(12) United States Patent
Steward et al.

(10) Patent No.: US 7,815,917 B2
(45) Date of Patent: \*Oct. 19, 2010

(54) BOTULINUM NEUROTOXIN SEROTYPE B ACTIVATABLE BOTULINUM NEUROTOXIN SEROTYPE BS

(75) Inventors: Lance E. Steward, Irvine, CA (US); Melvin S. Oka, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/434,074

(22) Filed: May 1, 2009

(65) Prior Publication Data

US 2010/0075396 A1    Mar. 25, 2010

Related U.S. Application Data

(63) Continuation of application No. 11/533,223, filed on Sep. 19, 2006, now Pat. No. 7,556,817.

(60) Provisional application No. 60/718,616, filed on Sep. 19, 2005.

(51) Int. Cl.
  *A61K 39/08* (2006.01)
  *C12N 1/21* (2006.01)
(52) U.S. Cl. ............... 424/239.1; 435/69.1; 435/252.3; 435/471; 530/350
(58) Field of Classification Search ....................... None
See application file for complete search history.

(56) References Cited

U.S. PATENT DOCUMENTS 5,707,826 A    1/1998    Wagner et al.
5,962,637 A   10/1999    Shone et al.
5,989,545 A   11/1999    Foster et al.
6,022,950 A    2/2000    Murphy
6,203,794 B1 *  3/2001   Dolly et al. ............... 424/184.1
6,221,355 B1    4/2001    Dowdy
6,337,386 B1 *  1/2002   Shone et al. ................ 530/329
6,395,513 B1    5/2002    Foster et al.

(Continued)

FOREIGN PATENT DOCUMENTS

WO    98/07864    2/1998

(Continued)

OTHER PUBLICATIONS

Wictome, Matthew et al, FEBS Letters, vol. 386, pp. 133-136, 1996, Substrate residues N-terminal to the cleavage site of botulinum type B neurotoxin play a role in determining the specificity of its endopeptidase activity.*

(Continued)

*Primary Examiner*—Robert B Mondesi
*Assistant Examiner*—Ginny Portner
(74) *Attorney, Agent, or Firm*—Dean G. Stathakis; Joel B. German; Allergan, Inc.

(57) ABSTRACT

The specification discloses modified Clostridial toxins comprising a Clostridial toxin substrate cleavage site located within the di-chain loop region; polynucleotide molecules encoding such modified Clostridial toxins comprising a Clostridial toxin substrate cleavage site located in the di-chain loop region; and method of producing modified Clostridial toxins comprising Clostridial toxin substrate cleavage site located within the di-chain loop region.

5 Claims, 18 Drawing Sheets

U.S. PATENT DOCUMENTS

| | | | |
|---|---|---|---|
| 6,426,075 B1 | | 7/2002 | Fitzgerald et al. |
| 6,461,617 B1 | | 10/2002 | Shone et al. |
| 6,461,834 B1 | * | 10/2002 | Dormady et al. ............ 435/68.1 |
| 6,504,006 B1 | | 1/2003 | Shine et al. |
| 6,787,517 B1 | * | 9/2004 | Gil et al. ........................ 514/1 |
| 6,831,059 B2 | * | 12/2004 | Donovan ........................ 514/2 |
| 7,132,259 B1 | * | 11/2006 | Dolly et al. ................ 435/69.1 |
| 7,183,066 B2 | | 2/2007 | Fernandez-Salas et al. |
| 7,192,596 B2 | | 3/2007 | Shone et al. |
| 7,208,285 B2 | | 4/2007 | Steward et al. |
| 7,273,722 B2 | * | 9/2007 | Lin et al. .................... 435/69.1 |
| 7,419,676 B2 | * | 9/2008 | Dolly et al. ............... 424/239.1 |
| 7,422,877 B2 | * | 9/2008 | Dolly et al. ................ 435/69.1 |
| 7,498,148 B2 | * | 3/2009 | Wagner et al. ............. 435/68.1 |
| 7,556,817 B2 | * | 7/2009 | Steward et al. ........... 424/239.1 |
| 2002/0137886 A1 | | 9/2002 | Lin et al. |
| 2002/0168727 A1 | | 11/2002 | Smith et al. |
| 2003/0143650 A1 | | 7/2003 | Steward et al. |
| 2003/0143651 A1 | | 7/2003 | Steward et al. |
| 2004/0018589 A1 | | 1/2004 | Zhong |
| 2004/0072270 A1 | | 4/2004 | Fernandez-Salas et al. |
| 2004/0219619 A1 | | 11/2004 | Fernandez-Salas et al. |
| 2006/0099672 A1 | | 5/2006 | Dolly et al. |
| 2006/0110410 A1 | | 5/2006 | Shone et al. |
| 2006/0134722 A1 | | 6/2006 | Chapman et al. |
| 2006/0154314 A9 | | 7/2006 | Steward et al. |
| 2006/0204524 A1 | | 9/2006 | Ichtchenko et al. |
| 2006/0211619 A1 | | 9/2006 | Steward et al. |
| 2007/0218001 A1 | | 9/2007 | Delagrave |
| 2007/0248626 A1 | | 10/2007 | Shone et al. |
| 2008/0032930 A1 | | 2/2008 | Steward et al. |
| 2008/0081355 A1 | | 4/2008 | Dolly et al. |
| 2008/0161226 A1 | | 7/2008 | Steward et al. |
| 2008/0221012 A1 | | 9/2008 | Steward et al. |
| 2008/0305510 A1 | * | 12/2008 | Williams et al. .............. 435/23 |
| 2008/0311622 A1 | | 12/2008 | Dolly et al. |
| 2009/0004224 A1 | | 1/2009 | Steward et al. |
| 2009/0005313 A1 | | 1/2009 | Steward et al. |
| 2009/0018081 A1 | | 1/2009 | Steward et al. |
| 2009/0030182 A1 | | 1/2009 | Dolly et al. |
| 2009/0030188 A1 | | 1/2009 | Dolly et al. |
| 2009/0042270 A1 | | 2/2009 | Dolly et al. |
| 2009/0069238 A1 | | 3/2009 | Steward et al. |
| 2009/0081730 A1 | | 3/2009 | Dolly et al. |
| 2009/0087458 A1 | | 4/2009 | Dolly et al. |

FOREIGN PATENT DOCUMENTS

| | | |
|---|---|---|
| WO | 00/61768 | 10/2000 |
| WO | WO 00/61192 | 10/2000 |
| WO | 01/14570 | 3/2001 |
| WO | 02/44199 | 6/2002 |
| WO | 03/020948 | 3/2003 |
| WO | 2004/024909 | 3/2004 |
| WO | 2005/023309 | 3/2005 |
| WO | 2006/026780 | 3/2006 |
| WO | 2006/059093 | 6/2006 |
| WO | 2006/059105 | 6/2006 |

OTHER PUBLICATIONS

Evans et al, Toxicon, vol. 46, pp. 446-453, 2005 Analysis of the substrate recognition domain determinants of Botulinum type B toxin using Phage Display.*

Ahmed, S.A., et al., Enzymatic Autocatalysis of Botulinum A Neurotoxin Light Chain, 20(3) J. Protein Chem. 221-231 (2001).

Breidenbach et al, "Substrate recognition strategy for botulinum neurotoxin serotype A", Nature, vol. 432, No. 7019, pp. 925-929, Dec. 2004.

Breidenbach et al, "New insights into clostridial neurotoxin-SNARE interactions", Trends in Molecular Medicine, vol. 11, No. 8, pp. 377-381, Aug. 2005.

Chaddock et al, "Expression and purification of catalytically active, non-toxic endopeptidase derivatives of Clostridium botulinum toxin type A", Protein Expression and Purification, vol. 25, No. 2, pp. 219-228, Jul. 2002.

Fasshauer, Dirk et al, PNAS, USA, vol. 95, pp. 15781-15786, Dec. 1998, Conserved structural features of the synaptic fusion complex: SNARE proteins reclassified as Q and R-SNAREs.

Johnson, "Clostridial Toxins as Therapeutic Agents: Benefits of Nature's Most Toxic Proteins", Annual Review of Microbiology, vol. 53, pp. 551-575, 1999.

Li, Y., et al., Recombinant Forms of Tetanus Toxin Engineered for Examining and Exploiting Neuronal Trafficking Pathways, 276(33) J. Biol. Chem. 31394-31401 (2001).

Rawlings et al, "MEROPS: the protease database", Nucleic Acids Research, vol. 30, No. 1, 343-346, 2002.

Rossi, Valeria et al, Biology of the Cell, vol. 96, pp. 251-256, 2004, VAMP subfamilies identified by specific R-SNARE motifs.

Sutton, J.M., et al., Preparation of Specifically Activatable Endopeptidase Derivatives of Clostridium botulinum Toxins Type A, B, and C and Their Applications, 40(2005) Protein Expr. Purif. 31-41 (2005).

Swiss Prot Accession No. P10845.

Turton et al, "Botulinum and tetanus neurotoxins: structure, function and therapeutic utility", vol. 27, No. 11, pp. 552-558, Nov. 2002.

Washbourne, Philip et al, FEBS letters, vol. 418, pp. 1-5, 1997, Botulinum neurotoxin types A and E require the SNARE motif in SNAP-25 for proteolysis.

* cited by examiner

FIG. 2b.

Toxin

1 Heavy Chain Binding Domain

Receptor System

2

Heavy Chain Translocation Domain

3

ATP → ADP
H⁺

Light Chain

BoNT/B Cleavage Site

| Enzymatic | Translocation | Binding | Single-chain Form
—SS—

↓ Di-chain Loop
BoNT/B

| Translocation | Binding |
SS
| Enzymatic |
Di-chain Form

FIG. 5b.

BoNT/D Cleavage Site

| Enzymatic | Translocation | Binding | Single-chain Form
—SS—

↓ Di-chain Loop
BoNT/D

| Translocation | Binding |
SS
| Enzymatic |
Di-chain Form

FIG. 5c.

BoNT/F Cleavage Site

| Enzymatic | Translocation | Binding | Single-chain Form
—SS—

Di-chain Loop
↓ BoNT/F

| Translocation | Binding |
SS
| Enzymatic |
Di-chain Form

FIG. 5d.

BoNT/G Cleavage Site

| Enzymatic | Translocation | Binding | Single-chain Form
—SS—

Di-chain Loop
↓ BoNT/G

| Translocation | Binding |
SS
| Enzymatic |
Di-chain Form

FIG. 6a.

BoNT/C1 Cleavage Site

| Enzymatic | Translocation | Binding | Single-chain Form
| SS |

Di-chain Loop

↓ BoNT/C1

| Translocation | Binding |
| SS |
| Enzymatic |

Di-chain Form

FIG. 6b.

BoNT/C1 Cleavage Site

| Enzymatic | Translocation | Binding | Single-chain Form
| SS |

Di-chain Loop

↓ BoNT/C1

| Translocation | Binding |
| SS |
| Enzymatic |

Di-chain Form

BoNT/A-BT35 pET29b/
BoNT/A-BT35
9.6 kb

FIG. 9.

BoNT/A-Csyn8 pET29b/
BoNT/A-Csyn8
9.4 kb

Csyn8, TD, BD, Trypsin, 6xHis, T7 TT, f1 origin, Kanamycin, pBR322 ori, lacI, P_T7, ED

Plasmid map: pET29b/BoNT/A-G8, 9.4 kb. Features: P_T7, ED, G8, TD, BD, Trypsin, 6xHis, T7 TT, f1 origin, Kanamycin, pBR322 ori, lacI. BoNT/A-G8 insert indicated.

SEQUENCE LISTING

```
<160> NUMBER OF SEQ ID NOS: 238

<210> SEQ ID NO 1
<211> LENGTH: 1296
<212> TYPE: PRT
<213> ORGANISM: Clostridium botulinum Serotype A
<220> FEATURE:
<221> NAME/KEY: DOMAIN
<222> LOCATION: (1)...(448)
<223> OTHER INFORMATION: Light chain comprising the enzymatic domain
<221> NAME/KEY: DOMAIN
<222> LOCATION: (449)...(1296)
<223> OTHER INFORMATION: Heavy chain comprising the translocation and
      binding domains
<221> NAME/KEY: DOMAIN
<222> LOCATION: (449)...(871)
<223> OTHER INFORMATION: Amino-terminal half of heavy chain comprising
      the translocation domain.
<221> NAME/KEY: DOMAIN
<222> LOCATION: (872)...(1296)
<223> OTHER INFORMATION: Carboxyl-terminal half of heavy chain
      comprising the binding domain.

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140
```

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
                195                 200                 205

Gly Ala Gly Lys Phe Ala Thr Asp Pro Ala Val Thr Leu Ala His Glu
                210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
                370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560
```

-continued

```
His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
        660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
        740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
        850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
        900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
```

-continued

```
                980                 985                 990
Ile Lys Gln Arg Val Val Phe Lys Tyr Ser Gln Met Ile Asn Ile Ser
        995                1000                1005
Asp Tyr Ile Asn Arg Trp Ile Phe Val Thr Ile Thr Asn Asn Arg Leu
       1010                1015                1020
Asn Asn Ser Lys Ile Tyr Ile Asn Gly Arg Leu Ile Asp Gln Lys Pro
1025                1030                1035                1040
Ile Ser Asn Leu Gly Asn Ile His Ala Ser Asn Asn Ile Met Phe Lys
                1045                1050                1055
Leu Asp Gly Cys Arg Asp Thr His Arg Tyr Ile Trp Ile Lys Tyr Phe
            1060                1065                1070
Asn Leu Phe Asp Lys Glu Leu Asn Glu Lys Glu Ile Lys Asp Leu Tyr
        1075                1080                1085
Asp Asn Gln Ser Asn Ser Gly Ile Leu Lys Asp Phe Trp Gly Asp Tyr
    1090                1095                1100
Leu Gln Tyr Asp Lys Pro Tyr Tyr Met Leu Asn Leu Tyr Asp Pro Asn
1105                1110                1115                1120
Lys Tyr Val Asp Val Asn Asn Val Gly Ile Arg Gly Tyr Met Tyr Leu
                1125                1130                1135
Lys Gly Pro Arg Gly Ser Val Met Thr Thr Asn Ile Tyr Leu Asn Ser
            1140                1145                1150
Ser Leu Tyr Arg Gly Thr Lys Phe Ile Ile Lys Lys Tyr Ala Ser Gly
        1155                1160                1165
Asn Lys Asp Asn Ile Val Arg Asn Asn Asp Arg Val Tyr Ile Asn Val
    1170                1175                1180
Val Val Lys Asn Lys Glu Tyr Arg Leu Ala Thr Asn Ala Ser Gln Ala
1185                1190                1195                1200
Gly Val Glu Lys Ile Leu Ser Ala Leu Glu Ile Pro Asp Val Gly Asn
                1205                1210                1215
Leu Ser Gln Val Val Val Met Lys Ser Lys Asn Asp Gln Gly Ile Thr
            1220                1225                1230
Asn Lys Cys Lys Met Asn Leu Gln Asp Asn Asn Gly Asn Asp Ile Gly
        1235                1240                1245
Phe Ile Gly Phe His Gln Phe Asn Asn Ile Ala Lys Leu Val Ala Ser
    1250                1255                1260
Asn Trp Tyr Asn Arg Gln Ile Glu Arg Ser Ser Arg Thr Leu Gly Cys
1265                1270                1275                1280
Ser Trp Glu Phe Ile Pro Val Asp Asp Gly Trp Gly Glu Arg Pro Leu
                1285                1290                1295
```

<210> SEQ ID NO 2
<211> LENGTH: 1291
<212> TYPE: PRT
<213> ORGANISM: Clostridium botulinum Serotype B
<220> FEATURE:
<221> NAME/KEY: DOMAIN
<222> LOCATION: (1)...(441)
<223> OTHER INFORMATION: Light chain comprising the enzymatic domain.
<221> NAME/KEY: DOMAIN
<222> LOCATION: (442)...(1291)
<223> OTHER INFORMATION: Heavy chain comprising teh translocation and
      binding domains
<221> NAME/KEY: DOMAIN
<222> LOCATION: (442)...(858)
<223> OTHER INFORMATION: Amino-terminal half of heavy chain comprising
      the translocation domain.
<221> NAME/KEY: DOMAIN
<222> LOCATION: (858)...(1291)
<223> OTHER INFORMATION: Carboxyl-terminal half of heavy chain comprising the binding domain.

<400> SEQUENCE: 2

```
Met Pro Val Thr Ile Asn Asn Phe Asn Tyr Asn Asp Pro Ile Asp Asn
  1               5                  10                  15

Asn Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
             100                 105                 110

Ile Asn Gly Ile Pro Tyr Leu Gly Asp Arg Arg Val Pro Leu Glu Glu
         115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400
```

-continued

Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu

```
                  820                 825                 830
Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Leu Ile Asp Leu Ser Gly
865                 870                 875                 880

Tyr Gly Ala Lys Val Glu Val Tyr Asp Gly Val Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu Ser
            1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
            1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
            1075                1080                1085

Gly Asn Pro Leu Met Tyr Asn Lys Glu Tyr Tyr Met Phe Asn Ala Gly
            1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
            1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
            1155                1160                1165

Leu Asp Phe Phe Asn Leu Asn Gln Glu Trp Arg Val Tyr Thr Tyr Lys
            1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
            1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
            1235                1240                1245
```

-continued

```
Val Phe Glu Glu Tyr Lys Asp Tyr Phe Cys Ile Ser Lys Trp Tyr Leu
    1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
            1285                1290

<210> SEQ ID NO 3
<211> LENGTH: 1291
<212> TYPE: PRT
<213> ORGANISM: Clostridium botulinum Serotype C1
<220> FEATURE:
<221> NAME/KEY: DOMAIN
<222> LOCATION: (1)...(449)
<223> OTHER INFORMATION: Light chain comprising the enzymatic domain.
<221> NAME/KEY: DOMAIN
<222> LOCATION: (450)...(1291)
<223> OTHER INFORMATION: Heavy chain comprising the translocation and
      binding domains.
<221> NAME/KEY: DOMAIN
<222> LOCATION: (450)...(866)
<223> OTHER INFORMATION: Amino-terminal half of heavy chain comprising
      the translocation domain.
<221> NAME/KEY: DOMAIN
<222> LOCATION: (867)...(1291)
<223> OTHER INFORMATION: Carboxyl-terminal half of heavy chain
      comprising the binding domain.

<400> SEQUENCE: 3

Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
     50                  55                  60

Thr Ser Pro Lys Ser Gly Tyr Tyr Asp Pro Asn Tyr Leu Ser Thr Asp
 65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240
```

-continued

```
Ile Ala Ile Pro Asn Asp Gln Thr Ile Ser Ser Val Thr Ser Asn Ile
            245                 250                 255
Phe Tyr Ser Gln Tyr Asn Val Lys Leu Glu Tyr Ala Glu Ile Tyr Ala
        260                 265                 270
Phe Gly Gly Pro Thr Ile Asp Leu Ile Pro Lys Ser Ala Arg Lys Tyr
    275                 280                 285
Phe Glu Glu Lys Ala Leu Asp Tyr Tyr Arg Ser Ile Ala Lys Arg Leu
290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Thr Val Asn Arg Asn Lys Phe Val Glu Leu Tyr Asn
            340                 345                 350
Glu Leu Thr Gln Ile Phe Thr Glu Phe Asn Tyr Ala Lys Ile Tyr Asn
        355                 360                 365
Val Gln Asn Arg Lys Ile Tyr Leu Ser Asn Val Tyr Thr Pro Val Thr
    370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg Ser Leu Tyr Asn
        435                 440                 445
Lys Thr Leu Asp Cys Arg Glu Leu Leu Val Lys Asn Thr Asp Leu Pro
    450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
                485                 490                 495
Val Asp Gln Val Ile Leu Ser Lys Asn Thr Ser Glu His Gly Gln Leu
            500                 505                 510
Asp Leu Leu Tyr Pro Ser Ile Asp Ser Glu Ser Glu Ile Leu Pro Gly
        515                 520                 525
Glu Asn Gln Val Phe Tyr Asp Asn Arg Thr Gln Asn Val Asp Tyr Leu
    530                 535                 540
Asn Ser Tyr Tyr Tyr Leu Glu Ser Gln Lys Leu Ser Asp Asn Val Glu
545                 550                 555                 560
Asp Phe Thr Phe Thr Arg Ser Ile Glu Glu Ala Leu Asp Asn Ser Ala
                565                 570                 575
Lys Val Tyr Thr Tyr Phe Pro Thr Leu Ala Asn Lys Val Asn Ala Gly
            580                 585                 590
Val Gln Gly Gly Leu Phe Leu Met Trp Ala Asn Asp Val Val Glu Asp
        595                 600                 605
Phe Thr Thr Asn Ile Leu Arg Lys Asp Thr Leu Asp Lys Ile Ser Asp
    610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
                645                 650                 655
Thr Ile Leu Leu Glu Ala Phe Pro Glu Phe Thr Ile Pro Ala Leu Gly
```

-continued

```
            660                 665                 670
Ala Phe Val Ile Tyr Ser Lys Val Gln Glu Arg Asn Glu Ile Ile Lys
                675                 680                 685
Thr Ile Asp Asn Cys Leu Glu Gln Arg Ile Lys Arg Trp Lys Asp Ser
            690                 695                 700
Tyr Glu Trp Met Met Gly Thr Trp Leu Ser Arg Ile Ile Thr Gln Phe
705                 710                 715                 720
Asn Asn Ile Ser Tyr Gln Met Tyr Asp Ser Leu Asn Tyr Gln Ala Gly
                725                 730                 735
Ala Ile Lys Ala Lys Ile Asp Leu Glu Tyr Lys Lys Tyr Ser Gly Ser
            740                 745                 750
Asp Lys Glu Asn Ile Lys Ser Gln Val Glu Asn Leu Lys Asn Ser Leu
            755                 760                 765
Asp Val Lys Ile Ser Glu Ala Met Asn Asn Ile Asn Lys Phe Ile Arg
            770                 775                 780
Glu Cys Ser Val Thr Tyr Leu Phe Lys Asn Met Leu Pro Lys Val Ile
785                 790                 795                 800
Asp Glu Leu Asn Glu Phe Asp Arg Asn Thr Lys Ala Lys Leu Ile Asn
                805                 810                 815
Leu Ile Asp Ser His Asn Ile Ile Leu Val Gly Glu Val Asp Lys Leu
                820                 825                 830
Lys Ala Lys Val Asn Asn Ser Phe Gln Asn Thr Ile Pro Phe Asn Ile
            835                 840                 845
Phe Ser Tyr Thr Asn Asn Ser Leu Leu Lys Asp Ile Ile Asn Glu Tyr
            850                 855                 860
Phe Asn Asn Ile Asn Asp Ser Lys Ile Leu Ser Leu Gln Asn Arg Lys
865                 870                 875                 880
Asn Thr Leu Val Asp Thr Ser Gly Tyr Asn Ala Glu Val Ser Glu Glu
                885                 890                 895
Gly Asp Val Gln Leu Asn Pro Ile Phe Pro Phe Asp Phe Lys Leu Gly
                900                 905                 910
Ser Ser Gly Glu Asp Arg Gly Lys Val Ile Val Thr Gln Asn Glu Asn
            915                 920                 925
Ile Val Tyr Asn Ser Met Tyr Glu Ser Phe Ser Ile Ser Phe Trp Ile
            930                 935                 940
Arg Ile Asn Lys Trp Val Ser Asn Leu Pro Gly Tyr Thr Ile Ile Asp
945                 950                 955                 960
Ser Val Lys Asn Asn Ser Gly Trp Ser Ile Gly Ile Ile Ser Asn Phe
                965                 970                 975
Leu Val Phe Thr Leu Lys Gln Asn Glu Asp Ser Glu Gln Ser Ile Asn
                980                 985                 990
Phe Ser Tyr Asp Ile Ser Asn Asn Ala Pro Gly Tyr Asn Lys Trp Phe
            995                 1000                1005
Phe Val Thr Val Thr Asn Asn Met Met Gly Asn Met Lys Ile Tyr Ile
            1010                1015                1020
Asn Gly Lys Leu Ile Asp Thr Ile Lys Val Lys Glu Leu Thr Gly Ile
1025                1030                1035                1040
Asn Phe Ser Lys Thr Ile Thr Phe Glu Ile Asn Lys Ile Pro Asp Thr
                1045                1050                1055
Gly Leu Ile Thr Ser Asp Ser Asp Asn Ile Asn Met Trp Ile Arg Asp
            1060                1065                1070
Phe Tyr Ile Phe Ala Lys Glu Leu Asp Gly Lys Asp Ile Asn Ile Leu
            1075                1080                1085
```

-continued

```
Phe Asn Ser Leu Gln Tyr Thr Asn Val Val Lys Asp Tyr Trp Gly Asn
    1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135

Arg Asn Asn Asn Asp Phe Asn Glu Gly Tyr Lys Ile Ile Ile Lys Arg
            1140                1145                1150

Ile Arg Gly Asn Thr Asn Asp Thr Arg Val Arg Gly Gly Asp Ile Leu
        1155                1160                1165

Tyr Phe Asp Met Thr Ile Asn Asn Lys Ala Tyr Asn Leu Phe Met Lys
    1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
        1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290

<210> SEQ ID NO 4
<211> LENGTH: 1276
<212> TYPE: PRT
<213> ORGANISM: Clostridium botulinum Serotype D
<220> FEATURE:
<221> NAME/KEY: DOMAIN
<222> LOCATION: (1)...(445)
<223> OTHER INFORMATION: Light chain comprising the enzymatic domain.
<221> NAME/KEY: DOMAIN
<222> LOCATION: (446)...(1276)
<223> OTHER INFORMATION: Heavy chain comprising the translocation and
      binding domains.
<221> NAME/KEY: DOMAIN
<222> LOCATION: (446)...(862)
<223> OTHER INFORMATION: Amino-terminal half of heavy chain comprising
      the translocation domain.
<221> NAME/KEY: DOMAIN
<222> LOCATION: (863)...(1276)
<223> OTHER INFORMATION: Carboxyl-terminal half of heavy chain
      comprising the binding domain.

<400> SEQUENCE: 4

Met Thr Trp Pro Val Lys Asp Phe Asn Tyr Ser Asp Pro Val Asn Asp
  1               5                  10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
     50                  55                  60

Thr Ser Lys Tyr Gln Ser Tyr Tyr Asp Pro Ser Tyr Leu Ser Thr Asp
65                  70                  75                  80
```

-continued

```
Glu Gln Lys Asp Thr Phe Leu Lys Gly Ile Ile Lys Leu Phe Lys Arg
                85                  90                  95
Ile Asn Glu Arg Asp Ile Gly Lys Lys Leu Ile Asn Tyr Leu Val Val
            100                 105                 110
Gly Ser Pro Phe Met Gly Asp Ser Ser Thr Pro Glu Asp Thr Phe Asp
            115                 120                 125
Phe Thr Arg His Thr Thr Asn Ile Ala Val Glu Lys Phe Glu Asn Gly
            130                 135                 140
Ser Trp Lys Val Thr Asn Ile Ile Thr Pro Ser Val Leu Ile Phe Gly
145                 150                 155                 160
Pro Leu Pro Asn Ile Leu Asp Tyr Thr Ala Ser Leu Thr Leu Gln Gly
                165                 170                 175
Gln Gln Ser Asn Pro Ser Phe Glu Gly Phe Gly Thr Leu Ser Ile Leu
            180                 185                 190
Lys Val Ala Pro Glu Phe Leu Leu Thr Phe Ser Asp Val Thr Ser Asn
            195                 200                 205
Gln Ser Ser Ala Val Leu Gly Lys Ser Ile Phe Cys Met Asp Pro Val
    210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
Phe Phe Ser Gln Asp Gly Pro Asn Val Gln Phe Glu Glu Leu Tyr Thr
            260                 265                 270
Phe Gly Gly Leu Asp Val Glu Ile Ile Pro Gln Ile Glu Arg Ser Gln
            275                 280                 285
Leu Arg Glu Lys Ala Leu Gly His Tyr Lys Asp Ile Ala Lys Arg Leu
    290                 295                 300
Asn Asn Ile Asn Lys Thr Ile Pro Ser Ser Trp Ile Ser Asn Ile Asp
305                 310                 315                 320
Lys Tyr Lys Lys Ile Phe Ser Glu Lys Tyr Asn Phe Asp Lys Asp Asn
                325                 330                 335
Thr Gly Asn Phe Val Val Asn Ile Asp Lys Phe Asn Ser Leu Tyr Ser
            340                 345                 350
Asp Leu Thr Asn Val Met Ser Glu Val Val Tyr Ser Ser Gln Tyr Asn
            355                 360                 365
Val Lys Asn Arg Thr His Tyr Phe Ser Arg His Tyr Leu Pro Val Phe
    370                 375                 380
Ala Asn Ile Leu Asp Asp Asn Ile Tyr Thr Ile Arg Asp Gly Phe Asn
385                 390                 395                 400
Leu Thr Asn Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
            420                 425                 430
Phe Thr Lys Val Cys Leu Arg Leu Thr Lys Asn Ser Arg Asp Asp Ser
            435                 440                 445
Thr Cys Ile Lys Val Lys Asn Asn Arg Leu Pro Tyr Val Ala Asp Lys
    450                 455                 460
Asp Ser Ile Ser Gln Glu Ile Phe Glu Asn Lys Ile Ile Thr Asp Glu
465                 470                 475                 480
Thr Asn Val Gln Asn Tyr Ser Asp Lys Phe Ser Leu Asp Glu Ser Ile
                485                 490                 495
Leu Asp Gly Gln Val Pro Ile Asn Pro Glu Ile Val Asp Pro Leu Leu
```

-continued

```
            500                 505                 510
Pro Asn Val Asn Met Glu Pro Leu Asn Leu Pro Gly Glu Glu Ile Val
            515                 520                 525

Phe Tyr Asp Asp Ile Thr Lys Tyr Val Asp Tyr Leu Asn Ser Tyr Tyr
        530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
        610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
        770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
        850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
        915                 920                 925
```

```
Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu Lys
    1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
            1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
    1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
            1140                1145                1150

Asp Asn Ile Ile Leu His Met Leu Tyr Asn Ser Arg Lys Tyr Met Ile
        1155                1160                1165

Ile Arg Asp Thr Asp Thr Ile Tyr Ala Thr Gln Gly Gly Glu Cys Ser
    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                1205                1210                1215

Cys Ser Gln Ile Phe Ser Ser Phe Arg Glu Asn Thr Met Leu Leu Ala
            1220                1225                1230

Asp Ile Tyr Lys Pro Trp Arg Phe Ser Phe Lys Asn Ala Tyr Thr Pro
        1235                1240                1245

Val Ala Val Thr Asn Tyr Glu Thr Lys Leu Leu Ser Thr Ser Ser Phe
    1250                1255                1260

Trp Lys Phe Ile Ser Arg Asp Pro Gly Trp Val Glu
1265                1270                1275

<210> SEQ ID NO 5
<211> LENGTH: 1252
<212> TYPE: PRT
<213> ORGANISM: Clostridium botulinum Serotype E
<220> FEATURE:
<221> NAME/KEY: DOMAIN
<222> LOCATION: (1)...(422)
<223> OTHER INFORMATION: Light chain comprising the enzymatic domain.
<221> NAME/KEY: DOMAIN
<222> LOCATION: (423)...(1252)
<223> OTHER INFORMATION: Heavy chain comprising the translocation and
```

-continued

```
      binding domains.
<221> NAME/KEY: DOMAIN
<222> LOCATION: (423)...(845)
<223> OTHER INFORMATION: Amino-terminal half of heavy chain comprising
      the translocation domain.
<221> NAME/KEY: DOMAIN
<222> LOCATION: (846)...(1252)
<223> OTHER INFORMATION: Carboxyl-terminal half of heavy chain
      comprising the binding domain.

<400> SEQUENCE: 5

Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
```

-continued

```
                355                 360                 365
Tyr Asn Ile Ser Glu Gly Tyr Asn Ile Asn Asn Leu Lys Val Asn Phe
        370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
        420                 425                 430
Glu Leu Phe Phe Val Ala Ser Glu Asn Ser Tyr Asn Asp Asp Asn Ile
        435                 440                 445
Asn Thr Pro Lys Glu Ile Asp Asp Thr Val Thr Ser Asn Asn Asn Tyr
450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
        515                 520                 525
Pro Glu Gly Glu Asn Asn Val Asn Leu Thr Ser Ser Ile Asp Thr Ala
        530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
        580                 585                 590
Val Asp Lys Ile Ala Asp Ile Ser Ile Val Val Pro Tyr Ile Gly Leu
        595                 600                 605
Ala Leu Asn Ile Gly Asn Glu Ala Gln Lys Gly Asn Phe Lys Asp Ala
        610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
                675                 680                 685
Trp Met Thr Lys Ile Asn Thr Gln Phe Asn Lys Arg Lys Glu Gln Met
        690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
        755                 760                 765
Tyr Leu Met Lys Leu Ile Asn Glu Val Lys Ile Asn Lys Leu Arg Glu
        770                 775                 780
```

-continued

```
Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
            805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
                900                 905                 910

Lys Asn Phe Ser Ile Ser Phe Trp Val Arg Ile Pro Asn Tyr Asp Asn
                915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
                980                 985                 990

Val Thr Ile Thr Asn Asp Arg Leu Gly Asp Ser Lys Leu Tyr Ile Asn
                995                 1000                1005

Gly Asn Leu Ile Asp Gln Lys Ser Ile Leu Asn Leu Gly Asn Ile His
            1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
            1060                1065                1070

Lys Asp Phe Trp Gly Asn Tyr Leu Leu Tyr Asp Lys Glu Tyr Tyr Leu
            1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
            1125                1130                1135

Thr Asn Asp Asn Leu Val Arg Lys Asn Asp Gln Val Tyr Ile Asn Phe
            1140                1145                1150

Val Ala Ser Lys Thr His Leu Phe Pro Leu Tyr Ala Asp Thr Ala Thr
            1155                1160                1165

Thr Asn Lys Glu Lys Thr Ile Lys Ile Ser Ser Ser Gly Asn Arg Phe
            1170                1175                1180

Asn Gln Val Val Val Met Asn Ser Val Gly Asn Asn Cys Thr Met Asn
1185                1190                1195                1200
```

-continued

```
Phe Lys Asn Asn Asn Gly Asn Ile Gly Leu Leu Gly Phe Lys Ala
            1205                1210                1215

Asp Thr Val Val Ala Ser Thr Trp Tyr Tyr Thr His Met Arg Asp His
            1220                1225                1230

Thr Asn Ser Asn Gly Cys Phe Trp Asn Phe Ile Ser Glu Glu His Gly
        1235                1240                1245

Trp Gln Glu Lys
    1250

<210> SEQ ID NO 6
<211> LENGTH: 1274
<212> TYPE: PRT
<213> ORGANISM: Clostridium botulinum Serotype F
<220> FEATURE:
<221> NAME/KEY: DOMAIN
<222> LOCATION: (1)...(439)
<223> OTHER INFORMATION: Light chain comprising the enzymatic domain.
<221> NAME/KEY: DOMAIN
<222> LOCATION: (440)...(1274)
<223> OTHER INFORMATION: Heavy chain comprising the translocation and
      binding domains.
<221> NAME/KEY: DOMAIN
<222> LOCATION: (440)...(864)
<223> OTHER INFORMATION: Amino-terminal half of heavy chain comprising
      the translocation domain.
<221> NAME/KEY: DOMAIN
<222> LOCATION: (865)...(1274)
<223> OTHER INFORMATION: Carboxyl-terminal half of heavy chain
      comprising the binding domain.

<400> SEQUENCE: 6

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
            85                  90                  95

Arg Ile Asn Ser Asn Pro Ala Gly Lys Val Leu Leu Gln Glu Ile Ser
        100                 105                 110

Tyr Ala Lys Pro Tyr Leu Gly Asn Asp His Thr Pro Ile Asp Glu Phe
    115                 120                 125

Ser Pro Val Thr Arg Thr Thr Ser Val Asn Ile Lys Leu Ser Thr Asn
        130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
            165                 170                 175

Asp Val Val Tyr Asp Pro Ser Asn Tyr Gly Phe Gly Ser Ile Asn Ile
        180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
```

```
            225                 230                 235                 240
Gly Val Thr Tyr Glu Glu Thr Ile Glu Val Lys Gln Ala Pro Leu Met
                245                 250                 255
Ile Ala Glu Lys Pro Ile Arg Leu Glu Glu Phe Leu Thr Phe Gly Gly
                260                 265                 270
Gln Asp Leu Asn Ile Ile Thr Ser Ala Met Lys Glu Lys Ile Tyr Asn
                275                 280                 285
Asn Leu Leu Ala Asn Tyr Glu Lys Ile Ala Thr Arg Leu Ser Glu Val
            290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
                325                 330                 335
Asn Glu Asn Lys Phe Asn Glu Ile Tyr Lys Lys Leu Tyr Ser Phe Thr
                340                 345                 350
Glu Ser Asp Leu Ala Asn Lys Phe Lys Val Lys Cys Arg Asn Thr Tyr
            355                 360                 365
Phe Ile Lys Tyr Glu Phe Leu Lys Val Pro Asn Leu Leu Asp Asp Asp
        370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
                405                 410                 415
Pro Asp Lys Gly Leu Val Glu Lys Ile Val Lys Phe Cys Lys Ser Val
                420                 425                 430
Ile Pro Arg Lys Gly Thr Lys Ala Pro Pro Arg Leu Cys Ile Arg Val
                435                 440                 445
Asn Asn Ser Glu Leu Phe Phe Val Ala Ser Glu Ser Tyr Asn Glu
            450                 455                 460
Asn Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
                485                 490                 495
Gln Thr Ile Pro Gln Ile Ser Asn Arg Thr Leu Asn Thr Leu Val Gln
                500                 505                 510
Asp Asn Ser Tyr Val Pro Arg Tyr Asp Ser Asn Gly Thr Ser Glu Ile
            515                 520                 525
Glu Glu Tyr Asp Val Val Asp Phe Asn Val Phe Phe Tyr Leu His Ala
            530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Asp Ile Phe Phe Ser Ser Glu
                565                 570                 575
Phe Ile Asp Thr Ile Asn Lys Pro Val Asn Ala Ala Leu Phe Ile Asp
                580                 585                 590
Trp Ile Ser Lys Val Ile Arg Asp Phe Thr Thr Glu Ala Thr Gln Lys
                595                 600                 605
Ser Thr Val Asp Lys Ile Ala Asp Ile Ser Leu Ile Val Pro Tyr Val
                610                 615                 620
Gly Leu Ala Leu Asn Ile Ile Ile Glu Ala Glu Lys Gly Asn Phe Glu
625                 630                 635                 640
Glu Ala Phe Glu Leu Leu Gly Val Gly Ile Leu Leu Glu Phe Val Pro
                645                 650                 655
```

-continued

```
Glu Leu Thr Ile Pro Val Ile Leu Val Phe Thr Ile Lys Ser Tyr Ile
            660                 665                 670
Asp Ser Tyr Glu Asn Lys Asn Lys Ala Ile Lys Ala Ile Asn Asn Ser
        675                 680                 685
Leu Ile Glu Arg Glu Ala Lys Trp Lys Glu Ile Tyr Ser Trp Ile Val
    690                 695                 700
Ser Asn Trp Leu Thr Arg Ile Asn Thr Gln Phe Asn Lys Arg Lys Glu
705                 710                 715                 720
Gln Met Tyr Gln Ala Leu Gln Asn Gln Val Asp Ala Ile Lys Thr Ala
                725                 730                 735
Ile Glu Tyr Lys Tyr Asn Asn Tyr Thr Ser Asp Glu Lys Asn Arg Leu
            740                 745                 750
Glu Ser Glu Tyr Asn Ile Asn Asn Ile Glu Glu Leu Asn Lys Lys
        755                 760                 765
Val Ser Leu Ala Met Lys Asn Ile Glu Arg Phe Met Thr Glu Ser Ser
    770                 775                 780
Ile Ser Tyr Leu Met Lys Leu Ile Asn Glu Ala Lys Val Gly Lys Leu
785                 790                 795                 800
Lys Lys Tyr Asp Asn His Val Lys Ser Asp Leu Leu Asn Tyr Ile Leu
                805                 810                 815
Asp His Arg Ser Ile Leu Gly Glu Gln Thr Asn Glu Leu Ser Asp Leu
            820                 825                 830
Val Thr Ser Thr Leu Asn Ser Ser Ile Pro Phe Glu Leu Ser Ser Tyr
        835                 840                 845
Thr Asn Asp Lys Ile Leu Ile Ile Tyr Phe Asn Arg Leu Tyr Lys Lys
    850                 855                 860
Ile Lys Asp Ser Ser Ile Leu Asp Met Arg Tyr Glu Asn Asn Lys Phe
865                 870                 875                 880
Ile Asp Ile Ser Gly Tyr Gly Ser Asn Ile Ser Ile Asn Gly Asn Val
                885                 890                 895
Tyr Ile Tyr Ser Thr Asn Arg Asn Gln Phe Gly Ile Tyr Asn Ser Arg
            900                 905                 910
Leu Ser Glu Val Asn Ile Ala Gln Asn Asn Asp Ile Ile Tyr Asn Ser
        915                 920                 925
Arg Tyr Gln Asn Phe Ser Ile Ser Phe Trp Val Arg Ile Pro Lys His
    930                 935                 940
Tyr Lys Pro Met Asn His Asn Arg Glu Tyr Thr Ile Ile Asn Cys Met
945                 950                 955                 960
Gly Asn Asn Asn Ser Gly Trp Lys Ile Ser Leu Arg Thr Val Arg Asp
                965                 970                 975
Cys Glu Ile Ile Trp Thr Leu Gln Asp Thr Ser Gly Asn Lys Glu Asn
            980                 985                 990
Leu Ile Phe Arg Tyr Glu Glu Leu Asn Arg Ile Ser Asn Tyr Ile Asn
        995                 1000                1005
Lys Trp Ile Phe Val Thr Ile Thr Asn Asn Arg Leu Gly Asn Ser Arg
    1010                1015                1020
Ile Tyr Ile Asn Gly Asn Leu Ile Val Glu Lys Ser Ile Ser Asn Leu
1025                1030                1035                1040
Gly Asp Ile His Val Ser Asp Asn Ile Leu Phe Lys Ile Val Gly Cys
                1045                1050                1055
Asp Asp Glu Thr Tyr Val Gly Ile Arg Tyr Phe Lys Val Phe Asn Thr
            1060                1065                1070
```

```
Glu Leu Asp Lys Thr Glu Ile Glu Thr Leu Tyr Ser Asn Glu Pro Asp
        1075                1080                1085

Pro Ser Ile Leu Lys Asn Tyr Trp Gly Asn Tyr Leu Leu Tyr Asn Lys
        1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
        1125                1130                1135

Ser Val Phe Leu Asn Tyr Lys Leu Tyr Glu Gly Val Glu Val Ile Ile
        1140                1145                1150

Arg Lys Asn Gly Pro Ile Asp Ile Ser Asn Thr Asp Asn Phe Val Arg
        1155                1160                1165

Lys Asn Asp Leu Ala Tyr Ile Asn Val Val Asp Arg Gly Val Glu Tyr
        1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
        1205                1210                1215

Gly Asn Asn Cys Thr Met Asn Phe Gln Asn Asn Asn Gly Ser Asn Ile
        1220                1225                1230

Gly Leu Leu Gly Phe His Ser Asn Asn Leu Val Ala Ser Ser Trp Tyr
        1235                1240                1245

Tyr Asn Asn Ile Arg Arg Asn Thr Ser Ser Asn Gly Cys Phe Trp Ser
        1250                1255                1260

Ser Ile Ser Lys Glu Asn Gly Trp Lys Glu
1265                1270

<210> SEQ ID NO 7
<211> LENGTH: 1297
<212> TYPE: PRT
<213> ORGANISM: Clostridium botulinum Serotype G
<220> FEATURE:
<221> NAME/KEY: DOMAIN
<222> LOCATION: (1)...(446)
<223> OTHER INFORMATION: Light chain comprising the enzymatic domain.
<221> NAME/KEY: DOMAIN
<222> LOCATION: (447)...(1297)
<223> OTHER INFORMATION: Heavy chain comprising the translocation and
      binding domains.
<221> NAME/KEY: DOMAIN
<222> LOCATION: (447)...(863)
<223> OTHER INFORMATION: Amino-terminal half of heavy chain comprising
      the translocation domain.
<221> NAME/KEY: DOMAIN
<222> LOCATION: (864)...(1297)
<223> OTHER INFORMATION: Carboxyl-terminal half of heavy chain
      comprising the binding domain.

<400> SEQUENCE: 7

Met Pro Val Asn Ile Lys Asn Phe Asn Tyr Asn Asp Pro Ile Asn Asn
1                5                  10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
        50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
```

```
                    85                  90                  95
Asn Arg Ile Asn Ser Lys Pro Ser Gly Gln Arg Leu Leu Asp Met Ile
            100                 105                 110
Val Asp Ala Ile Pro Tyr Leu Gly Asn Ala Ser Thr Pro Pro Asp Lys
            115                 120                 125
Phe Ala Ala Asn Val Ala Asn Val Ser Ile Asn Lys Lys Ile Ile Gln
            130                 135                 140
Pro Gly Ala Glu Asp Gln Ile Lys Gly Leu Met Thr Asn Leu Ile Ile
145                 150                 155                 160
Phe Gly Pro Gly Pro Val Leu Ser Asp Asn Phe Thr Asp Ser Met Ile
                165                 170                 175
Met Asn Gly His Ser Pro Ile Ser Glu Gly Phe Gly Ala Arg Met Met
            180                 185                 190
Ile Arg Phe Cys Pro Ser Cys Leu Asn Val Phe Asn Asn Val Gln Glu
            195                 200                 205
Asn Lys Asp Thr Ser Ile Phe Ser Arg Arg Ala Tyr Phe Ala Asp Pro
            210                 215                 220
Ala Leu Thr Leu Met His Glu Leu Ile His Val Leu His Gly Leu Tyr
225                 230                 235                 240
Gly Ile Lys Ile Ser Asn Leu Pro Ile Thr Pro Asn Thr Lys Glu Phe
                245                 250                 255
Phe Met Gln His Ser Asp Pro Val Gln Ala Glu Glu Leu Tyr Thr Phe
            260                 265                 270
Gly Gly His Asp Pro Ser Val Ile Ser Pro Ser Thr Asp Met Asn Ile
            275                 280                 285
Tyr Asn Lys Ala Leu Gln Asn Phe Gln Asp Ile Ala Asn Arg Leu Asn
            290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                325                 330                 335
Tyr Ser Val Asp Lys Asp Lys Phe Asp Lys Leu Tyr Lys Ala Leu Met
            340                 345                 350
Phe Gly Phe Thr Glu Thr Asn Leu Ala Gly Glu Tyr Gly Ile Lys Thr
            355                 360                 365
Arg Tyr Ser Tyr Phe Ser Glu Tyr Leu Pro Pro Ile Lys Thr Glu Lys
            370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
            420                 425                 430
Ile Ala Met Cys Lys Pro Val Met Tyr Lys Asn Thr Gly Lys Ser Glu
            435                 440                 445
Gln Cys Ile Ile Val Asn Asn Glu Asp Leu Phe Phe Ile Ala Asn Lys
            450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
            500                 505                 510
```

-continued

Glu Pro Phe Thr Asn Phe Asp Asp Ile Asp Ile Pro Val Tyr Ile Lys
    515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Lys Val Tyr Thr
                565                 570                 575

Phe Phe Ser Thr Asn Leu Val Glu Lys Ala Asn Thr Val Gly Ala
                580                 585                 590

Ser Leu Phe Val Asn Trp Val Lys Gly Val Ile Asp Asp Phe Thr Ser
    595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
    675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
    755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
                820                 825                 830

Val Asn Arg His Leu Lys Asp Ser Ile Pro Phe Asp Leu Ser Leu Tyr
    835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
    915                 920                 925

```
Met Phe Asp Asn Phe Ser Ile Asn Phe Trp Val Arg Thr Pro Lys Tyr
    930                 935                 940
Asn Asn Asn Asp Ile Gln Thr Tyr Leu Gln Asn Glu Tyr Thr Ile Ile
945                 950                 955                 960
Ser Cys Ile Lys Asn Asp Ser Gly Trp Lys Val Ser Ile Lys Gly Asn
                965                 970                 975
Arg Ile Ile Trp Thr Leu Ile Asp Val Asn Ala Lys Ser Lys Ser Ile
            980                 985                 990
Phe Phe Glu Tyr Ser Ile Lys Asp Asn Ile Ser Asp Tyr Ile Asn Lys
        995                 1000                1005
Trp Phe Ser Ile Thr Ile Thr Asn Asp Arg Leu Gly Asn Ala Asn Ile
    1010                1015                1020
Tyr Ile Asn Gly Ser Leu Lys Lys Ser Glu Lys Ile Leu Asn Leu Asp
1025                1030                1035                1040
Arg Ile Asn Ser Ser Asn Asp Ile Asp Phe Lys Leu Ile Asn Cys Thr
                1045                1050                1055
Asp Thr Thr Lys Phe Val Trp Ile Lys Asp Phe Asn Ile Phe Gly Arg
            1060                1065                1070
Glu Leu Asn Ala Thr Glu Val Ser Ser Leu Tyr Trp Ile Gln Ser Ser
        1075                1080                1085
Thr Asn Thr Leu Lys Asp Phe Trp Gly Asn Pro Leu Arg Tyr Asp Thr
    1090                1095                1100
Gln Tyr Tyr Leu Phe Asn Gln Gly Met Gln Asn Ile Tyr Ile Lys Tyr
1105                1110                1115                1120
Phe Ser Lys Ala Ser Met Gly Glu Thr Ala Pro Arg Thr Asn Phe Asn
                1125                1130                1135
Asn Ala Ala Ile Asn Tyr Gln Asn Leu Tyr Leu Gly Leu Arg Phe Ile
            1140                1145                1150
Ile Lys Lys Ala Ser Asn Ser Arg Asn Ile Asn Asn Asp Asn Ile Val
        1155                1160                1165
Arg Glu Gly Asp Tyr Ile Tyr Leu Asn Ile Asp Asn Ile Ser Asp Glu
    1170                1175                1180
Ser Tyr Arg Val Tyr Val Leu Val Asn Ser Lys Glu Ile Gln Thr Gln
1185                1190                1195                1200
Leu Phe Leu Ala Pro Ile Asn Asp Asp Pro Thr Phe Tyr Asp Val Leu
                1205                1210                1215
Gln Ile Lys Lys Tyr Tyr Glu Lys Thr Thr Tyr Asn Cys Gln Ile Leu
            1220                1225                1230
Cys Glu Lys Asp Thr Lys Thr Phe Gly Leu Phe Gly Ile Gly Lys Phe
        1235                1240                1245
Val Lys Asp Tyr Gly Tyr Val Trp Asp Thr Tyr Asp Asn Tyr Phe Cys
    1250                1255                1260
Ile Ser Gln Trp Tyr Leu Arg Arg Ile Ser Glu Asn Ile Asn Lys Leu
1265                1270                1275                1280
Arg Leu Gly Cys Asn Trp Gln Phe Ile Pro Val Asp Glu Gly Trp Thr
                1285                1290                1295
Glu

<210> SEQ ID NO 8
<211> LENGTH: 1315
<212> TYPE: PRT
<213> ORGANISM: Clostridium tetani
<220> FEATURE:
<221> NAME/KEY: DOMAIN
<222> LOCATION: (1)...(457)
```

-continued

```
<223> OTHER INFORMATION: Light chain comprising the enzymatic domain.
<221> NAME/KEY: DOMAIN
<222> LOCATION: (458)...(1315)
<223> OTHER INFORMATION: Heavy chain comprising the translocation and
      binding domains.
<221> NAME/KEY: DOMAIN
<222> LOCATION: (458)...(879)
<223> OTHER INFORMATION: Amino-terminal half of heavy chain comprising
      the translocation domain.
<221> NAME/KEY: DOMAIN
<222> LOCATION: (880)...(1315)
<223> OTHER INFORMATION: Carboxyl-terminal half of heavy chain
      comprising the binding domain.

<400> SEQUENCE: 8

Met Pro Ile Thr Ile Asn Asn Phe Arg Tyr Ser Asp Pro Val Asn Asn
 1               5                  10                  15

Asp Thr Ile Ile Met Met Glu Pro Pro Tyr Cys Lys Gly Leu Asp Ile
             20                  25                  30

Tyr Tyr Lys Ala Phe Lys Ile Thr Asp Arg Ile Trp Ile Val Pro Glu
         35                  40                  45

Arg Tyr Glu Phe Gly Thr Lys Pro Glu Asp Phe Asn Pro Pro Ser Ser
 50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335
```

```
Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
        370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
```

-continued

```
            755                 760                 765
Glu Gln Ile Ala Asp Glu Ile Asn Asn Leu Lys Asn Lys Leu Glu Glu
    770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                805                 810                 815
Leu Leu Glu Phe Asp Thr Gln Ser Lys Asn Ile Leu Met Gln Tyr Ile
                820                 825                 830
Lys Ala Asn Ser Lys Phe Ile Gly Ile Thr Glu Leu Lys Lys Leu Glu
                835                 840                 845
Ser Lys Ile Asn Lys Val Phe Ser Thr Pro Ile Pro Phe Ser Tyr Ser
    850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                885                 890                 895
Ser Asp Ile Ser Gly Phe Asn Ser Ser Val Ile Thr Tyr Pro Asp Ala
                900                 905                 910
Gln Leu Val Pro Gly Ile Asn Gly Lys Ala Ile His Leu Val Asn Asn
                915                 920                 925
Glu Ser Ser Glu Val Ile Val His Lys Ala Met Asp Ile Glu Tyr Asn
    930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                965                 970                 975
Ile Ser Ser Met Lys Lys His Ser Leu Ser Ile Gly Ser Gly Trp Ser
                980                 985                 990
Val Ser Leu Lys Gly Asn Asn Leu Ile Trp Thr Leu Lys Asp Ser Ala
                995                 1000                1005
Gly Glu Val Arg Gln Ile Thr Phe Arg Asp Leu Pro Asp Lys Phe Asn
    1010                1015                1020
Ala Tyr Leu Ala Asn Lys Trp Val Phe Ile Thr Ile Thr Asn Asp Arg
1025                1030                1035                1040
Leu Ser Ser Ala Asn Leu Tyr Ile Asn Gly Val Leu Met Gly Ser Ala
                1045                1050                1055
Glu Ile Thr Gly Leu Gly Ala Ile Arg Glu Asp Asn Asn Ile Thr Leu
                1060                1065                1070
Lys Leu Asp Arg Cys Asn Asn Asn Asn Gln Tyr Val Ser Ile Asp Lys
                1075                1080                1085
Phe Arg Ile Phe Cys Lys Ala Leu Asn Pro Lys Glu Ile Glu Lys Leu
                1090                1095                1100
Tyr Thr Ser Tyr Leu Ser Ile Thr Phe Leu Arg Asp Phe Trp Gly Asn
1105                1110                1115                1120
Pro Leu Arg Tyr Asp Thr Glu Tyr Tyr Leu Ile Pro Val Ala Ser Ser
                1125                1130                1135
Ser Lys Asp Val Gln Leu Lys Asn Ile Thr Asp Tyr Met Tyr Leu Thr
                1140                1145                1150
Asn Ala Pro Ser Tyr Thr Asn Gly Lys Leu Asn Ile Tyr Tyr Arg Arg
                1155                1160                1165
Leu Tyr Asn Gly Leu Lys Phe Ile Ile Lys Arg Tyr Thr Pro Asn Asn
    1170                1175                1180
```

```
Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
                1205                1210                1215

Ala Phe Asn Asn Leu Asp Arg Ile Leu Arg Val Gly Tyr Asn Ala Pro
                1220                1225                1230

Gly Ile Pro Leu Tyr Lys Lys Met Glu Ala Val Lys Leu Arg Asp Leu
                1235                1240                1245

Lys Thr Tyr Ser Val Gln Leu Lys Leu Tyr Asp Asp Lys Asn Ala Ser
                1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
                1285                1290                1295

Lys Ile Leu Gly Cys Asp Trp Tyr Phe Val Pro Thr Asp Glu Gly Trp
                1300                1305                1310

Thr Asn Asp
        1315

<210> SEQ ID NO 9
<211> LENGTH: 206
<212> TYPE: PRT
<213> ORGANISM: Homo sapiens SNAP-25A (Human)

<400> SEQUENCE: 9

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Asp Arg Val Glu Glu Gly Met
        50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 10
<211> LENGTH: 206
<212> TYPE: PRT
```

<213> ORGANISM: Homo sapiens SNAP-25B (Human)

<400> SEQUENCE: 10

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 11
<211> LENGTH: 211
<212> TYPE: PRT
<213> ORGANISM: Homo sapiens SNAP-23A (Human)

<400> SEQUENCE: 11

```
Met Asp Asn Leu Ser Ser Glu Glu Ile Gln Gln Arg Ala His Gln Ile
1               5                   10                  15

Thr Asp Glu Ser Leu Glu Ser Thr Arg Arg Ile Leu Gly Leu Ala Ile
                20                  25                  30

Glu Ser Gln Asp Ala Gly Ile Lys Thr Ile Thr Met Leu Asp Glu Gln
            35                  40                  45

Lys Glu Gln Leu Asn Arg Ile Glu Glu Gly Leu Asp Gln Ile Asn Lys
        50                  55                  60

Asp Met Arg Glu Thr Glu Lys Thr Leu Thr Glu Leu Asn Lys Cys Cys
65                  70                  75                  80

Gly Leu Cys Val Cys Pro Cys Asn Arg Thr Lys Asn Phe Glu Ser Gly
                85                  90                  95

Lys Ala Tyr Lys Thr Thr Trp Gly Asp Gly Gly Glu Asn Ser Pro Cys
            100                 105                 110

Asn Val Val Ser Lys Gln Pro Gly Pro Val Thr Asn Gly Gln Leu Gln
        115                 120                 125

Gln Pro Thr Thr Gly Ala Ala Ser Gly Gly Tyr Ile Lys Arg Ile Thr
130                 135                 140

Asn Asp Ala Arg Glu Asp Glu Met Glu Glu Asn Leu Thr Gln Val Gly
```

-continued

```
              145                 150                 155                 160
Ser Ile Leu Gly Asn Leu Lys Asp Met Ala Leu Asn Ile Gly Asn Glu
                165                 170                 175

Ile Asp Ala Gln Asn Pro Gln Ile Lys Arg Ile Thr Asp Lys Ala Asp
            180                 185                 190

Thr Asn Arg Asp Arg Ile Asp Ile Ala Asn Ala Arg Ala Lys Lys Leu
        195                 200                 205

Ile Asp Ser
    210

<210> SEQ ID NO 12
<211> LENGTH: 158
<212> TYPE: PRT
<213> ORGANISM: Homo sapiens SNAP-23B (Human)

<400> SEQUENCE: 12

Met Asp Asn Leu Ser Ser Glu Glu Ile Gln Gln Arg Ala His Gln Ile
1               5                   10                  15

Thr Asp Glu Ser Leu Glu Ser Thr Arg Arg Ile Leu Gly Leu Ala Ile
            20                  25                  30

Glu Ser Gln Asp Ala Gly Ile Lys Thr Ile Thr Met Leu Asp Glu Gln
        35                  40                  45

Lys Glu Gln Leu Asn Arg Ile Glu Glu Gly Leu Asp Gln Ile Asn Lys
    50                  55                  60

Asp Met Arg Glu Thr Glu Lys Thr Leu Thr Glu Leu Asn Lys Cys Cys
65                  70                  75                  80

Gly Leu Cys Val Cys Pro Cys Asn Ser Ile Thr Asn Asp Ala Arg Glu
                85                  90                  95

Asp Glu Met Glu Glu Asn Leu Thr Gln Val Gly Ser Ile Leu Gly Asn
            100                 105                 110

Leu Lys Asp Met Ala Leu Asn Ile Gly Asn Glu Ile Asp Ala Gln Asn
        115                 120                 125

Pro Gln Ile Lys Arg Ile Thr Asp Lys Ala Asp Thr Asn Arg Asp Arg
    130                 135                 140

Ile Asp Ile Ala Asn Ala Arg Ala Lys Lys Leu Ile Asp Ser
145                 150                 155

<210> SEQ ID NO 13
<211> LENGTH: 206
<212> TYPE: PRT
<213> ORGANISM: Macaca mulatta SNAP-25B (Rhesus monkey)

<400> SEQUENCE: 13

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
```

```
                   100                 105                 110
Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 14
<211> LENGTH: 206
<212> TYPE: PRT
<213> ORGANISM: Rattus norvegicus SNAP-25A (Rat)

<400> SEQUENCE: 14

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 15
<211> LENGTH: 206
<212> TYPE: PRT
<213> ORGANISM: Rattus norvegicus SNAP-25B (Rat)

<400> SEQUENCE: 15

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
```

-continued

```
                    20                  25                  30
Leu Gln Leu Val Glu Glu Ser Lys Asp Ala Gly Ile Arg Thr Leu Val
            35                  40                  45
Met Leu Asp Glu Gln Gly Glu Gln Leu Glu Arg Ile Glu Glu Gly Met
 50                  55                  60
Asp Gln Ile Asn Lys Asp Met Lys Glu Ala Glu Lys Asn Leu Thr Asp
 65                  70                  75                  80
Leu Gly Lys Phe Cys Gly Leu Cys Val Cys Pro Cys Asn Lys Leu Lys
                 85                  90                  95
Ser Ser Asp Ala Tyr Lys Lys Ala Trp Gly Asn Asn Gln Asp Gly Val
            100                 105                 110
Val Ala Ser Gln Pro Ala Arg Val Val Asp Glu Arg Glu Gln Met Ala
        115                 120                 125
Ile Ser Gly Gly Phe Ile Arg Arg Val Thr Asn Asp Ala Arg Glu Asn
    130                 135                 140
Glu Met Asp Glu Asn Leu Glu Gln Val Ser Gly Ile Ile Gly Asn Leu
145                 150                 155                 160
Arg His Met Ala Leu Asp Met Gly Asn Glu Ile Asp Thr Gln Asn Arg
                165                 170                 175
Gln Ile Asp Arg Ile Met Glu Lys Ala Asp Ser Asn Lys Thr Arg Ile
            180                 185                 190
Asp Glu Ala Asn Gln Arg Ala Thr Lys Met Leu Gly Ser Gly
        195                 200                 205

<210> SEQ ID NO 16
<211> LENGTH: 206
<212> TYPE: PRT
<213> ORGANISM: Mus musculus SNAP-25B (Mouse)

<400> SEQUENCE: 16

Met Ala Glu Asp Ala Asp Met Arg Asn Glu Leu Glu Glu Met Gln Arg
 1               5                  10                  15
Arg Ala Asp Gln Leu Ala Asp Glu Ser Leu Glu Ser Thr Arg Arg Met
            20                  25                  30
Leu Gln Leu Val Glu Glu Ser Lys Asp Ala Gly Ile Arg Thr Leu Val
        35                  40                  45
Met Leu Asp Glu Gln Gly Glu Gln Leu Glu Arg Ile Glu Glu Gly Met
 50                  55                  60
Asp Gln Ile Asn Lys Asp Met Lys Glu Ala Glu Lys Asn Leu Thr Asp
 65                  70                  75                  80
Leu Gly Lys Phe Cys Gly Leu Cys Val Cys Pro Cys Asn Lys Leu Lys
                 85                  90                  95
Ser Ser Asp Ala Tyr Lys Lys Ala Trp Gly Asn Asn Gln Asp Gly Val
            100                 105                 110
Val Ala Ser Gln Pro Ala Arg Val Val Asp Glu Arg Glu Gln Met Ala
        115                 120                 125
Ile Ser Gly Gly Phe Ile Arg Arg Val Thr Asn Asp Ala Arg Glu Asn
    130                 135                 140
Glu Met Asp Glu Asn Leu Glu Gln Val Ser Gly Ile Ile Gly Asn Leu
145                 150                 155                 160
Arg His Met Ala Leu Asp Met Gly Asn Glu Ile Asp Thr Gln Asn Arg
                165                 170                 175
Gln Ile Asp Arg Ile Met Glu Lys Ala Asp Ser Asn Lys Thr Arg Ile
            180                 185                 190
```

Asp Glu Ala Asn Gln Arg Ala Thr Lys Met Leu Gly Ser Gly
            195                 200                 205

<210> SEQ ID NO 17
<211> LENGTH: 210
<212> TYPE: PRT
<213> ORGANISM: Rattus norvegicus SNAP-23 (Rat)

<400> SEQUENCE: 17

Met Asp Asp Leu Ser Pro Glu Glu Ile Gln Leu Arg Ala His Gln Val
  1               5                  10                  15

Thr Asp Glu Ser Leu Glu Ser Thr Arg Arg Ile Leu Gly Leu Ala Ile
             20                  25                  30

Glu Ser Gln Asp Ala Gly Ile Lys Thr Ile Thr Met Leu Asp Glu Gln
         35                  40                  45

Gly Glu Gln Leu Asn Arg Ile Glu Glu Gly Met Asp Gln Ile Asn Lys
     50                  55                  60

Asp Met Arg Glu Ala Glu Lys Thr Leu Thr Glu Leu Asn Lys Cys Cys
 65                  70                  75                  80

Gly Leu Cys Val Cys Pro Cys Asn Arg Thr Lys Asn Phe Glu Ser Gly
                 85                  90                  95

Lys Asn Tyr Lys Ala Thr Trp Gly Asp Gly Gly Asp Ser Ser Pro Ser
            100                 105                 110

Asn Val Val Ser Lys Gln Pro Ser Arg Ile Thr Asn Gly Gln Pro Gln
        115                 120                 125

Gln Thr Thr Gly Ala Ala Ser Gly Gly Tyr Ile Lys Arg Ile Thr Asn
    130                 135                 140

Asp Ala Arg Glu Asp Glu Met Glu Glu Asn Leu Thr Gln Val Gly Ser
145                 150                 155                 160

Ile Leu Gly Asn Leu Lys Asn Met Ala Leu Asp Met Gly Asn Glu Ile
                165                 170                 175

Asp Ala Gln Asn Gln Gln Ile Gln Lys Ile Thr Glu Lys Ala Asp Thr
            180                 185                 190

Asn Lys Asn Arg Ile Asp Ile Ala Asn Thr Arg Ala Lys Lys Leu Ile
        195                 200                 205

Asp Ser
    210

<210> SEQ ID NO 18
<211> LENGTH: 210
<212> TYPE: PRT
<213> ORGANISM: Mus musculus SNAP-23 (Mouse)

<400> SEQUENCE: 18

Met Asp Asn Leu Ser Pro Glu Glu Val Gln Leu Arg Ala His Gln Val
  1               5                  10                  15

Thr Asp Glu Ser Leu Glu Ser Thr Arg Arg Ile Leu Gly Leu Ala Ile
             20                  25                  30

Glu Ser Gln Asp Ala Gly Ile Lys Thr Ile Thr Met Leu Asp Glu Gln
         35                  40                  45

Gly Glu Gln Leu Asn Arg Ile Glu Glu Gly Met Asp Gln Ile Asn Lys
     50                  55                  60

Asp Met Arg Glu Ala Glu Lys Thr Leu Thr Glu Leu Asn Lys Cys Cys
 65                  70                  75                  80

Gly Leu Cys Ile Cys Pro Cys Asn Arg Thr Lys Asn Phe Glu Ser Gly
                 85                  90                  95

```
Lys Asn Tyr Lys Ala Thr Trp Gly Asp Gly Asp Asn Ser Pro Ser
            100                 105                 110

Asn Val Val Ser Lys Gln Pro Ser Arg Ile Thr Asn Gly Gln Pro Gln
            115                 120                 125

Gln Thr Thr Gly Ala Ala Ser Gly Gly Tyr Ile Lys Arg Ile Thr Asn
        130                 135                 140

Asp Ala Arg Glu Asp Glu Met Glu Glu Asn Leu Thr Gln Val Gly Ser
145                 150                 155                 160

Ile Leu Gly Asn Leu Lys Asn Met Ala Leu Asp Met Gly Asn Glu Ile
                165                 170                 175

Asp Ala Gln Asn Gln Gln Ile Gln Lys Ile Thr Glu Lys Ala Asp Thr
            180                 185                 190

Asn Lys Asn Arg Ile Asp Ile Ala Asn Thr Arg Ala Lys Lys Leu Ile
            195                 200                 205

Asp Ser
    210

<210> SEQ ID NO 19
<211> LENGTH: 206
<212> TYPE: PRT
<213> ORGANISM: Gallus gallus SNAP-25B (Chicken)

<400> SEQUENCE: 19

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 20
<211> LENGTH: 204
<212> TYPE: PRT
<213> ORGANISM: Carassius auratus SNAP-25A (Goldfish)

<400> SEQUENCE: 20
```

Met Ala Glu Asp Ala Asp Met Arg Asn Glu Leu Ser Asp Met Gln Gln
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
            115                 120                 125

Gly Gly Phe Ile Arg Arg Val Thr Asp Asp Ala Arg Glu Asn Glu Met
130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
                180                 185                 190

Ala Asn Gln Arg Ala Thr Lys Met Leu Gly Ser Gly
            195                 200

<210> SEQ ID NO 21
<211> LENGTH: 203
<212> TYPE: PRT
<213> ORGANISM: Carassius auratus SNAP-25B (Goldfish)

<400> SEQUENCE: 21

Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
            115                 120                 125

Gly Phe Ile Arg Arg Val Thr Asn Asp Ala Arg Glu Asn Glu Met Asp
130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

```
Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200

<210> SEQ ID NO 22
<211> LENGTH: 204
<212> TYPE: PRT
<213> ORGANISM: Danio rerio SNAP-25A (Zebrafish)

<400> SEQUENCE: 22

Met Ala Glu Asp Ser Asp Met Arg Asn Glu Leu Ala Asp Met Gln Gln
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Ala Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200

<210> SEQ ID NO 23
<211> LENGTH: 203
<212> TYPE: PRT
<213> ORGANISM: Danio rerio SNAP-25B (Zebrafish)

<400> SEQUENCE: 23

Met Ala Asp Glu Ser Asp Met Arg Asn Glu Leu Asn Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95
```

```
Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
            115                 120                 125

Gly Phe Ile Arg Arg Val Thr Asn Asp Ala Arg Glu Asn Glu Met Asp
            130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
                180                 185                 190

Asn Gln Arg Ala Thr Lys Met Leu Gly Ser Gly
            195                 200

<210> SEQ ID NO 24
<211> LENGTH: 214
<212> TYPE: PRT
<213> ORGANISM: Danio rerio SNAP-23 (Zebrafish)

<400> SEQUENCE: 24

Met Ala Asp Met Thr Val Glu Asp Ile Thr Met Arg Ala Asn Gln Val
1               5                   10                  15

Thr Asp Glu Ser Leu Glu Ser Thr Arg Arg Met Leu Gln Met Ala Glu
            20                  25                  30

Glu Ser Arg Glu Thr Gly Val Lys Thr Met Thr Met Leu Asp Glu Gln
            35                  40                  45

Gly Glu Gln Leu Arg Arg Val Asp Gln Gly Met Asp Gln Ile Asn Gln
            50                  55                  60

Asp Met Arg Gln Ala Glu Lys Asn Leu Thr Asp Leu Ser Lys Cys Cys
65                  70                  75                  80

Gly Leu Cys Val Cys Pro Cys Glu Arg Val Thr Ser Ile Glu His Asp
                85                  90                  95

Gly Arg Tyr Lys Arg Thr Trp Gly Thr Gly Ser Asp Asn Ser Ser Thr
            100                 105                 110

Glu Gly Lys Glu Gly Gly Val Val Ser Ser Gln Pro Thr Ala Val Arg
            115                 120                 125

Asn Gly Gln Ala Val Ser Gly Gly Ser Ser Gly Ala Ser Gly Pro Tyr
            130                 135                 140

Ile Lys Arg Ile Thr Asn Asp Ala Arg Glu Asp Glu Met Glu Glu Asn
145                 150                 155                 160

Leu Asp Gln Val Gly Ser Ile Ile Gly Asn Leu Lys Asn Leu Ala Leu
                165                 170                 175

Asp Met Gly Asn Glu Ile Asp Lys Gln Asn Lys Thr Ile Asp Arg Ile
                180                 185                 190

Thr Asp Lys Ala Asp Met Asn Lys Ala Arg Ile Asp Glu Ala Asn Gln
            195                 200                 205

Arg Ala Asn Lys Leu Leu
        210

<210> SEQ ID NO 25
<211> LENGTH: 210
<212> TYPE: PRT
<213> ORGANISM: Torpedo marmorata SNAP-25 (Marbled electric ray)

<400> SEQUENCE: 25
```

```
Met Glu Asn Ser Val Glu Asn Ser Met Asp Pro Arg Ser Gln Glu
1               5                  10                  15

Glu Met Gln Arg Cys Ala Asp Gln Ile Thr Asp Glu Ser Leu Glu Ser
            20                  25                  30

Thr Arg Arg Met Leu Gln Leu Val Glu Glu Ser Lys Asp Ala Gly Ile
        35                  40                  45

Arg Thr Leu Val Met Leu Asp Glu Gln Gly Glu Gln Leu Glu Arg Ile
    50                  55                  60

Glu Glu Gly Met Asp Gln Ile Asn Lys Asp Met Lys Glu Ala Glu Lys
65                  70                  75                  80

Asn Leu Ser Asp Leu Gly Lys Cys Cys Gly Leu Cys Ser Cys Pro Cys
                85                  90                  95

Asn Lys Leu Lys Asn Phe Glu Ala Gly Gly Ala Tyr Lys Lys Val Trp
            100                 105                 110

Gly Asn Asn Gln Asp Gly Val Val Ala Ser Gln Pro Ala Arg Val Met
        115                 120                 125

Asp Asp Arg Glu Gln Met Ala Met Ser Gly Gly Tyr Ile Arg Arg Ile
    130                 135                 140

Thr Asp Asp Ala Arg Glu Asn Glu Met Glu Glu Asn Leu Asp Gln Val
145                 150                 155                 160

Gly Ser Ile Ile Gly Asn Leu Arg His Met Ala Leu Asp Met Ser Asn
                165                 170                 175

Glu Ile Gly Ser Gln Asn Ala Gln Ile Asp Arg Ile Val Val Lys Gly
            180                 185                 190

Asp Met Asn Lys Ala Arg Ile Asp Glu Ala Asn Lys His Ala Thr Lys
        195                 200                 205

Met Leu
    210

<210> SEQ ID NO 26
<211> LENGTH: 206
<212> TYPE: PRT
<213> ORGANISM: Xenopus laevis SNAP-25A (African clawed frog)

<400> SEQUENCE: 26

Met Ala Asp Asp Ala Asp Met Arg Asn Glu Leu Glu Glu Met Gln Arg
1               5                  10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Gly Ala Tyr Asn Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
```

```
                    145                 150                 155                 160
Arg His Met Ala Leu Asp Met Gly Asn Glu Ile Asp Thr Gln Asn Arg
                    165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205

<210> SEQ ID NO 27
<211> LENGTH: 206
<212> TYPE: PRT
<213> ORGANISM: Xenopus laevis SNAP-25B (African clawed frog)

<400> SEQUENCE: 27

Met Ala Asp Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Glu Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205

<210> SEQ ID NO 28
<211> LENGTH: 204
<212> TYPE: PRT
<213> ORGANISM: Xenopus laevis SNAP-23 (African clawed frog)

<400> SEQUENCE: 28

Met Asp Asp Met Thr Ala Glu Glu Ile Gln Leu Lys Ala Asn Gln Val
  1               5                  10                  15

Ala Asp Glu Ser Leu Glu Ser Thr Arg Arg Met Leu Asn Leu Ala Leu
            20                  25                  30

Glu Ser Gln Asp Ala Gly Ile Lys Thr Ile Thr Met Leu Asp Glu Gln
        35                  40                  45

Gly Glu Gln Leu Asp Arg Ile Glu Glu Gly Met Asp Gln Ile Asn Lys
    50                  55                  60

Asp Met Arg Glu Ala Glu Lys Asn Leu Thr Glu Leu Asn Lys Cys Cys
```

```
                65                  70                  75                  80
Gly Leu Cys Val Cys Pro Gly Lys Arg Ser Lys Asp Phe Glu Thr Gly
                        85                  90                  95

Glu Asn Tyr Lys Lys Ala Trp Gly Ser Lys Asp Asn Asp Ser Asp Val
                100                 105                 110

Val Ser Lys Gln Pro Gly Gln Thr Asn Gly Gln Leu Ser Gly Ala Gly
            115                 120                 125

Gln Ser Gly Pro Tyr Ile Lys Arg Ile Thr Asn Asp Arg Glu Asp
        130                 135                 140

Glu Met Asp Glu Asn Leu Val Gln Val Gly Ser Ile Leu Gly Asn Leu
145                 150                 155                 160

Lys Asn Met Ala Ile Asp Met Gly Asn Glu Leu Glu Ser His Asn Gln
                165                 170                 175

Gln Ile Gly Arg Ile Asn Glu Lys Ala Glu Thr Asn Lys Thr Arg Ile
            180                 185                 190

Asp Glu Ala Asn Thr Lys Ala Lys Lys Leu Ile Glu
        195                 200

<210> SEQ ID NO 29
<211> LENGTH: 212
<212> TYPE: PRT
<213> ORGANISM: Strongylocentrotus purpuratus SNAP-25 (Sea urchin)

<400> SEQUENCE: 29

Met Glu Asp Gln Asn Asp Met Asn Met Arg Ser Glu Leu Glu Glu Ile
  1               5                  10                  15

Gln Met Gln Ser Asn Met Gln Thr Asp Glu Ser Leu Glu Ser Thr Arg
             20                  25                  30

Arg Met Leu Gln Met Ala Glu Ser Gln Asp Met Gly Ile Lys Thr
         35                  40                  45

Leu Val Met Leu Asp Glu Gln Gly Glu Gln Leu Asp Arg Ile Glu Glu
     50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                 85                  90                  95

Leu Gly Asn Phe Glu Lys Gly Asp Asp Tyr Lys Lys Thr Trp Lys Gly
                100                 105                 110

Asn Asp Asp Gly Lys Val Asn Ser His Gln Pro Met Arg Met Glu Asp
            115                 120                 125

Asp Arg Asp Gly Cys Gly Gly Asn Ala Ser Met Ile Thr Arg Ile Thr
        130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210

<210> SEQ ID NO 30
<211> LENGTH: 212
```

<212> TYPE: PRT
<213> ORGANISM: Drosophila melanogaster SNAP-25 (Fruit fly)

<400> SEQUENCE: 30

Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
        210

<210> SEQ ID NO 31
<211> LENGTH: 212
<212> TYPE: PRT
<213> ORGANISM: Drosophila melanogaster SNAP-24 (Fruit fly)

<400> SEQUENCE: 31

Met Ala Ala Val Glu Asn Ala Glu Pro Arg Thr Glu Leu Gln Glu Leu
1               5                   10                  15

Gln Phe Lys Ser Gly Gln Val Ala Asp Glu Ser Leu Glu Ser Thr Arg
            20                  25                  30

Arg Met Leu Ala Leu Met Asp Glu Ser Lys Glu Ala Gly Ile Arg Thr
        35                  40                  45

Leu Val Ala Leu Asp Asp Gln Gly Glu Gln Leu Asp Arg Ile Glu Glu
    50                  55                  60

Gly Met Asp Arg Ile Asn Ala Asp Met Arg Glu Ala Glu Lys Asn Leu
65                  70                  75                  80

Ser Gly Met Glu Lys Cys Cys Gly Ile Cys Val Leu Pro Trp Lys Lys
                85                  90                  95

Val Asn Ile Lys Asp Asp Gly Glu Ser Ala Trp Lys Ala Asn Asp Asp
            100                 105                 110

Gly Lys Ile Val Ala Ser Gln Pro Gln Arg Val Ile Asp Glu Arg Glu
        115                 120                 125

```
Arg Gly Gly Met Gly Ala Pro Pro Gln Ser Gly Tyr Val Ala Arg Ile
    130                 135                 140

Thr Asn Asp Ala Arg Glu Asp Glu Met Asp Glu Asn Leu Gly Gln Val
145                 150                 155                 160

Asn Ser Met Leu Gly Asn Leu Arg Asn Met Ala Leu Asp Met Gly Ser
                165                 170                 175

Glu Leu Glu Asn Gln Asn Lys Gln Val Asp Arg Ile Asn Ala Lys Gly
            180                 185                 190

Asp Ala Asn Asn Ile Arg Met Asp Gly Val Asn Lys Arg Ala Asn Asn
        195                 200                 205

Leu Leu Lys Ser
    210

<210> SEQ ID NO 32
<211> LENGTH: 212
<212> TYPE: PRT
<213> ORGANISM: Hirudo medicinalis SNAP-25 (Leech)

<400> SEQUENCE: 32

Met Ala Lys Asp Ile Lys Pro Lys Pro Ala Asn Gly Arg Asp Ser Pro
1               5                   10                  15

Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80

Asp Ala Glu Lys Asn Leu Glu Gly Met Glu Lys Cys Cys Gly Leu Cys
                85                  90                  95

Ile Leu Pro Trp Lys Arg Thr Lys Asn Phe Asp Lys Gly Ala Glu Trp
            100                 105                 110

Asn Lys Gly Asp Glu Gly Lys Val Asn Thr Asp Gly Pro Arg Leu Val
        115                 120                 125

Val Gly Asp Gly Asn Met Gly Pro Ser Gly Gly Phe Ile Thr Lys Ile
    130                 135                 140

Thr Asn Asp Ala Arg Glu Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210

<210> SEQ ID NO 33
<211> LENGTH: 212
<212> TYPE: PRT
<213> ORGANISM: Loligo pealei SNAP-25 (Longfin squid)

<400> SEQUENCE: 33

Met Ser Ala Asn Gly Glu Val Glu Val Pro Lys Thr Glu Leu Glu Glu
1               5                   10                  15
```

```
Ile Gln Gln Gln Cys Asn Gln Val Thr Asp Asp Ser Leu Glu Ser Thr
            20                  25                  30

Arg Arg Met Leu Asn Met Cys Glu Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110

Lys Asp Asp Gly Pro Thr Asn Thr Asn Gly Pro Arg Val Thr Val
            115                 120                 125

Gly Asp Gln Asn Gly Met Gly Pro Ser Ser Gly Tyr Val Thr Arg Ile
    130                 135                 140

Thr Asn Asp Ala Arg Glu Asp Asp Met Glu Asn Asn Met Lys Glu Val
145                 150                 155                 160

Ser Ser Met Ile Gly Asn Leu Arg Asn Met Ala Ile Asp Met Gly Asn
                165                 170                 175

Glu Ile Gly Ser Gln Asn Arg Gln Val Asp Arg Ile Gln Gln Lys Ala
            180                 185                 190

Glu Ser Asn Glu Ser Arg Ile Asp Glu Ala Asn Lys Lys Ala Thr Lys
        195                 200                 205

Leu Leu Lys Asn
        210

<210> SEQ ID NO 34
<211> LENGTH: 220
<212> TYPE: PRT
<213> ORGANISM: Lymnaea stagnalis SNAP-25 (Great pond snail)

<400> SEQUENCE: 34

Met Thr Thr Asn Gly Glu Ile Leu Pro Val Gly Glu Glu Glu Glu
1               5                   10                  15

Glu Leu Gly Glu Asp Ala Leu Leu Arg Lys Gln Ile Asp Cys Asn Thr
            20                  25                  30

Asn Glu Ser Leu Glu Ser Thr Arg Arg Met Leu Ser Leu Cys Glu Glu
        35                  40                  45

Ser Lys Glu Ala Gly Ile Lys Thr Leu Val Met Leu Asp Glu Gln Gly
    50                  55                  60

Glu Gln Leu Asp Arg Ile Glu Glu Gly Met Gly Gln Ile Asn Gln Asp
65                  70                  75                  80

Met Arg Asp Ala Glu Lys Asn Leu Glu Gly Leu Glu Lys Cys Cys Gly
                85                  90                  95

Leu Cys Val Leu Pro Trp Lys Arg Ser Lys Asn Phe Glu Lys Gly Ser
            100                 105                 110

Asp Tyr Asn Lys Thr Trp Lys Ala Ser Glu Asp Gly Lys Ile Asn Thr
        115                 120                 125

Asn Gly Pro Arg Leu Val Val Asp Gln Gly Asn Gly Ser Gly Pro Thr
    130                 135                 140

Gly Gly Tyr Ile Thr Arg Ile Thr Asn Asp Ala Arg Glu Asp Glu Met
145                 150                 155                 160

Glu Gln Asn Ile Gly Glu Val Ala Gly Met Val Ser Asn Leu Arg Asn
                165                 170                 175
```

```
Met Ala Val Asp Met Gly Asn Glu Ile Glu Ser Gln Asn Lys Gln Leu
            180                 185                 190

Asp Arg Ile Asn Gln Lys Gly Gly Ser Leu Asn Val Arg Val Asp Glu
        195                 200                 205

Ala Asn Lys Arg Ala Asn Arg Ile Leu Arg Lys Gln
    210                 215                 220
```

<210> SEQ ID NO 35
<211> LENGTH: 207
<212> TYPE: PRT
<213> ORGANISM: Caenorhabditis elegans SNAP-25 (Round worm)

<400> SEQUENCE: 35

```
Met Ser Gly Asp Asp Ile Pro Glu Gly Leu Glu Ala Ile Asn Leu
1               5                   10                  15

Lys Met Asn Ala Thr Thr Asp Asp Ser Leu Glu Ser Thr Arg Arg Met
            20                  25                  30

Leu Ala Leu Cys Glu Glu Ser Lys Glu Ala Gly Ile Lys Thr Leu Val
        35                  40                  45

Met Leu Asp Asp Gln Gly Glu Gln Leu Glu Arg Cys Glu Gly Ala Leu
    50                  55                  60

Asp Thr Ile Asn Gln Asp Met Lys Glu Ala Glu Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
        115                 120                 125

Met Gly Pro Gln Gly Gly Tyr Ile Thr Lys Ile Thr Asn Asp Ala Arg
    130                 135                 140

Glu Asp Glu Met Asp Glu Asn Val Gln Gln Val Ser Thr Met Val Gly
145                 150                 155                 160

Asn Leu Arg Asn Met Ala Ile Asp Met Ser Thr Glu Val Ser Asn Gln
                165                 170                 175

Asn Arg Gln Leu Asp Arg Ile His Asp Lys Ala Gln Ser Asn Glu Val
            180                 185                 190

Arg Val Glu Ser Ala Asn Lys Arg Ala Lys Asn Leu Ile Thr Lys
        195                 200                 205
```

<210> SEQ ID NO 36
<211> LENGTH: 118
<212> TYPE: PRT
<213> ORGANISM: Homo sapiens VAMP-1-1 (Human)

<400> SEQUENCE: 36

```
Met Ser Ala Pro Ala Gln Pro Pro Ala Glu Gly Thr Glu Gly Thr Ala
1               5                   10                  15

Pro Gly Gly Gly Pro Pro Gly Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80
```

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
            115

<210> SEQ ID NO 37
<211> LENGTH: 117
<212> TYPE: PRT
<213> ORGANISM: Homo sapiens VAMP-1-2 (Human)

<400> SEQUENCE: 37

Met Ser Ala Pro Ala Gln Pro Pro Ala Glu Gly Thr Glu Gly Thr Ala
1               5                   10                  15

Pro Gly Gly Gly Pro Pro Gly Pro Pro Asn Met Thr Ser Asn Arg
            20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
        50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ser Lys Tyr Arg
        115

<210> SEQ ID NO 38
<211> LENGTH: 116
<212> TYPE: PRT
<213> ORGANISM: Homo sapiens VAMP-1-3 (Human)

<400> SEQUENCE: 38

Met Ser Ala Pro Ala Gln Pro Pro Ala Glu Gly Thr Glu Gly Thr Ala
1               5                   10                  15

Pro Gly Gly Gly Pro Pro Gly Pro Pro Asn Met Thr Ser Asn Arg
            20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
        50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Arg Arg Asp
        115

<210> SEQ ID NO 39
<211> LENGTH: 116
<212> TYPE: PRT
<213> ORGANISM: Homo sapiens VAMP-2 (Human)

```
<400> SEQUENCE: 39

Met Ser Ala Thr Ala Ala Thr Ala Pro Pro Ala Ala Pro Ala Gly Glu
1               5                   10                  15

Gly Gly Pro Pro Ala Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 40
<211> LENGTH: 116
<212> TYPE: PRT
<213> ORGANISM: Macaca mulatta VAMP-2 (Rhesus monkey)

<400> SEQUENCE: 40

Met Ser Ala Thr Ala Ala Thr Ala Pro Pro Ala Ala Pro Ala Gly Glu
1               5                   10                  15

Gly Gly Pro Pro Ala Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 41
<211> LENGTH: 100
<212> TYPE: PRT
<213> ORGANISM: Homo sapiens VAMP-3 (Human)

<400> SEQUENCE: 41

Met Ser Thr Gly Pro Thr Ala Ala Thr Gly Ser Asn Arg Arg Leu Gln
1               5                   10                  15

Gln Thr Gln Asn Gln Val Asp Glu Val Val Asp Ile Met Arg Val Asn
            20                  25                  30

Val Asp Lys Val Leu Glu Arg Asp Gln Lys Leu Ser Glu Leu Asp Asp
        35                  40                  45

Arg Ala Asp Ala Leu Gln Ala Gly Ala Ser Gln Phe Glu Thr Ser Ala
    50                  55                  60
```

```
Ala Lys Leu Lys Arg Lys Tyr Trp Trp Lys Asn Cys Lys Met Trp Ala
 65                  70                  75                  80

Ile Gly Ile Thr Val Leu Val Ile Phe Ile Ile Ile Ile Val Trp
             85                  90                  95

Val Val Ser Ser
            100
```

<210> SEQ ID NO 42
<211> LENGTH: 116
<212> TYPE: PRT
<213> ORGANISM: Bos tarsus VAMP-2

<400> SEQUENCE: 42

```
Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
         35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
             85                  90                  95

Ile Ile Leu Gly Val Ile Cys Ala Ile Ile Leu Ile Ile Ile Ile Val
            100                 105                 110

Tyr Phe Ser Ser
            115
```

<210> SEQ ID NO 43
<211> LENGTH: 118
<212> TYPE: PRT
<213> ORGANISM: Rattus norvegicus VAMP-1 (Rat)

<400> SEQUENCE: 43

```
Met Ser Ala Pro Ala Gln Pro Pro Ala Glu Gly Thr Glu Gly Ala Ala
 1               5                  10                  15

Pro Gly Gly Gly Pro Pro Gly Pro Pro Pro Asn Thr Thr Ser Asn Arg
             20                  25                  30

Arg Leu Gln Gln Thr Gln Ala Gln Val Glu Glu Val Val Asp Ile Ile
         35                  40                  45

Arg Val Asn Val Asp Lys Val Leu Glu Arg Asp Gln Lys Leu Ser Glu
 50                  55                  60

Leu Asp Asp Arg Ala Asp Ala Leu Gln Ala Gly Ala Ser Val Phe Glu
 65                  70                  75                  80

Ser Ser Ala Ala Lys Leu Lys Arg Lys Tyr Trp Trp Lys Asn Cys Lys
             85                  90                  95

Met Met Ile Met Leu Gly Ala Ile Cys Ala Ile Ile Val Val Val Ile
            100                 105                 110

Val Ile Tyr Ile Phe Thr
            115
```

<210> SEQ ID NO 44
<211> LENGTH: 117
<212> TYPE: PRT
<213> ORGANISM: Rattus norvegicus VAMP-1b (Rat)

-continued

```
<400> SEQUENCE: 44

Met Ser Ala Pro Ala Gln Pro Pro Ala Glu Gly Thr Glu Gly Ala Ala
1               5                   10                  15

Pro Gly Gly Gly Pro Gly Pro Pro Asn Thr Thr Ser Asn Arg
                20                  25                  30

Arg Leu Gln Gln Thr Gln Ala Gln Val Glu Glu Val Asp Ile Met
                35                  40                  45

Arg Val Asn Val Asp Lys Val Leu Glu Arg Asp Gln Lys Leu Ser Glu
50                  55                  60

Leu Asp Asp Arg Ala Asp Ala Leu Gln Ala Gly Ala Ser Val Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ser Lys Tyr Arg
                115

<210> SEQ ID NO 45
<211> LENGTH: 118
<212> TYPE: PRT
<213> ORGANISM: Mus musculus VAMP-1 (Mouse)

<400> SEQUENCE: 45

Met Ser Ala Pro Ala Gln Pro Pro Ala Glu Gly Thr Glu Gly Ala Ala
1               5                   10                  15

Pro Gly Gly Gly Pro Gly Pro Pro Asn Met Thr Ser Asn Arg
                20                  25                  30

Arg Leu Gln Gln Thr Gln Ala Gln Val Glu Glu Val Asp Ile Met
                35                  40                  45

Arg Val Asn Val Asp Lys Val Leu Glu Arg Asp Gln Lys Leu Ser Glu
50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ile Tyr Phe Phe Thr
                115

<210> SEQ ID NO 46
<211> LENGTH: 116
<212> TYPE: PRT
<213> ORGANISM: Rattus norvegicus VAMP-2 (Rat)

<400> SEQUENCE: 46

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
                35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
```

```
                            65                  70                  75                  80
Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115

<210> SEQ ID NO 47
<211> LENGTH: 135
<212> TYPE: PRT
<213> ORGANISM: Rattus norvegicus VAMP-2b (Rat)

<400> SEQUENCE: 47

Met Ser Ala Thr Ala Ala Thr Val Pro Pro Ala Ala Pro Ala Gly Glu
  1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
         35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Gly
            100                 105                 110

Glu Trp Ser Arg Ser Gly Gln Gly Pro Phe Pro Gly Val Glu Gly
        115                 120                 125

Phe Pro Val Gly Ser Gly Leu
        130                 135

<210> SEQ ID NO 48
<211> LENGTH: 116
<212> TYPE: PRT
<213> ORGANISM: Mus musculus VAMP-2 (Mouse)

<400> SEQUENCE: 48

Met Ser Ala Thr Ala Ala Thr Val Pro Pro Ala Ala Pro Ala Gly Glu
  1               5                  10                  15

Gly Gly Pro Pro Ala Pro Pro Pro Asn Leu Thr Ser Asn Arg Arg Leu
             20                  25                  30

Gln Gln Thr Gln Ala Gln Val Asp Glu Val Val Asp Ile Met Arg Val
         35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115
```

```
<210> SEQ ID NO 49
<211> LENGTH: 103
<212> TYPE: PRT
<213> ORGANISM: Rattus norvegicus VAMP-3 (Rat)

<400> SEQUENCE: 49

Met Ser Thr Gly Val Pro Ser Gly Ser Ser Ala Ala Thr Gly Ser Asn
1               5                   10                  15

Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
    50                  55                  60

Glu Thr Ser Ala Ala Lys Leu Lys Arg Lys Tyr Trp Trp Lys Asn Cys
65                  70                  75                  80

Lys Met Trp Ala Ile Gly Ile Ser Val Leu Val Ile Ile Val Ile Ile
                85                  90                  95

Ile Ile Val Trp Cys Val Ser
            100

<210> SEQ ID NO 50
<211> LENGTH: 103
<212> TYPE: PRT
<213> ORGANISM: Mus musculus VAMP-3 (Mouse)

<400> SEQUENCE: 50

Met Ser Thr Gly Val Pro Ser Gly Ser Ser Ala Ala Thr Gly Ser Asn
1               5                   10                  15

Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
    50                  55                  60

Glu Thr Ser Ala Ala Lys Leu Lys Arg Lys Tyr Trp Trp Lys Asn Cys
65                  70                  75                  80

Lys Met Trp Ala Ile Gly Ile Ser Val Leu Val Ile Ile Val Ile Ile
                85                  90                  95

Ile Ile Val Trp Cys Val Ser
            100

<210> SEQ ID NO 51
<211> LENGTH: 259
<212> TYPE: PRT
<213> ORGANISM: Gallus gallus VAMP-1 (Chicken)

<400> SEQUENCE: 51

Met His Gln Glu Asn Gln Thr Lys Gln Val Gln Val Ser Pro Ser
1               5                   10                  15

Val Asn Ala Ala Trp Lys Leu Leu Val Pro Val Phe Leu Pro Gly Gly
            20                  25                  30

Ser Thr Pro Ala Ala Pro Tyr Pro Asp Cys Cys Ser Thr Arg Ala Gln
        35                  40                  45

Arg Thr Leu Ala Ala Leu Ser Pro Ala Leu Ile Gly Arg Cys Gln Ala
    50                  55                  60

Gly Thr Gly Leu Asn Pro Gly Glu Ser Gly Gly Gln Arg Glu Ala Gly
65                  70                  75                  80
```

Leu Arg Glu Gly Ala Leu Phe Thr Gly Ala Ser Leu Arg Pro Ser Arg
                    85                  90                  95

Gly Ala Leu Ile Gly Phe Gly Glu Gly Glu Gly Gly Ala Asp Ser Arg
                100                 105                 110

Val Ser Ala Arg Pro Ser Cys Asp Tyr Phe Ser Leu Ala Ala Gly Pro
            115                 120                 125

Cys Gly Ala Gly Leu Phe Val Cys Ala Gly Trp Gly Met Ser Glu Pro
130                 135                 140

Ala Gln Gln Pro Ala Pro Gly Ala Pro Glu Gly Gly Ala Pro Ala Gly
145                 150                 155                 160

Gly Pro Pro Gly Pro Pro Asn Leu Ser Ser Asn Arg Arg Leu Gln
                165                 170                 175

Gln Thr Gln Ala Gln Val Glu Glu Val Val Asp Ile Met Arg Val Asn
            180                 185                 190

Val Asp Lys Val Leu Glu Arg Asp Gln Lys Leu Ser Glu Leu Asp Asp
                195                 200                 205

Arg Ala Asp Ala Leu Gln Ala Gly Ala Ser Val Phe Glu Ser Ser Ala
210                 215                 220

Ala Lys Leu Lys Arg Lys Tyr Trp Trp Lys Asn Cys Lys Met Met Ile
225                 230                 235                 240

Met Met Gly Val Ile Cys Ala Ile Val Val Val Ile Val Ile Tyr
                245                 250                 255

Phe Phe Thr

<210> SEQ ID NO 52
<211> LENGTH: 114
<212> TYPE: PRT
<213> ORGANISM: Gallus gallus VAMP-2 (Chicken)

<400> SEQUENCE: 52

Met Ser Ala Pro Ala Pro Thr Gln Gly Pro Thr Ser Thr Gly Ala Ala
1               5                   10                  15

Gly Pro Pro Pro Ala Thr Asn Val Ser Ser Asn Lys Arg Leu Gln Gln
            20                  25                  30

Thr Gln Ala Gln Val Asp Glu Val Val Asp Ile Met Arg Met Asn Val
        35                  40                  45

Asp Lys Val Leu Glu Arg Asp Gln Lys Leu Ser Glu Leu Asp Asn Arg
    50                  55                  60

Ala Asp Ala Leu Gln Ala Gly Ala Ser Gln Phe Glu Thr Ser Ala Ala
65                  70                  75                  80

Lys Leu Lys Arg Lys Tyr Trp Trp Lys Asn Cys Lys Met Met Ile Ile
                85                  90                  95

Leu Gly Val Val Cys Thr Val Ile Leu Ile Ile Ile Ile Tyr Phe
            100                 105                 110

Ser Thr

<210> SEQ ID NO 53
<211> LENGTH: 118
<212> TYPE: PRT
<213> ORGANISM: Gallus gallus VAMP-3 (Chicken)

<400> SEQUENCE: 53

Met Ser Ala Asn Val Pro Gly Asn Thr Asn Val Pro Ala Gly Ser Asn
1               5                   10                  15

Arg Arg Leu Gln Gln Thr Gln His Gln Val Asp Glu Val Val Asp Ile

```
                20                  25                  30
Met Arg Val Asn Val Asp Lys Val Leu Glu Arg Asp Gln Lys Leu Ser
            35                  40                  45

Glu Leu Asp Asp Arg Ala Asp Ala Leu Gln Ala Gly Ala Ser Gln Phe
        50                  55                  60

Glu Thr Ser Ala Ala Lys Leu Lys Arg Lys Tyr Trp Trp Lys Asn Cys
65                  70                  75                  80

Lys Met Trp Ala Ile Leu Ile Ala Val Val Ile Ile Ile Ile
                85                  90                  95

Ile Ile Val Val Ser Val Ser Ala Ala Leu Ser Ala Arg Leu Leu Leu
                100                 105                 110

Phe Lys Ala Lys Leu Phe
            115

<210> SEQ ID NO 54
<211> LENGTH: 119
<212> TYPE: PRT
<213> ORGANISM: Danio rerio VAMP-1 (Zebrafish)

<400> SEQUENCE: 54

Met Ser Ala Pro Asp Ala Ala Ala Ser Pro Gly Ala Pro Gly Ala Pro
1               5                   10                  15

Glu Gly Glu Gly Gly Ala Pro Ala Gln Pro Pro Asn Leu Thr Ser Asn
            20                  25                  30

Arg Arg Leu Gln Gln Thr Gln Ala Gln Val Asp Glu Val Val Asp Ile
            35                  40                  45

Met Arg Val Asn Val Asp Lys Val Leu Glu Arg Asp Gln Lys Leu Ser
        50                  55                  60

Glu Leu Asp Asp Arg Ala Asp Ala Leu Gln Ala Gly Ala Ser Gln Phe
65                  70                  75                  80

Glu Ser Ser Ala Ala Lys Leu Lys Asn Lys Tyr Trp Trp Lys Asn Met
                85                  90                  95

Lys Met Met Ile Ile Met Gly Ile Met Gly Ile Ile Leu Leu Gly Ile
                100                 105                 110

Ala Phe Met Tyr Phe Tyr Tyr
            115

<210> SEQ ID NO 55
<211> LENGTH: 110
<212> TYPE: PRT
<213> ORGANISM: Danio rerio VAMP-2 (Zebrafish)

<400> SEQUENCE: 55

Met Ser Ala Pro Ala Gly Ala Pro Ala Pro Glu Gly Gly Asn Gln Ala
1               5                   10                  15

Pro Pro Asn Leu Thr Ser Asn Arg Arg Leu Gln Gln Thr Gln Ala Gln
            20                  25                  30

Val Asp Glu Val Val Asp Ile Met Arg Val Asn Val Asp Lys Val Leu
            35                  40                  45

Glu Arg Asp Gln Lys Leu Ser Glu Leu Asp Asp Arg Ala Asp Ala Leu
        50                  55                  60

Gln Ala Gly Ala Ser Gln Phe Glu Thr Ser Ala Ala Lys Leu Lys Asn
65                  70                  75                  80

Lys Tyr Trp Trp Lys Asn Ala Lys Met Met Ile Ile Leu Gly Val Ile
                85                  90                  95

Cys Val Ile Val Leu Ile Ile Ile Ile Val Tyr Phe Ser Thr
```

-continued

```
                100                 105                 110
```

<210> SEQ ID NO 56
<211> LENGTH: 102
<212> TYPE: PRT
<213> ORGANISM: Danio rerio VAMP-3 (Zebrafish)

<400> SEQUENCE: 56

```
Met Ser Ala Pro Gly Ala Asp Ala Ser Gly Ser Gly Ser Asn Arg
 1               5                  10                  15

Arg Leu Gln Gln Thr Gln Ala Gln Val Asp Glu Val Val Asp Ile Met
                20                  25                  30

Arg Val Asn Val Asp Lys Val Leu Glu Arg Asp Gln Lys Leu Ser Glu
            35                  40                  45

Leu Asp Asp Arg Ala Asp Ala Leu Gln Ala Gly Ala Ser Gln Phe Glu
        50                  55                  60

Thr Ser Ala Ala Lys Leu Lys Arg Lys Phe Trp Trp Lys Asn Val Lys
 65                  70                  75                  80

Met Trp Ala Ile Leu Ile Ala Val Val Val Ile Ile Ile Ile Ile Ile
                85                  90                  95

Val Ile Trp Ser Gln Ser
            100
```

<210> SEQ ID NO 57
<211> LENGTH: 120
<212> TYPE: PRT
<213> ORGANISM: Torpedo marmorata VAMP-1 (Marbled electric ray)

<400> SEQUENCE: 57

```
Met Ser Ala Pro Pro Ser Gly Pro Ala Pro Asp Ala Gln Gly Gly Ala
 1               5                  10                  15

Pro Gly Gln Pro Thr Gly Pro Pro Gly Ala Pro Pro Asn Thr Thr Ser
                20                  25                  30

Asn Arg Arg Leu Gln Gln Thr Gln Ala Gln Val Glu Glu Val Val Asp
            35                  40                  45

Ile Ile Arg Val Asn Val Asp Lys Val Leu Glu Arg Asp Gln Lys Leu
        50                  55                  60

Ser Glu Leu Asp Asp Arg Ala Asp Ala Leu Gln Ala Gly Ala Ser Gln
 65                  70                  75                  80

Phe Glu Ser Ser Ala Ala Lys Leu Lys Arg Lys Tyr Trp Trp Lys Asn
                85                  90                  95

Cys Lys Met Met Ile Met Leu Gly Gly Ile Gly Ala Ile Ile Val Ile
            100                 105                 110

Val Ile Ile Ile Tyr Phe Phe Thr
        115                 120
```

<210> SEQ ID NO 58
<211> LENGTH: 114
<212> TYPE: PRT
<213> ORGANISM: Xenopus laevis VAMP-2 (African clawed frog)

<400> SEQUENCE: 58

```
Met Ser Ala Pro Ala Ala Gly Pro Pro Ala Ala Pro Gly Asp Gly
 1               5                  10                  15

Ala Pro Gln Gly Pro Pro Asn Leu Thr Ser Asn Arg Arg Leu Gln Gln
                20                  25                  30

Thr Gln Ala Gln Val Asp Glu Val Val Asp Ile Met Arg Val Asn Val
            35                  40                  45
```

```
Asp Lys Val Leu Glu Arg Asp Thr Lys Leu Ser Glu Leu Asp Asp Arg
     50                  55                  60

Ala Asp Ala Leu Gln Ala Gly Ala Ser Gln Phe Glu Thr Ser Ala Ala
 65                  70                  75                  80

Lys Leu Lys Arg Lys Tyr Trp Trp Lys Asn Met Lys Met Met Ile Ile
                 85                  90                  95

Met Gly Val Ile Cys Ala Ile Ile Leu Ile Ile Ile Ile Val Tyr Phe
                100                 105                 110

Ser Thr
```

```
<210> SEQ ID NO 59
<211> LENGTH: 101
<212> TYPE: PRT
<213> ORGANISM: Xenopus laevis VAMP-3 (African clawed frog)

<400> SEQUENCE: 59
```

```
Met Ser Thr Pro Gly Thr Ser Ala Thr Gly Asp Pro Gly Asn Arg Arg
  1               5                  10                  15

Leu Gln Gln Thr Gln Ala Gln Val Asp Glu Val Val Asp Ile Met Arg
                 20                  25                  30

Val Asn Val Asp Lys Val Leu Glu Arg Asp Gln Lys Leu Ser Glu Leu
                 35                  40                  45

Asp Asp Arg Ala Asp Ala Leu Gln Ala Gly Ala Ser Gln Phe Glu Thr
     50                  55                  60

Ser Ala Ala Lys Leu Lys Arg Lys Tyr Trp Trp Lys Asn Cys Lys Met
 65                  70                  75                  80

Trp Ala Ile Leu Ile Ala Val Val Leu Val Ile Ile Ile Ile Ile Ile
                 85                  90                  95

Val Trp Ser Val Ser
                100
```

```
<210> SEQ ID NO 60
<211> LENGTH: 104
<212> TYPE: PRT
<213> ORGANISM: Strongylocentrotus purpuratus VAMP (Sea urchin)

<400> SEQUENCE: 60
```

```
Met Ala Ala Pro Pro Pro Gln Pro Ala Pro Ser Asn Lys Arg Leu
  1               5                  10                  15

Gln Gln Thr Gln Ala Gln Val Asp Glu Val Val Asp Ile Met Arg Val
                 20                  25                  30

Asn Val Asp Lys Val Leu Glu Arg Asp Gln Ala Leu Ser Val Leu Asp
                 35                  40                  45

Asp Arg Ala Asp Ala Leu Gln Gln Gly Ala Ser Gln Phe Glu Thr Asn
     50                  55                  60

Ala Gly Lys Leu Lys Arg Lys Tyr Trp Trp Lys Asn Cys Lys Met Met
 65                  70                  75                  80

Ile Ile Leu Ala Ile Ile Ile Val Ile Leu Ile Ile Ile Val
                 85                  90                  95

Ala Ile Val Gln Ser Gln Lys Lys
                100
```

```
<210> SEQ ID NO 61
<211> LENGTH: 129
<212> TYPE: PRT
<213> ORGANISM: Drosophila melanogaster SynA1 (Fruit fly)
```

<400> SEQUENCE: 61

Met Glu Asn Asn Glu Ala Pro Ser Pro Ser Gly Ser Asn Asn Asn Glu
1               5                   10                  15

Asn Asn Asn Ala Ala Gln Lys Lys Leu Gln Gln Thr Gln Ala Lys Val
            20                  25                  30

Asp Glu Val Val Gly Ile Met Arg Val Asn Val Glu Lys Val Leu Glu
        35                  40                  45

Arg Asp Gln Lys Leu Ser Glu Leu Gly Glu Arg Ala Asp Gln Leu Glu
    50                  55                  60

Gln Gly Ala Ser Gln Phe Glu Gln Gln Ala Gly Lys Leu Lys Arg Lys
65                  70                  75                  80

Gln Trp Trp Ala Asn Met Lys Met Met Ile Ile Leu Gly Val Ile Ala
                85                  90                  95

Val Val Leu Leu Ile Ile Val Leu Val Ser Val Trp Pro Ser Ser Ser
            100                 105                 110

Asp Ser Gly Ser Gly Gly Gly Asn Lys Ala Ile Thr Gln Ala Pro Pro
        115                 120                 125

His

<210> SEQ ID NO 62
<211> LENGTH: 152
<212> TYPE: PRT
<213> ORGANISM: Drosophila melanogaster SynA2 (Fruit fly)

<400> SEQUENCE: 62

Met Glu Asn Asn Glu Ala Pro Ser Pro Ser Gly Ser Asn Asn Asn Asp
1               5                   10                  15

Phe Pro Ile Leu Pro Pro Pro Asn Ala Asn Asp Asn Tyr Asn Gln
            20                  25                  30

Phe Gly Asp His Gln Ile Arg Asn Asn Ala Ala Gln Lys Lys Leu
        35                  40                  45

Gln Gln Thr Gln Ala Lys Val Asp Glu Val Val Gly Ile Met Arg Val
    50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Ser Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
        115                 120                 125

Ser Val Trp Pro Ser Ser Ser Asp Ser Gly Ser Gly Gly Gly Asn Lys
    130                 135                 140

Ala Ile Thr Gln Ala Pro Pro His
145                 150

<210> SEQ ID NO 63
<211> LENGTH: 132
<212> TYPE: PRT
<213> ORGANISM: Drosophila melanogaster SynB1 (Fruit fly)

<400> SEQUENCE: 63

Met Glu Asn Asn Glu Ala Pro Ser Pro Ser Gly Ser Asn Asn Asn Asp
1               5                   10                  15

Phe Pro Ile Leu Pro Pro Pro Asn Ala Asn Asp Asn Tyr Asn Gln
            20                  25                  30

```
Phe Gly Asp His Gln Ile Arg Asn Asn Asn Ala Ala Gln Lys Lys Leu
            35                  40                  45

Gln Gln Thr Gln Ala Lys Val Asp Glu Val Val Gly Ile Met Arg Val
    50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Phe Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
            115                 120                 125

Ser Leu Phe Asn
    130

<210> SEQ ID NO 64
<211> LENGTH: 132
<212> TYPE: PRT
<213> ORGANISM: Drosophila melanogaster SynB2 (Fruit fly)

<400> SEQUENCE: 64

Met Glu Asn Asn Glu Ala Pro Ser Pro Ser Gly Ser Asn Asn Asn Asp
1               5                   10                  15

Phe Pro Ile Leu Pro Pro Pro Asn Ala Asn Asp Asn Tyr Asn Gln
            20                  25                  30

Phe Gly Asp His Gln Ile Arg Asn Asn Asn Ala Ala Gln Lys Lys Leu
            35                  40                  45

Gln Gln Thr Gln Ala Lys Val Asp Glu Val Val Gly Ile Met Arg Val
    50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Ser Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
            115                 120                 125

Ser Leu Phe Asn
    130

<210> SEQ ID NO 65
<211> LENGTH: 183
<212> TYPE: PRT
<213> ORGANISM: Drosophila melanogaster SynC (Fruit fly)

<400> SEQUENCE: 65

Met Ala Asp Ala Ala Pro Ala Gly Asp Ala Pro Asn Ala Gly Ala
1               5                   10                  15

Pro Ala Gly Glu Gly Gly Asp Gly Glu Ile Val Gly Gly Pro His Asn
            20                  25                  30

Pro Gln Gln Ile Ala Ala Gln Lys Arg Leu Gln Gln Thr Gln Ala Gln
            35                  40                  45

Val Asp Glu Val Val Asp Ile Met Arg Thr Asn Val Glu Lys Val Leu
    50                  55                  60

Glu Arg Asp Ser Lys Leu Ser Glu Leu Asp Asp Arg Ala Asp Ala Leu
65                  70                  75                  80
```

```
Gln Gln Gly Ala Ser Gln Phe Glu Gln Gln Ala Gly Lys Leu Lys Arg
                85                  90                  95

Lys Phe Trp Leu Gln Asn Leu Lys Met Met Ile Ile Met Gly Val Ile
            100                 105                 110

Gly Leu Val Val Gly Ile Ile Ala Asn Lys Leu Gly Leu Ile Gly
            115                 120                 125

Gly Glu Gln Pro Pro Gln Tyr Gln Tyr Pro Pro Gln Tyr Met Gln Pro
        130                 135                 140

Pro Pro Pro Pro Gln Gln Pro Ala Gly Gly Gln Ser Ser Leu Val
145                 150                 155                 160

Asp Ala Ala Gly Ala Gly Asp Gly Ala Gly Ala Gly Gly Ser Ala Gly
                165                 170                 175

Ala Gly Asp His Gly Gly Val
            180
```

```
<210> SEQ ID NO 66
<211> LENGTH: 221
<212> TYPE: PRT
<213> ORGANISM: Drosophila melanogaster SynD (Fruit fly)

<400> SEQUENCE: 66
```

```
Met Gly Lys Lys Asp Lys Asn Lys Glu Gln Ala Asp Ala Ala Pro Ala
1               5                   10                  15

Gly Asp Ala Pro Pro Asn Ala Gly Ala Pro Ala Gly Glu Gly Gly Asp
            20                  25                  30

Gly Glu Ile Val Gly Gly Pro His Asn Pro Gln Gln Ile Ala Ala Gln
        35                  40                  45

Lys Arg Leu Gln Gln Thr Gln Ala Gln Val Asp Glu Val Val Asp Ile
 50                  55                  60

Met Arg Thr Asn Val Glu Lys Val Leu Glu Arg Asp Ser Lys Leu Ser
65                  70                  75                  80

Glu Leu Asp Asp Arg Ala Asp Ala Leu Gln Gln Gly Ala Ser Gln Phe
                85                  90                  95

Glu Gln Gln Ala Gly Lys Leu Lys Arg Lys Phe Trp Leu Gln Asn Leu
            100                 105                 110

Lys Met Met Ile Ile Met Gly Val Ile Gly Leu Val Val Val Gly Ile
        115                 120                 125

Ile Ala Lys Arg Arg Arg Ile Ile Thr Gln Lys Ala Ser Ala Leu Tyr
130                 135                 140

Asn Phe Ile Asn His Lys Gln Ile Asn Leu Pro Asn Ile Thr Leu Tyr
145                 150                 155                 160

Lys Leu Gly Leu Ile Gly Gly Glu Gln Pro Gln Tyr Gln Tyr Pro
                165                 170                 175

Pro Gln Tyr Met Gln Pro Pro Pro Pro Pro Gln Gln Pro Ala Gly
            180                 185                 190

Gly Gln Ser Ser Leu Val Asp Ala Ala Gly Ala Gly Asp Gly Ala Gly
        195                 200                 205

Ala Gly Gly Ser Ala Gly Ala Gly Asp His Gly Gly Val
    210                 215                 220
```

```
<210> SEQ ID NO 67
<211> LENGTH: 192
<212> TYPE: PRT
<213> ORGANISM: Drosophila melanogaster SynE (Fruit fly)

<400> SEQUENCE: 67
```

Met Gly Lys Lys Asp Lys Asn Lys Glu Gln Ala Asp Ala Ala Pro Ala
1               5                   10                  15

Gly Asp Ala Pro Pro Asn Ala Gly Ala Pro Ala Gly Glu Gly Gly Asp
            20                  25                  30

Gly Glu Ile Val Gly Gly Pro His Asn Pro Gln Gln Ile Ala Ala Gln
        35                  40                  45

Lys Arg Leu Gln Gln Thr Gln Ala Gln Val Asp Glu Val Val Asp Ile
50                  55                  60

Met Arg Thr Asn Val Glu Lys Val Leu Glu Arg Asp Ser Lys Leu Ser
65                  70                  75                  80

Glu Leu Asp Asp Arg Ala Asp Ala Leu Gln Gln Gly Ala Ser Gln Phe
                85                  90                  95

Glu Gln Gln Ala Gly Lys Leu Lys Arg Lys Phe Trp Leu Gln Asn Leu
            100                 105                 110

Lys Met Met Ile Ile Met Gly Val Ile Gly Leu Val Val Val Gly Ile
        115                 120                 125

Ile Ala Asn Lys Leu Gly Leu Ile Gly Gly Glu Gln Pro Pro Gln Tyr
130                 135                 140

Gln Tyr Pro Pro Gln Tyr Met Gln Pro Pro Pro Pro Pro Gln Gln
145                 150                 155                 160

Pro Ala Gly Gly Gln Ser Ser Leu Val Asp Ala Ala Gly Ala Gly Asp
                165                 170                 175

Gly Ala Gly Ala Gly Gly Ser Ala Gly Ala Gly Asp His Gly Gly Val
            180                 185                 190

<210> SEQ ID NO 68
<211> LENGTH: 169
<212> TYPE: PRT
<213> ORGANISM: Hirudo medicinalis VAMP (Leech)

<400> SEQUENCE: 68

Met Ala Gln Pro Pro Lys Pro Ser Thr Gly Pro Gly Gly Leu Pro
1               5                   10                  15

Ala Pro Gly Ala Pro Pro Gln Pro Ala Pro Gln Ser Lys Arg Leu Gln
            20                  25                  30

Gln Ala Gln Ala Gln Val Asp Glu Val Val Asp Met Met Arg Val Asn
        35                  40                  45

Val Asp Lys Val Leu Glu Lys Asp Gln Lys Leu Ala Glu Leu Asp Gly
50                  55                  60

Arg Ala Asp Ala Leu Gln Ala Gly Ala Ser Gln Phe Glu Ala Ser Ala
65                  70                  75                  80

Gly Lys Leu Lys Arg Lys Phe Trp Trp Lys Asn Met Lys Met Met Leu
                85                  90                  95

Ile Met Gly Ala Val Val Ala Val Val Val Ile Phe Gly Ala Trp
            100                 105                 110

Ile Tyr Asn Lys Phe Ser Gly Thr Ser Ser Val Pro Gln Glu Gly Thr
        115                 120                 125

Pro Val Leu Gln Ser Pro Met Ala Gln Gln Pro Gln Ser Leu Pro Glu
130                 135                 140

Asn Ile Pro Pro Ala Ser Pro Val Gly Gly Gly Gly Gly Lys Lys
145                 150                 155                 160

Gly Lys Asn Lys Gln Pro His Ser Ser
                165

```
<210> SEQ ID NO 69
<211> LENGTH: 125
<212> TYPE: PRT
<213> ORGANISM: Loligo pealei VAMP (Longfin squid)

<400> SEQUENCE: 69

Met Ser Gly Pro Gln Asn Pro Gln Ala Gly Pro Gly Gly Pro Pro Ser
1               5                   10                  15

Gly Pro Pro Gln Pro Gly Gly Pro Pro Gly Pro Pro Gln Gly Pro Pro
            20                  25                  30

Gln Pro Val Gln Gln Ser Lys Arg Leu Gln Gln Thr Gln Ala Gln Val
        35                  40                  45

Glu Val Val Asp Ile Met Arg Val Asn Val Asp Lys Val Leu Glu
    50                  55                  60

Arg Asp Ser Lys Ile Ser Glu Leu Asp Asp Arg Ala Asp Ala Leu Gln
65                  70                  75                  80

Ala Gly Ala Ser Gln Phe Glu Ala Ser Ala Gly Lys Leu Lys Arg Lys
                85                  90                  95

Phe Trp Trp Lys Asn Cys Lys Met Met Ile Ile Leu Gly Ile Val
            100                 105                 110

Ala Val Ile Val Thr Val Ile Ile Val Trp Ala Ala Thr
            115                 120                 125

<210> SEQ ID NO 70
<211> LENGTH: 145
<212> TYPE: PRT
<213> ORGANISM: Lymnaea stagnalis VAMP (Great pond snail)

<400> SEQUENCE: 70

Met Ala Ala Ser Gln Asn Pro Gln Ala Gly Pro Gly Gly Pro Pro Ser
1               5                   10                  15

Ala Gly Pro Gly Gly Pro Gly Met Gln Pro Pro Arg Glu Gln Ser Lys
            20                  25                  30

Arg Leu Gln Gln Thr Gln Ala Gln Val Asp Glu Val Val Asp Ile Met
        35                  40                  45

Arg Val Asn Val Glu Lys Val Leu Asp Arg Asp Gln Lys Ile Ser Gln
    50                  55                  60

Leu Asp Asp Arg Ala Glu Ala Leu Gln Ala Gly Ala Ser Gln Phe Glu
65                  70                  75                  80

Ala Ser Ala Gly Lys Leu Lys Arg Lys Tyr Trp Trp Lys Asn Cys Lys
                85                  90                  95

Met Met Leu Ile Leu Gly Ala Ile Gly Ile Ile Cys Ile Ile Ile
            100                 105                 110

Ile Val Trp Val Val Thr Ser Thr Lys Gly Gly Asp Asp Lys Pro Thr
            115                 120                 125

Pro Gln Pro Ala Ile Ser Ser Thr Thr Gly Thr Pro Ser Pro Lys Thr
        130                 135                 140

Thr
145

<210> SEQ ID NO 71
<211> LENGTH: 180
<212> TYPE: PRT
<213> ORGANISM: Aplysia californica VAMP (California sea hare)

<400> SEQUENCE: 71

Met Ser Ala Gly Pro Gly Gly Pro Gln Gly Gly Met Gln Pro Pro Arg
1               5                   10                  15
```

```
Glu Gln Ser Lys Arg Leu Gln Gln Thr Gln Ala Gln Val Asp Glu Val
            20                  25                  30

Val Asp Ile Met Arg Val Asn Val Glu Lys Val Leu Asp Arg Asp Gln
        35                  40                  45

Lys Ile Ser Gln Leu Asp Asp Arg Ala Glu Ala Leu Gln Ala Gly Ala
    50                  55                  60

Ser Gln Phe Glu Ala Ser Ala Gly Lys Leu Lys Arg Lys Tyr Trp Trp
65                  70                  75                  80

Lys Asn Cys Lys Met Met Leu Ile Leu Gly Ala Ile Ile Gly Val Ile
                85                  90                  95

Val Ile Ile Ile Ile Val Trp Val Val Thr Ser Gln Asp Ser Gly Gly
            100                 105                 110

Asp Asp Ser Gly Ser Lys Thr Pro Ala Thr Ala Gly Thr Ser Pro Lys
            115                 120                 125

Pro Val Glu Ser Gly Val Gln Gly Gly Gly Arg Gln Gln Arg Pro
    130                 135                 140

His Ser Gln Leu Val Glu Arg Arg Asn Val Leu Arg Arg Thr Glu Asp
145                 150                 155                 160

His Ile Gly Cys Arg Pro His Ile His Ser Phe Ile His Ile Phe Met
                165                 170                 175

Ile Cys Leu Val
        180

<210> SEQ ID NO 72
<211> LENGTH: 109
<212> TYPE: PRT
<213> ORGANISM: Caenorhabditis elegans SNB1 (Round worm)

<400> SEQUENCE: 72

Met Asp Ala Gln Gly Asp Ala Gly Ala Gln Gly Gly Ser Gln Gly Gly
1               5                   10                  15

Pro Arg Pro Ser Asn Lys Arg Leu Gln Gln Thr Gln Ala Gln Val Asp
            20                  25                  30

Glu Val Val Gly Ile Met Lys Val Asn Val Glu Lys Val Leu Glu Arg
        35                  40                  45

Asp Gln Lys Leu Ser Gln Leu Asp Asp Arg Ala Asp Ala Leu Gln Glu
    50                  55                  60

Gly Ala Ser Gln Phe Glu Lys Ser Ala Ala Thr Leu Lys Arg Lys Tyr
65                  70                  75                  80

Trp Trp Lys Asn Ile Lys Met Met Ile Ile Met Cys Ala Ile Val Val
                85                  90                  95

Ile Leu Ile Ile Ile Val Leu Trp Ala Gly Gly Lys
            100                 105

<210> SEQ ID NO 73
<211> LENGTH: 118
<212> TYPE: PRT
<213> ORGANISM: Caenorhabditis elegans SNB1-like (Round worm)

<400> SEQUENCE: 73

Met Phe Ser Arg Met Ser Ala Asn Asn Glu Ala Asn Lys Asp Leu Glu
1               5                   10                  15

Ala Gly Asn Gly Glu Ala Gln Pro Pro Thr Gly Thr Tyr Asn Thr Lys
            20                  25                  30

Arg Met Gln Met Ala Gln Ala Gln Val Asn Glu Val Ile Asp Val Met
        35                  40                  45
```

Arg Asn Asn Val Asn Lys Val Met Glu Arg Asp Val Gln Leu Asn Ser
    50                  55                  60

Leu Asp His Arg Ala Glu Val Leu Gln Asn Gly Ala Ser Gln Phe Gln
65                  70                  75                  80

Gln Ser Ser Arg Thr Leu Arg Gln Lys Tyr Trp Trp Gln Asn Ile Arg
                85                  90                  95

Met Met Ile Ile Ile Gly Leu Ile Ala Phe Leu Val Gly Ile Phe
            100                 105                 110

Leu Ile Trp Ile Phe Asn
        115

<210> SEQ ID NO 74
<211> LENGTH: 288
<212> TYPE: PRT
<213> ORGANISM: Homo sapiens Syntaxin-1A (Human)

<400> SEQUENCE: 74

Met Lys Asp Arg Thr Gln Glu Leu Arg Thr Ala Lys Asp Ser Asp Asp
 1               5                  10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
        275                 280                 285

<210> SEQ ID NO 75
<211> LENGTH: 288
<212> TYPE: PRT
<213> ORGANISM: Homo sapiens Syntaxin-1B1 (Human)

<400> SEQUENCE: 75

Met Lys Asp Arg Thr Gln Val Leu Arg Thr Arg Arg Asn Ser Asp Asp
1               5                   10                  15

Lys Glu Glu Val Val His Val Asp Arg Asp His Phe Met Asp Glu Phe
            20                  25                  30

Phe Glu Gln Glu Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Arg Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Ser Thr Ala Pro Arg Pro Ile Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Pro Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Ile Ile Ile Cys Cys Val
            260                 265                 270

Val Leu Gly Val Val Leu Ala Ser Ser Ile Gly Cys Thr Leu Gly Leu
        275                 280                 285

<210> SEQ ID NO 76
<211> LENGTH: 288
<212> TYPE: PRT
<213> ORGANISM: Homo sapiens Syntaxin-1B2 (Human)

<400> SEQUENCE: 76

Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro

-continued

```
                50                  55                  60
Asn Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Gly Leu Asn Arg Ser Ser Ala Asp Leu
            100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
            165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
            195                 200                 205

Arg Glu Leu His Asp Met Phe Val Asp Met Ala Met Leu Val Glu Ser
            210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
            245                 250                 255

Gln Ser Lys Ala Arg Arg Lys Ile Met Ile Ile Cys Cys Val
            260                 265                 270

Val Leu Gly Val Val Leu Ala Ser Ser Ile Gly Gly Thr Leu Gly Leu
            275                 280                 285
```

<210> SEQ ID NO 77
<211> LENGTH: 287
<212> TYPE: PRT
<213> ORGANISM: Homo sapiens Syntaxin-2-1 (Human)

<400> SEQUENCE: 77

```
Met Arg Asp Arg Leu Pro Asp Leu Thr Ala Cys Arg Lys Asn Asp Asp
  1               5                  10                  15

Gly Asp Thr Val Val Val Val Glu Lys Asp His Phe Met Asp Asp Phe
             20                  25                  30

Phe His Gln Val Glu Glu Ile Arg Asn Ser Ile Asp Lys Ile Thr Gln
         35                  40                  45

Tyr Val Glu Glu Val Lys Lys Asn His Ser Ile Ile Leu Ser Ala Pro
 50                  55                  60

Asn Pro Glu Gly Lys Ile Lys Glu Glu Leu Glu Asp Leu Asn Lys Glu
 65                  70                  75                  80

Ile Lys Lys Thr Ala Asn Lys Ile Arg Ala Lys Leu Lys Ala Ile Glu
                 85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
            115                 120                 125

Ala Met Ala Glu Tyr Asn Glu Ala Gln Thr Leu Phe Arg Glu Arg Ser
130                 135                 140
```

```
Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Leu Met Phe Ile Ile Ile Cys Val Ile
            260                 265                 270

Val Leu Leu Val Ile Leu Gly Ile Ile Leu Ala Thr Thr Leu Ser
        275                 280                 285
```

<210> SEQ ID NO 78
<211> LENGTH: 288
<212> TYPE: PRT
<213> ORGANISM: Homo sapiens Syntaxin-2-2 (Human)

<400> SEQUENCE: 78

```
Met Arg Asp Arg Leu Pro Asp Leu Thr Ala Cys Arg Lys Asn Asp Asp
1               5                   10                  15

Gly Asp Thr Val Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240
```

```
Asp Tyr Val Glu His Ala Lys Glu Thr Lys Lys Ala Ile Lys Tyr
            245                 250                 255

Gln Ser Lys Ala Arg Arg Lys Lys Trp Ile Ile Ile Ala Val Ser Val
            260                 265                 270

Val Leu Val Ala Ile Ile Ala Leu Ile Ile Gly Leu Ser Val Gly Lys
        275                 280                 285

<210> SEQ ID NO 79
<211> LENGTH: 299
<212> TYPE: PRT
<213> ORGANISM: Homo sapiens Syntaxin-2-3 (Human)

<400> SEQUENCE: 79

Met Arg Asp Arg Leu Pro Asp Leu Thr Ala Cys Arg Lys Asn Asp Asp
  1               5                  10                  15

Gly Asp Thr Val Val Val Glu Lys Asp His Phe Met Asp Asp Phe
             20                  25                  30

Phe His Gln Val Glu Glu Ile Arg Asn Ser Ile Asp Lys Ile Thr Gln
             35                  40                  45

Tyr Val Glu Glu Val Lys Lys Asn His Ser Ile Ile Leu Ser Ala Pro
 50                  55                  60

Asn Pro Glu Gly Lys Ile Lys Glu Glu Leu Glu Asp Leu Asn Lys Glu
 65                  70                  75                  80

Ile Lys Lys Thr Ala Asn Lys Ile Ala Ala Lys Leu Lys Ala Ile Glu
                 85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Thr Lys Lys Ala Ile Lys Tyr
                245                 250                 255

Gln Ser Lys Ala Arg Arg Lys Lys Trp Ile Ile Ile Ala Val Ser Val
            260                 265                 270

Val Leu Val Val Tyr Arg Leu Phe Gly Leu Ser Leu Glu Tyr Val Val
        275                 280                 285

Arg Ser Ala Ala Ser Leu Pro Gly Trp Gly Asn
    290                 295

<210> SEQ ID NO 80
<211> LENGTH: 289
<212> TYPE: PRT
```

<213> ORGANISM: Homo sapiens Syntaxin-3 (Human)

<400> SEQUENCE: 80

```
Met Lys Asp Arg Leu Glu Gln Leu Lys Ala Lys Gln Leu Thr Gln Asp
1               5                   10                  15

Asp Asp Thr Asp Ala Val Glu Ile Ala Ile Asp Asn Thr Ala Phe Met
            20                  25                  30

Asp Glu Phe Phe Ser Glu Ile Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65              70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
        115                 120                 125

Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
            165                 170                 175

Phe Thr Ser Gly Ile Ile Asp Ser Gln Ile Ser Lys Gln Ala Leu Ser
        180                 185                 190

Glu Ile Glu Gly Arg His Lys Asp Ile Val Arg Leu Glu Ser Ser Ile
    195                 200                 205

Lys Glu Leu His Asp Met Phe Met Asp Ile Ala Met Leu Val Glu Asn
210                 215                 220

Gln Gly Glu Met Leu Asp Asn Ile Glu Leu Asn Val Met His Thr Val
225                 230                 235                 240

Asp His Val Glu Lys Ala Arg Asp Glu Ser Lys Lys Ala Val Lys Tyr
            245                 250                 255

Gln Ser Gln Ala Arg Lys Lys Leu Ile Ile Ile Val Leu Val Val
        260                 265                 270

Val Leu Leu Gly Ile Leu Ala Leu Ile Ile Gly Leu Ser Val Gly Leu
        275                 280                 285

Asn
```

<210> SEQ ID NO 81
<211> LENGTH: 288
<212> TYPE: PRT
<213> ORGANISM: Bos taurus Syntaxin-1A (Cow)

<400> SEQUENCE: 81

```
Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ser
        35                  40                  45

Glu Asn Val Glu Glu Val Lys Arg Lys His Ser Ala Ile Leu Ala Ser
    50                  55                  60
```

```
Pro Asn Pro Asp Glu Lys Thr Lys Glu Leu Glu Glu Leu Met Ser
 65                  70                  75                  80

Asp Ile Lys Lys Thr Ala Asn Lys Val Arg Ser Lys Leu Lys Ser Ile
                 85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ser
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Val Ile Cys Cys
            260                 265                 270

Val Val Leu Gly Ile Val Ile Ala Ser Thr Phe Gly Gly Ile Phe Gly
        275                 280                 285

<210> SEQ ID NO 82
<211> LENGTH: 288
<212> TYPE: PRT
<213> ORGANISM: Bos taurus Syntaxin-1B2 (Cow)

<400> SEQUENCE: 82

Met Lys Asp Arg Thr Gln Glu Leu Arg Ser Ala Lys Asp Ser Asp Asp
  1               5                  10                  15

Glu Glu Glu Val Val His Val Asp Arg Asp His Phe Met Asp Glu Phe
                 20                  25                  30

Phe Glu Gln Val Glu Glu Ile Arg Gly Cys Ile Glu Lys Leu Ser Glu
             35                  40                  45

Asp Val Glu Gln Val Lys Lys Gln His Ser Ala Ile Leu Ala Ala Pro
         50                  55                  60

Asn Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
130                 135                 140

Lys Asp Arg Ile Gln Arg Gln Leu Glu Ile Thr Gly Arg Thr Thr Thr
```

```
                   145                 150                 155                 160

Asn Glu Glu Leu Glu Asp Met Leu Glu Ser Gly Lys Leu Ala Ile Phe
                    165                 170                 175

Thr Asp Asp Ile Lys Met Asp Ser Gln Met Thr Lys Gln Ala Leu Asn
                180                 185                 190

Glu Ile Glu Thr Arg His Asn Glu Ile Ile Lys Leu Glu Thr Ser Ile
            195                 200                 205

Arg Glu Leu His Asp Met Phe Val Asp Met Ala Met Leu Val Glu Ser
        210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 83
<211> LENGTH: 288
<212> TYPE: PRT
<213> ORGANISM: Rattus norvegicus Syntaxin-1A (Rat)

<400> SEQUENCE: 83

Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
                20                  25                  30

Phe Phe Glu Gln Val Glu Glu Ile Arg Gly Phe Ile Asp Lys Ile Ala
            35                  40                  45

Glu Asn Val Glu Glu Val Lys Arg Lys His Ser Ala Ile Leu Ala Ser
        50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240
```

```
Val Asp Tyr Val Glu Arg Ala Val Ser Asp Thr Lys Lys Ala Val Lys
            245                 250                 255

Tyr Gln Ser Lys Ala Arg Arg Lys Lys Ile Met Ile Ile Ile Cys Cys
        260                 265                 270

Val Ile Leu Gly Ile Ile Ile Ala Ser Thr Ile Gly Gly Ile Phe Gly
        275                 280                 285

<210> SEQ ID NO 84
<211> LENGTH: 288
<212> TYPE: PRT
<213> ORGANISM: Rattus norvegicus Syntaxin-1B2 (Rat)

<400> SEQUENCE: 84

Met Lys Asp Arg Thr Gln Glu Leu Arg Ser Ala Lys Asp Ser Asp Asp
  1               5                  10                  15

Glu Glu Glu Val Val His Val Asp Arg Asp His Phe Met Asp Glu Phe
             20                  25                  30

Phe Glu Gln Val Glu Glu Ile Arg Gly Cys Ile Glu Lys Leu Ser Glu
         35                  40                  45

Asp Val Glu Gln Val Lys Lys Gln His Ser Ala Ile Leu Ala Ala Pro
 50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                 85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 85
<211> LENGTH: 288
<212> TYPE: PRT
<213> ORGANISM: Mus musculus Syntaxin-1A (Mouse)

<400> SEQUENCE: 85
```

```
Met Lys Asp Arg Thr Gln Glu Leu Arg Thr Ala Lys Asp Ser Asp Asp
 1               5                  10                  15

Asp Asp Asp Val Thr Val Thr Val Asp Arg Asp Arg Phe Met Asp Glu
             20                  25                  30

Phe Phe Glu Gln Val Glu Glu Ile Arg Gly Phe Ile Asp Lys Ile Ala
             35                  40                  45

Glu Asn Val Glu Glu Val Lys Arg Lys His Ser Ala Ile Leu Ala Ser
 50                  55                  60

Pro Asn Pro Asp Glu Lys Thr Lys Glu Glu Leu Glu Glu Leu Met Ser
 65                  70                  75                  80

Asp Ile Lys Lys Thr Ala Asn Lys Val Arg Ser Lys Leu Lys Ser Ile
                 85                  90                  95

Glu Gln Ser Ile Glu Gln Glu Glu Gly Leu Asn Arg Ser Ser Ala Asp
                100                 105                 110

Leu Arg Ile Arg Lys Thr Gln His Ser Thr Leu Ser Arg Lys Phe Val
             115                 120                 125

Glu Val Met Ser Glu Tyr Asn Ala Thr Gln Ser Asp Tyr Arg Glu Arg
             130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
             180                 185                 190

Ser Glu Ile Glu Thr Arg His Ser Glu Ile Ile Lys Leu Glu Thr Ser
             195                 200                 205

Ile Arg Glu Leu His Asp Met Phe Met Asp Met Ala Met Leu Val Glu
210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
             260                 265                 270

Val Ile Leu Gly Ile Ile Ala Ser Thr Ile Gly Gly Ile Phe Gly
             275                 280                 285

<210> SEQ ID NO 86
<211> LENGTH: 288
<212> TYPE: PRT
<213> ORGANISM: Mus musculus Syntaxin-1B1 (Mouse)

<400> SEQUENCE: 86

Met Lys Glu Trp Thr Gln Glu Arg Arg Ser Ala Lys Asp Ser Asp Asp
 1               5                  10                  15

Glu Glu Glu Val Val His Val Asp Arg Ala His Phe Met Ala Glu Phe
             20                  25                  30

Phe Glu Gln Val Glu Glu Ile Arg Gly Cys Ile Glu Lys Leu Ser Glu
             35                  40                  45

Asp Val Gly Arg Val Gly Gly Gln His Ser Ala Ile Leu Ala Ala Pro
 50                  55                  60

Lys Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
             85                  90                  95
```

-continued

Gln Gly Ile Glu Gln Glu Gly Leu Asn Arg Ser Ser Ala Asp Leu
                100                 105                 110

Arg Tyr Arg Thr Thr Gln His Ser Thr Val Ser Arg Asn Phe Val Glu
            115                 120                 125

Val Met Thr Glu Tyr Asn Ala Thr Lys Ser Lys Tyr Arg Asp Arg Cys
        130                 135                 140

Lys Asp Arg Leu Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Arg Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 87
<211> LENGTH: 288
<212> TYPE: PRT
<213> ORGANISM: Mus musculus Syntaxin-1B2 (Mouse)

<400> SEQUENCE: 87

Met Lys Asp Arg Thr Gln Glu Leu Arg Ser Ala Lys Asp Ser Asp Asp
 1               5                  10                  15

Glu Glu Glu Val Val His Val Asp Arg Asp His Phe Met Asp Glu Phe
                20                  25                  30

Phe Glu Gln Val Glu Glu Ile Arg Gly Cys Ile Glu Lys Leu Ser Glu
            35                  40                  45

Asp Val Glu Gln Val Lys Lys Gln His Ser Ala Ile Leu Ala Ala Pro
        50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
                100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn

```
                         180             185             190
Glu Ile Glu Thr Arg His Asn Glu Ile Ile Lys Leu Glu Thr Ser Ile
                195                 200                 205
Arg Glu Leu His Asp Met Phe Val Asp Met Ala Met Leu Val Glu Ser
            210                 215                 220
Gln Gly Glu Met Ile Asp Arg Ile Glu Tyr Asn Val Glu His Ser Val
225                 230                 235                 240
Asp Tyr Val Glu Arg Ala Val Ser Asp Thr Lys Lys Ala Val Lys Tyr
                245                 250                 255
Gln Ser Lys Ala Arg Arg Lys Lys Ile Met Ile Ile Ile Cys Cys Val
            260                 265                 270
Val Leu Gly Val Val Leu Ala Ser Ser Ile Gly Gly Thr Leu Gly Leu
                275                 280                 285

<210> SEQ ID NO 88
<211> LENGTH: 290
<212> TYPE: PRT
<213> ORGANISM: Rattus norvegicus Syntaxin-2 (Rat)

<400> SEQUENCE: 88

Met Arg Asp Arg Leu Pro Asp Leu Thr Ala Cys Arg Lys Ser Asp Asp
  1               5                  10                  15
Gly Asp Asn Ala Val Ile Ile Thr Val Glu Lys Asp His Phe Met Asp
                 20                  25                  30
Ala Phe Phe His Gln Val Glu Glu Ile Arg Ser Ser Ile Ala Arg Ile
             35                  40                  45
Ala Gln His Val Glu Asp Val Lys Lys Asn His Ser Ile Ile Leu Ser
         50                  55                  60
Ala Pro Asn Pro Glu Gly Lys Ile Lys Glu Glu Leu Glu Asp Leu Asn
 65                  70                  75                  80
Lys Glu Ile Lys Lys Thr Ala Asn Arg Ile Arg Gly Lys Leu Lys Ala
                 85                  90                  95
Ile Glu Gln Ser Cys Asp Gln Asp Glu Asn Gly Asn Arg Thr Ser Val
            100                 105                 110
Asp Leu Arg Ile Arg Arg Thr Gln His Ser Val Leu Ser Arg Lys Phe
        115                 120                 125
Val Asp Val Met Thr Glu Tyr Asn Glu Ala Gln Ile Leu Phe Arg Glu
    130                 135                 140
Arg Ser Lys Gly Arg Ile Gln Arg Gln Leu Glu Ile Thr Gly Arg Thr
145                 150                 155                 160
Thr Thr Asp Glu Glu Leu Glu Glu Met Leu Glu Ser Gly Lys Pro Ser
                165                 170                 175
Ile Phe Ile Ser Asp Ile Ile Ser Asp Ser Gln Ile Thr Arg Gln Ala
            180                 185                 190
Leu Asn Glu Ile Glu Ser Arg His Lys Asp Ile Met Lys Leu Glu Thr
        195                 200                 205
Ser Ile Arg Glu Leu His Glu Met Phe Met Asp Met Ala Met Phe Val
    210                 215                 220
Glu Thr Gln Gly Glu Met Val Asn Asn Ile Glu Arg Asn Val Val Asn
225                 230                 235                 240
Ser Val Asp Tyr Val Glu His Ala Lys Glu Glu Thr Lys Lys Ala Ile
                245                 250                 255
Lys Tyr Gln Ser Lys Ala Arg Arg Lys Lys Trp Ile Ile Ala Ala Val
            260                 265                 270
```

```
Val Val Ala Val Ile Ala Val Leu Ala Leu Ile Ile Gly Leu Ser Val
        275                 280                 285

Gly Lys
    290

<210> SEQ ID NO 89
<211> LENGTH: 289
<212> TYPE: PRT
<213> ORGANISM: Mus musculus Syntaxin-2 (Mouse)

<400> SEQUENCE: 89

Met Arg Asp Arg Leu Pro Asp Leu Thr Ala Cys Arg Thr Asn Asp Asp
  1               5                  10                  15

Gly Asp Thr Ala Val Val Ile Val Glu Lys Asp His Phe Met Asp Gly
             20                  25                  30

Phe Phe His Gln Val Glu Glu Ile Arg Ser Ser Ile Ala Arg Ile Ala
         35                  40                  45

Gln His Val Glu Asp Val Lys Lys Asn His Ser Ile Ile Leu Ser Ala
     50                  55                  60

Pro Asn Pro Glu Gly Lys Ile Lys Glu Glu Leu Glu Asp Leu Asn Lys
 65                  70                  75                  80

Glu Ile Lys Lys Thr Ala Asn Arg Ile Arg Gly Lys Leu Lys Ser Ile
                 85                  90                  95

Glu Gln Ser Cys Asp Gln Asp Glu Asn Gly Asn Arg Thr Ser Val Asp
            100                 105                 110

Leu Arg Ile Arg Arg Thr Gln His Ser Val Leu Ser Arg Lys Phe Val
        115                 120                 125

Asp Val Met Thr Glu Tyr Asn Glu Ala Gln Ile Leu Phe Arg Glu Arg
    130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                165                 170                 175

Phe Ile Ser Asp Ile Ile Ser Asp Ser Gln Ile Thr Arg Gln Ala Leu
            180                 185                 190

Asn Glu Ile Glu Ser Arg His Lys Asp Ile Met Lys Leu Glu Thr Ser
        195                 200                 205

Ile Arg Glu Leu His Glu Met Phe Met Asp Met Ala Met Phe Val Glu
    210                 215                 220

Thr Gln Gly Glu Met Val Asn Asn Ile Glu Arg Asn Val Val Asn Ser
225                 230                 235                 240

Val Asp Tyr Val Glu His Ala Lys Glu Glu Thr Lys Lys Ala Ile Lys
                245                 250                 255

Tyr Gln Ser Lys Ala Arg Arg Lys Lys Trp Ile Ile Ala Ala Val Ala
            260                 265                 270

Val Ala Val Ile Ala Val Leu Ala Leu Ile Ile Gly Leu Ser Val Gly
        275                 280                 285

Lys

<210> SEQ ID NO 90
<211> LENGTH: 289
<212> TYPE: PRT
<213> ORGANISM: Rattus norvegicus Syntaxin-3A (Rat)

<400> SEQUENCE: 90

Met Lys Asp Arg Leu Glu Gln Leu Lys Ala Lys Gln Leu Thr Gln Asp
```

-continued

```
                1               5                   10                  15
Asp Asp Thr Asp Glu Val Glu Ile Ala Ile Asp Asn Thr Ala Phe Met
                20                  25                  30

Asp Glu Phe Phe Ser Glu Ile Glu Thr Arg Leu Asn Ile Asp Lys
            35                  40                  45

Ile Ser Glu His Val Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
                100                 105                 110

Leu Arg Ile Arg Lys Ser Gln His Ser Val Leu Ser Arg Lys Phe Val
            115                 120                 125

Glu Val Met Thr Lys Tyr Asn Glu Ala Gln Val Asp Phe Arg Glu Arg
            130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
            195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Val Ile Val Val
            260                 265                 270

Val Leu Leu Gly Ile Leu Ala Leu Ile Ile Gly Leu Ser Val Gly Leu
        275                 280                 285

Lys

<210> SEQ ID NO 91
<211> LENGTH: 289
<212> TYPE: PRT
<213> ORGANISM: Mus musculus Syntaxin-3A (Mouse)

<400> SEQUENCE: 91

Met Lys Asp Arg Leu Glu Gln Leu Lys Ala Lys Gln Leu Thr Gln Asp
1               5                   10                  15

Asp Asp Thr Asp Glu Val Glu Ile Ala Ile Asp Asn Thr Ala Phe Met
                20                  25                  30

Asp Glu Phe Phe Ser Glu Ile Glu Thr Arg Leu Asn Ile Asp Lys
            35                  40                  45

Ile Ser Glu His Val Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
```

```
                        85                  90                  95
Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
            115                 120                 125

Glu Val Met Thr Lys Tyr Asn Glu Ala Gln Val Asp Phe Arg Glu Arg
            130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
            195                 200                 205

Lys Glu Leu His Asp Met Phe Met Asp Ile Ala Met Leu Val Glu Asn
210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Val Val Val Val Val
            260                 265                 270

Val Leu Leu Gly Ile Leu Ala Leu Ile Ile Gly Leu Ser Val Gly Leu
            275                 280                 285

Lys

<210> SEQ ID NO 92
<211> LENGTH: 283
<212> TYPE: PRT
<213> ORGANISM: Mus musculus Syntaxin-3B (Mouse)

<400> SEQUENCE: 92

Met Lys Asp Arg Leu Glu Gln Leu Lys Ala Lys Gln Leu Thr Gln Asp
 1               5                  10                  15

Asp Asp Thr Asp Glu Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
            35                  40                  45

Ile Ser Glu His Val Glu Glu Ala Lys Lys Leu Tyr Ser Ile Ile Leu
50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
            115                 120                 125

Glu Val Met Thr Lys Tyr Asn Glu Ala Gln Val Asp Phe Arg Glu Arg
            130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
```

```
                     165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Ala Met Ile Asp Arg Ile Glu Asn Asn Met Asp Gln Ser Val
225                 230                 235                 240

Gly Phe Val Glu Arg Ala Val Ala Asp Thr Lys Lys Ala Val Lys Tyr
                245                 250                 255

Gln Ser Glu Ala Arg Arg Lys Lys Ile Met Ile Met Ile Cys Cys Ile
            260                 265                 270

Ile Leu Ala Ile Ile Leu Ala Ser Thr Ile Gly
        275                 280

<210> SEQ ID NO 93
<211> LENGTH: 269
<212> TYPE: PRT
<213> ORGANISM: Mus musculus Syntaxin-3C (Mouse)

<400> SEQUENCE: 93

Met Lys Asp Arg Leu Glu Gln Leu Lys Ala Lys Gln Leu Thr Gln Asp
  1               5                  10                  15

Asp Asp Thr Asp Glu Val Glu Ile Ala Ile Asp Asn Thr Ala Phe Met
             20                  25                  30

Asp Glu Phe Phe Ser Glu Asn Phe His Gly Ile Leu Ser Tyr Leu Leu
         35                  40                  45

Arg Leu Ser Ser His Glu Thr Lys Asp Asp Leu Glu Gln Leu Thr Thr
     50                  55                  60

Glu Ile Lys Lys Arg Ala Asn Asn Val Arg Asn Lys Leu Lys Ser Met
 65                  70                  75                  80

Glu Lys His Ile Glu Glu Asp Glu Val Arg Ser Ser Ala Asp Leu Arg
                 85                  90                  95

Ile Arg Lys Ser Gln His Ser Val Leu Ser Arg Lys Phe Val Glu Val
            100                 105                 110

Met Thr Lys Tyr Asn Glu Ala Gln Val Asp Phe Arg Glu Arg Ser Lys
        115                 120                 125

Gly Arg Ile Gln Arg Gln Leu Glu Ile Thr Gly Lys Lys Thr Thr Asp
    130                 135                 140

Glu Glu Leu Glu Glu Met Leu Glu Ser Gly Asn Pro Ala Ile Phe Thr
145                 150                 155                 160

Ser Gly Ile Ile Asp Ser Gln Ile Ser Lys Gln Ala Leu Ser Glu Ile
                165                 170                 175

Glu Gly Arg His Lys Asp Ile Val Arg Leu Glu Ser Ser Ile Lys Glu
            180                 185                 190

Leu His Asp Met Phe Met Asp Ile Ala Met Leu Val Glu Asn Gln Gly
        195                 200                 205

Ala Met Ile Asp Arg Ile Glu Asn Asn Met Asp Gln Ser Val Gly Phe
    210                 215                 220

Val Glu Arg Ala Val Ala Asp Thr Lys Lys Ala Val Lys Tyr Gln Ser
225                 230                 235                 240

Glu Ala Arg Arg Lys Lys Ile Met Ile Met Ile Cys Cys Ile Ile Leu
                245                 250                 255
```

```
Ala Ile Ile Leu Ala Ser Thr Ile Gly Gly Ile Phe Ala
            260                 265
```

<210> SEQ ID NO 94
<211> LENGTH: 282
<212> TYPE: PRT
<213> ORGANISM: Gallus gallus Syntaxin-1B (Chicken)

<400> SEQUENCE: 94

```
Met Lys Asp Arg Thr Gln Glu Leu Arg His Ala Lys Asp Ser Asp Asp
1               5                   10                  15

Glu Glu Glu Val Val His Val Asp Arg Asn His Phe Met Asp Glu Phe
            20                  25                  30

Phe Glu Gln Val Glu Glu Ile Arg Gly Cys Ile Glu Lys Leu Phe Glu
        35                  40                  45

Asp Val Glu Gln Val Lys Lys Gln His Ser Ala Ile Leu Ala Ala Pro
    50                  55                  60

Asn Pro Asp Glu Arg Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Ala Asp Glu Glu Gly Leu Asn Arg Ser Ser Ala Asp Leu
            100                 105                 110

Arg Ile Arg Lys Thr His Val Arg Glu Val Met Thr Glu Tyr Asn Ala
        115                 120                 125

Thr Gln Ser Lys Tyr Arg Asp Arg Cys Lys Asp Arg Ile Gln Arg Leu
    130                 135                 140

Leu Glu Ile Thr Gly Arg Thr Thr Asn Glu Glu Leu Glu Asp Met
145                 150                 155                 160

Leu Glu Ser Gly Lys Leu Ala Val Phe Asn Asp Ile Lys Ile Asp
                165                 170                 175

Ser Gln Met Thr Lys Gln Ala Leu Asn Glu Ile Glu Thr Arg His Asn
            180                 185                 190

Glu Ile Ile Tyr Leu Glu Thr Ser Ile Arg Glu Leu His Asp Met Phe
        195                 200                 205

Val Asp Met Ala Met Leu Val Glu Ser His Gly Glu Ser Ile Arg Pro
    210                 215                 220

Ala Ser Ser Thr Thr Cys Val His Thr Val Asp Tyr Val Glu Pro Val
225                 230                 235                 240

Val Phe Val Thr Lys Ser Ala Val Met Tyr Gln Cys Lys Ser Arg Arg
                245                 250                 255

Lys Lys Ile Met Ile Ile Ile Phe Val Val Val Leu Gly Val Val Leu
            260                 265                 270

Ser Pro Val Ile Cys Gly Thr Leu Gly Leu
        275                 280
```

<210> SEQ ID NO 95
<211> LENGTH: 288
<212> TYPE: PRT
<213> ORGANISM: Gallus gallus Syntaxin-2 (Chicken)

<400> SEQUENCE: 95

```
Met Lys Asp Arg Leu Ala Asp Leu Ala Glu Cys Lys Gly Asn Glu Asp
1               5                   10                  15

Gly Glu Thr Val Ile Val Glu Lys Asp His Phe Met Asp Asp Phe Phe
            20                  25                  30
```

-continued

Gln Gln Val Glu Glu Ile Arg Asn Asn Ile Thr Lys Ile Ala Gln Asn
        35                  40                  45

Val Glu Glu Val Lys Lys Gln His Ser Ile Ile Leu Ser Ala Pro Asn
    50                  55                  60

Pro Glu Gly Arg Thr Lys Glu Glu Leu Glu Glu Leu Asn Glu Glu Ile
65                  70                  75                  80

Lys Lys Thr Ala Asn Lys Ile Arg Ala Arg Leu Lys Ala Ile Glu Gln
                85                  90                  95

Ser Val Asp Gln Ser Glu Asn Ala Asn Arg Thr Ser Val Asn Val Arg
            100                 105                 110

Ile Arg Lys Thr Gln His Ser Val Leu Ala His Lys Phe Val Glu Val
        115                 120                 125

Met Thr Glu Tyr Asn Glu Thr Gln Thr Leu Phe Arg Glu Arg Ser Lys
    130                 135                 140

Gly Arg Ile Gln Arg Gln Leu Glu Ile Thr Gly Lys Thr Thr Thr Asp
145                 150                 155                 160

Glu Glu Leu Glu Glu Met Leu Glu Ser Gly Asn Pro Ser Ile Phe Thr
                165                 170                 175

Ser Asp Ile Ile Ser Asp Ser Gln Ile Thr Arg Gln Ala Leu Asn Glu
            180                 185                 190

Ile Glu Ser Arg His Lys Asp Ile Met Lys Leu Glu Ser Ser Ile Arg
        195                 200                 205

Glu Leu His Glu Met Phe Met Asp Met Ala Met Phe Val Glu Thr Gln
    210                 215                 220

Gly Glu Met Ile Asn Asn Ile Glu Lys Asn Val Met Asn Ala Thr Asp
225                 230                 235                 240

Tyr Val Glu His Ala Lys Glu Glu Thr Lys Lys Ala Val Lys Tyr Gln
                245                 250                 255

Ser Lys Ala Arg Arg Lys Met Trp Ile Ile Ile Ile Val Ser Leu Val
            260                 265                 270

Leu Ile Ala Val Ile Gly Ile Ile Gly Leu Ser Val Gly Ile Arg
        275                 280                 285

<210> SEQ ID NO 96
<211> LENGTH: 288
<212> TYPE: PRT
<213> ORGANISM: Danio rerio Syntaxin-1B (Zebrafish)

<400> SEQUENCE: 96

Met Lys Asp Arg Thr Gln Glu Leu Arg Ser Ala Lys Asp Ser Asp Asp
1               5                   10                  15

Asp Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Thr Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
                180                 185                 190

Glu Ile Glu Thr Arg His Thr Glu Ile Ile Lys Leu Glu Asn Ser Ile
            195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Gln Ala Arg Lys Lys Lys Ile Met Ile Ile Cys Cys Val
                260                 265                 270

Ile Leu Gly Val Val Leu Arg Ser Ile Gly Gly Thr Leu Gly Phe
            275                 280                 285

<210> SEQ ID NO 97
<211> LENGTH: 288
<212> TYPE: PRT
<213> ORGANISM: Danio rerio Syntaxin-3 (Zebrafish)

<400> SEQUENCE: 97

Met Lys Asp Arg Leu Glu Gln Leu Lys Ala Thr Cys Asp His Asp Asp
1               5                   10                  15

Glu Asp Val Glu Ile Ala Val Asp Asn Ala Ala Phe Met Asp Glu Phe
                20                  25                  30

Phe Ser Gln Ile Glu Asp Ile Arg Asn Ser Ile Asp Lys Ile Asp Glu
            35                  40                  45

Asn Val Ala Glu Val Lys Lys Leu Tyr Ser Val Ile Leu Ser Ala Pro
    50                  55                  60

Thr Ser Asp Gln Lys Thr Gln Asp Asp Leu Glu Ala Leu Thr Asn Asp
65                  70                  75                  80

Ile Lys Lys Met Ala Asn Asn Ala Arg Asn Lys Leu Lys Thr Ile Glu
                85                  90                  95

Arg Asn Leu Glu Thr Glu Val Glu Arg Val Ser Ala Asp Met Arg
                100                 105                 110

Ile Arg Lys Ser Gln His Ala Val Leu Ser Arg Lys Phe Val Asp Val
            115                 120                 125

Met Thr Lys Tyr Asn Glu Ala Gln Val Asp Phe Arg Glu Lys Ser Lys
    130                 135                 140

Gly Arg Ile Gln Arg Gln Leu Glu Ile Thr Gly Lys Ala Thr Thr Asp
145                 150                 155                 160

Glu Glu Leu Glu Glu Met Leu Glu Gly Gly Asn Ala Ala Val Phe Thr
                165                 170                 175

Ala Gly Ile Val Asp Ser Gly Ile Ser Lys Gln Ala Leu Ser Glu Ile
                180                 185                 190

Glu Ala Arg His Lys Asp Ile Val Arg Leu Glu Ser Ser Ile Lys Glu
            195                 200                 205

Leu His Asp Met Phe Val Asp Ile Ala Met Leu Val Glu Ser Gln Gly

-continued

```
                210                 215                 220
Asn Met Val Asp Asn Ile Glu Val Asn Val Gly Lys Ala Val Asp His
225                 230                 235                 240

Val Glu Ala Ala Arg Asp Glu Thr Lys Lys Ala Val Arg Tyr Gln Ser
                245                 250                 255

Lys Ala Arg Lys Lys Ile Ile Ile Val Ser Val Val Leu Val Ile
                260                 265                 270

Leu Ala Ile Ile Ala Leu Ile Val Gly Leu Ser Val Gly Leu Lys Arg
                275                 280                 285
```

<210> SEQ ID NO 98
<211> LENGTH: 286
<212> TYPE: PRT
<213> ORGANISM: Strongylocentrotus purpuratus Syntaxin-1B (urchin)

<400> SEQUENCE: 98

```
Met Arg Asp Arg Leu Gly Ser Leu Lys Arg Asn Glu Glu Asp Val
1               5                   10                  15

Gly Gln Ser Arg Gly His Val Glu Ser Glu Lys Phe Met Glu Glu Phe
                20                  25                  30

Phe Glu Gln Val Glu Glu Val Arg Asn Asn Ile Asp Lys Ile Ser Lys
                35                  40                  45

Asn Val Asp Glu Val Lys Lys Lys His Ser Asp Ile Leu Ser Ala Pro
50                  55                  60

Gln Ala Asp Glu Lys Val Lys Asp Glu Leu Glu Glu Leu Met Ser Asp
65                  70                  75                  80

Ile Lys Lys Thr Ala Asn Lys Val Arg Val Lys Leu Lys Met Met Tyr
                85                  90                  95

Glu Ser Ile Glu Arg Arg Arg Val Leu Arg Arg Thr Gln Thr Asp Val
                100                 105                 110

Arg Ile Arg Lys Thr Gln His Ser Thr Leu Ser Arg Lys Phe Val Glu
                115                 120                 125

Val Met Thr Asp Tyr Asn Ser Thr Gln Thr Asp Tyr Arg Glu Arg Cys
130                 135                 140

Lys Gly Arg Ile Gln Arg Gln Leu Glu Ile Thr Gly Lys Ser Thr Thr
145                 150                 155                 160

Asp Ala Glu Leu Glu Asp Met Leu Glu Ser Gly Asn Pro Ala Ile Phe
                165                 170                 175

Thr Ser Gly Ile Ile Met Asp Thr Gln Gln Ala Lys Gln Thr Leu Arg
                180                 185                 190

Asp Ile Glu Ala Arg His Asn Asp Ile Ile Lys Leu Glu Ser Ser Ile
                195                 200                 205

Arg Glu Leu His Asp Met Phe Met Asp Met Ala Met Leu Val Glu Ser
                210                 215                 220

Gln Gly Glu Met Ile Asp Arg Ile Glu Tyr Asn Val Glu Gln Ser Val
225                 230                 235                 240

Asp Tyr Val Arg Arg Gln Asn Asp Thr Lys Lys Ala Val Lys Tyr Gln
                245                 250                 255

Ser Lys Ala Arg Arg Lys Lys Phe Tyr Ile Ala Ile Cys Cys Gly Val
                260                 265                 270

Ala Leu Gly Ile Leu Ile Leu Val Leu Ile Ile Val Leu Ala
                275                 280                 285
```

<210> SEQ ID NO 99
<211> LENGTH: 291

```
<212> TYPE: PRT
<213> ORGANISM: Drosophila melanogaster Syntaxin-1A (Fruit fly)

<400> SEQUENCE: 99

Met Thr Lys Asp Arg Leu Ala Ala Leu His Ala Ala Gln Ser Asp Asp
 1               5                   10                  15

Glu Glu Glu Thr Glu Val Ala Val Asn Val Asp Gly His Asp Ser Tyr
                20                  25                  30

Met Asp Asp Phe Phe Ala Gln Val Glu Glu Ile Arg Gly Met Ile Asp
             35                  40                  45

Lys Val Gln Asp Asn Val Glu Glu Val Lys Lys His Ser Ala Ile
 50                  55                  60

Leu Ser Ala Pro Gln Thr Asp Glu Lys Thr Lys Gln Glu Leu Glu Asp
 65                  70                  75                  80

Leu Met Ala Asp Ile Lys Lys Asn Ala Asn Arg Val Arg Gly Lys Leu
             85                  90                  95

Lys Gly Ile Glu Gln Asn Ile Glu Gln Glu Gln Gln Asn Lys Ser
                100                 105                 110

Ser Ala Asp Leu Arg Ile Arg Lys Thr Gln His Ser Thr Leu Ser Arg
             115                 120                 125

Lys Phe Val Glu Val Met Thr Glu Tyr Asn Arg Thr Gln Thr Asp Tyr
 130                 135                 140

Arg Glu Arg Cys Lys Gly Arg Ile Gln Arg Gln Leu Glu Ile Thr Gly
145                 150                 155                 160

Arg Pro Thr Asn Asp Asp Glu Leu Glu Lys Met Leu Glu Glu Gly Asn
                165                 170                 175

Ser Ser Val Phe Thr Gln Gly Ile Ile Met Glu Thr Gln Ala Lys
             180                 185                 190

Gln Thr Leu Ala Asp Ile Glu Ala Arg His Gln Asp Ile Met Lys Leu
             195                 200                 205

Glu Thr Ser Ile Lys Glu Leu His Asp Met Phe Met Asp Met Ala Met
             210                 215                 220

Leu Val Glu Ser Gln Gly Glu Met Ile Asp Arg Ile Glu Tyr His Val
225                 230                 235                 240

Glu His Ala Met Asp Tyr Val Gln Thr Ala Thr Gln Asp Thr Lys Lys
                245                 250                 255

Ala Leu Lys Tyr Gln Ser Lys Ala Arg Arg Lys Lys Ile Met Ile Leu
                260                 265                 270

Ile Cys Leu Thr Val Leu Gly Ile Leu Ala Ala Ser Tyr Val Ser Ser
             275                 280                 285

Tyr Phe Met
    290

<210> SEQ ID NO 100
<211> LENGTH: 295
<212> TYPE: PRT
<213> ORGANISM: Hirudo medicinalis Syntaxin-1A (Leech)

<400> SEQUENCE: 100

Met Thr Lys Asp Arg Leu Ala Ala Leu Lys Ala Ala Gln Ser Asp Asp
 1               5                   10                  15

Asp Asp Glu Pro Gly Glu His Met Pro Met Thr Met Asn Val Asp Gly
                20                  25                  30

Gly Lys Phe Met Glu Glu Phe Phe Glu Gln Val Asn Glu Ile Arg Glu
             35                  40                  45
```

-continued

```
Met Ile Asp Lys Ile Ala Val Asp Val Asp Glu Val Lys Lys His
 50                  55                  60

Ser Ala Ile Leu Ser Ala Pro Gln Thr Asp Asp Lys Thr Lys Glu Glu
 65                  70                  75                  80

Leu Glu Asp Leu Met Ala Glu Ile Lys Lys Thr Ala Asn Lys Val Arg
                 85                  90                  95

Gly Lys Leu Lys Val Leu Glu Gln Lys Ile Glu Gln Glu Glu Glu Thr
            100                 105                 110

Asn Lys Ser Ser Ala Asp Leu Arg Ile Arg Lys Thr Gln His Ser Thr
        115                 120                 125

Ile Leu Arg Lys Phe Ile Glu Val Met Asn Gln Tyr Asn Ala Ala Gln
    130                 135                 140

Val Asp Tyr Arg Asp Gly Cys Lys Lys Arg Leu Gln Arg Gln Met Glu
145                 150                 155                 160

Ile Thr Gly Arg Ala Thr Thr Asn Glu Glu Leu Glu Asp Met Leu Glu
                165                 170                 175

Ser Gly Asn Pro Ala Ile Phe Thr Gln Gly Ile Ile Thr Asp Thr Gln
            180                 185                 190

Gln Ala Lys Gln Ser Leu Met Asp Ile Glu Ala Arg His Asn Asp Ile
        195                 200                 205

Met Lys Leu Glu Gln Ser Ile Lys Glu Leu His Asp Met Phe Met Asp
    210                 215                 220

Met Ala Met Leu Val Glu Ser Gln Gly Glu Met Ile Asp Arg Ile Glu
225                 230                 235                 240

His Asn Val Glu Lys Ala Val Asp Tyr Val Glu Thr Ala Ala Ala Asp
                245                 250                 255

Thr Lys Lys Ala Met Lys Tyr Gln Ser Ala Ala Arg Lys Lys Lys Ile
            260                 265                 270

Ile Ile Leu Ile Cys Val Ser Val Leu Ile Leu Ile Val Gly Gly Ser
        275                 280                 285

Leu Leu Gly Ile Phe Ile Pro
    290                 295

<210> SEQ ID NO 101
<211> LENGTH: 292
<212> TYPE: PRT
<213> ORGANISM: Loligo pealei Syntaxin-1A (Longfin squid)

<400> SEQUENCE: 101

Met Thr Lys Asp Arg Leu Ala Ala Leu Lys Ala Ala Val Ser Asp Glu
  1               5                  10                  15

Glu Asp Val Glu Glu Val Ala Val Gln Val Asp Ser Gly Gly Gly Phe
             20                  25                  30

Met Glu Glu Phe Phe Glu Gln Val Glu Glu Ile Arg Ala Met Ile Asp
         35                  40                  45

Lys Ile Ser Asp Asn Val Asp Ala Val Lys Lys His Ser Asp Ile
 50                  55                  60

Leu Ser Ala Pro Gln Thr Asp Asp Gln Met Lys Glu Glu Leu Glu Glu
 65                  70                  75                  80

Leu Met Thr Asp Ile Lys Arg Thr Ala Asn Lys Val Arg Gly Lys Leu
                 85                  90                  95

Lys Thr Ile Glu Leu Asn Ile Glu Gln Glu Glu His Ser Asn Lys Ser
            100                 105                 110

Ser Ala Asp Leu Arg Ile Arg Lys Thr Gln Tyr Ser Thr Ile Ser Arg
        115                 120                 125
```

-continued

```
Lys Phe Val Glu Val Met Ser Asp Tyr Asn Thr Thr Gln Ile Asp Tyr
    130                 135                 140

Arg Asp Arg Cys Lys Ala Arg Ile Lys Arg Gln Met Glu Ile Thr Gly
145                 150                 155                 160

Arg Thr Thr Thr Asn Glu Glu Leu Glu Asp Met Leu Glu Ser Gly Asn
                165                 170                 175

Pro Ala Ile Phe Thr Gln Gly Ile Ile Met Glu Thr Gln Ala Lys
            180                 185                 190

Gln Thr Leu Ala Asp Ile Glu Ala Arg His Ala Asp Ile Met Lys Leu
        195                 200                 205

Glu Thr Ser Ile Arg Glu Leu His Asp Met Phe Met Asp Met Ala Met
    210                 215                 220

Leu Val Glu Ser Gln Gly Glu Met Ile Asp Arg Ile Glu Tyr Asn Val
225                 230                 235                 240

Glu Ala Ala Val Asp Tyr Ile Glu Thr Ala Lys Val Asp Thr Lys Lys
                245                 250                 255

Ala Val Lys Tyr Gln Ser Lys Ala Arg Gln Lys Lys Ile Ala Ile Leu
            260                 265                 270

Val Cys Leu Val Ile Leu Val Leu Val Ile Val Ser Thr Val Gly Gly
        275                 280                 285

Val Phe Gly Gly
    290

<210> SEQ ID NO 102
<211> LENGTH: 290
<212> TYPE: PRT
<213> ORGANISM: Lymnaea stagnalis Syntaxin-1A (Great pond snail)

<400> SEQUENCE: 102

Met Thr Lys Asp Arg Leu Ala Ala Leu Lys Ala Ala Gln Ser Asp Asp
1               5                   10                  15

Asp Glu Asn Asp Asp Val Ala Val Thr Val Asp Ser Ser Gly Phe Met
            20                  25                  30

Glu Glu Phe Phe Glu Gln Val Asp Glu Ile Arg Glu Met Ile Asp Lys
        35                  40                  45

Ile Ala Ser Asn Val Asp Glu Val Lys Lys His Ser Ala Ile Leu
    50                  55                  60

Ser Ala Pro Gln Thr Asp Asp Lys Met Lys Glu Glu Leu Glu Glu Leu
65                  70                  75                  80

Met Ser Glu Ile Lys Lys Asn Ala Asn Lys Val Arg Ala Lys Leu Lys
                85                  90                  95

Val Ile Glu Gln Asn Ile Glu Gln Glu Glu His Thr Asn Lys Ser Ser
            100                 105                 110

Ala Asp Leu Arg Ile Arg Lys Thr Gln His Ala Thr Leu Ser Arg Lys
        115                 120                 125

Phe Val Glu Val Met Asn Asp Tyr Asn Ala Cys Gln Ile Asp Tyr Arg
    130                 135                 140

Glu Arg Cys Lys Gly Arg Ile Lys Arg Gln Leu Ala Ile Thr Gly Lys
145                 150                 155                 160

Thr Thr Thr Asn Glu Glu Leu Glu Asp Met Ile Glu Ser Gly Asn Pro
                165                 170                 175

Ala Ile Phe Thr Gln Gly Ile Ile Met Glu Thr Gln Gln Ala Lys Gln
            180                 185                 190

Thr Leu Ala Asp Ile Glu Ala Arg His Asn Asp Ile Met Lys Leu Glu
```

```
                195                 200                 205
Thr Ser Ile Arg Asp Leu His Asp Met Phe Met Asp Met Ala Met Leu
        210                 215                 220

Val Glu Ser Gln Gly Glu Met Ile Asp Arg Ile Glu Tyr Asn Val Glu
225                 230                 235                 240

Gln Ala Val Asp Tyr Ile Glu Thr Ala Lys Met Asp Thr Lys Lys Ala
            245                 250                 255

Val Lys Tyr Gln Ser Lys Ala Arg Arg Lys Lys Ile Met Ile Ile Ile
                260                 265                 270

Cys Val Cys Val Leu Ile Ile Ile Leu Val Gly Ile Leu Gly Gly Thr
            275                 280                 285

Phe Gly
    290

<210> SEQ ID NO 103
<211> LENGTH: 290
<212> TYPE: PRT
<213> ORGANISM: Aplysia californica Syntaxin-1A (sea hare)

<400> SEQUENCE: 103

Met Thr Lys Asp Arg Leu Ala Ala Leu Lys Ala Ala Gln Ser Asp Asp
  1               5                  10                  15

Asp Asp Asn Asp Asp Val Ala Val Thr Val Asp Ser Ser Gly Phe Met
                20                  25                  30

Glu Glu Phe Phe Glu Gln Val Asp Glu Ile Arg Glu Met Ile Asp Lys
            35                  40                  45

Ile Ala Ser Asn Val Asp Glu Val Lys Lys Lys His Ser Ala Ile Leu
        50                  55                  60

Ser Ala Pro Gln Thr Asp Asp Lys Met Lys Glu Leu Glu Glu Leu
65                  70                  75                  80

Met Ser Glu Ile Lys Lys Asn Ala Asn Lys Val Arg Ala Lys Leu Lys
                85                  90                  95

Val Ile Glu Gln Asn Ile Glu Gln Glu Glu His Thr Asn Lys Ser Ser
            100                 105                 110

Ala Asp Leu Arg Ile Arg Lys Thr Gln His Ala Thr Leu Ser Arg Lys
        115                 120                 125

Phe Val Glu Val Met Asn Asp Tyr Asn Ala Cys Gln Ile Asp Tyr Arg
    130                 135                 140

Glu Arg Cys Lys Gly Arg Ile Lys Arg Gln Leu Ala Ile Thr Gly Lys
145                 150                 155                 160

Thr Thr Thr Asn Glu Glu Leu Glu Asp Met Ile Glu Ser Gly Asn Pro
                165                 170                 175

Ala Ile Phe Thr Gln Gly Ile Ile Met Glu Thr Gln Gln Ala Asn Glu
            180                 185                 190

Thr Leu Ala Asp Ile Glu Ala Arg His Asn Asp Ile Met Lys Leu Glu
        195                 200                 205

Thr Ser Ile Arg Asp Leu His Asp Met Phe Met Asp Met Ala Met Leu
    210                 215                 220

Val Glu Ser Gln Gly Glu Met Ile Asp Arg Ile Glu Tyr Asn Val Glu
225                 230                 235                 240

Gln Ala Val Asp Tyr Ile Glu Thr Ala Lys Met Asp Thr Lys Lys Ala
                245                 250                 255

Val Lys Tyr Gln Ser Lys Ala Arg Arg Lys Lys Ile Met Ile Leu Val
            260                 265                 270
```

```
Cys Leu Ala Ile Leu Ile Ile Ile Leu Val Gly Val Ile Gly Gly Thr
        275                 280                 285

Leu Gly
    290

<210> SEQ ID NO 104
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/A subtrate cleavage
      site.

<400> SEQUENCE: 104

Glu Ala Asn Gln Arg Ala Thr Lys
 1               5

<210> SEQ ID NO 105
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/A substrate cleavage
      site.

<400> SEQUENCE: 105

Glu Ala Asn Lys His Ala Thr Lys
 1               5

<210> SEQ ID NO 106
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/A substrate cleavage
      site.

<400> SEQUENCE: 106

Glu Ala Asn Lys His Ala Asn Lys
 1               5

<210> SEQ ID NO 107
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/B substrate cleavage
      site and a TeNT substrate cleavage site.

<400> SEQUENCE: 107

Gly Ala Ser Gln Phe Glu Thr Ser
 1               5

<210> SEQ ID NO 108
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/B substrate cleavage
``` site and a TeNT substrate cleavage site.

<400> SEQUENCE: 108

Gly Ala Ser Gln Phe Glu Ser Ser
 1               5

<210> SEQ ID NO 109
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/B substrate cleavage site and a TeNT substrate cleavage site.

<400> SEQUENCE: 109

Gly Ala Ser Gln Phe Glu Thr Asn
 1               5

<210> SEQ ID NO 110
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/B substrate cleavage site and a TeNT substrate cleavage site.

<400> SEQUENCE: 110

Gly Ala Ser Gln Phe Glu Gln Gln
 1               5

<210> SEQ ID NO 111
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/B substrate cleavage site and a TeNT substrate cleavage site.

<400> SEQUENCE: 111

Gly Ala Ser Gln Phe Glu Ala Ser
 1               5

<210> SEQ ID NO 112
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/B substrate cleavage site and a TeNT substrate cleavage site.

<400> SEQUENCE: 112

Gly Ala Ser Gln Phe Gln Gln Ser
 1               5

<210> SEQ ID NO 113
<211> LENGTH: 8
<212> TYPE: PRT
<213> ORGANISM: Artificial Sequence
<220> FEATURE:
<221> NAME/KEY: PEPTIDE
<222> LOCATION: (1)...(8)

```
<223> OTHER INFORMATION: Peptide comprising a BoNT/C1 substrate cleavage
      site.

<400> SEQUENCE: 113

Asp Thr Lys Lys Ala Val Lys Tyr
1               5

<210> SEQ ID NO 114
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/C1 substrate cleavage
      site.

<400> SEQUENCE: 114

Glu Thr Lys Lys Ala Ile Lys Tyr
1               5

<210> SEQ ID NO 115
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/C1 substrate cleavage
      site.

<400> SEQUENCE: 115

Glu Ser Lys Lys Ala Val Lys Tyr
1               5

<210> SEQ ID NO 116
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/C1 substrate cleavage
      site.

<400> SEQUENCE: 116

Glu Thr Lys Arg Ala Met Lys Tyr
1               5

<210> SEQ ID NO 117
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/C1 substrate cleavage
      site.

<400> SEQUENCE: 117

Glu Thr Lys Lys Ala Val Lys Tyr
1               5

<210> SEQ ID NO 118
<211> LENGTH: 8
<212> TYPE: PRT
<213> ORGANISM: Artificial Sequence
<220> FEATURE:
<221> NAME/KEY: PEPTIDE
```

```
<222> LOCATION: (1)...(8)
<223> OTHER INFORMATION: Peptide comprising a BoNT/C1 substrate cleavage
      site.

<400> SEQUENCE: 118

Asp Thr Lys Lys Ala Leu Lys Tyr
1               5

<210> SEQ ID NO 119
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/C1 substrate cleavage
      site.

<400> SEQUENCE: 119

Asp Thr Lys Lys Ala Met Lys Tyr
1               5

<210> SEQ ID NO 120
<211> LENGTH: 8
<212> TYPE: PRT
<213> ORGANISM: Artificial Sequence
<220> FEATURE:
<221> NAME/KEY: PEPTIDE
<222> LOCATION: (0)...(0)
<223> OTHER INFORMATION: Peptide comprising a BoNT/C1 substrate cleavage
      site.

<400> SEQUENCE: 120

Ala Asn Gln Arg Ala Thr Lys Met
1               5

<210> SEQ ID NO 121
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/C1 substrate cleavage
      site.

<400> SEQUENCE: 121

Ala Asn Gln Arg Ala His Gln Leu
1               5

<210> SEQ ID NO 122
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/D substrate cleavage
      site.

<400> SEQUENCE: 122

Arg Asp Gln Lys Leu Ser Glu Leu
1               5

<210> SEQ ID NO 123
<211> LENGTH: 8
<212> TYPE: PRT
<213> ORGANISM: Artificial Sequence
<220> FEATURE:
```

```
<221> NAME/KEY: PEPTIDE
<222> LOCATION: (1)...(8)
<223> OTHER INFORMATION: Peptide comprising a BoNT/D substrate cleavage
      site.

<400> SEQUENCE: 123

Lys Asp Gln Lys Leu Ala Glu Leu
1               5

<210> SEQ ID NO 124
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/E substrate cleavage
      site.

<400> SEQUENCE: 124

Gln Ile Asp Arg Ile Met Glu Lys
1               5

<210> SEQ ID NO 125
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/E substrate cleavage
      site.

<400> SEQUENCE: 125

Gln Ile Gln Lys Ile Thr Glu Lys
1               5

<210> SEQ ID NO 126
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/E substrate cleavage
      site.

<400> SEQUENCE: 126

Gln Ile Asp Arg Ile Met Asp Met
1               5

<210> SEQ ID NO 127
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: Peptide comprising a BoNT/E substrate cleavage
      site.

<400> SEQUENCE: 127

Gln Val Asp Arg Ile Gln Gln Lys
1               5

<210> SEQ ID NO 128
<211> LENGTH: 8
<212> TYPE: PRT
<213> ORGANISM: Artificial Sequence
```

```
<220> FEATURE:
<221> NAME/KEY: PEPTIDE
<222> LOCATION: (1)...(8)
<223> OTHER INFORMATION: Peptide comprising a BoNT/E substrate cleavage
      site.

<400> SEQUENCE: 128

Gln Leu Asp Arg Ile His Asp Lys
 1               5

<210> SEQ ID NO 129
<211> L

```
<213> ORGANISM: Artificial Sequence
<220> FEATURE:
<221> NAME/KEY: PEPTIDE
<222> LOCATION: (1)...(13)
<223> OTHER INFORMATION: Peptide comprising a BoNT/A substrate cleavage
      site.

<400> SEQUENCE: 133

Thr Arg Ile Asp Glu Ala Asn Gln Arg Ala Thr Lys Met
 1               5                  10

<210> SEQ ID NO 134
<211> LENGTH: 15
<212> TYPE: PRT
<213> ORGANISM: Artificial Sequence
<220> FEATURE:
<221> NAME/KEY: PEPTIDE
<222> LOCATION: (1)...(15)
<223> OTHER INFORMATION: Peptide comprising a BoNT/A substrate cleavage
      site.

<400> SEQUENCE: 134

Ser Asn Lys Thr Arg Ile Asp Glu Ala Asn Gln Arg Ala Thr Lys
 1               5                  10                  15

<210> SEQ ID NO 135
<211> LENGTH: 16
<212> TYPE: PRT
<213> ORGANISM: Artificial Sequence
<220> FEATURE:
<221> NAME/KEY: PEPTIDE
<222> LOCATION: (1)...(16)
<223> OTHER INFORMATION: Peptide comprising a BoNT/A substrate cleavage
      site.

<400> SEQUENCE: 135

Ser Asn Lys Thr Arg Ile Asp Glu Ala Asn Gln Arg Ala Thr Lys Met
 1               5                  10                  15

<210> SEQ ID NO 136
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site.

<400> SEQUENCE: 136

Ser Asn Lys Thr Arg Ile Asp Glu Ala Asn Gln Arg Ala Thr Lys Met
 1               5                  10                  15

Leu

<210> SEQ ID NO 137
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, M16A variant.

<400> SEQUENCE: 137

Ser Asn Lys Thr Arg Ile Asp Glu Ala Asn Gln Arg Ala Thr Lys Ala
 1               5                  10                  15

Leu
```

<210> SEQ ID NO 138
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage site, M16X variant.
<221> NAME/KEY: VARIANT
<222> LOCATION: (16)...(16)
<223> OTHER INFORMATION: Xaa=2-aminohexanoic acid (norleucine)

<400> SEQUENCE: 138

Ser Asn Lys Thr Arg Ile Asp Glu Ala Asn Gln Arg Ala Thr Lys Xaa
1               5                   10                  15

Leu

<210> SEQ ID NO 139
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage site, K15A variant.

<400> SEQUENCE: 139

Ser Asn Lys Thr Arg Ile Asp Glu Ala Asn Gln Arg Ala Thr Ala Met
1               5                   10                  15

Leu

<210> SEQ ID NO 140
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage site, T14S variant.

<400> SEQUENCE: 140

Ser Asn Lys Thr Arg Ile Asp Glu Ala Asn Gln Arg Ala Ser Lys Met
1               5                   10                  15

Leu

<210> SEQ ID NO 141
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage site, T14B variant.
<221> NAME/KEY: VARIANT
<222> LOCATION: (14)...(14)
<223> OTHER INFORMATION: Xaa=2-aminobutyric acid

<400> SEQUENCE: 141

Ser Asn Lys Thr Arg Ile Asp Glu Ala Asn Gln Arg Ala Xaa Lys Met
1               5                   10                  15

Leu

-continued

```
<210> SEQ ID NO 142
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, A13B variant.
<221> NAME/KEY: VARIANT
<222> LOCATION: (13)...(13)
<223> OTHER INFORMATION: Xaa=2-aminobutyric acid

<400> SEQUENCE: 142

Ser Asn Lys Thr Arg Ile Asp Glu Ala Asn Gln Arg Xaa Thr Lys Met
 1               5                  10                  15

Leu

<210> SEQ ID NO 143
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, Q11A variant.

<400> SEQUENCE: 143

Ser Asn Lys Thr Arg Ile Asp Glu Ala Asn Ala Arg Ala Thr Lys Met
 1               5                  10                  15

Leu

<210> SEQ ID NO 144
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, Q11B variant.
<221> NAME/KEY: VARIANT
<222> LOCATION: (11)...(11)
<223> OTHER INFORMATION: Xaa=2-aminobutyric acid

<400> SEQUENCE: 144

Ser Asn Lys Thr Arg Ile Asp Glu Ala Asn Xaa Arg Ala Thr Lys Met
 1               5                  10                  15

Leu

<210> SEQ ID NO 145
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, Q11N variant.

<400> SEQUENCE: 145

Ser Asn Lys Thr Arg Ile Asp Glu Ala Asn Asn Arg Ala Thr Lys Met
 1               5                  10                  15

Leu
```

```
<210> SEQ ID NO 146
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, N10A variant.

<400> SEQUENCE: 146

Ser Asn Lys Thr Arg Ile Asp Glu Ala Ala Gln Arg Ala Thr Lys Met
1               5                   10                  15

Leu

<210> SEQ ID NO 147
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, A9B variant.
<221> NAME/KEY: VARIANT
<222> LOCATION: (9)...(9)
<223> OTHER INFORMATION: Xaa=2-aminobutyric acid

<400> SEQUENCE: 147

Ser Asn Lys Thr Arg Ile Asp Glu Xaa Asn Gln Arg Ala Thr Lys Met
1               5                   10                  15

Leu

<210> SEQ ID NO 148
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, E8Q variant.

<400> SEQUENCE: 148

Ser Asn Lys Thr Arg Ile Asp Gln Ala Asn Gln Arg Ala Thr Lys Met
1               5                   10                  15

Leu

<210> SEQ ID NO 149
<211> LENGTH: 17
<212> TYPE: PRT
<213> ORGANISM: Artificial Sequence
<220> FEATURE:
<221> NAME/KEY: PEPTIDE
<222> LOCATION: (1)...(17)
<223> OTHER INFORMATION: Peptide comprising a BoNT/A substrate cleavage
      site, D7N variant.

<400> SEQUENCE: 149

Ser Asn Lys Thr Arg Ile Asn Glu Ala Asn Gln Arg Ala Thr Lys Met
1               5                   10                  15

Leu

<210> SEQ ID NO 150
<211> LENGTH: 17
<212> TYPE: PRT
<213> ORGANISM: Artificial Sequence
```

```
<220> FEATURE:
<221> NAME/KEY: PEPTIDE
<222> LOCATION: (1)...(17)
<223> OTHER INFORMATION: Peptide comprising a BoNT/A substrate cleavage
      site.

<400> SEQUENCE: 150

Asp Ser Asn Lys Thr Arg Ile Asp Glu Ala Asn Gln Arg Ala Thr Lys
1

-continued

```
<213> ORGANISM: Artificial Sequence
<220> FEATURE:
<221> NAME/KEY: PEPTIDE
<222> LOCATION: (1)...(39)
<223> OTHER INFORMATION: Peptide comprising a BoNT/D substrate cleavage
      site and a BoNT/F substrate cleavage site.

<400> SEQUENCE: 154

Ala Gln Val Asp Glu Val Val Asp Ile Met Arg Val Asn Val Asp Lys
 1               5                  10                  15

Val Leu Glu Arg Asp Gln Lys Leu Ser Glu Leu Asp Asp Arg Ala Asp
            20                  25                  30

Ala Leu Gln Ala Gly Ala Ser
        35

<210> SEQ ID NO 155
<211> LENGTH: 39
<212> TYPE: PRT
<213> ORGANISM: Artificial Sequence
<220> FEATURE:
<221> NAME/KEY: PEPTIDE
<222> LOCATION: (1)...(39)
<223> OTHER INFORMATION: Peptide comprising a BoNT/D substrate cleavage
      site and a BoNT/F substrate cleavage site.

<400> SEQUENCE: 155

Ala Gln Val Glu Glu Val Val Asp Ile Ile Arg Val Asn Val Asp Lys
 1               5                  10                  15

Val Leu Glu Arg Asp Gln Lys Leu Ser Glu Leu Asp Asp Arg Ala Asp
            20                  25                  30

Ala Leu Gln Ala Gly Ala Ser
        35

<210> SEQ ID NO 156
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: Flexible G-spacer

<400> SEQUENCE: 156

Gly Gly Gly Gly Ser
 1               5

<210> SEQ ID NO 157
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: Flexible A-spacer

<400> SEQUENCE: 157

Glu Ala Ala Ala Lys
 1               5

<210> SEQ ID NO 158
<211> LENGTH: 8
<212> TYPE: PRT
<213> ORGANISM: Artificial Sequence
<220> FEATURE:
<221> NAME/KEY: PEPTIDE
<222> LOCATION: (1)...(8)
<223> OTHER INFORMATION: FLAG epitope-binding region
```

```
<400> SEQUENCE: 158

Asp Tyr Lys Asp Asp Asp Asp Lys
1               5

<210> SEQ ID NO 159
<211> LENGTH: 9
<212> TYPE: PRT
<213> ORGANISM: Artificial Sequence
<220> FEATURE:
<221> NAME/KEY: PEPTIDE
<222> LOCATION: (1)...(9)
<223> OTHER INFORMATION: human Influenza virus hemagluttinin (HA)
      epitope-binding region

<400> SEQUENCE: 159

Tyr Pro Tyr Asp Val Pro Asp Tyr Ala
1               5

<210> SEQ ID NO 160
<211> LENGTH: 10
<212> TYPE: PRT
<213> ORGANISM: Artificial Sequence
<220> FEATURE:
<221> NAME/KEY: PEPTIDE
<222> LOCATION: (1)...(10)
<223> OTHER INFORMATION: human p62 c-Myc epitope-binding region

<400> SEQUENCE: 160

Glu Gln Lys Leu Ile Ser Glu Glu Asp Leu
1               5                   10

<210> SEQ ID NO 161
<211> LENGTH: 11
<212> TYPE: PRT
<213> ORGANISM: Artificial Sequence
<220> FEATURE:
<221> NAME/KEY: PEPTIDE
<222> LOCATION: (1)...(11)
<223> OTHER INFORMATION: Vesicular Stomatitis Virus Glycoprotein (VSV-G)
      epitope-binding region

<400> SEQUENCE: 161

Tyr Thr Asp Ile Glu Met Asn Arg Leu Gly Lys
1               5                   10

<210> SEQ ID NO 162
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Substance P epitope-binding region

<400> SEQUENCE: 162

Gln Phe Phe Gly Leu Met
1               5

<210> SEQ ID NO 163
<211> LENGTH: 11
<212> TYPE: PRT
<213> ORGANISM: Artificial Sequence
<220> FEATURE:
<221> NAME/KEY: PEPTIDE
<222> LOCATION: (1)...(11)
<223> OTHER INFORMATION: glycoprotein-D precursor of Herpes simplex
      virus epitope-binding region
```

```
<400> SEQUENCE: 163

Gln Pro Glu Leu Ala Pro Glu Asp Pro Glu Asp
 1               5                  10

<210> SEQ ID NO 164
<211> LENGTH: 14
<212> TYPE: PRT
<213> ORGANISM: Artificial Sequence
<220> FEATURE:
<221> NAME/KEY: PEPTIDE
<222> LOCATION: (1)...(14)
<223> OTHER INFORMATION: V5 epitope-binding region

<400> SEQUENCE: 164

Gly Lys Pro Ile Pro Asn Pro Leu Leu Gly Leu Asp Ser Thr
 1               5                  10

<210> SEQ ID NO 165
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: AU1 epitope-binding region

<400> SEQUENCE: 165

Asp Thr Tyr Arg Tyr Ile
 1               5

<210> SEQ ID NO 166
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: AU5 epitope-binding region

<400> SEQUENCE: 166

Thr Asp Phe Tyr Leu Lys
 1               5

<210> SEQ ID NO 167
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: HIS epitope-binding region

<400> SEQUENCE: 167

His His His His His His
 1               5

<210> SEQ ID NO 168
<211> LENGTH: 5
<212> TYPE: PRT
<213> ORGANISM: Artificial Sequence
<220> FEATURE:
<221> NAME/KEY: PEPTIDE
<222> LOCATION: (1)...(5)
<223> OTHER INFORMATION: Bovine enterokinase protease cleavage site.

<400> SEQUENCE: 168

Asp Asp Asp Asp Lys
 1               5
```

```
<210> SEQ ID NO 169
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 169

Glu Asn Leu Tyr Phe Gln Gly
1               5

<210> SEQ ID NO 170
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 170

Glu Asn Leu Tyr Phe Gln Ser
1               5

<210> SEQ ID NO 171
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 171

Glu Asn Ile Tyr Thr Gln Gly
1               5

<210> SEQ ID NO 172
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 172

Glu Asn Ile Tyr Thr Gln Ser
1               5

<210> SEQ ID NO 173
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 173

Glu Asn Ile Tyr Leu Gln Gly
```

-continued

```
<210> SEQ ID NO 174
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 174

Glu Asn Ile Tyr Leu Gln Ser
1               5

<210> SEQ ID NO 175
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 175

Glu Asn Val Tyr Phe Gln Gly
1               5

<210> SEQ ID NO 176
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 176

Glu Asn Val Tyr Ser Gln Ser
1               5

<210> SEQ ID NO 177
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 177

Glu Asn Val Tyr Ser Gln Gly
1               5

<210> SEQ ID NO 178
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Tobacco Etch Virus (TEV) protease cleavage
      site.

<400> SEQUENCE: 178
```

```
Glu Asn Val Tyr Ser Gln Ser
1               5

<210> SEQ ID NO 179
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Human Rhinovirus 3C protease cleavage site.

<400> SEQUENCE: 179

Glu Ala Leu Phe Gln Gly Pro
1               5

<210> SEQ ID NO 180
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Human Rhinovirus 3C protease cleavage site.

<400> SEQUENCE: 180

Glu Val Leu Phe Gln Gly Pro
1               5

<210> SEQ ID NO 181
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Human Rhinovirus 3C protease cleavage site.

<400> SEQUENCE: 181

Glu Leu Leu Phe Gln Gly Pro
1               5

<210> SEQ ID NO 182
<211> LENGTH: 7
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Human Rhinovirus 3C protease cleavage site.

<400> SEQUENCE: 182

Asp Ala Leu Phe Gln Gly Pro
1               5

<210> SEQ ID NO 183
<211> LENGTH: 7
<212> TYPE: PRT
<213> ORGANISM: Artificial Sequence
<220> FEATURE:
<223> OTHER INFORMATION: Human Rhinovirus 3C protease cleavage site.

<400> SEQUENCE: 183

Asp Val Leu Phe Gln Gly Pro
1               5

<210> SEQ ID NO 184
<211> LENGTH: 7
```

```
<212> TYPE: PRT
<213> ORGANISM: Artificial Sequence
<220> FEATURE:
<221> NAME/KEY: PEPTIDE
<222> LOCATION: (1)...(7)
<223> OTHER INFORMATION: Human Rhinovirus 3C protease cleavage site.

<400> SEQUENCE: 184

Asp Leu Leu Phe Gln Gly Pro
 1               5

<210> SEQ ID NO 185
<211> LENGTH: 98
<212> TYPE: PRT
<213> ORGANISM: Artificial Sequence
<220> FEATURE:
<223> OTHER INFORMATION: SUMO/ULP-1 protease cleavage site.

<400> SEQUENCE: 185

Met Ala Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 186
<211> LENGTH: 4
<212> TYPE: PRT
<213> ORGANISM: Artificial Sequence
<220> FEATURE:
<221> NAME/KEY: PEPTIDE
<222> LOCATION: (1)...(4)
<223> OTHER INFORMATION: Thrombin protease cleavage site.

<400> SEQUENCE: 186

Gly Val Arg Gly
 1

<210> SEQ ID NO 187
<211> LENGTH: 4
<212> TYPE: PRT
<213> ORGANISM: Artificial Sequence
<220> FEATURE:
<221> NAME/KEY: PEPTIDE
<222> LOCATION: (1)...(4)
<223> OTHER INFORMATION: Thrombin protease cleavage site.

<400> SEQUENCE: 187

Ser Ala Arg Gly
 1

<210> SEQ ID NO 188
<211> LENGTH: 4
<212> TYPE: PRT
<213> ORGANISM: Artificial Sequence
<220> FEATURE:
<221> NAME/KEY: PEPTIDE
```

```
<222> LOCATION: (1)...(4)
<223> OTHER INFORMATION: Thrombin protease cleavage site.

<400> SEQUENCE: 188

Ser Leu Arg Gly
 1

<210> SEQ ID NO 189
<211> LENGTH: 4
<212> TYPE: PRT
<213> ORGANISM: Artificial Sequence
<220> FEATURE:
<221> NAME/KEY: PEPTIDE
<222> LOCATION: (1)...(4)
<223> OTHER INFORMATION: Thrombin protease cleavage site.

<400> SEQUENCE: 189

Asp Gly Arg Ile
 1

<210> SEQ ID NO 190
<211> LENGTH: 4
<212> TYPE: PRT
<213> ORGANISM: Artificial Sequence
<220> FEATURE:
<221> NAME/KEY: PEPTIDE
<222> LOCATION: (1)...(4)
<223> OTHER INFORMATION: Thrombin protease cleavage site.

<400> SEQUENCE: 190

Gln Gly Lys Ile
 1

<210> SEQ ID NO 191
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 191

Leu Val Pro Arg Gly Ser
 1               5

<210> SEQ ID NO 192
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 192

Leu Val Pro Lys Gly Ser
 1               5

<210> SEQ ID NO 193
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 193
```

```
Phe Ile Pro Arg Thr Phe
1               5

<210> SEQ ID NO 194
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 194

Val Leu Pro Arg Ser Phe
1               5

<210> SEQ ID NO 195
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 195

Ile Val Pro Arg Ser Phe
1               5

<210> SEQ ID NO 196
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 196

Ile Val Pro Arg Gly Tyr
1               5

<210> SEQ ID NO 197
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 197

Val Val Pro Arg Gly Val
1               5

<210> SEQ ID NO 198
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 198

Val Leu Pro Arg Leu Ile
1               5
```

<210> SEQ ID NO 199
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 199

Val Met Pro Arg Ser Leu
1               5

<210> SEQ ID NO 200
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: Thrombin protease cleavage site.

<400> SEQUENCE: 200

Met Phe Pro Arg Ser Leu
1               5

<210> SEQ ID NO 201
<211> LENGTH: 4
<212> TYPE: PRT
<213> ORGANISM: Artificial Sequence
<220> FEATURE:
<221> NAME/KEY: PEPTIDE
<222> LOCATION: (1)...(4)
<223> OTHER INFORMATION: Coagulation Factor Xa protease cleavage site.

<400> SEQUENCE: 201

Ile Asp Gly Arg
1

<210> SEQ ID NO 202
<211> LENGTH: 4
<212> TYPE: PRT
<213> ORGANISM: Artificial Sequence
<220> FEATURE:
<221> NAME/KEY: PEPTIDE
<222> LOCATION: (1)...(4)
<223> OTHER INFORMATION: Coagulation Factor Xa protease cleavage site.

<400> SEQUENCE: 202

Ile Glu Gly Arg
1

<210> SEQ ID NO 203
<211> LENGTH: 1303
<212> TYPE: PRT
<213> ORGANISM: Artificial Sequence
<220> FEATURE:
<221> NAME/KEY: PEPTIDE
<222> LOCATION: (1)...(1303)
<223> OTHER INFORMATION: BoNT/A_A17

<400> SEQUENCE: 203

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg

-continued

```
            35                  40                  45
Asp Thr Phe Thr Asn Pro Glu Glu Gly Asp Leu Asn Pro Pro Glu
50                  55                  60
Ala Lys Gln Val Pro Val Ser Tyr Tyr Asp Ser Thr Tyr Leu Ser Thr
65                  70                  75                  80
Asp Asn Glu Lys Asp Asn Tyr Leu Lys Gly Val Thr Lys Leu Phe Glu
                85                  90                  95
Arg Ile Tyr Ser Thr Asp Leu Gly Arg Met Leu Leu Thr Ser Ile Val
                100                 105                 110
Arg Gly Ile Pro Phe Trp Gly Ser Thr Ile Asp Thr Glu Leu Lys
                115                 120                 125
Val Ile Asp Thr Asn Cys Ile Asn Val Ile Gln Pro Asp Gly Ser Tyr
130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
                180                 185                 190
Thr Phe Gly Phe Glu Glu Ser Leu Glu Val Asp Thr Asn Pro Leu Leu
                195                 200                 205
Gly Ala Gly Lys Phe Ala Thr Asp Pro Ala Val Thr Leu Ala His Glu
                210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Ser Asn Lys Thr Arg Ile Asp Glu Ala Asn
                435                 440                 445
Gln Arg Ala Thr Lys Met Leu Ala Leu Asn Asp Leu Cys Ile Lys Val
450                 455                 460
```

-continued

```
Asn Asn Trp Asp Leu Phe Phe Ser Pro Ser Glu Asp Asn Phe Thr Asn
465                 470                 475                 480

Asp Leu Asn Lys Gly Glu Ile Thr Ser Asp Thr Asn Ile Glu Ala
            485                 490                 495

Ala Glu Glu Asn Ile Ser Leu Asp Leu Ile Gln Gln Tyr Tyr Leu Thr
                500                 505                 510

Phe Asn Phe Asp Asn Glu Pro Glu Asn Ile Ser Ile Glu Asn Leu Ser
            515                 520                 525

Ser Asp Ile Ile Gly Gln Leu Glu Leu Met Pro Asn Ile Glu Arg Phe
530                 535                 540

Pro Asn Gly Lys Lys Tyr Glu Leu Asp Lys Tyr Thr Met Phe His Tyr
545                 550                 555                 560

Leu Arg Ala Gln Glu Phe Glu His Gly Lys Ser Arg Ile Ala Leu Thr
                565                 570                 575

Asn Ser Val Asn Glu Ala Leu Leu Asn Pro Ser Arg Val Tyr Thr Phe
            580                 585                 590

Phe Ser Ser Asp Tyr Val Lys Lys Val Asn Lys Ala Thr Glu Ala Ala
            595                 600                 605

Met Phe Leu Gly Trp Val Glu Gln Leu Val Tyr Asp Phe Thr Asp Glu
610                 615                 620

Thr Ser Glu Val Ser Thr Thr Asp Lys Ile Ala Asp Ile Thr Ile Ile
625                 630                 635                 640

Ile Pro Tyr Ile Gly Pro Ala Leu Asn Ile Gly Asn Met Leu Tyr Lys
                645                 650                 655

Asp Asp Phe Val Gly Ala Leu Ile Phe Ser Gly Ala Val Ile Leu Leu
            660                 665                 670

Glu Phe Ile Pro Glu Ile Ala Ile Pro Val Leu Gly Thr Phe Ala Leu
            675                 680                 685

Val Ser Tyr Ile Ala Asn Lys Val Leu Thr Val Gln Thr Ile Asp Asn
690                 695                 700

Ala Leu Ser Lys Arg Asn Glu Lys Trp Asp Glu Val Tyr Lys Tyr Ile
705                 710                 715                 720

Val Thr Asn Trp Leu Ala Lys Val Asn Thr Gln Ile Asp Leu Ile Arg
                725                 730                 735

Lys Lys Met Lys Glu Ala Leu Glu Asn Gln Ala Glu Ala Thr Lys Ala
            740                 745                 750

Ile Ile Asn Tyr Gln Tyr Asn Gln Tyr Thr Glu Glu Lys Asn Asn
            755                 760                 765

Ile Asn Phe Asn Ile Asp Asp Leu Ser Ser Lys Leu Asn Glu Ser Ile
            770                 775                 780

Asn Lys Ala Met Ile Asn Ile Asn Lys Phe Leu Asn Gln Cys Ser Val
785                 790                 795                 800

Ser Tyr Leu Met Asn Ser Met Ile Pro Tyr Gly Val Lys Arg Leu Glu
                805                 810                 815

Asp Phe Asp Ala Ser Leu Lys Asp Ala Leu Leu Lys Tyr Ile Tyr Asp
            820                 825                 830

Asn Arg Gly Thr Leu Ile Gly Gln Val Asp Arg Leu Lys Asp Lys Val
            835                 840                 845

Asn Asn Thr Leu Ser Thr Asp Ile Pro Phe Gln Leu Ser Lys Tyr Val
850                 855                 860

Asp Asn Gln Arg Leu Leu Ser Thr Phe Thr Glu Tyr Ile Lys Asn Ile
865                 870                 875                 880
```

-continued

```
Ile Asn Thr Ser Ile Leu Asn Leu Arg Tyr Glu Ser Asn His Leu Ile
                885                 890                 895

Asp Leu Ser Arg Tyr Ala Ser Lys Ile Asn Ile Gly Ser Lys Val Asn
            900                 905                 910

Phe Asp Pro Ile Asp Lys Asn Gln Ile Gln Leu Phe Asn Leu Glu Ser
        915                 920                 925

Ser Lys Ile Glu Val Ile Leu Lys Asn Ala Ile Val Tyr Asn Ser Met
    930                 935                 940

Tyr Glu Asn Phe Ser Thr Ser Phe Trp Ile Arg Ile Pro Lys Tyr Phe
945                 950                 955                 960

Asn Ser Ile Ser Leu Asn Asn Glu Tyr Thr Ile Ile Asn Cys Met Glu
                965                 970                 975

Asn Asn Ser Gly Trp Lys Val Ser Leu Asn Tyr Gly Glu Ile Ile Trp
            980                 985                 990

Thr Leu Gln Asp Thr Gln Glu Ile Lys Gln Arg Val Val Phe Lys Tyr
        995                 1000                1005

Ser Gln Met Ile Asn Ile Ser Asp Tyr Ile Asn Arg Trp Ile Phe Val
    1010                1015                1020

Thr Ile Thr Asn Asn Arg Leu Asn Asn Ser Lys Ile Tyr Ile Asn Gly
1025                1030                1035                1040

Arg Leu Ile Asp Gln Lys Pro Ile Ser Asn Leu Gly Asn Ile His Ala
                1045                1050                1055

Ser Asn Asn Ile Met Phe Lys Leu Asp Gly Cys Arg Asp Thr His Arg
            1060                1065                1070

Tyr Ile Trp Ile Lys Tyr Phe Asn Leu Phe Asp Lys Glu Leu Asn Glu
        1075                1080                1085

Lys Glu Ile Lys Asp Leu Tyr Asp Asn Gln Ser Asn Ser Gly Ile Leu
    1090                1095                1100

Lys Asp Phe Trp Gly Asp Tyr Leu Gln Tyr Asp Lys Pro Tyr Tyr Met
1105                1110                1115                1120

Leu Asn Leu Tyr Asp Pro Asn Lys Tyr Val Asp Val Asn Asn Val Gly
                1125                1130                1135

Ile Arg Gly Tyr Met Tyr Leu Lys Gly Pro Arg Gly Ser Val Met Thr
            1140                1145                1150

Thr Asn Ile Tyr Leu Asn Ser Ser Leu Tyr Arg Gly Thr Lys Phe Ile
        1155                1160                1165

Ile Lys Lys Tyr Ala Ser Gly Asn Lys Asp Asn Ile Val Arg Asn Asn
    1170                1175                1180

Asp Arg Val Tyr Ile Asn Val Val Val Lys Asn Lys Glu Tyr Arg Leu
1185                1190                1195                1200

Ala Thr Asn Ala Ser Gln Ala Gly Val Glu Lys Ile Leu Ser Ala Leu
                1205                1210                1215

Glu Ile Pro Asp Val Gly Asn Leu Ser Gln Val Val Val Met Lys Ser
            1220                1225                1230

Lys Asn Asp Gln Gly Ile Thr Asn Lys Cys Lys Met Asn Leu Gln Asp
        1235                1240                1245

Asn Asn Gly Asn Asp Ile Gly Phe Ile Gly Phe His Gln Phe Asn Asn
    1250                1255                1260

Ile Ala Lys Leu Val Ala Ser Asn Trp Tyr Asn Arg Gln Ile Glu Arg
1265                1270                1275                1280

Ser Ser Arg Thr Leu Gly Cys Ser Trp Glu Phe Ile Pro Val Asp Asp
                1285                1290                1295

Gly Trp Gly Glu Arg Pro Leu
```

```
                                  1300

<210> SEQ ID NO 204
<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_A8

<400> SEQUENCE: 204

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350
```

-continued

```
Asn Phe Val Lys Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Glu Ala Asn Gln Arg Ala Thr Lys Ala Leu
            435                 440                 445
Asn Asp Leu Cys Ile Lys Val Asn Asn Trp Asp Leu Phe Phe Ser Pro
450                 455                 460
Ser Glu Asp Asn Phe Thr Asn Asp Leu Asn Lys Gly Glu Glu Ile Thr
465                 470                 475                 480
Ser Asp Thr Asn Ile Glu Ala Ala Glu Glu Asn Ile Ser Leu Asp Leu
                485                 490                 495
Ile Gln Gln Tyr Tyr Leu Thr Phe Asn Phe Asp Asn Glu Pro Glu Asn
            500                 505                 510
Ile Ser Ile Glu Asn Leu Ser Ser Asp Ile Ile Gly Gln Leu Glu Leu
            515                 520                 525
Met Pro Asn Ile Glu Arg Phe Pro Asn Gly Lys Lys Tyr Glu Leu Asp
            530                 535                 540
Lys Tyr Thr Met Phe His Tyr Leu Arg Ala Gln Glu Phe Glu His Gly
545                 550                 555                 560
Lys Ser Arg Ile Ala Leu Thr Asn Ser Val Asn Glu Ala Leu Leu Asn
                565                 570                 575
Pro Ser Arg Val Tyr Thr Phe Phe Ser Ser Asp Tyr Val Lys Lys Val
            580                 585                 590
Asn Lys Ala Thr Glu Ala Ala Met Phe Leu Gly Trp Val Glu Gln Leu
            595                 600                 605
Val Tyr Asp Phe Thr Asp Glu Thr Ser Glu Val Ser Thr Thr Asp Lys
610                 615                 620
Ile Ala Asp Ile Thr Ile Ile Pro Tyr Ile Gly Pro Ala Leu Asn
625                 630                 635                 640
Ile Gly Asn Met Leu Tyr Lys Asp Asp Phe Val Gly Ala Leu Ile Phe
                645                 650                 655
Ser Gly Ala Val Ile Leu Leu Glu Phe Ile Pro Glu Ile Ala Ile Pro
            660                 665                 670
Val Leu Gly Thr Phe Ala Leu Val Ser Tyr Ile Ala Asn Lys Val Leu
            675                 680                 685
Thr Val Gln Thr Ile Asp Asn Ala Leu Ser Lys Arg Asn Glu Lys Trp
            690                 695                 700
Asp Glu Val Tyr Lys Tyr Ile Val Thr Asn Trp Leu Ala Lys Val Asn
705                 710                 715                 720
Thr Gln Ile Asp Leu Ile Arg Lys Lys Met Lys Glu Ala Leu Glu Asn
                725                 730                 735
Gln Ala Glu Ala Thr Lys Ala Ile Ile Asn Tyr Gln Tyr Asn Gln Tyr
            740                 745                 750
Thr Glu Glu Glu Lys Asn Asn Ile Asn Phe Asn Ile Asp Asp Leu Ser
            755                 760                 765
```

-continued

```
Ser Lys Leu Asn Glu Ser Ile Asn Lys Ala Met Ile Asn Ile Asn Lys
    770                 775                 780
Phe Leu Asn Gln Cys Ser Val Ser Tyr Leu Met Asn Ser Met Ile Pro
785                 790                 795                 800
Tyr Gly Val Lys Arg Leu Glu Asp Phe Asp Ala Ser Leu Lys Asp Ala
                805                 810                 815
Leu Leu Lys Tyr Ile Tyr Asp Asn Arg Gly Thr Leu Ile Gly Gln Val
                820                 825                 830
Asp Arg Leu Lys Asp Lys Val Asn Asn Thr Leu Ser Thr Asp Ile Pro
                835                 840                 845
Phe Gln Leu Ser Lys Tyr Val Asp Asn Gln Arg Leu Leu Ser Thr Phe
    850                 855                 860
Thr Glu Tyr Ile Lys Asn Ile Ile Asn Thr Ser Ile Leu Asn Leu Arg
865                 870                 875                 880
Tyr Glu Ser Asn His Leu Ile Asp Leu Ser Arg Tyr Ala Ser Lys Ile
                885                 890                 895
Asn Ile Gly Ser Lys Val Asn Phe Asp Pro Ile Asp Lys Asn Gln Ile
                900                 905                 910
Gln Leu Phe Asn Leu Glu Ser Ser Lys Ile Glu Val Ile Leu Lys Asn
    915                 920                 925
Ala Ile Val Tyr Asn Ser Met Tyr Glu Asn Phe Ser Thr Ser Phe Trp
    930                 935                 940
Ile Arg Ile Pro Lys Tyr Phe Asn Ser Ile Ser Leu Asn Asn Glu Tyr
945                 950                 955                 960
Thr Ile Ile Asn Cys Met Glu Asn Asn Ser Gly Trp Lys Val Ser Leu
                965                 970                 975
Asn Tyr Gly Glu Ile Ile Trp Thr Leu Gln Asp Thr Gln Glu Ile Lys
                980                 985                 990
Gln Arg Val Val Phe Lys Tyr Ser Gln Met Ile Asn Ile Ser Asp Tyr
                995                 1000                1005
Ile Asn Arg Trp Ile Phe Val Thr Ile Thr Asn Asn Arg Leu Asn Asn
    1010                1015                1020
Ser Lys Ile Tyr Ile Asn Gly Arg Leu Ile Asp Gln Lys Pro Ile Ser
1025                1030                1035                1040
Asn Leu Gly Asn Ile His Ala Ser Asn Asn Ile Met Phe Lys Leu Asp
                1045                1050                1055
Gly Cys Arg Asp Thr His Arg Tyr Ile Trp Ile Lys Tyr Phe Asn Leu
                1060                1065                1070
Phe Asp Lys Glu Leu Asn Glu Lys Glu Ile Lys Asp Leu Tyr Asp Asn
                1075                1080                1085
Gln Ser Asn Ser Gly Ile Leu Lys Asp Phe Trp Gly Asp Tyr Leu Gln
    1090                1095                1100
Tyr Asp Lys Pro Tyr Tyr Met Leu Asn Leu Tyr Asp Pro Asn Lys Tyr
1105                1110                1115                1120
Val Asp Val Asn Asn Val Gly Ile Arg Gly Tyr Met Tyr Leu Lys Gly
                1125                1130                1135
Pro Arg Gly Ser Val Met Thr Thr Asn Ile Tyr Leu Asn Ser Ser Leu
                1140                1145                1150
Tyr Arg Gly Thr Lys Phe Ile Ile Lys Lys Tyr Ala Ser Gly Asn Lys
                1155                1160                1165
Asp Asn Ile Val Arg Asn Asn Asp Arg Val Tyr Ile Asn Val Val Val
                1170                1175                1180
Lys Asn Lys Glu Tyr Arg Leu Ala Thr Asn Ala Ser Gln Ala Gly Val
```

-continued 1185 1190 1195 1200

Glu Lys Ile Leu Ser Ala Leu Glu Ile Pro Asp Val Gly Asn Leu Ser
1205 1210 1215

Gln Val Val Val Met Lys Ser Lys Asn Asp Gln Gly Ile Thr Asn Lys
1220 1225 1230

Cys Lys Met Asn Leu Gln Asp Asn Asn Gly Asn Asp Ile Gly Phe Ile
1235 1240 1245

Gly Phe His Gln Phe Asn Asn Ile Ala Lys Leu Val Ala Ser Asn Trp
1250 1255 1260

Tyr Asn Arg Gln Ile Glu Arg Ser Ser Arg Thr Leu Gly Cys Ser Trp
1265 1270 1275 1280

Glu Phe Ile Pro Val Asp Asp Gly Trp Gly Glu Arg Pro Leu
1285 1290

<210> SEQ ID NO 205
<211> LENGTH: 1321
<212> TYPE: PRT
<213> ORGANISM: Artificial Sequence
<220> FEATURE:
<221> NAME/KEY: PEPTIDE
<222> LOCATION: (1)...(1321)
<223> OTHER INFORMATION: BoNT/A_BT35

<400> SEQUENCE: 205

Met Pro Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

Leu Ile His Ala Gly His Arg Leu Tyr Gly Ile Ala Ile Asn Pro Asn
225 230 235 240

Arg Val Phe Lys Val Asn Thr Asn Ala Tyr Tyr Glu Met Ser Gly Leu
245 250 255

```
Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Leu Ser Glu Leu Asp Asp Arg Ala Asp Ala
            435                 440                 445

Leu Gln Ala Gly Ala Ser Gln Phe Glu Ser Ser Ala Ala Lys Leu Lys
            450                 455                 460

Arg Lys Tyr Trp Trp Lys Asn Cys Lys Ala Leu Asn Asp Leu Cys Ile
465                 470                 475                 480

Lys Val Asn Asn Trp Asp Leu Phe Phe Ser Pro Ser Glu Asp Asn Phe
                485                 490                 495

Thr Asn Asp Leu Asn Lys Gly Glu Glu Ile Thr Ser Asp Thr Asn Ile
            500                 505                 510

Glu Ala Ala Glu Glu Asn Ile Ser Leu Asp Leu Ile Gln Gln Tyr Tyr
            515                 520                 525

Leu Thr Phe Asn Phe Asp Asn Glu Pro Glu Asn Ile Ser Ile Glu Asn
            530                 535                 540

Leu Ser Ser Asp Ile Ile Gly Gln Leu Glu Leu Met Pro Asn Ile Glu
545                 550                 555                 560

Arg Phe Pro Asn Gly Lys Lys Tyr Glu Leu Asp Lys Tyr Thr Met Phe
                565                 570                 575

His Tyr Leu Arg Ala Gln Glu Phe Glu His Gly Lys Ser Arg Ile Ala
            580                 585                 590

Leu Thr Asn Ser Val Asn Glu Ala Leu Leu Asn Pro Ser Arg Val Tyr
            595                 600                 605

Thr Phe Phe Ser Ser Asp Tyr Val Lys Lys Val Asn Lys Ala Thr Glu
            610                 615                 620

Ala Ala Met Phe Leu Gly Trp Val Glu Gln Leu Val Tyr Asp Phe Thr
625                 630                 635                 640

Asp Glu Thr Ser Glu Val Ser Thr Thr Asp Lys Ile Ala Asp Ile Thr
                645                 650                 655

Ile Ile Ile Pro Tyr Ile Gly Pro Ala Leu Asn Ile Gly Asn Met Leu
            660                 665                 670
```

```
Tyr Lys Asp Asp Phe Val Gly Ala Leu Ile Phe Ser Gly Ala Val Ile
        675                 680                 685

Leu Leu Glu Phe Ile Pro Glu Ile Ala Ile Pro Val Leu Gly Thr Phe
        690                 695                 700

Ala Leu Val Ser Tyr Ile Ala Asn Lys Val Leu Thr Val Gln Thr Ile
705                 710                 715                 720

Asp Asn Ala Leu Ser Lys Arg Asn Glu Lys Trp Asp Glu Val Tyr Lys
                725                 730                 735

Tyr Ile Val Thr Asn Trp Leu Ala Lys Val Asn Thr Gln Ile Asp Leu
            740                 745                 750

Ile Arg Lys Lys Met Lys Glu Ala Leu Glu Asn Gln Ala Glu Ala Thr
        755                 760                 765

Lys Ala Ile Ile Asn Tyr Gln Tyr Asn Gln Tyr Thr Glu Glu Glu Lys
        770                 775                 780

Asn Asn Ile Asn Phe Asn Ile Asp Asp Leu Ser Ser Lys Leu Asn Glu
785                 790                 795                 800

Ser Ile Asn Lys Ala Met Ile Asn Ile Asn Lys Phe Leu Asn Gln Cys
                805                 810                 815

Ser Val Ser Tyr Leu Met Asn Ser Met Ile Pro Tyr Gly Val Lys Arg
            820                 825                 830

Leu Glu Asp Phe Asp Ala Ser Leu Lys Asp Ala Leu Leu Lys Tyr Ile
        835                 840                 845

Tyr Asp Asn Arg Gly Thr Leu Ile Gly Gln Val Asp Arg Leu Lys Asp
        850                 855                 860

Lys Val Asn Asn Thr Leu Ser Thr Asp Ile Pro Phe Gln Leu Ser Lys
865                 870                 875                 880

Tyr Val Asp Asn Gln Arg Leu Leu Ser Thr Phe Thr Glu Tyr Ile Lys
                885                 890                 895

Asn Ile Ile Asn Thr Ser Ile Leu Asn Leu Arg Tyr Glu Ser Asn His
            900                 905                 910

Leu Ile Asp Leu Ser Arg Tyr Ala Ser Lys Ile Asn Ile Gly Ser Lys
        915                 920                 925

Val Asn Phe Asp Pro Ile Asp Lys Asn Gln Ile Gln Leu Phe Asn Leu
        930                 935                 940

Glu Ser Ser Lys Ile Glu Val Ile Leu Lys Asn Ala Ile Val Tyr Asn
945                 950                 955                 960

Ser Met Tyr Glu Asn Phe Ser Thr Ser Phe Trp Ile Arg Ile Pro Lys
                965                 970                 975

Tyr Phe Asn Ser Ile Ser Leu Asn Asn Glu Tyr Thr Ile Ile Asn Cys
            980                 985                 990

Met Glu Asn Asn Ser Gly Trp Lys Val Ser Leu Asn Tyr Gly Glu Ile
        995                 1000                1005

Ile Trp Thr Leu Gln Asp Thr Gln Glu Ile Lys Gln Arg Val Val Phe
    1010                1015                1020

Lys Tyr Ser Gln Met Ile Asn Ile Ser Asp Tyr Ile Asn Arg Trp Ile
1025                1030                1035                1040

Phe Val Thr Ile Thr Asn Asn Arg Leu Asn Asn Ser Lys Ile Tyr Ile
                1045                1050                1055

Asn Gly Arg Leu Ile Asp Gln Lys Pro Ile Ser Asn Leu Gly Asn Ile
            1060                1065                1070

His Ala Ser Asn Asn Ile Met Phe Lys Leu Asp Gly Cys Arg Asp Thr
        1075                1080                1085

His Arg Tyr Ile Trp Ile Lys Tyr Phe Asn Leu Phe Asp Lys Glu Leu
```

-continued

```
           1090                1095                1100
Asn Glu Lys Glu Ile Lys Asp Leu Tyr Asp Asn Gln Ser Asn Ser Gly
1105                1110                1115                1120

Ile Leu Lys Asp Phe Trp Gly Asp Tyr Leu Gln Tyr Asp Lys Pro Tyr
                1125                1130                1135

Tyr Met Leu Asn Leu Tyr Asp Pro Asn Lys Tyr Val Asp Val Asn Asn
            1140                1145                1150

Val Gly Ile Arg Gly Tyr Met Tyr Leu Lys Gly Pro Arg Gly Ser Val
                1155                1160                1165

Met Thr Thr Asn Ile Tyr Leu Asn Ser Ser Leu Tyr Arg Gly Thr Lys
            1170                1175                1180

Phe Ile Ile Lys Lys Tyr Ala Ser Gly Asn Lys Asp Asn Ile Val Arg
1185                1190                1195                1200

Asn Asn Asp Arg Val Tyr Ile Asn Val Val Val Lys Asn Lys Glu Tyr
                1205                1210                1215

Arg Leu Ala Thr Asn Ala Ser Gln Ala Gly Val Glu Lys Ile Leu Ser
            1220                1225                1230

Ala Leu Glu Ile Pro Asp Val Gly Asn Leu Ser Gln Val Val Val Met
            1235                1240                1245

Lys Ser Lys Asn Asp Gln Gly Ile Thr Asn Lys Cys Lys Met Asn Leu
            1250                1255                1260

Gln Asp Asn Asn Gly Asn Asp Ile Gly Phe Ile Gly Phe His Gln Phe
1265                1270                1275                1280

Asn Asn Ile Ala Lys Leu Val Ala Ser Asn Trp Tyr Asn Arg Gln Ile
                1285                1290                1295

Glu Arg Ser Ser Arg Thr Leu Gly Cys Ser Trp Glu Phe Ile Pro Val
                1300                1305                1310

Asp Asp Gly Trp Gly Glu Arg Pro Leu
            1315                1320

<210> SEQ ID NO 206
<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_BT8

<400> SEQUENCE: 206

Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
 50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125
```

-continued

```
Val Ile Asp Thr Asn Cys Ile Asn Val Ile Gln Pro Asp Gly Ser Tyr
            130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Gly Ala Ser Gln Phe Glu Thr Ser Ala Leu
        435                 440                 445

Asn Asp Leu Cys Ile Lys Val Asn Asn Trp Asp Leu Phe Phe Ser Pro
    450                 455                 460

Ser Glu Asp Asn Phe Thr Asn Asp Leu Asn Lys Gly Glu Glu Ile Thr
465                 470                 475                 480

Ser Asp Thr Asn Ile Glu Ala Ala Glu Glu Asn Ile Ser Leu Asp Leu
                485                 490                 495

Ile Gln Gln Tyr Tyr Leu Thr Phe Asn Phe Asp Asn Glu Pro Glu Asn
            500                 505                 510

Ile Ser Ile Glu Asn Leu Ser Ser Asp Ile Ile Gly Gln Leu Glu Leu
        515                 520                 525

Met Pro Asn Ile Glu Arg Phe Pro Asn Gly Lys Lys Tyr Glu Leu Asp
    530                 535                 540
```

-continued

```
Lys Tyr Thr Met Phe His Tyr Leu Arg Ala Gln Glu Phe Glu His Gly
545                 550                 555                 560

Lys Ser Arg Ile Ala Leu Thr Asn Ser Val Asn Glu Ala Leu Leu Asn
            565                 570                 575

Pro Ser Arg Val Tyr Thr Phe Phe Ser Ser Asp Tyr Val Lys Lys Val
        580                 585                 590

Asn Lys Ala Thr Glu Ala Ala Met Phe Leu Gly Trp Val Glu Gln Leu
    595                 600                 605

Val Tyr Asp Phe Thr Asp Glu Thr Ser Glu Val Ser Thr Thr Asp Lys
610                 615                 620

Ile Ala Asp Ile Thr Ile Ile Pro Tyr Ile Gly Pro Ala Leu Asn
625                 630                 635                 640

Ile Gly Asn Met Leu Tyr Lys Asp Asp Phe Val Gly Ala Leu Ile Phe
                645                 650                 655

Ser Gly Ala Val Ile Leu Leu Glu Phe Ile Pro Glu Ile Ala Ile Pro
            660                 665                 670

Val Leu Gly Thr Phe Ala Leu Val Ser Tyr Ile Ala Asn Lys Val Leu
        675                 680                 685

Thr Val Gln Thr Ile Asp Asn Ala Leu Ser Lys Arg Asn Glu Lys Trp
    690                 695                 700

Asp Glu Val Tyr Lys Tyr Ile Val Thr Asn Trp Leu Ala Lys Val Asn
705                 710                 715                 720

Thr Gln Ile Asp Leu Ile Arg Lys Lys Met Lys Glu Ala Leu Glu Asn
                725                 730                 735

Gln Ala Glu Ala Thr Lys Ala Ile Ile Asn Tyr Gln Tyr Asn Gln Tyr
            740                 745                 750

Thr Glu Glu Glu Lys Asn Asn Ile Asn Phe Asn Ile Asp Asp Leu Ser
        755                 760                 765

Ser Lys Leu Asn Glu Ser Ile Asn Lys Ala Met Ile Asn Ile Asn Lys
    770                 775                 780

Phe Leu Asn Gln Cys Ser Val Ser Tyr Leu Met Asn Ser Met Ile Pro
785                 790                 795                 800

Tyr Gly Val Lys Arg Leu Glu Asp Phe Asp Ala Ser Leu Lys Asp Ala
                805                 810                 815

Leu Leu Lys Tyr Ile Tyr Asp Asn Arg Gly Thr Leu Ile Gly Gln Val
            820                 825                 830

Asp Arg Leu Lys Asp Lys Val Asn Asn Thr Leu Ser Thr Asp Ile Pro
        835                 840                 845

Phe Gln Leu Ser Lys Tyr Val Asp Asn Gln Arg Leu Leu Ser Thr Phe
    850                 855                 860

Thr Glu Tyr Ile Lys Asn Ile Ile Asn Thr Ser Ile Leu Asn Leu Arg
865                 870                 875                 880

Tyr Glu Ser Asn His Leu Ile Asp Leu Ser Arg Tyr Ala Ser Lys Ile
                885                 890                 895

Asn Ile Gly Ser Lys Val Asn Phe Asp Pro Ile Asp Lys Asn Gln Ile
            900                 905                 910

Gln Leu Phe Asn Leu Glu Ser Ser Lys Ile Glu Val Ile Leu Lys Asn
        915                 920                 925

Ala Ile Val Tyr Asn Ser Met Tyr Glu Asn Phe Ser Thr Ser Phe Trp
    930                 935                 940

Ile Arg Ile Pro Lys Tyr Phe Asn Ser Ile Ser Leu Asn Asn Glu Tyr
945                 950                 955                 960

Thr Ile Ile Asn Cys Met Glu Asn Asn Ser Gly Trp Lys Val Ser Leu
```

-continued

```
                965                 970                 975
Asn Tyr Gly Glu Ile Ile Trp Thr Leu Gln Asp Thr Gln Glu Ile Lys
            980                 985                 990
Gln Arg Val Val Phe Lys Tyr Ser Gln Met Ile Asn Ile Ser Asp Tyr
            995                1000                1005
Ile Asn Arg Trp Ile Phe Val Thr Ile Thr Asn Asn Arg Leu Asn Asn
           1010                1015                1020
Ser Lys Ile Tyr Ile Asn Gly Arg Leu Ile Asp Gln Lys Pro Ile Ser
1025               1030                1035                1040
Asn Leu Gly Asn Ile His Ala Ser Asn Asn Ile Met Phe Lys Leu Asp
           1045                1050                1055
Gly Cys Arg Asp Thr His Arg Tyr Ile Trp Ile Lys Tyr Phe Asn Leu
           1060                1065                1070
Phe Asp Lys Glu Leu Asn Glu Lys Glu Ile Lys Asp Leu Tyr Asp Asn
           1075                1080                1085
Gln Ser Asn Ser Gly Ile Leu Lys Asp Phe Trp Gly Asp Tyr Leu Gln
           1090                1095                1100
Tyr Asp Lys Pro Tyr Tyr Met Leu Asn Leu Tyr Asp Pro Asn Lys Tyr
1105               1110                1115                1120
Val Asp Val Asn Asn Val Gly Ile Arg Gly Tyr Met Tyr Leu Lys Gly
           1125                1130                1135
Pro Arg Gly Ser Val Met Thr Thr Asn Ile Tyr Leu Asn Ser Ser Leu
           1140                1145                1150
Tyr Arg Gly Thr Lys Phe Ile Ile Lys Lys Tyr Ala Ser Gly Asn Lys
           1155                1160                1165
Asp Asn Ile Val Arg Asn Asn Asp Arg Val Tyr Ile Asn Val Val Val
           1170                1175                1180
Lys Asn Lys Glu Tyr Arg Leu Ala Thr Asn Ala Ser Gln Ala Gly Val
1185               1190                1195                1200
Glu Lys Ile Leu Ser Ala Leu Glu Ile Pro Asp Val Gly Asn Leu Ser
           1205                1210                1215
Gln Val Val Val Met Lys Ser Lys Asn Asp Gln Gly Ile Thr Asn Lys
           1220                1225                1230
Cys Lys Met Asn Leu Gln Asp Asn Asn Gly Asn Asp Ile Gly Phe Ile
           1235                1240                1245
Gly Phe His Gln Phe Asn Asn Ile Ala Lys Leu Val Ala Ser Asn Trp
           1250                1255                1260
Tyr Asn Arg Gln Ile Glu Arg Ser Ser Arg Thr Leu Gly Cys Ser Trp
1265               1270                1275                1280
Glu Phe Ile Pro Val Asp Asp Gly Trp Gly Glu Arg Pro Leu
           1285                1290
```

<210> SEQ ID NO 207
<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_Csyn8

<400> SEQUENCE: 207

```
Met Pro Phe Val Asn Lys Gln Phe Asn Tyr Lys Asp Pro Val Asn Gly
1               5                  10                  15
Val Asp Ile Ala Tyr Ile Lys Ile Pro Asn Ala Gly Gln Met Gln Pro
            20                  25                  30
```

```
Val Lys Ala Phe Lys Ile His Asn Lys Ile Trp Val Ile Pro Glu Arg
        35                  40                  45
Asp Thr Phe Thr Asn Pro Glu Glu Gly Asp Leu Asn Pro Pro Pro Glu
     50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
             85                  90                  95
Arg Ile Tyr Ser Thr Asp Leu Gly Arg Met Leu Leu Thr Ser Ile Val
            100                 105                 110
Arg Gly Ile Pro Phe Trp Gly Ser Thr Ile Asp Thr Glu Leu Lys
            115                 120                 125
Val Ile Asp Thr Asn Cys Ile Asn Val Ile Gln Pro Asp Gly Ser Tyr
            130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Glu
            210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Asp Thr Lys Lys Ala Val Lys Tyr Ala Leu
            435                 440                 445
```

```
Asn Asp Leu Cys Ile Lys Val Asn Asn Trp Asp Leu Phe Ser Pro
    450                 455                 460
Ser Glu Asp Asn Phe Thr Asn Asp Leu Asn Lys Gly Glu Glu Ile Thr
465                 470                 475                 480
Ser Asp Thr Asn Ile Glu Ala Ala Glu Glu Asn Ile Ser Leu Asp Leu
                485                 490                 495
Ile Gln Gln Tyr Tyr Leu Thr Phe Asn Phe Asp Asn Glu Pro Glu Asn
            500                 505                 510
Ile Ser Ile Glu Asn Leu Ser Ser Asp Ile Ile Gly Gln Leu Glu Leu
        515                 520                 525
Met Pro Asn Ile Glu Arg Phe Pro Asn Gly Lys Lys Tyr Glu Leu Asp
    530                 535                 540
Lys Tyr Thr Met Phe His Tyr Leu Arg Ala Gln Glu Phe Glu His Gly
545                 550                 555                 560
Lys Ser Arg Ile Ala Leu Thr Asn Ser Val Asn Glu Ala Leu Leu Asn
                565                 570                 575
Pro Ser Arg Val Tyr Thr Phe Phe Ser Ser Asp Tyr Val Lys Lys Val
            580                 585                 590
Asn Lys Ala Thr Glu Ala Ala Met Phe Leu Gly Trp Val Glu Gln Leu
        595                 600                 605
Val Tyr Asp Phe Thr Asp Glu Thr Ser Glu Val Ser Thr Thr Asp Lys
    610                 615                 620
Ile Ala Asp Ile Thr Ile Ile Pro Tyr Ile Gly Pro Ala Leu Asn
625                 630                 635                 640
Ile Gly Asn Met Leu Tyr Lys Asp Asp Phe Val Gly Ala Leu Ile Phe
                645                 650                 655
Ser Gly Ala Val Ile Leu Leu Glu Phe Ile Pro Glu Ile Ala Ile Pro
            660                 665                 670
Val Leu Gly Thr Phe Ala Leu Val Ser Tyr Ile Ala Asn Lys Val Leu
        675                 680                 685
Thr Val Gln Thr Ile Asp Asn Ala Leu Ser Lys Arg Asn Glu Lys Trp
    690                 695                 700
Asp Glu Val Tyr Lys Tyr Ile Val Thr Asn Trp Leu Ala Lys Val Asn
705                 710                 715                 720
Thr Gln Ile Asp Leu Ile Arg Lys Lys Met Lys Glu Ala Leu Glu Asn
                725                 730                 735
Gln Ala Glu Ala Thr Lys Ala Ile Ile Asn Tyr Gln Tyr Asn Gln Tyr
            740                 745                 750
Thr Glu Glu Glu Lys Asn Asn Ile Asn Phe Asn Ile Asp Asp Leu Ser
        755                 760                 765
Ser Lys Leu Asn Glu Ser Ile Asn Lys Ala Met Ile Asn Ile Asn Lys
    770                 775                 780
Phe Leu Asn Gln Cys Ser Val Ser Tyr Leu Met Asn Ser Met Ile Pro
785                 790                 795                 800
Tyr Gly Val Lys Arg Leu Glu Asp Phe Asp Ala Ser Leu Lys Asp Ala
                805                 810                 815
Leu Leu Lys Tyr Ile Tyr Asp Asn Arg Gly Thr Leu Ile Gly Gln Val
            820                 825                 830
Asp Arg Leu Lys Asp Lys Val Asn Asn Thr Leu Ser Thr Asp Ile Pro
        835                 840                 845
Phe Gln Leu Ser Lys Tyr Val Asp Asn Gln Arg Leu Leu Ser Thr Phe
    850                 855                 860
Thr Glu Tyr Ile Lys Asn Ile Ile Asn Thr Ser Ile Leu Asn Leu Arg
```

-continued

```
            865                 870                 875                 880
Tyr Glu Ser Asn His Leu Ile Asp Leu Ser Arg Tyr Ala Ser Lys Ile
                885                 890                 895
Asn Ile Gly Ser Lys Val Asn Phe Asp Pro Ile Asp Lys Asn Gln Ile
            900                 905                 910
Gln Leu Phe Asn Leu Glu Ser Ser Lys Ile Glu Val Ile Leu Lys Asn
            915                 920                 925
Ala Ile Val Tyr Asn Ser Met Tyr Glu Asn Phe Ser Thr Ser Phe Trp
            930                 935                 940
Ile Arg Ile Pro Lys Tyr Phe Asn Ser Ile Ser Leu Asn Asn Glu Tyr
945                 950                 955                 960
Thr Ile Ile Asn Cys Met Glu Asn Asn Ser Gly Trp Lys Val Ser Leu
                965                 970                 975
Asn Tyr Gly Glu Ile Ile Trp Thr Leu Gln Asp Thr Gln Glu Ile Lys
            980                 985                 990
Gln Arg Val Val Phe Lys Tyr Ser Gln Met Ile Asn Ile Ser Asp Tyr
            995                 1000                1005
Ile Asn Arg Trp Ile Phe Val Thr Ile Thr Asn Asn Arg Leu Asn Asn
1010                1015                1020
Ser Lys Ile Tyr Ile Asn Gly Arg Leu Ile Asp Gln Lys Pro Ile Ser
1025                1030                1035                1040
Asn Leu Gly Asn Ile His Ala Ser Asn Asn Ile Met Phe Lys Leu Asp
                1045                1050                1055
Gly Cys Arg Asp Thr His Arg Tyr Ile Trp Ile Lys Tyr Phe Asn Leu
                1060                1065                1070
Phe Asp Lys Glu Leu Asn Glu Lys Glu Ile Lys Asp Leu Tyr Asp Asn
                1075                1080                1085
Gln Ser Asn Ser Gly Ile Leu Lys Asp Phe Trp Gly Asp Tyr Leu Gln
                1090                1095                1100
Tyr Asp Lys Pro Tyr Tyr Met Leu Asn Leu Tyr Asp Pro Asn Lys Tyr
1105                1110                1115                1120
Val Asp Val Asn Asn Val Gly Ile Arg Gly Tyr Met Tyr Leu Lys Gly
                1125                1130                1135
Pro Arg Gly Ser Val Met Thr Thr Asn Ile Tyr Leu Asn Ser Ser Leu
                1140                1145                1150
Tyr Arg Gly Thr Lys Phe Ile Ile Lys Lys Tyr Ala Ser Gly Asn Lys
                1155                1160                1165
Asp Asn Ile Val Arg Asn Asn Asp Arg Val Tyr Ile Asn Val Val Val
            1170                1175                1180
Lys Asn Lys Glu Tyr Arg Leu Ala Thr Asn Ala Ser Gln Ala Gly Val
1185                1190                1195                1200
Glu Lys Ile Leu Ser Ala Leu Glu Ile Pro Asp Val Gly Asn Leu Ser
                1205                1210                1215
Gln Val Val Val Met Lys Ser Lys Asn Asp Gln Gly Ile Thr Asn Lys
                1220                1225                1230
Cys Lys Met Asn Leu Gln Asp Asn Asn Gly Asn Asp Ile Gly Phe Ile
                1235                1240                1245
Gly Phe His Gln Phe Asn Asn Ile Ala Lys Leu Val Ala Ser Asn Trp
            1250                1255                1260
Tyr Asn Arg Gln Ile Glu Arg Ser Ser Arg Thr Leu Gly Cys Ser Trp
1265                1270                1275                1280
Glu Phe Ile Pro Val Asp Asp Gly Trp Gly Glu Arg Pro Leu
                1285                1290
```

<210> SEQ ID NO 208
<211> LENGTH: 1294
<212> TYPE: PRT
<213> ORGANISM: Artificial Sequence
<220> FEATURE:
<223> OTHER INFORMATION: BoNT/A_Csnp8

<400> SEQUENCE: 208

```
Met Pro Phe Val Asn Lys Gln Phe Asn Tyr Lys Asp P

```
Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Ala Asn Gln Arg Ala Thr Lys Met Ala Leu
        435                 440                 445

Asn Asp Leu Cys Ile Lys Val Asn Asn Trp Asp Leu Phe Phe Ser Pro
    450                 455                 460

Ser Glu Asp Asn Phe Thr Asn Asp Leu Asn Lys Gly Glu Glu Ile Thr
465                 470                 475                 480

Ser Asp Thr Asn Ile Glu Ala Ala Glu Glu Asn Ile Ser Leu Asp Leu
                485                 490                 495

Ile Gln Gln Tyr Tyr Leu Thr Phe Asn Phe Asp Asn Glu Pro Glu Asn
            500                 505                 510

Ile Ser Ile Glu Asn Leu Ser Ser Asp Ile Ile Gly Gln Leu Glu Leu
        515                 520                 525

Met Pro Asn Ile Glu Arg Phe Pro Asn Gly Lys Lys Tyr Glu Leu Asp
    530                 535                 540

Lys Tyr Thr Met Phe His Tyr Leu Arg Ala Gln Glu Phe Glu His Gly
545                 550                 555                 560

Lys Ser Arg Ile Ala Leu Thr Asn Ser Val Asn Glu Ala Leu Leu Asn
                565                 570                 575

Pro Ser Arg Val Tyr Thr Phe Phe Ser Ser Asp Tyr Val Lys Lys Val
            580                 585                 590

Asn Lys Ala Thr Glu Ala Ala Met Phe Leu Gly Trp Val Glu Gln Leu
        595                 600                 605

Val Tyr Asp Phe Thr Asp Glu Thr Ser Glu Val Ser Thr Thr Asp Lys
    610                 615                 620

Ile Ala Asp Ile Thr Ile Ile Pro Tyr Ile Gly Pro Ala Leu Asn Ile
625                 630                 635                 640

Ile Gly Asn Met Leu Tyr Lys Asp Asp Phe Val Gly Ala Leu Ile Phe
                645                 650                 655

Ser Gly Ala Val Ile Leu Leu Glu Phe Ile Pro Glu Ile Ala Ile Pro
            660                 665                 670

Val Leu Gly Thr Phe Ala Leu Val Ser Tyr Ile Ala Asn Lys Val Leu
        675                 680                 685

Thr Val Gln Thr Ile Asp Asn Ala Leu Ser Lys Arg Asn Glu Lys Trp
    690                 695                 700

Asp Glu Val Tyr Lys Tyr Ile Val Thr Asn Trp Leu Ala Lys Val Asn
705                 710                 715                 720

Thr Gln Ile Asp Leu Ile Arg Lys Lys Met Lys Glu Ala Leu Glu Asn
                725                 730                 735

Gln Ala Glu Ala Thr Lys Ala Ile Ile Asn Tyr Gln Tyr Asn Gln Tyr
            740                 745                 750

Thr Glu Glu Glu Lys Asn Asn Ile Asn Phe Asn Ile Asp Asp Leu Ser
        755                 760                 765

Ser Lys Leu Asn Glu Ser Ile Asn Lys Ala Met Ile Asn Ile Asn Lys
    770                 775                 780
```

-continued

```
Phe Leu Asn Gln Cys Ser Val Ser Tyr Leu Met Asn Ser Met Ile Pro
785                 790                 795                 800

Tyr Gly Val Lys Arg Leu Glu Asp Phe Asp Ala Ser Leu Lys Asp Ala
            805                 810                 815

Leu Leu Lys Tyr Ile Tyr Asp Asn Arg Gly Thr Leu Ile Gly Gln Val
        820                 825                 830

Asp Arg Leu Lys Asp Lys Val Asn Asn Thr Leu Ser Thr Asp Ile Pro
    835                 840                 845

Phe Gln Leu Ser Lys Tyr Val Asp Asn Gln Arg Leu Leu Ser Thr Phe
850                 855                 860

Thr Glu Tyr Ile Lys Asn Ile Ile Asn Thr Ser Ile Leu Asn Leu Arg
865                 870                 875                 880

Tyr Glu Ser Asn His Leu Ile Asp Leu Ser Arg Tyr Ala Ser Lys Ile
            885                 890                 895

Asn Ile Gly Ser Lys Val Asn Phe Asp Pro Ile Asp Lys Asn Gln Ile
        900                 905                 910

Gln Leu Phe Asn Leu Glu Ser Ser Lys Ile Glu Val Ile Leu Lys Asn
    915                 920                 925

Ala Ile Val Tyr Asn Ser Met Tyr Glu Asn Phe Ser Thr Ser Phe Trp
930                 935                 940

Ile Arg Ile Pro Lys Tyr Phe Asn Ser Ile Ser Leu Asn Asn Glu Tyr
945                 950                 955                 960

Thr Ile Ile Asn Cys Met Glu Asn Asn Ser Gly Trp Lys Val Ser Leu
            965                 970                 975

Asn Tyr Gly Glu Ile Ile Trp Thr Leu Gln Asp Thr Gln Glu Ile Lys
        980                 985                 990

Gln Arg Val Val Phe Lys Tyr Ser Gln Met Ile Asn Ile Ser Asp Tyr
    995                 1000                1005

Ile Asn Arg Trp Ile Phe Val Thr Ile Thr Asn Asn Arg Leu Asn Asn
    1010                1015                1020

Ser Lys Ile Tyr Ile Asn Gly Arg Leu Ile Asp Gln Lys Pro Ile Ser
1025                1030                1035                1040

Asn Leu Gly Asn Ile His Ala Ser Asn Asn Ile Met Phe Lys Leu Asp
                1045                1050                1055

Gly Cys Arg Asp Thr His Arg Tyr Ile Trp Ile Lys Tyr Phe Asn Leu
                1060                1065                1070

Phe Asp Lys Glu Leu Asn Glu Lys Glu Ile Lys Asp Leu Tyr Asp Asn
        1075                1080                1085

Gln Ser Asn Ser Gly Ile Leu Lys Asp Phe Trp Gly Asp Tyr Leu Gln
    1090                1095                1100

Tyr Asp Lys Pro Tyr Tyr Met Leu Asn Leu Tyr Asp Pro Asn Lys Tyr
1105                1110                1115                1120

Val Asp Val Asn Asn Val Gly Ile Arg Gly Tyr Met Tyr Leu Lys Gly
                1125                1130                1135

Pro Arg Gly Ser Val Met Thr Thr Asn Ile Tyr Leu Asn Ser Ser Leu
                1140                1145                1150

Tyr Arg Gly Thr Lys Phe Ile Ile Lys Lys Tyr Ala Ser Gly Asn Lys
        1155                1160                1165

Asp Asn Ile Val Arg Asn Asn Asp Arg Val Tyr Ile Asn Val Val Val
    1170                1175                1180

Lys Asn Lys Glu Tyr Arg Leu Ala Thr Asn Ala Ser Gln Ala Gly Val
1185                1190                1195                1200

Glu Lys Ile Leu Ser Ala Leu Glu Ile Pro Asp Val Gly Asn Leu Ser
```

-continued

```
                1205                1210                1215

Gln Val Val Val Met Lys Ser Lys Asn Asp Gln Gly Ile Thr Asn Lys
            1220                1225                1230

Cys Lys Met Asn Leu Gln Asp Asn Asn Gly Asn Asp Ile Gly Phe Ile
        1235                1240                1245

Gly Phe His Gln Phe Asn Asn Ile Ala Lys Leu Val Ala Ser Asn Trp
    1250                1255                1260

Tyr Asn Arg Gln Ile Glu Arg Ser Ser Arg Thr Leu Gly Cys Ser Trp
1265                1270                1275                1280

Glu Phe Ile Pro Val Asp Asp Gly Trp Gly Glu Arg Pro Leu
                1285                1290

<210> SEQ ID NO 209
<211> LENGTH: 1325
<212> TYPE: PRT
<213> ORGANISM: Artificial Sequence
<220> FEATURE:
<221> NAME/KEY: PEPTIDE
<222> LOCATION: (1)...(1325)
<223> OTHER INFORMATION: BoNT/A_DF39

<400> SEQUENCE: 209

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

```
Phe Ile Asp Ser Leu Gln Glu Asn Glu Phe Arg Leu Tyr Tyr Asn
        275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Ala Gln Val Glu Glu Val Val Asp Ile Ile
                435                 440                 445
Arg Val Asn Val Asp Lys Val Leu Glu Arg Asp Gln Lys Leu Ser Glu
        450                 455                 460
Leu Asp Asp Arg Ala Asp Ala Leu Gln Ala Gly Ala Ser Ala Leu Asn
465                 470                 475                 480
Asp Leu Cys Ile Lys Val Asn Asn Trp Asp Leu Phe Phe Ser Pro Ser
                485                 490                 495
Glu Asp Asn Phe Thr Asn Asp Leu Asn Lys Gly Glu Glu Ile Thr Ser
                500                 505                 510
Asp Thr Asn Ile Glu Ala Ala Glu Glu Asn Ile Ser Leu Asp Leu Ile
        515                 520                 525
Gln Gln Tyr Tyr Leu Thr Phe Asn Phe Asp Asn Glu Pro Glu Asn Ile
        530                 535                 540
Ser Ile Glu Asn Leu Ser Ser Asp Ile Ile Gly Gln Leu Glu Leu Met
545                 550                 555                 560
Pro Asn Ile Glu Arg Phe Pro Asn Gly Lys Lys Tyr Glu Leu Asp Lys
                565                 570                 575
Tyr Thr Met Phe His Tyr Leu Arg Ala Gln Glu Phe Glu His Gly Lys
                580                 585                 590
Ser Arg Ile Ala Leu Thr Asn Ser Val Asn Glu Ala Leu Leu Asn Pro
        595                 600                 605
Ser Arg Val Tyr Thr Phe Phe Ser Ser Asp Tyr Val Lys Lys Val Asn
        610                 615                 620
Lys Ala Thr Glu Ala Ala Met Phe Leu Gly Trp Val Glu Gln Leu Val
625                 630                 635                 640
Tyr Asp Phe Thr Asp Glu Thr Ser Glu Val Ser Thr Thr Asp Lys Ile
                645                 650                 655
Ala Asp Ile Thr Ile Ile Pro Tyr Ile Gly Pro Ala Leu Asn Ile
                660                 665                 670
Gly Asn Met Leu Tyr Lys Asp Asp Phe Val Gly Ala Leu Ile Phe Ser
                675                 680                 685
```

-continued

```
Gly Ala Val Ile Leu Glu Phe Ile Pro Glu Ile Ala Ile Pro Val
    690                 695                 700
Leu Gly Thr Phe Ala Leu Val Ser Tyr Ile Ala Asn Lys Val Leu Thr
705                 710                 715                 720
Val Gln Thr Ile Asp Asn Ala Leu Ser Lys Arg Asn Glu Lys Trp Asp
                725                 730                 735
Glu Val Tyr Lys Tyr Ile Val Thr Asn Trp Leu Ala Lys Val Asn Thr
            740                 745                 750
Gln Ile Asp Leu Ile Arg Lys Lys Met Lys Glu Ala Leu Glu Asn Gln
        755                 760                 765
Ala Glu Ala Thr Lys Ala Ile Ile Asn Tyr Gln Tyr Asn Gln Tyr Thr
770                 775                 780
Glu Glu Glu Lys Asn Asn Ile Asn Phe Asn Ile Asp Asp Leu Ser Ser
785                 790                 795                 800
Lys Leu Asn Glu Ser Ile Asn Lys Ala Met Ile Asn Ile Asn Lys Phe
                805                 810                 815
Leu Asn Gln Cys Ser Val Ser Tyr Leu Met Asn Ser Met Ile Pro Tyr
            820                 825                 830
Gly Val Lys Arg Leu Glu Asp Phe Asp Ala Ser Leu Lys Asp Ala Leu
        835                 840                 845
Leu Lys Tyr Ile Tyr Asp Asn Arg Gly Thr Leu Ile Gly Gln Val Asp
850                 855                 860
Arg Leu Lys Asp Lys Val Asn Asn Thr Leu Ser Thr Asp Ile Pro Phe
865                 870                 875                 880
Gln Leu Ser Lys Tyr Val Asp Asn Gln Arg Leu Leu Ser Thr Phe Thr
                885                 890                 895
Glu Tyr Ile Lys Asn Ile Ile Asn Thr Ser Ile Leu Asn Leu Arg Tyr
            900                 905                 910
Glu Ser Asn His Leu Ile Asp Leu Ser Arg Tyr Ala Ser Lys Ile Asn
        915                 920                 925
Ile Gly Ser Lys Val Asn Phe Asp Pro Ile Asp Lys Asn Gln Ile Gln
    930                 935                 940
Leu Phe Asn Leu Glu Ser Ser Lys Ile Glu Val Ile Leu Lys Asn Ala
945                 950                 955                 960
Ile Val Tyr Asn Ser Met Tyr Glu Asn Phe Ser Thr Ser Phe Trp Ile
                965                 970                 975
Arg Ile Pro Lys Tyr Phe Asn Ser Ile Ser Leu Asn Asn Glu Tyr Thr
            980                 985                 990
Ile Ile Asn Cys Met Glu Asn Asn Ser Gly Trp Lys Val Ser Leu Asn
        995                 1000                1005
Tyr Gly Glu Ile Ile Trp Thr Leu Gln Asp Thr Gln Glu Ile Lys Gln
    1010                1015                1020
Arg Val Val Phe Lys Tyr Ser Gln Met Ile Asn Ile Ser Asp Tyr Ile
1025                1030                1035                1040
Asn Arg Trp Ile Phe Val Thr Ile Thr Asn Asn Arg Leu Asn Asn Ser
                1045                1050                1055
Lys Ile Tyr Ile Asn Gly Arg Leu Ile Asp Gln Lys Pro Ile Ser Asn
            1060                1065                1070
Leu Gly Asn Ile His Ala Ser Asn Asn Ile Met Phe Lys Leu Asp Gly
        1075                1080                1085
Cys Arg Asp Thr His Arg Tyr Ile Trp Ile Lys Tyr Phe Asn Leu Phe
    1090                1095                1100
Asp Lys Glu Leu Asn Glu Lys Glu Ile Lys Asp Leu Tyr Asp Asn Gln
```

-continued

```
1105                1110                1115                1120

Ser Asn Ser Gly Ile Leu Lys Asp Phe Trp Gly Asp Tyr Leu Gln Tyr
                1125                1130                1135
Asp Lys Pro Tyr Tyr Met Leu Asn Leu Tyr Asp Pro Asn Lys Tyr Val
            1140                1145                1150
Asp Val Asn Asn Val Gly Ile Arg Gly Tyr Met Tyr Leu Lys Gly Pro
        1155                1160                1165

Arg Gly Ser Val Met Thr Thr Asn Ile Tyr Leu Asn Ser Ser Leu Tyr
    1170                1175                1180

Arg Gly Thr Lys Phe Ile Ile Lys Lys Tyr Ala Ser Gly Asn Lys Asp
1185                1190                1195                1200
Asn Ile Val Arg Asn Asn Asp Arg Val Tyr Ile Asn Val Val Val Lys
                1205                1210                1215
Asn Lys Glu Tyr Arg Leu Ala Thr Asn Ala Ser Gln Ala Gly Val Glu
            1220                1225                1230
Lys Ile Leu Ser Ala Leu Glu Ile Pro Asp Val Gly Asn Leu Ser Gln
        1235                1240                1245

Val Val Val Met Lys Ser Lys Asn Asp Gln Gly Ile Thr Asn Lys Cys
    1250                1255                1260

Lys Met Asn Leu Gln Asp Asn Asn Gly Asn Asp Ile Gly Phe Ile Gly
1265                1270                1275                1280
Phe His Gln Phe Asn Asn Ile Ala Lys Leu Val Ala Ser Asn Trp Tyr
                1285                1290                1295
Asn Arg Gln Ile Glu Arg Ser Ser Arg Thr Leu Gly Cys Ser Trp Glu
            1300                1305                1310
Phe Ile Pro Val Asp Asp Gly Trp Gly Glu Arg Pro Leu
        1315                1320                1325

<210> SEQ ID NO 210
<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_D8

<400> SEQUENCE: 210

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140
```

-continued

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Arg Asp Gln Lys Leu Ser Glu Leu Ala Leu
    435                 440                 445

Asn Asp Leu Cys Ile Lys Val Asn Asn Trp Asp Leu Phe Phe Ser Pro
450                 455                 460

Ser Glu Asp Asn Phe Thr Asn Asp Leu Asn Lys Gly Glu Glu Ile Thr
465                 470                 475                 480

Ser Asp Thr Asn Ile Glu Ala Ala Glu Glu Asn Ile Ser Leu Asp Leu
                485                 490                 495

Ile Gln Gln Tyr Tyr Leu Thr Phe Asn Phe Asp Asn Glu Pro Glu Asn
            500                 505                 510

Ile Ser Ile Glu Asn Leu Ser Ser Asp Ile Ile Gly Gln Leu Glu Leu
        515                 520                 525

Met Pro Asn Ile Glu Arg Phe Pro Asn Gly Lys Lys Tyr Glu Leu Asp
    530                 535                 540

Lys Tyr Thr Met Phe His Tyr Leu Arg Ala Gln Glu Phe Glu His Gly
545                 550                 555                 560
```

-continued

```
Lys Ser Arg Ile Ala Leu Thr Asn Ser Val Asn Glu Ala Leu Leu Asn
                565                 570                 575
Pro Ser Arg Val Tyr Thr Phe Phe Ser Ser Asp Tyr Val Lys Lys Val
            580                 585                 590
Asn Lys Ala Thr Glu Ala Ala Met Phe Leu Gly Trp Val Glu Gln Leu
        595                 600                 605
Val Tyr Asp Phe Thr Asp Glu Thr Ser Glu Val Ser Thr Thr Asp Lys
    610                 615                 620
Ile Ala Asp Ile Thr Ile Ile Pro Tyr Ile Gly Pro Ala Leu Asn
625                 630                 635                 640
Ile Gly Asn Met Leu Tyr Lys Asp Asp Phe Val Gly Ala Leu Ile Phe
                645                 650                 655
Ser Gly Ala Val Ile Leu Leu Glu Phe Ile Pro Glu Ile Ala Ile Pro
            660                 665                 670
Val Leu Gly Thr Phe Ala Leu Val Ser Tyr Ile Ala Asn Lys Val Leu
        675                 680                 685
Thr Val Gln Thr Ile Asp Asn Ala Leu Ser Lys Arg Asn Glu Lys Trp
    690                 695                 700
Asp Glu Val Tyr Lys Tyr Ile Val Thr Asn Trp Leu Ala Lys Val Asn
705                 710                 715                 720
Thr Gln Ile Asp Leu Ile Arg Lys Lys Met Lys Glu Ala Leu Glu Asn
                725                 730                 735
Gln Ala Glu Ala Thr Lys Ala Ile Ile Asn Tyr Gln Tyr Asn Gln Tyr
            740                 745                 750
Thr Glu Glu Glu Lys Asn Asn Ile Asn Phe Asn Ile Asp Asp Leu Ser
        755                 760                 765
Ser Lys Leu Asn Glu Ser Ile Asn Lys Ala Met Ile Asn Ile Asn Lys
    770                 775                 780
Phe Leu Asn Gln Cys Ser Val Ser Tyr Leu Met Asn Ser Met Ile Pro
785                 790                 795                 800
Tyr Gly Val Lys Arg Leu Glu Asp Phe Asp Ala Ser Leu Lys Asp Ala
                805                 810                 815
Leu Leu Lys Tyr Ile Tyr Asp Asn Arg Gly Thr Leu Ile Gly Gln Val
            820                 825                 830
Asp Arg Leu Lys Asp Lys Val Asn Asn Thr Leu Ser Thr Asp Ile Pro
        835                 840                 845
Phe Gln Leu Ser Lys Tyr Val Asp Asn Gln Arg Leu Leu Ser Thr Phe
    850                 855                 860
Thr Glu Tyr Ile Lys Asn Ile Ile Asn Thr Ser Ile Leu Asn Leu Arg
865                 870                 875                 880
Tyr Glu Ser Asn His Leu Ile Asp Leu Ser Arg Tyr Ala Ser Lys Ile
                885                 890                 895
Asn Ile Gly Ser Lys Val Asn Phe Asp Pro Ile Asp Lys Asn Gln Ile
            900                 905                 910
Gln Leu Phe Asn Leu Glu Ser Ser Lys Ile Glu Val Ile Leu Lys Asn
        915                 920                 925
Ala Ile Val Tyr Asn Ser Met Tyr Glu Asn Phe Ser Thr Ser Phe Trp
    930                 935                 940
Ile Arg Ile Pro Lys Tyr Phe Asn Ser Ile Ser Leu Asn Asn Glu Tyr
945                 950                 955                 960
Thr Ile Ile Asn Cys Met Glu Asn Asn Ser Gly Trp Lys Val Ser Leu
                965                 970                 975
Asn Tyr Gly Glu Ile Ile Trp Thr Leu Gln Asp Thr Gln Glu Ile Lys
```

-continued

```
                   980             985              990
Gln Arg Val Val Phe Lys Tyr Ser Gln Met Ile Asn Ile Ser Asp Tyr
            995                  1000                 1005

Ile Asn Arg Trp Ile Phe Val Thr Ile Thr Asn Asn Arg Leu Asn Asn
        1010                 1015                 1020

Ser Lys Ile Tyr Ile Asn Gly Arg Leu Ile Asp Gln Lys Pro Ile Ser
1025                 1030                 1035                 1040

Asn Leu Gly Asn Ile His Ala Ser Asn Asn Ile Met Phe Lys Leu Asp
                1045                 1050                 1055

Gly Cys Arg Asp Thr His Arg Tyr Ile Trp Ile Lys Tyr Phe Asn Leu
            1060                 1065                 1070

Phe Asp Lys Glu Leu Asn Glu Lys Glu Ile Lys Asp Leu Tyr Asp Asn
        1075                 1080                 1085

Gln Ser Asn Ser Gly Ile Leu Lys Asp Phe Trp Gly Asp Tyr Leu Gln
    1090                 1095                 1100

Tyr Asp Lys Pro Tyr Tyr Met Leu Asn Leu Tyr Asp Pro Asn Lys Tyr
1105                 1110                 1115                 1120

Val Asp Val Asn Asn Val Gly Ile Arg Gly Tyr Met Tyr Leu Lys Gly
                1125                 1130                 1135

Pro Arg Gly Ser Val Met Thr Thr Asn Ile Tyr Leu Asn Ser Ser Leu
            1140                 1145                 1150

Tyr Arg Gly Thr Lys Phe Ile Ile Lys Lys Tyr Ala Ser Gly Asn Lys
        1155                 1160                 1165

Asp Asn Ile Val Arg Asn Asn Asp Arg Val Tyr Ile Asn Val Val Val
    1170                 1175                 1180

Lys Asn Lys Glu Tyr Arg Leu Ala Thr Asn Ala Ser Gln Ala Gly Val
1185                 1190                 1195                 1200

Glu Lys Ile Leu Ser Ala Leu Glu Ile Pro Asp Val Gly Asn Leu Ser
                1205                 1210                 1215

Gln Val Val Val Met Lys Ser Lys Asn Asp Gln Gly Ile Thr Asn Lys
            1220                 1225                 1230

Cys Lys Met Asn Leu Gln Asp Asn Asn Gly Asn Asp Ile Gly Phe Ile
        1235                 1240                 1245

Gly Phe His Gln Phe Asn Asn Ile Ala Lys Leu Val Ala Ser Asn Trp
    1250                 1255                 1260

Tyr Asn Arg Gln Ile Glu Arg Ser Ser Arg Thr Leu Gly Cys Ser Trp
1265                 1270                 1275                 1280

Glu Phe Ile Pro Val Asp Asp Gly Trp Gly Glu Arg Pro Leu
                1285                 1290
```

<210> SEQ ID NO 211
<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_E8

<400> SEQUENCE: 211

```
Met Pro Phe Val Asn Lys Gln Phe Asn Tyr Lys Asp Pro Val Asn Gly
 1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45
```

-continued

```
Asp Thr Phe Thr Asn Pro Glu Glu Gly Asp Leu Asn Pro Pro Glu
    50                  55                  60
Ala Lys Gln Val Pro Val Ser Tyr Tyr Asp Ser Thr Tyr Leu Ser Thr
65                  70                  75                  80
Asp Asn Glu Lys Asp Asn Tyr Leu Lys Gly Val Thr Lys Leu Phe Glu
                85                  90                  95
Arg Ile Tyr Ser Thr Asp Leu Gly Arg Met Leu Leu Thr Ser Ile Val
            100                 105                 110
Arg Gly Ile Pro Phe Trp Gly Gly Ser Thr Ile Asp Thr Glu Leu Lys
        115                 120                 125
Val Ile Asp Thr Asn Cys Ile Asn Val Ile Gln Pro Asp Gly Ser Tyr
    130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
    210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Gln Ile Asp Arg Ile Met Glu Lys Ala Leu
        435                 440                 445
Asn Asp Leu Cys Ile Lys Val Asn Asn Trp Asp Leu Phe Phe Ser Pro
    450                 455                 460
```

-continued

```
Ser Glu Asp Asn Phe Thr Asn Asp Leu Asn Lys Gly Glu Glu Ile Thr
465                 470                 475                 480

Ser Asp Thr Asn Ile Glu Ala Ala Glu Glu Asn Ile Ser Leu Asp Leu
                485                 490                 495

Ile Gln Gln Tyr Tyr Leu Thr Phe Asn Phe Asp Asn Glu Pro Glu Asn
            500                 505                 510

Ile Ser Ile Glu Asn Leu Ser Ser Asp Ile Ile Gly Gln Leu Glu Leu
        515                 520                 525

Met Pro Asn Ile Glu Arg Phe Pro Asn Gly Lys Lys Tyr Glu Leu Asp
530                 535                 540

Lys Tyr Thr Met Phe His Tyr Leu Arg Ala Gln Glu Phe Glu His Gly
545                 550                 555                 560

Lys Ser Arg Ile Ala Leu Thr Asn Ser Val Asn Glu Ala Leu Leu Asn
                565                 570                 575

Pro Ser Arg Val Tyr Thr Phe Phe Ser Ser Asp Tyr Val Lys Lys Val
            580                 585                 590

Asn Lys Ala Thr Glu Ala Ala Met Phe Leu Gly Trp Val Glu Gln Leu
        595                 600                 605

Val Tyr Asp Phe Thr Asp Glu Thr Ser Glu Val Ser Thr Thr Asp Lys
610                 615                 620

Ile Ala Asp Ile Thr Ile Ile Pro Tyr Ile Gly Pro Ala Leu Asn
625                 630                 635                 640

Ile Gly Asn Met Leu Tyr Lys Asp Asp Phe Val Gly Ala Leu Ile Phe
                645                 650                 655

Ser Gly Ala Val Ile Leu Leu Glu Phe Ile Pro Glu Ile Ala Ile Pro
            660                 665                 670

Val Leu Gly Thr Phe Ala Leu Val Ser Tyr Ile Ala Asn Lys Val Leu
        675                 680                 685

Thr Val Gln Thr Ile Asp Asn Ala Leu Ser Lys Arg Asn Glu Lys Trp
690                 695                 700

Asp Glu Val Tyr Lys Tyr Ile Val Thr Asn Trp Leu Ala Lys Val Asn
705                 710                 715                 720

Thr Gln Ile Asp Leu Ile Arg Lys Lys Met Lys Glu Ala Leu Glu Asn
                725                 730                 735

Gln Ala Glu Ala Thr Lys Ala Ile Ile Asn Tyr Gln Tyr Asn Gln Tyr
            740                 745                 750

Thr Glu Glu Glu Lys Asn Asn Ile Asn Phe Asn Ile Asp Asp Leu Ser
        755                 760                 765

Ser Lys Leu Asn Glu Ser Ile Asn Lys Ala Met Ile Asn Ile Asn Lys
770                 775                 780

Phe Leu Asn Gln Cys Ser Val Ser Tyr Leu Met Asn Ser Met Ile Pro
785                 790                 795                 800

Tyr Gly Val Lys Arg Leu Glu Asp Phe Asp Ala Ser Leu Lys Asp Ala
                805                 810                 815

Leu Leu Lys Tyr Ile Tyr Asp Asn Arg Gly Thr Leu Ile Gly Gln Val
            820                 825                 830

Asp Arg Leu Lys Asp Lys Val Asn Asn Thr Leu Ser Thr Asp Ile Pro
        835                 840                 845

Phe Gln Leu Ser Lys Tyr Val Asp Asn Gln Arg Leu Leu Ser Thr Phe
850                 855                 860

Thr Glu Tyr Ile Lys Asn Ile Ile Asn Thr Ser Ile Leu Asn Leu Arg
865                 870                 875                 880

Tyr Glu Ser Asn His Leu Ile Asp Leu Ser Arg Tyr Ala Ser Lys Ile
```

-continued

```
                885                 890                 895
Asn Ile Gly Ser Lys Val Asn Phe Asp Pro Ile Asp Lys Asn Gln Ile
            900                 905                 910
Gln Leu Phe Asn Leu Glu Ser Ser Lys Ile Glu Val Ile Leu Lys Asn
        915                 920                 925
Ala Ile Val Tyr Asn Ser Met Tyr Glu Asn Phe Ser Thr Ser Phe Trp
    930                 935                 940
Ile Arg Ile Pro Lys Tyr Phe Asn Ser Ile Ser Leu Asn Asn Glu Tyr
945                 950                 955                 960
Thr Ile Ile Asn Cys Met Glu Asn Asn Ser Gly Trp Lys Val Ser Leu
                965                 970                 975
Asn Tyr Gly Glu Ile Ile Trp Thr Leu Gln Asp Thr Gln Glu Ile Lys
            980                 985                 990
Gln Arg Val Val Phe Lys Tyr Ser Gln Met Ile Asn Ile Ser Asp Tyr
        995                 1000                1005
Ile Asn Arg Trp Ile Phe Val Thr Ile Thr Asn Asn Arg Leu Asn Asn
    1010                1015                1020
Ser Lys Ile Tyr Ile Asn Gly Arg Leu Ile Asp Gln Lys Pro Ile Ser
1025                1030                1035                1040
Asn Leu Gly Asn Ile His Ala Ser Asn Asn Ile Met Phe Lys Leu Asp
                1045                1050                1055
Gly Cys Arg Asp Thr His Arg Tyr Ile Trp Ile Lys Tyr Phe Asn Leu
            1060                1065                1070
Phe Asp Lys Glu Leu Asn Glu Lys Glu Ile Lys Asp Leu Tyr Asp Asn
        1075                1080                1085
Gln Ser Asn Ser Gly Ile Leu Lys Asp Phe Trp Gly Asp Tyr Leu Gln
    1090                1095                1100
Tyr Asp Lys Pro Tyr Tyr Met Leu Asn Leu Tyr Asp Pro Asn Lys Tyr
1105                1110                1115                1120
Val Asp Val Asn Asn Val Gly Ile Arg Gly Tyr Met Tyr Leu Lys Gly
                1125                1130                1135
Pro Arg Gly Ser Val Met Thr Thr Asn Ile Tyr Leu Asn Ser Ser Leu
            1140                1145                1150
Tyr Arg Gly Thr Lys Phe Ile Ile Lys Lys Tyr Ala Ser Gly Asn Lys
        1155                1160                1165
Asp Asn Ile Val Arg Asn Asn Asp Arg Val Tyr Ile Asn Val Val Val
    1170                1175                1180
Lys Asn Lys Glu Tyr Arg Leu Ala Thr Asn Ala Ser Gln Ala Gly Val
1185                1190                1195                1200
Glu Lys Ile Leu Ser Ala Leu Glu Ile Pro Asp Val Gly Asn Leu Ser
                1205                1210                1215
Gln Val Val Val Met Lys Ser Lys Asn Asp Gln Gly Ile Thr Asn Lys
            1220                1225                1230
Cys Lys Met Asn Leu Gln Asp Asn Asn Gly Asn Asp Ile Gly Phe Ile
        1235                1240                1245
Gly Phe His Gln Phe Asn Asn Ile Ala Lys Leu Val Ala Ser Asn Trp
    1250                1255                1260
Tyr Asn Arg Gln Ile Glu Arg Ser Ser Arg Thr Leu Gly Cys Ser Trp
1265                1270                1275                1280
Glu Phe Ile Pro Val Asp Asp Gly Trp Gly Glu Arg Pro Leu
                1285                1290

<210> SEQ ID NO 212
```

<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_F8

<400> SEQUENCE: 212

```
Met Pro Phe Val Asn Lys Gln Phe As

-continued

```
Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Glu Arg Asp Gln Lys Leu Ser Glu Ala Leu
        435                 440                 445

Asn Asp Leu Cys Ile Lys Val Asn Asn Trp Asp Leu Phe Phe Ser Pro
    450                 455                 460

Ser Glu Asp Asn Phe Thr Asn Asp Leu Asn Lys Gly Glu Glu Ile Thr
465                 470                 475                 480

Ser Asp Thr Asn Ile Glu Ala Ala Glu Glu Asn Ile Ser Leu Asp Leu
                485                 490                 495

Ile Gln Gln Tyr Tyr Leu Thr Phe Asn Phe Asp Asn Glu Pro Glu Asn
            500                 505                 510

Ile Ser Ile Glu Asn Leu Ser Ser Asp Ile Ile Gly Gln Leu Glu Leu
        515                 520                 525

Met Pro Asn Ile Glu Arg Phe Pro Asn Gly Lys Lys Tyr Glu Leu Asp
    530                 535                 540

Lys Tyr Thr Met Phe His Tyr Leu Arg Ala Gln Glu Phe Glu His Gly
545                 550                 555                 560

Lys Ser Arg Ile Ala Leu Thr Asn Ser Val Asn Glu Ala Leu Leu Asn
                565                 570                 575

Pro Ser Arg Val Tyr Thr Phe Phe Ser Ser Asp Tyr Val Lys Lys Val
            580                 585                 590

Asn Lys Ala Thr Glu Ala Ala Met Phe Leu Gly Trp Val Glu Gln Leu
        595                 600                 605

Val Tyr Asp Phe Thr Asp Glu Thr Ser Glu Val Ser Thr Thr Asp Lys
    610                 615                 620

Ile Ala Asp Ile Thr Ile Ile Pro Tyr Ile Gly Pro Ala Leu Asn Ile
625                 630                 635                 640

Gly Asn Met Leu Tyr Lys Asp Asp Phe Val Gly Ala Leu Ile Phe
                645                 650                 655

Ser Gly Ala Val Ile Leu Leu Glu Phe Ile Pro Glu Ile Ala Ile Pro
            660                 665                 670

Val Leu Gly Thr Phe Ala Leu Val Ser Tyr Ile Ala Asn Lys Val Leu
        675                 680                 685

Thr Val Gln Thr Ile Asp Asn Ala Leu Ser Lys Arg Asn Glu Lys Trp
    690                 695                 700

Asp Glu Val Tyr Lys Tyr Ile Val Thr Asn Trp Leu Ala Lys Val Asn
705                 710                 715                 720

Thr Gln Ile Asp Leu Ile Arg Lys Lys Met Lys Glu Ala Leu Glu Asn
                725                 730                 735

Gln Ala Glu Ala Thr Lys Ala Ile Ile Asn Tyr Gln Tyr Asn Gln Tyr
            740                 745                 750

Thr Glu Glu Glu Lys Asn Asn Ile Asn Phe Asn Ile Asp Asp Leu Ser
        755                 760                 765

Ser Lys Leu Asn Glu Ser Ile Asn Lys Ala Met Ile Asn Ile Asn Lys
    770                 775                 780

Phe Leu Asn Gln Cys Ser Val Ser Tyr Leu Met Asn Ser Met Ile Pro
```

-continued

```
              785                 790                 795                 800
Tyr Gly Val Lys Arg Leu Glu Asp Phe Asp Ala Ser Leu Lys Asp Ala
                805                 810                 815

Leu Leu Lys Tyr Ile Tyr Asp Asn Arg Gly Thr Leu Ile Gly Gln Val
                820                 825                 830

Asp Arg Leu Lys Asp Lys Val Asn Asn Thr Leu Ser Thr Asp Ile Pro
                835                 840                 845

Phe Gln Leu Ser Lys Tyr Val Asp Asn Gln Arg Leu Leu Ser Thr Phe
                850                 855                 860

Thr Glu Tyr Ile Lys Asn Ile Ile Asn Thr Ser Ile Leu Asn Leu Arg
865                 870                 875                 880

Tyr Glu Ser Asn His Leu Ile Asp Leu Ser Arg Tyr Ala Ser Lys Ile
                885                 890                 895

Asn Ile Gly Ser Lys Val Asn Phe Asp Pro Ile Asp Lys Asn Gln Ile
                900                 905                 910

Gln Leu Phe Asn Leu Glu Ser Ser Lys Ile Glu Val Ile Leu Lys Asn
                915                 920                 925

Ala Ile Val Tyr Asn Ser Met Tyr Glu Asn Phe Ser Thr Ser Phe Trp
                930                 935                 940

Ile Arg Ile Pro Lys Tyr Phe Asn Ser Ile Ser Leu Asn Asn Glu Tyr
945                 950                 955                 960

Thr Ile Ile Asn Cys Met Glu Asn Asn Ser Gly Trp Lys Val Ser Leu
                965                 970                 975

Asn Tyr Gly Glu Ile Ile Trp Thr Leu Gln Asp Thr Gln Glu Ile Lys
                980                 985                 990

Gln Arg Val Val Phe Lys Tyr Ser Gln Met Ile Asn Ile Ser Asp Tyr
                995                 1000                1005

Ile Asn Arg Trp Ile Phe Val Thr Ile Thr Asn Asn Arg Leu Asn Asn
                1010                1015                1020

Ser Lys Ile Tyr Ile Asn Gly Arg Leu Ile Asp Gln Lys Pro Ile Ser
1025                1030                1035                1040

Asn Leu Gly Asn Ile His Ala Ser Asn Asn Ile Met Phe Lys Leu Asp
                1045                1050                1055

Gly Cys Arg Asp Thr His Arg Tyr Ile Trp Ile Lys Tyr Phe Asn Leu
                1060                1065                1070

Phe Asp Lys Glu Leu Asn Glu Lys Glu Ile Lys Asp Leu Tyr Asp Asn
                1075                1080                1085

Gln Ser Asn Ser Gly Ile Leu Lys Asp Phe Trp Gly Asp Tyr Leu Gln
                1090                1095                1100

Tyr Asp Lys Pro Tyr Tyr Met Leu Asn Leu Tyr Asp Pro Asn Lys Tyr
1105                1110                1115                1120

Val Asp Val Asn Asn Val Gly Ile Arg Gly Tyr Met Tyr Leu Lys Gly
                1125                1130                1135

Pro Arg Gly Ser Val Met Thr Thr Asn Ile Tyr Leu Asn Ser Ser Leu
                1140                1145                1150

Tyr Arg Gly Thr Lys Phe Ile Ile Lys Lys Tyr Ala Ser Gly Asn Lys
                1155                1160                1165

Asp Asn Ile Val Arg Asn Asn Asp Arg Val Tyr Ile Asn Val Val Val
                1170                1175                1180

Lys Asn Lys Glu Tyr Arg Leu Ala Thr Asn Ala Ser Gln Ala Gly Val
1185                1190                1195                1200

Glu Lys Ile Leu Ser Ala Leu Glu Ile Pro Asp Val Gly Asn Leu Ser
                1205                1210                1215
```

```
Gln Val Val Met Lys Ser Lys Asn Asp Gln Gly Ile Thr Asn Lys
            1220                1225                1230

Cys Lys Met Asn Leu Gln Asp Asn Asn Gly Asn Asp Ile Gly Phe Ile
        1235                1240                1245

Gly Phe His Gln Phe Asn Asn Ile Ala Lys Leu Val Ala Ser Asn Trp
        1250                1255                1260

Tyr Asn Arg Gln Ile Glu Arg Ser Ser Arg Thr Leu Gly Cys Ser Trp
1265                1270                1275                1280

Glu Phe Ile Pro Val Asp Asp Gly Trp Gly Glu Arg Pro Leu
                1285                1290

<210> SEQ ID NO 213
<211> LENGTH: 1294
<212> TYPE: PRT
<213> ORGANISM: Artificial Sequence
<220> FEATURE:
<221> NAME/KEY: PEPTIDE
<222> LOCATION: (1)...(1294)
<223> OTHER INFORMATION: BoNT/A_G8

<400> SEQUENCE: 213

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

-continued

```
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
        290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
        370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Glu Thr Ser Ala Ala Lys Leu Lys Ala Leu
                435                 440                 445
Asn Asp Leu Cys Ile Lys Val Asn Asn Trp Asp Leu Phe Phe Ser Pro
        450                 455                 460
Ser Glu Asp Asn Phe Thr Asn Asp Leu Asn Lys Gly Glu Glu Ile Thr
465                 470                 475                 480
Ser Asp Thr Asn Ile Glu Ala Ala Glu Glu Asn Ile Ser Leu Asp Leu
                485                 490                 495
Ile Gln Gln Tyr Tyr Leu Thr Phe Asn Phe Asp Asn Glu Pro Glu Asn
                500                 505                 510
Ile Ser Ile Glu Asn Leu Ser Ser Asp Ile Ile Gly Gln Leu Glu Leu
        515                 520                 525
Met Pro Asn Ile Glu Arg Phe Pro Asn Gly Lys Lys Tyr Glu Leu Asp
        530                 535                 540
Lys Tyr Thr Met Phe His Tyr Leu Arg Ala Gln Glu Phe Glu His Gly
545                 550                 555                 560
Lys Ser Arg Ile Ala Leu Thr Asn Ser Val Asn Glu Ala Leu Leu Asn
                565                 570                 575
Pro Ser Arg Val Tyr Thr Phe Phe Ser Ser Asp Tyr Val Lys Lys Val
                580                 585                 590
Asn Lys Ala Thr Glu Ala Ala Met Phe Leu Gly Trp Val Glu Gln Leu
                595                 600                 605
Val Tyr Asp Phe Thr Asp Glu Thr Ser Glu Val Ser Thr Thr Asp Lys
        610                 615                 620
Ile Ala Asp Ile Thr Ile Ile Pro Tyr Ile Gly Pro Ala Leu Asn
625                 630                 635                 640
Ile Gly Asn Met Leu Tyr Lys Asp Asp Phe Val Gly Ala Leu Ile Phe
                645                 650                 655
Ser Gly Ala Val Ile Leu Leu Glu Phe Ile Pro Glu Ile Ala Ile Pro
                660                 665                 670
Val Leu Gly Thr Phe Ala Leu Val Ser Tyr Ile Ala Asn Lys Val Leu
        675                 680                 685
Thr Val Gln Thr Ile Asp Asn Ala Leu Ser Lys Arg Asn Glu Lys Trp
```

-continued

```
            690                 695                 700
Asp Glu Val Tyr Lys Tyr Ile Val Thr Asn Trp Leu Ala Lys Val Asn
705                 710                 715                 720

Thr Gln Ile Asp Leu Ile Arg Lys Lys Met Lys Glu Ala Leu Glu Asn
                725                 730                 735

Gln Ala Glu Ala Thr Lys Ala Ile Ile Asn Tyr Gln Tyr Asn Gln Tyr
                    740                 745                 750

Thr Glu Glu Lys Asn Asn Ile Asn Phe Asn Ile Asp Asp Leu Ser
                755                 760                 765

Ser Lys Leu Asn Glu Ser Ile Asn Lys Ala Met Ile Asn Ile Asn Lys
770                 775                 780

Phe Leu Asn Gln Cys Ser Val Ser Tyr Leu Met Asn Ser Met Ile Pro
785                 790                 795                 800

Tyr Gly Val Lys Arg Leu Glu Asp Phe Asp Ala Ser Leu Lys Asp Ala
                    805                 810                 815

Leu Leu Lys Tyr Ile Tyr Asp Asn Arg Gly Thr Leu Ile Gly Gln Val
                820                 825                 830

Asp Arg Leu Lys Asp Lys Val Asn Asn Thr Leu Ser Thr Asp Ile Pro
                835                 840                 845

Phe Gln Leu Ser Lys Tyr Val Asp Asn Gln Arg Leu Leu Ser Thr Phe
850                 855                 860

Thr Glu Tyr Ile Lys Asn Ile Ile Asn Thr Ser Ile Leu Asn Leu Arg
865                 870                 875                 880

Tyr Glu Ser Asn His Leu Ile Asp Leu Ser Arg Tyr Ala Ser Lys Ile
                    885                 890                 895

Asn Ile Gly Ser Lys Val Asn Phe Asp Pro Ile Asp Lys Asn Gln Ile
                900                 905                 910

Gln Leu Phe Asn Leu Glu Ser Ser Lys Ile Glu Val Ile Leu Lys Asn
                915                 920                 925

Ala Ile Val Tyr Asn Ser Met Tyr Glu Asn Phe Ser Thr Ser Phe Trp
                930                 935                 940

Ile Arg Ile Pro Lys Tyr Phe Asn Ser Ile Ser Leu Asn Asn Glu Tyr
945                 950                 955                 960

Thr Ile Ile Asn Cys Met Glu Asn Asn Ser Gly Trp Lys Val Ser Leu
                965                 970                 975

Asn Tyr Gly Glu Ile Ile Trp Thr Leu Gln Asp Thr Gln Glu Ile Lys
                980                 985                 990

Gln Arg Val Val Phe Lys Tyr Ser Gln Met Ile Asn Ile Ser Asp Tyr
                995                 1000                1005

Ile Asn Arg Trp Ile Phe Val Thr Ile Thr Asn Asn Arg Leu Asn Asn
1010                1015                1020

Ser Lys Ile Tyr Ile Asn Gly Arg Leu Ile Asp Gln Lys Pro Ile Ser
1025                1030                1035                1040

Asn Leu Gly Asn Ile His Ala Ser Asn Asn Ile Met Phe Lys Leu Asp
                    1045                1050                1055

Gly Cys Arg Asp Thr His Arg Tyr Ile Trp Ile Lys Tyr Phe Asn Leu
                1060                1065                1070

Phe Asp Lys Glu Leu Asn Glu Lys Glu Ile Lys Asp Leu Tyr Asp Asn
                1075                1080                1085

Gln Ser Asn Ser Gly Ile Leu Lys Asp Phe Trp Gly Asp Tyr Leu Gln
                1090                1095                1100

Tyr Asp Lys Pro Tyr Tyr Met Leu Asn Leu Tyr Asp Pro Asn Lys Tyr
1105                1110                1115                1120
```

```
Val Asp Val Asn Asn Val Gly Ile Arg Gly Tyr Met Tyr Leu Lys Gly
        1125                1130                1135

Pro Arg Gly Ser Val Met Thr Thr Asn Ile Tyr Leu Asn Ser Ser Leu
    1140                1145                1150

Tyr Arg Gly Thr Lys Phe Ile Ile Lys Lys Tyr Ala Ser Gly Asn Lys
        1155                1160                1165

Asp Asn Ile Val Arg Asn Asn Asp Arg Val Tyr Ile Asn Val Val Val
    1170                1175                1180

Lys Asn Lys Glu Tyr Arg Leu Ala Thr Asn Ala Ser Gln Ala Gly Val
1185                1190                1195                1200

Glu Lys Ile Leu Ser Ala Leu Glu Ile Pro Asp Val Gly Asn Leu Ser
        1205                1210                1215

Gln Val Val Val Met Lys Ser Lys Asn Asp Gln Gly Ile Thr Asn Lys
        1220                1225                1230

Cys Lys Met Asn Leu Gln Asp Asn Asn Gly Asn Asp Ile Gly Phe Ile
        1235                1240                1245

Gly Phe His Gln Phe Asn Asn Ile Ala Lys Leu Val Ala Ser Asn Trp
    1250                1255                1260

Tyr Asn Arg Gln Ile Glu Arg Ser Ser Arg Thr Leu Gly Cys Ser Trp
1265                1270                1275                1280

Glu Phe Ile Pro Val Asp Asp Gly Trp Gly Glu Arg Pro Leu
        1285                1290
```

```
<210> SEQ ID NO 214
<211> LENGTH: 3918
<212> TYPE: DNA
<213> ORGANISM: Artificial Sequence
<220> FEATURE:
<221> NAME/KEY: mat_peptide
<222> LOCATION: (1)...(3915)
<223> OTHER INFORMATION: BoNT/A_A17

<400> SEQUENCE: 214
```

| | | | | | |
|---|---|---|---|---|---|
| atgccatttg | ttaataaaca | atttaattat | aaagatcctg | taaatggtgt | tgatattgct | 60 |
| tatataaaaa | ttccaaatgc | aggacaaatg | caaccagtaa | aagcttttaa | aattcataat | 120 |
| aaaatatggg | ttattccaga | agagatacca | tttacaaatc | ctgaagaagg | agatttaaat | 180 |
| ccaccaccag | aagcaaaaca | agttccagtt | tcatattatg | attcaacata | tttaagtaca | 240 |
| gataatgaaa | agataatta | tttaaaggga | gttacaaaat | tatttgagag | aatttattca | 300 |
| actgatcttg | gaagaatgtt | gttaacatca | atagtaaggg | gaataccatt | tgggggtgga | 360 |
| agtacaatag | atacagaatt | aaaagttatt | gatactaatt | gtattaatgt | gatacaacca | 420 |
| gatggtagtt | atagatcaga | agaacttaat | ctagtaataa | taggaccctc | agctgatatt | 480 |
| atacagtttg | aatgtaaaag | ctttggacat | gaagttttga | atcttacgcg | aaatggttat | 540 |
| ggctctactc | aatacattag | atttagccca | gattttacat | tggtttttga | ggagtcactt | 600 |
| gaagttgata | caaatcctct | tttaggtgca | ggcaaatttg | ctacagatcc | agcagtaaca | 660 |
| ttagcacatg | aacttataca | tgctggacat | agattatatg | gaatagcaat | taatccaaat | 720 |
| agggttttta | agtaaatac | taatgcctat | tatgaaatga | gtgggttaga | agtaagcttt | 780 |
| gaggaactta | gaacatttgg | gggacatgat | gcaaagttta | gatagtttt | acaggaaaac | 840 |
| gaatttcgtc | tatattatta | taataagttt | aaagatatag | caagtacact | aataaagct | 900 |
| aaatcaatag | taggtactac | tgcttcatta | cagtatatga | aaaatgtttt | taaagagaaa | 960 |
| tatctcctat | ctgaagatac | atctggaaaa | ttttcggtag | ataaattaaa | atttgataag | 1020 |

```
ttatacaaaa tgttaacaga gatttacaca gaggataatt tgttaagtt ttttaaagta    1080
cttaacagaa aaacatattt gaattttgat aaagccgtat ttaagataaa tatagtacct    1140
aaggtaaatt acacaatata tgatggattt aatttaagaa atacaaattt agcagcaaac    1200
tttaatggtc aaaatacaga aattaataat atgaatttta ctaaactaaa aaattttact    1260
ggattgtttg aatttttataa gttgctatgt gtaagaggga taataacttc taaatccaac   1320
aaaaccagaa ttgatgaggc caaccaacgt gcaacaaaga tgctgaataa ggcattaaat    1380
gatttatgta tcaaagttaa taattgggac ttgttttta gtccttcaga agataatttt    1440
actaatgatc taaataaagg agaagaaatt acatctgata ctaatataga agcagcagaa    1500
gaaaatatta gttagatttt aatacaacaa tattatttaa cctttaattt tgataatgaa    1560
cctgaaaata tttcaataga aaatctttca agtgacatta taggccaatt agaacttatg    1620
cctaatatag aaagatttcc taatggaaaa aagtatgagt tagataaaata tactatgttc    1680
cattatcttc gtgctcaaga atttgaacat ggtaaatcta ggattgcttt aacaaattct    1740
gttaacgaag cattattaaa tcctagtcgt gtttatacat tttttcttc agactatgta    1800
aagaaagtta ataaagctac ggaggcagct atgtttttag gctgggtaga acaattagta    1860
tatgatttta ccgatgaaac tagcgaagta agtactacgg ataaaattgc ggatataact    1920
ataattattc catatatagg acctgcttta aatataggta atatgttata taagatgat    1980
tttgtaggtg ctttaatatt ttcaggagct gttattctgt tagaatttat accagagatt    2040
gcaatacctg tattaggtac ttttgcactt gtatcatata ttgcgaataa ggttctaacc    2100
gttcaaacaa tagataatgc tttaagtaaa agaaatgaaa aatgggatga ggtctataaa    2160
tatatagtaa caaattggtt agcaaaggtt aatacacaga ttgatctaat aagaaaaaaa    2220
atgaaagaag ctttagaaaa tcaagcagaa gcaacaaagg ctataataaa ctatcagtat    2280
aatcaatata ctgaggaaga gaaaataat attaattttta atattgatga tttaagttcg    2340
aaacttaatg agtctataaa taaagctatg attaatataa ataaattttt gaatcaatgc    2400
tctgtttcat atttaatgaa ttctatgatc cctatggtg ttaaacggtt agaagatttt    2460
gatgctagtc ttaaagatgc attattaaag tatatatatg ataatagagg aactttaatt    2520
ggtcaagtag atagattaaa agataaagtt aataatacac ttagtacaga tatacctttt    2580
cagctttcca atacgtaga taatcaaaga ttattatcta catttactga atatattaag    2640
aatattatta atacttctat attgaattta agatatgaaa gtaatcattt aatagactta    2700
tctaggtatg catcaaaaat aaatattggt agtaaagtaa attttgatcc aatagataaa    2760
aatcaaattc aattatttaa tttagaaagt agtaaaattg aggtaatttt aaaaaatgct    2820
attgtatata atagtatgta tgaaaatttt agtactagct tttggataag aattcctaag    2880
tattttaaca gtataagtct aaataatgaa tatacaataa taaattgtat ggaaaataat    2940
tcaggatgga agtatcact taattatggt gaaataatct ggactttaca ggatactcag    3000
gaaataaaac aaagagtagt ttttaaatac agtcaaatga ttaatatatc agattatata    3060
aacagatgga tttttgtaac tatcactaat aatagattaa ataactctaa aatttatata    3120
aatggaagat taatagatca aaaaccaatt tcaaatttag gtaatattca tgctagtaat    3180
aatataatgt ttaaattaga tggttgtaga gatacacata gatatatttg gataaaatat    3240
tttaatcttt ttgataagga attaaatgaa aagaaaatca agatttata tgataatcaa    3300
tcaaattcag gtatttaaa agacttttgg ggtgattatt tacaatatga taaaccatac    3360
```

-continued

```
tatatgttaa atttatatga tccaaataaa tatgtcgatg taaataatgt aggtattaga   3420
ggttatatgt atcttaaagg gcctagaggt agcgtaatga ctacaaacat ttatttaaat   3480
tcaagtttgt ataggggggac aaaatttatt ataaaaaaat atgcttctgg aaataaagat   3540
aatattgtta gaaataatga tcgtgtatat attaatgtag tagttaaaaa taaagaatat   3600
aggttagcta ctaatgcgtc acaggcaggc gtagaaaaaa tactaagtgc attagaaata   3660
cctgatgtag gaaatctaag tcaagtagta gtaatgaagt caaaaaatga tcaaggaata   3720
acaaataaat gcaaaatgaa tttacaagat aataatggga atgatatagg ctttatagga   3780
tttcatcagt ttaataatat agctaaacta gtagcaagta attggtataa tagacaaata   3840
gaaagatcta gtaggacttt gggttgctca tgggaattta ttcctgtaga tgatggatgg   3900
ggagaaaggc cactgtaa                                                 3918
```

```
<210> SEQ ID NO 215
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_A8

<400> SEQUENCE: 215
```

```
atgccatttg ttaataaaca atttaattat aaagatcctg taaatggtgt tgatattgct     60
tatataaaaa ttccaaatgc aggacaaatg caaccagtaa aagcttttaa aattcataat    120
aaaatatggg ttattccaga aagagataca tttacaaatc ctgaagaagg agatttaaat    180
ccaccaccag aagcaaaaca agttccagtt tcatattatg attcaacata tttaagtaca    240
gataatgaaa aagataatta tttaaaggga gttacaaaat tatttgagag aatttattca    300
actgatcttg gaagaatgtt gttaacatca atagtaaggg gaataccatt ttggggtgga    360
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag ctttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaatttta ctaaactaaa aaattttact   1260
ggattgtttg aattttataa gttgctatgt gtaagaggga taataacttc taaagaggcc   1320
aaccaacgtg caacaaagaa taaggcatta aatgatttat gtatcaaagt taataattgg   1380
gacttgtttt ttagtccttc agaagataat tttactaatg atctaaataa aggagaagaa   1440
```

```
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740 cgtgttttata catttttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaacttta attggtcaag tagatagatt aaaagataaa   2520
gttaataata cacttagtac agatataccct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtattttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agttttaaaa   3000
tacagtcaaa tgattaatat atcagattat ataaacagat ggattttgt aactatcact    3060 aataatagat taaataactc taaaatttat ataaatggaa gattaataga tcaaaaacca   3120
atttcaaatt taggtaatat tcatgctagt aataatataa tgtttaaatt agatggttgt   3180
agagatacac atagatatat ttggataaaa tattttaatc ttttgataa ggaattaaat    3240 gaaaagaaa tcaaagattt atatgataat caatcaaatt caggtatttt aaaagacttt    3300
tggggtgatt atttacaata tgataaacca tactatatgt taaatttata tgatccaaat   3360
aaatatgtcg atgtaaataa tgtaggtatt agaggttata tgtatcttaa agggcctaga   3420
ggtagcgtaa tgactacaaa catttattta aattcaagtt tgtataggg gacaaaattt     3480 attataaaaa aatatgcttc tggaaataaa gataatattg ttagaaataa tgatcgtgta   3540
tatattaatg tagtagttaa aaataaagaa tataggttag ctactaatgc gtcacaggca   3600
ggcgtagaaa aaatactaag tgcattagaa atacctgatg taggaaatct aagtcaagta   3660
gtagtaatga agtcaaaaaa tgatcaagga ataacaaata aatgcaaaat gaatttacaa   3720
gataataatg ggaatgatat aggctttata ggatttcatc agtttaataa tatagctaaa   3780
```

| ctagtagcaa gtaattggta taatagacaa atagaaagat ctagtaggac tttgggttgc | 3840 |
| tcatgggaat ttattcctgt agatgatgga tggggagaaa ggccactgta a | 3891 |

<210> SEQ ID NO 216
<211> LENGTH: 3972
<212> TYPE: DNA
<213> ORGANISM: Artificial Sequence
<220> FEATURE:
<221> NAME/KEY: mat_peptide
<222> LOCATION: (1)...(3969)
<223> OTHER INFORMATION: BoNT/A_BT35

<400> SEQUENCE: 216

| atgccatttg ttaataaaca atttaattat aaagatcctg taaatggtgt tgatattgct | 60 |
| tatataaaaa ttccaaatgc aggacaaatg caaccagtaa aagcttttaa aattcataat | 120 |
| aaaatatggg ttattccaga aagagataca tttacaaatc ctgaagaagg agatttaaat | 180 |
| ccaccaccag aagcaaaaca agttccagtt tcatattatg attcaacata tttaagtaca | 240 |
| gataatgaaa agataatta tttaaaggga gttacaaaat tatttgagag aatttattca | 300 |
| actgatcttg gaagaatgtt gttaacatca atagtaaggg gaataccatt ttggggtgga | 360 |
| agtacaatag atacagaatt aaaagttatt gatactaatt gtattaatgt gatacaacca | 420 |
| gatggtagtt atagatcaga agaacttaat ctagtaataa taggaccctc agctgatatt | 480 |
| atacagtttg aatgtaaaag ctttggacat gaagttttga atcttacgcg aaatggttat | 540 |
| ggctctactc aatacattag atttagccca gattttacat ttggttttga ggagtcactt | 600 |
| gaagttgata caaatcctct tttaggtgca ggcaaatttg ctacagatcc agcagtaaca | 660 |
| ttagcacatg aacttataca tgctggacat agattatatg gaatagcaat taatccaaat | 720 |
| agggttttta aagtaaatac taatgcctat tatgaaatga gtgggttaga agtaagcttt | 780 |
| gaggaactta gaacatttgg gggacatgat gcaaagttta tagatagttt acaggaaaac | 840 |
| gaatttcgtc tatattatta taataagttt aaagatatag caagtacact aataaaagct | 900 |
| aaatcaatag taggtactac tgcttcatta cagtatatga aaaatgtttt taaagagaaa | 960 |
| tatctcctat ctgaagatac atctggaaaa ttttcggtag ataaattaaa atttgataag | 1020 |
| ttatacaaaa tgttaacaga gatttacaca gaggataatt ttgttaagtt ttttaaagta | 1080 |
| cttaacagaa aaacatattt gaattttgat aaagccgtat ttaagataaa tatagtacct | 1140 |
| aaggtaaatt acacaatata tgatggattt aatttaagaa atacaaattt agcagcaaac | 1200 |
| tttaatggtc aaaatacaga aattaataat atgaatttta ctaaactaaa aaatttact | 1260 |
| ggattgtttg aatttatata gttgctatgt gtaagaggga taataacttc taaactgtca | 1320 |
| gagctggatg accgagctga tgccttgcag gcaggagcat cacaatttga gagcagtgct | 1380 |
| gcaaagctaa agaggaagta ttggtggaaa aactgcaaga ataaggcatt aaatgattta | 1440 |
| tgtatcaaag ttaataattg ggacttgttt tttagtcctt cagaagataa ttttactaat | 1500 |
| gatctaaata aaggagaaga aattacatct gatactaata tagaagcagc agaagaaaat | 1560 |
| attagtttag atttaataca acaatattat ttaaccttta ttttgataa tgaacctgaa | 1620 |
| aatatttcaa tagaaaatct ttcaagtgac attataggcc aattagaact tatgcctaat | 1680 |
| atagaaagat ttcctaatgg aaaaaagtat gagttagata aatatactat gttccattat | 1740 |
| cttcgtgctc aagaatttga acatggtaaa tctaggattg ctttaacaaa ttctgttaac | 1800 |
| gaagcattat taaatcctag tcgtgtttat acatttttt cttcagacta tgtaaagaaa | 1860 |
| gttaataaag ctacggaggc agctatgttt ttaggctggg tagaacaatt agtatatgat | 1920 |

```
tttaccgatg aaactagcga agtaagtact acggataaaa ttgcggatat aactataatt    1980
attccatata taggacctgc tttaaatata ggtaatatgt tatataaaga tgattttgta    2040
ggtgctttaa tattttcagg agctgttatt ctgttagaat ttataccaga gattgcaata    2100
cctgtattag gtacttttgc acttgtatca tatattgcga ataaggttct aaccgttcaa    2160
acaatagata atgctttaag taaaagaaat gaaaaatggg atgaggtcta aaatatata     2220
gtaacaaatt ggttagcaaa ggttaataca cagattgatc taataagaaa aaaaatgaaa    2280
gaagctttag aaaatcaagc agaagcaaca aaggctataa taaactatca gtataatcaa    2340
tatactgagg aagagaaaaa taatattaat tttaatattg atgatttaag ttcgaaactt    2400
aatgagtcta taaataaagc tatgattaat ataaataaat ttttgaatca atgctctgtt    2460
tcatatttaa tgaattctat gatcccttat ggtgttaaac ggttagaaga ttttgatgct    2520
agtcttaaag atgcattatt aaagtatata tatgataata gaggaacttt aattggtcaa    2580
gtagatagat taaaagataa agttaataat acacttagta cagatatacc ttttcagctt    2640
tccaaatacg tagataatca aagattatta tctacattta ctgaatatat taagaatatt    2700
attaatactt ctatattgaa tttaagatat gaaagtaatc atttaataga cttatctagg    2760
tatgcatcaa aaataaatat tggtagtaaa gtaaattttg atccaataga taaaaatcaa    2820
attcaattat ttaatttaga aagtagtaaa attgaggtaa ttttaaaaaa tgctattgta    2880
tataatagta tgtatgaaaa ttttagtact agcttttgga taagaattcc taagtatttt    2940
aacagtataa gtctaaataa tgaatataca ataataaatt gtatggaaaa taattcagga    3000
tggaaagtat cacttaatta tggtgaaata atctggactt tacaggatac tcaggaaata    3060
aaacaaagag tagttttta aatacagtcaa atgattaata tatcagatta tataaacaga    3120
tggatttttg taactatcac taataatgaa ttaaataact ctaaaattta tataaatgga    3180
agattaatag atcaaaaacc aatttcaaat ttaggtaata ttcatgctag taataatata    3240
atgtttaaat tagatggttg tagagataca catagatata tttggataaa atattttaat    3300
cttttgata aggaattaaa tgaaaaagaa atcaaagatt tatatgataa tcaatcaaat    3360
tcaggtattt taaaagactt ttggggtgat tatttacaat atgataaacc atactatatg    3420
ttaaatttat atgatccaaa taaatatgtc gatgtaaata atgtaggtat tagaggttat    3480
atgtatctta aagggcctag aggtagcgta atgactacaa acatttattt aaattcaagt    3540
ttgtataggg ggacaaaatt tattataaaa aaatatgctt ctggaaataa agataatatt    3600
gttagaaata atgatcgtgt atatattaat gtagtagtta aaaataaaga atataggtta    3660
gctactaatg cgtcacaggc aggcgtagaa aaaatactaa gtgcattaga aatacctgat    3720
gtaggaaatc taagtcaagt agtagtaatg aagtcaaaaa atgatcaagg aataacaaat    3780
aaatgcaaaa tgaatttaca agataataat gggaatgata taggctttat aggatttcat    3840
cagtttaata atatagctaa actagtagca agtaattggt ataatagaca aatagaaaga    3900
tctagtagga ctttgggttg ctcatgggaa tttattcctg tagatgatgg atggggagaa    3960
aggccactgt aa                                                        3972
```

<210> SEQ ID NO 217
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)

<223> OTHER INFORMATION: BoNT/A_BT8

<400> SEQUENCE: 217

```
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttggggtgga     360
agtacaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gattttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta agtaaatac taatgcctat tatgaaatga gtgggttaga agtaagcttt     780
gaggaactta gaacatttgg gggacatgat gcaaagttta tagatagttt acaggaaaac     840
gaatttcgtc tatattatta taataagttt aaagatatag caagtacact taataaagct     900
aaatcaatag taggtactac tgcttcatta cagtatatga aaaatgtttt taaagagaaa     960
tatctcctat ctgaagatac atctggaaaa ttttcggtag ataaattaaa atttgataag    1020
ttatacaaaa tgttaacaga gatttacaca gaggataatt ttgttaagtt ttttaaagta    1080
cttaacagaa aaacatattt gaattttgat aaagccgtat ttaagataaa tatagtacct    1140
aaggtaaatt acacaatata tgatggattt aatttaagaa atacaaattt agcagcaaac    1200
tttaatggtc aaaatacaga aattaataat atgaatttta ctaaactaaa aaatttttact    1260
ggattgtttg aatttttataa gttgctatgt gtaagaggga taataacttc taaaggagca    1320
tcacaatttg agaccagtaa taaggcatta aatgattat gtatcaaagt taataattgg    1380
gacttgtttt ttagtccttc agaagataat tttactaatg atctaaataa aggaagaa     1440
attacatctg atactaatat agaagcagca gaagaaaata ttagtttaga tttaatacaa    1500
caatattatt taacctttaa ttttgataat gaacctgaaa atatttcaat agaaaatctt    1560
tcaagtgaca ttataggcca attagaactt atgcctaata tagaaagatt tcctaatgga    1620
aaaaagtatg agttagataa atatactatg ttccattatc ttcgtgctca agaatttgaa    1680
catggtaaat ctaggattgc tttaacaaat tctgttaacg aagcattatt aaatcctagt    1740
cgtgtttata catttttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tacttttgca    2040
cttgtatcat atattgcgaa taaggttcta accgttcaaa caatagataa tgctttaagt    2100
aaaagaaatg aaaaatggga tgaggtctat aaatatatag taacaaattg gttagcaaag    2160
gttaatacac agattgatct aataagaaaa aaaatgaaag aagctttaga aaatcaagca    2220
gaagcaacaa aggctataat aaactatcag tataatcaat atactgagga agagaaaaat    2280
```

-continued

```
aatattaatt ttaatattga tgatttaagt tcgaaactta atgagtctat aaataaagct    2340
atgattaata taaataaatt tttgaatcaa tgctctgttt catatttaat gaattctatg    2400
atcccttatg gtgttaaacg gttagaagat tttgatgcta gtcttaaaga tgcattatta    2460
aagtatatat atgataatag aggaacttta attggtcaag tagatagatt aaaagataaa    2520
gttaataata cacttagtac agatatacct tttcagcttt ccaaatacgt agataatcaa    2580
agattattat ctacatttac tgaatatatt aagaatatta ttaatacttc tatattgaat    2640
ttaagatatg aaagtaatca tttaatagac ttatctaggt atgcatcaaa ataaatatt     2700 ggtagtaaag taaattttga tccaatagat aaaaatcaaa ttcaattatt taatttagaa    2760
agtagtaaaa ttgaggtaat tttaaaaaat gctattgtat ataatagtat gtatgaaaat    2820
tttagtacta gcttttggat aagaattcct aagtatttta acagtataag tctaaataat    2880
gaatatacaa taataaattg tatggaaaat aattcaggat ggaaagtatc acttaattat    2940
ggtgaaataa tctggacttt acaggatact caggaaataa aacaaagagt agtttttaaa    3000
tacagtcaaa tgattaatat atcagattat ataaacagat ggattttgt aactatcact     3060 aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tattttaatc ttttgataaa ggaattaaat    3240 gaaaagaaa tcaaagattt atatgataat caatcaaatt caggtatttt aaaagacttt     3300
tggggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttatta aattcaagtt tgtataggg gacaaaattt      3480 attataaaaa aatatgcttc tggaaataaa gataatattg ttagaaataa tgatcgtgta    3540
tatattaatg tagtagttaa aaataaagaa tataggttag ctactaatgc gtcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 218
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_Csyn8

<400> SEQUENCE: 218

```
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat    180
ccaccaccag aagcaaaaca agttccagtt tcatatattg attcaacata tttaagtaca    240
gataatgaaa aagataatta tttaaaggga gttacaaaat atttgagag aatttattca     300 actgatcttg gaagaatgtt gttaacatca atagtaaggg gaataccatt ttggggtgga    360
```

-continued

```
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag ctttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaatttta ctaaactaaa aaattttact   1260
ggattgtttg aattttataa gttgctatgt gtaagaggga taataacttc taaagacacc   1320
aagaaggccg tcaagtacaa taaggcatta aatgatttat gtatcaaagt aataattgg    1380 gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata cattttttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tactttttgca   2040 cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaacttta attggtcaag tagatagatt aaaagataaa   2520
gttaataata cacttagtac agatataacct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
```

| | |
|---|---:|
| agtagtaaaa ttgaggtaat tttaaaaaat gctattgtat ataatagtat gtatgaaaat | 2820 |
| tttagtacta gcttttggat aagaattcct aagtatttta acagtataag tctaaataat | 2880 |
| gaatatacaa taataaattg tatggaaaat aattcaggat ggaaagtatc acttaattat | 2940 |
| ggtgaaataa tctggacttt acaggatact caggaaataa aacaaagagt agttttaaa | 3000 |
| tacagtcaaa tgattaatat atcagattat ataaacagat ggattttgt aactatcact | 3060 |
| aataatagat taaataactc taaaatttat ataaatggaa gattaataga tcaaaaacca | 3120 |
| atttcaaatt taggtaatat tcatgctagt aataatataa tgtttaaatt agatggttgt | 3180 |
| agagatacac atagatatat ttggataaaa tattttaatc tttttgataa ggaattaaat | 3240 |
| gaaaaagaaa tcaaagattt atatgataat caatcaaatt caggtatttt aaaagacttt | 3300 |
| tggggtgatt atttacaata tgataaacca tactatatgt taaatttata tgatccaaat | 3360 |
| aaatatgtcg atgtaaataa tgtaggtatt agaggttata tgtatcttaa agggcctaga | 3420 |
| ggtagcgtaa tgactacaaa catttattta aattcaagtt tgtataggggg gacaaaattt | 3480 |
| attataaaaa aatatgcttc tggaaataaa gataatattg ttagaaataa tgatcgtgta | 3540 |
| tatattaatg tagtagttaa aaataaagaa tataggttag ctactaatgc gtcacaggca | 3600 |
| ggcgtagaaa aaatactaag tgcattagaa atacctgatg taggaaatct aagtcaagta | 3660 |
| gtagtaatga agtcaaaaaa tgatcaagga ataacaaata aatgcaaaat gaatttacaa | 3720 |
| gataataatg ggaatgatat aggctttata ggatttcatc agtttaataa tatagctaaa | 3780 |
| ctagtagcaa gtaattggta taatagacaa atagaaagat ctagtaggac tttgggttgc | 3840 |
| tcatgggaat ttattcctgt agatgatgga tggggagaaa ggccactgta a | 3891 |

<210> SEQ ID NO 219
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_Csnp8

<400> SEQUENCE: 219

| | |
|---|---:|
| atgccatttg ttaataaaca atttaattat aaagatcctg taaatggtgt tgatattgct | 60 |
| tatataaaaa ttccaaatgc aggacaaatg caaccagtaa aagcttttaa aattcataat | 120 |
| aaaatatggg ttattccaga aagagataca tttacaaatc ctgaagaagg agatttaaat | 180 |
| ccaccaccag aagcaaaaca agttccagtt tcatatattatg attcaacata tttaagtaca | 240 |
| gataatgaaa aagataatta tttaaaggga gttacaaaat tatttgagag aatttattca | 300 |
| actgatcttg gaagaatgtt gttaacatca atagtaaggg gaataccatt tgggggtgga | 360 |
| agtacaatag atcagaatt aaaagttatt gatactaatt gtattaatgt gatacaacca | 420 |
| gatggtagtt atagatcaga agaacttaat ctagtaataa taggaccctc agctgatatt | 480 |
| atacagtttg aatgtaaaag ctttggacat aagttttga atcttacgcg aaatggttat | 540 |
| ggctctactc aatacattag atttagccca gattttacat ttgttttga ggagtcactt | 600 |
| gaagttgata caaatcctct tttaggtgca ggcaaatttg ctacagatcc agcagtaaca | 660 |
| ttagcacatg aacttataca tgctggacat agattatatg gaatagcaat taatccaaat | 720 |
| agggtttta agtaaatac taatgcctat tatgaaatga gtgggttaga agtaagcttt | 780 |
| gaggaactta aacatttggg gggacatgat gcaaagttta gatagttt acaggaaaac | 840 |

```
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaattta ctaaactaaa aaattttact   1260
ggattgtttg aattttataa gttgctatgt gtaagaggga taataacttc taaagccaac   1320
caacgtgcaa caaagatgaa taaggcatta aatgatttat gtatcaaagt taataattgg   1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata cattttttc ttcagactat gtaaagaaag ttaataaagc tacgaaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaactta attggtcaag tagatagatt aaaagataaa   2520
gttaataata cacttagtac agatataccct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa acaaagagt agttttaaa   3000
tacagtcaaa tgattaatat atcagattat ataaacagat ggattttgt aactatcact   3060
aataatagat aaataactc taaaattat ataaatggaa gattaataga tcaaaaacca   3120
atttcaaatt taggtaatat tcatgctagt aataataaa tgtttaaatt agatggttgt   3180
agagatacac atagatatat ttggataaaa tattttaatc tttttgataa ggaattaaat   3240
```

| | |
|---|---|
| gaaaaagaaa tcaaagattt atatgataat caatcaaatt caggtatttt aaaagacttt | 3300 |
| tggggtgatt atttacaata tgataaacca tactatatgt taaatttata tgatccaaat | 3360 |
| aaatatgtcg atgtaaataa tgtaggtatt agaggttata tgtatcttaa agggcctaga | 3420 |
| ggtagcgtaa tgactacaaa catttattta aattcaagtt tgtataggg gacaaaattt | 3480 |
| attataaaaa aatatgcttc tggaaataaa gataatattg ttagaaataa tgatcgtgta | 3540 |
| tatattaatg tagtagttaa aaataaagaa tataggttag ctactaatgc gtcacaggca | 3600 |
| ggcgtagaaa aaatactaag tgcattagaa atacctgatg taggaaatct aagtcaagta | 3660 |
| gtagtaatga agtcaaaaaa tgatcaagga ataacaaata aatgcaaaat gaatttacaa | 3720 |
| gataataatg ggaatgatat aggctttata ggatttcatc agtttaataa tatagctaaa | 3780 |
| ctagtagcaa gtaattggta taatagacaa atagaaagat ctagtaggac tttgggttgc | 3840 |
| tcatgggaat ttattcctgt agatgatgga tggggagaaa ggccactgta a | 3891 |

<210> SEQ ID NO 220
<211> LENGTH: 3984
<212> TYPE: DNA
<213> ORGANISM: Artificial Sequence
<220> FEATURE:
<221> NAME/KEY: mat_peptide
<222> LOCATION: (1)...(3981)
<223> OTHER INFORMATION: BoNT/A_DF39

<400> SEQUENCE: 220
atgccatttg ttaataaaca atttaattat aaagatcctg taaatggtgt tgatattgct 60
tatataaaaa ttccaaatgc aggacaaatg caaccagtaa aagcttttaa aattcataat 120
aaaatatggg ttattccaga aagagataca tttacaaatc ctgaagaagg agatttaaat 180
ccaccaccag aagcaaaaca agttccagtt tcatattatg attcaacata tttaagtaca 240
gataatgaaa aagataatta tttaaaggga gttacaaaat tatttgagag aatttattca 300
actgatcttg gaagaatgtt gttaacatca atagtaaggg gaataccatt ttggggtgga 360
agtacaatag atacagaatt aaaagttatt gatactaatt gtattaatgt gatacaacca 420
gatggtagtt atagatcaga agaacttaat ctagtaataa taggaccctc agctgatatt 480
atacagtttg aatgtaaaag ctttggacat gaagttttga atcttacgcg aaatggttat 540
ggctctactc aatacattag atttagccca gattttacat ttggttttga ggagtcactt 600
gaagttgata caaatcctct tttaggtgca ggcaaatttg ctacagatcc agcagtaaca 660
ttagcacatg aacttataca tgctggacat agattatatg gaatagcaat taatccaaat 720
agggttttta aagtaaatac taatgcctat tatgaaatga gtgggttaga agtaagcttt 780
gaggaactta gaacatttgg gggacatgat gcaaagttta tagatagttt acaggaaaac 840
gaatttcgtc tatattatta taataagttt aaagatatag caagtacact taataaagct 900
aaatcaatag taggtactac tgcttcatta cagtatatga aaaatgtttt taaagagaaa 960
tatctcctat ctgaagatac atctggaaaa ttttcggtag ataaattaaa atttgataag 1020
ttatacaaaa tgttaacaga gatttacaca gaggataatt ttgttaagtt ttttaaagta 1080
cttaacagaa aaacatattt gaattttgat aaagccgtat ttaagataaa tatagtacct 1140
aaggtaaatt acacaatata tgatggattt aatttaagaa atacaaattt agcagcaaac 1200
tttaatggtc aaaatacaga aattaataat atgaatttta ctaaactaaa aaattttact 1260
ggattgtttg aattttataa gttgctatgt gtaagaggga taataacttc taaagcacaa 1320

```
gtggaggagg tggtggacat catacgtgtg aacgtggaca aggtcctgga gagggaccag      1380
aagctgtcag agctggatga ccgagctgat gccttgcagg caggagcatc aaataaggca      1440
ttaaatgatt tatgtatcaa agttaataat tgggacttgt tttttagtcc ttcagaagat      1500
aattttacta atgatctaaa taaggagaa gaaattacat ctgatactaa tatagaagca       1560
gcagaagaaa atattagttt agatttaata caacaatatt atttaacctt taattttgat      1620
aatgaacctg aaaatatttc aatagaaaat ctttcaagtg acattatagg ccaattagaa      1680
cttatgccta atatagaaag atttcctaat ggaaaaaagt atgagttaga taaatatact      1740
atgttccatt atcttcgtgc tcaagaattt gaacatggta atctaggat tgctttaaca       1800 aattctgtta acgaagcatt attaaatcct agtcgtgttt atacattttt ttcttcagac      1860
tatgtaaaga aagttaataa agctacggag gcagctatgt ttttaggctg ggtagaacaa      1920
ttagtatatg atttaccga tgaaactagc gaagtaagta ctacggataa aattgcggat      1980
ataactataa ttattccata tataggacct gctttaaata taggtaatat gttatataaa      2040
gatgattttg taggtgcttt aatattttca ggagctgtta ttctgttaga atttatacca     2100
gagattgcaa tacctgtatt aggtactttt gcacttgtat catatattgc gaataaggtt     2160
ctaaccgttc aaacaataga taatgcttta agtaaaagaa atgaaaaatg ggatgaggtc     2220
tataaatata tagtaacaaa ttggttagca aaggttaata cacagattga tctaataaga     2280
aaaaaaatga agaagctttt agaaaatcaa gcagaagcaa caaaggctat aataaactat     2340
cagtataatc aatatactga ggaagagaaa aataatatta atttaatat tgatgattta      2400 agttcgaaac ttaatgagtc tataaataaa gctatgatta atataaataa attttttgaat    2460 caatgctctg tttcatatt taatgaattct atgatccctt atggtgttaa acggttagaa     2520
gattttgatg ctagtcttaa agatgcatta ttaaagtata tatatgataa tagaggaact     2580
ttaattggtc aagtagatag attaaaaagat aaagttaata atacacttag tacagatata   2640 cctttttcagc tttccaaata cgtagataat caaagattat tatctacatt tactgaatat   2700
attaagaata ttattaatac ttctatattg aatttaagat atgaaagtaa tcatttaata     2760
gacttatcta ggtatgcatc aaaaataaat attggtagta agtaaatttt tgatccaata    2820
gataaaaatc aaattcaatt atttaattta gaaagtagta aaattgaggt aattttaaaa    2880
aatgctattg tatataatag tatgtatgaa aattttagta ctagcttttg gataagaatt    2940
cctaagtatt ttaacagtat aagtctaaat aatgaatata caataataaa ttgtatggaa    3000
aataattcag gatggaaagt atcacttaat tatggtgaaa taatctggac tttacaggat    3060
actcaggaaa taaacaaag agtagttttt aaatacagtc aaatgattaa tatatcagat     3120
tatataaaca gatggatttt tgtaactatc actaataata gattaaataa ctctaaaatt    3180
tatataaatg gaagattaat agatcaaaaa ccaatttcaa atttaggtaa tattcatgct    3240
agtaataata taatgtttaa attagatggt tgtagagata cacatagata tatttggata    3300
aaatatttta atcttttga taaggaatta aatgaaaaag aaatcaaaga tttatatgat    3360
aatcaatcaa attcaggtat tttaaaagac ttttggggtg attatttaca atatgataaa    3420
ccatactata tgttaaattt atatgatcca aataaatatg tcgatgtaaa taatgtaggt    3480
attagaggtt atatgtatct taagggcct agaggtagcg taatgactac aaacattat     3540 ttaaattcaa gtttgtatag ggggacaaaa tttattataa aaaaatatgc ttctggaaat    3600
aaagataata ttgttagaaa taatgatcgt gtatatatta atgtagtagt taaaaataaa    3660
gaatataggt tagctactaa tgcgtcacag gcaggcgtag aaaaaatact aagtgcatta    3720
```
gaaatacctg atgtaggaaa tctaagtcaa gtagtagtaa tgaagtcaaa aaatgatcaa 3780
ggaataacaa ataaatgcaa aatgaattta caagataata atgggaatga tataggcttt 3840
ataggatttc atcagtttaa taatatagct aaactagtag caagtaattg gtataataga 3900
caaatagaaa gatctagtag gactttgggt tgctcatggg aatttattcc tgtagatgat 3960
ggatggggag aaaggccact gtaa 3984

<210> SEQ ID NO 221
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_D8

<400> SEQUENCE: 221
atgccatttg ttaataaaca atttaattat aaagatcctg taaatggtgt tgatattgct 60
tatataaaaa ttccaaatgc aggacaaatg caaccagtaa aagcttttaa aattcataat 120
aaaatatggg ttattccaga aagagataca tttacaaatc ctgaagaagg agatttaaat 180
ccaccaccag aagcaaaaca agttccagtt tcatattatg attcaacata tttaagtaca 240
gataatgaaa aagataatta tttaaaggga gttacaaaat tatttgagag aatttattca 300
actgatcttg gaagaatgtt gttaacatca atagtaaggg gaataccatt ttggggtgga 360
agtacaatag atacagaatt aaaagttatt gatactaatt gtattaatgt gatacaacca 420
gatggtagtt atagatcaga agaacttaat ctagtaataa taggaccctc agctgatatt 480
atacagtttg aatgtaaaag ctttggacat gaagttttga atcttacgcg aaatggttat 540
ggctctactc aatacattag atttagccca gattttacat ttggttttga ggagtcactt 600
gaagttgata caaatcctct tttaggtgca ggcaaatttg ctacagatcc agcagtaaca 660
ttagcacatg aacttataca tgctggacat agattatatg gaatagcaat taatccaaat 720
agggttttta aagtaaatac taatgcctat tatgaaatga gtgggttaga agtaagcttt 780
gaggaactta gaacatttgg gggacatgat gcaaagttta tagatagttt acaggaaaac 840
gaatttcgtc tatattatta taataagttt aaagatatag caagtacact taataaagct 900
aaatcaatag taggtactac tgcttcatta cagtatatga aaaatgtttt taaagagaaa 960
tatctcctat ctgaagatac atctggaaaa ttttcggtag ataaattaaa atttgataag 1020
ttatacaaaa tgttaacaga gatttacaca gaggataatt ttgttaagtt ttttaaagta 1080
cttaacagaa aaacatattt gaattttgat aaagccgtat ttaagataaa tatagtacct 1140
aaggtaaatt acacaatata tgatggattt aatttaagaa atacaaattt agcagcaaac 1200
tttaatggtc aaaatacaga aattaataat atgaatttta ctaaactaaa aaattttact 1260
ggattgtttg aattttataa gttgctatgt gtaagaggga taataacttc taaaagggac 1320
cagaagctgt cagagctgaa taaggcatta aatgatttat gtatcaaagt taataattgg 1380
gacttgtttt ttagtccttc agaagataat tttactaatg atctaaataa aggagaagaa 1440
attacatctg atactaatat agaagcagca gaagaaaata ttagtttaga tttaatacaa 1500
caatattatt taacctttaa ttttgataat gaacctgaaa atatttcaat agaaaatctt 1560
tcaagtgaca ttataggcca attagaactt atgcctaata tagaaagatt tcctaatgga 1620
aaaaagtatg agttagataa atatactatg ttccattatc ttcgtgctca agaatttgaa 1680

```
catggtaaat ctaggattgc tttaacaaat tctgttaacg aagcattatt aaatcctagt    1740
cgtgtttata cattttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tacttttgca    2040
cttgtatcat atattgcgaa taaggttcta accgttcaaa caatagataa tgctttaagt    2100
aaaagaaatg aaaaatggga tgaggtctat aaatatatag taacaaattg gttagcaaag    2160
gttaatacac agattgatct aataagaaaa aaaatgaaag aagctttaga aaatcaagca    2220
gaagcaacaa aggctataat aaactatcag tataatcaat atactgagga agagaaaaat    2280
aatattaatt ttaatattga tgatttaagt tcgaaactta atgagtctat aaataaagct    2340
atgattaata taaataaatt tttgaatcaa tgctctgttt catatttaat gaattctatg    2400
atcccttatg gtgttaaacg gttagaagat tttgatgcta gtcttaaaga tgcattatta    2460
aagtatatat atgataatag aggaacttta attggtcaag tagatagatt aaaagataaa    2520
gttaataata cacttagtac agatatacct tttcagcttt ccaaatacgt agataatcaa    2580
agattattat ctacatttac tgaatatatt aagaatatta ttaatacttc tatattgaat    2640
ttaagatatg aaagtaatca tttaatagac ttatctaggt atgcatcaaa aataaatatt    2700
ggtagtaaag taaatttga tccaatagat aaaaatcaaa ttcaattatt taatttagaa    2760
agtagtaaaa ttgaggtaat tttaaaaaat gctattgtat ataatagtat gtatgaaaat    2820
tttagtacta gctttggat aagaattcct aagtatttta acagtataag tctaaataat    2880
gaatatacaa taataaattg tatggaaaat aattcaggat ggaaagtatc acttaattat    2940
ggtgaaataa tctggacttt acaggatact caggaaataa acaaagagt agtttttaaa    3000
tacagtcaaa tgattaatat atcagattat ataaacagat ggattttgt aactatcact    3060
aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tattttaatc ttttgataa ggaattaaat    3240
gaaaagaaa tcaaagattt atatgataat caatcaaatt caggtatttt aaaagacttt    3300
tggggtgatt atttcaaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttattta aattcaagtt tgtataggg gacaaaattt    3480
attataaaaa aatatgcttc tggaaataaa gataatattg ttagaaataa tgatcgtgta    3540
tatattaatg tagtagttaa aaataaagaa tataggttag ctactaatgc gtcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg gaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a            3891
```

<210> SEQ ID NO 222
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_E8

<400> SEQUENCE: 222

```
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga agagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttggggtgga     360
agtacaatag atacagaatt aaaagttatt gatactaatt gtattaatgt gatacaacca     420
gatggtagtt atagatcaga gaacttaat ctagtaataa taggaccctc agctgatatt     480
atacagtttg aatgtaaaag cttggacat gaagttttga atcttacgcg aaatggttat     540
ggctctactc aatacattag atttagccca gattttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta aagtaaatac taatgcctat atgaaatga gtgggttaga agtaagcttt     780
gaggaactta gaacatttgg gggacatgat gcaaagttta tagatagtttt acaggaaaaac     840
gaatttcgtc tatattatta taataagttt aagatatag caagtacact aataaaagct     900
aaatcaatag taggtactac tgcttcatta cagtatatga aaaatgtttt taaagagaaa     960
tatctcctat ctgaagatac atctggaaaa ttttcggtag ataaattaaa atttgataag    1020
ttatacaaaa tgttaacaga gatttacaca gaggataatt tgttaagtt ttttaaagta    1080
cttaacagaa aaacatatttt gaattttgat aaagccgtat ttaagataaa tatagtacct    1140
aaggtaaatt acacaatata tgatggattt aatttaagaa atacaaattt agcagcaaac    1200
tttaatggtc aaaatacaga aattaataat atgaatttta ctaaactaaa aaatttttact    1260
ggattgtttg aattttataa gttgctatgt gtaagaggga ataacttc taaacagatc    1320
gacaggatca tggagaagaa taaggcatta aatgatttat gtatcaaagt taataattgg    1380
gacttgtttt ttagtccttc agaagataat tttactaatg atctaaataa aggagaagaa    1440
attacatctg atactaatat agaagcagca gaagaaaata ttagtttaga tttaatacaa    1500
caatattatt taaacttaa ttttgataat gaacctgaaa atatttcaat agaaaatctt    1560
tcaagtgaca ttataggcca attagaactt atgcctaata tagaaagatt tcctaatgga    1620
aaaaagtatg agttagataa atatactatg ttccattatc tccgtgctca gaatttgaa    1680
catggtaaat ctaggattgc tttaacaaat tctgttaacg aagcattatt aaatcctagt    1740
cgtgtttata catttttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tacttttgca    2040
cttgtatcat atattgcgaa taaggttcta accgttcaaa caatgataaa tgctttaagt    2100
aaagaaatg aaaaatggga tgaggtctat aaatatatag taacaattg gttagcaaag    2160
```

| | |
|---|---|
| gttaatacac agattgatct aataagaaaa aaaatgaaag aagctttaga aaatcaagca | 2220 |
| gaagcaacaa aggctataat aaactatcag tataatcaat atactgagga agagaaaaat | 2280 |
| aatattaatt ttaatattga tgatttaagt tcgaaactta atgagtctat aaataaagct | 2340 |
| atgattaata taaataaatt tttgaatcaa tgctctgttt catatttaat gaattctatg | 2400 |
| atcccttatg gtgttaaacg gttagaagat tttgatgcta gtcttaaaga tgcattatta | 2460 |
| aagtatatat atgataatag aggaacttta attggtcaag tagatagatt aaaagataaa | 2520 |
| gttaataata cacttagtac agatataacct tttcagcttt ccaaatacgt agataatcaa | 2580 |
| agattattat ctacatttac tgaatatatt aagaatatta ttaatacttc tatattgaat | 2640 |
| ttaagatatg aaagtaatca tttaatagac ttatctaggt atgcatcaaa aataaatatt | 2700 |
| ggtagtaaag taaattttga tccaatagat aaaaatcaaa ttcaattatt taatttagaa | 2760 |
| agtagtaaaa ttgaggtaat tttaaaaaat gctattgtat ataatagtat gtatgaaaat | 2820 |
| tttagtacta gcttttggat aagaattcct aagtatttta acagtataag tctaaataat | 2880 |
| gaatatacaa taataaattg tatggaaaat aattcaggat ggaaagtatc acttaattat | 2940 |
| ggtgaaaata tctggacttt acaggatact caggaaataa aacaaagagt agttttttaaa | 3000 |
| tacagtcaaa tgattaatat atcagattat ataaacagat ggatttttgt aactatcact | 3060 |
| aataatagat taaataactc taaaatttat ataaatggaa gattaataga tcaaaaacca | 3120 |
| atttcaaatt taggtaatat tcatgctagt aataatataa tgtttaaatt agatggttgt | 3180 |
| agagatacac atagatatat ttggataaaa tatttttaatc tttttgataa ggaattaaat | 3240 |
| gaaaagaaa tcaaagattt atatgataat caatcaaatt caggtatttt aaaagacttt | 3300 |
| tggggtgatt atttcacaata tgataaacca tactatatgt taaatttata tgatccaaat | 3360 |
| aaatatgtcg atgtaaataa tgtaggtatt agaggttata tgtatcttaa agggcctaga | 3420 |
| ggtagcgtaa tgactacaaa catttatttta aattcaagtt tgtataggg gacaaaattt | 3480 |
| attataaaaa aatatgcttc tggaaataaa gataatattg ttagaaataa tgatcgtgta | 3540 |
| tatattaatg tagtagttaa aaataaagaa tataggttag ctactaatgc gtcacaggca | 3600 |
| ggcgtagaaa aaatactaag tgcattagaa atacctgatg taggaaatct aagtcaagta | 3660 |
| gtagtaatga gtcaaaaaaa tgatcaagga ataacaaata aatgcaaaat gaatttacaa | 3720 |
| gataataatg ggaatgatat aggctttata ggatttcatc agtttaataa atatagctaaa | 3780 |
| ctagtagcaa gtaattggta taatagacaa atagaaagat ctagtaggac tttgggttgc | 3840 |
| tcatgggaat ttattcctgt agatgatgga tggggagaaa ggccactgta a | 3891 |

<210> SEQ ID NO 223
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_F8

<400> SEQUENCE: 223

| | |
|---|---|
| atgccatttg ttaataaaca atttaattat aaagatcctg taaatggtgt tgatattgct | 60 |
| tatataaaaa ttccaaatgc aggacaaatg caaccagtaa aagcttttaa aattcataat | 120 |
| aaaatatggg ttattccaga aagagataca tttacaaatc ctgaagaagg agatttaaat | 180 |
| ccaccaccag aagcaaaaca agttccagtt tcatattatg attcaacata tttaagtaca | 240 |
| gataatgaaa aagataatta tttaaaggga gttacaaaat tatttgagag aatttattca | 300 |

```
actgatcttg gaagaatgtt gttaacatca atagtaaggg gaataccatt ttggggtgga      360
agtacaatag atacagaatt aaaagttatt gatactaatt gtattaatgt gatacaacca      420
gatggtagtt atagatcaga agaacttaat ctagtaataa taggaccctc agctgatatt      480
atacagtttg aatgtaaaag ctttggacat gaagttttga atcttacgcg aaatggttat      540
ggctctactc aatacattag atttagccca gattttacat ttggttttga ggagtcactt      600
gaagttgata caaatcctct tttaggtgca ggcaaatttg ctacagatcc agcagtaaca      660
ttagcacatg aacttataca tgctggacat agattatatg gaatagcaat taatccaaat      720
agggttttta aagtaaatac taatgcctat tatgaaatga gtgggttaga agtaagcttt      780
gaggaactta aacatttgg gggacatgat gcaaagttta tagatagttt acaggaaaac      840
gaatttcgtc tatattatta taataagttt aaagatatag caagtacact aataaagct       900 aaatcaatag taggtactac tgcttcatta cagtatatga aaaatgtttt taaagagaaa      960
tatctcctat ctgaagatac atctggaaaa ttttcggtag ataaattaaa atttgataag     1020
ttatacaaaa tgttaacaga gatttacaca gaggataatt ttgttaagtt ttttaaagta     1080
cttaacagaa aaacatattt gaattttgat aaagccgtat ttaagataaa tatagtacct     1140
aaggtaaatt acacaatata tgatggattt aatttaagaa atacaaattt agcagcaaac     1200
tttaatggtc aaaatacaga aattaataat atgaatttta ctaaactaaa aaattttact     1260
ggattgtttg aatttttataa gttgctatgt gtaagaggga taataacttc taaagagagg     1320
gaccagaagc tgtcagagaa taaggcatta aatgatttat gtatcaaagt taataattgg     1380
gacttgtttt ttagtccttc agaagataat tttactaatg atctaaataa aggagaagaa     1440
attacatctg atactaatat agaagcagca gaagaaaata ttagtttaga tttaatacaa     1500
caatattatt taacctttaa ttttgataat gaacctgaaa atatttcaat agaaaatctt     1560
tcaagtgaca ttataggcca attagaactt atgcctaata tagaaagatt tcctaatgga     1620
aaaaagtatg agttagataa atatactatg ttccattatc ttcgtgctca agaatttgaa     1680
catggtaaat ctaggattgc tttaacaaat tctgttaacg aagcattatt aaatcctagt     1740
cgtgtttata cattttttc ttcagactat gtaaagaaag ttaataaagc tacggaggca     1800
gctatgtttt taggctgggt agaacaatta gtatatgatt ttaccgatga aactagcgaa     1860
gtaagtacta cggataaaat tgcggatata actataatta ttccatatat aggacctgct     1920
ttaaatatag gtaatatgtt atataaagat gattttgtag gtgctttaat attttcagga     1980
gctgttattc tgttagaatt tataccagag attgcaatac ctgtattagg tacttttgca     2040
cttgtatcat atattgcgaa taaggttcta accgttcaaa caatagataa tgctttaagt     2100
aaaagaaatg aaaaatggga tgaggtctat aaatatatag taacaaattg gttagcaaag     2160
gttaatacac agattgatct aataagaaaa aaaatgaaag aagctttaga aaatcaagca     2220
gaagcaacaa aggctataat aaactatcag tataatcaat atactgagga agagaaaaat     2280
aatattaatt ttaatattga tgatttaagt tcgaaactta atgagtctat aaataaagct     2340
atgattaata taaataaatt tttgaatcaa tgctctgttt catatttaat gaattctatg     2400
atcccttatg gtgttaaacg gttagaagat tttgatgcta gtcttaaaga tgcattatta     2460
aagtatatat atgataatag aggaacttta attggtcaag tagatagatt aaaagataaa     2520
gttaataata cacttagtac agatatacct tttcagcttt ccaaatacgt agataatcaa     2580
agattattat ctacatttac tgaatatatt aagaatatta ttaatacttc tatattgaat     2640
```

| | |
|---|---|
| ttaagatatg aaagtaatca tttaatagac ttatctaggt atgcatcaaa aataaatatt | 2700 |
| ggtagtaaag taaattttga tccaatagat aaaaatcaaa ttcaattatt taatttagaa | 2760 |
| agtagtaaaa ttgaggtaat tttaaaaaat gctattgtat ataatagtat gtatgaaaat | 2820 |
| tttagtacta gcttttggat aagaattcct aagtatttta acagtataag tctaaataat | 2880 |
| gaatatacaa taataaattg tatggaaaat aattcaggat ggaaagtatc acttaattat | 2940 |
| ggtgaaataa tctggacttt acaggatact caggaaataa aacaagagt agttttaaa | 3000 |
| tacagtcaaa tgattaatat atcagattat ataaacagat ggattttgt aactatcact | 3060 |
| aataatagat taaataactc taaaatttat ataaatggaa gattaataga tcaaaaacca | 3120 |
| atttcaaatt taggtaatat tcatgctagt aataatataa tgtttaaatt agatggttgt | 3180 |
| agagatacac atagatatat ttggataaaa tattttaatc tttttgataa ggaattaaat | 3240 |
| gaaaaagaaa tcaaagattt atatgataat caatcaaatt caggtatttt aaaagacttt | 3300 |
| tggggtgatt atttacaata tgataaacca tactatatgt taaatttata tgatccaaat | 3360 |
| aaatatgtcg atgtaaataa tgtaggtatt agaggttata tgtatcttaa agggcctaga | 3420 |
| ggtagcgtaa tgactacaaa catttattta aattcaagtt gtatagggg gacaaaattt | 3480 |
| attataaaaa aatatgcttc tggaaataaa gataatattg ttagaaataa tgatcgtgta | 3540 |
| tatattaatg tagtagttaa aaataaagaa tataggttag ctactaatgc gtcacaggca | 3600 |
| ggcgtagaaa aaatactaag tgcattagaa atacctgatg taggaaatct aagtcaagta | 3660 |
| gtagtaatga agtcaaaaaa tgatcaagga ataacaaata aatgcaaaat gaatttacaa | 3720 |
| gataataatg ggaatgatat aggctttata ggatttcatc agtttaataa tatagctaaa | 3780 |
| ctagtagcaa gtaattggta taatagacaa atagaaagat ctagtaggac tttgggttgc | 3840 |
| tcatgggaat ttattcctgt agatgatgga tggggagaaa ggccactgta a | 3891 |

<210> SEQ ID NO 224
<211> LENGTH: 3891
<212> TYPE: DNA
<213> ORGANISM: Artificial Sequence
<220> FEATURE:
<221> NAME/KEY: mat_peptide
<222> LOCATION: (1)...(3888)
<223> OTHER INFORMATION: BoNT/A_G8

<400> SEQUENCE: 224

```
atgccatttg ttaataaaca atttaattat aaagatcctg taaatggtgt tgatattgct     60
tatataaaaa ttccaaatgc aggacaaatg caaccagtaa aagcttttaa aattcataat    120
aaaatatggg ttattccaga aagagataca tttacaaatc ctgaagaagg agatttaaat    180
ccaccaccag aagcaaaaca agttccagtt tcatattatg attcaacata tttaagtaca    240
gataatgaaa aagataatta tttaaaggga gttacaaaat tatttgagag aatttattca    300
actgatcttg gaagaatgtt gttaacatca atagtaaggg gaataccatt ttggggtgga    360
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag ctttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
```

```
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gattacaca gaggataatt tgttaagtt ttttaaagta    1080 cttaacagaa aaacatattt gaatttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaattta ctaaactaaa aaattttact    1260
ggattgtttg aattttataa gttgctatgt gtaagaggga taataacttc taagaaaaca   1320
agcgcagcca agctcaagaa taaggcatta aatgattat gtatcaaagt taataattgg    1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taaccttta ttttgataat gaacctgaaa atatttcaat agaaaatctt    1560
tcaagtgaca ttataggcca attagaactt atgcctaata tagaaagatt tcctaatgga   1620 aaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata catttttttc ttcagactat gtaaagaaag ttaataaagc tacggaggca   1800
gctatgtttt taggctgggt agaacaatta gtatatgatt ttaccgatga aactagcgaa   1860
gtaagtacta cggataaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaacttta attggtcaag tagatagatt aaaagataaa   2520
gttaataata cacttagtac agatatacct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa ataaatatt    2700 ggtagtaaag taaatttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agttttaaa    3000 tacagtcaaa tgattaatat atcagattat ataaacagat ggattttgt aactatcact    3060 aataatagat taaataactc taaaatttat ataaatggaa gattaataga tcaaaaacca   3120
```

```
atttcaaatt taggtaatat tcatgctagt aataatataa tgtttaaatt agatggttgt    3180
agagatacac atagatatat ttggataaaa tattttaatc tttttgataa ggaattaaat    3240
gaaaaagaaa tcaaagattt atatgataat caatcaaatt caggtatttt aaaagacttt    3300
tggggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttattta aattcaagtt tgtatagggg acaaaatttt    3480
attataaaaa aatatgcttc tggaaataaa gataatattg ttagaaataa tgatcgtgta    3540
tatattaatg tagtagttaa aaataaagaa tataggttag ctactaatgc gtcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta aatagacaa atagaaagat ctagtaggac tttgggttgc    3840
tcatgggaat ttattcctgt agatgatgga tggggagaaa ggccactgta a             3891
```

<210> SEQ ID NO 225
<211> LENGTH: 3912
<212> TYPE: DNA
<213> ORGANISM: Artificial Sequence
<220> FEATURE:
<221> NAME/KEY: mat_peptide
<222> LOCATION: (1)...(3909)
<223> OTHER INFORMATION: Polynucleotide encoding BoNT/A-A17, optimized for E. coli expression

<400> SEQUENCE: 225

```
atgccgttcg ttaacaaaca gttcaactac aaagacccgg ttaacggcgt tgacatcgct     60
tacatcaaaa tcccgaacgc tggccagatg cagccggtta agctttcaa  atccacaac    120 aaaatctggg ttatcccgga acgtgacacc ttcaccaacc cggaagaagg tgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
actgacctgg gccgtatgct gctgactagc atcgttcgtg gcatcccgtt ctggggcggc    360
tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgacccg taacggctac    540
ggctccaccc agtacatccg tttctctccg gacttcacct tcggcttcga agaatccctg    600
gaagttgaca ctaacccgct gctgggcgct ggtaaattcg ctaccgaccc ggctgtaacc    660
ctggctcacg aactgatcca cgctggccac cgtctgtacg gcatcgctat caacccgaac    720
cgtgttttca agttaacac caacgcttac tacgaaatgt ccggcctgga agtttccttc    780
gaagaactgc gtaccttcgg cggccacgac gctaaattca tcgactccct gcaggaaaac    840
gaattccgtc tgtactatta caacaaattc aaagacatcg cttccaccct gaacaaagct    900
aaatccatcg ttggcaccac cgcttccctg cagtacatga agaacgtttt caaagagaag    960
tacctgctgt ccgaagacac ctccggcaaa ttctccgttg acaaactgaa attcgacaaa   1020
ctgtacaaaa tgctgaccga aatctacacc gaagacaact cgttaaatt cttcaaagtt   1080 ctgaaccgta aacctacct gaacttcgac aaagctgttt tcaaaatcaa catcgttccg   1140
aaagttaact acaccatcta cgacggcttc aacctgcgta acaccaacct ggctgctaac   1200
```

```
ttcaacggcc agaacaccga aatcaacaac atgaacttca ccaaactgaa gaacttcacc    1260
ggcctgttcg aattctacaa actgctgtgc gttcgtggca tcatcacctc caaatccaac    1320
aaaacccgta tcgacgaagc taaccagcgt gctaccaaaa tgctggctct gaacgacctg    1380
tgcatcaaag ttaacaactg ggacctgttc ttctccccgt ccgaagacaa cttcaccaac    1440
gacctgaaca aaggcgaaga aatcacctcc gacaccaaca tcgaagctgc tgaagaaaac    1500
atctccctgg acctgatcca gcagtactac ctgaccttca cttcgacaa cgaaccggaa    1560 aacatctcca tcgaaaacct gtcctccgac atcatcggcc agctggaact gatgccgaac    1620
atcgaacgtt tcccgaacgg caagaagtat gaactggaca aatacaccat gttccactac    1680
ctgcgtgctc aggaattcga acacggcaaa tcccgtatcg ctctgaccaa ctccgttaac    1740
gaagctctgc tgaacccgtc ccgtgtttac accttcttct cctccgacta cgttaagaag    1800
gttaacaaag ctaccgaagc tgctatgttc ctgggctggg ttgaacagct ggtttacgac    1860
ttcaccgacg aaacctccga gtttccacc ccgacaaaa tcgctgacat caccatcatt    1920
atcccgtaca tcggcccggc tctgaacatc ggcaacatgc tgtacaaaga cgacttcgtt    1980
ggcgctctga tcttctccgg cgctgttatc ctgctggaat tcatcccgga aatcgctatc    2040
ccggttctgg gcaccttcgc tctggttttcc tacatcgcta acaaagttct gaccgttcag    2100
accatcgaca acgctctgtc caaacgtaac gagaagtggg acgaagttta caaatacatc    2160
gttaccaact ggctggctaa agttaacacc cagatcgacc tgatccgtaa aagatgaaa    2220 gaagctctgg aaaaccaggc tgaagctacc aaagctatca tcaactacca gtacaaccag    2280
tacaccgaag aggaaaagaa caacatcaac ttcaacatcg acgacctgtc ctccaaactg    2340
aacgaatcca tcaacaaagc tatgatcaac atcaacaaat tcctgaacca gtgctccgtt    2400
tcctacctga tgaactccat gatcccgtac ggcgttaaac gtctggaaga cttcgacgct    2460
tccctgaaag acgctctgct gaaatacatc tacgacaacc gtggcaccct gatcggccag    2520
gttgaccgtc tgaaagacaa agttaacaac accctgtcca ccgacatccc gttccagctg    2580
tccaaatacg ttgacaacca gcgtctgctg tccaccttca ccgaatacat caagaacatc    2640
atcaacacct ccatcctgaa cctgcgttac gaatccaacc acctgatcga cctgtcccgt    2700
tacgcttcca aaatcaacat cggctccaaa gttaacttcg acccgatcga caagaaccag    2760
atccagctgt tcaacctgga atcctccaaa atcgaagtta tcctgaagaa cgctatcgtt    2820
tacaactcca gtacgaaaaa cttctccacc tccttctgga tccgtatccc gaaatacttc    2880
aactccatct ccctgaacaa cgaatacacc atcatcaact gcatggaaaa caactccggc    2940
tggaaagttt ccctgaacta cggcgaaatc atctggaccc tgcaggacac ccaggaaatc    3000
aaacagcgtg ttgttttcaa atactcccag atgatcaaca tctccgacta catcaaccgt    3060
tggatcttcg ttaccatcac caacaaccgt ctgaacaact ccaaaatcta catcaacggc    3120
cgtctgatcg accagaaacc gatctccaac ctgggcaaca tccacgcttc caacaacatc    3180
atgttcaaac tggacggctg ccgtgacacc caccgttaca tctggatcaa atacttcaac    3240
ctgttcgaca aagaactgaa cgagaaggaa atcaagacc tgtacgacaa ccagtccaac    3300
tccggcatcc tgaaagactt ctggggcgac tacctgcagt atgacaaacc gtactacatg    3360
ctgaacctgt acgacccgaa caatacgtt gacgttaaca cgttggcat ccgtggctac    3420 atgtacctga aaggcccgcg tggctccgtt atgaccacca acatctacct gaactcctcc    3480
ctgtaccgtg gcaccaaatt catcatcaag aagtacgctt ccggcaacaa agacaacatc    3540
gttcgtaaca acgaccgtgt ttacatcaac gttgtagtta agaacaaaga ataccgtctg    3600
```

-continued

```
gctaccaacg cttcccaggc tggcgttgag aagattctga gcgctctgga atcccggac      3660 gtaggcaacc tgtcccaagt tgtagttatg aaatccaaga acgaccaggg catcaccaac     3720
aagtgcaaga tgaacctgca ggacaacaac ggcaacgaca tcggcttcat cggcttccac     3780
cagttcaaca acatcgctaa actggttgct tccaactggt acaaccgtca gattgaacgt     3840
agctcccgta ccctgggctg cagctgggaa tttatcccgg tagacgacgg ctggggtgaa     3900
cgtccgctgt aa                                                         3912
```

<210> SEQ ID NO 226
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-A8, optimized for E. coli expression

<400> SEQUENCE: 226

```
atgccgttcg ttaacaaaca gttcaactac aaagacccgg ttaacggcgt tgacatcgct      60
tacatcaaaa tcccgaacgc tggccagatg cagccggtta agctttcaa atccacaac      120 aaaatctggg ttatcccgga acgtgacacc ttcaccaacc cggaagaagg cgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
accgacctgg ccgtatgct gctgacctcc atcgttcgtg catcccgtt ctggggcggc       360 tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgacccg taacggctac    540
ggctccaccc agtacatccg tttctccccg gacttcacct tcggcttcga agaatccctg    600
gaagttgaca ccaacccgct gctgggcgct ggcaaattcg ctaccgaccc ggctgttacc    660
ctggctcacg aactgatcca cgctggccac cgtctgtacg gcatcgctat caacccgaac    720
cgtgttttca aagttaacac caacgcttac tacgaaatgt ccggcctgga agtttccttc    780
gaagaactgc gtaccttcgg cggccacgac gctaaattca tcgactccct gcaggaaaac    840
gaattccgtc tgtactatta aacaaattc aaagacatcg cttccaccct gaacaaagct    900
aaatccatcg ttggcaccac cgcttccctg cagtacatga agaacgtttt caagagaag    960 tacctgctgt ccgaagacac ctccggcaaa ttctccgttg acaaactgaa attcgacaaa    1020
ctgtacaaga tgctgaccga atctacacc gaagacaact tcgttaaatt cttcaaagtt    1080
ctgaaccgta aaacctacct gaacttcgac aaagctgttt tcaaaatcaa catcgttccg    1140
aaagttaact acaccatcta cgacggcttc aacctgcgta caccaacct ggctgctaac    1200 ttcaacggcc agaacaccga atcaacaac atgaacttca ccaaactgaa gaacttcacc    1260
ggcctgttcg aattctacaa actgctgtgc gttcgtggca tcatcacctc caagaagct    1320 aaccagcgtg ctaccaaagc tctgaacgac ctgtgcatca agttaacaa ctgggacctg    1380 ttcttctccc cgtccgaaga caacttcacc aacgacctga caaaggcga gaaaatcacc    1440 tccgacacca catcgaagc tgctgaagaa acatctcccc tggacctgat ccagcagtac    1500
tacctgacct tcaacttcga caacgaaccg gaaaacatct ccatcgaaaa cctgtcctcc    1560
gacatcatcg ccagctgga actgatgccg aacatcgaac gttcccgaa cggcaagaag    1620
```

```
tatgaactgg acaaatacac catgttccac tacctgcgtg ctcaggaatt cgaacacggc    1680
aaatcccgta tcgctctgac caactccgtt aacgaagctc tgctgaaccc gtcccgtgtt    1740
tacaccttct tctcctccga ctacgttaag aaggttaaca aagctaccga agctgctatg    1800
ttcctgggct gggttgaaca gctggtttac gacttcaccg acgaaacctc cgaagtttcc    1860
accaccgaca aaatcgctga catcaccatc attatcccgt acatcggccc ggctctgaac    1920
atcggcaaca tgctgtacaa agacgacttc gttggcgctc tgatcttctc cggcgctgtt    1980
atcctgctgg aattcatccc ggaaatcgct atcccggttc tgggcacctt cgctctggtt    2040
tcctacatcg ctaacaaagt tctgaccgtt cagaccatcg acaacgctct gtccaaacgt    2100
aacgagaagt gggacgaagt ttacaaatac atcgttacca actggctggc taaagttaac    2160
acccagatcg acctgatccg taagaagatg aaagaagctc tggaaaacca ggctgaagct    2220
accaaagcta tcatcaacta ccagtacaac cagtacaccg aagaggaaaa gaacaacatc    2280
aacttcaaca tcgacgacct gtcctccaaa ctgaacgaat ccatcaacaa agctatgatc    2340
aacatcaaca aattcctgaa ccagtgctcc gtttcctacc tgatgaactc catgatcccg    2400
tacggcgtta acgtctggga agacttcgac gcttccctga agacgctct gctgaaatac    2460 atctacgaca accgtggcac cctgatcggc caggttgacc gtctgaaaga caaagttaac    2520
aacaccctgt ccaccgacat cccgttccag ctgtccaaat acgttgacaa ccagcgtctg    2580
ctgtccacct tcaccgaata catcaagaac atcatcaaca cctccatcct gaacctgcgt    2640
tacgaatcca accacctgat cgacctgtcc cgttacgctt ccaaaatcaa catcggctcc    2700
aaagttaact tcgacccgat cgacaagaac cagatccagc tgttcaacct ggaatcctcc    2760
aaaatcgaag ttatcctgaa gaacgctatc gtttacaact ccatgtacga aacttctcc     2820 acctccttct ggatccgtat cccgaaatac ttcaactcca tctccctgaa caacgaatac    2880
accatcatca actgcatgga aaacaactcc ggctggaaag tttccctgaa ctacggcgaa    2940
atcatctgga ccctgcagga cacccaggaa atcaaacagc gtgttgtttt caaatactcc    3000
cagatgatca acatctccga ctacatcaac cgttggatct tcgttaccat caccaacaac    3060
cgtctgaaca actccaaaat ctacatcaac ggccgtctga tcgaccagaa accgatctcc    3120
aacctgggca catccacgc ttccaacaac atcatgttca aactggacgg ctgccgtgac    3180
acccaccgtt acatctggat caaatacttc aacctgttcg acaaagaact gaacgagaag    3240
gaaatcaaag acctgtacga caaccagtcc aactccggca tcctgaaaga cttctggggc    3300
gactacctgc agtatgacaa accgtactac atgctgaacc tgtacgaccc gaacaaatac    3360
gttgacgtta acaacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgtccca agttgtagtt    3660
atgaaatcca agaacgacca gggcatcacc aacaagtgca aaatgaacct gcaggacaac    3720
aacggcaacg catcggcttc atcggcttc caccagttca acaacatcgc taaactggtt    3780
gcttccaact ggtacaaccg tcagatcgaa cgttcctccc gtaccctggg ctgctcctgg    3840
gaattcatcc cggttgacga cggctggggc gaacgtccgc tgtaa                   3885
```

<210> SEQ ID NO 227

<211> LENGTH: 3966
<212> TYPE: DNA
<213> ORGANISM: Artificial Sequence
<220> FEATURE:
<221> NAME/KEY: mat_peptide
<222> LOCATION: (1)...(3963)
<223> OTHER INFORMATION: Polynucleotide encoding BoNT/A-BT35, optimized for E. coli expression

<400> SEQUENCE: 227

```
atgccgttcg ttaacaaaca gttcaactac aaagacccgg ttaacggcgt tgacatcgct     60
tacatcaaaa tcccgaacgc tggccagatg cagccggtta aagctttcaa aatccacaac    120
aaaatctggg taatcccgga acgtgacacc ttcaccaacc cggaagaagg tgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
accgacctgg gccgtatgct gctgacctcc atcgttcgtg gcatcccgtt ctggggcggc    360
tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgacccg taacggctac    540
ggctccaccc agtacatccg tttctccccg gacttcacct tcggcttcga agaatccctg    600
gaagttgaca ctaacccgct gctgggcgct ggtaaattcg ctaccgaccc ggctgtaacc    660
ctggctcacg aactgatcca cgctggccac cgtctgtacg gcatcgctat caacccgaac    720
cgtgttttca aagttaacac caacgcttac tacgaaatgt ccggcctgga agtttccttc    780
gaagaactgc gtaccttcgg cggccacgac gctaaattca tcgactccct gcaggaaaac    840
gaattccgtc tgtactatta caacaaattc aaagacatcg cttccaccct gaacaaagct    900
aaatccatcg ttggcaccac cgcttccctg cagtacatga agaacgtttt caaagagaag    960
tacctgctgt ccgaagacac ctccggcaaa ttctccgttg acaaactgaa attcgacaaa   1020
ctgtacaaaa tgctgaccga aatctacacc gaagacaact tcgttaaatt cttcaaagtt   1080
ctgaaccgta aaacctacct gaacttcgac aaagctgttt tcaaaatcaa catcgttccg   1140
aaagttaact acaccatcta cgacggcttc aacctgcgta acaccaacct ggctgctaac   1200
ttcaacggcc agaacaccga aatcaacaac atgaacttca ccaaactgaa gaacttcacc   1260
ggcctgttcg aattctacaa actgctgtgc gttcgtggca tcatcacctc caaactgtct   1320
gaactggacg accgtgctga cgctctgcag gctggcgctt cccagttcga atcctccgct   1380
gctaaactga aacgtaaata ctggtggaag aactgcaaag ctctgaacga cctgtgcatc   1440
aaagttaaca actgggacct gttcttctcc ccgtccgaag acaacttcac caacgacctg   1500
aacaaaggcg aagaaatcac ctccgacacc aacatcgaag ctgctgaaga aaacatctcc   1560
ctggacctga tccagcagta ctacctgacc ttcaacttcg acaacgaacc ggaaaacatc   1620
tccatcgaaa acctgtcctc cgacatcatc ggccagctgg aactgatgcc gaacatcgaa   1680
cgtttcccga acggcaaaaa atatgaactg gacaaataca ccatgttcca ctacctgcgt   1740
gctcaggaat tcgaacacgg caaatcccgt atcgctctga ccaactccgt taacgaagct   1800
ctgctgaacc cgtcccgtgt ttacaccttc ttctcctccg actacgttaa gaaggttaac   1860
aaagctaccg aagctgctat gttcctgggc tgggttgaac agctggttta cgacttcacc   1920
gacgaaacct ccgaagtttc caccaccgac aaaatcgctg acatcaccat cattatcccg   1980
tacatcggcc cggctctgaa catcggcaac atgctgtaca aagacgactt cgttggcgct   2040
```

-continued

```
ctgatcttct ccggcgctgt tatcctgctg gaattcatcc cggaaatcgc tatcccggtt      2100
ctgggcacct tcgctctggt ttcctacatc gctaacaaag ttctgaccgt tcagaccatc      2160
gacaacgctc tgtccaaacg taacgagaag tgggacgaag tttacaaata catcgttacc      2220
aactggctgg ctaaagttaa cacccagatc gacctgatcc gtaagaagat gaaagaagct      2280
ctggaaaacc aggctgaagc taccaaagct atcatcaact accagtacaa ccagtacacc      2340
gaagaggaaa agaacaacat caacttcaac atcgacgacc tgtcctccaa actgaacgaa      2400
tccatcaaca agctatgat caacatcaac aaattcctga accagtgctc cgtttcctac      2460
ctgatgaact ccatgatccc gtacggcgtt aaacgtctgg aagacttcga cgcttccctg      2520
aaagacgctc tgctgaaata catctacgac aaccgtggca ccctgatcgg ccaggttgac      2580
cgtctgaaag acaagttaa caacccctg tccaccgaca tcccgttcca gctgtccaaa       2640
tacgttgaca ccagcgtct gctgtccacc ttcaccgaat acatcaagaa catcatcaac      2700
acctccatcc tgaacctgcg ttacgaatcc aaccacctga tcgacctgtc ccgttacgct      2760
tccaaaatca catcggctc caaagttaac ttcgacccga tcgacaagaa ccagatccag      2820
ctgttcaacc tggaatcctc caaaatcgaa gttatcctga gaacgctat cgtttacaac      2880 tccatgtacg aaaacttctc cacctccttc tggatccgta tcccgaaata cttcaactcc      2940 atctcccctga caacgaata caccatcatc aactgcatgg aaaacaactc cggctggaaa     3000
gtttccctga ctacggcga atcatctgg accctgcagg acacccagga atcaaacag        3060 cgtgttgttt tcaaatactc ccagatgatc aacatctccg actacatcaa ccgttggatc     3120
ttcgttacca tcaccaacaa ccgtctgaac aactccaaaa tctacatcaa cggccgtctg     3180
atcgaccaga aaccgatctc caacctgggc aacatccacg cttccaacaa catcatgttc     3240
aaactggacg gctgccgtga cacccaccgt tacatctgga tcaaatactt caacctgttc     3300
gacaaagaac tgaacgagaa ggaaatcaaa gacctgtacg acaaccagtc caactccggc     3360
atcctgaaag acttctgggg cgactacctg cagtatgaca aaccgtacta catgctgaac     3420
ctgtacgacc cgaacaaata cgttgacgtt aacaacgttg gcatccgtgg ctacatgtac     3480
ctgaaaggcc cgcgtggctc cgttatgacc accaacatct acctgaactc ctcccctgtac   3540 cgtggcacca aattcatcat caagaagtac gcttccggca caaagacaa catcgttcgt     3600 aacaacgacc gtgtttacat caacgttgta gttaagaaca agaataccg tctggctacc     3660 aacgcttccc aggctggcgt tgagaagatt ctgtccgctc tggaaatccc ggacgttggc    3720
aacctgtccc aagttgtagt tatgaaatcc aagaacgacc agggcatcac caacaagtgc   3780
aagatgaacc tgcaggacaa caacggcaac gacatcggct tcatcggctt ccaccagttc    3840
aacaacatcg ctaaactggt tgcttccaac tggtacaacc gtcagatcga acgttcctcc     3900 cgtacccctgg gctgtagctg ggaattcatc ccggttgacg acggctgggg cgaacgtccg    3960
ctgtaa                                                                 3966
```

<210> SEQ ID NO 228
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-BT8, optimized for E. coli expression

<400> SEQUENCE: 228

```
atgccgttcg ttaacaaaca gttcaactac aaagacccgg ttaacggcgt tgacatcgct      60
tacatcaaaa tcccgaacgc tggccagatg cagccggtta agctttcaa atccacaac      120 aaaatctggg taatcccgga acgtgacacc ttcaccaacc cggaagaagg tgacctgaac      180
ccgccgccgg aagctaaaca ggttccggtt tcctactacg actccaccta cctgtccacc      240
gacaacgaga aggacaacta cctgaaaggc gttaccaaac tgttcgaacg tatctactcc      300
actgacctgg gccgtatgct gctgacctcc atcgttcgtg gcatcccgtt ctggggcggc      360
tccaccatcg acaccgaact gaaagttatc gacaccaact gcatcaacgt tatccagccg      420
gacggctcct accgttccga agaactgaac ctggttatca tcggcccgtc cgctgacatc      480
atccagttcg aatgcaaatc cttcggccac gaagttctga acctgacccg taacggctac      540
ggctccaccc agtacatccg tttctccccg gacttcacct tcggcttcga agaatccctg      600
gaagttgaca ctaacccgct gctgggcgct ggtaaattcg ctaccgaccc ggctgttacc      660
ctggctcacg aactgatcca cgctggccac cgtctgtacg catcgctat caacccgaac      720 cgtgttttca agttaacac caacgcttac tacgaaatgt ccggcctgga gtttccttc      780 gaagaactgc gtaccttcgg cggccacgac gctaaattca tcgactccct gcaggaaaac      840
gaattccgtc tgtactatta caacaaattc aaagacatcg cttccaccct gaacaaagct      900
aaatccatct tggccaccac cgcttccctg cagtacatga gaacgtttt caaagagaag      960 tacctgctgt ccgaagacac ctccggcaaa ttctccgttg acaaactgaa attcgacaaa     1020
ctgtacaaaa tgctgaccga aatctacacc gaagacaact tcgttaaatt cttcaaagtt     1080
ctgaaccgta aacctacct gaacttcgac aaagctgttt tcaaaatcaa catcgttccg     1140
aaagttaact acaccatcta cgacggcttc aacctgcgta acaccaacct ggctgctaac     1200
ttcaacggcc agaacaccga atcaacaac atgaacttca ccaaactgaa gaacttcacc     1260
ggcctgttcg aattctacaa actgctgtgc gttcgtggca tcatcacctc caaaggcgct     1320
tcccagttcg aaacctccgc tctgaacgac ctgtgcatca aagttaacaa ctgggacctg     1380
ttcttctccc cgtccgaaga caacttcacc aacgacctga caaaggcga agaaatcacc     1440 tccgacacca acatcgaagc tgctgaagaa acatctcccc tggacctgat ccagcagtac     1500
tacctgacct tcaacttcga caacgaaccg gaaaacatct ccatcgaaaa cctgtcctcc     1560
gacatcatcg gccagctgga actgatgccg aacatcgaac gtttcccgaa cggcaagaag     1620
tatgaactgg acaaatacac catgttccac tacctgcgtg ctcaggaatt cgaacacggc     1680
aaatcccgta tcgctctgac caactccgtt aacgaagctc tgctgaaccc gtcccgtgtt     1740
tacaccttct tctcctccga ctacgttaag aaggttaaca aagctaccga agctgctatg     1800
ttcctgggct gggttgaaca gctggtttac gacttcaccg acgaaacctc cgaagtttcc     1860
accaccgaca aaatcgctga catcaccatc attatcccgt acatcggccc ggctctgaac     1920
atcggcaaca tgctgtacaa agacgacttc gttggcgctc tgatcttctc cggcgctgtt     1980
atcctgctgg aattcatccc ggaaatcgct atcccggttc tgggcacctt cgctctggtt     2040
tcctacatcg ctaacaaagt tctgaccgtt cagaccatcg acaacgctct gtccaaacgt     2100
aacgagaagt gggacgaagt ttacaaatac atcgttacca actggctggc taaagttaac     2160
acccagatcg acctgatccg taagaagatg aaagaagctc tggaaaacca ggctgaagct     2220
accaaagcta tcatcaacta ccagtacaac cagtacaccg aagaggaaaa gaacaacatc     2280
aacttcaaca tcgacgacct gtcctccaaa ctgaacgaat ccatcaacaa agctatgatc     2340
aacatcaaca aattcctgaa ccagtgctcc gtttcctacc tgatgaactc catgatcccg     2400
```

-continued

```
tacggcgtta aacgtctgga agacttcgac gcttccctga agacgctct gctgaaatac    2460 atctacgaca accgtggcac cctgatcggc caggttgacc gtctgaaaga caaagttaac    2520
aacaccctgt ccaccgacat cccgttccag ctgtccaaat acgttgacaa ccagcgtctg    2580
ctgtccacct tcaccgaata catcaagaac atcatcaaca cctccatcct gaacctgcgt    2640
tacgaatcca accacctgat cgacctgtcc cgttacgctt ccaaaatcaa catcggctcc    2700
aaagttaact tcgacccgat cgacaagaac cagatccagc tgttcaacct ggaatcctcc    2760
aaaatcgaag ttatcctgaa gaacgctatc gtttacaact ccatgtacga aaacttctcc    2820
acctccttct ggatccgtat cccgaaatac ttcaactcca tctccctgaa caacgaatac    2880
accatcatca actgcatgga aaacaactcc ggctggaaag tttccctgaa ctacggcgaa    2940
atcatctgga ccctgcagga cacccaggaa atcaaacagc gtgttgtttt caaatactcc    3000
cagatgatca acatctccga ctacatcaac cgttggatct tcgttaccat caccaacaac    3060
cgtctgaaca actccaaaat ctacatcaac ggccgtctga tcgaccagaa accgatctcc    3120
aacctgggca catccacgc ttccaacaac atcatgttca actggacgg ctgccgtgac    3180 acccaccgtt acatctggat caaatacttc aacctgttcg acaaagaact gaacgagaag    3240
gaaatcaaag acctgtacga caaccagtcc aactccggca tcctgaaaga cttctggggc    3300
gactacctgc agtatgacaa accgtactac atgctgaacc tgtacgaccc gaacaaatac    3360
gttgacgtta acaacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgtccca agttgtagtt    3660
atgaaatcca agaacgacca gggcatcacc aacaagtgca aaatgaacct gcaggacaac    3720
aacggcaacg acatcggctt catcggcttc caccagttca acaacatcgc taaactggtt    3780
gcttccaact ggtacaaccg tcagatcgaa cgttcctccc gtaccctggg ctgctcctgg    3840
gaattcatcc cggttgacga cggctggggc gaacgtccgc tgtaa               3885
```

<210> SEQ ID NO 229
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-Csyp8, optimized for E. coli expression

<400> SEQUENCE: 229

```
atgccgttcg ttaacaaaca gttcaactac aaagacccgg ttaacggcgt tgacatcgct      60
tacatcaaaa tcccgaacgc tggccagatg cagccggtta agctttcaa atcccacaac     120 aaaatctggg ttatcccgga acgtgacacc ttcaccaacc cggaagaagg cgacctgaac     180
ccgccgccgg aagctaaaca ggttccggtt cctactacg actccaccta cctgtccacc     240
gacaacgaga aggacaacta cctgaaaggc gttaccaaac tgttcgaacg tatctactcc     300
accgacctgg gccgtatgct gctgacctcc atcgttcgtg gcatcccgtt ctggggcggc     360
tccaccatcg acaccgaact gaaagttatc gacaccaact gcatcaacgt tatccagccg     420
gacggctcct accgttccga agaactgaac ctggttatca tcggcccgtc cgctgacatc     480
```

```
atccagttcg aatgcaaatc cttcggccac gaagttctga acctgacccg taacggctac    540
ggctccaccc agtacatccg tttctctccg gacttcacct tcggcttcga agaatccctg    600
gaagttgaca ccaacccgct gctgggcgct ggcaaattcg ctaccgaccc ggctgttacc    660
ctggctcacg aactgatcca cgctggccac cgtctgtacg gcatcgctat caacccgaac    720
cgtgtattta agttaacac caacgcttac tacgaaatgt ccggcctgga agtttccttc    780
gaagaactgc gtaccttcgg cggccacgac gctaaattca tcgactccct gcaggaaaac    840
gaattccgtc tgtactatta caacaaattc aaagacatcg cttccaccct gaacaaagct    900
aaatccatcg ttggcaccac cgcttccctg cagtacatga agaacgtttt caaagagaag    960
tacctgctgt ccgaagacac ctccggcaaa ttctccgttg acaaactgaa attcgacaaa   1020
ctgtacaaaa tgctgaccga atctacacc gaagacaact tcgttaaatt cttcaaagtt   1080
ctgaaccgta aacctacct gaacttcgac aaagctgttt tcaaaatcaa catcgttccg   1140
aaagttaact acaccatcta cgacggcttc aacctgcgta acaccaacct ggctgctaac   1200
ttcaacggcc agaacaccga atcaacaac atgaacttca ccaaactgaa gaacttcacc   1260
ggcctgttcg aattctacaa actgctgtgc gttcgtggca tcatcacctc caaagacacc   1320
aagaaggctg ttaaatacgc tctgaacgac ctgtgcatca agttaacaa ctgggacctg   1380 ttcttctctc cgtccgaaga caacttcacc aacgacctga caaaggcga agaaatcacc   1440 tccgacacca catcgaagc tgctgaagaa acatctccc tggacctgat ccagcagtac   1500
tacctgacct tcaacttcga caacgaaccg gaaaacatct ccatcgaaaa cctgtcctcc   1560
gacatcatcg ccagctgga actgatgccg aacatcgaac gtttcccgaa cggcaagaag   1620
tatgaactgg acaaatacac catgttccac tacctgcgtg ctcaggaatt cgaacacggc   1680
aaatcccgta tcgctctgac caactccgtt aacgaagctc tgctgaaccc gtcccgtgtt   1740 tacacctttct ctcctccga ctacgttaag aaggttaaca aagctaccga agctgctatg   1800
ttcctgggct gggttgaaca gctggtttac gacttcaccg acgaaacctc cgaagttcc   1860 accaccgaca aaatcgctga catcaccatc attatcccgt acatcggccc ggctctgaac   1920
atcggcaaca tgctgtacaa agacgacttc gttggcgctc tgatcttctc cggcgctgtt   1980
atcctgctgg aattcatccc ggaaatcgct atcccggttc tgggcacctt cgctctggtt   2040
tcctacatcg ctaacaaagt tctgaccgtt cagaccatcg acaacgctct gtccaaacgt   2100
aacgagaagt gggacgaagt ttacaaatac atcgttacca actggctggc taaagttaac   2160
acccagatcg acctgatccg taagaagatg aaagaagctc tggagaacca ggctgaagct   2220
accaaagcta tcatcaacta ccagtacaac cagtacaccg aagaggaaaa gaacaacatc   2280
aacttcaaca tcgacgacct gtcctccaaa ctgaacgaat ccatcaacaa agctatgatc   2340
aacatcaaca aattcctgaa ccagtgctcc gtttcctacc tgatgaactc catgatcccg   2400
tacggcgtta acgtctgga agacttcgac gcttccctga agacgctct gctgaaatac   2460 atctacgaca ccgtggcac cctgatcggc caggttgacc gtctgaaaga caaagttaac   2520
aacaccctgt ccaccgacat cccgttccag ctgtccaaat acgttgacaa ccagcgtctg   2580
ctgtccacct tcaccgaata catcaagaac atcatcaaca cctccatcct gaacctgcgt   2640
tacgaatcca ccacctgat cgacctgtcc cgttacgctt ccaagattaa catcggctcc   2700
aaagttaact cgacccgat cgacaagaac cagatccagc tgttcaacct ggaatcctcc   2760
aagattgaag ttatcctgaa gaacgctatc gtttacaact ccatgtacga aaacttctcc   2820
```

-continued

```
acctccttct ggatccgtat cccgaaatac ttcaactcca tctccctgaa caacgaatac    2880
accatcatca actgcatgga aaacaactcc ggctggaaag tttccctgaa ctacggcgaa    2940
atcatctgga ccctgcagga cacccaggaa atcaaacagc gtgttgtttt caaatactcc    3000
cagatgatca acatctccga ctacatcaac cgttggatct tcgttaccat caccaacaac    3060
cgtctgaaca actccaagat ttacatcaac ggccgtctga tcgaccagaa accgatctcc    3120
aacctgggca catccacgc ttccaacaac atcatgttca aactggacgg ctgccgtgac    3180
acccaccgtt acatctggat caaatacttc aacctgttcg acaagaact gaacgagaag    3240 gaaatcaaag acctgtacga caaccagtcc aactccggca tcctgaaaga cttctggggc    3300
gactacctgc agtatgacaa accgtactac atgctgaacc tgtacgaccc gaacaaatac    3360
gttgacgtta caacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgtccca gttgtagtt    3660 atgaaatcca agaacgacca gggcatcacc aacaagtgca aaatgaacct gcaggacaac    3720
aacggcaacg catcggctt catcggcttc accagttca acaacatcgc taaactggtt    3780
gcttccaact ggtacaaccg tcagatcgaa cgttcctccc gtaccctggg ctgctcctgg    3840
gaattcatcc cggttgacga cggctgggggc gaacgtccgc tgtaa                   3885
```

<210> SEQ ID NO 230
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-Csnp8, optimized for E. coli expression

<400> SEQUENCE: 230

```
atgccgttcg ttaacaaaca gttcaactac aaagacccgg ttaacggcgt tgacatcgct    60
tacatcaaaa tcccgaacgc tggccagatg cagccggtta agctttcaa aatccacaac    120 aaaatctggg ttatcccgga acgtgacacc ttcaccaacc cggaagaagg cgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
accgacctgg ccgtatgct gctgacctcc atcgttcgtg gcatcccgtt ctggggcggc    360
tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgaccc taacggctac    540 ggctccaccc agtacatccg tttctccccg gacttcacct tcggcttcga agaatccctg    600
gaagttgaca ccaacccgct gctgggcgct ggcaaattcg ctaccgaccc ggctgttacc    660
ctggctcacg aactgatcca cgctggccac cgtctgtacg gcatcgctat caacccgaac    720
cgtgttttca aagttaacac caacgcttac tacgaaatgt ccggcctgga agtttccttc    780
gaagaactgc gtaccttcgg cggccacgac gctaaattca tcgactccct gcaggaaaac    840
gaattccgtc tgtactatta caacaaattc aaagacatcg cttccaccct gaacaaagct    900
```

```
aaatccatcg ttggcaccac cgcttccctg cagtacatga agaacgtttt caaagagaag    960
tacctgctgt ccgaagacac ctccggcaaa ttctccgttg acaaactgaa attcgacaaa   1020
ctgtacaaaa tgctgaccga atctacacc gaagacaact tcgttaaatt cttcaaagtt   1080
ctgaaccgta aacctacct gaacttcgac aaagctgttt tcaaaatcaa catcgttccg   1140
aaagttaact acaccatcta cgacggcttc aacctgcgta acaccaacct ggctgctaac   1200
ttcaacggcc agaacaccga atcaacaac atgaacttca ccaaactgaa gaacttcacc   1260
ggcctgttcg aattctacaa actgctgtgc gttcgtggca tcatcacctc caaagctaac   1320
cagcgtgcta ccaaaatggc tctgaacgac ctgtgcatca agttaacaa ctgggacctg   1380
ttcttctccc cgtccgaaga caacttcacc aacgacctga caaaggcga agaaatcacc   1440
tccgacacca catcgaagc tgctgaagaa acatctccc tggacctgat ccagcagtac   1500
tacctgacct tcaacttcga caacgaaccg gaaaacatct ccatcgaaaa cctgtcctcc   1560
gacatcatcg ccagctgga actgatgccg aacatcgaac gtttcccgaa cggcaagaag   1620
tatgaactgg acaaatacac catgttccac tacctgcgtg ctcaggaatt cgaacacggc   1680
aaatcccgta tcgctctgac caactccgtt aacgaagctc tgctgaaccc gtcccgtgtt   1740
tacaccttct tctcctccga ctacgttaag aaggttaaca agctaccga agctgctatg   1800
ttcctgggct gggttgaaca gctggtttac gacttcaccg acgaaacctc cgaagtttcc   1860
accaccgaca aaatcgctga catcaccatc attatcccgt acatcggccc ggctctgaac   1920
atcggcaaca tgctgtacaa agacgacttc gttggcgctc tgatcttctc cggcgctgtt   1980
atcctgctgg aattcatccc ggaaatcgct atcccggttc tgggcacctt cgctctggtt   2040
tcctacatcg ctaacaaagt tctgaccgtt cagaccatcg acaacgctct gtccaaacgt   2100
aacgagaagt gggacgaagt ttacaaatac atcgttacca actggctggc taaagttaac   2160
acccagatcg acctgatccg taagaagatg aaagaagctc tggaaaacca ggctgaagct   2220
accaaagcta tcatcaacta ccagtacaac cagtacaccg aagaggaaaa gaacaacatc   2280
aacttcaaca tcgacgacct gtcctccaaa ctgaacgaat ccatcaacaa agctatgatc   2340
aacatcaaca aattcctgaa ccagtgctcc gtttcctacc tgatgaactc catgatcccg   2400
tacggcgtta acgtctggga agacttcgac gcttccctga agacgctct gctgaaatac   2460
atctacgaca accgtggcac cctgatcggc caggttgacc gtctgaaaga caaagttaac   2520
aacaccctgt ccaccgacat cccgttccag ctgtccaaat acgttgacaa ccagcgtctg   2580
ctgtccacct tcaccgaata catcaagaac atcatcaaca cctccatcct gaacctgcgt   2640
tacgaatcca accacctgat cgacctgtcc cgttacgctt ccaagattaa catcggctcc   2700
aaagttaact cgacccgat cgacaagaac cagatccagc tgttcaacct ggaatcctcc   2760
aagattgaag ttatcctgaa gaacgctatc gtttacaact ccatgtacga gaacttctcc   2820
acctccttct ggatccgtat cccgaaatac ttcaactcca tcccctgaa caacgaatac   2880
accatcatca actgcatgga aaacaactcc ggctggaaag tttccctgaa ctacggcgaa   2940
atcatctgga ccctgcagga cacccaggaa atcaaacagc gtgttgtttt caaatactcc   3000
cagatgatca acatctccga ctacatcaac cgttggatct tcgttaccat caccaacaac   3060
cgtctgaaca actccaaaat ctacatcaac ggccgtctga tcgaccagaa accgatctcc   3120
aacctgggca acatccacgc ttccaacaac atcatgttca aactggacgg ctgccgtgac   3180
acccaccgtt acatctggat caaatacttc aacctgttcg acaaagaact gaacgagaag   3240
gaaatcaaag acctgtacga caaccagtcc aactccggca tcctgaaaga cttctggggc   3300
```

```
gactacctgc agtatgacaa accgtactac atgctgaacc tgtacgaccc gaacaaatac    3360
gttgacgtta caacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgtccca agttgtagtt    3660
atgaaatcca gaacgacca gggcatcacc aacaagtgca agatgaacct gcaggacaac    3720
aacggcaacg acatcggctt catccggcttc caccagttca caacatcgc taaactggtt    3780 gcttccaact ggtacaaccg tcagatcgaa cgttcctccc gtaccctggg ctgctcctgg    3840
gaattcatcc cggttgacga cggctggggc gaacgtccgc tgtaa    3885

<210> SEQ ID NO 231
<211> LENGTH: 3978
<212> TYPE: DNA
<213> ORGANISM: Artificial Sequence
<220> FEATURE:
<221> NAME/KEY: mat_peptide
<222> LOCATION: (1)...(3975)
<223> OTHER INFORMATION: Polynucleotide encoding BoNT/A-DF39, optimized
      for E. coli expression

<400> SEQUENCE: 231
atgccgttcg ttaacaaaca gttcaactac aaagacccgg ttaacggcgt tgacatcgct     60
tacatcaaaa tcccgaacgc tggccagatg cagccggtta aagctttcaa atccacaac    120 aaaatctggg taatcccgga acgtgacacc ttcaccaacc cggaagaagg cgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
accgacctgg ccgtatgct gctgacctcc atcgttcgtg gcatcccgtt ctggggcggc    360
tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgacccg taacggctac    540
ggctccaccc agtacatccg tttctccccg gacttcacct tcggcttcga agaatccctg    600
gaagttgaca ccaacccgct gctgggcgct ggcaaattcg ctaccgaccc ggctgttacc    660
ctggctcacg aactgatcca cgctggccac cgtctgtacg gcatcgctat caacccgaac    720
cgtgttttca aagttaacac caacgcttac tacgaaatgt ccggcctgga agtttccttc    780
gaagaactgc gtaccttcgg cggccacgac gctaaattca tcgactccct gcaggaaaac    840
gaattccgtc tgtactatta caacaaattc aaagacatcg cttccaccct gaacaaagct    900
aaatccatcg ttggcaccac cgcttccctg cagtacatga gaacgttttt caagagaag    960 tacctgctgt ccgaagacac ctccggcaaa ttctccgttg acaaactgaa attcgacaaa    1020
ctgtacaaga tgctgaccga aatctacacc gaagacaact tcgttaaatt cttcaaagtt    1080
ctgaaccgta aaacctacct gaacttcgac aaagctgttt tcaaaatcaa catcgttccg    1140
aaagttaact acaccatcta cgacggcttc aacctgcgta caccaacct ggctgctaac    1200 ttcaacggcc agaacaccga aatcaacaac atgaacttca ccaaactgaa gaacttcacc    1260
ggcctgttcg aattctacaa actgctgtgc gttcgtggca tcatcacctc caaagctcag    1320
gttgaagaag ttgttgacat catccgtgtt aacgttgaca aagttctgga acgtgaccag    1380
```

```
aaactgtccg aactggacga ccgtgctgac gctctgcagg ctggcgcttc cgctctgaac    1440
gacctgtgca tcaaagttaa caactgggac ctgttcttct ccccgtccga agacaacttc    1500
accaacgacc tgaacaaagg cgaagaaatc acctccgaca ccaacatcga agctgctgaa    1560
gaaaacatct ccctggacct gatccagcag tactacctga ccttcaactt cgacaacgaa    1620
ccggaaaaca tctccatcga gaacctgtcc tccgacatca tcggccagct ggaactgatg    1680
ccgaacatcg aacgtttccc gaacggcaag aagtatgaac tggacaaata caccatgttc    1740
cactacctgc gtgctcagga attcgaacac ggcaaatccc gtatcgctct gaccaactcc    1800
gttaacgaag ctctgctgaa cccgtcccgt gtttacacct tcttctcctc cgactacgtt    1860
aagaaggtta acaaagctac cgaagctgct atgttcctgg gctgggttga acagctggtt    1920
tacgacttca ccgacgaaac ctccgaagtt tccaccaccg acaagattgc tgacatcacc    1980
atcattatcc cgtacatcgg cccggctctg aacatcggca catgctgta caaagacgac    2040
ttcgttggcg ctctgatctt ctccggcgct gttatcctgc tggaattcat cccggaaatc    2100
gctatcccgg ttctgggcac cttcgctctg gtttcctaca tcgctaacaa agttctgacc    2160
gttcagacca tcgacaacgc tctgtccaaa cgtaacgaga agtgggacga agtttacaaa    2220
tacatcgtta ccaactggct ggctaaagtt aacacccaga tcgacctgat ccgtaagaag    2280
atgaaagaag ctctggagaa ccaggctgaa gctaccaaag ctatcatcaa ctaccagtac    2340
aaccagtaca ccgaagaaga gaagaacaac atcaacttca acatcgacga cctgtcctcc    2400
aaactgaacg aatccatcaa caaagctatg atcaacatca acaaattcct gaaccagtgc    2460
tccgtttcct acctgatgaa ctccatgatc ccgtacggcg ttaaacgtct ggaagacttc    2520
gacgcttccc tgaaagacgc tctgctgaaa tacatctacg acaaccgtgg caccctgatc    2580
ggccaggttg accgtctgaa agacaaagtt aacaacaccc tgtccaccga catcccgttc    2640
cagctgtcca aatacgttga caaccagcgt ctgctgtcca ccttcaccga atacatcaag    2700
aacatcatca acacctccat cctgaacctg cgttacgaat ccaaccacct gatcgacctg    2760
tcccgttacg cttccaagat taacatcggc tccaaagtta acttcgaccc gatcgacaag    2820
aaccagatcc agctgttcaa cctggaatcc tccaagattg aagttatcct gaagaacgct    2880
atcgtttaca actccatgta cgagaacttc tccacctcct tctggatccg tatcccgaaa    2940
tacttcaact ccatctccct gaacaacgaa tacaccatca tcaactgcat ggaaaacaac    3000
tccggctgga agtttcccct gaactacggc gaaatcatct ggaccctgca ggacacccag    3060
gaaatcaaac agcgtgttgt tttcaaatac tcccagatga tcaacatctc cgactacatc    3120
aaccgttgga tcttcgttac catcaccaac aaccgtctga caactccaa atctacatc    3180
aacggccgtc tgatcgacca gaaaccgatc tccaacctgg gcaacatcca cgcttccaac    3240
aacatcatgt tcaaactgga cggctgccgt gacacccacc gttacatctg gatcaaatac    3300
ttcaacctgt tcgacaaaga actgaacgag aaggaaatca agacctgta cgacaaccag    3360
tccaactccg gcatcctgaa agacttctgg ggcgactacc tgcagtatga caaaccgtac    3420
tacatgctga acctgtacga cccgaacaaa tacgttgacg ttaacaacgt tggcatccgt    3480
ggctacatgt acctgaaagg cccgcgtggc tccgttatga ccaccaacat ctacctgaac    3540
tcctccctgt accgtggcac caaattcatc atcaagaagt acgcttccgg caacaaagac    3600
aacatcgttc gtaacaacga ccgtgtttac atcaacgttg tagttaagaa caaagaatac    3660
cgtctggcta ccaacgcttc ccaggctggc gttgagaaga ttctgtccgc tctggaaatc    3720
```

```
ccggacgttg gcaacctgtc ccaagttgta gttatgaaat ccaagaacga ccagggcatc   3780
accaacaagt gcaagatgaa cctgcaggac aacaacggca acgacatcgg cttcatcggc   3840
ttccaccagt tcaacaacat cgctaaactg gttgcttcca actggtacaa ccgtcagatc   3900
gaacgttcct cccgtaccct gggctgtagc tgggaattca tcccggttga cgacggctgg   3960
ggcgaacgtc cgctgtaa                                                 3978

<210> SEQ ID NO 232
<211> LENGTH: 3885
<212> TYPE: DNA
<213> ORGANISM: Artificial Sequence
<220> FEATURE:
<223> OTHER INFORMATION: Polynucleotide encoding BoNT/A-D8, optimized
      for E. coli expression

<400> SEQUENCE: 232
atgccgttcg ttaacaaaca gttcaactac aaagacccgg ttaacggcgt tgacatcgct     60
tacatcaaaa tcccgaacgc tggccagatg cagccggtta agctttcaa aatccacaac    120 aaaatctggg ttatcccgga acgtgacacc ttcaccaacc cggaagaagg cgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
accgacctgg ccgtatgct gctgacctcc atcgttcgtg gcatcccgtt ctggggcggc    360
tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgacccg taacggctac    540
ggctccaccc agtacatccg tttctccccg gacttcacct tcggcttcga agaatccctg    600
gaagttgaca ccaacccgct gctgggcgct ggcaaattcg ctaccgaccc ggctgttacc    660
ctggctcacg aactgatcca cgctggccac cgtctgtacg gcatcgctat caacccgaac    720 cgtgtttca agttaacac caacgcttac tacgaaatgt ccggcctgga agttcccttc    780
gaagaactgc gtaccttcgg cggccacgac gctaaattca tcgactccct gcaggaaaac    840
gaattccgtc tgtactatta caacaaattc aaagacatcg cttccaccct gaacaaagct    900
aaatccatct tggcaccac cgcttcccctg cagtacatga gaacgttttt caagagaag    960 tacctgctgt ccgaagacac ctccggcaaa ttctccgttg acaaactgaa attcgacaaa   1020
ctgtacaaga tgctgaccga aatctacacc gaagacaact tcgttaaatt cttcaaagtt   1080
ctgaaccgta aacctacct gaacttcgac aaagctgttt caaaatcaa catcgttccg   1140 aaagttaact acaccatcta cgacggcttc aacctgcgta caccaacct ggctgctaac   1200 ttcaacggcc agaacaccga atcaacaac atgaacttca ccaaactgaa gaacttcacc   1260
ggcctgttcg aattctacaa actgctgtgc gttcgtggca tcatcacctc caaacgtgac   1320
cagaaactgt ccgaactggc tctgaacgac ctgtgcatca agttaacaa ctgggacctg   1380 ttcttctccc cgtccgaaga caacttcacc aacgacctga caaaggcga agaaatcacc   1440 tccgacacca catcgaagc tgctgaagaa acatctcccc tggacctgat ccagcagtac   1500
tacctgacct tcaacttcga caacgaaccg gaaacatct ccatcgaaaa cctgtcctcc   1560
gacatcatcg ccagctgga actgatgccg aacatcgaac gtttcccgaa cggcaagaag   1620
tacgaactgg acaaatacac catgttccac tacctgcgtg ctcaggaatt cgaacacggc   1680
aaatcccgta tcgctctgac caactccgtt aacgaagctc tgctgaaccc gtcccgtgtt   1740
```

```
tacaccttct tctcctccga ctacgttaag aaggttaaca aagctaccga agctgctatg    1800
ttcctgggct gggttgaaca gctggttac gacttcaccg acgaaacctc cgaagtttcc    1860
accaccgaca aaatcgctga catcaccatc attatcccgt acatcggccc ggctctgaac    1920
atcggcaaca tgctgtacaa agacgacttc gttggcgctc tgatcttctc cggcgctgtt    1980
atcctgctgg aattcatccc ggaaatcgct atcccggttc tgggcacctt cgctctggtt    2040
tcctacatcg ctaacaaagt tctgaccgtt cagaccatcg acaacgctct gtccaaacgt    2100
aacgagaagt gggacgaagt ttacaaatac atcgttacca actggctggc taaagttaac    2160
acccagatcg acctgatccg taagaagatg aaagaagctc tggaaaacca ggctgaagct    2220
accaaagcta tcatcaacta ccagtacaac cagtacaccg aagaagagaa gaacaacatc    2280
aacttcaaca tcgacgacct gtcctccaaa ctgaacgaat ccatcaacaa agctatgatc    2340
aacatcaaca aattcctgaa ccagtgctcc gtttcctacc tgatgaactc catgatcccg    2400
tacggcgtta aacgtctgga agacttcgac gcttccctga agacgctct gctgaaatac    2460 atctacgaca accgtggcac cctgatcggc caggttgacc gtctgaaaga caaagttaac    2520
aacaccctgt ccaccgacat cccgttccag ctgtccaaat acgttgacaa ccagcgtctg    2580
ctgtccacct tcaccgaata catcaagaac atcatcaaca cctccatcct gaacctgcgt    2640
tacgaatcca accacctgat cgacctgtcc cgttacgctt ccaaaatcaa catcggctcc    2700
aaagttaact tcgacccgat cgacaagaac cagatccagc tgttcaacct ggaatcctcc    2760
aaaatcgaag ttatcctgaa gaacgctatc gtttacaact ccatgtacga aaacttctcc    2820
acctccttct ggatccgtat cccgaaatac ttcaactcca tctccctgaa caacgaatac    2880
accatcatca actgcatgga gaacaactcc ggctggaaag tttccctgaa ctacggcgaa    2940
atcatctgga ccctgcagga cacccaggaa atcaaacagc gtgttgtttt caaatactcc    3000
cagatgatca acatctccga ctacatcaac cgttggatct tcgttaccat caccaacaac    3060
cgtctgaaca actccaaaat ctacatcaac ggccgtctga tcgaccagaa accgatctcc    3120
aacctgggca acatccacgc ttccaacaac atcatgttca aactggacgg ctgccgtgac    3180
acccaccgtt acatctggat caaatacttc aacctgttcg acaaagaact gaacgagaag    3240
gaaatcaaag acctgtacga caaccagtcc aactccggca tcctgaaaga cttctggggc    3300
gactacctgc agtacgacaa accgtactac atgctgaacc tgtacgaccc gaacaaatac    3360
gttgacgtta acaacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgtccca ggttgtagtt    3660
atgaaatcca gaacgacca gggcatcacc aacaaatgca aatgaacct gcaggacaac    3720 aacggcaacg acatcggctt catcggcttc caccagttca acaacatcgc taaactggtt    3780
gcttccaact ggtacaaccg tcagatcgaa cgttcctccc gtaccctggg ctgctcctgg    3840
gaattcatcc cggttgacga cggctggggc gaacgtccgc tgtaa                   3885
```

<210> SEQ ID NO 233
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-E8, optimized for E. coli expression

<400> SEQUENCE: 233

| | | | | | |
|---|---|---|---|---|---|
| atgccgttcg | ttaacaaaca | gttcaactac | aaagacccgg | ttaacggcgt | tgacatcgct | 60 |
| tacatcaaaa | tcccgaacgc | tggccagatg | cagccggtta | aagctttcaa | aatccacaac | 120 |
| aagatttggg | taatcccgga | acgtgacacc | ttcaccaacc | cggaagaagg | cgacctgaac | 180 |
| ccgccgccgg | aagctaaaca | ggttccggtt | cctactacg | actccaccta | cctgtccacc | 240 |
| gacaacgaga | aggacaacta | cctgaaaggc | gttaccaaac | tgttcgaacg | tatctactcc | 300 |
| accgacctgg | ccgtatgct | gctgacctcc | atcgttcgtg | gcatcccgtt | ctggggcggc | 360 |
| tccaccatcg | acaccgaact | gaaagttatc | gacaccaact | gcatcaacgt | tatccagccg | 420 |
| gacggctcct | accgttccga | agaactgaac | ctggttatca | tcggcccgtc | cgctgacatc | 480 |
| atccagttcg | aatgcaaatc | cttcggccac | gaagttctga | acctgacccg | taacggctac | 540 |
| ggctccaccc | agtacatccg | tttctccccg | gacttcacct | tcggcttcga | agaatccctg | 600 |
| gaagttgaca | ccaacccgct | gctgggcgct | ggcaaattcg | ctaccgaccc | ggctgttacc | 660 |
| ctggctcacg | aactgatcca | cgctggccac | cgtctgtacg | gcatcgctat | caacccgaac | 720 |
| cgtgttttca | agttaacac | caacgcttac | tacgaaatgt | ccggcctgga | agtttccttc | 780 |
| gaagaactgc | gtaccttcgg | cggccacgac | gctaaattca | tcgactccct | gcaggaaaac | 840 |
| gaattccgtc | tgtactatta | caacaaattc | aaagacatcg | cttccaccct | gaacaaagct | 900 |
| aaatccatcg | ttggcaccac | cgcttccctg | cagtacatga | agaacgtttt | caagagaag | 960 |
| tacctgctgt | ccgaagacac | ctccggcaaa | ttctccgttg | acaaactgaa | attcgacaaa | 1020 |
| ctgtacaaaa | tgctgaccga | aatctacacc | gaagacaact | tcgttaaatt | cttcaaagtt | 1080 |
| ctgaaccgta | aaacctacct | gaacttcgac | aaagctgttt | tcaaaatcaa | catcgttccg | 1140 |
| aaagttaact | acaccatcta | cgacggcttc | aacctgcgta | acaccaacct | ggctgctaac | 1200 |
| ttcaacggcc | agaacaccga | aatcaacaac | atgaacttca | ccaaactgaa | gaacttcacc | 1260 |
| ggcctgttcg | aattctacaa | actgctgtgc | gttcgtggca | tcatcacctc | caaacagatc | 1320 |
| gaccgtatca | tggagaaggc | tctgaacgac | ctgtgcatca | agttaacaa | ctgggacctg | 1380 |
| ttcttctctc | cgtccgaaga | acttcacc | aacgacctga | caaaggcga | agaaatcacc | 1440 |
| tccgacacca | catcgaagc | tgctgaagaa | acatctcccc | tggacctgat | ccagcagtac | 1500 |
| tacctgacct | tcaacttcga | caacgaaccg | gaaacatcc | ccatcgaaaa | cctgtcctcc | 1560 |
| gacatcatcg | ccagctgga | actgatgccg | aacatcgaac | gtttcccgaa | cggcaagaag | 1620 |
| tatgaactgg | acaaatacac | catgttccac | tacctgcgtg | ctcaggaatt | cgaacacggc | 1680 |
| aaatcccgta | tcgctctgac | caactccgtt | aacgaagctc | tgctgaaccc | gtcccgtgtt | 1740 |
| tacaccttct | tctcctccga | ctacgttaag | aaggttaaca | aagctaccga | agctgctatg | 1800 |
| ttcctgggct | gggttgaaca | gctggtttac | gacttcaccg | acgaaacctc | cgaagtttcc | 1860 |
| accaccgaca | agattgctga | catcaccatc | attatcccgt | acatcggccc | ggctctgaac | 1920 |
| atcggcaaca | tgctgtacaa | agacgacttc | gttggcgctc | tgatcttctc | cggcgctgtt | 1980 |
| atcctgctgg | aattcatccc | ggaaatcgct | atcccggttc | tgggcacctt | cgctctggtt | 2040 |
| tcctacatcg | ctaacaaagt | tctgaccgtt | cagaccatcg | acaacgctct | gtccaaacgt | 2100 |
| aacgagaagt | gggacgaagt | ttacaaatac | atcgttacca | ctggctggc | taaagttaac | 2160 |
| acccagatcg | acctgatccg | taagaagatg | aaagaagctc | tggagaacca | ggctgaagct | 2220 |

```
accaaagcta tcatcaacta ccagtacaac cagtacaccg aagaggaaaa gaacaacatc    2280
aacttcaaca tcgacgacct gtcctccaaa ctgaacgaat ccatcaacaa agctatgatc    2340
aacatcaaca aattcctgaa ccagtgctcc gtttcctacc tgatgaactc catgatcccg    2400
tacggcgtta acgtctgga gacttcgac gcttccctga agacgctct gctgaaatac       2460 atctacgaca accgtggcac cctgatcggc caggttgacc gtctgaaaga caaagttaac    2520
aacaccctgt ccaccgacat cccgttccag ctgtccaaat acgttgacaa ccagcgtctg    2580
ctgtccacct tcaccgaata catcaagaac atcatcaaca cctccatcct gaacctgcgt    2640
tacgaatcca accacctgat cgacctgtcc cgttacgctt ccaagattaa catcggctcc    2700
aaagttaact tcgaccccgat cgacaagaac cagatccagc tgttcaacct ggaatcctcc    2760
aagattgaag ttatcctgaa gaacgctatc gtttacaact ccatgtacga gaacttctcc    2820
acctccttct ggatccgtat cccgaaatac ttcaactcca tctccctgaa caacgaatac    2880
accatcatca actgcatgga aaacaactcc ggctggaaag tttccctgaa ctacggcgaa    2940
atcatctgga ccctgcagga cacccaggaa atcaaacagc gtgttgtttt caaatactcc    3000
cagatgatca acatctccga ctacatcaac cgttggatct tcgttaccat caccaacaac    3060
cgtctgaaca actccaaaat ctacatcaac ggccgtctga tcgaccagaa accgatctcc    3120
aacctgggca catccacgc ttccaacaac atcatgttca aactggacgg ctgccgtgac    3180
acccaccgtt acatctggat caaatacttc aacctgttcg acaagaact gaacgagaag    3240 gaaatcaaag acctgtacga caaccagtcc aactccggca tcctgaaaga cttctggggc    3300
gactacctgc agtatgacaa accgtactac atgctgaacc tgtacgaccc gaacaaatac    3360
gttgacgtta caacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgagcca agttgtagtt    3660
atgaaatcca agaacgacca gggcatcacc aacaagtgca agatgaacct gcaggacaac    3720
aacggcaacg catcggctt catcggcttc caccagttca caacatcgc taaactggtt    3780 gcttccaact ggtacaaccg tcagatcgaa cgttcctccc gtaccctggg ctgctcctgg    3840
gaattcatcc cggttgacga cggctggggt gaacgtccgc tgtaa                    3885
```

<210> SEQ ID NO 234
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-F8, optimized
    for E. coli expression

<400> SEQUENCE: 234

```
atgccgttcg ttaacaaaca gttcaactac aaagacccgg ttaacggcgt tgacatcgct    60
tacatcaaaa tcccgaacgc tggccagatg cagccggtta agctttcaa aatccacaac    120 aaaatctggg ttatcccgga acgtgacacc ttcaccaacc cggaagaagg cgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
```

-continued

| | |
|---|---|
| accgacctgg gccgtatgct gctgacctcc atcgttcgtg gcatcccgtt ctggggcggc | 360 |
| tccaccatcg acaccgaact gaaagttatc gacaccaact gcatcaacgt tatccagccg | 420 |
| gacggctcct accgttccga agaactgaac ctggttatca tcggcccgtc cgctgacatc | 480 |
| atccagttcg aatgcaaatc cttcggccac gaagttctga acctgacccg taacggctac | 540 |
| ggctccaccc agtacatccg tttctccccg gacttcacct tcggcttcga agaatccctg | 600 |
| gaagttgaca ccaacccgct gctgggcgct ggcaaattcg ctaccgaccc ggctgttacc | 660 |
| ctggctcacg aactgatcca cgctggccac cgtctgtacg gcatcgctat caacccgaac | 720 |
| cgtgttttca agttaacac caacgcttac tacgaaatgt ccggcctgga gtttccttc | 780 |
| gaagaactgc gtaccttcgg cggccacgac gctaaattca tcgactccct gcaggagaac | 840 |
| gaattccgtc tgtactatta caacaaattc aaagacatcg cttccaccct gaacaaagct | 900 |
| aaatccatcg ttggcaccac cgcttccctg cagtacatga gaacgttttt caagagaag | 960 |
| tacctgctgt ccgaagacac ctccggcaaa ttctccgttg acaaactgaa attcgacaaa | 1020 |
| ctgtacaaga tgctgaccga aatctacacc gaagacaact tcgttaaatt cttcaaagtt | 1080 |
| ctgaaccgta agacttacct gaacttcgac aaagctgttt tcaaaatcaa catcgttccg | 1140 |
| aaagttaact acaccatcta cgacggcttc aacctgcgta acaccaacct ggctgctaac | 1200 |
| ttcaacggcc agaacaccga aatcaacaac atgaacttca ccaaactgaa gaacttcacc | 1260 |
| ggcctgttcg aattctacaa actgctgtgc gttcgtggca tcatcacctc caaagaacgt | 1320 |
| gaccagaaac tgtccgaagc tctgaacgac ctgtgcatca agttaacaa ctgggacctg | 1380 |
| ttcttctctc cgtccgaaga caacttcacc aacgacctga caaaggcga agaaatcacc | 1440 |
| tccgacacca catcgaagc tgctgaagag aacatctccc tggacctgat ccagcagtac | 1500 |
| tacctgacct tcaacttcga caacgaaccg gaaaacatct ccatcgaaaa cctgtcctcc | 1560 |
| gacatcatcg ccagctgga actgatgccg aacatcgaac gtttcccgaa cggcaagaag | 1620 |
| tatgaactgg acaaatacac catgttccac tacctgcgtg ctcaggaatt cgaacacggc | 1680 |
| aaatcccgta tcgctctgac caactccgtt aacgaagctc tgctgaaccc gtcccgtgtt | 1740 |
| tacaccttct tctcctccga ctacgttaag aaggttaaca aagctaccga agctgctatg | 1800 |
| ttcctgggct gggttgaaca gctggtttac gacttcaccg acgaaacctc cgaagtttcc | 1860 |
| accaccgaca agattgctga catcaccatc attatcccgt acatcggccc ggctctgaac | 1920 |
| atcggcaaca tgctgtacaa agacgacttc gttggcgctc tgatcttctc cggcgctgtt | 1980 |
| atcctgctgg aattcatccc ggaaatcgct atcccggttc tgggcacctt cgctctggtt | 2040 |
| tcctacatcg ctaacaaagt tctgaccgtt cagaccatcg acaacgctct gtccaaacgt | 2100 |
| aacgagaagt gggacgaagt ttacaaatac atcgttacca actggctggc taaagttaac | 2160 |
| acccagatcg acctgatccg taagaagatg aaagaagctc tggagaacca ggctgaagct | 2220 |
| accaaagcta tcatcaacta ccagtacaac cagtacaccg aagaggaaaa gaacaacatc | 2280 |
| aacttcaaca tcgacgacct gtcctccaaa ctgaacgaat ccatcaacaa agctatgatc | 2340 |
| aacatcaaca aattcctgaa ccagtgctcc gtttcctacc tgatgaactc catgatcccg | 2400 |
| tacggcgtta acgtctggga agacttcgac gcttccctga agacgctct gctgaaatac | 2460 |
| atctacgaca accgtggcac cctgatcggc caggttgacc gtctgaaaga caaagttaac | 2520 |
| aacaccctgt ccaccgacat cccgttccag ctgtccaaat acgttgacaa ccagcgtctg | 2580 |
| ctgtccacct tcaccgaata catcaagaac atcatcaaca cctccatcct gaacctgcgt | 2640 |

```
tacgaatcca accacctgat cgacctgtcc cgttacgctt ccaagattaa catcggctcc   2700
aaagttaact tcgacccgat cgacaagaac cagatccagc tgttcaacct ggaatcctcc   2760
aagattgaag ttatcctgaa gaacgctatc gtttacaact ccatgtacga gaacttctcc   2820
acctccttct ggatccgtat cccgaaatac ttcaactcca tctccctgaa caacgaatac   2880
accatcatca actgcatgga aaacaactcc ggctggaaag tttccctgaa ctacggcgaa   2940
atcatctgga ccctgcagga cacccaggaa atcaaacagc gtgttgtttt caaatactcc   3000
cagatgatca acatctccga ctacatcaac cgttggatct tcgttaccat caccaacaac   3060
cgtctgaaca actccaaaat ctacatcaac ggccgtctga tcgaccagaa accgatctcc   3120
aacctgggca catccacgc ttccaacaac atcatgttca aactggacgg ctgccgtgac   3180
acccaccgtt acatctggat caaatacttc aacctgttcg acaagaact gaacgagaag   3240 gaaatcaaag acctgtacga caaccagtcc aactccggca tcctgaaaga cttctggggc   3300
gactacctgc agtatgacaa accgtactac atgctgaacc tgtacgaccc gaacaaatac   3360
gttgacgtta caacgttgg catccgtggc tacatgtacc tgaaaggccc gcgtggctcc   3420
gttatgacca ccaacatcta cctgaactcc tccctgtacc gtggcaccaa attcatcatc   3480
aagaagtacg cttccggcaa caaagacaac atcgttcgta caacgaccg tgtttacatc   3540 aacgttgtag ttaagaacaa agaataccgt ctggctacca acgcttccca ggctggcgtt   3600
gagaagattc tgtccgctct ggaaatcccg gacgttggca acctgtccca agttgtagtt   3660
atgaaatcca agaacgacca gggcatcacc aacaagtgca agatgaacct gcaggacaac   3720
aacggcaacg acatcggctt catcggcttc caccagttca acaacatcgc taaactggtt   3780
gcttccaact ggtacaaccg tcagatcgaa cgttcctccc gtaccctggg ctgctcctgg   3840
gaattcatcc cggttgacga cggctggggc gaacgtccgc tgtaa   3885
```

<210> SEQ ID NO 235
<211> LENGTH: 3885
<212> TYPE: DNA
<213> ORGANISM: Artificial Sequence
<220> FEATURE:
<221> NAME/KEY: mat_peptide
<222> LOCATION: (1)...(3882)
<223> OTHER INFORMATION: Polynucleotide encoding BoNT/A-G8, optimized
      for E. coli expression

<400> SEQUENCE: 235

```
atgccgttcg ttaacaaaca gttcaactac aaagacccgg ttaacggcgt tgacatcgct     60
tacatcaaaa tcccgaacgc tggccagatg cagccggtta agctttcaa atccacaac     120 aaaatctggg ttatcccgga acgtgacacc ttcaccaacc cggaagaagg cgacctgaac    180
ccgccgccgg aagctaaaca ggttccggtt tcctactacg actccaccta cctgtccacc    240
gacaacgaga aggacaacta cctgaaaggc gttaccaaac tgttcgaacg tatctactcc    300
accgacctgg gccgtatgct gctgacctcc atcgttcgtg gcatcccgtt ctggggcggc    360
tccaccatcg acaccgaact gaaagttatc gacaccaact gcatcaacgt tatccagccg    420
gacggctcct accgttccga agaactgaac ctggttatca tcggcccgtc cgctgacatc    480
atccagttcg aatgcaaatc cttcggccac gaagttctga acctgacccg taacggctac    540
ggctccaccc agtacatccg tttctcccg gacttcacct tcggcttcga agaatccctg    600
gaagttgaca ccaacccgct gctgggcgct ggcaaattcg ctaccgaccc ggctgttacc    660
ctggctcacg aactgatcca cgctggccac cgtctgtacg gcatcgctat caacccgaac    720
```

-continued

```
cgtgttttca aagttaacac caacgcttac tacgaaatgt ccggcctgga agtttccttc      780
gaagaactgc gtaccttcgg cggccacgac gctaaattca tcgactccct gcaggaaaac      840
gaattccgtc tgtactatta caacaaattc aaagacatcg cttccaccct gaacaaagct      900
aaatccatcg ttggcaccac cgcttccctg cagtacatga agaacgtttt caaagagaag      960
tacctgctgt ccgaagacac ctccggcaaa ttctccgttg acaaactgaa attcgacaaa     1020
ctgtacaaaa tgctgaccga aatctacacc gaagacaact tcgttaaatt cttcaaagtt     1080
ctgaaccgta aacctacct gaacttcgac aaagctgttt tcaaaatcaa catcgttccg       1140
aaagttaact acaccatcta cgacggcttc aacctgcgta acaccaacct ggctgctaac     1200
ttcaacggcc agaacaccga atcaacaac atgaacttca ccaaactgaa gaacttcacc       1260
ggcctgttcg aattctacaa actgctgtgc gttcgtggca tcatcacctc caagaaaacc     1320
tccgctgcta aactgaaagc tctgaacgac ctgtgcatca agttaacaa ctgggacctg       1380
ttcttctccc cgtccgaaga caacttcacc aacgacctga caaaggcga gaaaatcacc       1440
tccgacacca acatcgaagc tgctgaagaa aacatctccc tggacctgat ccagcagtac     1500
tacctgacct tcaacttcga caacgaaccg gaaaacatct ccatcgagaa cctgtcctcc     1560
gacatcatcg gccagctgga actgatgccg aacatcgaac gtttcccgaa cggcaagaag     1620
tatgaactgg acaaatacac catgttccac tacctgcgtg ctcaggaatt cgaacacggc     1680
aaatcccgta tcgctctgac caactccgtt aacgaagctc tgctgaaccc gtcccgtgtt     1740
tacacccttct tctcctccga ctacgttaag aaggttaaca agctaccga agctgctatg     1800
ttcctgggct gggttgaaca gctggtttac gacttcaccg acgaaacctc cgaagtttcc     1860
accaccgaca agattgctga catcaccatc attatcccgt acatcggccc ggctctgaac     1920
atcggcaaca tgctgtacaa agacgacttc gttggcgctc tgatcttctc cggcgctgtt     1980
atcctgctgg aattcatccc ggaaatcgct atcccggttc tgggcacctt cgtctctggtt   2040
tcctacatcg ctaacaaagt tctgaccgtt cagaccatcg acaacgctct gtccaaacgt     2100
aacgagaagt gggacgaagt ttacaaatac atcgttacca actggctggc taaagttaac     2160
acccagatcg acctgatccg taagaagatg aaagaagctc tggagaacca ggctgaagct     2220
accaaagcta tcatcaacta ccagtacaac cagtacaccg aagaggaaaa gaacaacatc     2280
aacttcaaca tcgacgacct gtcctccaaa ctgaacgaat ccatcaacaa agctatgatc     2340
aacatcaaca aattcctgaa ccagtgctcc gtttcctacc tgatgaactc catgatcccg     2400
tacggcgtta acgtctgga agacttcgac gcttccctga agacgctct gctgaaatac       2460
atctacgaca accgtggcac cctgatcggc caggttgacc gtctgaaaga caaagttaac     2520
aacaccctgt ccaccgacat cccgttccag ctgtccaaat acgttgacaa ccagcgtctg     2580
ctgtccacct tcaccgaata catcaagaac atcatcaaca cctccatcct gaacctgcgt     2640
tacgaatcca accacctgat cgacctgtcc cgttacgctt ccaagattaa catcggctcc     2700
aaagttaact tcgacccgat cgacaagaac cagatccagc tgttcaacct ggaatcctcc     2760
aagattgaag ttatcctgaa gaacgctatc gtttacaact ccatgtacga aaacttctcc     2820
acctccttct ggatccgtat cccgaaatac ttcaactcca tctccctgaa caacgaatac     2880
accatcatca actgcatgga aaacaactcc ggctggaaag tttccctgaa ctacggcgaa     2940
atcatctgga ccctgcagga cacccaggaa atcaaacagc gtgttgtttt caaatactcc     3000
cagatgatca acatctccga ctacatcaac cgttggatct tcgttaccat caccaacaac     3060
cgtctgaaca actccaaaat ctacatcaac ggccgtctga tcgaccagaa accgatctcc     3120
```

```
aacctgggca acatccacgc ttccaacaac atcatgttca aactggacgg ctgccgtgac    3180
acccaccgtt acatctggat caaatacttc aacctgttcg acaaagaact gaacgagaag    3240
gaaatcaaag acctgtacga caaccagtcc aactccggca tcctgaaaga cttctggggc    3300
gactacctgc agtatgacaa accgtactac atgctgaacc tgtacgaccc gaacaaatac    3360
gttgacgtta acaacgttgg catccgtggc tacatgtacc tgaaaggccc gcgtggctcc    3420
gttatgacca ccaacatcta cctgaactcc tccctgtacc gtggcaccaa attcatcatc    3480
aagaagtacg cttccggcaa caaagacaac atcgttcgta caacgaccg tgtttacatc    3540 aacgttgtag ttaagaacaa agaataccgt ctggctacca acgcttccca ggctggcgtt    3600
gagaagattc tgtccgctct ggaaatcccg gacgttggca acctgtccca agttgtagtt    3660
atgaaatcca agaacgacca gggcatcacc aacaagtgca agatgaacct gcaggacaac    3720
aacggcaacg catcggcttc catcggcttc caccagttca caacatcgc taaactggtt    3780 gcttccaact ggtacaaccg tcagatcgaa cgttcctccc gtaccctggg ctgctcctgg    3840
gaattcatcc cggttgacga cggctggggc gaacgtccgc tgtaa              3885
```

<210> SEQ ID NO 236
<211> LENGTH: 3912
<212> TYPE: DNA
<213> ORGANISM: Artificial Sequence
<220> FEATURE:
<221> NAME/KEY: mat_peptide
<222> LOCATION: (1)...(3909)
<223> OTHER INFORMATION: Polynucleotide encoding BoNT/A-A17, optimized for P. pastoris expression.

<400> SEQUENCE: 236

```
atgccatttg ttaacaagca atttaactac aaggatccag ttaacggtgt tgatattgct      60
tacattaaaa ttccaaacgc tggtcaaatg caaccagtta aggcattcaa gattcataac     120
aagatttggg ttattccaga aagagatact tttactaacc cagaagaagg tgatttgaac     180
ccacctccag aagctaagca agttccagtt tcttactacg attctactta cttgtcactg     240
gataacgaga agataactta cttgaagggt gttactaagt tgtttgaaag aatttactct     300
actgatttgg gtagaatgtt gttgacttct attgttagag gtattccatt tgggggtggt     360
tctactattg atactgaatt gaaggttatt gatactaact gtattaacgt tattcaacca     420
gatggttctt acagatctga agaattgaac ttggttatta ttggtccatc tgctgatatt     480
attcaatttg aatgtaagtc cttcggtcat gaagtttga acttgactag aaacggttac     540
ggttctactc aatacattag attctcccca gacttcactt ttggttttga agaatctttg     600
gaagttgata ctaacccatt gttgggtgct ggtaagtttg ctactgatcc agctgttact     660
ttggctcatg aattgattca tgctggtcat agattgtacg gtattgctat taacccaaac    720
agagtcttca aggttaacac taacgcttac tacgaaatgt ctggtttgga agtttccttc    780
gaagaattga aacttttgg tggtcacgac gctaagttta tgattctttt gcaagaaaac    840
gaatttagat tgtactatta acaagtttt aaggatattg cttctacttt gaacaaggct    900
aagtctattg ttggtactac tgcttctttg caatacatga agaacgtctt caaggagaaa    960
tacttgttgt ctgaagatac ttctggtaag ttctccgttg ataagttgaa gtttgataag    1020
ttgtacaaga tgttgactga aatttacact gaagataact tgttaagtt cttcaaggtt    1080 ttgaacagaa agacttactt gaactttgat aaggctgtct tcaagattaa cattgttcca    1140
aaggttaact acactatttt cgacggtttt aacttgagaa acactaactt ggctgctaac    1200
```

```
tttaacggtc aaaacactga aattaacaac atgaactttta ctaagttgaa gaactttact   1260
ggtttgtttg aattttacaa gttgttgtgt gttagaggta ttattacttc taagtctaac   1320
aagactagaa ttgacgaagc taaccaacgt gctactaaga tgttggcttt gaacgatttg   1380
tgtattaagg ttaacaactg ggatttgttc ttctccccat ctgaagataa ctttactaac   1440
gatttgaaca agggtgaaga aattacttct gatactaaca ttgaagctgc tgaagaaaac   1500
atttctttgg atttgattca acaatactac ttgactttta actttgataa cgaaccagaa   1560
aacatttcta ttgaaaactt gtcttctgat attattggtc aacttgaatt gatgccaaac   1620
attgaaagat ttccaaacgg taagaagtat gaacttgata aatacactat gtttcattac   1680
ttgagagctc aagaatttga acacggtaag tctagaattg ctttgactaa ctctgttaac   1740
gaagctttgt tgaacccatc tagagtttac acattcttct cctctgatta cgttaagaag   1800
gttaacaaag ctactgaagc tgctatgttc cttggttggg ttgaacaatt ggtttacgat   1860
tttactgacg aaacttctga gtttctact actgataaga ttgctgatat tactattatc   1920
attccataca ttggtccagc tttgaacatt ggtaacatgt tgtacaagga tgattttgtt   1980
ggtgctttga tcttctccgg tgctgttatt ttgttggaat ttattccaga aattgctatt   2040
ccagttttgg gtacattcgc tttggttct tacattgcta acaaggtttt gactgttcaa   2100
actattgata acgctttgtc taagagaaac gaaaagtggg acgaagttta caagtacatt   2160
gttactaact ggttggctaa ggttaacact caaattgatt tgattagaaa gaagatgaag   2220
gaagctttgg agaatcaagc tgaagctact aaggctatta ttaactacca atacaaccaa   2280
tacactgaag aggaaaagaa caacattaac tttaacattg acgatttgtc ttctaagttg   2340
aatgaatcta ttaacaaggc tatgattaac attaacaagt tccttaacca atgttctgtt   2400
tcttacttga tgaactctat gattccatac ggtgttaaga gattggaaga ttttgacgct   2460
tctttgaagg acgctttgtt gaagtacatt tacgataaca gaggtacttt gattggtcaa   2520
gttgatagat tgaaggataa ggttaacaac actttgtcta ctgatattcc atttcaattg   2580
tctaagtacg ttgataacca aagattgttg tctacttta ctgaatacat taagaacatt   2640
attaacactt ctattttgaa cttgagatac gaatctaacc atttgattga tttgtctaga   2700
tacgcttcta agattaacat tggttctaag gttaactttg atccaattga taagaaccaa   2760
attcaattgt ttaacttgga atcttctaag attgaagtta ttttgaaaaa cgctattgtt   2820
tacaactcta tgtacgaaaa cttctccact tccttctgga ttagaattcc aaagtacttt   2880
aactctattt ctttgaacaa tgaatacact attattaact gtatggaaaa caactctggt   2940
tggaaggttt ctttgaacta cggtgaaatt atttggactt tgcaagatac tcaagaaatt   3000
aagcaaagag ttgtcttcaa atactctcaa atgattaaca tttctgatta cattaacaga   3060
tggatcttcg ttactattac taacaacaga ttgaacaact ctaagattta cattaacggt   3120
agattgattg atcaaaagcc aatttctaac ttgggtaaca ttcatgcttc taacaacatt   3180
atgtttaagt tggatggttg tagagatact catagataca tttggattaa gtactttaac   3240
ttgtttgata aggaattgaa cgaaaaggaa attaaggatt tgtacgataa ccaatctaac   3300
tctggtattt tgaaggactt ctggggtgat tacttgcaat atgataagcc atactacatg   3360
ttgaacttgt acgatccaaa caagtacgtt gacgttaaca cgttggtat tagaggttac   3420 atgtacttga agggtccaag aggttctgtt atgactacta acatttactt gaactcttct   3480
ttgtacagag gtactaagtt tattattaag aagtacgctt ctggtaacaa ggataacatt   3540
```

```
gttagaaaca acgatagagt ttacattaac gttgtcgtta agaacaagga atacagattg    3600
gctactaacg cttctcaagc tggtgttgaa aagattttgt ctgctttgga aattccagac    3660
gttggtaact tgtctcaagt tgtcgttatg aagtctaaga acgatcaagg tattactaac    3720
aagtgtaaga tgaacttgca agataacaac ggtaacgata ttggttttat tggttttcat    3780
caatttaaca acattgctaa gttggttgct tctaactggt acaacagaca aattgaaaga    3840
tcttctagaa ctttgggttg ttcttgggaa tttattccag ttgacgatgg ttggggtgaa    3900
agaccattgt aa                                                        3912

<210> SEQ ID NO 237
<211> LENGTH: 3912
<212> TYPE: DNA
<213> ORGANISM: Artificial Sequence
<220> FEATURE:
<221> NAME/KEY: mat_peptide
<222> LOCATION: (1)...(3909)
<223> OTHER INFORMATION: Polynucleotide encoding BoNT/A-A17, optimized
      for S. frugiperda expression.

<400> SEQUENCE: 237
atgcccttcg tgaacaagca gttcaactac aaggaccccg tgaacggtgt ggacatcgct      60
tacatcaaaa tccccaacgc tggtcagatg cagcccgtga aggctttcaa gatccacaac     120
aagatctggg tgatcccgga cgtgacacc ttcaccaacc ccgaggaggg tgacctgaat     180
ccccctcccg aggctaagca ggtgcccgtg tcctactacg actccaccta cctgtccacc     240
gacaacgaga aggacaacta cctgaagggt gtgaccaagc tgttcgagcg tatctactcc     300
accgacctgg tcgtatgct gctgacctcc atcgtgcgtg gtatcccctt ctggggtggt     360
tccaccatcg acaccgagct gaaggtgatc gacaccaact gcatcaacgt gatccagccc     420
gacggttcct accgttccga ggagctgaac ctggtgatca tcggtccctc cgctgacatc     480
atccagttcg agtgcaagtc cttcggtcac gaggtgctga acctgacccg taacggttac     540
ggttccaccc agtacatccg tttctctcct gacttcacct tcggtttcga ggagtccctg     600
gaggtggaca ccaatcctct cctgggtgct ggtaagttcg ctaccgatcc tgctgtgacc     660
ctggctcacg agctgatcca cgctggtcac cgtctgtacg gtatcgctat caaccccaac     720
cgtgtgttca aggtgaacac caacgcttac tacgagatgc ccgtctggga ggtgtccttc     780
gaggagctgc gtaccttcgg tggtcacgac gctaagttca tcgactccct gcaggagaac     840
gagttccgtc tgtactatta caacaagttc aaggacatcg cttccaccct gaacaaggct     900
aagtccatcg tgggtaccac cgcttccctg cagtacatga agaacgtgtt caaggagaag     960
tacctgctgt ccgaggacac ctccggtaag ttctccgtgg acaagctgaa gttcgacaag    1020
ctgtacaaga tgctgaccga gatctacacc gaggacaact tcgtgaagtt cttcaaggtg    1080
ctgaaccgta agacctacct gaacttcgac aaggctgtgt tcaagatcaa catcgtgccc    1140
aaggtgaact acaccatcta cgacggtttc aacctgcgta caccaacct ggctgctaac    1200 ttcaacggtc aaaacaccga gatcaacaac atgaacttca ccaagctgaa gaacttcacc    1260
ggtctgttcg agttctacaa gctgctgtgc gtgcgtggta tcatcacctc caagtccaac    1320
aagacccgta tcgacgaagc taaccagcgt gctaccaaga tgctggctct gaacgacctg    1380
tgcatcaagg tgaacaactg ggacctgttc ttctctcctt ccgaggacaa cttcaccaac    1440
gacctgaaca agggtgagga gatcacctcc gacaccaaca tcgaggctgc tgaggagaac    1500
atctccctgg acctgatcca gcagtactac ctgaccttca acttcgacaa cgagcccgag    1560
```

```
aacatctcca tcgagaacct gtcctccgac atcatcggtc agctcgagct gatgcccaac   1620
atcgagcgtt tccccaacgg taagaagtat gagctggaca aatacaccat gttccactac   1680
ctgcgtgctc aggagttcga gcacggtaag tcccgtatcg ctctgaccaa ctccgtgaac   1740
gaggctctgc tgaacccctc ccgtgtgtac accttcttct cctccgacta cgtgaagaag   1800
gtgaacaagg ctaccgaagc tgctatgttc ctgggttggg tggagcagct ggtgtacgac   1860
ttcaccgacg agacctccga ggtgtccacc accgacaaga tcgctgacat caccatcatt   1920
atcccttaca tcggtcccgc tctgaacatc ggtaacatgc tgtacaagga cgacttcgtg   1980
ggtgctctga tcttctccgg tgctgtgatc ctgctggagt tcatccccga gatcgctatc   2040
cccgtgctgg gtaccttcgc tctggtgtcc tacatcgcta acaaggtgct gaccgtgcag   2100
accatcgaca acgctctgtc caagcgtaac gagaagtggg acgaggtgta caagtacatc   2160
gtgaccaact ggctggctaa ggtgaacacc cagatcgacc tgatccgtaa gaagatgaag   2220
gaggctctgg agaaccaggc tgaggctacc aaggctatca tcaactacca gtacaaccag   2280
tacaccgagg aagagaagaa caacatcaac ttcaacatcg acgacctgtc ctccaagctg   2340
aatgagtcca tcaacaaggc tatgatcaac atcaacaagt tcctgaacca gtgctccgtg   2400
agctacctga tgaactccat gattccttac ggtgtgaagc gtcttgagga cttcgacgct   2460
tccctgaagg acgctctgct gaagtacatc tacgacaata ggggtaccct gataggtcag   2520
gttgaccgtc tgaaggacaa ggtgaacaac accctgtcca ccgacatccc cttccagctg   2580
tccaagtacg tggacaacca gcgtctgctg tccaccttca ccgagtacat caagaacatc   2640
atcaacacct ccatcctgaa cctgcgttac gagtccaacc acctgatcga cctgtcccgt   2700
tacgcttcca agatcaacat cggttccaag gtgaacttcg accccatcga caagaaccag   2760
atccagctgt tcaacctgga gtcctccaag atcgaggtga tcctgaaaaa cgctatcgtg   2820
tacaactcca tgtacgagaa cttctccacc tccttctgga tccgtattcc taagtacttc   2880
aactccatct ccctgaacaa tgaatacacc atcatcaact gcatggagaa caactccggt   2940
tggaaggtgt ccctgaacta cggtgagatc atctggaccc tgcaggacac ccaggagatc   3000
aagcagcgtg tggtgttcaa atactcccag atgatcaaca tctccgacta catcaaccgt   3060
tggatcttcg tgaccatcac caacaaccgt ctgaacaact ccaagatcta catcaacggt   3120
cgtctgatcg accagaagcc catctccaac ctgggtaaca tccacgcttc caacaacatc   3180
atgttcaagc tggacggttg ccgtgacacc caccgttaca tctggatcaa gtacttcaac   3240
ctgttcgaca aggagctgaa cgagaaggag atcaaggacc tgtacgacaa ccagtccaac   3300
tccggtatcc tgaaggactt ctggggtgac tacctgcagt atgacaagcc ctactacatg   3360
ctgaacctgt acgaccccaa caagtacgtg gacgtgaaca acgtgggtat ccgtggttac   3420
atgtacctga agggtcctcg cggttccgtg atgaccacca acatctacct gaactcctcc   3480
ctgtaccgtg gtaccaagtt catcatcaag aagtacgctt ccggtaacaa ggacaacatc   3540
gtgcgtaaca acgaccgtgt gtacatcaac gtggtcgtga agaacaagga gtaccgtctg   3600
gctaccaacg cttcccaggc tggtgtggag aagatcctgt ccgctctgga gatccccgac   3660
gtgggtaacc tgtcccaagt cgtcgtgatg aagtccaaga acgaccaggg tatcaccaac   3720
aagtgcaaga tgaacctgca ggacaacaac ggtaacgaca tcggtttcat cggtttccac   3780
cagttcaaca acatagctaa gctggtggct tccaactggt acaaccgtca gatcgagcgt   3840
tcctcccgta ccctgggttg ctcctgggag ttcattcctg tggacgacgg ttggggtgag   3900
cgtcctctct aa                                                       3912
```

<210> SEQ ID NO 238
<211> LENGTH: 3912
<212> TYPE: DNA
<213> ORGANISM: Artificial Sequence
<220> FEATURE:
<221> NAME/KEY: mat_peptide
<222> LOCATION: (1)...(3909)
<223> OTHER INFORMATION: Polynucleotide encoding BoNT/A-A17, optimized for H. sapiens expression.

<400> SEQUENCE: 238

```
atgcccttcg tgaacaagca gttcaactac aaggaccccg tgaacggcgt ggacatcgcc      60
tacatcaaaa tcccaaacgc cggccagatg cagcccgtga aggccttcaa gatccacaac     120
aagatctggg tgatccccga gagacacacc ttcaccaacc ccgaggaggg cgacctgaat     180
ccaccaccag aggccaagca ggtgcccgtg agctactacg acagcaccta cctgagcacc     240
gacaacgaga aggacaacta cctgaagggc gtgaccaagc tgttcgagag aatctacagc     300
accgacctgg gcagaatgct gctgaccagc atcgtgagag gcattccatt ctggggcggc     360
agcaccatcg acaccgagct gaaggtgatc gacaccaact gcatcaacgt gatccagccc     420
gacggcagct acagaagcga ggagctgaac ctggtgatca tcggaccaag cgccgacatc     480
atccagttcg agtgcaagag cttcggccac gaggtgctga acctgaccag aaacggctac     540
ggcagcaccc agtacatcag attctctccg gacttcacct tcggcttcga ggagagcctg     600
gaggtggaca ccaatccact cctgggcgcc ggcaagttcg ccaccgaccc cgccgtgacc     660
ctggcccacg agctgatcca cgccggccac agactgtacg gcatagccat caatccaaac     720
agagtgttca aggtgaacac caacgcctac tacgagatgt caggcctgga ggtgagcttc     780
gaggagctga gaaccttcgg cggccacgac gccaagttca tcgacagcct gcaggagaac     840
gagttcagac tgtactatta acaacaagttc aaggacatcg ccagcaccct gaacaaggcc     900
aagagcatcg tgggcaccac cgccagcctg cagtacatga agaacgtgtt caaggagaag     960
tacctgctga gcgaggacac cagcggcaag ttcagcgtgg acaagctgaa gttcgacaag    1020
ctgtacaaga tgctgaccga gatctacacc gaggacaact cgtgaagtt cttcaaggtg    1080
ctgaacagaa agacctacct gaacttcgac aaggccgtgt tcaagatcaa catcgtgccc    1140
aaggtgaact acaccatcta cgacggcttc aacctgagaa acaccaacct ggccgccaac    1200
ttcaacggcc aaaacaccga gatcaacaac atgaacttca ccaagctgaa gaacttcacc    1260
ggcctgttcg agttctacaa gctgctgtgc gtgagaggca tcatcaccag caagaccaac    1320
aagaccagaa tcgacgaagc caaccagaga gccaccaaga tgctggccct gaacgacctg    1380
tgcatcaagg tgaacaactg gaccctgttc ttcagcccca gcgaggacaa cttcaccaac    1440
gacctgaaca agggcgagga gatcaccagc gacaccaaca tcgaggccgc cgaggagaac    1500
atcagcctgg acctgatcca gcagtactac ctgaccttca acttcgacaa cgagcccgag    1560
aacatcagca tcgagaacct gagcagcgac atcatcggcc agctcgagct gatgcccaac    1620
atcgagagat tccaaacggc aagaagtat gagctggaca atacaccat gttccactac    1680
ctgagagccc aggagttcga gcacggcaag agcagaatcg ccctgaccaa cagcgtgaac    1740
gaggccctgc tgaaccccag cagagtgtac accttcttca gcagcgacta cgtgaagaag    1800
gtgaacaaag ccaccgaagc cgccatgttc ctgggctggg tggagcagct ggtgtacgac    1860
ttcaccgacg agaccagcga ggtgagcacc accgacaaga tcgccgacat caccatcatt    1920
atcccctaca tcggaccagc cctgaacatc ggcaacatgc tgtacaagga cgacttcgta    1980
```

```
                                          -continued
ggcgcgctga tcttcagcgg cgccgtgatc ctgctggagt tcatccccga gatcgccatt      2040
ccagtgctgg gcaccttcgc cctggtgagc tacatcgcca acaaggtgct gaccgtgcag      2100
accatcgaca acgccctgag caagagaaac gagaagtggg acgaggtgta caagtacatc      2160
gtgaccaact ggctggccaa ggtgaacacc cagatcgacc tgatcagaaa gaagatgaag      2220
gaggccctgg agaaccaggc cgaggccacc aaggccatca tcaactacca gtacaaccag      2280
tacaccgagg aagagaagaa caacatcaac ttcaacatcg acgacctgag cagcaagctg      2340
aatgaaagca tcaacaaggc catgatcaac atcaacaagt tcctgaacca gtgcagcgtg      2400
agctacctga tgaacagcat gatcccctac ggcgtgaaga gactggagga cttcgacgcc      2460
agcctgaagg acgccctgct gaagtacatc tacgacaaca gaggcaccct gatcggccag      2520
gtggacagac tgaaggacaa ggtgaacaac accctgagca ccgacattcc attccagctg      2580
agcaagtacg tggacaacca gagactgctg agcaccttca ccgagtacat caagaacatc      2640
atcaacacca gcatcctgaa cctgagatac gagagcaacc acctgatcga cctgagcaga      2700
tacgccagca agatcaacat cggcagcaag gtgaacttcg accccatcga caagaaccag      2760
atccagctgt tcaacctgga gagcagcaag atcgaggtga tcctgaagaa tgccatcgtg      2820
tacaacagca tgtacgagaa cttcagcacc agcttctgga tcagaatccc caagtacttc      2880
aacagcatca gcctgaacaa tgaatacacc atcatcaact gcatggagaa caacagcggc      2940
tggaaggtga gcctgaacta cggcgagatc atctggaccc tgcaggacac ccaggagatc      3000
aagcagagag tggtgttcaa atacagccag atgatcaaca tcagcgacta catcaacaga      3060
tggatcttcg tgaccatcac caacaacaga ctgaacaaca gcaagatcta catcaacggc      3120
agactgatcg accagaagcc catcagcaac ctgggcaaca tccacgcctc caacaacatc      3180
atgttcaagc tggacggctg cagagacacc cacagataca tctggatcaa gtacttcaac      3240
ctgttcgaca aggagctgaa cgagaaggag atcaaggacc tgtacgacaa ccagagcaac      3300
agcggcatcc tgaaggactt ctggggcgac tacctgcagt atgacaagcc ctactacatg      3360
ctgaacctgt acgatccaaa caagtacgtg gacgtgaaca acgtgggcat cagaggctac      3420
atgtacctga agggcccccag aggcagcgtg atgaccacca acatctacct gaacagcagc      3480
ctgtacagag gcaccaagtt catcatcaag aagtacgcca gcggcaacaa ggacaacatc      3540
gtgagaaaca acgacagagt gtacatcaac gtggtcgtga agaacaagga gtacagactg      3600
gccaccaacg ccagccaggc cggcgtggag aagatcctga gcgccctgga gattccagac      3660
gtgggcaacc tgagccaagt cgtcgtgatg aagagcaaga acgaccaggg catcaccaac      3720
aagtgcaaga tgaacctgca ggacaacaac ggcaacgaca tcggcttcat cggcttccac      3780
cagttcaaca acatagccaa gctggtggcc agcaactggt acaacagaca gatcgagaga      3840
agcagcagaa ccctgggctg tagctgggag ttcattccag tggacgacgg ctggggcgag      3900
agaccactct ga                                                         3912
```

BOTULINUM NEUROTOXIN SEROTYPE B ACTIVATABLE BOTULINUM NEUROTOXIN SEROTYPE BS

This patent application is a continuation and claims priority pursuant to 35 U.S.C. §120(e) to U.S. patent application Ser. No. 11/533,223 filed on Sep. 19, 2006, a patent application that claims priority pursuant to 35 U.S.C. §119(e) to U.S. provisional patent application Ser. No. 60/718,616 filed on Sep. 19, 2005, each of which is hereby incorporated by reference in its entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, Tetanus neurotoxin (TeNT), Baratium neurotoxin (BaNT) and Butyricum neurotoxin (BuNT) to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Linurase® (Prollenium, Inc., Ontario, Canada), Neuronox® (Medy-Tox, Inc., Ochang-myeon, South Korea) BTX-A (Lanzhou Institute Biological Products, China) and Xeomin® (Merz Pharmaceuticals, GmbH., Frankfurt, Germany); and BoNT/B preparations, such as, e.g., MyoBloc™/NeuroBloc™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

The increasing use of Clostridial toxin therapies in treating a wider range of human afflictions necessitates increasing the efficiency with which these toxins are produced. However, meeting the needs for the ever increasing demand for such toxin treatments may become difficult. One outstanding problem is that all Clostridial toxins need to be converted into the di-chain form of the molecule in order to achieve optimal activity. Historically, this conversion has been done in one of two ways. The first method simply purifies a Clostridial toxin from the bacterial strain itself, thereby relying on the naturally-occurring endogenous protease used to convert the single-chain form of the toxin into the di-chain form. The second method utilizes an exogenous protease that converts the single-chain form into the di-chain by either taking advantage of a fortuitous cleavage site found in the appropriate location or by genetically engineering a protease cleavage site of commonly used, commercially available exogenous proteases. However, there are several drawbacks to both of these methods. For example, methods employing an endogenous protease produce low toxin yields because native Clostridial strains usually produce little toxin. In addition these strains are poorly suited for research, thus hindering the efforts to genetic manipulation Clostridial toxins to improve their therapeutic and cosmetic attributes. Lastly, several Clostridial strains do not produce the endogenous protease necessary to convert the single-chain form of the toxin to the di-chain form. A drawback to the use of exogenous proteases is a lack of protease specificity that results in inactive toxin because of proteolytic cleavage in inappropriate locations. In addition, many of the currently available proteases are from animal sources that lack Good Manufacture Standard (GMS) approval, requiring additional purification steps during the manufacturing process. Thus, methods currently used to convert the single-chain form of the toxin into the di-chain form are inefficient, cumbersome and lead to higher overall production costs. These drawbacks represent a significant obstacle to the overall commercial production of Clostridial toxins and are thus a major problem since di-chain forms of these toxins are needed for scientific, therapeutic and cosmetic applications. In addition, both the amount of Clostridial toxins anticipated for future therapies and the demand for toxins with enhanced therapeutic properties are increasing. Therefore, there is a need to develop better methods for producing Clostridial toxin di-chain molecules in order to meet this need.

The present invention provides modified Clostridial toxins that rely on a novel method of converting the single-chain form of the toxin into the di-chain form. These and related advantages are useful for various clinical, therapeutic and cosmetic applications, such as, e.g., the treatment of neuromuscular disorders, neuropathic disorders, eye disorders, pain, muscle injuries, headache, cardiovascular diseases, neuropsychiatric disorders, endocrine disorders, cancers, otic disorders and hyperkinetic facial lines, as well as, other disorders where a Clostridial toxin administration to a mammal can produce a beneficial effect.

BRIEF DESCRIPTION OF THE DRAWINGS

FIG. 2 shows a schematic of the current paradigm of neurotransmitter release and Clostridial toxin intoxication in a central and peripheral neuron. FIG. 2b shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events result in the release of the active light chain into the cytoplasm; and 4) enzymatic target modification, where the active light chain of Clostridial toxin proteolytically cleaves its target SNARE substrate, such as, e.g., SNAP-25, VAMP or Syntaxin, thereby preventing vesicle docking and neurotransmitter release.

FIG. 3 shows a schematic of the subcellular localization and cleavage sites of SNAP-25, VAMP and Syntaxin. VAMP is localized to synaptic vesicle membrane, whereas SNAP-25 and Syntaxin are localized to the plasma membrane. BoNT/A and BoNT/E cleave SNAP-25 close to the carboxyl-terminus, releasing nine or 26 residues, respectively. BoNT/B, BoNT/D, BoNT/F, BoNT/G and TeNT act on the conserved central portion of VAMP (white box) and release the amino-terminal cytosolic half of VAMP into the cytosol. BoNT/C1 cleaves SNAP-25 close to the carboxyl-terminus as well as cleaving Syntaxin at a single site near the cytosolic membrane surface. The action of BoNT/C1 results in release of a large portion of the cytosolic domain of Syntaxin, while only a small portion of SNAP-25 is released by selective proteolysis of BoNT/C1.

FIG. 4 shows a schematic of modified Clostridial toxins.

FIG. 5 shows a schematic of modified Clostridial toxins. FIG. 5a shows a modified Clostridial toxin comprising an enzymatic domain, a translocation domain and a binding domain and a di-chain loop including a Clostridial toxin substrate cleavage site comprising a BoNT/B cleavage site, derived, e.g., from a member of the VAMP family susceptible to BoNT/B cleavage. Cleavage of the BoNT/B cleavage site by BoNT/B converts the single-chain form of the modified toxin into the di-chain form. FIG. 5b shows a modified Clostridial toxin comprising an enzymatic domain, a translocation domain and a binding domain and a di-chain loop including a Clostridial toxin substrate cleavage site comprising a BoNT/D cleavage site, derived, e.g., from a member of the VAMP family susceptible to BoNT/D cleavage. Cleavage of the BoNT/D cleavage site by BoNT/D converts the single-chain form of the modified toxin into the di-chain form. FIG. 5c shows a modified Clostridial toxin comprising an enzymatic domain, a translocation domain and a binding domain and a di-chain loop including a Clostridial toxin substrate cleavage site comprising a BoNT/F cleavage site, derived, e.g., from a member of the VAMP family susceptible to BoNT/F cleavage. Cleavage of the BoNT/F cleavage site by BoNT/F converts the single-chain form of the modified toxin into the di-chain form. FIG. 5d shows a modified Clostridial toxin comprising an enzymatic domain, a translocation domain and a binding domain and a di-chain loop including a Clostridial toxin substrate cleavage site comprising a BoNT/G cleavage site, derived, e.g., from a member of the VAMP family susceptible to BoNT/G cleavage. Cleavage of the BoNT/G cleavage site by BoNT/G converts the single-chain form of the modified toxin into the di-chain form.

FIG. 6 shows a schematic of modified Clostridial toxins. FIG. 6a shows a modified Clostridial toxin comprising an enzymatic domain, a translocation domain and a binding domain and a di-chain loop including a Clostridial toxin substrate cleavage site comprising a BoNT/C1 cleavage site, derived, e.g., from a member of the Syntaxin family susceptible to BoNT/C1 cleavage. Cleavage of the BoNT/C1 cleavage site by BoNT/C1 converts the single-chain form of the modified toxin into the di-chain form. FIG. 6b shows a modified Clostridial toxin comprising an enzymatic domain, a translocation domain and a binding domain and a di-chain loop including a Clostridial toxin substrate cleavage site comprising a BoNT/C1 cleavage site, derived, e.g., from a member of the SNAP-25 family susceptible to BoNT/C1 cleavage. Cleavage of the BoNT/C1 cleavage site by BoNT/C1 converts the single-chain form of the modified toxin into the di-chain form.

FIG. 7 shows a plasmid map of prokaryotic expression construct pET29b/BoNT/A-A17 comprising a polynucleotide molecule of SEQ ID NO: 225 encoding a modified BoNT/A of SEQ ID NO: 203, operably-linked to a carboxyl-terminal polyhistidine binding polypeptide. A Trypsin protease cleavage site is operably-linked between the polyhistidine binding polypeptide and the modified BoNT/A. Abbreviations are as follows: $P_{T7}$, a bacteriophage T7 promoter region; ED, a polynucleotide molecule encoding a BoNT/A enzymatic domain; A17, a polynucleotide molecule encoding a BoNT/A substrate cleavage site; TD, a polynucleotide molecule encoding a BoNT/A translocation domain; BD, a polynucleotide molecule encoding a BoNT/A binding domain; Trypsin, a polynucleotide molecule encoding Trypsin cleavage site; 6×His, a polynucleotide molecule encoding a polyhistidine binding polypeptide; T7 TT, a bacteriophage T7 transcription termination region; f1 origin, a bacteriophage f1 origin of replication; Kanamycin, a polynucleotide molecule encoding an aminophosphotransferase that confers Kanamycin resistance; pBR322 ori, a pBR322 origin of plasmid replication region; lacI, a polynucleotide molecule encoding a lactose I.

FIG. 8 shows a plasmid map of prokaryotic expression construct pET29b/BoNT/A-BT35 comprising a polynucleotide molecule of SEQ ID NO: 227 encoding a modified BoNT/A of SEQ ID NO: 205, operably-linked to a carboxyl-terminal polyhistidine binding polypeptide. A Trypsin protease cleavage site is operably-linked between the polyhistidine binding polypeptide and the modified BoNT/A. Abbreviations are as follows: $P_{T7}$, a bacteriophage T7 promoter region; ED, a polynucleotide molecule encoding a BoNT/A enzymatic domain; BT35, a polynucleotide molecule encoding a BoNT/B substrate cleavage site and a TeNT substrate cleavage site; TD, a polynucleotide molecule encoding a BoNT/A translocation domain; BD, a polynucleotide molecule encoding a BoNT/A binding domain; Trypsin, a polynucleotide molecule encoding Trypsin cleavage site; 6×His, a polynucleotide molecule encoding a polyhistidine binding polypeptide; T7 TT, a bacteriophage T7 transcription termination region; f1 origin, a bacteriophage f1 origin of replication; Kanamycin, a polynucleotide molecule encoding an aminophosphotransferase that confers Kanamycin resistance; pBR322 ori, a pBR322 origin of plasmid replication region; lacI, a polynucleotide molecule encoding a lactose I.

FIG. 9 shows a plasmid map of prokaryotic expression construct pET29b/BoNT/A-Csyn8 comprising a polynucleotide molecule of SEQ ID NO: 229 encoding a modified BoNT/A of SEQ ID NO: 207, operably-linked to a carboxyl-terminal polyhistidine binding polypeptide. A Trypsin protease cleavage site is operably-linked between the polyhistidine binding polypeptide and the modified BoNT/A. Abbreviations are as follows: $P_{T7}$, a bacteriophage T7 promoter region; ED, a polynucleotide molecule encoding a BoNT/A enzymatic domain; Csyn8, a polynucleotide molecule encoding a BoNT/C1 substrate cleavage site; TD, a polynucleotide molecule encoding a BoNT/A translocation domain; BD, a polynucleotide molecule encoding a BoNT/A binding domain; Trypsin, a polynucleotide molecule encoding Trypsin cleavage site; 6×His, a polynucleotide molecule encoding a polyhistidine binding polypeptide; T7 TT, a bacteriophage T7 transcription termination region; f1 origin, a bacteriophage f1 origin of replication; Kanamycin, a polynucleotide molecule encoding an aminophosphotransferase that confers Kanamycin resistance; pBR322 ori, a pBR322 origin of plasmid replication region; lacI, a polynucleotide molecule encoding a lactose I.

FIG. 10 shows a plasmid map of prokaryotic expression construct pET29b/BoNT/A-DF39 comprising a polynucleotide molecule of SEQ ID NO: 231 encoding a modified BoNT/A of SEQ ID NO: 209, operably-linked to a carboxyl-terminal polyhistidine binding polypeptide. A Trypsin protease cleavage site is operably-linked between the polyhistidine binding polypeptide and the modified BoNT/A. Abbreviations are as follows: $P_{T7}$, a bacteriophage T7 promoter region; ED, a polynucleotide molecule encoding a BoNT/A enzymatic domain; DF39, a polynucleotide molecule encoding a BoNT/D substrate cleavage site and a BoNT/F substrate cleavage site; TD, a polynucleotide molecule encoding a BoNT/A translocation domain; BD, a polynucleotide molecule encoding a BoNT/A binding domain; Trypsin, a polynucleotide molecule encoding Trypsin cleavage site; 6×His, a polynucleotide molecule encoding a polyhistidine binding polypeptide; T7 TT, a bacteriophage T7 transcription termination region; f1 origin, a bacteriophage f1 origin of replication; Kanamycin, a polynucleotide molecule encoding an aminophosphotransferase that confers Kanamycin resistance; pBR322 ori, a pBR322 origin of plasmid replication region; lacI, a polynucleotide molecule encoding a lactose I.

FIG. 11 shows a plasmid map of prokaryotic expression construct pET29b/BoNT/A-E8 comprising a polynucleotide molecule of SEQ ID NO: 233 encoding a modified BoNT/A of SEQ ID NO: 211, operably-linked to a carboxyl-terminal polyhistidine binding polypeptide. A Trypsin protease cleavage site is operably-linked between the polyhistidine binding polypeptide and the modified BoNT/A. Abbreviations are as follows: $P_{T7}$, a bacteriophage T7 promoter region; ED, a polynucleotide molecule encoding a BoNT/A enzymatic domain; E8, a polynucleotide molecule encoding a BoNT/E substrate cleavage site; TD, a polynucleotide molecule encoding a BoNT/A translocation domain; BD, a polynucleotide molecule encoding a BoNT/A binding domain; Trypsin, a polynucleotide molecule encoding Trypsin cleavage site; 6×His, a polynucleotide molecule encoding a polyhistidine binding polypeptide; T7 TT, a bacteriophage T7 transcription termination region; f1 origin, a bacteriophage f1 origin of replication; Kanamycin, a polynucleotide molecule encoding an aminophosphotransferase that confers Kanamycin resistance; pBR322 ori, a pBR322 origin of plasmid replication region; lacI, a polynucleotide molecule encoding a lactose I.

FIG. 12 shows a plasmid map of prokaryotic expression construct pET29b/BoNT/A-G8 comprising a polynucleotide molecule of SEQ ID NO: 235 encoding a modified BoNT/A of SEQ ID NO: 213, operably-linked to a carboxyl-terminal polyhistidine binding polypeptide. A Trypsin protease cleavage site is operably-linked between the polyhistidine binding polypeptide and the modified BoNT/A. Abbreviations are as follows: $P_{T7}$, a bacteriophage T7 promoter region; ED, a polynucleotide molecule encoding a BoNT/A enzymatic domain; G8, a polynucleotide molecule encoding a BoNT/G substrate cleavage site; TD, a polynucleotide molecule encoding a BoNT/A translocation domain; BD, a polynucleotide molecule encoding a BoNT/A binding domain; Trypsin, a polynucleotide molecule encoding Trypsin cleavage site; 6×His, a polynucleotide molecule encoding a polyhistidine binding polypeptide; T7 TT, a bacteriophage T7 transcription termination region; f1 origin, a bacteriophage f1 origin of replication; Kanamycin, a polynucleotide molecule encoding an aminophosphotransferase that confers Kanamycin resistance; pBR322 ori, a pBR322 origin of plasmid replication region; lacI, a polynucleotide molecule encoding a lactose I.

FIG. 13 shows a plasmid map of yeast expression construct pPICZ A/BoNT/A-A17 comprising a polynucleotide molecule of SEQ ID NO: 236 encoding a modified BoNT/A of SEQ ID NO: 203, operably-linked to carboxyl-terminal c-myc and polyhistidine binding polypeptides. Abbreviations are as follows: $P_{AOX1}$, an aldehyde oxidase 1 promoter region; ED, a polynucleotide molecule encoding a BoNT/A enzymatic domain; A17, a polynucleotide molecule encoding a BoNT/A substrate cleavage site; TD, a polynucleotide molecule encoding a BoNT/A translocation domain; BD, a polynucleotide molecule encoding a BoNT/A binding domain; c-myc, a polynucleotide molecule encoding a c-myc binding polypeptide; 6×His, a polynucleotide molecule encoding a polyhistidine binding polypeptide; AOX1 TT, an aldehyde oxidase 1 transcription termination region; Zeocin™, a polynucleotide molecule encoding a Zeocin™ resistance polypeptide; pUC ori, a pUC origin of plasmid replication region.

FIG. 14 shows a plasmid map of baculovirus transfer construct pBACgus3/BoNT/A-A17 comprising a polynucleotide molecule of SEQ ID NO: 237 encoding a modified BoNT/A of SEQ ID NO: 203, operably-linked to carboxyl-terminal polyhistidine binding polypeptide. A Thrombin protease cleavage site is operably-linked between the modified BoNT/A and the polyhistidine binding polypeptide. Abbreviations are as follows: $P_{PH}$, an polyhedrin promoter region; gp64, a polynucleotide molecule encoding a gp64 signal polypeptide; ED, a polynucleotide molecule encoding a BoNT/A enzymatic domain; A17, a polynucleotide molecule encoding a BoNT/A substrate cleavage site; TD, a polynucleotide molecule encoding a BoNT/A translocation domain; BD, a polynucleotide molecule encoding a BoNT/A binding domain; Thrombin, a polynucleotide molecule encoding a Thrombin protease cleavage site; 6×His, a polynucleotide molecule encoding a polyhistidine binding polypeptide; pUC ori, a pUC origin of plasmid replication region; Ampicillin, a polynucleotide molecule encoding a β-lactamase that confers Ampicillin resistance; f1 ori, a bacteriophage f1 origin of replication; gus, a polynucleotide molecule encoding a β-glucuronidase.

FIG. 15 shows a plasmid map of mammalian expression construct pSecTag2/BoNT/A-A17 comprising a polynucleotide molecule of SEQ ID NO: 238 encoding a modified BoNT/A of SEQ ID NO: 203, operably-linked to carboxyl-terminal c-myc and polyhistidine binding polypeptides. Abbreviations are as follows: $P_{CMV}$, an cytomegalovirus promoter region; IgK, a polynucleotide molecule encoding an immunoglobulin K polypeptide; ED, a polynucleotide molecule encoding a BoNT/A enzymatic domain; A17, a polynucleotide molecule encoding a BoNT/A substrate cleavage site; TD, a polynucleotide molecule encoding a BoNT/A translocation domain; BD, a polynucleotide molecule encoding a BoNT/A binding domain; c-myc, a polynucleotide molecule encoding a c-myc binding polypeptide; 6×His, a polynucleotide molecule encoding a polyhistidine binding polypeptide; BGH pA, a bovine growth hormone polyadenylation site; f1 ori, a bacteriophage f1 origin of replication; $P_{SV40}$, a simian virus 40 promoter region; Zeocin™, a region encoding an Zeocin™ resistance polypeptide; pUC ori, a pUC origin of plasmid replication region; Ampicillin, a polynucleotide molecule encoding a β-lactamase that confers Ampicillin resistance.

DETAILED DESCRIPTION

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other species of Clostridia, *C. baratii* and *C. butyricum*, also produce toxins, BaNT and BuNT respectively, which are similar to BoNT/F and BoNT/E, respectively.

Figure 1:
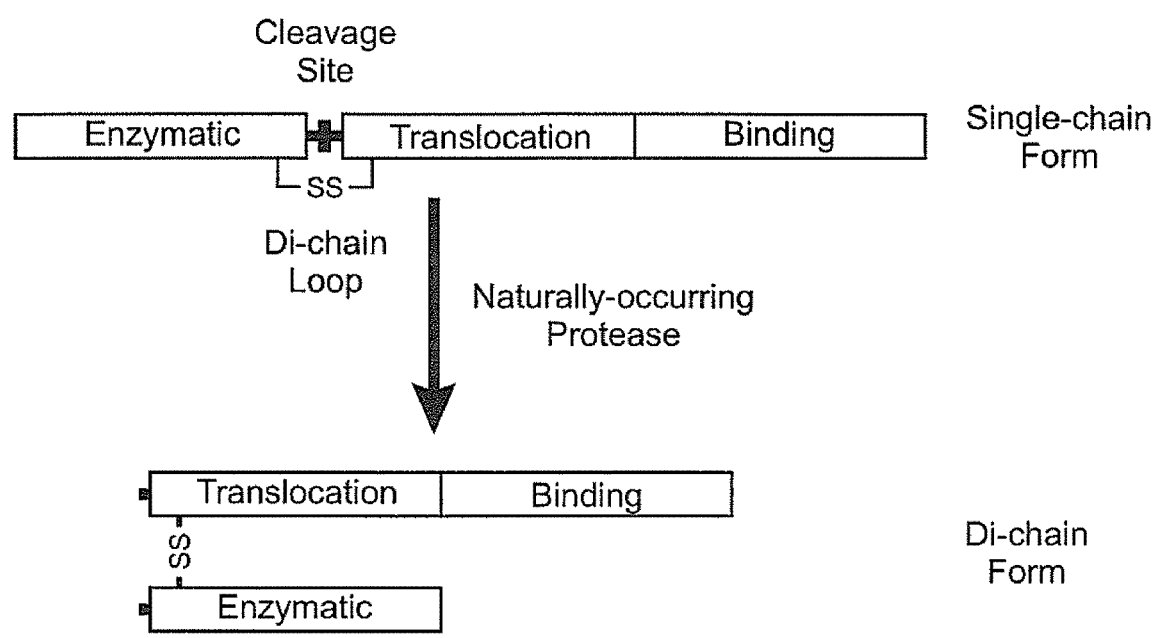
FIG. 1 shows a schematic of the current paradigm of Clostridial toxin posttranslational processing. Clostridial toxins are translated as a single-chain polypeptide of approximately 150 kDa comprising an enzymatic domain, a translocation domain and a binding domain. A disulfide bridge formed from a cysteine residue in the enzymatic domain and a cysteine residue from the translocation domain form a di-chain loop. Within this di-chain loop is a protease cleavage site for a naturally-occurring protease that can be produced endogenously from the Clostridial strain synthesizing the toxin, or exogenously from a source found in the environment. Cleavage of the protease cleavage site by the naturally-occurring protease converts the single-chain form of the toxin into the di-chain form. The di-chain form of the toxin is held together by the disulfide bond and non-covalent interactions between the two chains.

Clostridial toxins are each translated as a single chain polypeptide of approximately 150 kDa that is subsequently cleaved by proteolytic scission within a disulfide loop by a naturally-occurring protease (FIG. 1). This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single chain molecule into the di-chain is currently not known. In some serotypes, such as, e.g., BoNT/A, the naturally-occurring protease is produced endogenously by the bacteria serotype and cleavage occurs within the cell before the toxin is release into the environment. However, in other serotypes, such as, e.g., BoNT/E, the bacterial strain appears not to produce an endogenous protease capable of converting the single chain form of the toxin into the di-chain form. In these situations, the toxin is released from the cell as a single-chain toxin which is subsequently converted into the di-chain form by a naturally-occurring protease found in the environment.

TABLE 1

Clostridial Toxin Reference Sequences and Regions

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus (Table 1); 2) a translocation domain contained within the amino-terminal half of the HC($H_N$) that facilitates release of the LC from intracellular vesicles into the cytoplasm of the target cell (Table 1); and 3) a binding domain found within the carboxyl-terminal half of the HC ($H_C$) that determines the binding activity and binding specificity of the toxin to the receptor complex located at the surface of the target cell (Table 1).

Figure 2A:
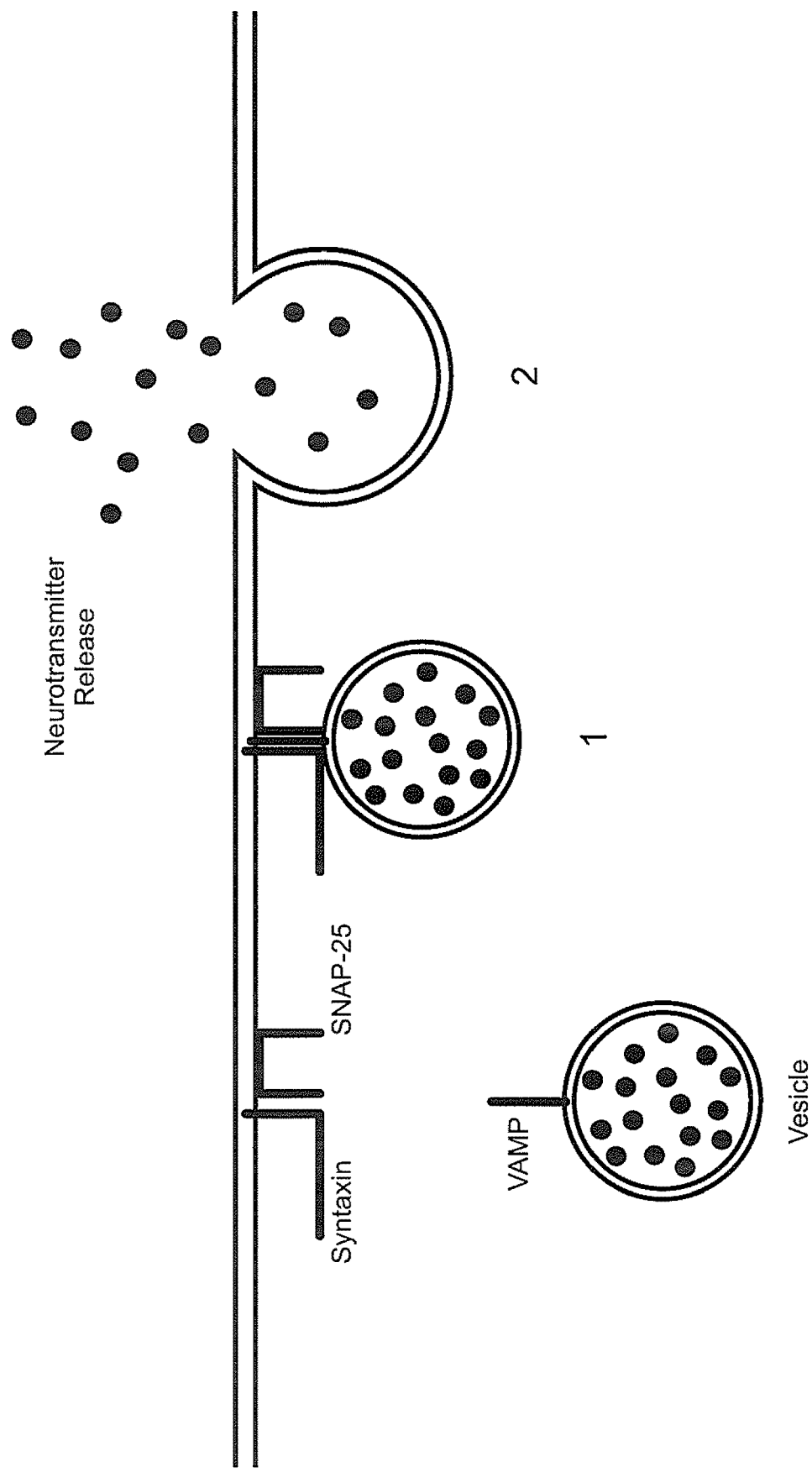
FIG. 2a shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.
Figure 4A:
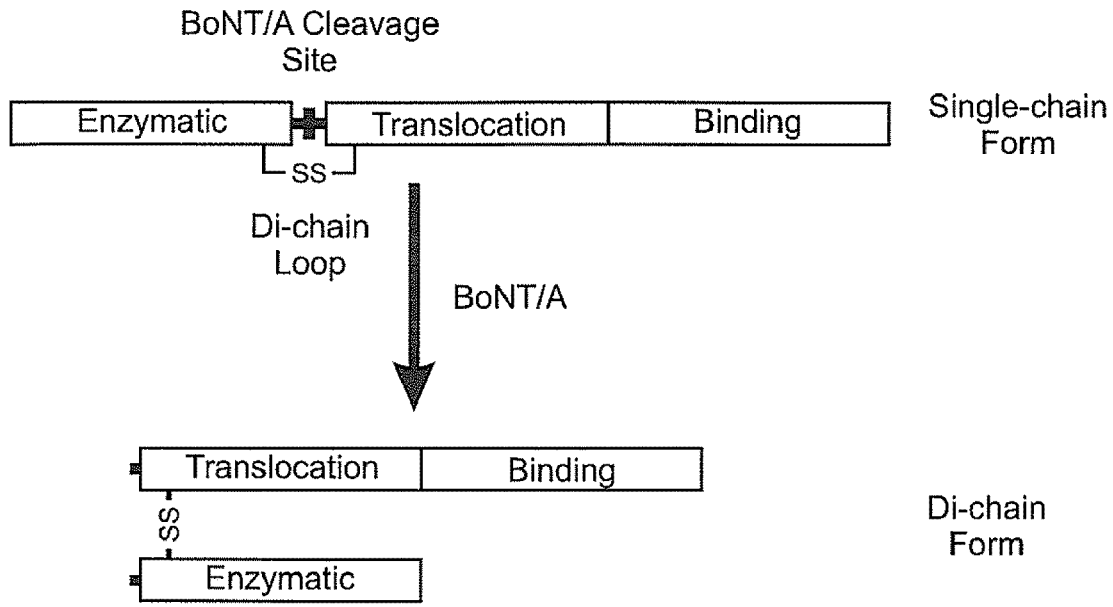
FIG. 4a shows a modified Clostridial toxin comprising an enzymatic domain, a translocation domain and a binding domain and a di-chain loop including a Clostridial toxin substrate cleavage site comprising a BoNT/A cleavage site, derived, e.g., from a member of the SNAP-25 family susceptible to BoNT/A cleavage. Cleavage of the BoNT/A cleavage site by BoNT/A converts the single-chain form of the modified toxin into the di-chain form.
Figure 4B:
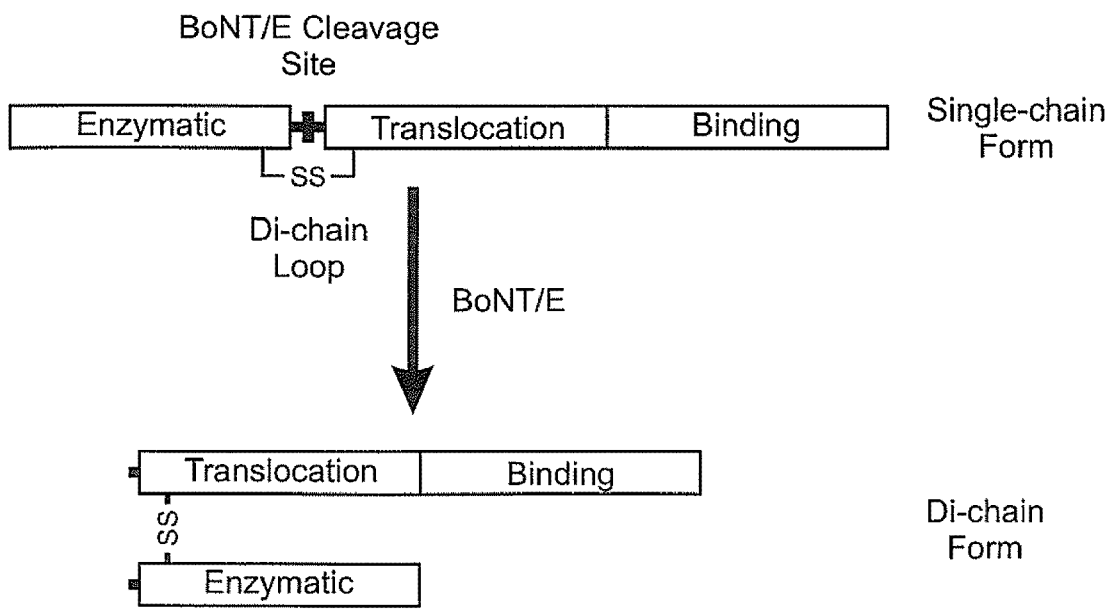
FIG. 4b shows a modified Clostridial toxin comprising an enzymatic domain, a translocation domain and a binding domain and a di-chain loop including a Clostridial toxin substrate cleavage site comprising a BoNT/E cleavage site, derived, e.g., from a member of the SNAP-25 family susceptible to BoNT/E cleavage. Cleavage of the BoNT/E cleavage site by BoNT/E converts the single-chain form of the modified toxin into the di-chain form.
Figure 5E:
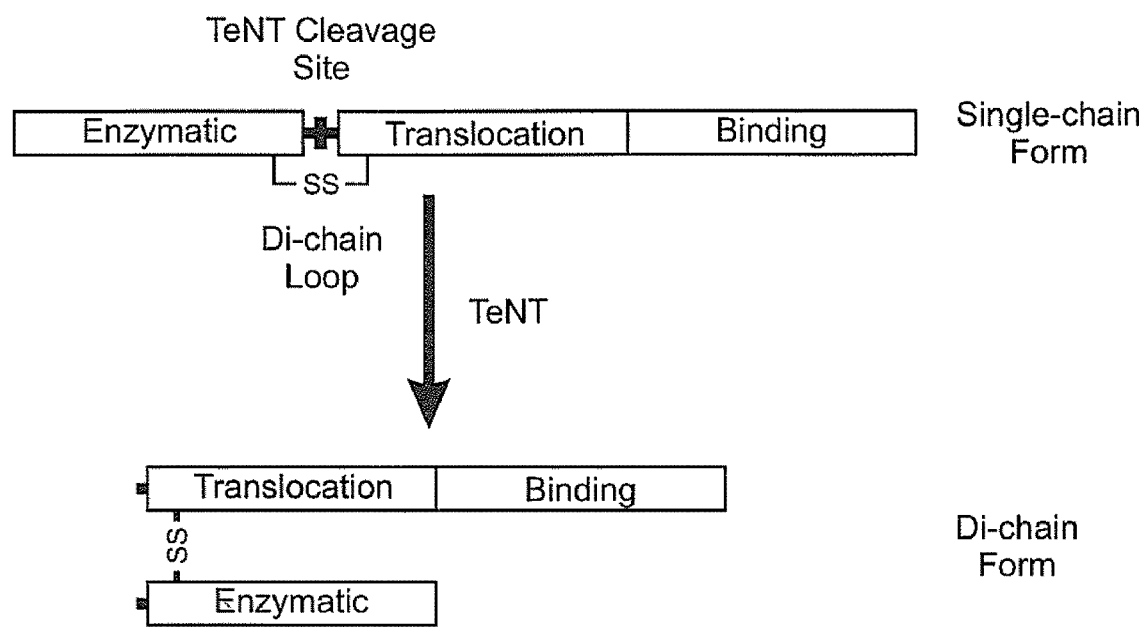
FIG. 5e shows a modified Clostridial toxin comprising an enzymatic domain, a translocation domain and a binding domain and a di-chain loop including a Clostridial toxin substrate cleavage site comprising a TeNT cleavage site, derived, e.g., from a member of the VAMP family susceptible to TeNT cleavage. Cleavage of the TeNT cleavage site by TeNT converts the single-chain form of the modified toxin into the di-chain form.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of type. Although the applicants have no wish to be limited by the following description, the intoxication mechanism can be described as comprising at least four steps: 1) receptor binding, 2) complex internalization, 3) light chain translocation, and 4) enzymatic target modification (see FIG. 2). The process is initiated when the $H_C$ domain of a Clostridial toxin binds to a toxin-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); Giovanna Lalli et al., *The Journey of Tetanus and Botulinum Neurotoxins in Neurons*, 11 (9) Trends Microbiol. 431-437, (2003).

The present invention discloses modified Clostridial toxins that can be converted from the single-chain polypeptide form into the di-chain form using the enzymatic activity of a Clostridial toxin. This is accomplished by replacing the naturally-occurring protease cleavage site found within the di-chain loop region with a Clostridial toxin substrate cleavage site. In a modification where the Clostridial toxin substrate cleavage site replacement is the substrate for the Clostridial toxin, activation is accomplished using a Clostridial toxin having BoNT/A enzymatic activity. This cleavage site replacement will enable these modified toxins to activate one another, eliminating the reliance of a different protease. For example, a modified BoNT/A comprising a BoNT/A substrate cleavage site will enable a Clostridial toxin having BoNT/A enzymatic activity to cleave the BoNT/A substrate cleavage site of the modified BoNT/A, thereby producing the di-chain form of the toxin. In a modification where the Clostridial toxin substrate cleavage site replacement is the substrate for a different Clostridial toxin, activation is accomplished using a Clostridial toxin having BoNT/C1 enzymatic activity. For example, a modified BoNT/A comprising a BoNT/C1 substrate cleavage site will enable a Clostridial toxin having BoNT/C1 enzymatic activity to cleave the BoNT/C1 substrate cleavage site of the modified BoNT/A, thereby producing the di-chain form of the toxin.

Aspects of the present invention provide modified Clostridial toxins comprising a Clostridial toxin substrate cleavage site, wherein the Clostridial toxin substrate cleavage site is located within a di-chain loop region of the modified Clostridial toxin. It is envisioned that any Clostridial toxin substrate cleavage site can be used, including, without limitation, a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site and a BuNT substrate cleavage site.

Other aspects of the present invention provide polynucleotide molecules encoding modified Clostridial toxins comprising Clostridial toxin substrate cleavage site, wherein the Clostridial toxin substrate cleavage site is located within the di-chain loop region.

Other aspects of the present invention provide methods of producing a modified Clostridial toxin comprising Clostridial toxin substrate cleavage site, wherein the Clostridial toxin substrate cleavage site is located within the di-chain loop region. Other aspects of the present invention provide methods of producing in a cell a modified Clostridial toxin comprising Clostridial toxin substrate cleavage site, wherein the Clostridial toxin substrate cleavage site is located within the di-chain loop region and expressing the expression construct in the cell.

Aspects of the present invention provide, in part, a Clostridial toxin. As used herein, the term "Clostridial toxin" means any polypeptide that can execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate.

A Clostridial toxin includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. As used herein, the term "Clostridial toxin variant," whether naturally-occurring or non-naturally-occurring, means a Clostridial toxin that has at least one amino acid change from the corresponding region of the disclosed reference sequences (see Table 1) and can be described in percent identity to the corresponding region of that reference sequence. As non-limiting examples, a BoNT/A variant comprising amino acids 1-1296 of SEQ ID NO: 1 will have at least one amino acid difference, such as, e.g., an amino acid substitution, deletion or addition, as compared to the amino acid region 1-1296 of SEQ ID NO: 1; a BoNT/B variant comprising amino acids 1-1291 of SEQ ID NO: 2 will have at least one amino acid difference, such as, e.g., an amino acid substitution, deletion or addition, as compared to the amino acid region 1-1291 of SEQ ID NO: 2; a BoNT/C1 variant comprising amino acids 1-1291 of SEQ ID NO: 3 will have at least one amino acid difference, such as, e.g., an amino acid substitution, deletion or addition, as compared to the amino acid region 1-1291 of SEQ ID NO: 3; a BoNT/D variant comprising amino acids 1-1276 of SEQ ID NO: 4 will have at least one amino acid difference, such as, e.g., an amino acid substitution, deletion or addition, as compared to the amino acid region 1-1276 of SEQ ID NO: 4; a BoNT/E variant comprising amino acids 1-1252 of SEQ ID NO: 5 will have at least one amino acid difference, such as, e.g., an amino acid substitution, deletion or addition, as compared to the amino acid region 1-1252 of SEQ ID NO: 5; a BoNT/F variant comprising amino acids 1-1274 of SEQ ID NO: 6 will have at least one amino acid difference, such as, e.g., an amino acid substitution, deletion or addition, as compared to the amino acid region 1-1274 of SEQ ID NO: 6; a BoNT/G variant comprising amino acids 1-1297 of SEQ ID NO: 7 will have at least one amino acid difference, such as, e.g., an amino acid substitution, deletion or addition, as compared to the amino acid region 1-1297 of SEQ ID NO: 7; and a TeNT variant comprising amino acids 1-1315 of SEQ ID NO: 8 will have at least one amino acid difference, such as, e.g., an amino acid substitution, deletion or addition, as compared to the amino acid region 1-1315 of SEQ ID NO: 8.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

As used herein, the term "naturally occurring Clostridial toxin variant" means any Clostridial toxin produced without the aid of any human manipulation, including, without limitation, Clostridial toxin isoforms produced from alternatively-spliced transcripts, Clostridial toxin isoforms produced by spontaneous mutation and Clostridial toxin subtypes. Non-limiting examples of a Clostridial toxin isoform include, e.g., BoNT/A isoforms, BoNT/B isoforms, BoNT/C1 isoforms, BoNT/D isoforms, BoNT/E isoforms, BoNT/F isoforms, BoNT/G isoforms, and TeNT isoforms. Non-limiting examples of a Clostridial toxin subtype include, e.g., BoNT/A subtypes BoNT/A1, BoNT/A2, BoNT/A3 and BoNT/A4; BoNT/B subtypes BoNT/B1, BoNT/B2, BoNT/B bivalent and BoNT/B nonproteolytic; BoNT/C1 subtypes BoNT/C1-1 and BoNT/C1-2; BoNT/E subtypes BoNT/E1, BoNT/E2 and BoNT/E3; and BoNT/F subtypes BoNT/F1, BoNT/F2, BoNT/F3 and BoNT/F4.

As used herein, the term "non-naturally occurring Clostridial toxin variant" means any Clostridial toxin produced with the aid of human manipulation, including, without limitation, Clostridial toxins produced by genetic engineering using random mutagenesis or rational design and Clostridial toxins produced by chemical synthesis. Non-limiting examples of non-naturally occurring Clostridial toxin variants include, e.g., conservative Clostridial toxin variants, non-conservative Clostridial toxin variants, Clostridial toxin chimeric variants and active Clostridial toxin fragments.

As used herein, the term "conservative Clostridial toxin variant" means a Clostridial toxin that has at least one amino acid substituted by another amino acid or an amino acid analog that has at least one property similar to that of the original amino acid from the reference Clostridial toxin sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin variant can function in substantially the same manner as the reference Clostridial toxin on which the conservative Clostridial toxin variant is based, and can be substituted for the reference Clostridial toxin in any aspect of the present invention. A conservative Clostridial toxin variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin on which the conservative Clostridial toxin variant is based. A conservative Clostridial toxin variant can also substitute at least 10 contiguous amino acids, at least 15 contiguous amino acids, at least 20 contiguous amino acids, or at least 25 contiguous amino acids from the reference Clostridial toxin on which the conservative Clostridial toxin variant is based, that possess at least 50% amino acid identity, 65% amino acid identity, 75% amino acid identity, 85% amino acid identity or 95% amino acid identity to the reference Clostridial toxin on which the conservative Clostridial toxin variant is based. Non-limiting examples of a conservative Clostridial toxin variant include, e.g., conservative BoNT/A variants, conservative BoNT/B variants, conservative BoNT/C1 variants, conservative BoNT/D variants, conservative BoNT/E variants, conservative BoNT/F variants, conservative BoNT/G variants, and conservative TeNT variants.

As used herein, the term "non-conservative Clostridial toxin variant" means a Clostridial toxin in which 1) at least one amino acid is deleted from the reference Clostridial toxin on which the non-conservative Clostridial toxin variant is based; 2) at least one amino acid added to the reference Clostridial toxin on which the non-conservative Clostridial toxin is based; or 3) at least one amino acid is substituted by another amino acid or an amino acid analog that does not share any property similar to that of the original amino acid from the reference Clostridial toxin sequence (Table 1). A non-conservative Clostridial toxin variant can function in substantially the same manner as the reference Clostridial toxin on which the non-conservative Clostridial toxin variant is based, and can be substituted for the reference Clostridial toxin in any aspect of the present invention. A non-conservative Clostridial toxin variant can delete one or more amino acids, two or more amino acids, three or more amino acids, four or more amino acids, five or more amino acids, and ten or more amino acids from the reference Clostridial toxin on which the non-conservative Clostridial toxin variant is based. A non-conservative Clostridial toxin variant can add one or more amino acids, two or more amino acids, three or more amino acids, four or more amino acids, five or more amino acids, and ten or more amino acids to the reference Clostridial toxin on which the non-conservative Clostridial toxin variant is based. A non-conservative Clostridial toxin variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin on which the non-conservative Clostridial toxin variant is based. A non-conservative Clostridial toxin variant can also substitute at least 10 contiguous amino acids, at least 15 contiguous amino acids, at least 20 contiguous amino acids, or at least 25 contiguous amino acids from the reference Clostridial toxin on which the non-conservative Clostridial toxin variant is based, that possess at least 50% amino acid identity, 65% amino acid identity, 75% amino acid identity, 85% amino acid identity or 95% amino acid identity to the reference Clostridial toxin on which the non-conservative Clostridial toxin variant is based. Non-limiting examples of a non-conservative Clostridial toxin variant include, e.g., non-conservative BoNT/A variants, non-conservative BoNT/B variants, non-conservative BoNT/C1 variants, non-conservative BoNT/D variants, non-conservative BoNT/E variants, non-conservative BoNT/F variants, non-conservative BoNT/G variants, and non-conservative TeNT variants.

As used herein, the term "Clostridial toxin chimeric variant" means a molecule comprising at least a portion of a Clostridial toxin and at least a portion of at least one other protein to form a toxin with at least one property different from the reference Clostridial toxins of Table 1. One class of Clostridial toxin chimeric variant comprises a modified Clostridial toxin were the endogenous cell binding domain of a naturally-occurring Clostridial toxin is either modified or replaced with a cell binding domain of another molecule. Such modified Clostridial toxin possesses an altered cell binding activity because the modified toxin can, e.g., use the same receptor present on the surface of a naturally occurring Clostridial toxin target cell, referred to as an enhanced cell binding activity for a naturally-occurring Clostridial toxin target cell; use a different receptor present on the surface of a naturally occurring Clostridial toxin target cell, referred to as an altered cell binding activity for a naturally-occurring Clostridial toxin target cell, or use a different receptor present on the surface of the non-Clostridial toxin target cell, referred to as an altered cell binding activity for a non-naturally-occurring Clostridial toxin target cell.

A Clostridial toxin chimeric variant can be a modified Clostridial toxin with an enhanced cell binding activity capable of intoxicating a naturally occurring Clostridial toxin target cell, e.g., a motor neuron. One way this enhanced binding activity is achieved by modifying the endogenous targeting domain of a naturally-occurring Clostridial toxin in order to enhance a cell binding activity of the toxin for its naturally-occurring receptor. Such modifications to a targeting domain result in, e.g., a enhanced cell binding activity that increases binding affinity for an endogenous Clostridial toxin receptor present on a naturally-occurring Clostridial toxin target cell; an enhanced cell binding activity that increases binding specificity for a subgroup of endogenous Clostridial toxin receptors present on a naturally-occurring Clostridial toxin target cell; or an enhanced cell binding activity that increases both binding affinity and binding specificity. Non-limiting examples of modified Clostridial toxins an enhanced cell binding activity for a naturally-occurring Clostridial toxin receptor are described in, e.g., Lance E. Steward, et al., Modified Clostridial Toxins with Enhanced Targeting Capabilities For Endogenous Clostridial Toxin Receptors, International Patent Publication No. 2006/008956 (Mar. 14, 2006); Lance E. Steward, Modified Clostridial Toxins with Enhanced Translocation Capability, and Enhanced Targeting Activity, U.S. Provisional Patent Application No. 60/807,063 (Jul. 11, 2006); the content of which are all hereby incorporated by reference in their entirety.

A Clostridial toxin chimeric variant can be a modified Clostridial toxin with an altered cell binding activity capable of intoxicating a naturally occurring Clostridial toxin target cell, e.g., a motor neuron. One way this altered capability is achieved by replacing the endogenous targeting domain of a naturally-occurring Clostridial toxin with a targeting domain of another molecule that selectively binds to a different receptor present on the surface of a naturally occurring Clostridial toxin target cell. Such a modification to a targeting domain results in a modified toxin that is able to selectively bind to a non-Clostridial toxin receptor (target receptor) present on a Clostridial toxin target cell. This enhanced binding activity for a naturally occurring Clostridial toxin target cell allows for lower effective doses of a modified Clostridial toxin to be administered to an individual because more toxin will be delivered to the target cell. Thus, modified Clostridial toxins with an enhanced binding activity will reduce the undesirable dispersal of the toxin to areas not targeted for treatment, thereby reducing or preventing the undesirable side-effects associated with diffusion of a Clostridial toxin to an unwanted location. Non-limiting examples of modified Clostridial toxins with an altered cell binding capability for a Clostridial toxin target cell are described in, e.g., Lance E. Steward et al., Modified Clostridial Toxins with Altered Targeting Capabilities For Clostridial Toxin Target Cells, International Patent Publication No. 2006/009831 (Mar. 14, 2005); Lance E. Steward et al., Multivalent Clostridial Toxin Derivatives and Methods of Their Use, U.S. patent application Ser. No. 11/376,696 (Mar. 15, 2006); and Lance E. Steward, Modified Clostridial Toxins with Enhanced Translocation Capabilities and Altered Targeting Activity for Clostridial Toxin Target Cells, U.S. Provisional Patent Application No. 60/807,062, (Jul. 11, 2006); the contents of all of which are hereby incorporated by reference in their entirety.

A Clostridial toxin chimeric variant can be a modified Clostridial toxin with an altered cell binding activity capable of intoxicating a cell other than a naturally occurring Clostridial toxin target cell, e.g., a cell other than a motor neuron. These modified toxins achieve this intoxication by using a target receptor present on non-Clostridial toxin target cell. This re-targeted capability is achieved by replacing a naturally-occurring targeting domain of a Clostridial toxin with a targeting domain showing a selective binding activity for a non-Clostridial toxin receptor present in a non-Clostridial toxin target cell. Such modifications to a targeting domain result in a modified toxin that is able to selectively bind to a non-Clostridial toxin receptor (target receptor) present on a non-Clostridial toxin target cell (re-targeted). A modified Clostridial toxin with an altered targeting activity for a non-Clostridial toxin target cell can bind to a target receptor, translocate into the cytoplasm, and exert its proteolytic effect on the SNARE complex of the non-Clostridial toxin target cell. Non-limiting examples of modified Clostridial toxins with an altered targeting activity for a non-Clostridial toxin target cell are described in, e.g., Keith A. Foster et al., Clostridial Toxin Derivatives Able To Modify Peripheral Sensory Afferent Functions, U.S. Pat. No. 5,989, 545 (Nov. 23, 1999); Clifford C. Shone et al., Recombinant Toxin Fragments, U.S. Pat. No. 6,461,617 (Oct. 8, 2002); Conrad P. Quinn et al., Methods and Compounds for the Treatment of Mucus Hypersecretion, U.S. Pat. No. 6,632,440 (Oct. 14, 2003); Lance E. Steward et al., Methods And Compositions For The Treatment Of Pancreatitis, U.S. Pat. No. 6,843,998 (Jan. 18, 2005); Stephan Donovan, Clostridial Toxin Derivatives and Methods For Treating Pain, U.S. Patent Publication 2002/0037833 (Mar. 28, 2002); Keith A. Foster et al., Inhibition of Secretion from Non-neural Cells, U.S. Patent Publication 2003/0180289 (Sep. 25, 2003); J. Oliver Dolly et al., Activatable Recombinant Neurotoxins, WO 2001/014570 (Mar. 1, 2001); Keith A. Foster et al., Re-targeted Toxin Conjugates, International Patent Publication WO 2005/023309 (Mar. 17, 2005); Lance E. Steward et al., Multivalent Clostridial Toxin Derivatives and Methods of Their Use, U.S. patent application Ser. No. 11/376,696 (Mar. 15, 2006); and Lance E. Steward, Modified Clostridial Toxins with Enhanced Translocation Capabilities and Altered Targeting Capabilities for Non-Clostridial Toxin Target Cells, U.S. Provisional Patent Application No. 60/807,059, (Jul. 11, 2006); the contents of all of which are hereby incorporated by reference in their entirety. The ability to re-target the therapeutic effects associated with Clostridial toxins has greatly extended the number of medicinal applications able to use a Clostridial toxin therapy. As a non-limiting example, modified Clostridial toxins retargeted to sensory neurons are useful in treating various kinds of chronic pain, such as, e.g., hyperalgesia and allodynia, neuropathic pain and inflammatory pain, see, e.g., Foster, supra, (1999); and Donovan, supra, (2002); and Stephan Donovan, Method For Treating Neurogenic Inflammation Pain with Botulinum Toxin and Substance P Components, U.S. Pat. No. 7,022,329 (Apr. 4, 2006). As another non-limiting example, modified Clostridial toxins retargeted to pancreatic cells are useful in treating pancreatitis, see, e.g., Steward, supra, (2005).

Thus, in an embodiment, a Clostridial toxin chimeric variant can comprise a modified Clostridial toxin disclosed in the present specification where the binding domain comprises an enhanced cell binding activity capable of intoxicating a naturally occurring Clostridial toxin target cell. In another embodiment, a Clostridial toxin chimeric variant can comprise a modified Clostridial toxin disclosed in the present specification where the binding domain comprises an altered cell binding activity capable of intoxicating a naturally occurring Clostridial toxin target cell. In still another embodiment, a Clostridial toxin chimeric variant can comprise a modified Clostridial toxin disclosed in the present specification where the binding domain comprises an altered cell binding activity capable of intoxicating a non-naturally occurring Clostridial toxin target cell.

It is also envisioned that any of a variety of Clostridial toxin fragments can be useful in aspects of the present invention with the proviso that these active fragments can execute the overall cellular mechanism whereby a Clostridial toxin proteolytically cleaves a substrate. Thus, aspects of this embodiment can include Clostridial toxin fragments having a length of, e.g., at least 300 amino acids, at least 400 amino acids, at least 500 amino acids, at least 600 amino acids, at least 700 amino acids, at least 800 amino acids, at least 900 amino acids, at least 1000 amino acids, at least 1100 amino acids and at least 1200 amino acids. Other aspects of this embodiment, can include Clostridial toxin fragments having a length of, e.g., at most 300 amino acids, at most 400 amino acids, at most 500 amino acids, at most 600 amino acids, at most 700 amino acids, at most 800 amino acids, at most 900 amino acids, at most 1000 amino acids, at most 1100 amino acids and at most 1200 amino acids.

It is also envisioned that any of a variety of Clostridial toxin fragments comprising the light chain can be useful in aspects of the present invention with the proviso that these light chain fragments can specifically target the core components of the neurotransmitter release apparatus and thus participate in executing the overall cellular mechanism whereby a Clostridial toxin proteolytically cleaves a substrate. The light chains of Clostridial toxins are approximately 420-460 amino acids in length and comprise an enzymatic domain (Table 1). Research has shown that the entire length of a Clostridial toxin light chain is not necessary for the enzymatic activity of the enzymatic domain. As a non-limiting example, the first eight amino acids of the BoNT/A light chain (residues 1-8 of SEQ ID NO: 1) are not required for enzymatic activity. As another non-limiting example, the first eight amino acids of the TeNT light chain (residues 1-8 of SEQ ID NO: 8) are not required for enzymatic activity. Likewise, the carboxyl-terminus of the light chain is not necessary for activity. As a non-limiting example, the last 32 amino acids of the BoNT/A light chain (residues 417-448 of SEQ ID NO: 1) are not required for enzymatic activity. As another non-limiting example, the last 31 amino acids of the TeNT light chain (residues 427-457 of SEQ ID NO: 8) are not required for enzymatic activity. Thus, aspects of this embodiment can include Clostridial toxin light chains comprising an enzymatic domain having a length of, e.g., at least 350 amino acids, at least 375 amino acids, at least 400 amino acids, at least 425 amino acids and at least 450 amino acids. Other aspects of this embodiment can include Clostridial toxin light chains comprising an enzymatic domain having a length of, e.g., at most 350 amino acids, at most 375 amino acids, at most 400 amino acids, at most 425 amino acids and at most 450 amino acids.

It is also envisioned that any of a variety of Clostridial toxin $H_N$ regions comprising a translocation domain can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The $H_N$ regions from the heavy chains of Clostridial toxins are approximately 410-430 amino acids in length and comprise a translocation domain (Table 1). Research has shown that the entire length of a $H_N$ region from a Clostridial toxin heavy chain is not necessary for the translocating activity of the translocation domain. Thus, aspects of this embodiment can include Clostridial toxin $H_N$ regions comprising a translocation domain having a length of, e.g., at least 350 amino acids, at least 375 amino acids, at least 400 amino acids and at least 425 amino acids. Other aspects of this embodiment can include Clostridial toxin $H_N$ regions comprising translocation domain having a length of, e.g., at most 350 amino acids, at most 375 amino acids, at most 400 amino acids and at most 425 amino acids.

It is also envisioned that any of a variety of Clostridial toxin $H_C$ regions comprising a binding domain can be useful in aspects of the present invention with the proviso that these active fragments can determine the binding activity and binding specificity of the toxin to the receptor complex located at the surface of the target cell execute the overall cellular mechanism whereby a Clostridial toxin proteolytically cleaves a substrate. The $H_C$ regions from the heavy chains of Clostridial toxins are approximately 400-440 amino acids in length and comprise a binding domain (Table 1). Research has shown that the entire length of a $H_C$ region from a Clostridial toxin heavy chain is not necessary for the binding activity of the binding domain. Thus, aspects of this embodiment can include Clostridial toxin $H_C$ regions comprising a binding domain having a length of, e.g., at least 350 amino acids, at least 375 amino acids, at least 400 amino acids and at least 425 amino acids. Other aspects of this embodiment can include Clostridial toxin $H_C$ regions comprising a binding domain having a length of, e.g., at most 350 amino acids, at most 375 amino acids, at most 400 amino acids and at most 425 amino acids.

Thus, in an embodiment, a Clostridial toxin comprises a Clostridial toxin enzymatic domain, a Clostridial toxin translocation domain and a Clostridial toxin binding domain. In an aspect of this embodiment, a Clostridial toxin comprises a naturally occurring Clostridial toxin variant, such as, e.g., a Clostridial toxin isoform or a Clostridial toxin subtype. In another aspect of this embodiment, a Clostridial toxin comprises a non-naturally occurring Clostridial toxin variant, such as, e.g., a conservative Clostridial toxin variant, a non-conservative Clostridial toxin variant or an active Clostridial toxin fragment, or any combination thereof. In another aspect of this embodiment, a Clostridial toxin comprises a Clostridial toxin enzymatic domain or an active fragment thereof, a Clostridial toxin translocation domain or an active fragment thereof, a Clostridial toxin binding domain or an active fragment thereof, or any combination thereof. In other aspects of this embodiment, a Clostridial toxin can comprise a BoNT/A, a BoNT/B, a BoNT/C1, a BoNT/D, a BoNT/E, a BoNT/F, a BoNT/G or a TeNT.

In another embodiment, a Clostridial toxin comprises a BoNT/A. In an aspect of this embodiment, a BoNT/A comprises a BoNT/A enzymatic domain, a BoNT/A translocation domain and a BoNT/A binding domain. In another aspect of this embodiment, a BoNT/A comprises SEQ ID NO: 1. In another aspect of this embodiment, a BoNT/A comprises a naturally occurring BoNT/A variant, such as, e.g., a BoNT/A isoform or a BoNT/A subtype. In another aspect of this embodiment, a BoNT/A comprises a naturally occurring BoNT/A variant of SEQ ID NO: 1, such as, e.g., a BoNT/A isoform of SEQ ID NO: 1 or a BoNT/A subtype of SEQ ID NO: 1. In still another aspect of this embodiment, a BoNT/A comprises a non-naturally occurring BoNT/A variant, such as, e.g., a conservative BoNT/A variant, a non-conservative BoNT/A variant or an active BoNT/A fragment, or any combination thereof. In still another aspect of this embodiment, a BoNT/A comprises a non-naturally occurring BoNT/A variant of SEQ ID NO: 1, such as, e.g., a conservative BoNT/A variant of SEQ ID NO: 1, a non-conservative BoNT/A variant of SEQ ID NO: 1 or an active BoNT/A fragment of SEQ ID NO: 1, or any combination thereof. In yet another aspect of this embodiment, a BoNT/A comprises a BoNT/A enzymatic domain or an active fragment thereof, a BoNT/A translocation domain or an active fragment thereof, a BoNT/A binding domain or an active fragment thereof, or any combination thereof. In yet another aspect of this embodiment, a BoNT/A comprising a BoNT/A enzymatic domain of amino acids 1-448 from SEQ ID NO: 1 or an active fragment thereof, a BoNT/A translocation domain of amino acids 449-871 from SEQ ID NO: 1 or an active fragment thereof, a BoNT/A binding domain of amino acids 872-1296 from SEQ ID NO: 1 or an active fragment thereof, and any combination thereof.

In other aspects of this embodiment, a BoNT/A comprises a polypeptide having, e.g., at least 70% amino acid identity with SEQ ID NO: 1, at least 75% amino acid identity with the SEQ ID NO: 1, at least 80% amino acid identity with SEQ ID NO: 1, at least 85% amino acid identity with SEQ ID NO: 1, at least 90% amino acid identity with SEQ ID NO: 1 or at least 95% amino acid identity with SEQ ID NO: 1. In yet other aspects of this embodiment, a BoNT/A comprises a polypeptide having, e.g., at most 70% amino acid identity with SEQ ID NO: 1, at most 75% amino acid identity with the SEQ ID NO: 1, at most 80% amino acid identity with SEQ ID NO: 1, at most 85% amino acid identity with SEQ ID NO: 1, at most 90% amino acid identity with SEQ ID NO: 1 or at most 95% amino acid identity with SEQ ID NO: 1.

In other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 1. In yet other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid deletions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid deletions relative to SEQ ID NO: 1. In still other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid additions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid additions relative to SEQ ID NO: 1.

In other aspects of this embodiment, a BoNT/A comprises a polypeptide having, e.g., at most one, two, three, four, five, six, seven, eight, nine, 10, 20, 30, 40, 50, 100, 200 or 500 contiguous amino acid substitutions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid substitutions relative to SEQ ID NO: 1. In yet other aspects of this embodiment, a BoNT/A comprises a polypeptide having, e.g., at most one, two, three, four, five, six, seven, eight, nine, 10, 20, 30, 40, 50, 100, 200 or 500 contiguous amino acid deletions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid deletions relative to SEQ ID NO: 1. In still other aspects of this embodiment, a BoNT/A comprises a polypeptide having, e.g., at most one, two, three, four, five, six, seven, eight, nine, 10, 20, 30, 40, 50, 100, 200 or 500 contiguous amino acid additions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid additions relative to SEQ ID NO: 1.

In another embodiment, a Clostridial toxin comprises a BoNT/B. In an aspect of this embodiment, a BoNT/B comprises a BoNT/B enzymatic domain, a BoNT/B translocation domain and a BoNT/B binding domain. In another aspect of this embodiment, a BoNT/B comprises SEQ ID NO: 2. In another aspect of this embodiment, a BoNT/B comprises a naturally occurring BoNT/B variant, such as, e.g., a BoNT/B isoform or a BoNT/B subtype. In another aspect of this embodiment, a BoNT/B comprises a naturally occurring BoNT/B variant of SEQ ID NO: 2, such as, e.g., a BoNT/B isoform of SEQ ID NO: 2 or a BoNT/B subtype of SEQ ID NO: 2. In still another aspect of this embodiment, a BoNT/B comprises a non-naturally occurring BoNT/B variant, such as, e.g., a conservative BoNT/B variant, a non-conservative BoNT/B variant or an active BoNT/B fragment, or any combination thereof. In still another aspect of this embodiment, a BoNT/B comprises a non-naturally occurring BoNT/B variant of SEQ ID NO: 2, such as, e.g., a conservative BoNT/B variant of SEQ ID NO: 2, a non-conservative BoNT/B variant of SEQ ID NO: 2 or an active BoNT/B fragment of SEQ ID NO: 2, or any combination thereof. In yet another aspect of this embodiment, a BoNT/B comprising a BoNT/B enzymatic domain or an active fragment thereof, a BoNT/B translocation domain or active fragment thereof, a BoNT/B binding domain or active fragment thereof, and any combination thereof. In yet another aspect of this embodiment, a BoNT/B comprising a BoNT/B enzymatic domain of amino acids 1-441 from SEQ ID NO: 2 or active fragment thereof, a BoNT/B translocation domain of amino acids 442-858 from SEQ ID NO: 2 or active fragment thereof, a BoNT/B binding domain of amino acids 859-1291 from SEQ ID NO: 2 or active fragment thereof, and any combination thereof.

In other aspects of this embodiment, a BoNT/B comprises a polypeptide having, e.g., at least 70% amino acid identity with SEQ ID NO: 2, at least 75% amino acid identity with the SEQ ID NO: 2, at least 80% amino acid identity with SEQ ID NO: 2, at least 85% amino acid identity with SEQ ID NO: 2, at least 90% amino acid identity with SEQ ID NO: 2 or at least 95% amino acid identity with SEQ ID NO: 2. In yet other aspects of this embodiment, a BoNT/B comprises a polypeptide having, e.g., at most 70% amino acid identity with SEQ ID NO: 2, at most 75% amino acid identity with the SEQ ID NO: 2, at most 80% amino acid identity with SEQ ID NO: 2, at most 85% amino acid identity with SEQ ID NO: 2, at most 90% amino acid identity with SEQ ID NO: 2 or at most 95% amino acid identity with SEQ ID NO: 2.

In other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 2. In yet other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid deletions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid deletions relative to SEQ ID NO: 2. In still other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid additions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid additions relative to SEQ ID NO: 2.

In other aspects of this embodiment, a BoNT/B comprises a polypeptide having, e.g., at most one, two, three, four, five, six, seven, eight, nine, 10, 20, 30, 40, 50, 100, 200 or 500 contiguous amino acid substitutions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid substitutions relative to SEQ ID NO: 2. In yet other aspects of this embodiment, a BoNT/B comprises a polypeptide having, e.g., at most one, two, three, four, five, six, seven, eight, nine, 10, 20, 30, 40, 50, 100, 200 or 500 contiguous amino acid deletions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid deletions relative to SEQ ID NO: 2. In still other aspects of this embodiment, a BoNT/B comprises a polypeptide having, e.g., at most one, two, three, four, five, six, seven, eight, nine, 10, 20, 30, 40, 50, 100, 200 or 500 contiguous amino acid additions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid additions relative to SEQ ID NO: 2.

In another embodiment, a Clostridial toxin comprises a BoNT/C1. In an aspect of this embodiment, a BoNT/C1 comprises a BoNT/C1 enzymatic domain, a BoNT/C1 translocation domain and a BoNT/C1 binding domain. In another aspect of this embodiment, a BoNT/C1 comprises SEQ ID NO: 3. In another aspect of this embodiment, a BoNT/C1 comprises a naturally occurring BoNT/C1 variant, such as, e.g., a BoNT/C1 isoform or a BoNT/C1 subtype. In another aspect of this embodiment, a BoNT/C1 comprises a naturally occurring BoNT/C1 variant of SEQ ID NO: 3, such as, e.g., a BoNT/C1 isoform of SEQ ID NO: 3 or a BoNT/C1 subtype of SEQ ID NO: 3. In still another aspect of this embodiment, a BoNT/C1 comprises a non-naturally occurring BoNT/C1 variant, such as, e.g., a conservative BoNT/C1 variant, a non-conservative BoNT/C1 variant or an active BoNT/C1 fragment, or any combination thereof. In still another aspect of this embodiment, a BoNT/C1 comprises a non-naturally occurring BoNT/C1 variant of SEQ ID NO: 3, such as, e.g., a conservative BoNT/C1 variant of SEQ ID NO: 3, a non-conservative BoNT/C1 variant of SEQ ID NO: 3 or an active BoNT/C1 fragment of SEQ ID NO: 3, or any combination thereof. In yet another aspect of this embodiment, a BoNT/C1 comprises a BoNT/C1 enzymatic domain or active fragment thereof, a BoNT/C1 translocation domain or active fragment thereof, a BoNT/C1 binding domain or active fragment thereof, and any combination thereof. In yet another aspect of this embodiment, a BoNT/C1 comprises a BoNT/C1 enzymatic domain of amino acid 1-449 from SEQ ID NO: 3 or active fragment thereof, a BoNT/C1 translocation domain of amino acids 450-866 from SEQ ID NO: 3 or active fragment thereof, a BoNT/C1 binding domain of amino acids 867-1291 from SEQ ID NO: 3 or active fragment thereof, and any combination thereof.

In other aspects of this embodiment, a BoNT/C1 comprises a polypeptide having, e.g., at least 70% amino acid identity with SEQ ID NO: 3, at least 75% amino acid identity with the SEQ ID NO: 3, at least 80% amino acid identity with SEQ ID NO: 3, at least 85% amino acid identity with SEQ ID NO: 3, at least 90% amino acid identity with SEQ ID NO: 3 or at least 95% amino acid identity with SEQ ID NO: 3. In yet other aspects of this embodiment, a BoNT/C1 comprises a polypeptide having, e.g., at most 70% amino acid identity with SEQ ID NO: 3, at most 75% amino acid identity with the SEQ ID NO: 3, at most 80% amino acid identity with SEQ ID NO: 3, at most 85% amino acid identity with SEQ ID NO: 3, at most 90% amino acid identity with SEQ ID NO: 3 or at most 95% amino acid identity with SEQ ID NO: 3.

In other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 3. In yet other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid deletions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid deletions relative to SEQ ID NO: 3. In still other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid additions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid additions relative to SEQ ID NO: 3.

In other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid substitutions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid substitutions relative to SEQ ID NO: 3. In yet other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid deletions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid deletions relative to SEQ ID NO: 3. In still other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid additions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid additions relative to SEQ ID NO: 3.

In another embodiment, a Clostridial toxin comprises a BoNT/D. In an aspect of this embodiment, a BoNT/D comprises a BoNT/D enzymatic domain, a BoNT/D translocation domain and a BoNT/D binding domain. In another aspect of this embodiment, a BoNT/D comprises SEQ ID NO: 4. In another aspect of this embodiment, a BoNT/D comprises a naturally occurring BoNT/D variant, such as, e.g., a BoNT/D isoform or a BoNT/D subtype. In another aspect of this embodiment, a BoNT/D comprises a naturally occurring BoNT/D variant of SEQ ID NO: 4, such as, e.g., a BoNT/D isoform of SEQ ID NO: 4 or a BoNT/D subtype of SEQ ID NO: 4. In still another aspect of this embodiment, a BoNT/D comprises a non-naturally occurring BoNT/D variant, such as, e.g., a conservative BoNT/D variant, a non-conservative BoNT/D variant or an active BoNT/D fragment, or any combination thereof. In still another aspect of this embodiment, a BoNT/D comprises a non-naturally occurring BoNT/D variant of SEQ ID NO: 4, such as, e.g., a conservative BoNT/D variant of SEQ ID NO: 4, a non-conservative BoNT/D variant of SEQ ID NO: 4 or an active BoNT/D fragment of SEQ ID NO: 4, or any combination thereof. In yet another aspect of this embodiment, a BoNT/D comprises a BoNT/D enzymatic domain or an active fragment thereof, a BoNT/D translocation domain or an active fragment thereof, a BoNT/D binding domain or an active fragment thereof, or any combination thereof. In yet another aspect of this embodiment, a BoNT/D comprising a BoNT/D enzymatic domain of amino acids 1-445 from SEQ ID NO: 4 or an active fragment thereof, a BoNT/D translocation domain of amino acids 446-862 from SEQ ID NO: 4 or an active fragment thereof, a BoNT/D binding domain of amino acids 863-1276 from SEQ ID NO: 4 or an active fragment thereof, and any combination thereof.

In other aspects of this embodiment, a BoNT/D comprises a polypeptide having, e.g., at least 70% amino acid identity with SEQ ID NO: 4, at least 75% amino acid identity with the SEQ ID NO: 4, at least 80% amino acid identity with SEQ ID NO: 4, at least 85% amino acid identity with SEQ ID NO: 4, at least 90% amino acid identity with SEQ ID NO: 4 or at least 95% amino acid identity with SEQ ID NO: 4. In yet other aspects of this embodiment, a BoNT/D comprises a polypeptide having, e.g., at most 70% amino acid identity with SEQ ID NO: 4, at most 75% amino acid identity with the SEQ ID NO: 4, at most 80% amino acid identity with SEQ ID NO: 4, at most 85% amino acid identity with SEQ ID NO: 4, at most 90% amino acid identity with SEQ ID NO: 4 or at most 95% amino acid identity with SEQ ID NO: 4.

In other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 4. In yet other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid deletions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid deletions relative to SEQ ID NO: 4. In still other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid additions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid additions relative to SEQ ID NO: 4.

In other aspects of this embodiment, a BoNT/D comprises a polypeptide having, e.g., at most one, two, three, four, five, six, seven, eight, nine, 10, 20, 30, 40, 50, 100, 200 or 500 contiguous amino acid substitutions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid substitutions relative to SEQ ID NO: 4. In yet other aspects of this embodiment, a BoNT/D comprises a polypeptide having, e.g., at most one, two, three, four, five, six, seven, eight, nine, 10, 20, 30, 40, 50, 100, 200 or 500 contiguous amino acid deletions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid deletions relative to SEQ ID NO: 4. In still other aspects of this embodiment, a BoNT/D comprises a polypeptide having, e.g., at most one, two, three, four, five, six, seven, eight, nine, 10, 20, 30, 40, 50, 100, 200 or 500 contiguous amino acid additions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid additions relative to SEQ ID NO: 4.

In another embodiment, a Clostridial toxin comprises a BoNT/E. In an aspect of this embodiment, a BoNT/E comprises a BoNT/E enzymatic domain, a BoNT/E translocation domain and a BoNT/E binding domain. In another aspect of this embodiment, a BoNT/E comprises SEQ ID NO: 5. In another aspect of this embodiment, a BoNT/E comprises a naturally occurring BoNT/E variant, such as, e.g., a BoNT/E isoform or a BoNT/E subtype. In another aspect of this embodiment, a BoNT/E comprises a naturally occurring BoNT/E variant of SEQ ID NO: 5, such as, e.g., a BoNT/E isoform of SEQ ID NO: 5 or a BoNT/E subtype of SEQ ID NO: 5. In still another aspect of this embodiment, a BoNT/E comprises a non-naturally occurring BoNT/E variant, such as, e.g., a conservative BoNT/E variant, a non-conservative BoNT/E variant or an active BoNT/E fragment, or any combination thereof. In still another aspect of this embodiment, a BoNT/E comprises a non-naturally occurring BoNT/E variant of SEQ ID NO: 5, such as, e.g., a conservative BoNT/E variant of SEQ ID NO: 5, a non-conservative BoNT/E variant of SEQ ID NO: 5 or an active BoNT/E fragment of SEQ ID NO: 5, or any combination thereof. In yet another aspect of this embodiment, a BoNT/E comprising a BoNT/E enzymatic domain or an active fragment thereof, a BoNT/E translocation domain or active fragment thereof, a BoNT/E binding domain or active fragment thereof, and any combination thereof. In yet another aspect of this embodiment, a BoNT/E comprising a BoNT/E enzymatic domain of amino acids 1-422 from SEQ ID NO: 5 or active fragment thereof, a BoNT/E translocation domain of amino acids 423-845 from SEQ ID NO: 5 or active fragment thereof, a BoNT/E binding domain of amino acids 846-1252 from SEQ ID NO: 5 or active fragment thereof, and any combination thereof.

In other aspects of this embodiment, a BoNT/E comprises a polypeptide having, e.g., at least 70% amino acid identity with SEQ ID NO: 5, at least 75% amino acid identity with the SEQ ID NO: 5, at least 80% amino acid identity with SEQ ID NO: 5, at least 85% amino acid identity with SEQ ID NO: 5, at least 90% amino acid identity with SEQ ID NO: 5 or at least 95% amino acid identity with SEQ ID NO: 5. In yet other aspects of this embodiment, a BoNT/E comprises a polypeptide having, e.g., at most 70% amino acid identity with SEQ ID NO: 5, at most 75% amino acid identity with the SEQ ID NO: 5, at most 80% amino acid identity with SEQ ID NO: 5, at most 85% amino acid identity with SEQ ID NO: 5, at most 90% amino acid identity with SEQ ID NO: 5 or at most 95% amino acid identity with SEQ ID NO: 5.

In other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 5. In yet other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid deletions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid deletions relative to SEQ ID NO: 5. In still other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid additions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid additions relative to SEQ ID NO: 5.

In other aspects of this embodiment, a BoNT/E comprises a polypeptide having, e.g., at most one, two, three, four, five, six, seven, eight, nine, 10, 20, 30, 40, 50, 100, 200 or 500 contiguous amino acid substitutions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid substitutions relative to SEQ ID NO: 5. In yet other aspects of this embodiment, a BoNT/E comprises a polypeptide having, e.g., at most one, two, three, four, five, six, seven, eight, nine, 10, 20, 30, 40, 50, 100, 200 or 500 contiguous amino acid deletions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid deletions relative to SEQ ID NO: 5. In still other aspects of this embodiment, a BoNT/E comprises a polypeptide having, e.g., at most one, two, three, four, five, six, seven, eight, nine, 10, 20, 30, 40, 50, 100, 200 or 500 contiguous amino acid additions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid additions relative to SEQ ID NO: 5.

In another embodiment, a Clostridial toxin comprises a BoNT/F. In an aspect of this embodiment, a BoNT/F comprises a BoNT/F enzymatic domain, a BoNT/F translocation domain and a BoNT/F binding domain. In another aspect of this embodiment, a BoNT/F comprises SEQ ID NO: 6. In another aspect of this embodiment, a BoNT/F comprises a naturally occurring BoNT/F variant, such as, e.g., a BoNT/F isoform or a BoNT/F subtype. In another aspect of this embodiment, a BoNT/F comprises a naturally occurring BoNT/F variant of SEQ ID NO: 6, such as, e.g., a BoNT/F isoform of SEQ ID NO: 6 or a BoNT/F subtype of SEQ ID NO: 6. In still another aspect of this embodiment, a BoNT/F comprises a non-naturally occurring BoNT/F variant, such as, e.g., a conservative BoNT/F variant, a non-conservative BoNT/F variant or an active BoNT/F fragment, or any combination thereof. In still another aspect of this embodiment, a BoNT/F comprises a non-naturally occurring BoNT/F variant of SEQ ID NO: 6, such as, e.g., a conservative BoNT/F variant of SEQ ID NO: 6, a non-conservative BoNT/F variant of SEQ ID NO: 6 or an active BoNT/F fragment of SEQ ID NO: 6, or any combination thereof. In yet another aspect of this embodiment, a BoNT/F comprises a BoNT/F enzymatic domain or active fragment thereof, a BoNT/F translocation domain or active fragment thereof, a BoNT/F binding domain or active fragment thereof, and any combination thereof. In yet another aspect of this embodiment, a BoNT/F comprises a BoNT/F enzymatic domain of amino acid 1-439 from SEQ ID NO: 6 or active fragment thereof, a BoNT/F translocation domain of amino acids 440-864 from SEQ ID NO: 6 or active fragment thereof, a BoNT/F binding domain of amino acids 865-1274 from SEQ ID NO: 6 or active fragment thereof, and any combination thereof.

In other aspects of this embodiment, a BoNT/F comprises a polypeptide having, e.g., at least 70% amino acid identity with SEQ ID NO: 6, at least 75% amino acid identity with the SEQ ID NO: 6, at least 80% amino acid identity with SEQ ID NO: 6, at least 85% amino acid identity with SEQ ID NO: 6, at least 90% amino acid identity with SEQ ID NO: 6 or at least 95% amino acid identity with SEQ ID NO: 6. In yet other aspects of this embodiment, a BoNT/F comprises a polypeptide having, e.g., at most 70% amino acid identity with SEQ ID NO: 6, at most 75% amino acid identity with the SEQ ID NO: 6, at most 80% amino acid identity with SEQ ID NO: 6, at most 85% amino acid identity with SEQ ID NO: 6, at most 90% amino acid identity with SEQ ID NO: 6 or at most 95% amino acid identity with SEQ ID NO: 6.

In other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 6. In yet other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid deletions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid deletions relative to SEQ ID NO: 6. In still other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid additions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid additions relative to SEQ ID NO: 6.

In other aspects of this embodiment, a BoNT/F comprises a polypeptide having, e.g., at most one, two, three, four, five, six, seven, eight, nine, 10, 20, 30, 40, 50, 100, 200 or 500 contiguous amino acid substitutions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid substitutions relative to SEQ ID NO: 6. In yet other aspects of this embodiment, a BoNT/F comprises a polypeptide having, e.g., at most one, two, three, four, five, six, seven, eight, nine, 10, 20, 30, 40, 50, 100, 200 or 500 contiguous amino acid deletions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid deletions relative to SEQ ID NO: 6. In still other aspects of this embodiment, a BoNT/F comprises a polypeptide having, e.g., at most one, two, three, four, five, six, seven, eight, nine, 10, 20, 30, 40, 50, 100, 200 or 500 contiguous amino acid additions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid additions relative to SEQ ID NO: 6.

In another embodiment, a Clostridial toxin comprises a BoNT/G. In an aspect of this embodiment, a BoNT/G comprises a BoNT/G enzymatic domain, a BoNT/G translocation domain and a BoNT/G binding domain. In another aspect of this embodiment, a BoNT/G comprises SEQ ID NO: 7. In another aspect of this embodiment, a BoNT/G comprises a naturally occurring BoNT/G variant, such as, e.g., a BoNT/G isoform or a BoNT/G subtype. In another aspect of this embodiment, a BoNT/G comprises a naturally occurring BoNT/G variant of SEQ ID NO: 7, such as, e.g., a BoNT/G isoform of SEQ ID NO: 7 or a BoNT/G subtype of SEQ ID NO: 7. In still another aspect of this embodiment, a BoNT/G comprises a non-naturally occurring BoNT/G variant, such as, e.g., a conservative BoNT/G variant, a non-conservative BoNT/G variant or an active BoNT/G fragment, or any combination thereof. In still another aspect of this embodiment, a BoNT/D comprises a non-naturally occurring BoNT/G variant of SEQ ID NO: 7, such as, e.g., a conservative BoNT/G variant of SEQ ID NO: 7, a non-conservative BoNT/G variant of SEQ ID NO: 7 or an active BoNT/G fragment of SEQ ID NO: 7, or any combination thereof. In yet another aspect of this embodiment, a BoNT/G comprises a BoNT/G enzymatic domain or an active fragment thereof, a BoNT/G translocation domain or an active fragment thereof, a BoNT/G binding domain or an active fragment thereof, or any combination thereof. In yet another aspect of this embodiment, a BoNT/G comprising a BoNT/G enzymatic domain of amino acids 1-446 from SEQ ID NO: 7 or an active fragment thereof, a BoNT/G translocation domain of amino acids 447-863 from SEQ ID NO: 7 or an active fragment thereof, a BoNT/G binding domain of amino acids 864-1297 from SEQ ID NO: 7 or an active fragment thereof, and any combination thereof.

In other aspects of this embodiment, a BoNT/G comprises a polypeptide having, e.g., at least 70% amino acid identity with SEQ ID NO: 7, at least 75% amino acid identity with the SEQ ID NO: 7, at least 80% amino acid identity with SEQ ID NO: 7, at least 85% amino acid identity with SEQ ID NO: 7, at least 90% amino acid identity with SEQ ID NO: 7 or at least 95% amino acid identity with SEQ ID NO: 7. In yet other aspects of this embodiment, a BoNT/G comprises a polypeptide having, e.g., at most 70% amino acid identity with SEQ ID NO: 7, at most 75% amino acid identity with the SEQ ID NO: 7, at most 80% amino acid identity with SEQ ID NO: 7, at most 85% amino acid identity with SEQ ID NO: 7, at most 90% amino acid identity with SEQ ID NO: 7 or at most 95% amino acid identity with SEQ ID NO: 7.

In other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 7. In yet other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid deletions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid deletions relative to SEQ ID NO: 7. In still other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid additions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid additions relative to SEQ ID NO: 7.

In other aspects of this embodiment, a BoNT/G comprises a polypeptide having, e.g., at most one, two, three, four, five, six, seven, eight, nine, 10, 20, 30, 40, 50, 100, 200 or 500 contiguous amino acid substitutions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid substitutions relative to SEQ ID NO: 7. In yet other aspects of this embodiment, a BoNT/G comprises a polypeptide having, e.g., at most one, two, three, four, five, six, seven, eight, nine, 10, 20, 30, 40, 50, 100, 200 or 500 contiguous amino acid deletions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid deletions relative to SEQ ID NO: 7. In still other aspects of this embodiment, a BoNT/G comprises a polypeptide having, e.g., at most one, two, three, four, five, six, seven, eight, nine, 10, 20, 30, 40, 50, 100, 200 or 500 contiguous amino acid additions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid additions relative to SEQ ID NO: 7.

In another embodiment, a Clostridial toxin comprises a TeNT. In an aspect of this embodiment, a TeNT comprises a TeNT enzymatic domain, a TeNT translocation domain and a TeNT binding domain. In an aspect of this embodiment, a TeNT comprises SEQ ID NO: 8. In another aspect of this embodiment, a TeNT comprises a naturally occurring TeNT variant, such as, e.g., a TeNT isoform or a TeNT subtype. In another aspect of this embodiment, a TeNT comprises a naturally occurring TeNT variant of SEQ ID NO: 8, such as, e.g., a TeNT isoform of SEQ ID NO: 8 or a TeNT subtype of SEQ ID NO: 8. In still another aspect of this embodiment, a TeNT comprises a non-naturally occurring TeNT variant, such as, e.g., a conservative TeNT variant, a non-conservative TeNT variant or an active TeNT fragment, or any combination thereof. In still another aspect of this embodiment, a TeNT comprises a non-naturally occurring TeNT variant of SEQ ID NO: 8, such as, e.g., a conservative TeNT variant of SEQ ID NO: 8, a non-conservative TeNT variant of SEQ ID NO: 8 or an active TeNT fragment of SEQ ID NO: 8, or any combination thereof. In yet another aspect of this embodiment, a TeNT comprising a TeNT enzymatic domain or an active fragment thereof, a TeNT translocation domain or active fragment thereof, a TeNT binding domain or active fragment thereof, and any combination thereof. In yet another aspect of this embodiment, a TeNT comprising a TeNT enzymatic domain of amino acids 1-457 from SEQ ID NO: 8 or active fragment thereof, a TeNT translocation domain of amino acids 458-879 from SEQ ID NO: 8 or active fragment thereof, a TeNT binding domain of amino acids 880-1315 from SEQ ID NO: 8 or active fragment thereof, and any combination thereof.

In other aspects of this embodiment, a TeNT comprises a polypeptide having, e.g., at least 70% amino acid identity with SEQ ID NO: 8, at least 75% amino acid identity with the SEQ ID NO: 8, at least 80% amino acid identity with SEQ ID NO: 8, at least 85% amino acid identity with SEQ ID NO: 8, at least 90% amino acid identity with SEQ ID NO: 8 or at least 95% amino acid identity with SEQ ID NO: 8. In yet other aspects of this embodiment, a TeNT comprises a polypeptide having, e.g., at most 70% amino acid identity with SEQ ID NO: 8, at most 75% amino acid identity with the SEQ ID NO: 8, at most 80% amino acid identity with SEQ ID NO: 8, at most 85% amino acid identity with SEQ ID NO: 8, at most 90% amino acid identity with SEQ ID NO: 8 or at most 95% amino acid identity with SEQ ID NO: 8.

In other aspects of this embodiment, a TeNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 8. In yet other aspects of this embodiment, a TeNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 8. In still other aspects of this embodiment, a TeNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 8.

In other aspects of this embodiment, a TeNT comprises a polypeptide having, e.g., at most one, two, three, four, five, six, seven, eight, nine, 10, 20, 30, 40, 50, 100, 200 or 500 contiguous amino acid substitutions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 8. In yet other aspects of this embodiment, a TeNT comprises a polypeptide having, e.g., at most one, two, three, four, five, six, seven, eight, nine, 10, 20, 30, 40, 50, 100, 200 or 500 contiguous amino acid deletions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid deletions relative to SEQ ID NO: 8. In still other aspects of this embodiment, a TeNT comprises a polypeptide having, e.g., at most one, two, three, four, five, six, seven, eight, nine, 10, 20, 30, 40, 50, 100, 200 or 500 contiguous amino acid additions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid additions relative to SEQ ID NO: 8.

Aspects of the present invention provide, in part, a Clostridial toxin substrate cleavage site. As used herein, the term "Clostridial toxin substrate cleavage site" means a scissile bond together with adjacent or non-adjacent recognition elements, or both, sufficient for detectable proteolysis at the scissile bond by a Clostridial toxin under conditions suitable for Clostridial toxin protease activity. By definition, a Clostridial toxin substrate cleavage site is susceptible to cleavage by at least one Clostridial toxin under conditions suitable for Clostridial toxin protease activity. It is envisioned that a Clostridial toxin substrate cleavage site of any and all lengths can be useful in aspects of the present invention with the proviso that the Clostridial toxin substrate cleavage site is capable of being cleaved by a Clostridial toxin. Thus, in aspects of this embodiment, a Clostridial toxin substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a Clostridial toxin substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A Clostridial toxin substrate cleavage site useful in aspects of the invention includes, without limitation, naturally occurring Clostridial toxin substrate cleavage site; naturally occurring Clostridial toxin substrate cleavage site variants; and non-naturally-occurring Clostridial toxin substrate cleavage site variants, such as, e.g., conservative Clostridial toxin substrate cleavage site variants, non-conservative Clostridial toxin substrate cleavage site variants and Clostridial toxin substrate cleavage site peptidomimetics. As used herein, the term "Clostridial toxin substrate cleavage site variant," whether naturally-occurring or non-naturally-occurring, means a Clostridial toxin substrate cleavage site that has at least one amino acid change from the corresponding region of the disclosed reference sequences and can be described in percent identity to the corresponding region of that reference sequence. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

As used herein, the term "naturally occurring Clostridial toxin substrate cleavage site variant" means any Clostridial toxin substrate cleavage site produced without the aid of any human manipulation, including, without limitation, Clostridial toxin substrate cleavage site isoforms produced from alternatively-spliced transcripts, Clostridial toxin substrate cleavage site isoforms produced by spontaneous mutation and Clostridial toxin substrate cleavage site subtypes.

As used herein, the term "non-naturally occurring Clostridial toxin substrate cleavage site variant" means any Clostridial toxin substrate cleavage site produced with the aid of human manipulation, including, without limitation, Clostridial toxin substrate cleavage site variants produced by genetic engineering using random mutagenesis or rational design and Clostridial toxin substrate cleavage site variants produced by chemical synthesis. Non-limiting examples of non-naturally occurring Clostridial toxin substrate cleavage site variants include, e.g., conservative Clostridial toxin substrate cleavage site variants, non-conservative Clostridial toxin substrate cleavage site variants and Clostridial toxin substrate cleavage site peptidomimetics.

As used herein, the term "conservative Clostridial toxin substrate cleavage site variant" means a Clostridial toxin substrate cleavage site that has at least one amino acid substituted by another amino acid or an amino acid analog that has at least one property similar to that of the original amino acid from the reference Clostridial toxin substrate cleavage site sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin substrate cleavage site variant can function in substantially the same manner as the reference Clostridial toxin substrate cleavage site on which the conservative Clostridial toxin substrate cleavage site variant is based, and can be substituted for the reference Clostridial toxin substrate cleavage site in any aspect of the present invention. A conservative Clostridial toxin substrate cleavage site variant may substitute one or more amino acids, two or more amino acids, three or more amino acids, four or more amino acids or five or more amino acids from the reference Clostridial toxin substrate cleavage site on which the conservative Clostridial toxin substrate cleavage site variant is based. A conservative Clostridial toxin substrate cleavage site variant can also possess at least 50% amino acid identity, 65% amino acid identity, 75% amino acid identity, 85% amino acid identity or 95% amino acid identity to the reference Clostridial toxin substrate cleavage site on which the conservative Clostridial toxin substrate cleavage site variant is based. Non-limiting examples of a conservative Clostridial toxin substrate cleavage site variant include, e.g., conservative BoNT/A substrate cleavage site variants, conservative BoNT/B substrate cleavage site variants, conservative BoNT/C1 substrate cleavage site variants, conservative BoNT/D substrate cleavage site variants, conservative BoNT/E substrate cleavage site variants, conservative BoNT/F substrate cleavage site variants, conservative BoNT/G substrate cleavage site variants, conservative TeNT substrate cleavage site variants, conservative BaNT substrate cleavage site variants and conservative BuNT substrate cleavage site variants.

As used herein, the term "non-conservative Clostridial toxin substrate cleavage site variant" means a Clostridial toxin substrate cleavage site in which 1) at least one amino acid is deleted from the reference Clostridial toxin substrate cleavage site on which the non-conservative Clostridial toxin substrate cleavage site variant is based; 2) at least one amino acid added to the reference Clostridial toxin substrate cleavage site on which the non-conservative Clostridial toxin substrate cleavage site is based; or 3) at least one amino acid is substituted by another amino acid or an amino acid analog that does not share any property similar to that of the original amino acid from the reference Clostridial toxin substrate cleavage site sequence (Table 3). A non-conservative Clostridial toxin substrate cleavage site variant can function in substantially the same manner as the reference Clostridial toxin substrate cleavage site on which the non-conservative Clostridial toxin substrate cleavage site is based, and can be substituted for the reference Clostridial toxin substrate cleavage site in any aspect of the present invention. A non-conservative Clostridial toxin substrate cleavage site variant can add one or more amino acids, two or more amino acids, three or more amino acids, four or more amino acids, five or more amino acids, and ten or more amino acids to the reference Clostridial toxin substrate cleavage site on which the non-conservative Clostridial toxin substrate cleavage site variant is based. A non-conservative Clostridial toxin substrate cleavage site may substitute one or more amino acids, two or more amino acids, three or more amino acids, four or more amino acids or five or more amino acids from the reference Clostridial toxin substrate cleavage site on which the non-conservative Clostridial toxin substrate cleavage site variant is based. A non-conservative Clostridial toxin substrate cleavage site variant can also possess at least 50% amino acid identity, 65% amino acid identity, 75% amino acid identity, 85% amino acid identity or 95% amino acid identity to the reference Clostridial toxin substrate cleavage site on which the non-conservative Clostridial toxin substrate cleavage site variant is based. Non-limiting examples of a non-conservative Clostridial toxin substrate cleavage site variant include, e.g., non-conservative BoNT/A substrate cleavage site variants, non-conservative BoNT/B substrate cleavage site variants, non-conservative BoNT/C1 substrate cleavage site variants, non-conservative BoNT/D substrate cleavage site variants, non-conservative BoNT/E substrate cleavage site variants, non-conservative BoNT/F substrate cleavage site variants, non-conservative BoNT/G substrate cleavage site variants, non-conservative TeNT substrate cleavage site variants, non-conservative BaNT substrate cleavage site variants and non-conservative BuNT substrate cleavage site variants.

As used herein, the term "Clostridial toxin substrate cleavage site peptidomimetic" means a Clostridial toxin substrate cleavage site that has at least one amino acid substituted by a non-natural oligomer that has at least one property similar to that of the first amino acid. Examples of properties include, without limitation, topography of a peptide primary structural element, functionality of a peptide primary structural element, topology of a peptide secondary structural element, functionality of a peptide secondary structural element, of the like, or any combination thereof. A Clostridial toxin substrate cleavage site peptidomimetic can function in substantially the same manner as the reference Clostridial toxin substrate cleavage site on which the Clostridial toxin substrate cleavage site peptidomimetic is based, and can be substituted for the reference Clostridial toxin substrate cleavage site in any aspect of the present invention. A Clostridial toxin substrate cleavage site peptidomimetic may substitute one or more amino acids, two or more amino acids, three or more amino acids, four or more amino acids or five or more amino acids from the reference Clostridial toxin substrate cleavage site on which the Clostridial toxin substrate cleavage site peptidomimetic is based. A Clostridial toxin substrate cleavage site peptidomimetic can also possess at least 50% amino acid identity, at least 65% amino acid identity, at least 75% amino acid identity, at least 85% amino acid identity or at least 95% amino acid identity to the reference Clostridial toxin substrate cleavage site on which the Clostridial toxin substrate cleavage site peptidomimetic is based. For examples of peptidomimetic methods see, e.g., Amy S. Ripka & Daniel H. Rich, Peptidomimetic design, 2(4) CURR. OPIN. CHEM. BIOL. 441-452 (1998); and M. Angels Estiarte & Daniel H. Rich, Peptidomimetics for Drug Design, 803-861 (BURGER'S MEDICINAL CHEMISTRY AND DRUG DISCOVERY Vol. 1 PRINCIPLE AND PRACTICE, Donald J. Abraham ed., Wiley-Interscience, 6th ed 2003). Non-limiting examples of a conservative Clostridial toxin substrate cleavage site variant include, e.g., BoNT/A substrate cleavage site peptidomimetics, BoNT/B substrate cleavage site peptidomimetics, BoNT/C1 substrate cleavage site peptidomimetics, BoNT/D substrate cleavage site peptidomimetics, BoNT/E substrate cleavage site peptidomimetics, BoNT/F substrate cleavage site peptidomimetics, BoNT/G substrate cleavage site peptidomimetics, TeNT substrate cleavage site peptidomimetics, BaNT substrate cleavage site peptidomimetics and BuNT substrate cleavage site peptidomimetics.

One type of Clostridial toxin substrate cleavage site is derived from in vivo substrate targets of Clostridial toxins, such as, e.g., the SNARE proteins. The natural SNARE targets of the Clostridial toxins include, without limitation, the SNAP-25 family, the VAMP family and the Syntaxin family. SNAP-25 and Syntaxin are associated with the plasma membrane, whereas VAMP is associated with the synaptic vesicle membrane (see FIG. 3). BoNT/A and BoNT/E recognize and specifically cleave SNAP-25 at two different sites in the carboxyl-terminal portion of the protein (Table 2). TeNT and BoNT/B, BoNT/D, BoNT/F, and BoNT/G specifically target the conserved central portion of VAMPs (also known as synaptobrevin) at distinct bonds, depending on the toxin (Table 3). BoNT/C1 cleaves Syntaxin at a single site near the cytosolic membrane surface in addition to SNAP-25 near the carboxyl-terminus (Tables 2 & 4). The three protein targets of these Clostridial toxins are conserved from yeast to humans although cleavage sites and toxin susceptibility are not necessarily conserved, see below; see, also, e.g., Humeau, supra, (2000); Heiner Niemann et al., Clostridial Neurotoxins: New Tools for Dissecting Exocytosis, 4(5) Trends Cell Biol. 179-185 (1994); and Rossella Pellizzari et al., Tetanus and Botulinum Neurotoxins: Mechanism of Action and Therapeutic Uses, 354(1381) Philos. Trans. R. Soc. Lond. B Biol. Sci. 259-268 (1999).

Figure 3:
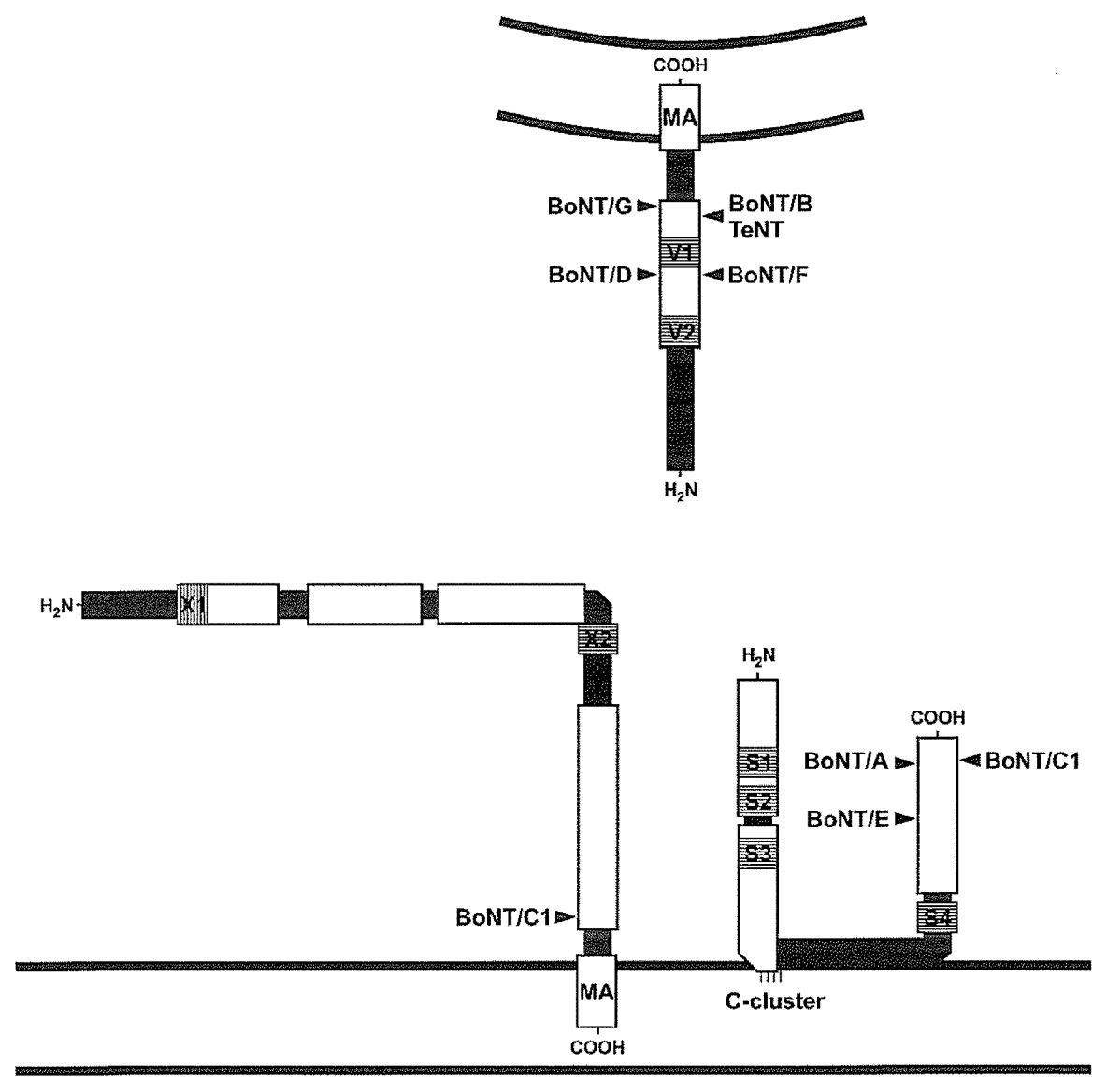

Naturally occurring SNAP-25, a protein of about 206 residues lacking a transmembrane segment, is associated with the cytosolic surface of the nerve plasmalemma (see FIG. 3). SNAP-25 is required for axonal growth during development and may be required for nerve terminal plasticity in the mature nervous system. SNAP-25 has been isolated from a variety of vertebrate and invertebrate species including, e.g., species belonging to the genera Homo, Macaca, Bos, Rattus, Mus, Gallus, Carassius, Danio, Torpedo, Xenopus, Strongylocentrotus, Drosophila, Hirudo, Loligo, Lymnaea and Caenorhabditis (Table 2). In humans, at least two isoforms are differentially expressed during development; isoform a is constitutively expressed during fetal development, while isoform b appears at birth and predominates in adult life. SNAP-25 analogues such as SNAP-23 also are expressed outside the nervous system, for example, in pancreatic cells.

TABLE 2

Cleavage of SNAP-25 and Related Proteins[a,b,c]

| Organism | Isoform | Cleavage Sites | | | | | | | | Cleavage Susceptibility |
|---|---|---|---|---|---|---|---|---|---|---|
| | | BoNT/E ▼ | | | | BoNT/A ▼ | | BoNT/C1 ▼ | | |
| Primate | SNAP-25A SNAP-25B | MALDMGNEIDTQNRQIDR | * | IMEKADSNKTRIDEANQ | * | R | * | ATKMLGSG | | BoNT/A; BoNT/C1; BoNT/E |
| Primate | SNAP-23A SNAP-23B | MALNIGNEIDAQNPQIKR | — | ITDKADTNRDRIDIANA | — | R | — | AKKLIDS | | None[b] |
| Rodent | SNAP-25A SNAP-25B | MALDMGNEIDTQNRQIDR | * | IMEKADSNKTRIDEANQ | * | R | * | ATKMLGSG | | BoNT/A; BoNT/C1; BoNT/E |
| Rodent | SNAP-23 | MALDMGNEIDAQNQQIQK | * | ITEKADTNKNRIDIANT | — | R | — | AKKLIDS | | BoNT/E |

TABLE 2-continued

Cleavage of SNAP-25 and Related Proteins[a,b,c]

| Organism | Isoform | Cleavage Sites | | | | | | | Cleavage Susceptibility |
|---|---|---|---|---|---|---|---|---|---|
| | | | BoNT/E ▼ | | BoNT/A ▼ | | BoNT/C1 ▼ | | |
| Bird | SNAP-25B | MALDMGNEIDTQNRQIDR | * | IMEKADSNKTRIDEANQ | — | R | — | ATKMLGSG | BoNT/E |
| Amphibian | SNAP-25A SNAP-25B | MALDMGNEIDTQNRQIDR | ND | IMEKADSNKARIDEAN[K] | ND | [H] | ND | ATKMLGSG | ND |
| Amphibian | SNAP-23 | MAIDMGNELESHNQQIGR | ND | INEKAETNKTRIDEAN[T] | ND | K | ND | AKKLIE | ND |
| Fish | SNAP-25A | MALDMGNEIDTQNRQIDR | * | IMEKADSNKTRIDEANQ | * | R | * | ATKMLGSG | BoNT/A; BoNT/C1; |
| | SNAP-25B | MALDMGNEIDTQNRQIDR | * | IMDMADSNKTRIDEANQ | * | R | * | ATKMLGSG | BoNT/E |
| Fish | SNAP-23 | LALDMGNEIDKQNKTIDR | ND | ITDKADMNKARIDEANQ | ND | R | ND | ANKLL | ND |
| Ray | SNAP-25 | MALDMSNEIGSQNAQIDR | —[c] | IV[V]KGDMNKARIDEAN[K] | * | [H] | ND | ATKML | BoNT/A |
| Sea urchin | SNAP-25 | MAIDMQSEIGAQNSQVGR | ND | ITSKAESNEGRINSAD[K] | ND | R | ND | AKNILRNK | ND |
| Insect | SNAP-25 | MALDMGSELENQNRQIDR | — | INRKGESNEARIAVANQ | — | R | * | AHQLLK | BoNT/C1 |
| Insect | SNAP-24 | MALDMGSELENQNKQVDR | ND | INAKGDANNIRMDGVN[K] | ND | R | ND | ANNLLKS | ND |
| Segmented worm | SNAP-25 | MAVDMGSEIDSQNRQVDR | ND | INNKMTSNOLRISDAN[K] | — | R | ND | ASKLLKE | ND |
| Cephalopod | SNAP-25 | MAIDMGNEIGSQNRQVDR | ND | IQQKAESNESRIDEAN[K] | ND | [K] | ND | ATKLLKN | ND |
| Gastropod | SNAP-25 | MAVDMGNEIESQNKQLDR | ND | INQKGGSLNVRVDEAN[K] | ND | R | ND | ANRILRKQ | ND |
| Round worm | SNAP-25 | MAIDMSTEVSNQNRQLDR | * | IHDKAQSNEVRVESAN[K] | — | R | — | AKNLITK | BoNT/E |

Proteolytic cleavage occurs at this site (*); Proteolytic cleavage not detected at this site (—); Proteolytic cleavage not determined at this site (ND)
[a] = In vitro cleavage of SNAP-25 requires 1000-fold higher BoNT/C concentration than BoNT/A or /E.
[b] = Substitution of P182R, or K185DD (boxes) induces susceptibility toward BoNT/E.
[c] = Resistance to BoNT/E possibly due to D189 or E189 substitution by V189, see box.

Table 2—Cleavage of SNAP-25 and related proteins. Primate: Human SNAP-25A residues 163-206 of SEQ ID NO: 9; Human SNAP-25B residues 163-206 of SEQ ID NO: 10; Human SNAP-23A residues 169-211 of SEQ ID NO: 11; Human SNAP-23B residues 116-158 of SEQ ID NO: 12; Monkey SNAP-25B residues 163-206 of SEQ ID NO: 13; Rodent: Rat SNAP-25A residues 163-206 of SEQ ID NO: 14; Rat SNAP-25B residues 163-206 of SEQ ID NO: 15; Mouse SNAP-25B residues 163-206 of SEQ ID NO: 16; Rat SNAP-23 residues 168-210 of SEQ ID NO: 17; Mouse SNAP-23 residues 168-210 of SEQ ID NO: 18; Bird: Chicken SNAP-25B residues 163-206 of SEQ ID NO: 19; Fish: Goldfish SNAP-25A residues 161-204 of SEQ ID NO: 20; Goldfish SNAP-25B residues 160-203 of SEQ ID NO: 21; Zebrafish SNAP-25A residues 161-204 of SEQ ID NO: 22; Zebrafish SNAP-25B residues 160-203 of SEQ ID NO: 23; Zebrafish SNAP-23 residues 174-214 of SEQ ID NO: 24; Ray: marbled electric ray SNAP-25 residues 170-210 of SEQ ID NO: 25; Amphibian: Frog SNAP-25A residues 163-206 of SEQ ID NO: 26; Frog SNAP-25B residues 163-206 of SEQ ID NO: 27; Frog SNAP-23 residues 163-204 of SEQ ID NO: 28; Sea urchin SNAP-25 residues 169-212 of SEQ ID NO: 29; Insect: Fruit fly SNAP-25 residues 171-212 of SEQ ID NO: 30; Fruit fly SNAP-24 residues 170-212 of SEQ ID NO: 31; Segmented worm: Leech SNAP-25 residues 170-212 of SEQ ID NO: 32; Cephalopod: squid SNAP-25 residues 245-267 of SEQ ID NO: 33; Gastropod: Pond snail SNAP-25 residues 244-266 of SEQ ID NO: 34; Round worm: Nematode worm SNAP-25 residues 165-207 of SEQ ID NO: 35.

Naturally occurring VAMP is a protein of about 120 residues, with the exact length depending on the species and isoform. As shown in FIG. 3, VAMP contains a short carboxyl-terminal segment inside the vesicle lumen while most of the molecule is exposed to the cytosol. The proline-rich amino-terminal thirty residues are divergent among species and isoforms while the central portion of VAMP, which is rich in charged and hydrophilic residues and includes known cleavage sites, is highly conserved (Table 3). VAMP colocalizes with synaptophysin on synaptic vesicle membranes. VAMP has been isolated from a variety of vertebrate and invertebrate species including, e.g., species belonging to the genera *Homo, Macaca, Bos, Rattus, Mus, Gallus, Danio, Torpedo, Xenopus, Strongylocentrotus, Drosophila, Hirudo, Loligo, Lymnaea, Aplysia* and *Caenorhabditis*. In addition, multiple isoforms of VAMP have been identified including VAMP-1, VAMP-2 and VAMP-3/cellubrevin, and forms insensitive to toxin cleavage have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 orthologs have a valine in place of the glutamine present in human and mouse VAMP-1 at the TeNT or BoNT/B cleavage site. The substitution does not affect BoNT/D, /F or /G, which cleave both VAMP-1 and VAMP-2 with similar rates.

TABLE 3

Cleavage of VAMP and Related Proteins

| Organism | Isoform | | BoNT/F ▼ | | BoNT/D ▼ | |
|---|---|---|---|---|---|---|
| | | | Cleavage Sites | | | |
| Primate | VAMP1-1<br>VAMP1-2<br>VAMP1-3 | RVNVDKVLERDQ | * | K | * | LSELDDRADALQAGASQ |
| Primate | VAMP2 | RVNVDKVLERDQ | * | K | * | LSELDDRADALQAGASQ |
| Primate | VAMP3 | RVNVDKVLERDQ | * | K | * | LSELDDRADALQAGASQ |
| Bovine | VAMP2 | RVNVDKVLERDQ | * | K | * | LSELDDRADALQAGASQ |
| Rodent | VAMP1/1b | RVNVDKVLERDQ | * | K | * | LSELDDRADALQAGAS[V] |
| Rodent | VAMP1<br>VAMP2<br>VAMP2-b | RVNVDKVLERDQ<br>RVNVDKVLERDQ | *<br>* | K<br>K | *<br>* | LSELDDRADALQAGASQ<br>LSELDDRADALQAGASQ |
| Rodent | VAMP3 | RVNVDKVLERDQ | * | K | * | LSELDDRADALQAGASQ |
| Bird | VAMP1 | RVNVDKVLERDQ | * | K | * | LSELDDRADALQAGAS[V] |
| Bird | VAMP2 | RMNVDKVLERDQ | * | K | * | LSELDNRADALQAGASQ |
| Bird | VAMP3 | RVNVDKVLERDQ | ND | K | ND | LSELDDRADALQAGASQ |
| Amphibian | VAMP2 | RVNVDKVLERD[I] | ND | K | ND | LSELDDRADALQAGASQ |
| Amphibian | VAMP3 | RVNVDKVLERDQ | ND | K | ND | LSELDDRADALQAGASQ |
| Fish | VAMP1 | RVNVDKVLERDQ | ND | K | ND | LSELDDRADALQAGASQ |
| Fish | VAMP2 | RVNVDKVLERDQ | ND | K | ND | LSELDDRADALQAGASQ |
| Fish | VAMP-3 | RVNVDKVLERDQ | ND | K | ND | LSELDDRADALQAGASQ |
| Ray | VAMP1 | RVNVDKVLERDQ | * | K | * | LSELDDRADALQAGASQ |
| Sea Urchin | VAMP | RVNVDKVLERDQ | — | [A] | — | LSVLDDRADALQQGASQ |
| Insect | Syn-A1<br>Syn-B1 | RVNVEKVLERDQ | * | K | * | LSELGERADQLEQGASQ |
| Insect | Syn-A2<br>Syn-B2 | RVNVEKVLERDQ | * | K | * | LSELGERADQLEQGASQ |
| Insect | Syn-C<br>Syn-D<br>Syn-E | RTNVEKVLERD[S] | — | K | * | LSELDDRADALQQGASQ |
| Segmented worm | VAMP | RVNVDKVLEKDQ | * | K | * | LAELDGRADALQAGASQ |
| Cephalopod | VAMP | RVNVDKVLERD[S] | ND | K | ND | [I]SELDDRADALQAGASQ |
| Gastropod | VAMP | RVNVEKVLDRDQ | ND | K | ND | [I]SQLDDRAEALQAGASQ |
| Round worm | SNB1 | KVNVEKVLERDQ | ND | K | ND | LSQLDDRADALQEGASQ |
| | SNB-like | RNNVNKVMERD[V] | — | [Q] | — | LNSLDHRAEVLQNGASQ |

| Organism | Isoform | TeNT<br>BoNT/B ▼ | | BoNT/G ▼ | | Cleaved Susceptibility |
|---|---|---|---|---|---|---|
| | | | Cleavage Sites | | | |
| Primate | VAMP1-1<br>VAMP1-2<br>VAMP1-3 | * | FESSA | * | AKLKRKYWW | BoNT/B; BoNT/D; BoNT/F;<br>BoNT/G; TeNT |
| Primate | VAMP2 | * | FETSA | * | AKLKRKYWW | BoNT/B; BoNT/D; BoNT/F;<br>BoNT/G; TeNT |
| Primate | VAMP3 | * | FETSA | * | AKLKRKYWW | BoNT/B; BoNT/D; BoNT/F;<br>BoNT/G; TeNT |
| Bovine | VAMP2 | * | FETSA | * | AKLKRKYWW | BoNT/B; BoNT/D; BoNT/F;<br>BoNT/G; TeNT |
| Rodent | VAMP1/1b | —[a]<br>* | FESSA<br>FESSA | *<br>* | AKLKRKYWW<br>AKLKRKYWW | BoNT/B; BoNT/D; BoNT/F;<br>BoNT/G; TeNT |

TABLE 3-continued

Cleavage of VAMP and Related Proteins

| | | | | | | |
|---|---|---|---|---|---|---|
| Rodent | VAMP2 | * | FETSA | * | AKLKRKYWW | BoNT/B; BoNT/D; BoNT/F; BoNT/G; TeNT |
| | VAMP2-b | | | | | |
| Rodent | VAMP3 | * | FETSA | * | AKLKRKYWW | BoNT/B; BoNT/D; BoNT/F; BoNT/G; TeNT |
| Bird | VAMP1 | — | FESSA | * | AKLKRKYWW | BoNT/D; BoNT/F; BoNT/G |
| Bird | VAMP2 | * | FETSA | * | AKLKRKYWW | BoNT/B; BoNT/D; BoNT/F; BoNT/G; TeNT |
| Bird | VAMP3 | ND | FETSA | ND | AKLKRKYWW | ND |
| Amphibian | VAMP2 | ND | FETSA | ND | AKLKRKYWW | ND |
| Amphibian | VAMP3 | ND | FETSA | ND | AKLKRKYWW | ND |
| Fish | VAMP1 | ND | FESSA | ND | AKLKNKYWW | ND |
| Fish | VAMP2 | ND | FETSA | ND | AKLKNKYWW | ND |
| Fish | VAMP-3 | ND | FETSA | ND | AKLKRKYWW | ND |
| Ray | VAMP1 | * | FESSA | * | AKLKRKYWW | BoNT/B; BoNT/D; BoNT/F; BoNT/G; TeNT |
| Sea Urchin | VAMP | * | FETNA | — | GKLKRKYWW | BoNT/B; TeNT |
| Insect | Syn-A1 | * | FEQQA | — | GKLKRKQWW | BoNT/B; BoNT/D; BoNT/F; TeNT |
| Insect | Syn-A2 | — | SEQQA | — | GKLKRKQWW | BoNT/D; BoNT/F |
| Insect | Syn-B2 Syn-C | * | FEQQA | — | GKLKRKFWL | BoNT/B; BoNT/D; TeNT |
| Segmented worm | Syn-D Syn-E VAMP | * | FEASA | — | GKLKRKFWW | BoNT/B; BoNT/D; BoNT/F; TeNT |
| Cephalopod | VAMP | ND | FEASA | ND | GKLKRKFWW | ND |
| Gastropod | VAMP | ND | FEASA | ND | GKLKRKYWW | ND |
| Round worm | SNB1 | ND | FEKSA | ND | ATLKRKYWW | BoNT/B; TeNT |
| | SNB-like | * | FQQSS | — | RTLRQKYWW | |

Proteolytic cleavage occurs at this site (*); Proteolytic cleavage not detected at this site (—); Proteolytic cleavage not determined at this site (ND)
$^a$= Rat VAMP1 resistance to BoNT/B and TeNT possibly due to Q189V substitution, see box.

Table 3—Cleavage of VAMP and related proteins. Primate: Human VAMP-1-1 residues 49-92 of SEQ ID NO: 36; Human VAMP-1-2 residues 49-92 of SEQ ID NO: 37; Human VAMP-1-3 residues 49-92 of SEQ ID NO: 38; Human VAMP-2 residues 47-90 of SEQ ID NO: 39; Monkey VAMP-2 residues 47-90 of SEQ ID NO: 40; Human VAMP-3/cellubrevin residues 30-73 of SEQ ID NO: 41; Bovine: Cow VAMP-2 residues 47-90 of SEQ ID NO: 42; Rodent: Rat VAMP-1 residues 49-92 of SEQ ID NO: 43; Rat VAMP-1-b residues 49-92 of SEQ ID NO: 44; Mouse VAMP-1 residues 49-92 of SEQ ID NO: 45; Rat VAMP-2 residues 47-90 of SEQ ID NO: 46; Rat VAMP-2-b residues 47-90 of SEQ ID NO: 47; Mouse VAMP-2 residues 47-90 of SEQ ID NO: 48; Rat VAMP-3/cellubrevin residues 34-77 of SEQ ID NO: 49; Mouse VAMP-3/cellubrevin residues 34-77 of SEQ ID NO: 50; Bird: Chicken VAMP-1 residues 190-233 of SEQ ID NO: 51; Chicken VAMP-2 residues 47-88 of SEQ ID NO: 52; Chicken VAMP-3/cellubrevin residues 34-77 of SEQ ID NO: 53; Fish: Zebrafish VAMP-1 residues 50-93 of SEQ ID NO: 54; Zebrafish VAMP-2 residues 41-84 of SEQ ID NO: 55; Zebrafish VAMP-3 residues 33-60 of SEQ ID NO: 56; Ray: marbled electric ray VAMP-1 residues 51-94 of SEQ ID NO: 57; Amphibian: Frog VAMP-2 residues 45-88 of SEQ ID NO: 58; Frog VAMP-3 residues 32-75 of SEQ ID NO: 59; Sea urchin VAMP residues 31-74 of SEQ ID NO: 60; Insect: Fruit fly SynA1 residues 40-83 of SEQ ID NO: 61; Fruit fly SynA2 residues 63-106 of SEQ ID NO: 62; Fruit fly SynB1 residues 63-106 of SEQ ID NO: 63; Fruit fly SynB2 residues 63-106 of SEQ ID NO: 64; Fruit fly SynC residues 57-100 of SEQ ID NO: 65; Fruit fly SynD residues 66-109 of SEQ ID NO: 66; Fruit fly SynE residues 57-100 of SEQ ID NO: 67; Segmented worm: Leech VAMP residues 45-88 of SEQ ID NO: 68; Cephalopod: squid VAMP residues 56-99 of SEQ ID NO: 69; Gastropod: Pond snail VAMP residues 49-92 of SEQ ID NO: 70; sea hare VAMP residues 37-80 of SEQ ID NO: 71; Round worm: Nematode worm SNB1 residues 72-115 of SEQ ID NO: 72; Nematode worm SNB-like residues 82-115 of SEQ ID NO: 73.

Naturally occurring Syntaxin is located on the cytosolic surface of the nerve plasmalemma and is membrane-anchored via a carboxyl-terminal segment, with most of the protein exposed to the cytosol (see FIG. 3). Syntaxin colocalizes with calcium channels at the active zones of the presynaptic membrane, where neurotransmitter release takes place. In addition, syntaxin interacts with synaptotagmin, a protein of the SSV membrane that forms a functional bridge between the plasmalemma and the vesicles. Syntaxin has been isolated from a variety of vertebrate and invertebrate species including, e.g., species belonging to the genera *Homo, Bos, Rattus, Mus, Gallus, Danio, Strongylocentrotus, Drosophila, Hirudo, Loligo, Lymnaea* and *Aplysia* (Table 4). Three isoforms of slightly different length (285 and 288 residues) have been identified in nerve cells (isoforms 1A, 1B1 and 1B2), with isoforms 2, 3, 4 and 5 expressed in other tissues. The different isoforms have varying sensitivities to BoNT/C1, with the 1A, 1B1, 1B2, 2 and 3 syntaxin isoforms cleaved by this toxin.

TABLE 4

Cleavage of Syntaxin and Related Proteins

| Organism | Isoform | Cleavage Site BoNT/C1 ▼ | | | Cleaved Susceptibility |
|---|---|---|---|---|---|
| Primate | Syntaxin1A<br>Syntaxin1B1<br>Syntaxin1B2 | DYVERAVSDTKK | * | AVKYQSKARRK | BoNT/C1 |
| Primate | Syntaxin2-1<br>Syntaxin2-2<br>Syntaxin2-3 | DYVEHAKEETKK | ND | AIKYQSKARRK | ND |
| Primate | Syntaxin3A | DHVEKARDESKK | ND | AVKYQSQARKK | ND |
| Bovine | Syntaxin1A<br>Syntaxin1B2 | DYVERAVSDTKK | * | AVKYQSKARRK | BoNT/C1 |
| Rodent | Syntaxin1A<br>Syntaxin1B1<br>Syntaxin1B2 | DYVERAVSDTKK | * | AVKYQSKARRK | BoNT/C1 |
| Rodent | Syntaxin2 | DYVEHAKEETKK | * | AIKYQSKARRK | BoNT/C1 |
| Rodent | Syntaxin3A | DHVEKARDETKR | * | AMKYQGQARKK | BoNT/C1 |
| Rodent | Syntaxin3B<br>Syntaxin3C | GFVERAVADTKK | ND | AVKYQSEARRK | ND |
| Bird | Syntaxin1B | DYVEPVVFVTKS | ND | AVMYQCKSRRK | ND |
| Bird | Syntaxin2 | DYVEHAKEETKK | ND | AVKYQSKARRK | ND |
| Fish | Syntaxin1B | DYVERAVSDTKK | * | AVKYQSQARKK | BoNT/C1 |
| Fish | Syntaxin3 | DHVEAARDETKK | ND | AVRYQSKARKK | ND |
| Sea urchin | Syntaxin1B | DYVRRQNDTKK | * | AVKYQSKARRK | BoNT/C1 |
| Insect | Syntaxin1A | DYVQTATQDTKK | * | ALKYQSKARRK | BoNT/C1 |
| Segmented worm | Syntaxin1A | DYVETAAADTKK | * | AMKYQSAARKK | BoNT/C1 |
| Cephalopod | Syntaxin1A | DYIETAKVDTKK | * | AVKYQSKARQK | BoNT/C1 |
| Gastropod | Syntaxin1A | DYIETAKMDTKK | * | AVKYQSKARRK | BoNT/C1 |

Proteolytic cleavage occurs at this site (*); Proteolytic cleavage not detected at this site (—); Proteolytic cleavage not determined at this site (ND)

Table 4—Cleavage of Syntaxin and related proteins. Primate: Human Syntaxin1A residues 242-264 of SEQ ID NO: 74; Human Syntaxin1B1 residues 241-263 of SEQ ID NO: 75; Human Syntaxin1B2 residues 241-263 of SEQ ID NO: 76; Human Syntaxin2-1 residues 241-263 of SEQ ID NO: 77; Human Syntaxin2-2 residues 241-263 of SEQ ID NO: 78; Human Syntaxin2-3 residues 241-263 of SEQ ID NO: 79; Human Syntaxin3 residues 241-263 of SEQ ID NO: 80; Bovine: Cow Syntaxin1A residues 242-264 of SEQ ID NO: 81; Cow Syntaxin1B2 residues 241-263 of SEQ ID NO: 82; Rodent: Rat Syntaxin1A residues 242-264 of SEQ ID NO: 83; Rat Syntaxin1B2 residues 241-263 of SEQ ID NO: 84; Mouse Syntaxin1A residues 242-264 of SEQ ID NO: 85; Mouse Syntaxin1B1 residues 241-263 of SEQ ID NO: 86; Mouse Syntaxin1B2 residues 241-263 of SEQ ID NO: 87; Rat Syntaxin2 residues 243-265 of SEQ ID NO: 88; Mouse Syntaxin2 residues 242-264 of SEQ ID NO: 89; Rat Syntaxin3A residues 241-263 of SEQ ID NO: 90; Mouse Syntaxin3A residues 241-263 of SEQ ID NO: 91; Mouse Syntaxin3B residues 241-263 of SEQ ID NO: 92; Mouse Syntaxin3C residues 223-245 of SEQ ID NO: 93; Bird: Chicken Syntaxin1B residues 235-257 of SEQ ID NO: 94; Chicken Syntaxin2 residues 240-262 of SEQ ID NO: 95; Fish: Zebrafish Syntaxin1B residues 241-263 of SEQ ID NO: 96; Zebrafish Syntaxin3 residues 239-261 of SEQ ID NO: 97; sea urchin Syntaxin1B residues 241-263 of SEQ ID NO: 98; Insect: Fruit fly Syntaxin1A residues 245-267 of SEQ ID NO: 99; Segmented worm: leech Syntaxin1A residues 248-270 of SEQ ID NO: 100; Cephalopod: squid Syntaxin1A residues 245-267 of SEQ ID NO: 101; Gastropod: Pond snail Syntaxin1A residues 244-266 of SEQ ID NO: 102; sea hare Syntaxin1A residues 244-266 of SEQ ID NO: 103.

TABLE 5

Bonds Cleaved in SNAP-25, VAMP, or Syntaxin

| Toxin | Target | $P_4$-$P_3$-$P_2$-$P_1$—$P_1'$-$P_2'$-$P_3'$-$P_4'$ | SEQ ID NO: |
|---|---|---|---|
| BoNT/A | SNAP-25 | Glu-Ala-Asn-Gln—Arg* -Ala-Thr-Lys | 104 |
| BoNT/A | SNAP-25 | Glu-Ala-Asn-Lys—His* -Ala-Thr-Lys | 105 |
| BoNT/A | SNAP-25 | Glu-Ala-Asn-Lys—His* -Ala-Ans-Lys | 106 |
| BoNT/B & TeNT | VAMP | Gly-Ala-Ser-Gln—Phe* -Glu-Thr-Ser | 107 |

TABLE 5-continued

Bonds Cleaved in SNAP-25, VAMP, or Syntaxin

| Toxin | Target | $P_4$-$P_3$-$P_2$-$P_1$—$P_1$'-$P_2$'-$P_3$'-$P_4$' | SEQ ID NO: |
|---|---|---|---|
| BoNT/B & TeNT | VAMP | Gly-Ala-Ser-Gln—Phe\*-Glu-Ser-Ser | 108 |
| BoNT/B & TeNT | VAMP | Gly-Ala-Ser-Gln—Phe\*-Glu-Thr-Asn | 109 |
| BoNT/B & TeNT | VAMP | Gly-Ala-Ser-Gln—Phe\*-Glu-Gln-Gln | 110 |
| BoNT/B & TeNT | VAMP | Gly-Ala-Ser-Gln—Phe\*-Glu-Ala-Ser | 111 |
| BoNT/B & TeNT | VAMP | Gly-Ala-Ser-Gln—Phe\*-Gln-Gln-Ser | 112 |
| BoNT/C1 | Syntaxin | Asp-Thr-Lys-Lys—Ala\*-Val-Lys-Tyr | 113 |
| BoNT/C1 | Syntaxin | Glu-Thr-Lys-Lys—Ala\*-Ile-Lys-Tyr | 114 |
| BoNT/C1 | Syntaxin | Glu-Ser-Lys-Lys—Ala\*-Val-Lys-Tyr | 115 |
| BoNT/C1 | Syntaxin | Glu-Thr-Lys-Arg—Ala\*-Met-Lys-Tyr | 116 |
| BoNT/C1 | Syntaxin | Glu-Thr-Lys-Lys—Ala\*-Val-Lys-Tyr | 117 |
| BoNT/C1 | Syntaxin | Asp-Thr-Lys-Lys—Ala\*-Leu-Lys-Tyr | 118 |
| BoNT/C1 | Syntaxin | Asp-Thr-Lys-Lys—Ala\*-Met-Lys-Tyr | 119 |
| BoNT/C1 | SNAP-25 | Ala-Asn-Gln-Arg—Ala\*-Thr-Lys-Met | 120 |
| BoNT/C1 | SNAP-25 | Ala-Asn-Gln-Arg—Ala\*-His-Gln-Leu | 121 |
| BoNT/D | VAMP | Arg-Asp-Gln-Lys—Leu\*-Ser-Glu-Leu | 122 |
| BoNT/D | VAMP | Lys-Asp-Gln-Lys—Leu\*-Ala-Glu-Leu | 123 |
| BoNT/E | SNAP-25 | Gln-Ile-Asp-Arg—Ile\*-Met-Glu-Lys | 124 |
| BoNT/E | SNAP-25 | Gln-Ile-Gln-Lys—Ile\*-Thr-Glu-Lys | 125 |
| BoNT/E | SNAP-25 | Gln-Ile-Asp-Arg—Ile\*-Met-Asp-Met | 126 |
| BoNT/E | SNAP-25 | Gln-Val-Asp-Arg—Ile\*-Gln-Gln-Lys | 127 |
| BoNT/E | SNAP-25 | Gln-Leu-Asp-Arg—Ile\*-His-Asp-Lys | 128 |
| BoNT/F | VAMP | Glu-Arg-Asp-Gln—Lys\*-Leu-Ser-Glu | 129 |
| BoNT/F | VAMP | Glu-Lys-Asp-Gln—Lys\*-Leu-Ala-Glu | 130 |
| BoNT/G | VAMP | Glu-Thr-Ser-Ala—Ala\*-Lys-Leu-Lys | 131 |
| BoNT/G | VAMP | Glu-Ser-Ser-Ala—Ala\*-Lys-Leu-Lys | 132 |

*Scissile bond shown in bold

A wide variety of Clostridial toxin substrate cleavage sites are useful in aspects of the invention and specific and distinct cleavage sites for different Clostridial toxins are well known in the art. As non-limiting examples, BoNT/A cleaves a Gln-Arg bond and a Lys-His bond; BoNT/B and TeNT cleave a Gln-Phe bond; BoNT/C1 cleaves a Lys-Ala or Arg-Ala bond; BoNT/D cleaves a Lys-Leu bond; BoNT/E cleaves an Arg-Ile bond and a Lys-Ile bond; BoNT/F cleaves a Gln-Lys bond; and BoNT/G cleaves an Ala-Ala bond (see Table 5). In standard nomenclature, the sequence surrounding a Clostridial toxin cleavage site is denoted $P_5$—$P_4$—$P_3$—$P_2$—$P_1$—$P_1$'—$P_2$'—$P_3$'—$P_4$'—$P_5$', with $P_1$—$P_1$' representing the scissile bond. It is understood that a $P_1$ or $P_1$' site, or both, can be substituted with another amino acid or amino acid mimetic in place of the naturally occurring residue. As an example, BoNT/A substrates have been prepared in which the $P_1$ position (Gln) is modified to be an alanine, 2-aminobutyric acid or asparagine residue; these substrates were hydrolyzed by BoNT/A at the $P_1$-Arg bond, see, e.g., James J. Schmidt & Karen A Bostian, *Endoproteinase Activity of Type A Botulinum Neurotoxin: Substrate Requirements and Activation by Serum Albumin,* 16(1) J. Protein Chem. 19-26 (1997). While it is recognized that substitutions can be introduced at the $P_1$ position of the scissile bond, for example, a BoNT/A scissile bond, it is further recognized that conservation of the $P_1$' residue can be advantageous, see, e.g., Vadakkanchery V. Vaidyanathan et al., *Proteolysis of SNAP-25 Isoforms by Botulinum Neurotoxin Types A, C, and E: Domains and Amino Acid Residues Controlling the Formation of Enzyme-Substrate Complexes and Cleavage,* 72(1) J. Neurochem. 327-337 (1999).

Thus, in an embodiment, a modified Clostridial toxin substrate comprises a Clostridial toxin substrate cleavage site in which the $P_1$' residue is not modified or substituted relative to the naturally occurring residue in a target protein cleaved by the Clostridial toxin. In aspects of this embodiment, a Clostridial toxin substrate cleavage site in which the P$_1$' residue is not modified or substituted relative to the naturally occurring residue in a target protein cleaved by the Clostridial toxin can be, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site.

In another embodiment, a modified Clostridial toxin substrate comprises a Clostridial toxin substrate cleavage site in which the P$_1$ residue is modified or substituted relative to the naturally occurring residue in a target protein cleaved by the Clostridial toxin; such a Clostridial toxin substrate retains susceptibility to peptide bond cleavage between the P$_1$ and P$_1$' residues. In aspects of this embodiment, a Clostridial toxin substrate cleavage site in which the P$_1$' residue is modified or substituted relative to the naturally occurring residue in a target protein cleaved by the Clostridial toxin can be, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site.

In an aspect of the invention, a modified Clostridial toxin comprises a BoNT/A substrate cleavage site. As used herein, the term "botulinum toxin serotype A substrate cleavage site" is synonymous with "BoNT/A substrate cleavage site" and means a scissile bond together with adjacent or non-adjacent recognition elements, or both, sufficient for detectable proteolysis at the scissile bond by a BoNT/A under conditions suitable for Clostridial toxin protease activity. A scissile bond cleaved by BoNT/A can be, for example, Gln-Arg or Lys-His. It is envisioned that a BoNT/A substrate cleavage site of any and all lengths can be useful in aspects of the present invention with the proviso that the BoNT/A substrate cleavage site is capable of being cleaved by BoNT/A. Thus, in aspects of this embodiment, a BoNT/A substrate cleavage site can be, e.g., at least 6 amino acids in length, at least 7 amino acids in length, at least 8 amino acids in length, at least 9 amino acids in length, at least 10 amino acids in length, at least amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/A substrate cleavage site can be, e.g., at most 6 amino acids in length, at most 7 amino acids in length, at most 8 amino acids in length, at most 9 amino acids in length, at most 10 amino acids in length, at most 15 amino acids in length, at most amino acids in length, at most 25 amino acids in length, at most 30 amino acids in length, at most 40 amino acids in length, at most 50 amino acids in length or at most 60 amino acids in length.

A BoNT/A substrate cleavage sites useful in aspects of the invention can correspond to a segment of a protein that is sensitive to cleavage by BoNT/A, or can be substantially similar to a segment of a BoNT/A-sensitive protein. As shown in Table 2, a variety of naturally occurring proteins sensitive to cleavage by BoNT/A are known in the art and include, for example, human, rat, mouse, Danio, Carassius, SNAP-25A and SNAP-25B; and Torpedo SNAP-25. Thus, a BoNT/A substrate cleavage site can correspond, for example, to a segment of human SNAP-25A or SNAP-25B; bovine SNAP-25A or SNAP-25B; rat SNAP-25A or SNAP-25B; mouse SNAP-25A or SNAP-25B; Xenopus SNAP-25A or SNAP-25B; Danio SNAP-25A or SNAP-25B; Carassius SNAP-25A or SNAP-25B; Torpedo SNAP-25; Strongylocentrotus SNAP-25; Loligo SNAP-25; Lymnaea SNAP-25; Aplysia SNAP-25, isoforms thereof, or another naturally occurring protein sensitive to cleavage by BoNT/A. Furthermore, comparison of native SNAP-25 amino acid sequences cleaved by BoNT/A reveals that such sequences are not absolutely conserved (Table 2). This finding indicates that a variety of amino acid substitutions and modifications relative to a naturally occurring BoNT/A-sensitive SNAP-25 sequence can be tolerated in a BoNT/A substrate cleavage site useful in aspects of the present invention. It is understood that a similar BoNT/A recognition sequence can be prepared, if desired, from a corresponding (homologous) segment of another BoNT/A-sensitive SNAP-25 isoform, paralog or ortholog, such as, the BoNT/A substrate cleavage site contain in the SNAP-25 proteins identified in the organisms listed above and in Table 2.

TABLE 6

Kinetic Parameters of BoNT/A Synthetic Peptide Substrates

| Peptide | Sequence$^a$ | SEQ ID NO: | Relative Rate$^b$ |
|---|---|---|---|
| [1-15] | SNKTRIDEANQRATK | 134 | 0.03 |
| [1-16] | SNKTRIDEANQRATKM | 135 | 1.17 |
| [1-17] | SNKTRIDEANQRATKML | 136 | 1.00 |
| M16A | SNKTRIDEANQRATKAL | 137 | 0.38 |
| M16X | SNKTRIDEANQRATKXL | 138 | 1.20 |
| K15A | SNKTRIDEANQRATAML | 139 | 0.12 |
| T14S | SNKTRIDEANQRASKML | 140 | 0.26 |
| T14B | SNKTRIDEANQRABKML | 141 | 1.20 |
| A13B | SNKTRIDEANQRBTKML | 142 | 0.79 |
| Q11A | SNKTRIDEANARATKML | 143 | 0.19 |
| Q11B | SNKTRIDEANBRATKML | 144 | 0.25 |
| Q11N | SNKTRIDEANNRATKML | 145 | 0.66 |
| N10A | SNKTRIDEAAQRATKML | 146 | 0.06 |
| A9B | SNKTRIDEBNQRATKML | 147 | 0.38 |
| E8Q | SNKTRIDQANQRATKML | 148 | 2.08 |
| D7N | SNKTRINEANQRATKML | 149 | 0.23 |

$^a$Nonstandard abbreviations: B, 2-aminobutyric acid; X, 2-aminohexanoic acid (norleucine)
$^b$Initial hydrolysis rates relative to peptide [1-17]. Peptide concentrations were 1.0 mM.

Furthermore, experimental manipulation of the amino acid sequence comprising a native BoNT/A substrate cleavage site cleaved by BoNT/A reveals that such sequences are not absolutely conserved. These results indicate that a variety of residues can be substituted in a BoNT/A toxin substrate cleavage site as compared to a naturally occurring toxin-sensitive sequence. As a non-limiting example, as compared to a 17-mer corresponding to residues 187 to 203 of human SNAP-25, substitution of Asp193 with Asparagine in the BoNT/A substrate resulted in a relative rate of proteolysis of 0.23; substitution of Glu194 with Glutamine resulted in a relative rate of 2.08; substitution of Ala195 with 2-aminobutyric acid resulted in a relative rate of 0.38; and substitution of Gln197 with Asparagine, 2-aminobutyric acid or Alanine resulted in a relative rate of 0.66, 0.25, or 0.19, respectively (see Table 6). Furthermore, substitution of Ala199 with 2-aminobutyric acid resulted in a relative rate of 0.79; substitution of Thr200 with Serine or 2-aminobutyric acid resulted in a relative rate of 0.26 or 1.20, respectively; substitution of Lys201 with Alanine resulted in a relative rate of 0.12; and substitution of Met202 with Alanine or norleucine resulted in a relative rate of 0.38 or 1.20, respectively, see, e.g., Schmidt & Bostian, supra, (1997). In a separate study, Gln197 of SNAP-25 could be substituted with Methionine, Serine, Threonine, Glutamine or Lysine and still be cleaved efficiently by BoNT/A, see, e.g., Vadakkanchery V. Vaidyanathan et al., *Proteolysis of SNAP-25 Isoforms by Botulinum Neurotoxin Types A, C, and E: Domains and Amino Acid Residues Controlling the Formation of Enzyme-Substrate Complexes and Cleavage,* 72 J. Neurochem. 327-337 (1999). These results indicate that residues including but not limited to Glu194, Ala195, Gln197, Ala199, Thr200 and Met202, Leu203, Gly204, Ser205, and Gly206, as well as residues more distal from the Gln-Arg scissile bond, can be substituted or conjugated.

A variety of BoNT/A substrate cleavage sites are well known in the art or can be defined by routine methods. A BoNT/A substrate cleavage site can have, for example, residues 46-206, residues 134 to 206, residues 137 to 206 or 146-206 of human SNAP-25, see, e.g., Teresa A. Ekong et al., *Recombinant SNAP-25 is an Effective Substrate for Clostridium botulinum Type A Toxin Endopeptidase Activity in vitro,* 143 (Pt 10) Microbiology 3337-3347 (1997); Clifford C. Shone et al., Toxin Assays, U.S. Pat. No. 5,962,637 (Oct. 5, 1999); and Vaidyanathan et al., supra, (1999). A BoNT/A substrate cleavage site also can comprise, without limitation, the sequence Thr-Arg-Ile-Asp-Glu-Ala-Asn-Gln-Arg-Ala-Thr-Lys-Met (SEQ ID NO: 133) or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 134) or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO: 135) or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 136) or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 150) or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 151) or a peptidomimetic thereof, which corresponds to residues 186 to 203 of human SNAP-25. See, for example, James J. Schmidt & Karen A Bostian, *Proteolysis of Synthetic Peptides by Type A Botulinum Neurotoxin,* 14(8) J. Protein Chem. 703-708 (1995); Schmidt & Bostian, supra, (1997); James J. Schmidt et al., *Type A Botulinum Neurotoxin Proteolytic Activity: Development of Competitive Inhibitors and Implications For Substrate Specificity at the S1' Binding Subsite,* 435(1) FEBS Lett. 61-64 (1998); and James J. Schmidt & Karen A Bostian, Assay for the Proteolytic Activity of Serotype a From *Clostridium botulinum,* U.S. Pat. No. 5,965,699 (Oct. 12, 1999).

Thus, in an embodiment, a modified Clostridial toxin comprises a BoNT/A substrate cleavage site. In an aspect of this embodiment, a BoNT/A substrate cleavage site comprises at least six consecutive residues of SNAP-25 including Gln-Arg. In another aspect of this embodiment, a BoNT/A substrate cleavage site comprises at least six consecutive residues of SNAP-25 including Lys-His. In other aspects of this embodiment, a BoNT/A substrate cleavage site comprises, e.g., the amino acid sequence Glu-Ala-Asn-Gln-Arg-Ala-Thr-Lys (SEQ ID NO: 104); the amino acid sequence Glu-Ala-Asn-Lys-His-Ala-Thr-Lys (SEQ ID NO: 105); the amino acid sequence Glu-Ala-Asn-Lys-His-Ala-Asn-Lys (SEQ ID NO: 106). In another aspect of this embodiment, a BoNT/A substrate cleavage site comprises a naturally occurring BoNT/A substrate cleavage site variant. In another aspect of this embodiment, a BoNT/A substrate cleavage site comprises a naturally occurring BoNT/A substrate cleavage site variant of SEQ ID NO: 104, SEQ ID NO: 105 or SEQ ID NO: 106, such as, e.g., a BoNT/A substrate cleavage site isoform of SEQ ID NO: 104, SEQ ID NO: 105 or SEQ ID NO: 106; or a BoNT/A substrate cleavage site subtype of SEQ ID NO: 104, SEQ ID NO: 105 or SEQ ID NO: 106. In still another aspect of this embodiment, a BoNT/A substrate cleavage site comprises a non-naturally occurring BoNT/A substrate cleavage site variant, such as, e.g., a conservative BoNT/A substrate cleavage site variant, a non-conservative BoNT/A substrate cleavage site variant or a BoNT/A substrate cleavage site peptidomimetic, or any combination thereof. In still another aspect of this embodiment, a BoNT/A substrate cleavage site comprises a non-naturally occurring BoNT/A substrate cleavage site variant of SEQ ID NO: 104, SEQ ID NO: 105 or SEQ ID NO: 106; such as, e.g., a conservative BoNT/A substrate cleavage site variant of SEQ ID NO: 104, SEQ ID NO: 105 or SEQ ID NO: 106; a non-conservative BoNT/A substrate cleavage site variant of SEQ ID NO: 104, SEQ ID NO: 105 or SEQ ID NO: 106; a BoNT/A substrate cleavage site peptidomimetic of SEQ ID NO: 104, SEQ ID NO: 105 or SEQ ID NO: 106; or any combination thereof. In still other aspects of this embodiment, a BoNT/A substrate cleavage site comprises, e.g., SEQ ID NO: 133, SEQ ID NO: 134, SEQ ID NO: 135, SEQ ID NO: 136, SEQ ID NO: 138, SEQ ID NO: 141, SEQ ID NO: 148, SEQ ID NO: 150 or SEQ ID NO: 151.

In other aspects of this embodiment, a BoNT/A substrate cleavage site comprises a polypeptide having, e.g., at least 50% amino acid identity with SEQ ID NO: 104, at least 62.5% amino acid identity with the SEQ ID NO: 104, at least 75% amino acid identity with SEQ ID NO: 104 or at least 87.5% amino acid identity with SEQ ID NO: 104. In still other aspects of this embodiment, a BoNT/A substrate cleavage site comprises a polypeptide having, e.g., at most 50% amino acid identity with SEQ ID NO: 104, at most 62.5% amino acid identity with the SEQ ID NO: 104, at most 75% amino acid identity with SEQ ID NO: 104 or at most 87.5% amino acid identity with SEQ ID NO: 104.

In other aspects of this embodiment, a BoNT/A substrate cleavage site comprises a polypeptide having, e.g., at most one, two, three or four non-contiguous amino acid substitutions relative to SEQ ID NO: 104. In still other aspects of this embodiment, a BoNT/A substrate cleavage site comprises a polypeptide having, e.g., at least one, two, three or four non-contiguous amino acid substitutions relative to SEQ ID NO: 104. In yet other aspects of this embodiment, a BoNT/A substrate cleavage site comprises a polypeptide having, e.g., at most one, two, three, four, five, six, seven, eight, nine or ten non-contiguous amino acid additions relative to SEQ ID NO: 104. In yet other aspects of this embodiment, a BoNT/A substrate cleavage site comprises a polypeptide having, e.g., at least one, two, three, four, five, six, seven, eight, nine or ten non-contiguous amino acid additions relative to SEQ ID NO:

104. In still other aspects of this embodiment, a BoNT/A substrate cleavage site comprises a polypeptide having, e.g., at most one, two or three non-contiguous amino acid deletions relative to SEQ ID NO: 104. In still other aspects of this embodiment, a BoNT/A substrate cleavage site comprises a polypeptide having, e.g., at least one, two or three non-contiguous amino acid deletions relative to SEQ ID NO: 104.

In other aspects of this embodiment, a BoNT/A substrate cleavage site comprises a polypeptide having, e.g., at most two, three or four contiguous amino acid substitutions relative to SEQ ID NO: 104. In still other aspects of this embodiment, a BoNT/A substrate cleavage site comprises a polypeptide having, e.g., at least two, three or four contiguous amino acid substitutions relative to SEQ ID NO: 104. In yet other aspects of this embodiment, a BoNT/A substrate cleavage site comprises a polypeptide having, e.g., at most two, three, four, five, six, seven, eight, nine or ten contiguous amino acid additions relative to SEQ ID NO: 104. In yet other aspects of this embodiment, a BoNT/A substrate cleavage site comprises a polypeptide having, e.g., at least two, three, four, five, six, seven, eight, nine or ten contiguous amino acid additions relative to SEQ ID NO: 104. In still other aspects of this embodiment, a BoNT/A substrate cleavage site comprises a polypeptide having, e.g., at most two or three contiguous amino acid deletions relative to SEQ ID NO: 104. In still other aspects of this embodiment, a BoNT/A substrate cleavage site comprises a polypeptide having, e.g., at least two or three contiguous amino acid deletions relative to SEQ ID NO: 104.

In an aspect of the invention, a modified Clostridial toxin comprises a BoNT/B substrate cleavage site. As used herein, the term "botulinum toxin serotype B substrate cleavage site" is synonymous with "BoNT/B substrate cleavage site" and means a scissile bond together with adjacent or non-adjacent recognition elements, or both, sufficient for detectable proteolysis at the scissile bond by a BoNT/B under conditions suitable for Clostridial toxin protease activity. A scissile bond cleaved by BoNT/B can be, for example, Gln-Phe. It is envisioned that a BoNT/B substrate cleavage site of any and all lengths can be useful in aspects of the present invention with the proviso that the BoNT/B substrate cleavage site is capable of being cleaved by BoNT/B. Thus, in aspects of this embodiment, a BoNT/B substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/B substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A BoNT/B substrate cleavage sites useful in aspects of the invention can correspond to a segment of a protein that is sensitive to cleavage by BoNT/B, or can be substantially similar to a segment of a BoNT/B-sensitive protein. As shown in Table 3, a variety of naturally occurring proteins sensitive to cleavage by BoNT/B are known in the art and include, for example, human and mouse VAMP-1, VAMP-2 and VAMP-3/cellubrevin; bovine VAMP-2; rat VAMP-2 and VAMP-3; chicken VAMP-2; *Torpedo* VAMP-1; Strongylocentrotus VAMP; *Drosophila* sybA, synB, sync, synD and synE; *Hirudo* VAMP; and *Caenorhabditis* SNB1-like. Thus, a BoNT/B substrate cleavage site can correspond, for example, to a segment of human VAMP-1, VAMP-2 or VAMP-3; bovine VAMP-2; rat VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; Strongylocentrotus VAMP; *Drosophila* sybA, synB, sync, synD or synE; *Hirudo* VAMP; *Loligo* VAMP; *Lymnaea* VAMP; *Aplysia* VAMP; *Caenorhabditis* SNB1, isoforms thereof, or another naturally occurring protein sensitive to cleavage by BoNT/B. Furthermore, comparison of native VAMP amino acid sequences cleaved by BoNT/B reveals that such sequences are not absolutely conserved (Table 3). This finding indicates that a variety of amino acid substitutions and modifications relative to a naturally occurring BoNT/B-sensitive VAMP sequence can be tolerated in a BoNT/B substrate cleavage site useful in aspects of the present invention. It is understood that a similar BoNT/B substrate cleavage site can be prepared, if desired, from a corresponding (homologous) segment of another BoNT/B-sensitive VAMP-1 or VAMP-2 isoform, paralog or ortholog, such as, the BoNT/B substrate cleavage site contain in the VAMP-1 and VAMP-2 proteins identified in the organisms listed above and in Table 3.

A variety of BoNT/B substrate cleavage sites are well known in the art or can be defined by routine methods. Such BoNT/B substrate cleavage sites can include, for example, a sequence corresponding to some or all of the hydrophilic core of a VAMP protein such as human VAMP-1 or human VAMP-2. A BoNT/B substrate cleavage sites can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 39), or residues 60 to 94 of human VAMP-1-1 (SEQ ID NO: 36), VAMP-1-2 (SEQ ID NO: 37) and VAMP-1-3 (SEQ ID NO: 38), see, e.g., Shone et al., Eur. J. Biochem. 217: 965-971 (1993); and Shone et al., supra, (Oct. 5, 1999). A BoNT/B substrate cleavage sites also can include, without limitation, the sequence Leu-Ser-Glu-Leu-Asp-Asp-Arg-Ala-Asp-Ala-Leu-Gln-Ala-Gly-Ala-Ser-Gln-Phe-Glu-Thr-Ser-Ala-Ala-Lys-Leu-Lys-Arg-Lys-Tyr-Trp-Trp-Lys-Asn-Leu-Lys (SEQ ID NO: 152) or a peptidomimetic thereof, which corresponds to residues 60 to 94 of human VAMP-2, see, e.g., James J. Schmidt & Robert G. Stafford, High Throughput Assays for the Proteolytic Activities of Clostridial Neurotoxins, U.S. Pat. No. 6,762,280 (Jul. 13, 2004) and the BoNT/B recognition sequence Leu-Ser-Glu-Leu-Asp-Asp-Arg-Ala-Asp-Ala-Leu-Gln-Ala-Gly-Ala-Ser-Gln-Phe-Glu-Ser-Ser-Ala-Ala-Lys-Leu-Lys-Arg-Lys-Tyr-Trp-Trp-Lys-Asn-Cys-Lys (SEQ ID NO: 153) or a peptidomimetic thereof, which corresponds to residues 62 to 96 of human VAMP-1.

Thus, in an embodiment, a modified Clostridial toxin comprises a BoNT/B substrate cleavage site. In an aspect of this embodiment, a BoNT/B substrate cleavage site comprises at least six consecutive residues of VAMP including Gln-Phe. In other aspects of this embodiment, a BoNT/B substrate cleavage site comprises, e.g., the amino acid sequence Gly-Ala-Ser-Gln-Phe-Glu-Thr-Ser (SEQ ID NO: 107); the amino acid sequence Gly-Ala-Ser-Gln-Phe-Glu-Ser-Ser (SEQ ID NO: 108); the amino acid sequence Gly-Ala-Ser-Gln-Phe-Glu-Thr-Asn (SEQ ID NO: 109); the amino acid sequence Gly-Ala-Ser-Gln-Phe-Glu-Gln-Gln (SEQ ID NO: 110); the amino acid sequence Gly-Ala-Ser-Gln-Phe-Glu-Ala-Ser (SEQ ID NO: 111); or the amino acid sequence Gly-Ala-Ser-Gln-Phe-Gln-Gln-Ser (SEQ ID NO: 112). In another aspect of this embodiment, a BoNT/B substrate cleavage site comprises a naturally occurring BoNT/B substrate cleavage site variant.

In another aspect of this embodiment, a BoNT/B substrate cleavage site comprises a naturally occurring BoNT/B substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; or a BoNT/B substrate cleavage site subtype of SEQ ID NO: 107, SEQ ID NO: 108, SEQ ID NO: 109, SEQ ID NO: 110, SEQ ID NO: 111 or SEQ ID NO: 112. In still another aspect of this embodiment, a BoNT/B substrate cleavage site comprises a non-naturally occurring BoNT/B substrate cleavage site variant, such as, e.g., a conservative BoNT/B substrate cleavage site variant, a non-conservative BoNT/B substrate cleavage site variant or a BoNT/B substrate cleavage site peptidomimetic, or any combination thereof. In still another aspect of this embodiment, a BoNT/B substrate cleavage site comprises a non-naturally occurring BoNT/B substrate cleavage site variant of SEQ ID NO: 107, SEQ ID NO: 108, SEQ ID NO: 109, SEQ ID NO: 110, SEQ ID NO: 111 or SEQ ID NO: 112; such as, e.g., a conservative BoNT/B substrate cleavage site variant of SEQ ID NO: 107, SEQ ID NO: 108, SEQ ID NO: 109, SEQ ID NO: 110, SEQ ID NO: 111 or SEQ ID NO: 112; a non-conservative BoNT/B substrate cleavage site variant of SEQ ID NO: 107, SEQ ID NO: 108, SEQ ID NO: 109, SEQ ID NO: 110, SEQ ID NO: 111 or SEQ ID NO: 112; a BoNT/B substrate cleavage site peptidomimetic of SEQ ID NO: 107, SEQ ID NO: 108, SEQ ID NO: 109, SEQ ID NO: 110, SEQ ID NO: 111 or SEQ ID NO: 112; or any combination thereof.

In other aspects of this embodiment, a BoNT/B substrate cleavage site comprises a polypeptide having, e.g., at least 50% amino acid identity with SEQ ID NO: 107, at least 62.5% amino acid identity with the SEQ ID NO: 107, at least 75% amino acid identity with SEQ ID NO: 107 or at least 87.5% amino acid identity with SEQ ID NO: 107. In still other aspects of this embodiment, a BoNT/B substrate cleavage site comprises a polypeptide having, e.g., at most 50% amino acid identity with SEQ ID NO: 107, at most 62.5% amino acid identity with the SEQ ID NO: 107, at most 75% amino acid identity with SEQ ID NO: 107 or at most 87.5% amino acid identity with SEQ ID NO: 107.

In other aspects of this embodiment, a BoNT/B substrate cleavage site comprises a polypeptide having, e.g., at most one, two, three or four non-contiguous amino acid substitutions relative to SEQ ID NO: 107. In still other aspects of this embodiment, a BoNT/B substrate cleavage site comprises a polypeptide having, e.g., at least one, two, three or four non-contiguous amino acid substitutions relative to SEQ ID NO: 107. In yet other aspects of this embodiment, a BoNT/B substrate cleavage site comprises a polypeptide having, e.g., at most one, two, three, four, five, six, seven, eight, nine or ten non-contiguous amino acid additions relative to SEQ ID NO: 107. In yet other aspects of this embodiment, a BoNT/B substrate cleavage site comprises a polypeptide having, e.g., at least one, two, three, four, five, six, seven, eight, nine or ten non-contiguous amino acid additions relative to SEQ ID NO: 107. In still other aspects of this embodiment, a BoNT/B substrate cleavage site comprises a polypeptide having, e.g., at most one, two or three non-contiguous amino acid deletions relative to SEQ ID NO: 107. In still other aspects of this embodiment, a BoNT/B substrate cleavage site comprises a polypeptide having, e.g., at least one, two or three non-contiguous amino acid deletions relative to SEQ ID NO: 107.

In other aspects of this embodiment, a BoNT/B substrate cleavage site comprises a polypeptide having, e.g., at most two, three or four contiguous amino acid substitutions relative to SEQ ID NO: 107. In still other aspects of this embodiment, a BoNT/B substrate cleavage site comprises a polypeptide having, e.g., at least two, three or four contiguous amino acid substitutions relative to SEQ ID NO: 107. In yet other aspects of this embodiment, a BoNT/B substrate cleavage site comprises a polypeptide having, e.g., at most two, three, four, five, six, seven, eight, nine or ten contiguous amino acid additions relative to SEQ ID NO: 107. In yet other aspects of this embodiment, a BoNT/B substrate cleavage site comprises a polypeptide having, e.g., at least two, three, four, five, six, seven, eight, nine or ten contiguous amino acid additions relative to SEQ ID NO: 107. In still other aspects of this embodiment, a BoNT/B substrate cleavage site comprises a polypeptide having, e.g., at most two or three contiguous amino acid deletions relative to SEQ ID NO: 107. In still other aspects of this embodiment, a BoNT/B substrate cleavage site comprises a polypeptide having, e.g., at least two or three contiguous amino acid deletions relative to SEQ ID NO: 107.

In an aspect of the invention, a modified Clostridial toxin comprises a BoNT/C1 substrate cleavage site. As used herein, the term "botulinum toxin serotype C1 substrate cleavage site" is synonymous with "BoNT/C1 substrate cleavage site" and means a scissile bond together with adjacent or non-adjacent recognition elements, or both, sufficient for detectable proteolysis at the scissile bond by a BoNT/C1 under appropriate conditions. A scissile bond cleaved by BoNT/C1 can be, for example, Lys-Ala or Arg-Ala. It is envisioned that a BoNT/C1 substrate cleavage site of any and all lengths can be useful in aspects of the present invention with the proviso that the BoNT/C1 substrate cleavage site is capable of being cleaved by BoNT/C1. Thus, in aspects of this embodiment, a BoNT/C1 substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/C1 substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A BoNT/C1 substrate cleavage sites useful in aspects of the invention can correspond to a segment of a protein that is sensitive to cleavage by BoNT/C1, or can be substantially similar to a segment of a BoNT/C1-sensitive protein. As further shown in Table 4, a variety of naturally occurring proteins sensitive to cleavage by BoNT/C1 are known in the art and include, for example, human and mouse Syntaxin 1A, Syntaxin 1B1 and Syntaxin 1B2; bovine and rat Syntaxin 1A and Syntaxin 1B2; rat Syntaxin 2 and Rat syntaxin 3; *Strongylocentrotus* Syntaxin; *Drosophila* Syntaxin 1A; *Hirudo* Syntaxin1A; *Loligo* Syntaxin 1A; *Aplysia* Syntaxin 1A. Thus, a BoNT/C1 substrate cleavage site can correspond, for example, to a segment of human Syntaxin 1A, Syntaxin 1B1, Syntaxin 1B2, Syntaxin 2-1, Syntaxin 2-2, Syntaxin 2-3 or Syntaxin 3A; bovine Syntaxin 1A, Syntaxin 1B1 or Syntaxin 1B2; rat Syntaxin 1A, Syntaxin 1B1, Syntaxin 1B2, Syntaxin 2 or Syntaxin 3A; mouse Syntaxin 1A, Syntaxin 1B1, Syntaxin 1B2, Syntaxin 2, Syntaxin 3A, Syntaxin 3B or Syntaxin 3C; chicken Syntaxin 1A or Syntaxin 2; *Xenopus* Syntaxin 1A or Syntaxin 1B; *Danio* Syntaxin 1A, Syntaxin 1B or Syntaxin 3; *Torpedo* Syntaxin 1A or Syntaxin 1B; *Strongylocentrotus* Syntaxin 1A or Syntaxin 1B; *Drosophila* Syntaxin 1A or Syntaxin 1B; *Hirudo* Syntaxin 1A or Syntaxin 1B; *Loligo* Syntaxin 1A or Syntaxin 1B; *Lymnaea* Syntaxin 1A or Syntaxin 1B, isoforms thereof, or another naturally occurring protein sensitive to cleavage by BoNT/C1. Furthermore, comparison of native syntaxin amino acid sequences cleaved by BoNT/C1 reveals that such sequences are not absolutely conserved (see Table 4), indicating that a variety of amino acid substitutions and modifications relative to a naturally occurring BoNT/C1-sensitive syntaxin sequence can be tolerated in a BoNT/C1 substrate cleavage site useful in aspects of the present invention. It is understood that a similar BoNT/C1 substrate cleavage site can be prepared, if desired, from a corresponding (homologous) segment of another BoNT/C1-sensitive syntaxin isoform, paralog or ortholog, such as, the BoNT/C1 substrate cleavage site contain in the syntaxin proteins identified in the organisms listed above and in Table 4.

Although not extensively studied, a variety of BoNT/C1 substrate cleavage sites can be defined by routine methods. The minimum optimal fragment for BoNT/C1 substrate cleavage sites can include, without limitation, residues 93 to 202 of human SNAP-25A (SEQ ID NO: 9), or residues 93 to 202 of human SNAP-25B (SEQ ID NO: 10), see, e.g., Vaidyanathan et al., supra, (1999). However, as with substrates for other BoNTs, it is suspected that a much smaller substrate fragment can be effectively cleaved by BoNT/C1.

As further shown in Table 2, a variety of naturally occurring proteins sensitive to cleavage by BoNT/C1 are known in the art and include, for example, human, rat, mouse, *Danio, Carassius* SNAP-25A and SNAP-25B; and *Drosophila* SNAP-25. Thus, a BoNT/C1 substrate cleavage site can correspond, for example, to a segment of human SNAP-25A or SNAP-25B; bovine SNAP-25A or SNAP-25B; rat SNAP-25A or SNAP-25B; mouse SNAP-25A or SNAP-25B; *Xenopus* SNAP-25A or SNAP-25B; *Danio* SNAP-25A or SNAP-25B; *Carassius* SNAP-25A or SNAP-25B; *Torpedo* SNAP-25; *Strongylocentrotus* SNAP-25; *Drosophila* SNAP-25 or SNAP-24; *Hirudo* SNAP-25; *Loligo* SNAP-25; *Lymnaea* SNAP-25, isoforms thereof, or another naturally occurring protein sensitive to cleavage by BoNT/C1. As discussed above in regard to variants of naturally occurring syntaxin sequences, comparison of native SNAP-25 amino acid sequences cleaved by BoNT/C1 reveals significant sequence variability (Table 2), indicating that a variety of amino acid substitutions and modifications relative to a naturally occurring BoNT/C1-sensitive SNAP-25 sequence can be tolerated in a BoNT/C1 substrate cleavage site disclosed in the present specification. It is understood that a similar BoNT/C1 substrate cleavage site can be prepared, if desired, from a corresponding (homologous) segment of another BoNT/C1-sensitive SNAP-25 isoform, paralog or ortholog, such as, the BoNT/A substrate cleavage site contain in the SNAP-25 proteins identified in the organisms listed above and in Table 2.

Thus, in an embodiment, a modified Clostridial toxin comprises a BoNT/C1 substrate cleavage site. In an aspect of this embodiment, a BoNT/C1 substrate cleavage site comprises at least six consecutive residues of Syntaxin including Lys-Ala. In another aspect of this embodiment, a BoNT/C1 substrate cleavage site comprises at least six consecutive residues of Syntaxin including Arg-Ala. In other aspects of this embodiment, a BoNT/C1 substrate cleavage site comprises, e.g., the amino acid sequence Asp-Thr-Lys-Lys-Ala-Val-Lys-Tyr (SEQ ID NO: 113); the amino acid sequence Glu-Thr-Lys-Ala-Ile-Lys-Tyr (SEQ ID NO: 114); the amino acid sequence Glu-Ser-Lys-Lys-Ala-Val-Lys-Tyr (SEQ ID NO: 115); the amino acid sequence Glu-Thr-Lys-Arg-Ala-Met-Lys-Tyr (SEQ ID NO: 116); the amino acid sequence Glu-Thr-Lys-Lys-Ala-Val-Lys-Tyr (SEQ ID NO: 117); the amino acid sequence Asp-Thr-Lys-Lys-Ala-Leu-Lys-Tyr (SEQ ID NO: 118); or the amino acid sequence Asp-Thr-Lys-Lys-Ala-Met-Lys-Tyr (SEQ ID NO: 119). In another aspect of this embodiment, a BoNT/C1 substrate cleavage site comprises a naturally occurring BoNT/C1 substrate cleavage site variant. In another aspect of this embodiment, a BoNT/C1 substrate cleavage site comprises a naturally occurring BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119, such as, e.g., a BoNT/C1 substrate cleavage site isoform of SEQ ID NO: 113, SEQ ID NO: 114, SEQ ID NO: 115, SEQ ID NO: 116, SEQ ID NO: 117, SEQ ID NO: 118 or SEQ ID NO: 119; or a BoNT/C1 substrate cleavage site subtype of SEQ ID NO: 113, SEQ ID NO: 114, SEQ ID NO: 115, SEQ ID NO: 116, SEQ ID NO: 117, SEQ ID NO: 118 or SEQ ID NO: 119. In still another aspect of this embodiment, a BoNT/C1 substrate cleavage site comprises a non-naturally occurring BoNT/C1 substrate cleavage site variant, such as, e.g., a conservative BoNT/C1 substrate cleavage site variant, a non-conservative BoNT/C1 substrate cleavage site variant or a BoNT/C1 substrate cleavage site peptidomimetic, or any combination thereof. In still another aspect of this embodiment, a BoNT/C1 substrate cleavage site comprises a non-naturally occurring BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119; such as, e.g., a conservative BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119; a non-conservative BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119; a BoNT/C1 substrate cleavage site peptidomimetic of SEQ ID NO: 113, SEQ ID NO: 114, SEQ ID NO: 115, SEQ ID NO: 116, SEQ ID NO: 117, SEQ ID NO: 118 or SEQ ID NO: 119; or any combination thereof.

In other aspects of this embodiment, a BoNT/C1 substrate cleavage site comprises a polypeptide having, e.g., at least 50% amino acid identity with SEQ ID NO: 113, at least 62.5% amino acid identity with the SEQ ID NO: 113, at least 75% amino acid identity with SEQ ID NO: 113 or at least 87.5% amino acid identity with SEQ ID NO: 113. In still other aspects of this embodiment, a BoNT/C1 substrate cleavage site comprises a polypeptide having, e.g., at most 50% amino acid identity with SEQ ID NO: 113, at most 62.5% amino acid identity with the SEQ ID NO: 113, at most 75% amino acid identity with SEQ ID NO: 113 or at most 87.5% amino acid identity with SEQ ID NO: 113.

In other aspects of this embodiment, a BoNT/C1 substrate cleavage site comprises a polypeptide having, e.g., at most one, two, three or four non-contiguous amino acid substitutions relative to SEQ ID NO: 113. In still other aspects of this embodiment, a BoNT/C1 substrate cleavage site comprises a polypeptide having, e.g., at least one, two, three or four non-contiguous amino acid substitutions relative to SEQ ID NO: 113. In yet other aspects of this embodiment, a BoNT/C1 substrate cleavage site comprises a polypeptide having, e.g., at most one, two, three, four, five, six, seven, eight, nine or ten non-contiguous amino acid additions relative to SEQ ID NO: 113. In yet other aspects of this embodiment, a BoNT/C1 substrate cleavage site comprises a polypeptide having, e.g., at least one, two, three, four, five, six, seven, eight, nine or ten non-contiguous amino acid additions relative to SEQ ID NO:

113. In still other aspects of this embodiment, a BoNT/C1 substrate cleavage site comprises a polypeptide having, e.g., at most one, two or three non-contiguous amino acid deletions relative to SEQ ID NO: 113. In still other aspects of this embodiment, a BoNT/C1 substrate cleavage site comprises a polypeptide having, e.g., at least one, two or three non-contiguous amino acid deletions relative to SEQ ID NO: 113.

In other aspects of this embodiment, a BoNT/C1 substrate cleavage site comprises a polypeptide having, e.g., at most two, three or four contiguous amino acid substitutions relative to SEQ ID NO: 113. In still other aspects of this embodiment, a BoNT/C1 substrate cleavage site comprises a polypeptide having, e.g., at least two, three or four contiguous amino acid substitutions relative to SEQ ID NO: 113. In yet other aspects of this embodiment, a BoNT/C1 substrate cleavage site comprises a polypeptide having, e.g., at most two, three, four, five, six, seven, eight, nine or ten contiguous amino acid additions relative to SEQ ID NO: 113. In yet other aspects of this embodiment, a BoNT/C1 substrate cleavage site comprises a polypeptide having, e.g., at least two, three, four, five, six, seven, eight, nine or ten contiguous amino acid additions relative to SEQ ID NO: 113. In still other aspects of this embodiment, a BoNT/C1 substrate cleavage site comprises a polypeptide having, e.g., at most two or three contiguous amino acid deletions relative to SEQ ID NO: 113. In still other aspects of this embodiment, a BoNT/C1 substrate cleavage site comprises a polypeptide having, e.g., at least two or three contiguous amino acid deletions relative to SEQ ID NO: 113.

In another aspect of this embodiment, a BoNT/C1 substrate cleavage site comprises at least six consecutive residues of SNAP-25 including Arg-Ala. In other aspects of this embodiment, a BoNT/C1 toxin substrate cleavage site comprises, e.g., the amino acid sequence Ala-Asn-Gln-Arg-Ala-Thr-Lys-Met (SEQ ID NO: 120); or the amino acid sequence Ala-Asn-Gln-Arg-Ala-His-Gln-Leu (SEQ ID NO: 121). In another aspect of this embodiment, a BoNT/C1 substrate cleavage site comprises a naturally occurring BoNT/C1 substrate cleavage site variant. In another aspect of this embodiment, a BoNT/C1 substrate cleavage site comprises a naturally occurring BoNT/C1 substrate cleavage site variant of SEQ ID NO: 120 or SEQ ID NO: 121, such as, e.g., a BoNT/C1 substrate cleavage site isoform of SEQ ID NO: 120 or SEQ ID NO: 121; or a BoNT/C1 substrate cleavage site subtype of SEQ ID NO: 120 or SEQ ID NO: 121. In still another aspect of this embodiment, a BoNT/C1 substrate cleavage site comprises a non-naturally occurring BoNT/C1 substrate cleavage site variant, such as, e.g., a conservative BoNT/C1 substrate cleavage site variant, a non-conservative BoNT/C1 substrate cleavage site variant or a BoNT/C1 substrate cleavage site peptidomimetic, or any combination thereof. In still another aspect of this embodiment, a BoNT/C1 substrate cleavage site comprises a non-naturally occurring BoNT/C1 substrate cleavage site variant of SEQ ID NO: 120 or SEQ ID NO: 121; such as, e.g., a conservative BoNT/C1 substrate cleavage site variant of SEQ ID NO: 120 or SEQ ID NO: 121; a non-conservative BoNT/C1 substrate cleavage site variant of SEQ ID NO: 120 or SEQ ID NO: 121; a BoNT/C1 substrate cleavage site peptidomimetic of SEQ ID NO: 120 or SEQ ID NO: 121; or any combination thereof.

In other aspects of this embodiment, a BoNT/C1 substrate cleavage site comprises a polypeptide having, e.g., at least 50% amino acid identity with SEQ ID NO: 120, at least 62.5% amino acid identity with the SEQ ID NO: 120, at least 75% amino acid identity with SEQ ID NO: 120 or at least 87.5% amino acid identity with SEQ ID NO: 120. In still other aspects of this embodiment, a BoNT/C1 substrate cleavage site comprises a polypeptide having, e.g., at most 50% amino acid identity with SEQ ID NO: 120, at most 62.5% amino acid identity with the SEQ ID NO: 120, at most 75% amino acid identity with SEQ ID NO: 120 or at most 87.5% amino acid identity with SEQ ID NO: 120.

In other aspects of this embodiment, a BoNT/C1 substrate cleavage site comprises a polypeptide having, e.g., at most one, two, three or four non-contiguous amino acid substitutions relative to SEQ ID NO: 120. In still other aspects of this embodiment, a BoNT/C1 substrate cleavage site comprises a polypeptide having, e.g., at least one, two, three or four non-contiguous amino acid substitutions relative to SEQ ID NO: 120. In yet other aspects of this embodiment, a BoNT/C1 substrate cleavage site comprises a polypeptide having, e.g., at most one, two, three, four, five, six, seven, eight, nine or ten non-contiguous amino acid additions relative to SEQ ID NO: 120. In yet other aspects of this embodiment, a BoNT/C1 substrate cleavage site comprises a polypeptide having, e.g., at least one, two, three, four, five, six, seven, eight, nine or ten non-contiguous amino acid additions relative to SEQ ID NO: 120. In still other aspects of this embodiment, a BoNT/C1 substrate cleavage site comprises a polypeptide having, e.g., at most one, two or three non-contiguous amino acid deletions relative to SEQ ID NO: 120. In still other aspects of this embodiment, a BoNT/C1 substrate cleavage site comprises a polypeptide having, e.g., at least one, two or three non-contiguous amino acid deletions relative to SEQ ID NO: 120.

In other aspects of this embodiment, a BoNT/C1 substrate cleavage site comprises a polypeptide having, e.g., at most two, three or four contiguous amino acid substitutions relative to SEQ ID NO: 120. In still other aspects of this embodiment, a BoNT/C1 substrate cleavage site comprises a polypeptide having, e.g., at least two, three or four contiguous amino acid substitutions relative to SEQ ID NO: 120. In yet other aspects of this embodiment, a BoNT/C1 substrate cleavage site comprises a polypeptide having, e.g., at most two, three, four, five, six, seven, eight, nine or ten contiguous amino acid additions relative to SEQ ID NO: 120. In yet other aspects of this embodiment, a BoNT/C1 substrate cleavage site comprises a polypeptide having, e.g., at least two, three, four, five, six, seven, eight, nine or ten contiguous amino acid additions relative to SEQ ID NO: 120. In still other aspects of this embodiment, a BoNT/C1 substrate cleavage site comprises a polypeptide having, e.g., at most two or three contiguous amino acid deletions relative to SEQ ID NO: 120. In still other aspects of this embodiment, a BoNT/C1 substrate cleavage site comprises a polypeptide having, e.g., at least two or three contiguous amino acid deletions relative to SEQ ID NO: 120.

In an aspect of the invention, a modified Clostridial toxin comprises a BoNT/D substrate cleavage site. As used herein, the term "botulinum toxin serotype D substrate cleavage site" is synonymous with "BoNT/D substrate cleavage site" and means a scissile bond together with adjacent or non-adjacent recognition elements, or both, sufficient for detectable proteolysis at the scissile bond by a BoNT/D under appropriate conditions. A scissile bond cleaved by BoNT/D can be, for example, Lys-Leu. It is envisioned that a BoNT/D substrate cleavage site of any and all lengths can be useful in aspects of the present invention with the proviso that the BoNT/D substrate cleavage site is capable of being cleaved by BoNT/D. Thus, in aspects of this embodiment, a BoNT/D substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/D substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A BoNT/D substrate cleavage sites useful in aspects of the invention can correspond to a segment of a protein that is sensitive to cleavage by BoNT/D, or can be substantially similar to a segment of a BoNT/D-sensitive protein. As shown in Table 3, a variety of naturally occurring proteins sensitive to cleavage by BoNT/D are known in the art and include, for example, human, rat and mouse VAMP-1, VAMP-2 and VAMP-3/cellubrevin; bovine VAMP-2; chicken VAMP-1, VAMP-2 and VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD, synE; *Hirudo* VAMP; *Loligo* VAMP; *Lymnaea* VAMP; *Aplysia* VAMP; and *Caenorhabditis* SNB1. Thus, a BoNT/D substrate cleavage site can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD, synE; *Hirudo* VAMP; *Loligo* VAMP; *Lymnaea* VAMP; *Aplysia* VAMP; *Caenorhabditis* SNB1, isoforms thereof, or another naturally occurring protein sensitive to cleavage by BoNT/D. Furthermore, comparison of native VAMP amino acid sequences cleaved by BoNT/D reveals that such sequences are not absolutely conserved (Table 3). This finding indicates that a variety of amino acid substitutions and modifications relative to a naturally occurring BoNT/D-sensitive VAMP sequence can be tolerated in a BoNT/D substrate cleavage site useful in aspects of the present invention. It is understood that a similar BoNT/D substrate cleavage site can be prepared, if desired, from a corresponding (homologous) segment of another BoNT/D-sensitive VAMP-1 or VAMP-2 isoform, paralog or ortholog, such as, the BoNT/D substrate cleavage site contain in the VAMP-1 and VAMP-2 proteins identified in the organisms listed above and in Table 3.

A variety of BoNT/D substrate cleavage sites are well known in the art or can be defined by routine methods. A BoNT/D substrate cleavage site can include, for example, residues 27 to 116; residues 37 to 116; residues 1 to 86; residues 1 to 76; or residues 1 to 69 of rat VAMP-2 (SEQ ID NO: 46), see, e.g., Shinji Yamasaki et al., Cleavage of members of the synaptobrevin/VAMP family by types D and F botulinum neurotoxins and tetanus toxin, 269(17) J. Biol. Chem. 12764-12772 (1994). Thus, a BoNT/D substrate cleavage site can include, for example, residues 27 to 69 or residues 37 to 69 of rat VAMP-2. A BoNT/D substrate cleavage site also can include, without limitation, the sequence Ala-Gln-Val-Asp-Glu-Val-Val-Asp-Ile-Met-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 154) or a peptidomimetic thereof, which corresponds to residues 37 to 75 of human VAMP-2, see, e.g., Schmidt & Stafford, supra, (Jul. 13, 2004) and the BoNT/D recognition sequence Ala-Gln-Val-Glu-Glu-Val-Val-Asp-Ile-Ile-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 155) or a peptidomimetic thereof, which corresponds to residues 39 to 77 of the human VAMP-1 isoforms, VAMP-1-1, VAMP-1-2 and VAMP-1-3.

Thus, in an embodiment, a modified Clostridial toxin comprises a BoNT/D substrate cleavage site. In an aspect of this embodiment, a BoNT/D substrate cleavage site comprises at least six consecutive residues of VAMP including Lys-Leu. In other aspects of this embodiment, a BoNT/D substrate cleavage site comprises, e.g., the amino acid sequence Arg-Asp-Gln-Lys-Leu-Ser-Glu-Leu (SEQ ID NO: 122); or the amino acid sequence Lys-Asp-Gln-Lys-Leu-Ala-Glu-Leu (SEQ ID NO: 123). In another aspect of this embodiment, a BoNT/D substrate cleavage site comprises a naturally occurring BoNT/D substrate cleavage site variant. In another aspect of this embodiment, a BoNT/D substrate cleavage site comprises a naturally occurring BoNT/D substrate cleavage site variant of SEQ ID NO: 122 or SEQ ID NO: 123, such as, e.g., a BoNT/D substrate cleavage site isoform of SEQ ID NO: 122 or SEQ ID NO: 123; or a BoNT/D substrate cleavage site subtype of SEQ ID NO: 122 or SEQ ID NO: 123. In still another aspect of this embodiment, a BoNT/D substrate cleavage site comprises a non-naturally occurring BoNT/D substrate cleavage site variant, such as, e.g., a conservative BoNT/D substrate cleavage site variant, a non-conservative BoNT/D substrate cleavage site variant or a BoNT/D substrate cleavage site peptidomimetic, or any combination thereof. In still another aspect of this embodiment, a BoNT/D substrate cleavage site comprises a non-naturally occurring BoNT/D substrate cleavage site variant of SEQ ID NO: 122 or SEQ ID NO: 123; such as, e.g., a conservative BoNT/D substrate cleavage site variant of SEQ ID NO: 122 or SEQ ID NO: 123; a non-conservative BoNT/C1 substrate cleavage site variant of SEQ ID NO: 122 or SEQ ID NO: 123; a BoNT/D substrate cleavage site peptidomimetic of SEQ ID NO: 122 or SEQ ID NO: 123; or any combination thereof.

In other aspects of this embodiment, a BoNT/D substrate cleavage site comprises a polypeptide having, e.g., at least 50% amino acid identity with SEQ ID NO: 122, at least 62.5% amino acid identity with the SEQ ID NO: 122, at least 75% amino acid identity with SEQ ID NO: 122 or at least 87.5% amino acid identity with SEQ ID NO: 122. In still other aspects of this embodiment, a BoNT/D substrate cleavage site comprises a polypeptide having, e.g., at most 50% amino acid identity with SEQ ID NO: 122, at most 62.5% amino acid identity with the SEQ ID NO: 122, at most 75% amino acid identity with SEQ ID NO: 122 or at most 87.5% amino acid identity with SEQ ID NO: 122.

In other aspects of this embodiment, a BoNT/D substrate cleavage site comprises a polypeptide having, e.g., at most one, two, three or four non-contiguous amino acid substitutions relative to SEQ ID NO: 122. In still other aspects of this embodiment, a BoNT/D substrate cleavage site comprises a polypeptide having, e.g., at least one, two, three or four non-contiguous amino acid substitutions relative to SEQ ID NO: 122. In yet other aspects of this embodiment, a BoNT/D substrate cleavage site comprises a polypeptide having, e.g., at most one, two, three, four, five, six, seven, eight, nine or ten non-contiguous amino acid additions relative to SEQ ID NO: 122. In yet other aspects of this embodiment, a BoNT/D substrate cleavage site comprises a polypeptide having, e.g., at least one, two, three, four, five, six, seven, eight, nine or ten non-contiguous amino acid additions relative to SEQ ID NO: 122. In still other aspects of this embodiment, a BoNT/D substrate cleavage site comprises a polypeptide having, e.g., at most one, two or three non-contiguous amino acid deletions relative to SEQ ID NO: 122. In still other aspects of this embodiment, a BoNT/D substrate cleavage site comprises a polypeptide having, e.g., at least one, two or three non-contiguous amino acid deletions relative to SEQ ID NO: 122.

In other aspects of this embodiment, a BoNT/D substrate cleavage site comprises a polypeptide having, e.g., at most two, three or four contiguous amino acid substitutions relative to SEQ ID NO: 122. In still other aspects of this embodiment, a BoNT/D substrate cleavage site comprises a polypeptide having, e.g., at least two, three or four contiguous amino acid substitutions relative to SEQ ID NO: 122. In yet other aspects of this embodiment, a BoNT/D substrate cleavage site comprises a polypeptide having, e.g., at most two, three, four, five, six, seven, eight, nine or ten contiguous amino acid additions relative to SEQ ID NO: 122. In yet other aspects of this embodiment, a BoNT/D substrate cleavage site comprises a polypeptide having, e.g., at least two, three, four, five, six, seven, eight, nine or ten contiguous amino acid additions relative to SEQ ID NO: 122. In still other aspects of this embodiment, a BoNT/D substrate cleavage site comprises a polypeptide having, e.g., at most two or three contiguous amino acid deletions relative to SEQ ID NO: 122. In still other aspects of this embodiment, a BoNT/D substrate cleavage site comprises a polypeptide having, e.g., at least two or three contiguous amino acid deletions relative to SEQ ID NO: 122.

In an aspect of the invention, a modified Clostridial toxin comprises a BoNT/E substrate cleavage site. As used herein, the term "botulinum toxin serotype E substrate cleavage site" is synonymous with "BoNT/E substrate cleavage site" and means a scissile bond together with adjacent or non-adjacent recognition elements, or both, sufficient for detectable proteolysis at the scissile bond by a BoNT/E under appropriate conditions. A scissile bond cleaved by BoNT/E can be, for example, Arg-Ile or Lys-Ile. It is envisioned that a BoNT/E substrate cleavage site of any and all lengths can be useful in aspects of the present invention with the proviso that the BoNT/E substrate cleavage site is capable of being cleaved by BoNT/E. Thus, in aspects of this embodiment, a BoNT/E substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/E substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A BoNT/E substrate cleavage sites useful in aspects of the invention can correspond to a segment of a protein that is sensitive to cleavage by BoNT/E, or can be substantially similar to a segment of a BoNT/E-sensitive protein. As shown in Table 2, a variety of naturally occurring proteins sensitive to cleavage by BoNT/E are known in the art and include, for example, human, chicken, *Danio, Carassius* SNAP-25A and SNAP-25B; rat and mouse SNAP-25A, SNAP-25B and SNAP-23; and *Caenorhabditis* SNAP-25. Thus, a BoNT/E substrate cleavage site can correspond, for example, to a segment of human SNAP-25A or SNAP-25B; bovine SNAP-25A or SNAP-25B; rat SNAP-25A, SNAP-25B or SNAP-23; mouse SNAP-25A, SNAP-25B or SNAP-23; *Xenopus* SNAP-25A or SNAP-25B; *Danio* SNAP-25A or SNAP-25B; *Carassius* SNAP-25A or SNAP-25B; *Strongylocentrotus* SNAP-25; *Drosophila* SNAP-24; Hirudo SNAP-25; *Loligo* SNAP-25; *Lymnaea* SNAP-25; *Caenorhabditis* SNAP-25, isoforms thereof, or another naturally occurring protein sensitive to cleavage by BoNT/C1. Furthermore, comparison of native SNAP-23 and SNAP-25 amino acid sequences cleaved by BoNT/E reveals that such sequences are not absolutely conserved (Table 2). This finding indicates that a variety of amino acid substitutions and modifications relative to a naturally occurring BoNT/E-sensitive SNAP-23 or SNAP-25 sequence can be tolerated in a BoNT/E substrate cleavage site useful in aspects of the present invention. It is understood that a similar BoNT/E substrate cleavage site can be prepared, if desired, from a corresponding (homologous) segment of another BoNT/E-sensitive SNAP-25 isoform, paralog or ortholog, such as, the BoNT/E recognition sequence contain in the SNAP-25 proteins identified in the organisms listed above and in Table 2.

A variety of BoNT/E substrate cleavage sites are well known in the art or can be defined by routine methods. A BoNT/E substrate cleavage site can have, for example, residues 46-206, residues 92 to 206, residues, residues 134 to 206, residues, 137 to 206; 146-206, 156-206 or 146-186 of human SNAP-25A (SEQ ID NO: 9) and human SNAP-25B (SEQ ID NO: 10), see, e.g., Vaidyanathan et al., supra, (1999); and Schmidt & Stafford, supra, (Jul. 13, 2004).

Thus, in an embodiment, a modified Clostridial toxin comprises a BoNT/E substrate cleavage site. In an aspect of this embodiment, a BoNT/E substrate cleavage site comprises at least six consecutive residues of SNAP-25 including Arg-Ile. In another aspect of this embodiment, a BoNT/E substrate cleavage site comprises at least six consecutive residues of SNAP-25 including Lys-Ile. In other aspects of this embodiment, a BoNT/E substrate cleavage site comprises, e.g., the amino acid sequence Gln-Ile-Asp-Arg-Ile-Met-Glu-Lys (SEQ ID NO: 124); the amino acid sequence Gln-Ile-Gln-Lys-Ile-Thr-Glu-Lys (SEQ ID NO: 125); the amino acid sequence Gln-Ile-Asp-Arg-Ile-Met-Asp-Met (SEQ ID NO: 126); the amino acid sequence Gln-Val-Asp-Arg-Ile-Gln-Gln-Lys (SEQ ID NO: 127); or the amino acid sequence Gln-Leu-Asp-Arg-Ile-His-Asp-Lys (SEQ ID NO: 128). In another aspect of this embodiment, a BoNT/E substrate cleavage site comprises a naturally occurring BoNT/E substrate cleavage site variant. In another aspect of this embodiment, a BoNT/E substrate cleavage site comprises a naturally occurring BoNT/E substrate cleavage site variant of SEQ ID NO: 124, SEQ ID NO: 125, SEQ ID NO: 126, SEQ ID NO: 127 or SEQ ID NO: 128, such as, e.g., a BoNT/E substrate cleavage site isoform of SEQ ID NO: 124, SEQ ID NO: 125, SEQ ID NO: 126, SEQ ID NO: 127 or SEQ ID NO: 128; or a BoNT/E substrate cleavage site subtype of SEQ ID NO: 124, SEQ ID NO: 125, SEQ ID NO: 126, SEQ ID NO: 127 or SEQ ID NO: 128. In still another aspect of this embodiment, a BoNT/E substrate cleavage site comprises a non-naturally occurring BoNT/E substrate cleavage site variant, such as, e.g., a conservative BoNT/E substrate cleavage site variant, a non-conservative BoNT/E substrate cleavage site variant or a BoNT/E substrate cleavage site peptidomimetic, or any combination thereof. In still another aspect of this embodiment, a BoNT/E substrate cleavage site comprises a non-naturally occurring BoNT/E substrate cleavage site variant of SEQ ID NO: 124, SEQ ID NO: 125, SEQ ID NO: 126, SEQ ID NO: 127 or SEQ ID NO: 128; such as, e.g., a conservative BoNT/E substrate cleavage site variant of SEQ ID NO: 124, SEQ ID NO: 125, SEQ ID NO: 126, SEQ ID NO: 127 or SEQ ID NO: 128; a non-conservative BoNT/E substrate cleavage site variant of SEQ ID NO: 124, SEQ ID NO: 125, SEQ ID NO: 126, SEQ ID NO: 127 or SEQ ID NO: 128; a BoNT/E substrate cleavage site peptidomimetic of SEQ ID NO: 124, SEQ ID NO: 125, SEQ ID NO: 126, SEQ ID NO: 127 or SEQ ID NO: 128 or SEQ ID NO: XX; or any combination thereof.

In other aspects of this embodiment, a BoNT/E substrate cleavage site comprises a polypeptide having, e.g., at least 50% amino acid identity with SEQ ID NO: 124, at least 62.5% amino acid identity with the SEQ ID NO: 124, at least 75% amino acid identity with SEQ ID NO: 124 or at least 87.5% amino acid identity with SEQ ID NO: 124. In still other aspects of this embodiment, a BoNT/E substrate cleavage site comprises a polypeptide having, e.g., at most 50% amino acid identity with SEQ ID NO: 124, at most 62.5% amino acid identity with the SEQ ID NO: 124, at most 75% amino acid identity with SEQ ID NO: 124 or at most 87.5% amino acid identity with SEQ ID NO: 124.

In other aspects of this embodiment, a BoNT/E substrate cleavage site comprises a polypeptide having, e.g., at most one, two, three or four non-contiguous amino acid substitutions relative to SEQ ID NO: 124. In still other aspects of this embodiment, a BoNT/E substrate cleavage site comprises a polypeptide having, e.g., at least one, two, three or four non-contiguous amino acid substitutions relative to SEQ ID NO: 124. In yet other aspects of this embodiment, a BoNT/E substrate cleavage site comprises a polypeptide having, e.g., at most one, two, three, four, five, six, seven, eight, nine or ten non-contiguous amino acid additions relative to SEQ ID NO: 124. In yet other aspects of this embodiment, a BoNT/E substrate cleavage site comprises a polypeptide having, e.g., at least one, two, three, four, five, six, seven, eight, nine or ten non-contiguous amino acid additions relative to SEQ ID NO: 124. In still other aspects of this embodiment, a BoNT/E substrate cleavage site comprises a polypeptide having, e.g., at most one, two or three non-contiguous amino acid deletions relative to SEQ ID NO: 124. In still other aspects of this embodiment, a BoNT/E substrate cleavage site comprises a polypeptide having, e.g., at least one, two or three non-contiguous amino acid deletions relative to SEQ ID NO: 124.

In other aspects of this embodiment, a BoNT/E substrate cleavage site comprises a polypeptide having, e.g., at most two, three or four contiguous amino acid substitutions relative to SEQ ID NO: 124. In still other aspects of this embodiment, a BoNT/E substrate cleavage site comprises a polypeptide having, e.g., at least two, three or four contiguous amino acid substitutions relative to SEQ ID NO: 124. In yet other aspects of this embodiment, a BoNT/E substrate cleavage site comprises a polypeptide having, e.g., at most two, three, four, five, six, seven, eight, nine or ten contiguous amino acid additions relative to SEQ ID NO: 124. In yet other aspects of this embodiment, a BoNT/E substrate cleavage site comprises a polypeptide having, e.g., at least two, three, four, five, six, seven, eight, nine or ten contiguous amino acid additions relative to SEQ ID NO: 124. In still other aspects of this embodiment, a BoNT/E substrate cleavage site comprises a polypeptide having, e.g., at most two or three contiguous amino acid deletions relative to SEQ ID NO: 124. In still other aspects of this embodiment, a BoNT/E substrate cleavage site comprises a polypeptide having, e.g., at least two or three contiguous amino acid deletions relative to SEQ ID NO: 124.

In an aspect of the invention, a modified Clostridial toxin comprises a BoNT/F substrate cleavage site. As used herein, the term "botulinum toxin serotype F substrate cleavage site" is synonymous with "BoNT/F substrate cleavage site" and means a scissile bond together with adjacent or non-adjacent recognition elements, or both, sufficient for detectable proteolysis at the scissile bond by a BoNT/F under appropriate conditions. A scissile bond cleaved by BoNT/F can be, for example, Gln-Lys. It is envisioned that a BoNT/F substrate cleavage site of any and all lengths can be useful in aspects of the present invention with the proviso that the BoNT/F substrate cleavage site is capable of being cleaved by BoNT/F. Thus, in aspects of this embodiment, a BoNT/F substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/F substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A BoNT/F substrate cleavage sites useful in aspects of the invention can correspond to a segment of a protein that is sensitive to cleavage by BoNT/F, or can be substantially similar to a segment of a BoNT/F-sensitive protein. As shown in Table 3, a variety of naturally occurring proteins sensitive to cleavage by BoNT/F are known in the art and include, for example, human, rat and mouse VAMP-1, VAMP-2 and VAMP-3/cellubrevin; bovine VAMP-2; chicken VAMP-1 and VAMP-2; *Torpedo* VAMP-1; and *Drosophila* sybA and synB. Thus, a BoNT/F substrate cleavage site can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Drosophila* sybA and synB; *Hirudo* VAMP; Loligo VAMP; *Lymnaea* VAMP; *Aplysia* VAMP; *Caenorhabditis* SNB1, isoforms thereof, or another naturally occurring protein sensitive to cleavage by BoNT/F. Thus, a BoNT/F substrate cleavage site can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, *Aplysia* VAMP, *Drosophila* syb, leech VAMP, or another naturally occurring protein sensitive to cleavage by BoNT/F. Furthermore, comparison of native VAMP amino acid sequences cleaved by BoNT/F reveals that such sequences are not absolutely conserved (Table 3). This finding indicates that a variety of amino acid substitutions and modifications relative to a naturally occurring BoNT/F-sensitive VAMP sequence can be tolerated in a BoNT/F substrate cleavage site useful in aspects of the present invention. It is understood that a similar BoNT/F substrate cleavage site can be prepared, if desired, from a corresponding (homologous) segment of another BoNT/F-sensitive VAMP-1 or VAMP-2 isoform, paralog or ortholog, such as, the BoNT/F substrate cleavage site contain in the VAMP-1 and VAMP-2 identified in the organisms listed above and in Table 3.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2 (SEQ ID NO: 46), see, e.g., Yamasaki et al., supra, (1994). These a BoNT/F recognition sequence also can comprise, for example, residues 27 to 69 or residues 37 to 69 of rat VAMP-2. It is understood that a similar BoNT/F recognition sequence can be prepared, if desired, from a corresponding (homologous) segment of another BoNT/F-sensitive VAMP isoform, paralog or ortholog, such as, e.g., human VAMP-1 or human VAMP-2. A BoNT/F recognition sequence also can include, without limitation, the sequence Ala-Gln-Val-Asp-Glu-Val-Val-Asp-Ile-Met-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 154) or a peptidomimetic thereof, which corresponds to residues 37 to 75 of human VAMP-2, see, e.g., Schmidt & Stafford, supra, (Jul. 13, 2004) and the BoNT/F recognition sequence Ala-Gln-Val-Glu-Glu-Val-Val-Asp-Ile-Ile-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 155) or a peptidomimetic thereof, which corresponds to residues 39 to 77 of human VAMP-1.

Thus, in an embodiment, a modified Clostridial toxin comprises a BoNT/F substrate cleavage site. In an aspect of this embodiment, a BoNT/F substrate cleavage site comprises at least six consecutive residues of VAMP including Gln-Lys. In other aspects of this embodiment, a BoNT/F substrate cleavage site comprises, e.g., the amino acid sequence Glu-Arg-Asp-Gln-Lys-Leu-Ser-Glu (SEQ ID NO: 129); or the amino acid sequence Glu-Lys-Asp-Gln-Lys-Leu-Ala-Glu (SEQ ID NO: 130). In another aspect of this embodiment, a BoNT/F substrate cleavage site comprises a naturally occurring BoNT/F substrate cleavage site variant. In another aspect of this embodiment, a BoNT/F substrate cleavage site comprises a naturally occurring BoNT/F substrate cleavage site variant of SEQ ID NO: 129 or SEQ ID NO: 130, such as, e.g., a BoNT/F substrate cleavage site isoform of SEQ ID NO: 129 or SEQ ID NO: 130; or a BoNT/F substrate cleavage site subtype of SEQ ID NO: 129 or SEQ ID NO: 130. In still another aspect of this embodiment, a BoNT/F substrate cleavage site comprises a non-naturally occurring BoNT/F substrate cleavage site variant, such as, e.g., a conservative BoNT/F substrate cleavage site variant, a non-conservative BoNT/F substrate cleavage site variant or a BoNT/F substrate cleavage site peptidomimetic, or any combination thereof. In still another aspect of this embodiment, a BoNT/F substrate cleavage site comprises a non-naturally occurring BoNT/F substrate cleavage site variant of SEQ ID NO: 129 or SEQ ID NO: 130; such as, e.g., a conservative BoNT/F substrate cleavage site variant of SEQ ID NO: 129 or SEQ ID NO: 130; a non-conservative BoNT/F substrate cleavage site variant of SEQ ID NO: 129 or SEQ ID NO: 130; a BoNT/F substrate cleavage site peptidomimetic of SEQ ID NO: 129 or SEQ ID NO: 130; or any combination thereof.

In other aspects of this embodiment, a BoNT/F substrate cleavage site comprises a polypeptide having, e.g., at least 50% amino acid identity with SEQ ID NO: 129, at least 62.5% amino acid identity with the SEQ ID NO: 129, at least 75% amino acid identity with SEQ ID NO: 129 or at least 87.5% amino acid identity with SEQ ID NO: 129. In still other aspects of this embodiment, a BoNT/F substrate cleavage site comprises a polypeptide having, e.g., at most 50% amino acid identity with SEQ ID NO: 129, at most 62.5% amino acid identity with the SEQ ID NO: 129, at most 75% amino acid identity with SEQ ID NO: 129 or at most 87.5% amino acid identity with SEQ ID NO: 129.

In other aspects of this embodiment, a BoNT/F substrate cleavage site comprises a polypeptide having, e.g., at most one, two, three or four non-contiguous amino acid substitutions relative to SEQ ID NO: 129. In still other aspects of this embodiment, a BoNT/F substrate cleavage site comprises a polypeptide having, e.g., at least one, two, three or four non-contiguous amino acid substitutions relative to SEQ ID NO: 129. In yet other aspects of this embodiment, a BoNT/F substrate cleavage site comprises a polypeptide having, e.g., at most one, two, three, four, five, six, seven, eight, nine or ten non-contiguous amino acid additions relative to SEQ ID NO: 129. In yet other aspects of this embodiment, a BoNT/F substrate cleavage site comprises a polypeptide having, e.g., at least one, two, three, four, five, six, seven, eight, nine or ten non-contiguous amino acid additions relative to SEQ ID NO: 129. In still other aspects of this embodiment, a BoNT/F substrate cleavage site comprises a polypeptide having, e.g., at most one, two or three non-contiguous amino acid deletions relative to SEQ ID NO: 129. In still other aspects of this embodiment, a BoNT/F substrate cleavage site comprises a polypeptide having, e.g., at least one, two or three non-contiguous amino acid deletions relative to SEQ ID NO: 129.

In other aspects of this embodiment, a BoNT/F substrate cleavage site comprises a polypeptide having, e.g., at most two, three or four contiguous amino acid substitutions relative to SEQ ID NO: 129. In still other aspects of this embodiment, a BoNT/F substrate cleavage site comprises a polypeptide having, e.g., at least two, three or four contiguous amino acid substitutions relative to SEQ ID NO: 129. In yet other aspects of this embodiment, a BoNT/F substrate cleavage site comprises a polypeptide having, e.g., at most two, three, four, five, six, seven, eight, nine or ten contiguous amino acid additions relative to SEQ ID NO: 129. In yet other aspects of this embodiment, a BoNT/F substrate cleavage site comprises a polypeptide having, e.g., at least two, three, four, five, six, seven, eight, nine or ten contiguous amino acid additions relative to SEQ ID NO: 129. In still other aspects of this embodiment, a BoNT/F substrate cleavage site comprises a polypeptide having, e.g., at most two or three contiguous amino acid deletions relative to SEQ ID NO: 129. In still other aspects of this embodiment, a BoNT/F substrate cleavage site comprises a polypeptide having, e.g., at least two or three contiguous amino acid deletions relative to SEQ ID NO: 129.

In an aspect of the invention, a modified Clostridial toxin comprises a BoNT/G substrate cleavage site. As used herein, the term "botulinum toxin serotype G substrate cleavage site" is synonymous with "BoNT/G substrate cleavage site" and means a scissile bond together with adjacent or non-adjacent recognition elements, or both, sufficient for detectable proteolysis at the scissile bond by a BoNT/G under appropriate conditions. A scissile bond cleaved by BoNT/G can be, for example, Ala-Ala. It is envisioned that a BoNT/G substrate cleavage site of any and all lengths can be useful in aspects of the present invention with the proviso that the BoNT/G substrate cleavage site is capable of being cleaved by BoNT/G. Thus, in aspects of this embodiment, a BoNT/G substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a BoNT/G substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A BoNT/G substrate cleavage sites useful in aspects of the invention can correspond to a segment of a protein that is sensitive to cleavage by BoNT/G, or can be substantially similar to a segment of a BoNT/G-sensitive protein. As shown in Table 3, a variety of naturally occurring proteins sensitive to cleavage by BoNT/G are known in the art and include, for example, human, rat and mouse VAMP-1, VAMP-2 and VAMP-3/cellubrevin; bovine VAMP-2; chicken VAMP-1, and VAMP-2; and *Torpedo* VAMP-1. Thus, a BoNT/G recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Caenorhabditis* SNB1, isoforms thereof, or another naturally occurring protein sensitive to cleavage by BoNT/G. Furthermore, comparison of native VAMP amino acid sequences cleaved by BoNT/G reveals that such sequences are not absolutely conserved (Table 3). This finding indicates that a variety of amino acid substitutions and modifications relative to a naturally occurring BoNT/G-sensitive VAMP sequence can be tolerated in a BoNT/G substrate cleavage site useful in aspects of the present invention. It is understood that a similar BoNT/G recognition sequence can be prepared, if desired, from a corresponding (homologous) segment of another BoNT/G-sensitive VAMP-1 or VAMP-2 isoform, paralog or ortholog, such as, the BoNT/G recognition sequence contain in the VAMP-1 and VAMP-2 identified in the organisms listed above and in Table 3.

Thus, in an embodiment, a modified Clostridial toxin comprises a BoNT/G substrate cleavage site. In an aspect of this embodiment, a BoNT/G substrate cleavage site comprises at least six consecutive residues of VAMP including Ala-Ala. In other aspects of this embodiment, a BoNT/G substrate cleavage site comprises, e.g., the amino acid sequence Glu-Thr-Ser-Ala-Ala-Lys-Leu-Lys (SEQ ID NO: 131); or the amino acid sequence Glu-Ser-Ser-Ala-Ala-Lys-Leu-Lys (SEQ ID NO: 132). In another aspect of this embodiment, a BoNT/G substrate cleavage site comprises a naturally occurring BoNT/G substrate cleavage site variant. In another aspect of this embodiment, a BoNT/G substrate cleavage site comprises a naturally occurring BoNT/G substrate cleavage site variant of SEQ ID NO: 131 or SEQ ID NO: 132, such as, e.g., a BoNT/G substrate cleavage site isoform of SEQ ID NO: 131 or SEQ ID NO: 132; or a BoNT/G substrate cleavage site subtype of SEQ ID NO: 131 or SEQ ID NO: 132. In still another aspect of this embodiment, a BoNT/G substrate cleavage site comprises a non-naturally occurring BoNT/F substrate cleavage site variant, such as, e.g., a conservative BoNT/G substrate cleavage site variant, a non-conservative BoNT/G substrate cleavage site variant or a BoNT/G substrate cleavage site peptidomimetic, or any combination thereof. In still another aspect of this embodiment, a BoNT/G substrate cleavage site comprises a non-naturally occurring BoNT/G substrate cleavage site variant of SEQ ID NO: 131 or SEQ ID NO: 132; such as, e.g., a conservative BoNT/G substrate cleavage site variant of SEQ ID NO: 131 or SEQ ID NO: 132; a non-conservative BoNT/G substrate cleavage site variant of SEQ ID NO: 131 or SEQ ID NO: 132; a BoNT/G substrate cleavage site peptidomimetic of SEQ ID NO: 131 or SEQ ID NO: 132; or any combination thereof.

In other aspects of this embodiment, a BoNT/G substrate cleavage site comprises a polypeptide having, e.g., at least 50% amino acid identity with SEQ ID NO: 131, at least 62.5% amino acid identity with the SEQ ID NO: 131, at least 75% amino acid identity with SEQ ID NO: 131 or at least 87.5% amino acid identity with SEQ ID NO: 131. In still other aspects of this embodiment, a BoNT/G substrate cleavage site comprises a polypeptide having, e.g., at most 50% amino acid identity with SEQ ID NO: 131, at most 62.5% amino acid identity with the SEQ ID NO: 131, at most 75% amino acid identity with SEQ ID NO: 131 or at most 87.5% amino acid identity with SEQ ID NO: 131.

In other aspects of this embodiment, a BoNT/G substrate cleavage site comprises a polypeptide having, e.g., at most one, two, three or four non-contiguous amino acid substitutions relative to SEQ ID NO: 131. In still other aspects of this embodiment, a BoNT/G substrate cleavage site comprises a polypeptide having, e.g., at least one, two, three or four non-contiguous amino acid substitutions relative to SEQ ID NO: 131. In yet other aspects of this embodiment, a BoNT/G substrate cleavage site comprises a polypeptide having, e.g., at most one, two, three, four, five, six, seven, eight, nine or ten non-contiguous amino acid additions relative to SEQ ID NO: 131. In yet other aspects of this embodiment, a BoNT/G substrate cleavage site comprises a polypeptide having, e.g., at least one, two, three, four, five, six, seven, eight, nine or ten non-contiguous amino acid additions relative to SEQ ID NO: 131. In still other aspects of this embodiment, a BoNT/G substrate cleavage site comprises a polypeptide having, e.g., at most one, two or three non-contiguous amino acid deletions relative to SEQ ID NO: 131. In still other aspects of this embodiment, a BoNT/G substrate cleavage site comprises a polypeptide having, e.g., at least one, two or three non-contiguous amino acid deletions relative to SEQ ID NO: 131.

In other aspects of this embodiment, a BoNT/G substrate cleavage site comprises a polypeptide having, e.g., at most two, three or four contiguous amino acid substitutions relative to SEQ ID NO: 131. In still other aspects of this embodiment, a BoNT/G substrate cleavage site comprises a polypeptide having, e.g., at least two, three or four contiguous amino acid substitutions relative to SEQ ID NO: 131. In yet other aspects of this embodiment, a BoNT/G substrate cleavage site comprises a polypeptide having, e.g., at most two, three, four, five, six, seven, eight, nine or ten contiguous amino acid additions relative to SEQ ID NO: 131. In yet other aspects of this embodiment, a BoNT/G substrate cleavage site comprises a polypeptide having, e.g., at least two, three, four, five, six, seven, eight, nine or ten contiguous amino acid additions relative to SEQ ID NO: 131. In still other aspects of this embodiment, a BoNT/G substrate cleavage site comprises a polypeptide having, e.g., at most two or three contiguous amino acid deletions relative to SEQ ID NO: 131. In still other aspects of this embodiment, a BoNT/G substrate cleavage site comprises a polypeptide having, e.g., at least two or three contiguous amino acid deletions relative to SEQ ID NO: 131.

In an aspect of the invention, a modified Clostridial toxin comprises a TeNT substrate cleavage site. As used herein, the term "tetanus toxin substrate cleavage site" is synonymous with "TeNT substrate cleavage site" and means a scissile bond together with adjacent or non-adjacent recognition elements, or both, sufficient for detectable proteolysis at the scissile bond by a TeNT under appropriate conditions. A scissile bond cleaved by TeNT can be, for example, Gln-Phe. It is envisioned that a TeNT substrate cleavage site of any and all lengths can be useful in aspects of the present invention with the proviso that the TeNT substrate cleavage site is capable of being cleaved by TeNT. Thus, in aspects of this embodiment, a TeNT substrate cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, a TeNT substrate cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

A TeNT substrate cleavage sites useful in aspects of the invention can correspond to a segment of a protein that is sensitive to cleavage by TeNT, or can be substantially similar to a segment of a TeNT-sensitive protein. As shown in Table 3, a variety of naturally occurring proteins sensitive to cleavage by TeNT are known in the art and include, for example, human and mouse VAMP-1, VAMP-2 and VAMP-3/cellubrevin; bovine VAMP-2; rat VAMP-2 and VAMP-3; chicken VAMP-2; *Torpedo* VAMP-1; *Strongylocentrotus* VAMP; *Drosophila* sybA, synB, synC, synD and synE; *Hirudo* VAMP; and *Caenorhabditis* SNB1-like. Thus, a TeNT substrate cleavage site can correspond, for example, to a segment of human VAMP-1, VAMP-2 or VAMP-3; bovine VAMP-2; rat VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD or synE; *Hirudo* VAMP; *Loligo* VAMP; *Lymnaea* VAMP; *Aplysia* VAMP; *Caenorhabditis* SNB1 and SNB-like, isoforms thereof, or another naturally occurring protein sensitive to cleavage by TeNT. Furthermore, comparison of native VAMP amino acid sequences cleaved by TeNT reveals that such sequences are not absolutely conserved (Table 3). This finding indicates that a variety of amino acid substitutions and modifications relative to a naturally occurring TeNT-sensitive VAMP sequence can be tolerated in a TeNT substrate cleavage site useful in aspects of the present invention. It is understood that a similar TeNT substrate cleavage site can be prepared, if desired, from a corresponding (homologous) segment of another TeNT-sensitive VAMP-1 or VAMP-2 isoform, paralog or ortholog, such as, the TeNT substrate cleavage site contain in the VAMP-1 and VAMP-2 identified in the organisms listed above and in Table 3.

A variety of TeNT recognition sequences are well known in the art or can be defined by routine methods and include sequences corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 39); F. Cornille et al., *Solid-Phase Synthesis, Conformational Analysis and In Vitro Cleavage Of Synthetic Human Synaptobrevin II 1-93 by Tetanus Toxin L chain*, 222(1) Eur. J. Biochem. 173-181 (1994); Patrick Foran et al., *Differences in the Protease Activities of Tetanus and Botulinum B Toxins Revealed By the Cleavage of Vesicle-Associated Membrane Protein and Various Sized Fragments*, 33(51) Biochemistry 15365-15374 (1994); residues 51 to 93 or residues 1 to 86 of rat VAMP-2, see, e.g., Yamasaki et al., supra, (1994); or residues 33 to 94 of human VAMP-1-1 (SEQ ID NO: 36), residues 33 to 94 of human VAMP-1-2 (SEQ ID NO: 37) and residues 33 to 94 of human VAMP-1-3 (SEQ ID NO: 38). A TeNT recognition sequence also can include, for example, residues 25 to 86, residues 33 to 86 or residues 51 to 86 of human VAMP-2 (SEQ ID NO: 39) or rat VAMP-2 (SEQ ID NO: 46). It is understood that a similar TeNT recognition sequence can be prepared, if desired, from a corresponding (homologous) segment of another TeNT-sensitive VAMP isoform or species homolog such as human VAMP-1 or sea urchin or *Aplysia* VAMP.

Thus, in an embodiment, a modified Clostridial toxin comprises a TeNT substrate cleavage site. In an aspect of this embodiment, a TeNT substrate cleavage site comprises at least six consecutive residues of VAMP including Gln-Phe. In other aspects of this embodiment, a TeNT substrate cleavage site comprises, e.g., the amino acid sequence Gly-Ala-Ser-Gln-Phe-Glu-Thr-Ser (SEQ ID NO: 107); the amino acid sequence Gly-Ala-Ser-Gln-Phe-Glu-Ser-Ser (SEQ ID NO: 108); the amino acid sequence Gly-Ala-Ser-Gln-Phe-Glu-Thr-Asn (SEQ ID NO: 109); the amino acid sequence Gly-Ala-Ser-Gln-Phe-Glu-Gln-Gln (SEQ ID NO: 110); the amino acid sequence Gly-Ala-Ser-Gln-Phe-Glu-Ala-Ser (SEQ ID NO: 111); or the amino acid sequence Gly-Ala-Ser-Gln-Phe-Gln-Gln-Ser (SEQ ID NO: 112). In another aspect of this embodiment, a TeNT substrate cleavage site comprises a naturally occurring TeNT substrate cleavage site variant. In another aspect of this embodiment, a TeNT substrate cleavage site comprises a naturally occurring TeNT substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a TeNT substrate cleavage site isoform of SEQ ID NO: 107, SEQ ID NO: 108, SEQ ID NO: 109, SEQ ID NO: 110, SEQ ID NO: 111 or SEQ ID NO: 112; or a TeNT substrate cleavage site subtype of SEQ ID NO: 107, SEQ ID NO: 108, SEQ ID NO: 109, SEQ ID NO: 110, SEQ ID NO: 111 or SEQ ID NO: 112. In still another aspect of this embodiment, a TeNT substrate cleavage site comprises a non-naturally occurring TeNT substrate cleavage site variant, such as, e.g., a conservative TeNT substrate cleavage site variant, a non-conservative TeNT substrate cleavage site variant or a TeNT substrate cleavage site peptidomimetic, or any combination thereof. In still another aspect of this embodiment, a TeNT substrate cleavage site comprises a non-naturally occurring TeNT substrate cleavage site variant of SEQ ID NO: 107, SEQ ID NO: 108, SEQ ID NO: 109, SEQ ID NO: 110, SEQ ID NO: 111 or SEQ ID NO: 112; such as, e.g., a conservative TeNT substrate cleavage site variant of SEQ ID NO: 107, SEQ ID NO: 108, SEQ ID NO: 109, SEQ ID NO: 110, SEQ ID NO: 111 or SEQ ID NO: 112; a non-conservative TeNT substrate cleavage site variant of SEQ ID NO: 107, SEQ ID NO: 108, SEQ ID NO: 109, SEQ ID NO: 110, SEQ ID NO: 111 or SEQ ID NO: 112; a TeNT substrate cleavage site peptidomimetic of SEQ ID NO: 107, SEQ ID NO: 108, SEQ ID NO: 109, SEQ ID NO: 110, SEQ ID NO: 111 or SEQ ID NO: 112; or any combination thereof.

In other aspects of this embodiment, a TeNT substrate cleavage site comprises a polypeptide having, e.g., at least 50% amino acid identity with SEQ ID NO: 107, at least 62.5% amino acid identity with the SEQ ID NO: 107, at least 75% amino acid identity with SEQ ID NO: 107 or at least 87.5% amino acid identity with SEQ ID NO: 107. In still other aspects of this embodiment, a TeNT substrate cleavage site comprises a polypeptide having, e.g., at most 50% amino acid identity with SEQ ID NO: 107, at most 62.5% amino acid identity with the SEQ ID NO: 107, at most 75% amino acid identity with SEQ ID NO: 107 or at most 87.5% amino acid identity with SEQ ID NO: 107.

In other aspects of this embodiment, a TeNT substrate cleavage site comprises a polypeptide having, e.g., at most one, two, three or four non-contiguous amino acid substitutions relative to SEQ ID NO: 107. In still other aspects of this embodiment, a TeNT substrate cleavage site comprises a polypeptide having, e.g., at least one, two, three or four non-contiguous amino acid substitutions relative to SEQ ID NO:

107. In yet other aspects of this embodiment, a TeNT substrate cleavage site comprises a polypeptide having, e.g., at most one, two, three, four, five, six, seven, eight, nine or ten non-contiguous amino acid additions relative to SEQ ID NO: 107. In yet other aspects of this embodiment, a TeNT substrate cleavage site comprises a polypeptide having, e.g., at least one, two, three, four, five, six, seven, eight, nine or ten non-contiguous amino acid additions relative to SEQ ID NO: 107. In still other aspects of this embodiment, a TeNT substrate cleavage site comprises a polypeptide having, e.g., at most one, two or three non-contiguous amino acid deletions relative to SEQ ID NO: 107. In still other aspects of this embodiment, a TeNT substrate cleavage site comprises a polypeptide having, e.g., at least one, two or three non-contiguous amino acid deletions relative to SEQ ID NO: 107.

In other aspects of this embodiment, a TeNT substrate cleavage site comprises a polypeptide having, e.g., at most two, three or four contiguous amino acid substitutions relative to SEQ ID NO: 107. In still other aspects of this embodiment, a TeNT substrate cleavage site comprises a polypeptide having, e.g., at least two, three or four contiguous amino acid substitutions relative to SEQ ID NO: 107. In yet other aspects of this embodiment, a TeNT substrate cleavage site comprises a polypeptide having, e.g., at most two, three, four, five, six, seven, eight, nine or ten contiguous amino acid additions relative to SEQ ID NO: 107. In yet other aspects of this embodiment, a TeNT substrate cleavage site comprises a polypeptide having, e.g., at least two, three, four, five, six, seven, eight, nine or ten contiguous amino acid additions relative to SEQ ID NO: 107. In still other aspects of this embodiment, a TeNT substrate cleavage site comprises a polypeptide having, e.g., at most two or three contiguous amino acid deletions relative to SEQ ID NO: 107. In still other aspects of this embodiment, a TeNT substrate cleavage site comprises a polypeptide having, e.g., at least two or three contiguous amino acid deletions relative to SEQ ID NO: 107.

Another type of Clostridial toxin substrate cleavage site is derived from autocatalytic fragments of the Clostridial toxins themselves. It has been noted that a Clostridial toxin can undergo autocatalytic fragmentation resulting in the formation of two major polypeptide fragments. For example, peptide bonds susceptible to autocatalytic cleavage have been located in two regions of BoNT/A. The first region comprises amino acids 250-267 of SEQ ID NO: 1, where bonds Tyr250-Tyr251 and Phe266-Gly267 are susceptible to cleaved. The second region comprises residues 419-439 of SEQ ID NO: 1, where bonds Phe419-Thr420, Phe423-Glu424, Leu429-Cys430, Cys430-Val431, Arg432-Gly433 and Lys438-Thr439 are susceptible to autocatalytic cleavage. The BoNT/A region corresponding to amino acids 250-267 of SEQ ID NO: 1 is highly conserved among Clostridial toxins (Table 7).

TABLE 7

Autocatalytic Region of Clostridial Toxins

| Toxin | SEQ ID NO: | Autocatalytic Region |
|---|---|---|
| BoNT/A | 1 | NTNAY*YEMSGLEVSFEELRTF*GGHDA |
| BoNT/B | 2 | NEKKF*FMQSTDAIQAEELYTF*GGQDP |
| BoNT/C1 | 3 | TSNIF*YSQYNVKLEYAEIYAF*GGPTI |
| BoNT/D | 4 | VSEGF*FSQDGPNVQFEELYTF*GGLDV |
| BoNT/E | 5 | QKQNP*LTINIRGTNIEEFLTF*GGTDL |

TABLE 7-continued

Autocatalytic Region of Clostridial Toxins

| Toxin | SEQ ID NO: | Autocatalytic Region |
|---|---|---|
| BoNT/F | 6 | VKQAP*LMIAEKPIRLEEFLTF*GGQDL |
| BoNT/G | 7 | NTKEF*FMQHSDPVQAEELYTF*GGHDP |
| TeNT | 8 | SKQEI*YMQHTYPISAEELFTF*GGQDA |

The amino acid sequence displayed are as follows: BoNT/A, residues 246-271 of SEQ ID NO: 1; BoNT/B, residues 252-277 of SEQ ID NO: 2; BoNT/C1, residues 253-278 of SEQ ID NO: 3; BoNT/D, residues 253-278 of SEQ ID NO: 4; BoNT/E, residues 235-260 of SEQ ID NO: 5; BoNT/F, residues 250-275 of SEQ ID NO: 6; BoNT/G, residues 252-277 of SEQ ID NO: 7; and TeNT, residues 255-280 of SEQ ID NO: 8.
An asterisks (*) indicates the peptide bond of the $P_1$-$P_1$, cleavage site that is cleaved by a Clostridial toxin protease.

Thus, in an embodiment, a modified Clostridial toxin comprises a Clostridial toxin autocatalytic substrate cleavage site. In aspects of this embodiment, a Clostridial toxin autocatalytic substrate cleavage site comprises at least six consecutive residues of a Clostridial toxin including the BoNT/A residues 250Tyr-251Tyr, the BoNT/B residues 256Phe-257Phe, the BoNT/C1 residues 257Phe-258Tyr, the BoNT/D residues 257Phe-258Phe, the BoNT/E residues 239Pro-240Leu, the BoNT/F residues 254Pro-255Leu, the BoNT/G residues 256Phe-257Phe or the TeNT residues 259Ile-260Tyr. In another aspect of this embodiment, a Clostridial toxin autocatalytic substrate cleavage site comprises at least six consecutive residues of a Clostridial toxin including Phe-Gly. In other aspects of this embodiment, a Clostridial toxin autocatalytic substrate cleavage site comprises at least six consecutive residues of a Clostridial toxin including the BoNT/A residues Phe266-Gly267, the BoNT/B residues Phe272-Gly273, the BoNT/C1 residues Phe273-Gly274, the BoNT/D residues Phe273-Gly274, the BoNT/E residues Phe255-Gly256, the BoNT/F residues Phe270-Gly271, the BoNT/G residues Phe272-Gly273 or the TeNT residues Phe275-Gly276.

In other aspects of this embodiment, a Clostridial toxin autocatalytic substrate cleavage site comprises, e.g., the BoNT/A residues 246-271 of SEQ ID NO: 1; the BoNT/B residues 252-277 of SEQ ID NO: 2; the BoNT/C1 residues 253-278 of SEQ ID NO: 3; the BoNT/D residues 253-278 of SEQ ID NO: 4; the BoNT/E residues 235-260 of SEQ ID NO: 5; the BoNT/F residues 250-275 of SEQ ID NO: 6; the BoNT/G residues 252-277 of SEQ ID NO: 7; or the TeNT residues 255-280 of SEQ ID NO: 8. In still other aspects of this embodiment, a Clostridial toxin autocatalytic substrate cleavage site comprises, e.g., the BoNT/A residues 247-254 of SEQ ID NO: 1; the BoNT/B residues 253-260 of SEQ ID NO: 2; the BoNT/C1 residues 254-261 of SEQ ID NO: 3; the BoNT/D residues 254-261 of SEQ ID NO: 4; the BoNT/E residues 236-243 of SEQ ID NO: 5; the BoNT/F residues 251-258 of SEQ ID NO: 6; the BoNT/G residues 253-260 of SEQ ID NO: 7; or the TeNT residues 256-263 of SEQ ID NO: 8. In yet other aspects of this embodiment, a Clostridial toxin autocatalytic substrate cleavage site comprises, e.g., the BoNT/A residues 263-270 of SEQ ID NO: 1; the BoNT/B residues 269-276 of SEQ ID NO: 2; the BoNT/C1 residues 270-277 of SEQ ID NO: 3; the BoNT/D residues 270-277 of SEQ ID NO: 4; the BoNT/E residues 252-259 of SEQ ID NO: 5; the BoNT/F residues 267-274 of SEQ ID NO: 6; the BoNT/G residues 269-276 of SEQ ID NO: 7; or the TeNT residues 272-279 of SEQ ID NO: 8.

In other aspects of this embodiment, a Clostridial toxin autocatalytic substrate cleavage site comprises a polypeptide having, e.g., at least 50% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at least 60% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at least 70% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at least 80% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at least 90% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; or at least 95% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In still other aspects of this embodiment, a Clostridial toxin autocatalytic substrate cleavage site comprises a polypeptide having, e.g., at most 50% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at most 60% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at most 70% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at most 80% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; at most 90% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8; or at most 95% amino acid identity with the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In other aspects of this embodiment, a Clostridial toxin autocatalytic substrate cleavage site comprises a polypeptide having, e.g., at most one, two, three or four non-contiguous amino acid substitutions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8. In still other aspects of this embodiment, a Clostridial toxin autocatalytic substrate cleavage site comprises a polypeptide having, e.g., at least one, two, three or four non-contiguous amino acid substitutions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In yet other aspects of this embodiment, a Clostridial toxin autocatalytic substrate cleavage site comprises a polypeptide having, e.g., at most one, two, three, four, five, six, seven, eight, nine or ten non-contiguous amino acid additions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8. In yet other aspects of this embodiment, a Clostridial toxin autocatalytic substrate cleavage site comprises a polypeptide having, e.g., at least one, two, three, four, five, six, seven, eight, nine or ten non-contiguous amino acid additions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In still other aspects of this embodiment, a Clostridial toxin autocatalytic substrate cleavage site comprises a polypeptide having, e.g., at most one, two or three non-contiguous amino acid deletions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8. In still other aspects of this embodiment, a Clostridial toxin autocatalytic substrate cleavage site comprises a polypeptide having, e.g., at least one, two or three non-contiguous amino acid deletions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In other aspects of this embodiment, a Clostridial toxin autocatalytic substrate cleavage site comprises a polypeptide having, e.g., at most two, three or four contiguous amino acid substitutions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8. In still other aspects of this embodiment, a Clostridial toxin autocatalytic substrate cleavage site comprises a polypeptide having, e.g., at least two, three or four contiguous amino acid substitutions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In yet other aspects of this embodiment, a Clostridial toxin autocatalytic substrate cleavage site comprises a polypeptide having, e.g., at most two, three, four, five, six, seven, eight, nine or ten contiguous amino acid additions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8. In yet other aspects of this embodiment, a Clostridial toxin autocatalytic substrate cleavage site comprises a polypeptide having, e.g., at least two, three, four, five, six, seven, eight, nine or ten contiguous amino acid additions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In still other aspects of this embodiment, a Clostridial toxin autocatalytic substrate cleavage site comprises a polypeptide having, e.g., at most two or three contiguous amino acid deletions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8. In still other aspects of this embodiment, a Clostridial toxin autocatalytic substrate cleavage site comprises a polypeptide having, e.g., at least two or three contiguous amino acid deletions relative to the BoNT/A residues 246-271 of SEQ ID NO: 1, the BoNT/B residues 252-277 of SEQ ID NO: 2, the BoNT/C1 residues 253-278 of SEQ ID NO: 3, the BoNT/D residues 253-278 of SEQ ID NO: 4, the BoNT/E residues 235-260 of SEQ ID NO: 5, the BoNT/F residues 250-275 of SEQ ID NO: 6, the BoNT/G residues 252-277 of SEQ ID NO: 7 or the TeNT residues 255-280 of SEQ ID NO: 8.

In an aspect of the invention, a Clostridial toxin substrate cleavage site is located within the di-chain loop region. As used herein, the term "di-chain loop region" means the amino acid sequence of a Clostridial toxin containing a protease cleavage site used to convert the single-chain form of a Clostridial toxin into the di-chain form. As non-limiting examples, the di-chain loop region of BoNT/A comprises amino acids 430-454 of SEQ ID NO: 1; the di-chain loop region of BoNT/B comprises amino acids 437-446 of SEQ ID NO: 2; the di-chain loop region of BoNT/C1 comprises amino acids 437-453 of SEQ ID NO: 3; the di-chain loop region of BoNT/D comprises amino acids 437-450 of SEQ ID NO: 4; the di-chain loop region of BoNT/E comprises amino acids 412-426 of SEQ ID NO: 5; the di-chain loop region of BoNT/F comprises amino acids 429-445 of SEQ ID NO: 6; the di-chain loop region of BoNT/G comprises amino acids 436-450 of SEQ ID NO: 7; and the di-chain loop region of TeNT comprises amino acids 439-467 of SEQ ID NO: 8.

TABLE 8

Di-chain Loop Region of Clostridial Toxins

| Toxin | SEQ ID NO: | Light Chain Region | Di-chain Loop Region Containing the Naturally-occurring Di-chain Protease Cleavage Site | Heavy Chain Region |
|---|---|---|---|---|
| BoNT/A | 1 | NMNFTKLKNFTGLFEFYKLL | DVRGIITSKTKSLDKGYNK*----ALNDLC | IKVNNWDL |
| BoNT/B | 2 | KQAYYYISKEHALVYKIQM | CKSVK*------------------APGIC | IDVDNEDL |
| BoNT/C1 | 3 | PALRKVNPENMLYLFTKF | CHKAIDGRSLYNK*------------TLDC | RELLVKNTDL |

TABLE 8-continued

Di-chain Loop Region of Clostridial Toxins

| Toxin | SEQ ID NO: | Light Chain Region | Di-chain Loop Region Containing the Naturally-occurring Di-chain Protease Cleavage Site | Heavy Chain Region |
|---|---|---|---|---|
| BoNT/D | 4 | PALQKLSSESVVDLFTKV | CLRLTKNSR*--------------DDSTC | IKVKNNRL |
| BoNT/E | 5 | IITPITGRGLVKKIIRF | CKNIVSVKGIR*-------------KSIC | IEINNGEL |
| BoNT/F | 6 | IIDSIPDKGLVEKIVKF | CKSVIPRKGTK*-----------APPRLC | IRVNNSEL |
| BoNT/G | 7 | KEAYEEISLEHLVIYRIAM | CKPVMYKNTGK*-------------SEQC | IIVNNEDL |
| TeNT | 8 | TNAFRNVDGSGLVSKLIGL | CKKIIPPTNIRENLYNRTA*SLTDLGGELC | IKIKNEDL |

The amino acid sequence displayed are as follows: BoNT/A, residues 325-462 of SEQ ID NO: 1; BoNT/B, residues 332-454 of SEQ ID NO: 2; BoNT/C1, residues 334-463 of SEQ ID NO: 3; BoNT/D, residues 334-458 of SEQ ID NO: 4; BoNT/E, residues 311-434 of SEQ ID NO: 5; BoNT/F, residues 328-453 of SEQ ID NO: 6; BoNT/G, residues 331-458 of SEQ ID NO: 7; and TeNT, residues 334-474 of SEQ ID NO: 8. An asterisks (*) indicates the peptide bond of the $P_1$–$P_{1'}$ cleavagesite that is believed to be cleaved by a Clostridial toxin protease.

As mentioned above, a Clostridial toxin is converted from a single polypeptide form into a di-chain molecule by proteolytic cleavage. While the identity of the naturally-occurring protease is currently unknown, the location of the di-chain loop protease cleavage site for many Clostridial toxins has been determined (Table 8). Cleavage within the di-chain loop does not appear to be confined to a single peptide bond. Thus, cleavage of a Clostridial toxin with a naturally-occurring di-chain loop protease results in the lost of several residues centered around the original cleavage site. This loss is limited to a few amino acids located between the two cysteine residues that form the disulfide bridge. As a non-limiting example, BoNT/A single-chain polypeptide cleavage ultimately results in the loss of a ten amino acids within the di-chain loop. For BoNTs, cleavage at K448-A449 converts the single-chain form of BoNT/A into the di-chain form; cleavage at K441-A442 converts the single-chain form of BoNT/B into the di-chain form; cleavage at K449-T450 converts the single-chain form of BoNT/C1 into the di-chain form; cleavage at R445-D446 converts the single-chain form of BoNT/D into the di-chain form; cleavage at R422-K423 converts the single-chain form of BoNT/E into the di-chain form; cleavage at K439-A440 converts the single-chain form of BoNT/F into the di-chain form; and cleavage at K446-S447 converts the single-chain form of BoNT/G into the di-chain form. Proteolytic cleavage of the single-chain form of TeNT at of A457-S458 results in the di-chain form.

However, it should also be noted that additional cleavage sites within the di-chain loop also appear to be cleaved resulting in the generation of a small peptide fragment being lost. As a non-limiting example, BoNT/A single-chain polypeptide cleavage ultimately results in the loss of a ten amino acid fragment within the di-chain loop. Thus, cleavage at S441-L442 converts the single polypeptide form of BoNT/A into the di-chain form; cleavage at G444-1445 converts the single polypeptide form of BoNT/B into the di-chain form; cleavage at S445-L446 converts the single polypeptide form of BoNT/C1 into the di-chain form; cleavage at K442-N443 converts the single polypeptide form of BoNT/D into the di-chain form; cleavage at K419-G420 converts the single polypeptide form of BoNT/E into the di-chain form; cleavage at K423-S424 converts the single polypeptide form of BoNT/E into the di-chain form; cleavage at K436-G437 converts the single polypeptide form of BoNT/F into the di-chain form; cleavage at T444-G445 converts the single polypeptide form of BoNT/G into the di-chain form; and cleavage at E448-Q449 converts the single polypeptide form of BoNT/G into the di-chain form.

The di-chain loop region can be modified to include a Clostridial toxin substrate cleavage site in addition to the naturally-occurring di-chain loop protease cleavage site. In this type of modification, both cleavage site are operably-linked in-frame to a modified Clostridial toxin as a fusion protein and both sites can be cleaved by their respective proteases. As a non-limiting example, a modified BoNT/A that comprises a di-chain loop containing both the naturally-occurring di-chain loop protease cleavage site and a BoNT/A substrate cleavage site can be cleaved by either the endogenous di-chain loop protease found in C. botulinum serotype A or by BoNT/A. As another non-limiting example, a modified BoNT/A that comprises a di-chain loop containing both the naturally-occurring di-chain loop protease cleavage site and a BoNT/E substrate cleavage site can be cleaved by either the endogenous di-chain loop protease found in C. botulinum serotype A or by BoNT/E.

The di-chain loop region can also be modified to replace the naturally-occurring di-chain loop protease cleavage site with a Clostridial toxin substrate cleavage site. In this type of modification, the naturally-occurring protease cleavage site is made inoperable and thus can not be cleaved by its protease. Only the Clostridial toxin substrate cleavage site can be cleaved by its corresponding toxin. Such a Clostridial toxin substrate cleavage site is operably-linked in-frame to a modified Clostridial toxin as a fusion protein. As a non-limiting example, a single-chain modified BoNT/A that comprises a di-chain loop containing only a BoNT/A substrate cleavage site can be cleaved BoNT/A, but not the endogenous di-chain loop protease found in C. botulinum serotype A. As another non-limiting example, a single-chain modified BoNT/A that comprises a di-chain loop containing only a BoNT/E substrate cleavage site can be cleaved BoNT/E, but not the endogenous di-chain loop protease found in C. botulinum serotype A.

The naturally-occurring di-chain loop protease cleavage site can be made inoperable by altering at least the one of the amino acids flanking the peptide bond cleaved by the naturally-occurring protease. More extensive alterations can be made, with the proviso that the two cysteine residues of the di-chain loop region remain intact and formation of the disulfide bridge can still be achieved. Non-limiting examples of an amino acid alteration include deletion of an amino acid or replacement of the original amino acid with a different amino acid. These alterations can be made using standard mutagenesis procedures known to a person skilled in the art. In addition, non-limiting examples of mutagenesis procedures, as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures within the scope of one skilled in the art and from the teaching herein.

Thus, in one embodiment, a naturally-occurring di-chain loop protease cleavage site is made inoperable by altering at least one of the amino acids flanking the peptide bond cleaved by a naturally-occurring protease. In aspects of this embodiment, the $P_1$ amino acid of the di-chain loop protease cleavage site is altered or the $P_{1'}$ amino acid of the di-chain loop protease cleavage site is altered. In other aspects of this embodiment, either K448 or A449 of BoNT/A is altered; either S441 or L442 of BoNT/A is altered; either K441 or A442 of BoNT/B is altered; either G444 or I445 of BoNT/B is altered; either K449 or T450 of BoNT/C1 is altered; either S445 or L446 of BoNT/C1 is altered; either R445 or D446 of BoNT/D is altered; either K442 or N443 of BoNT/D is altered; either R422 or K423 of BoNT/E is altered; either K419 or G420 of BoNT/E is altered; either K423 or S424 of BoNT/E is altered; either K439 or A440 of BoNT/F is altered; either K436 or G437 of BoNT/F is altered; either K446 or S447 of BoNT/G is altered; either T444 or G445 of BoNT/G is altered; either E448 or Q449 of BoNT/G is altered; or either A457 or S458 of TeNT is altered.

In another embodiment, a naturally-occurring di-chain loop protease cleavage site is made inoperable by altering the two amino acids flanking the peptide bond cleaved by a naturally-occurring protease, i.e., $P_1$ and $P_{1'}$. In other aspects of this embodiment, both K448 and A449 of BoNT/A are altered; both S441 and L442 of BoNT/A are altered; both K441 and A442 of BoNT/B are altered; both G444 and I445 of BoNT/B are altered; both K449 and T450 of BoNT/C1 are altered; both S445 and L446 of BoNT/C1 are altered; both R445 and D446 of BoNT/D are altered; both K442 and N443 of BoNT/D are altered; both R422 and K423 of BoNT/E are altered; both K419 and G420 of BoNT/E are altered; both K423 and S424 of BoNT/E are altered; both K439 and A440 of BoNT/F are altered; both K436 and G437 of BoNT/F are altered; both K446 and S447 of BoNT/G are altered; both T444 and G445 of BoNT/G are altered; both E448 and Q449 of BoNT/G are altered; or both A457 and S458 of TeNT are altered.

In other aspects of this embodiment, a naturally-occurring di-chain loop protease cleavage site is made inoperable by altering, e.g., at least two amino acids within the dischain loop region; at least three amino acids within the dischain loop region; at least four amino acids within the dischain loop region; at least five amino acids within the dischain loop region; at least six amino acids within the dischain loop region; at least seven amino acids within the dischain loop region; at least eight amino acids within the dischain loop region; at least nine amino acids within the dischain loop region; at least ten amino acids within the dischain loop region; or at least 15 amino acids within the dischain loop region. In still other aspects of this embodiment, a naturally-occurring di-chain loop protease cleavage site is made inoperable by altering one of the amino acids flanking the peptide bond cleaved by a naturally-occurring protease and, e.g., at least one more amino acid within the dischain loop region; at least two more amino acids within the dischain loop region; at least three more amino acids within the dischain loop region; at least four more amino acids within the dischain loop region; at least five more amino acids within the dischain loop region; at least six more amino acids within the dischain loop region; at least seven more amino acids within the dischain loop region; at least eight more amino acids within the dischain loop region; at least nine more amino acids within the dischain loop region; at least ten more amino acids within the dischain loop region; at least 15 more amino acids within the dischain loop region. In yet other aspects of this embodiment, a naturally-occurring di-chain loop protease cleavage site is made inoperable by altering the two amino acids flanking the peptide bond cleaved by a naturally-occurring protease and, e.g., at least one more amino acid within the dischain loop region; at least two more amino acids within the dischain loop region; at least three more amino acids within the dischain loop region; at least four more amino acids within the dischain loop region; at least five more amino acids within the dischain loop region; at least six more amino acids within the dischain loop region; at least seven more amino acids within the dischain loop region; at least eight more amino acids within the dischain loop region; at least nine more amino acids within the dischain loop region; at least ten more amino acids within the dischain loop region; at least 15 more amino acids within the dischain loop region.

In other aspects of this embodiment, a naturally-occurring di-chain loop protease cleavage site is made inoperable by altering, e.g., at most two amino acids within the dischain loop region; at most three amino acids within the dischain loop region; at most four amino acids within the dischain loop region; at most five amino acids within the dischain loop region; at most six amino acids within the dischain loop region; at most seven amino acids within the dischain loop region; at most eight amino acids within the dischain loop region; at most nine amino acids within the dischain loop region; at most ten amino acids within the dischain loop region; or at most 15 amino acids within the dischain loop region. In still other aspects of this embodiment, a naturally-occurring di-chain loop protease cleavage site is made inoperable by altering one of the amino acids flanking the peptide bond cleaved by a naturally-occurring protease and, e.g., at most one more amino acid within the dischain loop region; at most two more amino acids within the dischain loop region; at most three more amino acids within the dischain loop region; at most four more amino acids within the dischain loop region; at most five more amino acids within the dischain loop region; at most six more amino acids within the dischain loop region; at most seven more amino acids within the dischain loop region; at most eight more amino acids within the dischain loop region; at most nine more amino acids within the dischain loop region; at most ten more amino acids within the dischain loop region; at most 15 more amino acids within the dischain loop region. In yet other aspects of this embodiment, a naturally-occurring di-chain loop protease cleavage site is made inoperable by altering the two amino acids flanking the peptide bond cleaved by a naturally-occurring protease and, e.g., at most one more amino acid within the dischain loop region; at most two more amino acids within the dischain loop region; at most three more amino acids within the dischain loop region; at most four more amino acids within the dischain loop region; at most five more amino acids within the dischain loop region; at most six more amino acids within the dischain loop region; at most seven more amino acids within the dischain loop region; at most eight more amino acids within the dischain loop region; at most nine more amino acids within the dischain loop region; at most ten more amino acids within the dischain loop region; at most 15 more amino acids within the dischain loop region.

It is envisioned that the di-chain loop region of a Clostridial toxin can be modified to include any and all Clostridial toxin substrate cleavage sites. In aspects of this embodiment, a di-chain loop of a Clostridial toxin disclosed in the present specification can be modified to comprise, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site. In other aspects of this embodiment, a di-chain loop of a Clostridial toxin, in addition to the naturally-occurring protease cleavage site, can be modified to comprise, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, or a TeNT substrate cleavage site. In still other aspects of this embodiment, a di-chain loop of a Clostridial toxin can be modified to replace a naturally-occurring protease cleavage site with, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site.

The location of the Clostridial toxin substrate cleavage site can be anywhere in the Clostridial toxin, with the proviso that cleavage of the site must occur between the two cysteine residues that form the single disulfide bridge of toxin. Thus, in aspects of this embodiment, location of a Clostridial toxin substrate cleavage site can be, e.g., anywhere in the BoNT/A of SEQ ID NO: 1, with the proviso that cleavage occurs between cysteine 430 and cysteine 454; anywhere in the BoNT/B of SEQ ID NO: 2, with the proviso that cleavage occurs between cysteine 437 and cysteine 446; anywhere in the BoNT/C1 of SEQ ID NO: 2, with the proviso that cleavage occurs between cysteine 437 and cysteine 453; anywhere in the BoNT/D of SEQ ID NO: 4, with the proviso that cleavage occurs between cysteine 437 and cysteine 450; anywhere in the BoNT/E of SEQ ID NO: 5, with the proviso that cleavage occurs between cysteine 412 and cysteine 426; anywhere in the BoNT/F of SEQ ID NO: 6, with the proviso that cleavage occurs between cysteine 429 and cysteine 445; anywhere in the BoNT/G of SEQ ID NO: 7, with the proviso that cleavage occurs between cysteine 436 and cysteine 450; or anywhere in the TeNT of SEQ ID NO: 8, with the proviso that cleavage occurs between cysteine 439 and cysteine 467.

It is understood that a modified Clostridial toxin disclosed in the present specification can optionally include one or more additional components. As a non-limiting example of an optional component, a modified Clostridial toxin can further comprise a flexible region comprising a flexible spacer. Non-limiting examples of a flexible spacer include, e.g., a G-spacer GGGGS (SEQ ID NO: 156) or an A-spacer EAAAK (SEQ ID NO: 157). A flexible region comprising flexible spacers can be used to adjust the length of a polypeptide region in order to optimize a characteristic, attribute or property of a polypeptide. Such a flexible region is operably-linked in-frame to the modified Clostridial toxin as a fusion protein. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present a ligand domain, thereby facilitating the binding of that ligand domain to its binding domain on a receptor.

Thus, in an embodiment, a modified Clostridial toxin disclosed in the present specification can further comprise a flexible region comprising a flexible spacer. In another embodiment, a modified Clostridial toxin disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a modified Clostridial toxin can comprise a flexible region comprising one or more copies of the same flexible spacers, one or more copies of different flexible-spacer regions, or any combination thereof.

As another non-limiting example of an optional component, a modified Clostridial toxin can further comprise an epitope-binding region. An epitope-binding region can be used in a wide variety of procedures involving, e.g., protein purification and protein visualization. Such an epitope-binding region is operably-linked in-frame to a modified Clostridial toxin as a fusion protein. Non-limiting examples of an epitope-binding region include, e.g., FLAG, Express™ (SEQ ID NO: 158), human Influenza virus hemagglutinin (HA) (SEQ ID NO: 159), human $p62^{c\text{-}Myc}$ protein (c-MYC) (SEQ ID NO: 160), Vesicular Stomatitis Virus Glycoprotein (VSV-G) (SEQ ID NO: 161), Substance P (SEQ ID NO: 162), glycoprotein-D precursor of Herpes simplex virus (HSV) (SEQ ID NO: 163), V5 (SEQ ID NO: 164), AU1 (SEQ ID NO: 165) and AU5 (SEQ ID NO: 166); affinity-binding, such as, e.g., polyhistidine (HIS) (SEQ ID NO: 167), streptavidin binding peptide (strep), and biotin or a biotinylation sequence; peptide-binding regions, such as, e.g., the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Epitope Tagging, pp. 17.90-17.93 (Sambrook and Russell, eds., MOLECULAR CLONING A LABORATORY MANUAL, Vol. 3, 3$^{rd}$ ed. 2001); ANTIBODIES: A LABORATORY MANUAL (Edward Harlow & David Lane, eds., Cold Spring Harbor Laboratory Press, 2$^{nd}$ ed. 1998); and USING ANTIBODIES: A LABORATORY MANUAL: PORTABLE PROTOCOL No. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a modified Clostridial toxin disclosed in the present specification can further comprise an epitope-binding region. In another embodiment, a modified Clostridial toxin disclosed in the present specification can further comprises a plurality of epitope-binding regions. In aspects of this embodiment, a modified Clostridial toxin can comprise, e.g., at least 1 epitope-binding region, at least 2 epitope-binding regions, at least 3 epitope-binding regions, at least 4 epitope-binding regions or at least 5 epitope-binding regions. In other aspects of this embodiment, a modified Clostridial toxin can comprise, e.g., at most 1 epitope-binding region, at most 2 epitope-binding regions, at most 3 epitope-binding regions, at most 4 epitope-binding regions or at most 5 epitope-binding regions. In another aspect of this embodiment, a modified Clostridial toxin can comprise one or more copies of the same epitope-binding region, one or more copies of different epitope-binding regions, or any combination thereof.

The location of an epitope-binding region can be in various positions, including, without limitation, at the amino terminus of a modified Clostridial toxin, within a modified Clostridial toxin, or at the carboxyl terminus of a modified Clostridial toxin. Thus, in an embodiment, an epitope-binding region is located at the amino-terminus of a modified Clostridial toxin. In such a location, a start methionine should be placed in front of the epitope-binding region. In addition, it is known in the art that when adding a polypeptide that is operationally-linked to the amino terminus of another polypeptide comprising the start methionine that the original methionine residue can be deleted. This is due to the fact that the added polypeptide will contain a new start methionine and that the original start methionine may reduce optimal expression of the fusion protein. In aspects of this embodiment, an epitope-binding region located at the amino-terminus of a modified Clostridial toxin disclosed in the present specification can be, e.g., a FLAG, Express™ epitope-binding region, a human Influenza virus hemagglutinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In another embodiment, an epitope-binding region is located at the carboxyl-terminus of a modified Clostridial toxin. In aspects of this embodiment, an epitope-binding region located at the carboxyl-terminus of a modified Clostridial toxin disclosed in the present specification can be, e.g., a FLAG, Express™ epitope-binding region, a human Influenza virus hemagglutinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

As still another non-limiting example of an optional component, a modified Clostridial toxin can further comprise an exogenous protease cleavage site. An exogenous protease cleavage site can be used in a wide variety of procedures involving, e.g., removal of an epitope-binding region by proteolytic cleavage. Such an exogenous protease cleavage site is operably-linked in-frame to a modified Clostridial toxin as a fusion protein. Non-limiting examples of protease cleavage sites include, e.g., an enterokinase cleavage site (Table 9); a Thrombin cleavage site (Table 9); a Factor Xa cleavage site (Table 9); a human rhinovirus 3C protease cleavage site (Table 9); a tobacco etch virus (TEV) protease cleavage site (Table 9); a dipeptidyl aminopeptidase cleavage site and a small ubiquitin-like modifier (SUMO)/ubiquitin-like protein-1(ULP-1) protease cleavage site, such as, e.g., MAD-SEVNQEAKPEVKPEVKPETHINLKVSDGSS EIFFKIKKTTPLRRLMEAFAKRQGKEMD-SLRFLYDGIRIQADQTPEDLDMEDNDIIEAHREQIGG (SEQ ID. NO: 185).

TABLE 9

Exogenous Protease Cleavage Sites

| Protease Cleavage Site | Consensus Sequence | Non-limiting Examples | SEQ ID NO: |
|---|---|---|---|
| Bovine enterokinase | DDDK* | DDDDK* | 168 |
| Tobacco Etch Virus (TEV) | E P$^5$ P$^5$YP$^2$Q* (G/S), where P$^2$, P$^4$ and P$^5$ can be any amino acid | ENLYFQ*G | 169 |
|  |  | ENLYFQ*S | 170 |
|  |  | ENIYTQ*G | 171 |
|  |  | ENIYTQ*S | 172 |
|  |  | ENIYLQ*G | 173 |
|  |  | ENIYLQ*S | 174 |
|  |  | ENVYFQ*G | 175 |
|  |  | ENVYSQ*S | 176 |
|  |  | ENVYSQ*G | 177 |
|  |  | ENVYSQ*S | 178 |
| Human Rhinovirus 3C | P$^5$P$^4$LFQ*GP where P$^4$ is G, A, V, L, I, M, S or T and P$^5$ can any amino acid, with D or E preferred. | EALFQ*GP | 179 |
|  |  | EVLFQ*GP | 180 |
|  |  | ELLFQ*GP | 181 |
|  |  | DALFQ*GP | 182 |
|  |  | DVLFQ*GP | 183 |
|  |  | DLLFQ*GP | 184 |

TABLE 9-continued

Exogenous Protease Cleavage Sites

| Protease Cleavage Site | Consensus Sequence | Non-limiting Examples | SEQ ID NO: |
|---|---|---|---|
| SUMO/ULP-1 | Tertiary structure | polypeptide-G* | 185 |
| Thrombin | $P^3P^2(R/K)*P^1$, where $P^3$ is any amino acid and $P^2$ or $P^1$ is G with the other position being any amino acid | GVR*G<br>SAR*G<br>SLR*G<br>DGR*I<br>QGK*I | 186<br>187<br>188<br>189<br>190 |
| Thrombin | $P^4P^3P(R/K)*P^{1'}P^{2'}$ where $P^{1'}$ and $P^{2'}$ can be any amino acid except for acidic amino acids like D or E; and $P^3$ and $P^4$ are hydrophobic amino acids like F, L, I, Y, W, V, M, P, C or A | LVPR*GS<br>LVPK*GS<br>FIPR*TF<br>VLPR*SF<br>IVPR*SF<br>IVPR*GY<br>VVPR*GV<br>VLPR*LI<br>VMPR*SL<br>MFPR*SL | 191<br>192<br>193<br>194<br>195<br>196<br>197<br>198<br>199<br>200 |
| Coagulation Factor Xa | I(E/D)GR* | IDGR*<br>IEGR* | 201<br>202 |

An asterisk (*) indicates the peptide bond of the $P_1$–$P_{1'}$ cleavage site that is cleaved by the indicated protease.

Thus, in an embodiment, a modified Clostridial toxin disclosed in the present specification can further comprise an exogenous protease cleavage site. In another embodiment, a modified Clostridial toxin disclosed in the present specification can further comprises a plurality of exogenous protease cleavage sites. In aspects of this embodiment, a modified Clostridial toxin can comprise, e.g., at least 1 exogenous protease cleavage site, at least 2 exogenous protease cleavage sites, at least 3 exogenous protease cleavage sites, at least 4 exogenous protease cleavage sites or at least 5 exogenous protease cleavage sites. In other aspects of this embodiment, a modified Clostridial toxin can comprise, e.g., at most 1 exogenous protease cleavage site, at most 2 exogenous protease cleavage sites, at most 3 exogenous protease cleavage sites, at most 4 exogenous protease cleavage sites or at most 5 exogenous protease cleavage sites. In another aspect of this embodiment, a modified Clostridial toxin can comprise one or more copies of the same exogenous protease cleavage site, one or more copies of different exogenous protease cleavage sites, or any combination thereof.

The location of an exogenous protease cleavage site may be in a variety of positions, including, without limitation, between an epitope-binding region and a modified Clostridial toxin in order to facilitate removal of the epitope-binding region by proteolytic cleavage. It is envisioned that an exogenous protease cleavage site can be used to remove an epitope-binding region. As mentioned above, epitope binding regions can be used in protein purification procedures and it is often desirable to remove such epitope binding regions after the protein is purified. A common way of doing so is to have a protease cleavage site in between the protein of interest and the epitope binding region, whereby proteolytic cleavage of the protease cleavage site separates the protein of interest from the epitope binding region. Non-limiting examples of protease cleavage sites used for the removal of epitope-binding regions as well as well-characterized proteases, reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. The selection, making and use of an appropriate protease cleavage site are routine procedures within the scope of one skilled in the art and from the teaching herein.

Thus, in an embodiment, an exogenous protease cleavage site is located between an epitope-binding peptide and a modified Clostridial toxin. In other aspects of this embodiment, a bovine enterokinase cleavage site is located between an epitope-binding region and a modified Clostridial toxin, a Tobacco Etch Virus protease cleavage site is located between an epitope-binding region and a modified Clostridial toxin, a Human Rhinovirus 3C protease cleavage site is located between an epitope-binding region and a modified Clostridial toxin, a SUMO/ULP-1 protease cleavage site is located between an epitope-binding region and a modified Clostridial toxin, a Thrombin protease cleavage site is located between an epitope-binding region and a modified Clostridial toxin, or a Coagulation Factor Xa protease cleavage site is located between an epitope-binding region and a modified Clostridial toxin. In other aspects of the embodiment, the bovine enterokinase protease cleavage site located between an epitope-binding region and a modified Clostridial toxin comprises SEQ ID NO: 168. In other aspects of the embodiment, the Tobacco Etch Virus protease cleavage site located between an epitope-binding region and a modified Clostridial toxin comprises SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177 or SEQ ID NO: 178. In still other aspects of the embodiment, the Human Rhinovirus 3C protease cleavage site located between an epitope-binding region and a modified Clostridial toxin comprises SEQ ID NO: 179, SEQ ID NO: 180, SEQ ID NO: 181, SEQ ID NO: 182, SEQ ID NO: 183 or SEQ ID NO: 184. In yet other aspects of the embodiment, the SUMO/ULP-1 protease cleavage site located between an epitope-binding region and a modified Clostridial toxin comprises SEQ ID NO: 185. In further other aspects of the embodiment, the Thrombin protease cleavage site located between an epitope-binding region and a modified Clostridial toxin comprises SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199 or SEQ ID NO: 200. In other aspects of the embodiment, the Coagulation Factor Xa protease cleavage site located between an epitope-binding region and a modified Clostridial toxin comprises SEQ ID NO: 201 or SEQ ID NO: 202.

Aspects of the present invention provide, in part modified Clostridial toxins. As used herein, the term "modified Clostridial toxin" means any naturally-occurring Clostridial toxin or non-naturally-occurring Clostridial toxin comprising at least the replacement of a naturally-occurring di-chain protease cleavage site with a Clostridial toxin substrate cleavage site as disclosed in the present specification, or the addition of a Clostridial toxin substrate cleavage site as disclosed in the present specification into the di-chain loop region. Non-limiting examples of modified Clostridial toxins disclosed in the present specification include, e.g., a modified Clostridial toxin comprising a Clostridial toxin substrate cleavage site, where the substrate cleavage site replaced the naturally-occurring di-chain loop protease cleavage site; a modified Clostridial toxin comprising a Clostridial toxin substrate cleavage site, where the substrate cleavage site is added into the di-chain loop region; a modified Clostridial toxin comprising a Clostridial toxin substrate cleavage site and a cell binding domain having an enhanced cell binding activity capable of intoxicating a naturally occurring Clostridial toxin target cell, where the substrate cleavage site replaced the naturally-occurring di-chain loop protease cleavage site; a modified Clostridial toxin comprising a Clostridial toxin substrate cleavage site and a cell binding domain having an enhanced cell binding activity capable of intoxicating a naturally occurring Clostridial toxin target cell, where the substrate cleavage site is added into the di-chain loop region; a modified Clostridial toxin comprising a Clostridial toxin substrate cleavage site and a cell binding domain having an altered cell binding activity capable of intoxicating a naturally occurring Clostridial toxin target cell, where the substrate cleavage site replaced the naturally-occurring di-chain loop protease cleavage site; a modified Clostridial toxin comprising a Clostridial toxin substrate cleavage site and a cell binding domain having an altered cell binding activity capable of intoxicating a naturally occurring Clostridial toxin target cell, where the substrate cleavage site is added into the di-chain loop region; a modified Clostridial toxin comprising a Clostridial toxin substrate cleavage site and a cell binding domain having an altered cell binding activity capable of intoxicating a non-naturally occurring Clostridial toxin target cell, where the substrate cleavage site replaced the naturally-occurring di-chain loop protease cleavage site; and a modified Clostridial toxin comprising a Clostridial toxin substrate cleavage site and a cell binding domain having an altered cell binding activity capable of intoxicating a non-naturally occurring Clostridial toxin target cell, where the substrate cleavage site is added into the di-chain loop region.

Non-limiting examples of Clostridial toxin modifications disclosed in the present specification include, e.g., replacement of a naturally-occurring di-chain protease cleavage site with a Clostridial toxin substrate cleavage site, addition of a Clostridial toxin substrate cleavage site, addition of an exogenous protease cleavage site, replacement of an endogenous cell binding domain with a cell binding domain having an enhanced cell binding activity capable of intoxicating a naturally occurring Clostridial toxin target cell, addition of a cell binding domain having an enhanced cell binding activity capable of intoxicating a naturally occurring Clostridial toxin target cell, replacement of an endogenous cell binding domain with a cell binding domain with a cell binding domain having an altered cell binding activity capable of intoxicating a naturally occurring Clostridial toxin target cell, addition of a cell binding domain having an altered cell binding activity capable of intoxicating a naturally occurring Clostridial toxin target cell, replacement of an endogenous cell binding domain with a cell binding domain having an altered cell binding activity capable of intoxicating a non-naturally occurring Clostridial toxin target cell, addition of a cell binding domain having an altered cell binding activity capable of intoxicating a non-naturally occurring Clostridial toxin target cell, addition of an exogenous protease cleavage site, rearrangement of the enzymatic, translocation and binding domains, addition of a spacer region and addition of an epitope-binding region.

It is understood that all such modifications do not substantially affect the ability of a Clostridial toxin to intoxicate a cell. As used herein, the term "do not substantially affect" means a Clostridial toxin can still execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. In aspects of this embodiment, the modified Clostridial toxin is, e.g., at least 10% as toxic as a naturally-occurring Clostridial toxin, at least 20% as toxic as a naturally-occurring Clostridial toxin, at least 30% as toxic as a naturally-occurring Clostridial toxin, at least 40% as toxic as a naturally-occurring Clostridial toxin, at least 50% as toxic as a naturally-occurring Clostridial toxin, at least 60% as toxic as a naturally-occurring Clostridial toxin, at least 70% as toxic as a naturally-occurring Clostridial toxin, at least 80% as toxic as a naturally-occurring Clostridial toxin, at least 90% as toxic as a naturally-occurring Clostridial toxin or at least 95% as toxic as a naturally-occurring Clostridial toxin. In aspects of this embodiment, the modified Clostridial toxin is, e.g., at most 10% as toxic as a naturally-occurring Clostridial toxin, at most 20% as toxic as a naturally-occurring Clostridial toxin, at most 30% as toxic as a naturally-occurring Clostridial toxin, at most 40% as toxic as a naturally-occurring Clostridial toxin, at most 50% as toxic as a naturally-occurring Clostridial toxin, at most 60% as toxic as a naturally-occurring Clostridial toxin, at most 70% as toxic as a naturally-occurring Clostridial toxin, at most 80% as toxic as a naturally-occurring Clostridial toxin, at most 90% as toxic as a naturally-occurring Clostridial toxin or at most 95% as toxic as a naturally-occurring Clostridial toxin.

Aspects of the present invention provide, in part, polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a modified Clostridial toxin disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagemid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Thus, in an embodiment, a polynucleotide molecule encodes a modified Clostridial toxin comprising a Clostridial toxin enzymatic domain, a Clostridial toxin translocation domain and a Clostridial toxin binding domain. In an aspect of this embodiment, a polynucleotide molecule encodes a Clostridial toxin comprises a naturally occurring Clostridial toxin variant, such as, e.g., a Clostridial toxin isoform or a Clostridial toxin subtype. In another aspect of this embodiment, a polynucleotide molecule encodes a Clostridial toxin comprises a non-naturally occurring Clostridial toxin variant, such as, e.g., a conservative Clostridial toxin variant, a non-conservative Clostridial toxin variant or an active Clostridial toxin fragment, or any combination thereof. In another aspect of this embodiment, a polynucleotide molecule encodes a Clostridial toxin comprises a Clostridial toxin enzymatic domain or an active fragment thereof, a Clostridial toxin translocation domain or an active fragment thereof, a Clostridial toxin binding domain or an active fragment thereof, or any combination thereof. In other aspects of this embodiment, a Clostridial toxins comprises a BoNT/A, a BoNT/B, a BoNT/C1, a BoNT/D, a BoNT/E, a BoNT/F, a BoNT/G or a TeNT.

In another embodiment, a polynucleotide molecule encodes a modified Clostridial toxin comprising a BoNT/A. In an aspect of this embodiment, a polynucleotide molecule encodes a BoNT/A comprising a BoNT/A enzymatic domain, a BoNT/A translocation domain and a BoNT/A binding domain. In another aspect of this embodiment, a polynucleotide molecule encodes a BoNT/A comprising SEQ ID NO: 1. In another aspect of this embodiment, a polynucleotide molecule encodes a BoNT/A comprising a naturally occurring BoNT/A variant, such as, e.g., a BoNT/A isoform or a BoNT/A subtype. In another aspect of this embodiment, a polynucleotide molecule encodes a BoNT/A comprising a naturally occurring BoNT/A variant of SEQ ID NO: 1, such as, e.g., a BoNT/A isoform of SEQ ID NO: 1 or a BoNT/A subtype of SEQ ID NO: 1. In still another aspect of this embodiment, a polynucleotide molecule encodes a BoNT/A comprising a non-naturally occurring BoNT/A variant, such as, e.g., a conservative BoNT/A variant, a non-conservative BoNT/A variant or an active BoNT/A fragment, or any combination thereof. In still another aspect of this embodiment, a polynucleotide molecule encodes a BoNT/A comprising a non-naturally occurring BoNT/A variant of SEQ ID NO: 1, such as, e.g., a conservative BoNT/A variant of SEQ ID NO: 1, a non-conservative BoNT/A variant of SEQ ID NO: 1 or an active BoNT/A fragment of SEQ ID NO: 1, or any combination thereof. In yet another aspect of this embodiment, a polynucleotide molecule encodes a BoNT/A comprising a BoNT/A enzymatic domain or an active fragment thereof, a BoNT/A translocation domain or an active fragment thereof, a BoNT/A binding domain or an active fragment thereof, or any combination thereof. In yet another aspect of this embodiment, a BoNT/A comprising a BoNT/A enzymatic domain of amino acids 1-448 from SEQ ID NO: 1 or an active fragment thereof, a BoNT/A translocation domain of amino acids 449-860 from SEQ ID NO: 1 or an active fragment thereof, a BoNT/A binding domain of amino acids 861-1296 from SEQ ID NO: 1 or an active fragment thereof, and any combination thereof.

In other aspects of this embodiment, a polynucleotide molecule encodes a BoNT/A comprising a polypeptide having, e.g., at least 70% amino acid identity with SEQ ID NO: 1, at least 75% amino acid identity with the SEQ ID NO: 1, at least 80% amino acid identity with SEQ ID NO: 1, at least 85% amino acid identity with SEQ ID NO: 1, at least 90% amino acid identity with SEQ ID NO: 1 or at least 95% amino acid identity with SEQ ID NO: 1. In yet other aspects of this embodiment, a polynucleotide molecule encodes a BoNT/A comprising a polypeptide having, e.g., at most 70% amino acid identity with SEQ ID NO: 1, at most 75% amino acid identity with the SEQ ID NO: 1, at most 80% amino acid identity with SEQ ID NO: 1, at most 85% amino acid identity with SEQ ID NO: 1, at most 90% amino acid identity with SEQ ID NO: 1 or at most 95% amino acid identity with SEQ ID NO: 1.

In other aspects of this embodiment, a polynucleotide molecule encodes a BoNT/A comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 1. In other aspects of this embodiment, a polynucleotide molecule encodes a BoNT/A comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 1. In yet other aspects of this embodiment, a polynucleotide molecule encodes a BoNT/A comprising a polypeptide having, e.g., at most one, two, three, four, five, six, seven, eight, nine, 10, 20, 30, 40, 50, 100, 200 or 500 non-contiguous amino acid deletions relative to SEQ ID NO: 1. In other aspects of this embodiment, a polynucleotide molecule encodes a BoNT/A comprising a polypeptide having, e.g., at least one, two, three, four, five, six, seven, eight, nine, 10, 20, 30, 40, 50, 100, 200 or 500 non-contiguous amino acid deletions relative to SEQ ID NO: 1. In still other aspects of this embodiment, a polynucleotide molecule encodes a BoNT/A comprising a polypeptide having, e.g., at most one, two, three, four, five, six, seven, eight, nine, 10, 20, 30, 40, 50, 100, 200 or 500 non-contiguous amino acid additions relative to SEQ ID NO: 1. In other aspects of this embodiment, a polynucleotide molecule encodes a BoNT/A comprising a polypeptide having, e.g., at least one, two, three, four, five, six, seven, eight, nine, 10, 20, 30, 40, 50, 100, 200 or 500 non-contiguous amino acid additions relative to SEQ ID NO: 1.

In other aspects of this embodiment, a polynucleotide molecule encodes a BoNT/A comprising a polypeptide having, e.g., at most one, two, three, four, five, six, seven, eight, nine, 10, 20, 30, 40, 50, 100, 200 or 500 contiguous amino acid substitutions relative to SEQ ID NO: 1. In other aspects of this embodiment, a polynucleotide molecule encodes a BoNT/A comprising a polypeptide having, e.g., at least one, two, three, four, five, six, seven, eight, nine, 10, 20, 30, 40, 50, 100, 200 or 500 contiguous amino acid substitutions relative to SEQ ID NO: 1. In yet other aspects of this embodiment, a polynucleotide molecule encodes a BoNT/A comprising a polypeptide having, e.g., at most one, two, three, four, five, six, seven, eight, nine, 10, 20, 30, 40, 50, 100, 200 or 500 contiguous amino acid deletions relative to SEQ ID NO: 1. In other aspects of this embodiment, a polynucleotide molecule encodes a BoNT/A comprising a polypeptide having, e.g., at least one, two, three, four, five, six, seven, eight, nine, 10, 20, 30, 40, 50, 100, 200 or 500 contiguous amino acid deletions relative to SEQ ID NO: 1. In still other aspects of this embodiment, a polynucleotide molecule encodes a BoNT/A comprising a polypeptide having, e.g., at most one, two, three, four, five, six, seven, eight, nine, 10, 20, 30, 40, 50, 100, 200 or 500 contiguous amino acid additions relative to SEQ ID NO: 1. In other aspects of this embodiment, a polynucleotide molecule encodes a BoNT/A comprising a polypeptide having, e.g., at least one, two, three, four, five, six, seven, eight, nine, 10, 20, 30, 40, 50, 100, 200 or 500 contiguous amino acid additions relative to SEQ ID NO: 1.

In another embodiment, a polynucleotide molecule encodes a modified Clostridial toxin comprising a BoNT/B. In an aspect of this embodiment, a polynucleotide molecule encodes a BoNT/B comprising a BoNT/B enzymatic domain, a BoNT/B translocation domain and a BoNT/B binding domain. In another aspect of this embodiment, a polynucleotide molecule encodes a BoNT/B comprising SEQ ID NO: 2. In another aspect of this embodiment, a polynucleotide molecule encodes a BoNT/B comprising a naturally occurring BoNT/B variant, such as, e.g., a BoNT/B isoform or a BoNT/B subtype. In another aspect of this embodiment, a polynucleotide molecule encodes a BoNT/B comprising a naturally occurring BoNT/B variant of SEQ ID NO: 2, such as, e.g., a BoNT/B isoform of SEQ ID NO: 2 or a BoNT/B subtype of SEQ ID NO: 2. In still another aspect of this embodiment, a polynucleotide molecule encodes a BoNT/B comprising a non-naturally occurring BoNT/B variant, such as, e.g., a conservative BoNT/B variant, a non-conservative BoNT/B variant or an active BoNT/B fragment, or any combination thereof. In still another aspect of this embodiment, a polynucleotide molecule encodes a BoNT/B comprising a non-naturally occurring BoNT/B variant of SEQ ID NO: 2, such as, e.g., a conservative BoNT/B variant of SEQ ID NO: 2, a non-conservative BoNT/B variant of SEQ ID NO: 2 or an active BoNT/B fragment of SEQ ID NO: 2, or any combination thereof. In yet another aspect of this embodiment, a BoNT/B comprising a BoNT/B enzymatic domain or an active fragment thereof, a BoNT/B translocation domain or active fragment thereof, a BoNT/B binding domain or active fragment thereof, and any combination thereof. In yet another aspect of this embodiment, a BoNT/B comprising a BoNT/B enzymatic domain of amino acids 1-441 from SEQ ID NO: 2 or active fragment thereof, a BoNT/B translocation domain of amino acids 442-847 from SEQ ID NO: 2 or active fragment thereof, a BoNT/B binding domain of amino acids 848-1291 from SEQ ID NO: 2 or active fragment thereof, and any combination thereof.

In other aspects of this embodiment, a polynucleotide molecule encodes a BoNT/B comprising a polypeptide having, e.g., at least 70% amino acid identity with SEQ ID NO: 2, at least 75% amino acid identity with the SEQ ID NO: 2, at least 80% amino acid identity with SEQ ID NO: 2, at least 85% amino acid identity with SEQ ID NO: 2, at least 90% amino acid identity with SEQ ID NO: 2 or at least 95% amino acid identity with SEQ ID NO: 2. In yet other aspects of this embodiment, a polynucleotide molecule encodes a BoNT/B comprising a polypeptide having, e.g., at most 70% amino acid identity with SEQ ID NO: 2, at most 75% amino acid identity with the SEQ ID NO: 2, at most 80% amino acid identity with SEQ ID NO: 2, at most 85% amino acid identity with SEQ ID NO: 2, at most 90% amino acid identity with SEQ ID NO: 2 or at most 95% amino acid identity with SEQ ID NO: 2.

In other aspects of this embodiment, a polynucleotide molecule encodes a BoNT/B comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 2. In other aspects of this embodiment, a polynucleotide molecule encodes a BoNT/B comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 2. In yet other aspects of this embodiment, a polynucleotide molecule encodes a BoNT/B comprising a polypeptide having, e.g., at most one, two, three, four, five, six, seven, eight, nine, 10, 20, 30, 40, 50, 100, 200 or 500 non-contiguous amino acid deletions relative to SEQ ID NO: 2. In other aspects of this embodiment, a polynucleotide molecule encodes a BoNT/B comprising a polypeptide having, e.g., at least one, two, three, four, five, six, seven, eight, nine, 10, 20, 30, 40, 50, 100, 200 or 500 non-contiguous amino acid deletions relative to SEQ ID NO: 2. In still other aspects of this embodiment, a polynucleotide molecule encodes a BoNT/B comprising a polypeptide having, e.g., at most one, two, three, four, five, six, seven, eight, nine, 10, 20, 30, 40, 50, 100, 200 or 500 non-contiguous amino acid additions relative to SEQ ID NO: 2. In other aspects of this embodiment, a polynucleotide molecule encodes a BoNT/B comprising a polypeptide having, e.g., at least one, two, three, four, five, six, seven, eight, nine, 10, 20, 30, 40, 50, 100, 200 or 500 non-contiguous amino acid additions relative to SEQ ID NO: 2.

In other aspects of this embodiment, a polynucleotide molecule encodes a BoNT/B comprising a polypeptide having, e.g., at most one, two, three, four, five, six, seven, eight, nine, 10, 20, 30, 40, 50, 100, 200 or 500 contiguous amino acid substitutions relative to SEQ ID NO: 2. In other aspects of this embodiment, a polynucleotide molecule encodes a BoNT/B comprising a polypeptide having, e.g., at least one, two, three, four, five, six, seven, eight, nine, 10, 20, 30, 40, 50, 100, 200 or 500 contiguous amino acid substitutions relative to SEQ ID NO: 2. In yet other aspects of this embodiment, a polynucleotide molecule encodes a BoNT/B comprising a polypeptide having, e.g., at most one, two, three, four, five, six, seven, eight, nine, 10, 20, 30, 40, 50, 100, 200 or 500 contiguous amino acid deletions relative to SEQ ID NO: 2. In other aspects of this embodiment, a polynucleotide molecule encodes a BoNT/B comprising a polypeptide having, e.g., at least one, two, three, four, five, six, seven, eight, nine, 10, 20, 30, 40, 50, 100, 200 or 500 contiguous amino acid deletions relative to SEQ ID NO: 2. In still other aspects of this embodiment, a polynucleotide molecule encodes a BoNT/B comprising a polypeptide having, e.g., at most one, two, three, four, five, six, seven, eight, nine, 10, 20, 30, 40, 50, 100, 200 or 500 contiguous amino acid additions relative to SEQ ID NO: 2. In other aspects of this embodiment, a polynucleotide molecule encodes a BoNT/B comprising a polypeptide having, e.g., at least one, two, three, four, five, six, seven, eight, nine, 10, 20, 30, 40, 50, 100, 200 or 500 contiguous amino acid additions relative to SEQ ID NO: 2.

In another embodiment, a polynucleotide molecule encodes a modified Clostridial toxin comprising a BoNT/C1. In an aspect of this embodiment, a polynucleotide molecule encodes a BoNT/C1 comprising a BoNT/C1 enzymatic domain, a BoNT/C1 translocation domain and a BoNT/C1 binding domain. In another aspect of this embodiment, a polynucleotide molecule encodes a BoNT/C1 comprising SEQ ID NO: 3. In another aspect of this embodiment, a polynucleotide molecule encodes a BoNT/C1 comprising a naturally occurring BoNT/C1 variant, such as, e.g., a BoNT/C1 isoform or a BoNT/C1 subtype. In another aspect of this embodiment, a polynucleotide molecule encodes a BoNT/C1 comprising a naturally occurring BoNT/C1 variant of SEQ ID NO: 3, such as, e.g., a BoNT/C1 isoform of SEQ ID NO: 3 or a BoNT/C1 subtype of SEQ ID NO: 3. In still another aspect of this embodiment, a polynucleotide molecule encodes a BoNT/C1 comprising a non-naturally occurring BoNT/C1 variant, such as, e.g., a conservative BoNT/C1 variant, a non-conservative BoNT/C1 variant or an active BoNT/C1 fragment, or any combination thereof. In still another aspect of this embodiment, a polynucleotide molecule encodes a BoNT/C1 comprising a non-naturally occurring BoNT/C1 variant of SEQ ID NO: 3, such as, e.g., a conservative BoNT/C1 variant of SEQ ID NO: 3, a non-conservative BoNT/C1 variant of SEQ ID NO: 3 or an active BoNT/C1 fragment of SEQ ID NO: 3, or any combination thereof. In yet another aspect of this embodiment, a polynucleotide molecule encodes a BoNT/C1 comprising a BoNT/C1 enzymatic domain or active fragment thereof, a BoNT/C1 translocation domain or active fragment thereof, a BoNT/C1 binding domain or active fragment thereof, and any combination thereof. In yet another aspect of this embodiment, a polynucleotide molecule encodes a BoNT/C1 comprising a BoNT/C1 enzymatic domain of amino acid 1-449 from SEQ ID NO: 3 or active fragment thereof, a BoNT/C1 translocation domain of amino acids 450-855 from SEQ ID NO: 3 or active fragment thereof, a BoNT/C1 binding domain of amino acids 856-1291 from SEQ ID NO: 3 or active fragment thereof, and any combination thereof.

In other aspects of this embodiment, a polynucleotide molecule encodes a BoNT/C1 comprising a polypeptide having, e.g., at least 70% amino acid identity with SEQ ID NO: 3, at least 75% amino acid identity with the SEQ ID NO: 3, at least 80% amino acid identity with SEQ ID NO: 3, at least 85% amino acid identity with SEQ ID NO: 3, at least 90% amino acid identity with SEQ ID NO: 3 or at least 95% amino acid identity with SEQ ID NO: 3. In yet other aspects of this embodiment, a polynucleotide molecule encodes a BoNT/C1 comprising a polypeptide having, e.g., at most 70% amino acid identity with SEQ ID NO: 3, at most 75% amino acid identity with the SEQ ID NO: 3, at most 80% amino acid identity with SEQ ID NO: 3, at most 85% amino acid identity with SEQ ID NO: 3, at most 90% amino acid identity with SEQ ID NO: 3 or at most 95% amino acid identity with SEQ ID NO: 3.

In other aspects of this embodiment, a polynucleotide molecule encodes a BoNT/C1 comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 3. In other aspects of this embodiment, a polynucleotide molecule encodes a BoNT/C1 comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 3. In yet other aspects of this embodiment, a polynucleotide molecule encodes a BoNT/C1 comprising a polypeptide having, e.g., at most one, two, three, four, five, six, seven, eight, nine, 10, 20, 30, 40, 50, 100, 200 or 500 non-contiguous amino acid deletions relative to SEQ ID NO: 3. In other aspects of this embodiment, a polynucleotide molecule encodes a BoNT/C1 comprising a polypeptide having, e.g., at least one, two, three, four, five, six, seven, eight, nine, 10, 20, 30, 40, 50, 100, 200 or 500 non-contiguous amino acid deletions relative to SEQ ID NO: 3. In still other aspects of this embodiment, a polynucleotide molecule encodes a BoNT/C1 comprising a polypeptide having, e.g., at most one, two, three, four, five, six, seven, eight, nine, 10, 20, 30, 40, 50, 100, 200 or 500 non-contiguous amino acid additions relative to SEQ ID NO: 3. In other aspects of this embodiment, a polynucleotide molecule encodes a BoNT/C1 comprising a polypeptide having, e.g., at least one, two, three, four, five, six, seven, eight, nine, 10, 20, 30, 40, 50, 100, 200 or 500 non-contiguous amino acid additions relative to SEQ ID NO: 3.

In other aspects of this embodiment, a polynucleotide molecule encodes a BoNT/C1 comprising a polypeptide having, e.g., at most one, two, three, four, five, six, seven, eight, nine, 10, 20, 30, 40, 50, 100, 200 or 500 contiguous amino acid substitutions relative to SEQ ID NO: 3. In other aspects of this embodiment, a polynucleotide molecule encodes a BoNT/C1 comprising a polypeptide having, e.g., at least one, two, three, four, five, six, seven, eight, nine, 10, 20, 30, 40, 50, 100, 200 or 500 contiguous amino acid substitutions relative to SEQ ID NO: 3. In yet other aspects of this embodiment, a polynucleotide molecule encodes a BoNT/C1 comprising a polypeptide having, e.g., at most one, two, three, four, five, six, seven, eight, nine, 10, 20, 30, 40, 50, 100, 200 or 500 contiguous amino acid deletions relative to SEQ ID NO: 3. In other aspects of this embodiment, a polynucleotide molecule encodes a BoNT/C1 comprising a polypeptide having, e.g., at least one, two, three, four, five, six, seven, eight, nine, 10, 20, 30, 40, 50, 100, 200 or 500 contiguous amino acid deletions relative to SEQ ID NO: 3. In still other aspects of this embodiment, a polynucleotide molecule encodes a BoNT/C1 comprising a polypeptide having, e.g., at most one, two, three, four, five, six, seven, eight, nine, 10, 20, 30, 40, 50, 100, 200 or 500 contiguous amino acid additions relative to SEQ ID NO: 3. In other aspects of this embodiment, a polynucleotide molecule encodes a BoNT/C1 comprising a polypeptide having, e.g., at least one, two, three, four, five, six, seven, eight, nine, 10, 20, 30, 40, 50, 100, 200 or 500 contiguous amino acid additions relative to SEQ ID NO: 3.

In another embodiment, a polynucleotide molecule encodes a modified Clostridial toxin comprising a BoNT/D. In an aspect of this embodiment, a polynucleotide molecule encodes a BoNT/D comprising a BoNT/D enzymatic domain, a BoNT/D translocation domain and a BoNT/D binding domain. In another aspect of this embodiment, a polynucleotide molecule encodes a BoNT/D comprising SEQ ID NO: 4. In another aspect of this embodiment, a polynucleotide molecule encodes a BoNT/D comprising a naturally occurring BoNT/D variant, such as, e.g., a BoNT/D isoform or a BoNT/D subtype. In another aspect of this embodiment, a polynucleotide molecule encodes a BoNT/D comprising a naturally occurring BoNT/D variant of SEQ ID NO: 4, such as, e.g., a BoNT/D isoform of SEQ ID NO: 4 or a BoNT/D subtype of SEQ ID NO: 4. In still another aspect of this embodiment, a polynucleotide molecule encodes a BoNT/D comprising a non-naturally occurring BoNT/D variant, such as, e.g., a conservative BoNT/D variant, a non-conservative BoNT/D variant or an active BoNT/D fragment, or any combination thereof. In still another aspect of this embodiment, a polynucleotide molecule encodes a BoNT/D comprising a non-naturally occurring BoNT/D variant of SEQ ID NO: 4, such as, e.g., a conservative BoNT/D variant of SEQ ID NO: 4, a non-conservative BoNT/D variant of SEQ ID NO: 4 or an active BoNT/D fragment of SEQ ID NO: 4, or any combination thereof. In yet another aspect of this embodiment, a polynucleotide molecule encodes a BoNT/D comprising a BoNT/D enzymatic domain or an active fragment thereof, a BoNT/D translocation domain or an active fragment thereof, a BoNT/D binding domain or an active fragment thereof, or any combination thereof. In yet another aspect of this embodiment, a BoNT/D comprising a BoNT/D enzymatic domain of amino acids 1-442 from SEQ ID NO: 4 or an active fragment thereof, a BoNT/D translocation domain of amino acids 443-851 from SEQ ID NO: 4 or an active fragment thereof, a BoNT/D binding domain of amino acids 852-1276 from SEQ ID NO: 4 or an active fragment thereof, and any combination thereof.

In other aspects of this embodiment, a polynucleotide molecule encodes a BoNT/D comprising a polypeptide having, e.g., at least 70% amino acid identity with SEQ ID NO: 4, at least 75% amino acid identity with the SEQ ID NO: 4, at least 80% amino acid identity with SEQ ID NO: 4, at least 85% amino acid identity with SEQ ID NO: 4, at least 90% amino acid identity with SEQ ID NO: 4 or at least 95% amino acid identity with SEQ ID NO: 4. In yet other aspects of this embodiment, a polynucleotide molecule encodes a BoNT/D comprising a polypeptide having, e.g., at most 70% amino acid identity with SEQ ID NO: 4, at most 75% amino acid identity with the SEQ ID NO: 4, at most 80% amino acid identity with SEQ ID NO: 4, at most 85% amino acid identity with SEQ ID NO: 4, at most 90% amino acid identity with SEQ ID NO: 4 or at most 95% amino acid identity with SEQ ID NO: 4.

In other aspects of this embodiment, a polynucleotide molecule encodes a BoNT/D comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 4. In other aspects of this embodiment, a polynucleotide molecule encodes a BoNT/D comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 4. In yet other aspects of this embodiment, a polynucleotide molecule encodes a BoNT/D comprising a polypeptide having, e.g., at most one, two, three, four, five, six, seven, eight, nine, 10, 20, 30, 40, 50, 100, 200 or 500 non-contiguous amino acid deletions relative to SEQ ID NO: 4. In other aspects of this embodiment, a polynucleotide molecule encodes a BoNT/D comprising a polypeptide having, e.g., at least one, two, three, four, five, six, seven, eight, nine, 10, 20, 30, 40, 50, 100, 200 or 500 non-contiguous amino acid deletions relative to SEQ ID NO: 4. In still other aspects of this embodiment, a polynucleotide molecule encodes a BoNT/D comprising a polypeptide having, e.g., at most one, two, three, four, five, six, seven, eight, nine, 10, 20, 30, 40, 50, 100, 200 or 500 non-contiguous amino acid additions relative to SEQ ID NO: 4. In other aspects of this embodiment, a polynucleotide molecule encodes a BoNT/D comprising a polypeptide having, e.g., at least one, two, three, four, five, six, seven, eight, nine, 10, 20, 30, 40, 50, 100, 200 or 500 non-contiguous amino acid additions relative to SEQ ID NO: 4.

In other aspects of this embodiment, a polynucleotide molecule encodes a BoNT/D comprising a polypeptide having, e.g., at most one, two, three, four, five, six, seven, eight, nine, 10, 20, 30, 40, 50, 100, 200 or 500 contiguous amino acid substitutions relative to SEQ ID NO: 4. In other aspects of this embodiment, a polynucleotide molecule encodes a BoNT/D comprising a polypeptide having, e.g., at least one, two, three, four, five, six, seven, eight, nine, 10, 20, 30, 40, 50, 100, 200 or 500 contiguous amino acid substitutions relative to SEQ ID NO: 4. In yet other aspects of this embodiment, a polynucleotide molecule encodes a BoNT/D comprising a polypeptide having, e.g., at most one, two, three, four, five, six, seven, eight, nine, 10, 20, 30, 40, 50, 100, 200 or 500 contiguous amino acid deletions relative to SEQ ID NO: 4. In other aspects of this embodiment, a polynucleotide molecule encodes a BoNT/D comprising a polypeptide having, e.g., at least one, two, three, four, five, six, seven, eight, nine, 10, 20, 30, 40, 50, 100, 200 or 500 contiguous amino acid deletions relative to SEQ ID NO: 4. In still other aspects of this embodiment, a polynucleotide molecule encodes a BoNT/D comprising a polypeptide having, e.g., at most one, two, three, four, five, six, seven, eight, nine, 10, 20, 30, 40, 50, 100, 200 or 500 contiguous amino acid additions relative to SEQ ID NO: 4. In other aspects of this embodiment, a polynucleotide molecule encodes a BoNT/D comprising a polypeptide having, e.g., at least one, two, three, four, five, six, seven, eight, nine, 10, 20, 30, 40, 50, 100, 200 or 500 contiguous amino acid additions relative to SEQ ID NO: 4.

In another embodiment, a polynucleotide molecule encodes a modified Clostridial toxin comprising a BoNT/E. In an aspect of this embodiment, a polynucleotide molecule encodes a BoNT/E comprising a BoNT/E enzymatic domain, a BoNT/E translocation domain and a BoNT/E binding domain. In another aspect of this embodiment, a polynucleotide molecule encodes a BoNT/E comprising SEQ ID NO: 5. In another aspect of this embodiment, a polynucleotide molecule encodes a BoNT/E comprising a naturally occurring BoNT/E variant, such as, e.g., a BoNT/E isoform or a BoNT/E subtype. In another aspect of this embodiment, a polynucleotide molecule encodes a BoNT/E comprising a naturally occurring BoNT/E variant of SEQ ID NO: 5, such as, e.g., a BoNT/E isoform of SEQ ID NO: 5 or a BoNT/E subtype of SEQ ID NO: 5. In still another aspect of this embodiment, a polynucleotide molecule encodes a BoNT/E comprising a non-naturally occurring BoNT/E variant, such as, e.g., a conservative BoNT/E variant, a non-conservative BoNT/E variant or an active BoNT/E fragment, or any combination thereof. In still another aspect of this embodiment, a polynucleotide molecule encodes a BoNT/E comprising a non-naturally occurring BoNT/E variant of SEQ ID NO: 5, such as, e.g., a conservative BoNT/E variant of SEQ ID NO: 5, a non-conservative BoNT/E variant of SEQ ID NO: 5 or an active BoNT/E fragment of SEQ ID NO: 5, or any combination thereof. In yet another aspect of this embodiment, a BoNT/E comprising a BoNT/E enzymatic domain or an active fragment thereof, a BoNT/E translocation domain or active fragment thereof, a BoNT/E binding domain or active fragment thereof, and any combination thereof. In yet another aspect of this embodiment, a BoNT/E comprising a BoNT/E enzymatic domain of amino acids 1-422 from SEQ ID NO: 5 or active fragment thereof, a BoNT/E translocation domain of amino acids 423-834 from SEQ ID NO: 5 or active fragment thereof, a BoNT/E binding domain of amino acids 835-1252 from SEQ ID NO: 5 or active fragment thereof, and any combination thereof.

In other aspects of this embodiment, a polynucleotide molecule encodes a BoNT/E comprising a polypeptide having, e.g., at least 70% amino acid identity with SEQ ID NO: 5, at least 75% amino acid identity with the SEQ ID NO: 5, at least 80% amino acid identity with SEQ ID NO: 5, at least 85% amino acid identity with SEQ ID NO: 5, at least 90% amino acid identity with SEQ ID NO: 5 or at least 95% amino acid identity with SEQ ID NO: 5. In yet other aspects of this embodiment, a polynucleotide molecule encodes a BoNT/E comprising a polypeptide having, e.g., at most 70% amino acid identity with SEQ ID NO: 5, at most 75% amino acid identity with the SEQ ID NO: 5, at most 80% amino acid identity with SEQ ID NO: 5, at most 85% amino acid identity with SEQ ID NO: 5, at most 90% amino acid identity with SEQ ID NO: 5 or at most 95% amino acid identity with SEQ ID NO: 5.

In other aspects of this embodiment, a polynucleotide molecule encodes a BoNT/E comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 5. In other aspects of this embodiment, a polynucleotide molecule encodes a BoNT/E comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 5. In yet other aspects of this embodiment, a polynucleotide molecule encodes a BoNT/E comprising a polypeptide having, e.g., at most one, two, three, four, five, six, seven, eight, nine, 10, 20, 30, 40, 50, 100, 200 or 500 non-contiguous amino acid deletions relative to SEQ ID NO:

5. In other aspects of this embodiment, a polynucleotide molecule encodes a BoNT/E comprising a polypeptide having, e.g., at least one, two, three, four, five, six, seven, eight, nine, 10, 20, 30, 40, 50, 100, 200 or 500 non-contiguous amino acid deletions relative to SEQ ID NO: 5. In still other aspects of this embodiment, a polynucleotide molecule encodes a BoNT/E comprising a polypeptide having, e.g., at most one, two, three, four, five, six, seven, eight, nine, 10, 20, 30, 40, 50, 100, 200 or 500 non-contiguous amino acid additions relative to SEQ ID NO: 5. In other aspects of this embodiment, a polynucleotide molecule encodes a BoNT/E comprising a polypeptide having, e.g., at least one, two, three, four, five, six, seven, eight, nine, 10, 20, 30, 40, 50, 100, 200 or 500 non-contiguous amino acid additions relative to SEQ ID NO: 5.

In other aspects of this embodiment, a polynucleotide molecule encodes a BoNT/E comprising a polypeptide having, e.g., at most one, two, three, four, five, six, seven, eight, nine, 10, 20, 30, 40, 50, 100, 200 or 500 contiguous amino acid substitutions relative to SEQ ID NO: 5. In other aspects of this embodiment, a polynucleotide molecule encodes a BoNT/E comprising a polypeptide having, e.g., at least one, two, three, four, five, six, seven, eight, nine, 10, 20, 30, 40, 50, 100, 200 or 500 contiguous amino acid substitutions relative to SEQ ID NO: 5. In yet other aspects of this embodiment, a polynucleotide molecule encodes a BoNT/E comprising a polypeptide having, e.g., at most one, two, three, four, five, six, seven, eight, nine, 10, 20, 30, 40, 50, 100, 200 or 500 contiguous amino acid deletions relative to SEQ ID NO: 5. In other aspects of this embodiment, a polynucleotide molecule encodes a BoNT/E comprising a polypeptide having, e.g., at least one, two, three, four, five, six, seven, eight, nine, 10, 20, 30, 40, 50, 100, 200 or 500 contiguous amino acid deletions relative to SEQ ID NO: 5. In still other aspects of this embodiment, a polynucleotide molecule encodes a BoNT/E comprising a polypeptide having, e.g., at most one, two, three, four, five, six, seven, eight, nine, 10, 20, 30, 40, 50, 100, 200 or 500 contiguous amino acid additions relative to SEQ ID NO: 5. In other aspects of this embodiment, a polynucleotide molecule encodes a BoNT/E comprising a polypeptide having, e.g., at least one, two, three, four, five, six, seven, eight, nine, 10, 20, 30, 40, 50, 100, 200 or 500 contiguous amino acid additions relative to SEQ ID NO: 5.

In another embodiment, a polynucleotide molecule encodes a modified Clostridial toxin comprising a BoNT/F. In an aspect of this embodiment, a polynucleotide molecule encodes a BoNT/F comprising a BoNT/F enzymatic domain, a BoNT/F translocation domain and a BoNT/F binding domain. In another aspect of this embodiment, a polynucleotide molecule encodes a BoNT/F comprising SEQ ID NO: 6. In another aspect of this embodiment, a polynucleotide molecule encodes a BoNT/F comprising a naturally occurring BoNT/F variant, such as, e.g., a BoNT/F isoform or a BoNT/F subtype. In another aspect of this embodiment, a polynucleotide molecule encodes a BoNT/F comprising a naturally occurring BoNT/F variant of SEQ ID NO: 6, such as, e.g., a BoNT/F isoform of SEQ ID NO: 6 or a BoNT/F subtype of SEQ ID NO: 6. In still another aspect of this embodiment, a polynucleotide molecule encodes a BoNT/F comprising a non-naturally occurring BoNT/F variant, such as, e.g., a conservative BoNT/F variant, a non-conservative BoNT/F variant or an active BoNT/F fragment, or any combination thereof. In still another aspect of this embodiment, a polynucleotide molecule encodes a BoNT/F comprising a non-naturally occurring BoNT/F variant of SEQ ID NO: 6, such as, e.g., a conservative BoNT/F variant of SEQ ID NO: 6, a non-conservative BoNT/F variant of SEQ ID NO: 6 or an active BoNT/F fragment of SEQ ID NO: 6, or any combination thereof. In yet another aspect of this embodiment, a polynucleotide molecule encodes a BoNT/F comprising a BoNT/F enzymatic domain or active fragment thereof, a BoNT/F translocation domain or active fragment thereof, a BoNT/F binding domain or active fragment thereof, and any combination thereof. In yet another aspect of this embodiment, a polynucleotide molecule encodes a BoNT/F comprising a BoNT/F enzymatic domain of amino acid 1-436 from SEQ ID NO: 6 or active fragment thereof, a BoNT/F translocation domain of amino acids 437-852 from SEQ ID NO: 6 or active fragment thereof, a BoNT/F binding domain of amino acids 853-1274 from SEQ ID NO: 6 or active fragment thereof, and any combination thereof.

In other aspects of this embodiment, a polynucleotide molecule encodes a BoNT/F comprising a polypeptide having, e.g., at least 70% amino acid identity with SEQ ID NO: 6, at least 75% amino acid identity with the SEQ ID NO: 6, at least 80% amino acid identity with SEQ ID NO: 6, at least 85% amino acid identity with SEQ ID NO: 6, at least 90% amino acid identity with SEQ ID NO: 6 or at least 95% amino acid identity with SEQ ID NO: 6. In yet other aspects of this embodiment, a polynucleotide molecule encodes a BoNT/F comprising a polypeptide having, e.g., at most 70% amino acid identity with SEQ ID NO: 6, at most 75% amino acid identity with the SEQ ID NO: 6, at most 80% amino acid identity with SEQ ID NO: 6, at most 85% amino acid identity with SEQ ID NO: 6, at most 90% amino acid identity with SEQ ID NO: 6 or at most 95% amino acid identity with SEQ ID NO: 6.

In other aspects of this embodiment, a polynucleotide molecule encodes a BoNT/F comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 6. In other aspects of this embodiment, a polynucleotide molecule encodes a BoNT/F comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 6. In yet other aspects of this embodiment, a polynucleotide molecule encodes a BoNT/F comprising a polypeptide having, e.g., at most one, two, three, four, five, six, seven, eight, nine, 10, 20, 30, 40, 50, 100, 200 or 500 non-contiguous amino acid deletions relative to SEQ ID NO: 6. In other aspects of this embodiment, a polynucleotide molecule encodes a BoNT/F comprising a polypeptide having, e.g., at least one, two, three, four, five, six, seven, eight, nine, 10, 20, 30, 40, 50, 100, 200 or 500 non-contiguous amino acid deletions relative to SEQ ID NO: 6. In still other aspects of this embodiment, a polynucleotide molecule encodes a BoNT/F comprising a polypeptide having, e.g., at most one, two, three, four, five, six, seven, eight, nine, 10, 20, 30, 40, 50, 100, 200 or 500 non-contiguous amino acid additions relative to SEQ ID NO: 6. In other aspects of this embodiment, a polynucleotide molecule encodes a BoNT/F comprising a polypeptide having, e.g., at least one, two, three, four, five, six, seven, eight, nine, 10, 20, 30, 40, 50, 100, 200 or 500 non-contiguous amino acid additions relative to SEQ ID NO: 6.

In other aspects of this embodiment, a polynucleotide molecule encodes a BoNT/F comprising a polypeptide having, e.g., at most one, two, three, four, five, six, seven, eight, nine, 10, 20, 30, 40, 50, 100, 200 or 500 contiguous amino acid substitutions relative to SEQ ID NO: 6. In other aspects of this embodiment, a polynucleotide molecule encodes a BoNT/F comprising a polypeptide having, e.g., at least one, two, three, four, five, six, seven, eight, nine, 10, 20, 30, 40, 50, 100, 200 or 500 contiguous amino acid substitutions relative to SEQ ID NO: 6. In yet other aspects of this embodiment, a polynucleotide molecule encodes a BoNT/F comprising a polypeptide having, e.g., at most one, two, three, four, five, six, seven, eight, nine, 10, 20, 30, 40, 50, 100, 200 or 500 contiguous amino acid deletions relative to SEQ ID NO: 6. In other aspects of this embodiment, a polynucleotide molecule encodes a BoNT/F comprising a polypeptide having, e.g., at least one, two, three, four, five, six, seven, eight, nine, 10, 20, 30, 40, 50, 100, 200 or 500 contiguous amino acid deletions relative to SEQ ID NO: 6. In still other aspects of this embodiment, a polynucleotide molecule encodes a BoNT/F comprising a polypeptide having, e.g., at most one, two, three, four, five, six, seven, eight, nine, 10, 20, 30, 40, 50, 100, 200 or 500 contiguous amino acid additions relative to SEQ ID NO: 6. In other aspects of this embodiment, a polynucleotide molecule encodes a BoNT/F comprising a polypeptide having, e.g., at least one, two, three, four, five, six, seven, eight, nine, 10, 20, 30, 40, 50, 100, 200 or 500 contiguous amino acid additions relative to SEQ ID NO: 6.

In another embodiment, a polynucleotide molecule encodes a modified Clostridial toxin comprising a BoNT/G. In an aspect of this embodiment, a polynucleotide molecule encodes a BoNT/G comprising a BoNT/G enzymatic domain, a BoNT/G translocation domain and a BoNT/G binding domain. In another aspect of this embodiment, a polynucleotide molecule encodes a BoNT/G comprising SEQ ID NO: 7. In another aspect of this embodiment, a polynucleotide molecule encodes a BoNT/G comprising a naturally occurring BoNT/G variant, such as, e.g., a BoNT/G isoform or a BoNT/G subtype. In another aspect of this embodiment, a polynucleotide molecule encodes a BoNT/G comprising a naturally occurring BoNT/G variant of SEQ ID NO: 7, such as, e.g., a BoNT/G isoform of SEQ ID NO: 7 or a BoNT/G subtype of SEQ ID NO: 7. In still another aspect of this embodiment, a polynucleotide molecule encodes a BoNT/G comprising a non-naturally occurring BoNT/G variant, such as, e.g., a conservative BoNT/G variant, a non-conservative BoNT/G variant or an active BoNT/G fragment, or any combination thereof. In still another aspect of this embodiment, a polynucleotide molecule encodes a BoNT/D comprising a non-naturally occurring BoNT/G variant of SEQ ID NO: 7, such as, e.g., a conservative BoNT/G variant of SEQ ID NO: 7, a non-conservative BoNT/G variant of SEQ ID NO: 7 or an active BoNT/G fragment of SEQ ID NO: 7, or any combination thereof. In yet another aspect of this embodiment, a polynucleotide molecule encodes a BoNT/G comprising a BoNT/G enzymatic domain or an active fragment thereof, a BoNT/G translocation domain or an active fragment thereof, a BoNT/G binding domain or an active fragment thereof, or any combination thereof. In yet another aspect of this embodiment, a BoNT/G comprising a BoNT/G enzymatic domain of amino acids 1-442 from SEQ ID NO: 7 or an active fragment thereof, a BoNT/G translocation domain of amino acids 443-852 from SEQ ID NO: 7 or an active fragment thereof, a BoNT/G binding domain of amino acids 853-1297 from SEQ ID NO: 7 or an active fragment thereof, and any combination thereof.

In other aspects of this embodiment, a polynucleotide molecule encodes a BoNT/G comprising a polypeptide having, e.g., at least 70% amino acid identity with SEQ ID NO: 7, at least 75% amino acid identity with the SEQ ID NO: 7, at least 80% amino acid identity with SEQ ID NO: 7, at least 85% amino acid identity with SEQ ID NO: 7, at least 90% amino acid identity with SEQ ID NO: 7 or at least 95% amino acid identity with SEQ ID NO: 7. In yet other aspects of this embodiment, a polynucleotide molecule encodes a BoNT/G comprising a polypeptide having, e.g., at most 70% amino acid identity with SEQ ID NO: 7, at most 75% amino acid identity with the SEQ ID NO: 7, at most 80% amino acid identity with SEQ ID NO: 7, at most 85% amino acid identity with SEQ ID NO: 7, at most 90% amino acid identity with SEQ ID NO: 7 or at most 95% amino acid identity with SEQ ID NO: 7.

In other aspects of this embodiment, a polynucleotide molecule encodes a BoNT/G comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 7. In other aspects of this embodiment, a polynucleotide molecule encodes a BoNT/G comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 7. In yet other aspects of this embodiment, a polynucleotide molecule encodes a BoNT/G comprising a polypeptide having, e.g., at most one, two, three, four, five, six, seven, eight, nine, 10, 20, 30, 40, 50, 100, 200 or 500 non-contiguous amino acid deletions relative to SEQ ID NO: 7. In other aspects of this embodiment, a polynucleotide molecule encodes a BoNT/G comprising a polypeptide having, e.g., at least one, two, three, four, five, six, seven, eight, nine, 10, 20, 30, 40, 50, 100, 200 or 500 non-contiguous amino acid deletions relative to SEQ ID NO: 7. In still other aspects of this embodiment, a polynucleotide molecule encodes a BoNT/G comprising a polypeptide having, e.g., at most one, two, three, four, five, six, seven, eight, nine, 10, 20, 30, 40, 50, 100, 200 or 500 non-contiguous amino acid additions relative to SEQ ID NO: 7. In other aspects of this embodiment, a polynucleotide molecule encodes a BoNT/G comprising a polypeptide having, e.g., at least one, two, three, four, five, six, seven, eight, nine, 10, 20, 30, 40, 50, 100, 200 or 500 non-contiguous amino acid additions relative to SEQ ID NO: 7.

In other aspects of this embodiment, a polynucleotide molecule encodes a BoNT/G comprising a polypeptide having, e.g., at most one, two, three, four, five, six, seven, eight, nine, 10, 20, 30, 40, 50, 100, 200 or 500 contiguous amino acid substitutions relative to SEQ ID NO: 7. In other aspects of this embodiment, a polynucleotide molecule encodes a BoNT/G comprising a polypeptide having, e.g., at least one, two, three, four, five, six, seven, eight, nine, 10, 20, 30, 40, 50, 100, 200 or 500 contiguous amino acid substitutions relative to SEQ ID NO: 7. In yet other aspects of this embodiment, a polynucleotide molecule encodes a BoNT/G comprising a polypeptide having, e.g., at most one, two, three, four, five, six, seven, eight, nine, 10, 20, 30, 40, 50, 100, 200 or 500 contiguous amino acid deletions relative to SEQ ID NO: 7. In other aspects of this embodiment, a polynucleotide molecule encodes a BoNT/G comprising a polypeptide having, e.g., at least one, two, three, four, five, six, seven, eight, nine, 10, 20, 30, 40, 50, 100, 200 or 500 contiguous amino acid deletions relative to SEQ ID NO: 7. In still other aspects of this embodiment, a polynucleotide molecule encodes a BoNT/G comprising a polypeptide having, e.g., at most one, two, three, four, five, six, seven, eight, nine, 10, 20, 30, 40, 50, 100, 200 or 500 contiguous amino acid additions relative to SEQ ID NO: 7. In other aspects of this embodiment, a polynucleotide molecule encodes a BoNT/G comprising a polypeptide having, e.g., at least one, two, three, four, five, six, seven, eight, nine, 10, 20, 30, 40, 50, 100, 200 or 500 contiguous amino acid additions relative to SEQ ID NO: 7.

In another embodiment, a polynucleotide molecule encodes a modified Clostridial toxin comprising a TeNT. In an aspect of this embodiment, a polynucleotide molecule encodes a TeNT comprising a TeNT enzymatic domain, a TeNT translocation domain and a TeNT binding domain. In an aspect of this embodiment, a polynucleotide molecule encodes a TeNT comprising SEQ ID NO: 8. In another aspect of this embodiment, a polynucleotide molecule encodes a TeNT comprising a naturally occurring TeNT variant, such as, e.g., a TeNT isoform or a TeNT subtype. In another aspect of this embodiment, a polynucleotide molecule encodes a TeNT comprising a naturally occurring TeNT variant of SEQ ID NO: 8, such as, e.g., a TeNT isoform of SEQ ID NO: 8 or a TeNT subtype of SEQ ID NO: 8. In still another aspect of this embodiment, a polynucleotide molecule encodes a TeNT comprising a non-naturally occurring TeNT variant, such as, e.g., a conservative TeNT variant, a non-conservative TeNT variant or an active TeNT fragment, or any combination thereof. In still another aspect of this embodiment, a polynucleotide molecule encodes a TeNT comprising a non-naturally occurring TeNT variant of SEQ ID NO: 8, such as, e.g., a conservative TeNT variant of SEQ ID NO: 8, a non-conservative TeNT variant of SEQ ID NO: 8 or an active TeNT fragment of SEQ ID NO: 8, or any combination thereof. In yet another aspect of this embodiment, a TeNT comprising a TeNT enzymatic domain or an active fragment thereof, a TeNT translocation domain or active fragment thereof, a TeNT binding domain or active fragment thereof, and any combination thereof. In yet another aspect of this embodiment, a TeNT comprising a TeNT enzymatic domain of amino acids 1-441 from SEQ ID NO: 8 or active fragment thereof, a TeNT translocation domain of amino acids 442-870 from SEQ ID NO: 8 or active fragment thereof, a TeNT binding domain of amino acids 871-1315 from SEQ ID NO: 8 or active fragment thereof, and any combination thereof.

In other aspects of this embodiment, a polynucleotide molecule encodes a TeNT comprising a polypeptide having, e.g., at least 70% amino acid identity with SEQ ID NO: 8, at least 75% amino acid identity with the SEQ ID NO: 8, at least 80% amino acid identity with SEQ ID NO: 8, at least 85% amino acid identity with SEQ ID NO: 8, at least 90% amino acid identity with SEQ ID NO: 8 or at least 95% amino acid identity with SEQ ID NO: 8. In yet other aspects of this embodiment, a polynucleotide molecule encodes a TeNT comprising a polypeptide having, e.g., at most 70% amino acid identity with SEQ ID NO: 8, at most 75% amino acid identity with the SEQ ID NO: 8, at most 80% amino acid identity with SEQ ID NO: 8, at most 85% amino acid identity with SEQ ID NO: 8, at most 90% amino acid identity with SEQ ID NO: 8 or at most 95% amino acid identity with SEQ ID NO: 8.

In other aspects of this embodiment, a polynucleotide molecule encodes a TeNT comprising a polypeptide having, e.g., at most one, two, three, four, five, six, seven, eight, nine, 10, 20, 30, 40, 50, 100, 200 or 500 non-contiguous amino acid substitutions relative to SEQ ID NO: 8. In other aspects of this embodiment, a polynucleotide molecule encodes a TeNT comprising a polypeptide having, e.g., at least one, two, three, four, five, six, seven, eight, nine, 10, 20, 30, 40, 50, 100, 200 or 500 non-contiguous amino acid substitutions relative to SEQ ID NO: 8. In yet other aspects of this embodiment, a polynucleotide molecule encodes a TeNT comprising a polypeptide having, e.g., at most one, two, three, four, five, six, seven, eight, nine, 10, 20, 30, 40, 50, 100, 200 or 500 non-contiguous amino acid deletions relative to SEQ ID NO: 8. In other aspects of this embodiment, a polynucleotide molecule encodes a TeNT comprising a polypeptide having, e.g., at least one, two, three, four, five, six, seven, eight, nine, 10, 20, 30, 40, 50, 100, 200 or 500 non-contiguous amino acid deletions relative to SEQ ID NO: 8. In still other aspects of this embodiment, a polynucleotide molecule encodes a TeNT comprising a polypeptide having, e.g., at most one, two, three, four, five, six, seven, eight, nine, 10, 20, 30, 40, 50, 100, 200 or 500 non-contiguous amino acid additions relative to SEQ ID NO: 8. In other aspects of this embodiment, a polynucleotide molecule encodes a TeNT comprising a polypeptide having, e.g., at least one, two, three, four, five, six, seven, eight, nine, 10, 20, 30, 40, 50, 100, 200 or 500 non-contiguous amino acid additions relative to SEQ ID NO: 8.

In other aspects of this embodiment, a polynucleotide molecule encodes a TeNT comprising a polypeptide having, e.g., at most one, two, three, four, five, six, seven, eight, nine, 10, 20, 30, 40, 50, 100, 200 or 500 contiguous amino acid substitutions relative to SEQ ID NO: 8. In other aspects of this embodiment, a polynucleotide molecule encodes a TeNT comprising a polypeptide having, e.g., at least one, two, three, four, five, six, seven, eight, nine, 10, 20, 30, 40, 50, 100, 200 or 500 contiguous amino acid substitutions relative to SEQ ID NO: 8. In yet other aspects of this embodiment, a polynucleotide molecule encodes a TeNT comprising a polypeptide having, e.g., at most one, two, three, four, five, six, seven, eight, nine, 10, 20, 30, 40, 50, 100, 200 or 500 contiguous amino acid deletions relative to SEQ ID NO: 8. In other aspects of this embodiment, a polynucleotide molecule encodes a TeNT comprising a polypeptide having, e.g., at least one, two, three, four, five, six, seven, eight, nine, 10, 20, 30, 40, 50, 100, 200 or 500 contiguous amino acid deletions relative to SEQ ID NO: 8. In still other aspects of this embodiment, a polynucleotide molecule encodes a TeNT comprising a polypeptide having, e.g., at most one, two, three, four, five, six, seven, eight, nine, 10, 20, 30, 40, 50, 100, 200 or 500 contiguous amino acid additions relative to SEQ ID NO: 8. In other aspects of this embodiment, a polynucleotide molecule encodes a TeNT comprising a polypeptide having, e.g., at least one, two, three, four, five, six, seven, eight, nine, 10, 20, 30, 40, 50, 100, 200 or 500 contiguous amino acid additions relative to SEQ ID NO: 8.

In still another embodiment, a polynucleotide molecule encodes a modified Clostridial toxin comprising a Clostridial toxin substrate cleavage site. In aspects of this embodiment, a polynucleotide molecule encodes a Clostridial toxin substrate cleavage site comprising a naturally occurring Clostridial toxin substrate cleavage site variant, such as, e.g., a Clostridial toxin substrate cleavage site isoform or a Clostridial toxin substrate cleavage site subtype. In other aspects of this embodiment, a polynucleotide molecule encodes a Clostridial toxin substrate cleavage site comprising a non-naturally occurring Clostridial toxin substrate cleavage site variant, such as, e.g., a conservative Clostridial toxin substrate cleavage site variant, a non-conservative Clostridial toxin substrate cleavage site variant or a Clostridial toxin substrate cleavage site peptidomimetic, or any combination thereof.

In still other aspects of this embodiment, a polynucleotide molecule encodes a modified Clostridial toxin substrate comprising a Clostridial toxin substrate cleavage site in which the $P_1'$ residue is not modified or substituted relative to the naturally occurring residue in a target protein cleaved by the Clostridial toxin. In still other aspects of this embodiment, a polynucleotide molecule encodes a Clostridial toxin substrate cleavage site in which the $P_1'$ residue is not modified or substituted relative to the naturally occurring residue in a target protein cleaved by the Clostridial toxin can be, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site.

In still other aspects of this embodiment, a polynucleotide molecule encodes a modified Clostridial toxin substrate comprises a Clostridial toxin substrate cleavage site in which the $P_1$ residue is modified or substituted relative to the naturally occurring residue in a target protein cleaved by the Clostridial toxin; such a Clostridial toxin substrate retains susceptibility to peptide bond cleavage between the $P_1$ and $P_1'$ residues. In still other aspects of this embodiment, a polynucleotide molecule encodes a Clostridial toxin substrate cleavage site in which the $P_1'$ residue is modified or substituted relative to the naturally occurring residue in a target protein cleaved by the Clostridial toxin can be, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site.

In still another embodiment, a polynucleotide molecule encodes a modified Clostridial toxin comprising a BoNT/A substrate cleavage site. In an aspect of this embodiment, a polynucleotide molecule encodes a BoNT/A substrate cleavage site comprising at least six consecutive residues of SNAP-25 including Gln-Arg. In other aspects of this embodiment, a polynucleotide molecule encodes a BoNT/A substrate cleavage site comprises, e.g., the amino acid sequence Glu-Ala-Asn-Gln-Arg-Ala-Thr-Lys (SEQ ID NO: 104); the amino acid sequence Glu-Ala-Asn-Lys-His-Ala-Thr-Lys (SEQ ID NO: 105); the amino acid sequence Glu-Ala-Asn-Lys-His-Ala-Asn-Lys (SEQ ID NO: 106). In another aspect of this embodiment, a polynucleotide molecule encodes a BoNT/A substrate cleavage site comprising a naturally occurring BoNT/A substrate cleavage site variant. In another aspect of this embodiment, a polynucleotide molecule encodes a BoNT/A substrate cleavage site comprises a naturally occurring BoNT/A substrate cleavage site variant of SEQ ID NO: 104, SEQ ID NO: 105 or SEQ ID NO: 106, such as, e.g., a BoNT/A substrate cleavage site isoform of SEQ ID NO: 104, SEQ ID NO: 105 or SEQ ID NO: 106; or a BoNT/A substrate cleavage site subtype of SEQ ID NO: 104, SEQ ID NO: 105 or SEQ ID NO: 106. In still another aspect of this embodiment, a polynucleotide molecule encodes a BoNT/A substrate cleavage site comprising a non-naturally occurring BoNT/A substrate cleavage site variant, such as, e.g., a conservative BoNT/A substrate cleavage site variant, a non-conservative BoNT/A substrate cleavage site variant or a BoNT/A substrate cleavage site peptidomimetic, or any combination thereof. In still another aspect of this embodiment, a polynucleotide molecule encodes a BoNT/A substrate cleavage site comprising a non-naturally occurring BoNT/A substrate cleavage site variant of SEQ ID NO: 104, SEQ ID NO: 105 or SEQ ID NO: 106; such as, e.g., a conservative BoNT/A substrate cleavage site variant of SEQ ID NO: 104, SEQ ID NO: 105 or SEQ ID NO: 106; a non-conservative BoNT/A substrate cleavage site variant of SEQ ID NO: 104, SEQ ID NO: 105 or SEQ ID NO: 106; a BoNT/A substrate cleavage site peptidomimetic of SEQ ID NO: 104, SEQ ID NO: 105 or SEQ ID NO: 106; or any combination thereof. In still other aspects of this embodiment, a polynucleotide molecule encodes a BoNT/A substrate cleavage site comprising, e.g., SEQ ID NO: 133, SEQ ID NO: 134, SEQ ID NO: 135, SEQ ID NO: 136, SEQ ID NO: 138, SEQ ID NO: 141, SEQ ID NO: 148, SEQ ID NO: 150 or SEQ ID NO: 151.

In other aspects of this embodiment, a polynucleotide molecule encodes a BoNT/A substrate cleavage site comprising a polypeptide having, e.g., at least 50% amino acid identity with SEQ ID NO: 104, at least 62.5% amino acid identity with the SEQ ID NO: 104, at least 75% amino acid identity with SEQ ID NO: 104 or at least 87.5% amino acid identity with SEQ ID NO: 104. In still other aspects of this embodiment, a polynucleotide molecule encodes a BoNT/A substrate cleavage site comprising a polypeptide having, e.g., at most 50% amino acid identity with SEQ ID NO: 104, at most 62.5% amino acid identity with the SEQ ID NO: 104, at most 75% amino acid identity with SEQ ID NO: 104 or at most 87.5% amino acid identity with SEQ ID NO: 104.

In other aspects of this embodiment, a polynucleotide molecule encodes a BoNT/A substrate cleavage site comprising a polypeptide having, e.g., at most one, two, three or four non-contiguous amino acid substitutions relative to SEQ ID NO: 104. In still other aspects of this embodiment, a polynucleotide molecule encodes a BoNT/A substrate cleavage site comprising a polypeptide having, e.g., at least one, two, three or four non-contiguous amino acid substitutions relative to SEQ ID NO: 104. In yet other aspects of this embodiment, a polynucleotide molecule encodes a BoNT/A substrate cleavage site comprising a polypeptide having, e.g., at most one, two, three, four, five, six, seven, eight, nine or ten non-contiguous amino acid additions relative to SEQ ID NO: 104. In yet other aspects of this embodiment, a polynucleotide molecule encodes BoNT/A substrate cleavage site comprising a polypeptide having, e.g., at least one, two, three, four, five, six, seven, eight, nine or ten non-contiguous amino acid additions relative to SEQ ID NO: 104. In still other aspects of this embodiment, a polynucleotide molecule encodes a BoNT/A substrate cleavage site comprising a polypeptide having, e.g., at most one, two or three non-contiguous amino acid deletions relative to SEQ ID NO: 104. In still other aspects of this embodiment, a polynucleotide molecule encodes a BoNT/A substrate cleavage site comprising a polypeptide having, e.g., at least one, two or three non-contiguous amino acid deletions relative to SEQ ID NO: 104.

In other aspects of this embodiment, a polynucleotide molecule encodes a BoNT/A substrate cleavage site comprising a polypeptide having, e.g., at most two, three or four contiguous amino acid substitutions relative to SEQ ID NO: 104. In still other aspects of this embodiment, a polynucleotide molecule encodes a BoNT/A substrate cleavage site comprising a polypeptide having, e.g., at least two, three or four contiguous amino acid substitutions relative to SEQ ID NO: 104. In yet other aspects of this embodiment, a polynucleotide molecule encodes a BoNT/A substrate cleavage site comprising a polypeptide having, e.g., at most two, three, four, five, six, seven, eight, nine or ten contiguous amino acid additions relative to SEQ ID NO: 104. In yet other aspects of this embodiment, a polynucleotide molecule encodes a BoNT/A substrate cleavage site comprising a polypeptide having, e.g., at least two, three, four, five, six, seven, eight, nine or ten contiguous amino acid additions relative to SEQ ID NO: 104. In still other aspects of this embodiment, a polynucleotide molecule encodes a BoNT/A substrate cleavage site comprising a polypeptide having, e.g., at most two or three contiguous amino acid deletions relative to SEQ ID NO: 104. In still other aspects of this embodiment, a polynucleotide molecule encodes a BoNT/A substrate cleavage site comprising a polypeptide having, e.g., at least two or three contiguous amino acid deletions relative to SEQ ID NO: 104.

In still another embodiment, a polynucleotide molecule encodes a modified Clostridial toxin comprising a BoNT/B substrate cleavage site. In an aspect of this embodiment, a polynucleotide molecule encodes a BoNT/B substrate cleavage site comprising at least six consecutive residues of VAMP including Gln-Phe. In other aspects of this embodiment, a polynucleotide molecule encodes a BoNT/B substrate cleavage site comprising, e.g., the amino acid sequence Gly-Ala-Ser-Gln-Phe-Glu-Thr-Ser (SEQ ID NO: 107); the amino acid sequence Gly-Ala-Ser-Gln-Phe-Glu-Ser-Ser (SEQ ID NO: 108); the amino acid sequence Gly-Ala-Ser-Gln-Phe-Glu-Thr-Asn (SEQ ID NO: 109); the amino acid sequence Gly-Ala-Ser-Gln-Phe-Glu-Gln-Gln (SEQ ID NO: 110); the amino acid sequence Gly-Ala-Ser-Gln-Phe-Glu-Ala-Ser (SEQ ID NO: 111); or the amino acid sequence Gly-Ala-Ser-Gln-Phe-Gln-Gln-Ser (SEQ ID NO: 112). In another aspect of this embodiment, a polynucleotide molecule encodes a BoNT/B substrate cleavage site comprising a naturally occurring BoNT/B substrate cleavage site variant. In another aspect of this embodiment, a polynucleotide molecule encodes a BoNT/B substrate cleavage site comprising a naturally occurring BoNT/B substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; or a BoNT/B substrate cleavage site subtype of SEQ ID NO: 107, SEQ ID NO: 108, SEQ ID NO: 109, SEQ ID NO: 110, SEQ ID NO: 111 or SEQ ID NO: 112. In still another aspect of this embodiment, a polynucleotide molecule encodes a BoNT/B substrate cleavage site comprising a non-naturally occurring BoNT/B substrate cleavage site variant, such as, e.g., a conservative BoNT/B substrate cleavage site variant, a non-conservative BoNT/B substrate cleavage site variant or a BoNT/B substrate cleavage site peptidomimetic, or any combination thereof. In still another aspect of this embodiment, a polynucleotide molecule encodes a BoNT/B substrate cleavage site comprising a non-naturally occurring BoNT/B substrate cleavage site variant of SEQ ID NO: 107, SEQ ID NO: 108, SEQ ID NO: 109, SEQ ID NO: 110, SEQ ID NO: 111 or SEQ ID NO: 112; such as, e.g., a conservative BoNT/B substrate cleavage site variant of SEQ ID NO: 107, SEQ ID NO: 108, SEQ ID NO: 109, SEQ ID NO: 110, SEQ ID NO: 111 or SEQ ID NO: 112; a non-conservative BoNT/B substrate cleavage site variant of SEQ ID NO: 107, SEQ ID NO: 108, SEQ ID NO: 109, SEQ ID NO: 110, SEQ ID NO: 111 or SEQ ID NO: 112; a BoNT/B substrate cleavage site peptidomimetic of SEQ ID NO: 107, SEQ ID NO: 108, SEQ ID NO: 109, SEQ ID NO: 110, SEQ ID NO: 111 or SEQ ID NO: 112; or any combination thereof.

In other aspects of this embodiment, a polynucleotide molecule encodes a BoNT/B substrate cleavage site comprising a polypeptide having, e.g., at least 50% amino acid identity with SEQ ID NO: 107, at least 62.5% amino acid identity with the SEQ ID NO: 107, at least 75% amino acid identity with SEQ ID NO: 107 or at least 87.5% amino acid identity with SEQ ID NO: 107. In still other aspects of this embodiment, a polynucleotide molecule encodes a BoNT/B substrate cleavage site comprising a polypeptide having, e.g., at most 50% amino acid identity with SEQ ID NO: 107, at most 62.5% amino acid identity with the SEQ ID NO: 107, at most 75% amino acid identity with SEQ ID NO: 107 or at most 87.5% amino acid identity with SEQ ID NO: 107.

In other aspects of this embodiment, a polynucleotide molecule encodes a BoNT/B substrate cleavage site comprising a polypeptide having, e.g., at most one, two, three or four non-contiguous amino acid substitutions relative to SEQ ID NO: 107. In still other aspects of this embodiment, a polynucleotide molecule encodes a BoNT/B substrate cleavage site comprising a polypeptide having, e.g., at least one, two, three or four non-contiguous amino acid substitutions relative to SEQ ID NO: 107. In yet other aspects of this embodiment, a polynucleotide molecule encodes a BoNT/B substrate cleavage site comprising a polypeptide having, e.g., at most one, two, three, four, five, six, seven, eight, nine or ten non-contiguous amino acid additions relative to SEQ ID NO: 107. In yet other aspects of this embodiment, a polynucleotide molecule encodes BoNT/B substrate cleavage site comprising a polypeptide having, e.g., at least one, two, three, four, five, six, seven, eight, nine or ten non-contiguous amino acid additions relative to SEQ ID NO: 107. In still other aspects of this embodiment, a polynucleotide molecule encodes a BoNT/B substrate cleavage site comprising a polypeptide having, e.g., at most one, two or three non-contiguous amino acid deletions relative to SEQ ID NO: 107. In still other aspects of this embodiment, a polynucleotide molecule encodes a BoNT/B substrate cleavage site comprising a polypeptide having, e.g., at least one, two or three non-contiguous amino acid deletions relative to SEQ ID NO: 107.

In other aspects of this embodiment, a polynucleotide molecule encodes a BoNT/B substrate cleavage site comprising a polypeptide having, e.g., at most two, three or four contiguous amino acid substitutions relative to SEQ ID NO: 107. In still other aspects of this embodiment, a polynucleotide molecule encodes a BoNT/B substrate cleavage site comprising a polypeptide having, e.g., at least two, three or four contiguous amino acid substitutions relative to SEQ ID NO: 107. In yet other aspects of this embodiment, a polynucleotide molecule encodes a BoNT/B substrate cleavage site comprising a polypeptide having, e.g., at most two, three, four, five, six, seven, eight, nine or ten contiguous amino acid additions relative to SEQ ID NO: 107. In yet other aspects of this embodiment, a polynucleotide molecule encodes a BoNT/B substrate cleavage site comprising a polypeptide having, e.g., at least two, three, four, five, six, seven, eight, nine or ten contiguous amino acid additions relative to SEQ ID NO: 107. In still other aspects of this embodiment, a polynucleotide molecule encodes a BoNT/B substrate cleavage site comprising a polypeptide having, e.g., at most two or three contiguous amino acid deletions relative to SEQ ID NO: 107. In still other aspects of this embodiment, a polynucleotide molecule encodes a BoNT/B substrate cleavage site comprising a polypeptide having, e.g., at least two or three contiguous amino acid deletions relative to SEQ ID NO: 107.

In still another embodiment, a polynucleotide molecule encodes a modified Clostridial toxin comprising a BoNT/C1 substrate cleavage site. In an aspect of this embodiment, a polynucleotide molecule encodes a BoNT/C1 substrate cleavage site comprising at least six consecutive residues of Syntaxin including Lys-Ala. In other aspects of this embodiment, a polynucleotide molecule encodes a BoNT/C1 substrate cleavage site comprising, e.g., the amino acid sequence Asp-Thr-Lys-Lys-Ala-Val-Lys-Tyr (SEQ ID NO: 113); the amino acid sequence Glu-Thr-Lys-Lys-Ala-Ile-Lys-Tyr (SEQ ID NO: 114); the amino acid sequence Glu-Ser-Lys-Lys-Ala-Val-Lys-Tyr (SEQ ID NO: 115); the amino acid sequence Glu-Thr-Lys-Arg-Ala-Met-Lys-Tyr (SEQ ID NO: 116); the amino acid sequence Glu-Thr-Lys-Lys-Ala-Val-Lys-Tyr (SEQ ID NO: 117); the amino acid sequence Asp-Thr-Lys-Lys-Ala-Leu-Lys-Tyr (SEQ ID NO: 118); or the amino acid sequence Asp-Thr-Lys-Lys-Ala-Met-Lys-Tyr (SEQ ID NO: 119). In another aspect of this embodiment, a polynucleotide molecule encodes a BoNT/C1 substrate cleavage site comprising a naturally occurring BoNT/C1 substrate cleavage site variant. In another aspect of this embodiment, a polynucleotide molecule encodes a BoNT/C1 substrate cleavage site comprising a naturally occurring BoNT/C1 substrate cleavage site variant of SEQ ID NO: 113, SEQ ID NO: 114, SEQ ID NO: 115, SEQ ID NO: 116, SEQ ID NO:

117, SEQ ID NO: 118 or SEQ ID NO: 119, such as, e.g., a BoNT/C1 substrate cleavage site isoform of SEQ ID NO: 113, SEQ ID NO: 114, SEQ ID NO: 115, SEQ ID NO: 116, SEQ ID NO: 117, SEQ ID NO: 118 or SEQ ID NO: 119; or a BoNT/C1 substrate cleavage site subtype of SEQ ID NO: 113, SEQ ID NO: 114, SEQ ID NO: 115, SEQ ID NO: 116, SEQ ID NO: 117, SEQ ID NO: 118 or SEQ ID NO: 119. In still another aspect of this embodiment, a polynucleotide molecule encodes a BoNT/C1 substrate cleavage site comprising a non-naturally occurring BoNT/C1 substrate cleavage site variant, such as, e.g., a conservative BoNT/C1 substrate cleavage site variant, a non-conservative BoNT/C1 substrate cleavage site variant or a BoNT/C1 substrate cleavage site peptidomimetic, or any combination thereof. In still another aspect of this embodiment, a polynucleotide molecule encodes a BoNT/C1 substrate cleavage site comprising a non-naturally occurring BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119; such as, e.g., a conservative BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119; a non-conservative BoNT/C1 substrate cleavage site variant of SEQ ID NO: 113, SEQ ID NO: 114, SEQ ID NO: 115, SEQ ID NO: 116, SEQ ID NO: 117, SEQ ID NO: 118 or SEQ ID NO: 119; a BoNT/C1 substrate cleavage site peptidomimetic of SEQ ID NO: 113, SEQ ID NO: 114, SEQ ID NO: 115, SEQ ID NO: 116, SEQ ID NO: 117, SEQ ID NO: 118 or SEQ ID NO: 119; or any combination thereof.

In other aspects of this embodiment, a polynucleotide molecule encodes a BoNT/C1 substrate cleavage site comprising a polypeptide having, e.g., at least 50% amino acid identity with SEQ ID NO: 113, at least 62.5% amino acid identity with the SEQ ID NO: 113, at least 75% amino acid identity with SEQ ID NO: 113 or at least 87.5% amino acid identity with SEQ ID NO: 113. In still other aspects of this embodiment, a polynucleotide molecule encodes a BoNT/C1 substrate cleavage site comprising a polypeptide having, e.g., at most 50% amino acid identity with SEQ ID NO: 113, at most 62.5% amino acid identity with the SEQ ID NO: 113, at most 75% amino acid identity with SEQ ID NO: 113 or at most 87.5% amino acid identity with SEQ ID NO: 113.

In other aspects of this embodiment, a polynucleotide molecule encodes a BoNT/CA substrate cleavage site comprising a polypeptide having, e.g., at most one, two, three or four non-contiguous amino acid substitutions relative to SEQ ID NO: 113. In still other aspects of this embodiment, a polynucleotide molecule encodes a BoNT/C1 substrate cleavage site comprising a polypeptide having, e.g., at least one, two, three or four non-contiguous amino acid substitutions relative to SEQ ID NO: 113. In yet other aspects of this embodiment, a polynucleotide molecule encodes a BoNT/C1 substrate cleavage site comprising a polypeptide having, e.g., at most one, two, three, four, five, six, seven, eight, nine or ten non-contiguous amino acid additions relative to SEQ ID NO: 113. In yet other aspects of this embodiment, a polynucleotide molecule encodes BoNT/C1 substrate cleavage site comprising a polypeptide having, e.g., at least one, two, three, four, five, six, seven, eight, nine or ten non-contiguous amino acid additions relative to SEQ ID NO: 113. In still other aspects of this embodiment, a polynucleotide molecule encodes a BoNT/C1 substrate cleavage site comprising a polypeptide having, e.g., at most one, two or three non-contiguous amino acid deletions relative to SEQ ID NO: 113. In still other aspects of this embodiment, a polynucleotide molecule encodes a BoNT/C1 substrate cleavage site comprising a polypeptide having, e.g., at least one, two or three non-contiguous amino acid deletions relative to SEQ ID NO: 113.

In other aspects of this embodiment, a polynucleotide molecule encodes a BoNT/C1 substrate cleavage site comprising a polypeptide having, e.g., at most two, three or four contiguous amino acid substitutions relative to SEQ ID NO: 113. In still other aspects of this embodiment, a polynucleotide molecule encodes a BoNT/C1 substrate cleavage site comprising a polypeptide having, e.g., at least two, three or four contiguous amino acid substitutions relative to SEQ ID NO: 113. In yet other aspects of this embodiment, a polynucleotide molecule encodes a BoNT/C1 substrate cleavage site comprising a polypeptide having, e.g., at most two, three, four, five, six, seven, eight, nine or ten contiguous amino acid additions relative to SEQ ID NO: 113. In yet other aspects of this embodiment, a polynucleotide molecule encodes a BoNT/C1 substrate cleavage site comprising a polypeptide having, e.g., at least two, three, four, five, six, seven, eight, nine or ten contiguous amino acid additions relative to SEQ ID NO: 113. In still other aspects of this embodiment, a polynucleotide molecule encodes a BoNT/C1 substrate cleavage site comprising a polypeptide having, e.g., at most two or three contiguous amino acid deletions relative to SEQ ID NO: 113. In still other aspects of this embodiment, a polynucleotide molecule encodes a BoNT/C1 substrate cleavage site comprising a polypeptide having, e.g., at least two or three contiguous amino acid deletions relative to SEQ ID NO: 113.

In another aspect of this embodiment, a polynucleotide molecule encodes a BoNT/C1 substrate cleavage site comprising at least six consecutive residues of SNAP-25 including Arg-Ala. In other aspects of this embodiment, a polynucleotide molecule encodes a BoNT/C1 toxin substrate cleavage site comprising, e.g., the amino acid sequence Ala-Asn-Gln-Arg-Ala-Thr-Lys-Met (SEQ ID NO: 120); or the amino acid sequence Ala-Asn-Gln-Arg-Ala-His-Gln-Leu (SEQ ID NO: 121). In another aspect of this embodiment, a polynucleotide molecule encodes a BoNT/C1 substrate cleavage site comprising a naturally occurring BoNT/C1 substrate cleavage site variant. In another aspect of this embodiment, a polynucleotide molecule encodes a BoNT/C1 substrate cleavage site comprising a naturally occurring BoNT/C1 substrate cleavage site variant of SEQ ID NO: 120 or SEQ ID NO: 121, such as, e.g., a BoNT/C1 substrate cleavage site isoform of SEQ ID NO: 120 or SEQ ID NO: 121; or a BoNT/C1 substrate cleavage site subtype of SEQ ID NO: 120 or SEQ ID NO: 121. In still another aspect of this embodiment, a polynucleotide molecule encodes a BoNT/C1 substrate cleavage site comprising a non-naturally occurring BoNT/C1 substrate cleavage site variant, such as, e.g., a conservative BoNT/C1 substrate cleavage site variant, a non-conservative BoNT/C1 substrate cleavage site variant or a BoNT/C1 substrate cleavage site peptidomimetic, or any combination thereof. In still another aspect of this embodiment, a polynucleotide molecule encodes a BoNT/C1 substrate cleavage site comprising a non-naturally occurring BoNT/C1 substrate cleavage site variant of SEQ ID NO: 120 or SEQ ID NO: 121; such as, e.g., a conservative BoNT/C1 substrate cleavage site variant of SEQ ID NO: 99 or SEQ ID NO: XX; a non-conservative BoNT/C1 substrate cleavage site variant of SEQ ID NO: 120 or SEQ ID NO: 121; a BoNT/C1 substrate cleavage site peptidomimetic of SEQ ID NO: 120 or SEQ ID NO: 121; or any combination thereof.

In other aspects of this embodiment, a polynucleotide molecule encodes a BoNT/C1 substrate cleavage site comprising a polypeptide having, e.g., at least 50% amino acid identity with SEQ ID NO: 120, at least 62.5% amino acid identity with the SEQ ID NO: 120, at least 75% amino acid identity with SEQ ID NO: 120 or at least 87.5% amino acid identity with SEQ ID NO: 120. In still other aspects of this embodiment, a polynucleotide molecule encodes a BoNT/C1 substrate cleavage site comprising a polypeptide having, e.g., at most 50% amino acid identity with SEQ ID NO: 120, at most 62.5% amino acid identity with the SEQ ID NO: 120, at most 75% amino acid identity with SEQ ID NO: 120 or at most 87.5% amino acid identity with SEQ ID NO: 120.

In other aspects of this embodiment, a polynucleotide molecule encodes a BoNT/C1 substrate cleavage site comprising a polypeptide having, e.g., at most one, two, three or four non-contiguous amino acid substitutions relative to SEQ ID NO: 120. In still other aspects of this embodiment, a polynucleotide molecule encodes a BoNT/C1 substrate cleavage site comprising a polypeptide having, e.g., at least one, two, three or four non-contiguous amino acid substitutions relative to SEQ ID NO: 120. In yet other aspects of this embodiment, a polynucleotide molecule encodes a BoNT/C1 substrate cleavage site comprising a polypeptide having, e.g., at most one, two, three, four, five, six, seven, eight, nine or ten non-contiguous amino acid additions relative to SEQ ID NO: 120. In yet other aspects of this embodiment, a polynucleotide molecule encodes BoNT/C1 substrate cleavage site comprising a polypeptide having, e.g., at least one, two, three, four, five, six, seven, eight, nine or ten non-contiguous amino acid additions relative to SEQ ID NO: 120. In still other aspects of this embodiment, a polynucleotide molecule encodes a BoNT/C1 substrate cleavage site comprising a polypeptide having, e.g., at most one, two or three non-contiguous amino acid deletions relative to SEQ ID NO: 120. In still other aspects of this embodiment, a polynucleotide molecule encodes a BoNT/C1 substrate cleavage site comprising a polypeptide having, e.g., at least one, two or three non-contiguous amino acid deletions relative to SEQ ID NO: 120.

In other aspects of this embodiment, a polynucleotide molecule encodes a BoNT/C1 substrate cleavage site comprising a polypeptide having, e.g., at most two, three or four contiguous amino acid substitutions relative to SEQ ID NO: 120. In still other aspects of this embodiment, a polynucleotide molecule encodes a BoNT/C1 substrate cleavage site comprising a polypeptide having, e.g., at least two, three or four contiguous amino acid substitutions relative to SEQ ID NO: 120. In yet other aspects of this embodiment, a polynucleotide molecule encodes a BoNT/C1 substrate cleavage site comprising a polypeptide having, e.g., at most two, three, four, five, six, seven, eight, nine or ten contiguous amino acid additions relative to SEQ ID NO: 120. In yet other aspects of this embodiment, a polynucleotide molecule encodes a BoNT/C1 substrate cleavage site comprising a polypeptide having, e.g., at least two, three, four, five, six, seven, eight, nine or ten contiguous amino acid additions relative to SEQ ID NO: 120. In still other aspects of this embodiment, a polynucleotide molecule encodes a BoNT/C1 substrate cleavage site comprising a polypeptide having, e.g., at most two or three contiguous amino acid deletions relative to SEQ ID NO: 120. In still other aspects of this embodiment, a polynucleotide molecule encodes a BoNT/C1 substrate cleavage site comprising a polypeptide having, e.g., at least two or three contiguous amino acid deletions relative to SEQ ID NO: 120.

In still another embodiment, a polynucleotide molecule encodes a modified Clostridial toxin comprising a BoNT/D substrate cleavage site. In an aspect of this embodiment, a polynucleotide molecule encodes a BoNT/D substrate cleavage site comprising at least six consecutive residues of VAMP including Lys-Leu. In other aspects of this embodiment, a polynucleotide molecule encodes a BoNT/D substrate cleavage site comprising, e.g., the amino acid sequence Arg-Asp-Gln-Lys-Leu-Ser-Glu-Leu (SEQ ID NO: 122); or the amino acid sequence Lys-Asp-Gln-Lys-Leu-Ala-Glu-Leu (SEQ ID NO: 123). In another aspect of this embodiment, a polynucleotide molecule encodes a BoNT/D substrate cleavage site comprising a naturally occurring BoNT/D substrate cleavage site variant. In another aspect of this embodiment, a polynucleotide molecule encodes a BoNT/D substrate cleavage site comprising a naturally occurring BoNT/D substrate cleavage site variant of SEQ ID NO: 122 or SEQ ID NO: 123, such as, e.g., a BoNT/D substrate cleavage site isoform of SEQ ID NO: 122 or SEQ ID NO: 123; or a BoNT/D substrate cleavage site subtype of SEQ ID NO: 122 or SEQ ID NO: 123. In still another aspect of this embodiment, a polynucleotide molecule encodes a BoNT/D substrate cleavage site comprising a non-naturally occurring BoNT/D substrate cleavage site variant, such as, e.g., a conservative BoNT/D substrate cleavage site variant, a non-conservative BoNT/D substrate cleavage site variant or a BoNT/D substrate cleavage site peptidomimetic, or any combination thereof. In still another aspect of this embodiment, a polynucleotide molecule encodes a BoNT/D substrate cleavage site comprising a non-naturally occurring BoNT/D substrate cleavage site variant of SEQ ID NO: 122 or SEQ ID NO: 123; such as, e.g., a conservative BoNT/D substrate cleavage site variant of SEQ ID NO: 122 or SEQ ID NO: 123; a non-conservative BoNT/C1 substrate cleavage site variant of SEQ ID NO: 122 or SEQ ID NO: 123; a BoNT/D substrate cleavage site peptidomimetic of SEQ ID NO: 122 or SEQ ID NO: 123; or any combination thereof.

In other aspects of this embodiment, a polynucleotide molecule encodes a BoNT/D substrate cleavage site comprising a polypeptide having, e.g., at least 50% amino acid identity with SEQ ID NO: 122, at least 62.5% amino acid identity with the SEQ ID NO: 122, at least 75% amino acid identity with SEQ ID NO: 122 or at least 87.5% amino acid identity with SEQ ID NO: 122. In still other aspects of this embodiment, a polynucleotide molecule encodes a BoNT/D substrate cleavage site comprising a polypeptide having, e.g., at most 50% amino acid identity with SEQ ID NO: 122, at most 62.5% amino acid identity with the SEQ ID NO: 122, at most 75% amino acid identity with SEQ ID NO: 122 or at most 87.5% amino acid identity with SEQ ID NO: 122.

In other aspects of this embodiment, a polynucleotide molecule encodes a BoNT/D substrate cleavage site comprising a polypeptide having, e.g., at most one, two, three or four non-contiguous amino acid substitutions relative to SEQ ID NO: 122. In still other aspects of this embodiment, a polynucleotide molecule encodes a BoNT/D substrate cleavage site comprising a polypeptide having, e.g., at least one, two, three or four non-contiguous amino acid substitutions relative to SEQ ID NO: 122. In yet other aspects of this embodiment, a polynucleotide molecule encodes a BoNT/D substrate cleavage site comprising a polypeptide having, e.g., at most one, two, three, four, five, six, seven, eight, nine or ten non-contiguous amino acid additions relative to SEQ ID NO: 122. In yet other aspects of this embodiment, a polynucleotide molecule encodes BoNT/D substrate cleavage site comprising a polypeptide having, e.g., at least one, two, three, four, five, six, seven, eight, nine or ten non-contiguous amino acid additions relative to SEQ ID NO: 122. In still other aspects of this embodiment, a polynucleotide molecule encodes a BoNT/D substrate cleavage site comprising a polypeptide having, e.g., at most one, two or three non-contiguous amino acid deletions relative to SEQ ID NO: 122. In still other aspects of this embodiment, a polynucleotide molecule encodes a BoNT/D substrate cleavage site comprising a polypeptide having, e.g., at least one, two or three non-contiguous amino acid deletions relative to SEQ ID NO: 122.

In other aspects of this embodiment, a polynucleotide molecule encodes a BoNT/D substrate cleavage site comprising a polypeptide having, e.g., at most two, three or four contiguous amino acid substitutions relative to SEQ ID NO: 122. In still other aspects of this embodiment, a polynucleotide molecule encodes a BoNT/D substrate cleavage site comprising a polypeptide having, e.g., at least two, three or four contiguous amino acid substitutions relative to SEQ ID NO: 122. In yet other aspects of this embodiment, a polynucleotide molecule encodes a BoNT/D substrate cleavage site comprising a polypeptide having, e.g., at most two, three, four, five, six, seven, eight, nine or ten contiguous amino acid additions relative to SEQ ID NO: 122. In yet other aspects of this embodiment, a polynucleotide molecule encodes a BoNT/D substrate cleavage site comprising a polypeptide having, e.g., at least two, three, four, five, six, seven, eight, nine or ten contiguous amino acid additions relative to SEQ ID NO: 122. In still other aspects of this embodiment, a polynucleotide molecule encodes a BoNT/D substrate cleavage site comprising a polypeptide having, e.g., at most two or three contiguous amino acid deletions relative to SEQ ID NO: 122. In still other aspects of this embodiment, a polynucleotide molecule encodes a BoNT/D substrate cleavage site comprising a polypeptide having, e.g., at least two or three contiguous amino acid deletions relative to SEQ ID NO: 122.

In still another embodiment, a polynucleotide molecule encodes a modified Clostridial toxin comprising a BoNT/E substrate cleavage site. In an aspect of this embodiment, a polynucleotide molecule encodes a BoNT/E substrate cleavage site comprising at least six consecutive residues of VAMP including Arg-Ile. In other aspects of this embodiment, a polynucleotide molecule encodes a BoNT/E substrate cleavage site comprising, e.g., the amino acid sequence Gln-Ile-Asp-Arg-Ile-Met-Glu-Lys (SEQ ID NO: 124); the amino acid sequence Gln-Ile-Gln-Lys-Ile-Thr-Glu-Lys (SEQ ID NO: 125); the amino acid sequence Gln-Ile-Asp-Arg-Ile-Met-Asp-Met (SEQ ID NO: 126); the amino acid sequence Gln-Val-Asp-Arg-Ile-Gln-Gln-Lys (SEQ ID NO: 127); or the amino acid sequence Gln-Leu-Asp-Arg-Ile-His-Asp-Lys (SEQ ID NO: 128). In another aspect of this embodiment, a polynucleotide molecule encodes a BoNT/E substrate cleavage site comprising a naturally occurring BoNT/E substrate cleavage site variant. In another aspect of this embodiment, a polynucleotide molecule encodes a BoNT/E substrate cleavage site comprising a naturally occurring BoNT/E substrate cleavage site variant of SEQ ID NO: 124, SEQ ID NO: 125, SEQ ID NO: 126, SEQ ID NO: 127 or SEQ ID NO: 128, such as, e.g., a BoNT/E substrate cleavage site isoform of SEQ ID NO: 124, SEQ ID NO: 125, SEQ ID NO: 126, SEQ ID NO: 127 or SEQ ID NO: 128; or a BoNT/E substrate cleavage site subtype of SEQ ID NO: 124, SEQ ID NO: 125, SEQ ID NO: 126, SEQ ID NO: 127 or SEQ ID NO: 128. In still another aspect of this embodiment, a polynucleotide molecule encodes a BoNT/E substrate cleavage site comprising a non-naturally occurring BoNT/E substrate cleavage site variant, such as, e.g., a conservative BoNT/E substrate cleavage site variant, a non-conservative BoNT/E substrate cleavage site variant or a BoNT/E substrate cleavage site peptidomimetic, or any combination thereof. In still another aspect of this embodiment, a polynucleotide molecule encodes a BoNT/E substrate cleavage site comprising a non-naturally occurring BoNT/E substrate cleavage site variant of SEQ ID NO: 124, SEQ ID NO: 125, SEQ ID NO: 126, SEQ ID NO: 127 or SEQ ID NO: 128; such as, e.g., a conservative BoNT/E substrate cleavage site variant of SEQ ID NO: 124, SEQ ID NO: 125, SEQ ID NO: 126, SEQ ID NO: 127 or SEQ ID NO: 128; a non-conservative BoNT/E substrate cleavage site variant of SEQ ID NO: 124, SEQ ID NO: 125, SEQ ID NO: 126, SEQ ID NO: 127 or SEQ ID NO: 128; a BoNT/E substrate cleavage site peptidomimetic of SEQ ID NO: 124, SEQ ID NO: 125, SEQ ID NO: 126, SEQ ID NO: 127 or SEQ ID NO: 128; or any combination thereof.

In other aspects of this embodiment, a polynucleotide molecule encodes a BoNT/E substrate cleavage site comprising a polypeptide having, e.g., at least 50% amino acid identity with SEQ ID NO: 124, at least 62.5% amino acid identity with the SEQ ID NO: 124, at least 75% amino acid identity with SEQ ID NO: 124 or at least 87.5% amino acid identity with SEQ ID NO: 124. In still other aspects of this embodiment, a polynucleotide molecule encodes a BoNT/E substrate cleavage site comprising a polypeptide having, e.g., at most 50% amino acid identity with SEQ ID NO: 124, at most 62.5% amino acid identity with the SEQ ID NO: 124, at most 75% amino acid identity with SEQ ID NO: 124 or at most 87.5% amino acid identity with SEQ ID NO: 124.

In other aspects of this embodiment, a polynucleotide molecule encodes a BoNT/E substrate cleavage site comprising a polypeptide having, e.g., at most one, two, three or four non-contiguous amino acid substitutions relative to SEQ ID NO: 124. In still other aspects of this embodiment, a polynucleotide molecule encodes a BoNT/E substrate cleavage site comprising a polypeptide having, e.g., at least one, two, three or four non-contiguous amino acid substitutions relative to SEQ ID NO: 124. In yet other aspects of this embodiment, a polynucleotide molecule encodes a BoNT/E substrate cleavage site comprising a polypeptide having, e.g., at most one, two, three, four, five, six, seven, eight, nine or ten non-contiguous amino acid additions relative to SEQ ID NO: 124. In yet other aspects of this embodiment, a polynucleotide molecule encodes BoNT/E substrate cleavage site comprising a polypeptide having, e.g., at least one, two, three, four, five, six, seven, eight, nine or ten non-contiguous amino acid additions relative to SEQ ID NO: 124. In still other aspects of this embodiment, a polynucleotide molecule encodes a BoNT/E substrate cleavage site comprising a polypeptide having, e.g., at most one, two or three non-contiguous amino acid deletions relative to SEQ ID NO: 124. In still other aspects of this embodiment, a polynucleotide molecule encodes a BoNT/E substrate cleavage site comprising a polypeptide having, e.g., at least one, two or three non-contiguous amino acid deletions relative to SEQ ID NO: 124.

In other aspects of this embodiment, a polynucleotide molecule encodes a BoNT/E substrate cleavage site comprising a polypeptide having, e.g., at most two, three or four contiguous amino acid substitutions relative to SEQ ID NO: 124. In still other aspects of this embodiment, a polynucleotide molecule encodes a BoNT/E substrate cleavage site comprising a polypeptide having, e.g., at least two, three or four contiguous amino acid substitutions relative to SEQ ID NO: 124. In yet other aspects of this embodiment, a polynucleotide molecule encodes a BoNT/E substrate cleavage site comprising a polypeptide having, e.g., at most two, three, four, five, six, seven, eight, nine or ten contiguous amino acid additions relative to SEQ ID NO: 124. In yet other aspects of this embodiment, a polynucleotide molecule encodes a BoNT/E substrate cleavage site comprising a polypeptide having, e.g., at least two, three, four, five, six, seven, eight, nine or ten contiguous amino acid additions relative to SEQ ID NO: 124. In still other aspects of this embodiment, a polynucleotide molecule encodes a BoNT/E substrate cleavage site comprising a polypeptide having, e.g., at most two or three contiguous amino acid deletions relative to SEQ ID NO: 124. In still other aspects of this embodiment, a polynucleotide molecule encodes a BoNT/E substrate cleavage site comprising a polypeptide having, e.g., at least two or three contiguous amino acid deletions relative to SEQ ID NO: 124.

In still another embodiment, a polynucleotide molecule encodes a modified Clostridial toxin comprising a BoNT/F substrate cleavage site. In an aspect of this embodiment, a polynucleotide molecule encodes a BoNT/F substrate cleavage site comprising at least six consecutive residues of VAMP including Gln-Lys. In other aspects of this embodiment, a polynucleotide molecule encodes a BoNT/F substrate cleavage site comprising, e.g., the amino acid sequence Glu-Arg-Asp-Gln-Lys-Leu-Ser-Glu (SEQ ID NO: 129); or the amino acid sequence Glu-Lys-Asp-Gln-Lys-Leu-Ala-Glu (SEQ ID NO: 130). In another aspect of this embodiment, a polynucleotide molecule encodes a BoNT/F substrate cleavage site comprising a naturally occurring BoNT/F substrate cleavage site variant. In another aspect of this embodiment, a polynucleotide molecule encodes a BoNT/F substrate cleavage site comprising a naturally occurring BoNT/F substrate cleavage site variant of SEQ ID NO: 129 or SEQ ID NO: 130, such as, e.g., a BoNT/F substrate cleavage site isoform of SEQ ID NO: 129 or SEQ ID NO: 130; or a BoNT/F substrate cleavage site subtype of SEQ ID NO: 129 or SEQ ID NO: 130. In still another aspect of this embodiment, a polynucleotide molecule encodes a BoNT/F substrate cleavage site comprising a non-naturally occurring BoNT/F substrate cleavage site variant, such as, e.g., a conservative BoNT/F substrate cleavage site variant, a non-conservative BoNT/F substrate cleavage site variant or a BoNT/F substrate cleavage site peptidomimetic, or any combination thereof. In still another aspect of this embodiment, a polynucleotide molecule encodes a BoNT/F substrate cleavage site comprising a non-naturally occurring BoNT/F substrate cleavage site variant of SEQ ID NO: 129 or SEQ ID NO: 130; such as, e.g., a conservative BoNT/F substrate cleavage site variant of SEQ ID NO: 129 or SEQ ID NO: 130; a non-conservative BoNT/F substrate cleavage site variant of SEQ ID NO: 129 or SEQ ID NO: 130; a BoNT/F substrate cleavage site peptidomimetic of SEQ ID NO: 129 or SEQ ID NO: 130; or any combination thereof.

In other aspects of this embodiment, a polynucleotide molecule encodes a BoNT/F substrate cleavage site comprising a polypeptide having, e.g., at least 50% amino acid identity with SEQ ID NO: 129, at least 62.5% amino acid identity with the SEQ ID NO: 129, at least 75% amino acid identity with SEQ ID NO: 129 or at least 87.5% amino acid identity with SEQ ID NO: 129. In still other aspects of this embodiment, a polynucleotide molecule encodes a BoNT/F substrate cleavage site comprising a polypeptide having, e.g., at most 50% amino acid identity with SEQ ID NO: 129, at most 62.5% amino acid identity with the SEQ ID NO: 129, at most 75% amino acid identity with SEQ ID NO: 129 or at most 87.5% amino acid identity with SEQ ID NO: 129.

In other aspects of this embodiment, a polynucleotide molecule encodes a BoNT/F substrate cleavage site comprising a polypeptide having, e.g., at most one, two, three or four non-contiguous amino acid substitutions relative to SEQ ID NO: 129. In still other aspects of this embodiment, a polynucleotide molecule encodes a BoNT/F substrate cleavage site comprising a polypeptide having, e.g., at least one, two, three or four non-contiguous amino acid substitutions relative to SEQ ID NO: 129. In yet other aspects of this embodiment, a polynucleotide molecule encodes a BoNT/F substrate cleavage site comprising a polypeptide having, e.g., at most one, two, three, four, five, six, seven, eight, nine or ten non-contiguous amino acid additions relative to SEQ ID NO: 129. In yet other aspects of this embodiment, a polynucleotide molecule encodes BoNT/F substrate cleavage site comprising a polypeptide having, e.g., at least one, two, three, four, five, six, seven, eight, nine or ten non-contiguous amino acid additions relative to SEQ ID NO: 129. In still other aspects of this embodiment, a polynucleotide molecule encodes a BoNT/F substrate cleavage site comprising a polypeptide having, e.g., at most one, two or three non-contiguous amino acid deletions relative to SEQ ID NO: 129. In still other aspects of this embodiment, a polynucleotide molecule encodes a BoNT/F substrate cleavage site comprising a polypeptide having, e.g., at least one, two or three non-contiguous amino acid deletions relative to SEQ ID NO: 129.

In other aspects of this embodiment, a polynucleotide molecule encodes a BoNT/F substrate cleavage site comprising a polypeptide having, e.g., at most two, three or four contiguous amino acid substitutions relative to SEQ ID NO: 129. In still other aspects of this embodiment, a polynucleotide molecule encodes a BoNT/F substrate cleavage site comprising a polypeptide having, e.g., at least two, three or four contiguous amino acid substitutions relative to SEQ ID NO: 129. In yet other aspects of this embodiment, a polynucleotide molecule encodes a BoNT/F substrate cleavage site comprising a polypeptide having, e.g., at most two, three, four, five, six, seven, eight, nine or ten contiguous amino acid additions relative to SEQ ID NO: 129. In yet other aspects of this embodiment, a polynucleotide molecule encodes a BoNT/F substrate cleavage site comprising a polypeptide having, e.g., at least two, three, four, five, six, seven, eight, nine or ten contiguous amino acid additions relative to SEQ ID NO: 129. In still other aspects of this embodiment, a polynucleotide molecule encodes a BoNT/F substrate cleavage site comprising a polypeptide having, e.g., at most two or three contiguous amino acid deletions relative to SEQ ID NO: 129. In still other aspects of this embodiment, a polynucleotide molecule encodes a BoNT/F substrate cleavage site comprising a polypeptide having, e.g., at least two or three contiguous amino acid deletions relative to SEQ ID NO: 129.

In still another embodiment, a polynucleotide molecule encodes a modified Clostridial toxin comprising a BoNT/G substrate cleavage site. In an aspect of this embodiment, a polynucleotide molecule encodes a BoNT/G substrate cleavage site comprising at least six consecutive residues of VAMP including Ala-Ala. In other aspects of this embodiment, a polynucleotide molecule encodes a BoNT/G substrate cleavage site comprising, e.g., the amino acid sequence Glu-Thr-Ser-Ala-Ala-Lys-Leu-Lys (SEQ ID NO: 131); or the amino acid sequence Glu-Ser-Ser-Ala-Ala-Lys-Leu-Lys (SEQ ID NO: 132). In another aspect of this embodiment, a polynucleotide molecule encodes a BoNT/G substrate cleavage site comprising a naturally occurring BoNT/G substrate cleavage site variant. In another aspect of this embodiment, a polynucleotide molecule encodes a BoNT/G substrate cleavage site comprising a naturally occurring BoNT/G substrate cleavage site variant of SEQ ID NO: 131 or SEQ ID NO: 132, such as, e.g., a BoNT/G substrate cleavage site isoform of SEQ ID NO: 131 or SEQ ID NO: 132; or a BoNT/G substrate cleavage site subtype of SEQ ID NO: 131 or SEQ ID NO: 132. In still another aspect of this embodiment, a polynucleotide molecule encodes a BoNT/G substrate cleavage site comprising a non-naturally occurring BoNT/F substrate cleavage site variant, such as, e.g., a conservative BoNT/G substrate cleavage site variant, a non-conservative BoNT/G substrate cleavage site variant or a BoNT/G substrate cleavage site peptidomimetic, or any combination thereof. In still another aspect of this embodiment, a polynucleotide molecule encodes a BoNT/G substrate cleavage site comprising a non-naturally occurring BoNT/G substrate cleavage site variant of SEQ ID NO: 131 or SEQ ID NO: 132; such as, e.g., a conservative BoNT/G substrate cleavage site variant of SEQ ID NO: 131 or SEQ ID NO: 132; a non-conservative BoNT/G substrate cleavage site variant of SEQ ID NO: 131 or SEQ ID NO: 132; a BoNT/G substrate cleavage site peptidomimetic of SEQ ID NO: 131 or SEQ ID NO: 132; or any combination thereof.

In other aspects of this embodiment, a polynucleotide molecule encodes a BoNT/G substrate cleavage site comprising a polypeptide having, e.g., at least 50% amino acid identity with SEQ ID NO: 131, at least 62.5% amino acid identity with the SEQ ID NO: 131, at least 75% amino acid identity with SEQ ID NO: 131 or at least 87.5% amino acid identity with SEQ ID NO: 131. In still other aspects of this embodiment, a polynucleotide molecule encodes a BoNT/G substrate cleavage site comprising a polypeptide having, e.g., at most 50% amino acid identity with SEQ ID NO: 131, at most 62.5% amino acid identity with the SEQ ID NO: 131, at most 75% amino acid identity with SEQ ID NO: 131 or at most 87.5% amino acid identity with SEQ ID NO: 131.

In other aspects of this embodiment, a polynucleotide molecule encodes a BoNT/G substrate cleavage site comprising a polypeptide having, e.g., at most one, two, three or four non-contiguous amino acid substitutions relative to SEQ ID NO: 131. In still other aspects of this embodiment, a polynucleotide molecule encodes a BoNT/G substrate cleavage site comprising a polypeptide having, e.g., at least one, two, three or four non-contiguous amino acid substitutions relative to SEQ ID NO: 131. In yet other aspects of this embodiment, a polynucleotide molecule encodes a BoNT/G substrate cleavage site comprising a polypeptide having, e.g., at most one, two, three, four, five, six, seven, eight, nine or ten non-contiguous amino acid additions relative to SEQ ID NO: 131. In yet other aspects of this embodiment, a polynucleotide molecule encodes BoNT/G substrate cleavage site comprising a polypeptide having, e.g., at least one, two, three, four, five, six, seven, eight, nine or ten non-contiguous amino acid additions relative to SEQ ID NO: 131. In still other aspects of this embodiment, a polynucleotide molecule encodes a BoNT/G substrate cleavage site comprising a polypeptide having, e.g., at most one, two or three non-contiguous amino acid deletions relative to SEQ ID NO: 131. In still other aspects of this embodiment, a polynucleotide molecule encodes a BoNT/G substrate cleavage site comprising a polypeptide having, e.g., at least one, two or three non-contiguous amino acid deletions relative to SEQ ID NO: 131.

In other aspects of this embodiment, a polynucleotide molecule encodes a BoNT/G substrate cleavage site comprising a polypeptide having, e.g., at most two, three or four contiguous amino acid substitutions relative to SEQ ID NO: 131. In still other aspects of this embodiment, a polynucleotide molecule encodes a BoNT/G substrate cleavage site comprising a polypeptide having, e.g., at least two, three or four contiguous amino acid substitutions relative to SEQ ID NO: 131. In yet other aspects of this embodiment, a polynucleotide molecule encodes a BoNT/G substrate cleavage site comprising a polypeptide having, e.g., at most two, three, four, five, six, seven, eight, nine or ten contiguous amino acid additions relative to SEQ ID NO: 131. In yet other aspects of this embodiment, a polynucleotide molecule encodes a BoNT/G substrate cleavage site comprising a polypeptide having, e.g., at least two, three, four, five, six, seven, eight, nine or ten contiguous amino acid additions relative to SEQ ID NO: 131. In still other aspects of this embodiment, a polynucleotide molecule encodes a BoNT/G substrate cleavage site comprising a polypeptide having, e.g., at most two or three contiguous amino acid deletions relative to SEQ ID NO: 131. In still other aspects of this embodiment, a polynucleotide molecule encodes a BoNT/G substrate cleavage site comprising a polypeptide having, e.g., at least two or three contiguous amino acid deletions relative to SEQ ID NO: 131.

In still another embodiment, a polynucleotide molecule encodes a modified Clostridial toxin comprising a TeNT substrate cleavage site. In an aspect of this embodiment, a polynucleotide molecule encodes a TeNT substrate cleavage site comprising at least six consecutive residues of VAMP including Gln-Phe. In other aspects of this embodiment, a polynucleotide molecule encodes a TeNT substrate cleavage site comprising, e.g., the amino acid sequence Gly-Ala-Ser-Gln-Phe-Glu-Thr-Ser (SEQ ID NO: 107); the amino acid sequence Gly-Ala-Ser-Gln-Phe-Glu-Ser-Ser (SEQ ID NO: 108); the amino acid sequence Gly-Ala-Ser-Gln-Phe-Glu-Thr-Asn (SEQ ID NO: 109); the amino acid sequence Gly-Ala-Ser-Gln-Phe-Glu-Gln-Gln (SEQ ID NO: 110); the amino acid sequence Gly-Ala-Ser-Gln-Phe-Glu-Ala-Ser (SEQ ID NO: 111); or the amino acid sequence Gly-Ala-Ser-Gln-Phe-Gln-Gln-Ser (SEQ ID NO: 112). In another aspect of this embodiment, a polynucleotide molecule encodes a TeNT substrate cleavage site comprising a naturally occurring TeNT substrate cleavage site variant. In another aspect of this embodiment, a polynucleotide molecule encodes a TeNT substrate cleavage site comprising a naturally occurring TeNT substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112, such as, e.g., a TeNT substrate cleavage site isoform of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; or a TeNT substrate cleavage site subtype of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112. In still another aspect of this embodiment, a polynucleotide molecule encodes a TeNT substrate cleavage site comprising a non-naturally occurring TeNT substrate cleavage site variant, such as, e.g., a conservative TeNT substrate cleavage site variant, a non-conservative TeNT substrate cleavage site variant or a TeNT substrate cleavage site peptidomimetic, or any combination thereof. In still another aspect of this embodiment, a polynucleotide molecule encodes a TeNT substrate cleavage site comprising a non-naturally occurring TeNT substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; such as, e.g., a conservative TeNT substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; a non-conservative TeNT substrate cleavage site variant of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; a TeNT substrate cleavage site peptidomimetic of SEQ ID NO: 107, SEQ ID NO: 108, SEQ ID NO: 109, SEQ ID NO: 110, SEQ ID NO: 111 or SEQ ID NO: 112, such as, e.g., a BoNT/B substrate cleavage site isoform of SEQ ID NO: 107, SEQ ID NO: 108, SEQ ID NO: 109, SEQ ID NO: 110, SEQ ID NO: 111 or SEQ ID NO: 112; or any combination thereof.

In other aspects of this embodiment, a polynucleotide molecule encodes a TeNT substrate cleavage site comprising a polypeptide having, e.g., at least 50% amino acid identity with SEQ ID NO: 107, at least 62.5% amino acid identity with the SEQ ID NO: 107, at least 75% amino acid identity with SEQ ID NO: 107 or at least 87.5% amino acid identity with SEQ ID NO: 107. In still other aspects of this embodiment, a polynucleotide molecule encodes a TeNT substrate cleavage site comprising a polypeptide having, e.g., at most 50% amino acid identity with SEQ ID NO: 107, at most 62.5% amino acid identity with the SEQ ID NO: 107, at most 75% amino acid identity with SEQ ID NO: 107 or at most 87.5% amino acid identity with SEQ ID NO: 107.

In other aspects of this embodiment, a polynucleotide molecule encodes a TeNT substrate cleavage site comprising a polypeptide having, e.g., at most one, two, three or four non-contiguous amino acid substitutions relative to SEQ ID NO: 107. In still other aspects of this embodiment, a polynucleotide molecule encodes a TeNT substrate cleavage site comprising a polypeptide having, e.g., at least one, two, three or four non-contiguous amino acid substitutions relative to SEQ ID NO: 107. In yet other aspects of this embodiment, a polynucleotide molecule encodes a TeNT substrate cleavage site comprising a polypeptide having, e.g., at most one, two, three, four, five, six, seven, eight, nine or ten non-contiguous amino acid additions relative to SEQ ID NO: 107. In yet other aspects of this embodiment, a polynucleotide molecule encodes TeNT substrate cleavage site comprising a polypeptide having, e.g., at least one, two, three, four, five, six, seven, eight, nine or ten non-contiguous amino acid additions relative to SEQ ID NO: 107. In still other aspects of this embodiment, a polynucleotide molecule encodes a TeNT substrate cleavage site comprising a polypeptide having, e.g., at most one, two or three non-contiguous amino acid deletions relative to SEQ ID NO: 107. In still other aspects of this embodiment, a polynucleotide molecule encodes a TeNT substrate cleavage site comprising a polypeptide having, e.g., at least one, two or three non-contiguous amino acid deletions relative to SEQ ID NO: 107.

In other aspects of this embodiment, a polynucleotide molecule encodes a TeNT substrate cleavage site comprising a polypeptide having, e.g., at most two, three or four contiguous amino acid substitutions relative to SEQ ID NO: 107. In still other aspects of this embodiment, a polynucleotide molecule encodes a TeNT substrate cleavage site comprising a polypeptide having, e.g., at least two, three or four contiguous amino acid substitutions relative to SEQ ID NO: 107. In yet other aspects of this embodiment, a polynucleotide molecule encodes a TeNT substrate cleavage site comprising a polypeptide having, e.g., at most two, three, four, five, six, seven, eight, nine or ten contiguous amino acid additions relative to SEQ ID NO: 107. In yet other aspects of this embodiment, a polynucleotide molecule encodes a TeNT substrate cleavage site comprising a polypeptide having, e.g., at least two, three, four, five, six, seven, eight, nine or ten contiguous amino acid additions relative to SEQ ID NO: 107. In still other aspects of this embodiment, a polynucleotide molecule encodes a TeNT substrate cleavage site comprising a polypeptide having, e.g., at most two or three contiguous amino acid deletions relative to SEQ ID NO: 107. In still other aspects of this embodiment, a polynucleotide molecule encodes a TeNT substrate cleavage site comprising a polypeptide having, e.g., at least two or three contiguous amino acid deletions relative to SEQ ID NO: 107.

In yet another embodiment, a polynucleotide molecule encoding a modified Clostridial toxin disclosed in the present specification can further comprise a polynucleotide molecule encoding a flexible region comprising a flexible spacer. In another embodiment, a polynucleotide molecule encoding a modified Clostridial toxin disclosed in the present specification can further comprise a polynucleotide molecule encoding a flexible region comprising a plurality of flexible spacers in tandem. In aspects of this embodiment, a polynucleotide molecule encoding a flexible region can comprise in tandem, e.g., at least 1 G-spacer, at least 2 G-spacers, at least 3 G-spacers, at least 4 G-spacers or at least 5 G-spacers. In other aspects of this embodiment, a polynucleotide molecule encoding a flexible region can comprise in tandem, e.g., at most 1 G-spacer, at most 2 G-spacers, at most 3 G-spacers, at most 4 G-spacers or at most 5 G-spacers. In still other aspects of this embodiment, a polynucleotide molecule encoding a flexible region can comprise in tandem, e.g., at least 1 A-spacer, at least 2 A-spacers, at least 3 A-spacers, at least 4 A-spacers or at least 5 A-spacers. In still other aspects of this embodiment, a polynucleotide molecule encoding a flexible region can comprise in tandem, e.g., at most 1 A-spacer, at most 2 A-spacers, at most 3 A-spacers, at most 4 A-spacers or at most 5 A-spacers. In another aspect of this embodiment, a polynucleotide molecule encoding a modified Clostridial toxin can comprise a polynucleotide molecule encoding a flexible region comprising one or more copies of the same flexible spacers, one or more copies of different flexible-spacers region, or any combination thereof.

In yet another embodiment, a polynucleotide molecule encoding a modified Clostridial toxin disclosed in the present specification can further comprises a polynucleotide molecule encoding an epitope-binding region. In another embodiment, a polynucleotide molecule encoding a modified Clostridial toxin disclosed in the present specification can further comprises a polynucleotide molecule encoding a plurality of epitope-binding regions. In aspects of this embodiment, a polynucleotide molecule encoding a modified Clostridial toxin can comprise, e.g., at least 1 polynucleotide molecule encoding an epitope-binding region, at least 2 polynucleotide molecules encoding epitope-binding regions, at least 3 polynucleotide molecules encoding epitope-binding regions, at least 4 polynucleotide molecules encoding epitope-binding regions or at least 5 polynucleotide molecules encoding epitope-binding regions. In other aspects of this embodiment, a polynucleotide molecule encoding a modified Clostridial toxin can comprise, e.g., at most 1 polynucleotide molecule encoding an epitope-binding region, at most 2 polynucleotide molecules encoding epitope-binding regions, at most 3 polynucleotide molecules encoding epitope-binding regions, at most 4 polynucleotide molecules encoding epitope-binding regions or at most 5 polynucleotide molecules encoding epitope-binding regions. In another aspect of this embodiment, a polynucleotide molecule encoding a modified Clostridial toxin can comprise one or more copies of the same polynucleotide molecules encoding epitope-binding region, one or more copies of different polynucleotide molecules encoding epitope-binding region, or any combination thereof. The location of a polynucleotide molecule encoding an epitope-binding region can be in various positions, including, without limitation, at the amino terminus of a modified Clostridial toxin, within a modified Clostridial toxin, or at the carboxyl terminus of a modified Clostridial toxin.

In an aspect of this embodiment, a polynucleotide molecule encoding an epitope-binding region is located at the amino-terminus of a modified Clostridial toxin. In aspects of this embodiment, a polynucleotide molecule encoding an epitope-binding region located at the amino-terminus of a modified Clostridial toxin disclosed in the present specification can be, e.g., a FLAG, Express™ epitope-binding region, a human Influenza virus hemagglutinin (HA) epitope-binding region, a human p62$^{c-Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In another aspect of this embodiment, a polynucleotide molecule encoding an epitope-binding region is located at the carboxyl-terminus of a modified Clostridial toxin. In aspects of this embodiment, a polynucleotide molecule encoding an epitope-binding region located at the carboxyl-terminus of a modified Clostridial toxin disclosed in the present specification can be, e.g., a FLAG, Express™ epitope-binding region, a human Influenza virus hemagglutinin (HA) epitope-binding region, a human p62$^{c-Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In yet another embodiment, polynucleotide molecules encoding a modified Clostridial toxin disclosed in the present specification can further comprise a polynucleotide molecule encoding an exogenous protease cleavage site. In another embodiment, a polynucleotide molecule encoding a modified Clostridial toxin disclosed in the present specification can further comprises a plurality of polynucleotide molecules encoding exogenous protease cleavage sites. In aspects of this embodiment, a polynucleotide molecule encoding a modified Clostridial toxin can comprise, e.g., at least 1 polynucleotide molecule encoding an exogenous protease cleavage site, at least 2 polynucleotide molecules encoding exogenous protease cleavage sites, at least 3 polynucleotide molecules encoding exogenous protease cleavage sites, at least 4 polynucleotide molecules encoding exogenous protease cleavage sites or at least 5 polynucleotide molecules encoding exogenous protease cleavage sites. In other aspects of this embodiment, polynucleotide molecules encoding a modified Clostridial toxin can comprise, e.g., at most 1 polynucleotide molecule encoding an exogenous protease cleavage site, at most 2 polynucleotide molecules encoding exogenous protease cleavage sites, at most 3 polynucleotide molecules encoding exogenous protease cleavage sites, at most 4 polynucleotide molecules encoding exogenous protease cleavage sites or at most 5 polynucleotide molecules encoding exogenous protease cleavage sites. In another aspect of this embodiment, a polynucleotide molecule encoding a modified Clostridial toxin can comprise one or more copies of the same exogenous protease cleavage site, one or more copies of different exogenous protease cleavage site, or any combination thereof.

In yet another embodiment, a polynucleotide molecule encoding an exogenous protease cleavage site is located between a polynucleotide molecule encoding an epitope-binding peptide and a polynucleotide molecule encoding a modified Clostridial toxin. In other aspects of this embodiment, a polynucleotide molecule encoding a bovine enterokinase cleavage site is located between a polynucleotide molecule encoding an epitope-binding region and a polynucleotide molecule encoding a modified Clostridial toxin, a polynucleotide molecule encoding a Tobacco Etch Virus protease cleavage site is located between a polynucleotide molecule encoding an epitope-binding region and a polynucleotide molecule encoding a modified Clostridial toxin, a polynucleotide molecule encoding a Human Rhinovirus 3C protease cleavage site is located between a polynucleotide molecule encoding an epitope-binding region and a polynucleotide molecule encoding a modified Clostridial toxin, a polynucleotide molecule encoding a SUMO/ULP-1 protease cleavage site is located between a polynucleotide molecule encoding an epitope-binding region and a polynucleotide molecule encoding a modified Clostridial toxin, a polynucleotide molecule encoding a Thrombin protease cleavage site is located between a polynucleotide molecule encoding an epitope-binding region and a polynucleotide molecule encoding a modified Clostridial toxin, or a polynucleotide molecule encoding a Coagulation Factor Xa protease cleavage site is located between a polynucleotide molecule encoding an epitope-binding region and a polynucleotide molecule encoding a modified Clostridial toxin. In other aspects of the embodiment, a polynucleotide molecule encoding the bovine enterokinase protease cleavage site of SEQ ID NO: 168 is located between a polynucleotide molecule encoding an epitope-binding region and a polynucleotide molecule encoding a modified Clostridial toxin. In other aspects of the embodiment, a polynucleotide molecule encoding the Tobacco Etch Virus protease cleavage site of SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177 or SEQ ID NO: 178 is located between a polynucleotide molecule encoding an epitope-binding region and a polynucleotide molecule encoding a modified Clostridial toxin. In still other aspects of the embodiment, a polynucleotide molecule encoding the Human Rhinovirus 3C protease cleavage site of SEQ ID NO: 179, SEQ ID NO: 180, SEQ ID NO: 181, SEQ ID NO: 182, SEQ ID NO: 183 or SEQ ID NO: 184 is located between a polynucleotide molecule encoding an epitope-binding region and a polynucleotide molecule encoding a modified Clostridial toxin. In yet other aspects of the embodiment, a polynucleotide molecule encoding the SUMO/ULP-1 protease cleavage site of SEQ ID NO: 185 is located between a polynucleotide molecule encoding an epitope-binding region and a polynucleotide molecule encoding a modified Clostridial toxin. In further other aspects of the embodiment, a polynucleotide molecule encoding the Thrombin protease cleavage site of SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199 or SEQ ID NO: 200 is located between a polynucleotide molecule encoding an epitope-binding region and a polynucleotide molecule encoding a modified Clostridial toxin. In other aspects of the embodiment, a polynucleotide molecule encoding the Coagulation Factor Xa protease cleavage site of SEQ ID NO: 201 or SEQ ID NO: 202 is located between a polynucleotide molecule encoding an epitope-binding region and a polynucleotide molecule encoding a modified Clostridial toxin.

Another aspect of the present invention provides a method of producing a modified Clostridial toxin comprising Clostridial toxin substrate cleavage site, wherein the Clostridial toxin substrate cleavage site is located within the di-chain loop region, such method comprising the step of expressing a polynucleotide molecule encoding a modified Clostridial toxin in a cell. Another aspect of the present invention provides a method of producing a modified Clostridial toxin comprising Clostridial toxin substrate cleavage site, wherein the Clostridial toxin substrate cleavage site is located within the di-chain loop region, such method comprising the steps of introducing an expression construct comprising a polynucleotide molecule encoding a modified Clostridial toxin into a cell and expressing the expression construct in the cell.

The methods disclosed in the present specification include, in part, a Clostridial toxin. It is envisioned that any and all Clostridial toxins disclosed in the present specification can be produced using the methods disclosed in the present specification. Thus, aspects of this embodiment include producing, without limitation, naturally occurring Clostridial toxins, naturally occurring Clostridial toxins variants, such as, e.g., Clostridial toxins isoforms and Clostridial toxins subtypes, non-naturally occurring Clostridial toxins variants, such as, e.g., conservative Clostridial toxins variants, non-conservative Clostridial toxins variants and Clostridial toxins fragments thereof, or any combination thereof.

The methods disclosed in the present specification include, in part, Clostridial toxin substrate cleavage site. It is envisioned that any and all Clostridial toxin substrate cleavage site disclosed in the present specification can be produced using the methods disclosed in the present specification. Thus, aspects of this embodiment include producing, without limitation, naturally occurring Clostridial toxin substrate cleavage sites, naturally occurring Clostridial toxin substrate cleavage site variants, such as, e.g., Clostridial toxin substrate cleavage site isoforms and Clostridial toxin substrate cleavage site subtypes, non-naturally occurring Clostridial toxin substrate cleavage site variants, such as, e.g., conservative Clostridial toxin substrate cleavage site variants, non-conservative Clostridial toxin substrate cleavage site variants and Clostridial toxin substrate cleavage site peptidomimetics thereof, or any combination thereof.

The methods disclosed in the present specification include, in part, a polynucleotide molecule. It is envisioned that any and all polynucleotide molecules disclosed in the present specification can be used. Thus, aspects of this embodiment include, without limitation, polynucleotide molecules encoding naturally occurring Clostridial toxins; polynucleotide molecules encoding naturally occurring Clostridial toxins variants, such as, e.g., Clostridial toxins isoforms and Clostridial toxins subtypes; polynucleotide molecules encoding non-naturally occurring Clostridial toxins variants, such as, e.g., conservative Clostridial toxins variants, non-conservative Clostridial toxins variants and Clostridial toxins fragments thereof, or any combination thereof.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a modified Clostridial toxin, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a modified Clostridial toxin under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Thus, aspects of this embodiment include, without limitation, a viral expression vector operably-linked to a polynucleotide molecule encoding a modified Clostridial toxin; a prokaryotic expression vector operably-linked to a polynucleotide molecule encoding a modified Clostridial toxin; a yeast expression vector operably-linked to a polynucleotide molecule encoding a modified Clostridial toxin; an insect expression vector operably-linked to a polynucleotide molecule encoding a modified Clostridial toxin; and a mammalian expression vector operably-linked to a polynucleotide molecule encoding a modified Clostridial toxin. Other aspects of this embodiment include, without limitation, expression constructs suitable for expressing a modified Clostridial toxin disclosed in the present specification using a cell-free extract comprising a cell-free extract expression vector operably linked to a polynucleotide molecule encoding a modified Clostridial toxin. Other aspects of this embodiment include, without limitation, expression constructs comprising polynucleotide molecules comprising any one of SEQ ID NO: 109 through SEQ ID NO: 132 and SEQ ID NO: 136 through SEQ ID NO: 159. Other aspects of this embodiment include, without limitation, expression constructs comprising polynucleotide molecules encoding a modified Clostridial toxin comprising any one of SEQ ID NO: 85 through SEQ ID NO: 108.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection (2004); European Collection of Cell Cultures (2204); and the German Collection of Microorganisms and Cell Cultures (2004). Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, $4^{th}$ ed. 2000); ANIMAL CELL CULTURE: A PRACTICAL APPROACH (John R. W. Masters ed., Oxford University Press, $3^{rd}$ ed. 2000); MOLECULAR CLONING A LABORATORY MANUAL, supra, (2001); BASIC CELL CULTURE: A PRACTICAL APPROACH (John M. Davis, Oxford Press, $2^{nd}$ ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell a polynucleotide molecule. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a nucleic acid molecule into a cell include, without limitation, chemical-mediated transfection, such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated transfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a polynucleotide molecule encoding a modified Clostridial toxin into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, *Transfection of Adherent and Suspended Cells by Calcium Phosphate*, 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., *Polyethylenimine Strategies for Plasmid Delivery to Brain-Derived Cells*, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a polynucleotide molecule encoding a modified Clostridial toxin into a cell. Physical techniques include, without limitation, electroporation, biolistic and microinjection. Biolistics and microinjection techniques perforate the cell wall in order to introduce the nucleic acid molecule into the cell, see, e.g., Jeike E. Biewenga et al., *Plasmid-Mediated Gene Transfer in Neurons Using the Biolistics Technique*, 71 (1) J. Neurosci. Methods. 67-75 (1997); and John O'Brien & Sarah C. R. Lummis, *Biolistic and Diolistic Transfection: Using the Gene Gun to Deliver DNA and Lipophilic Dyes into Mammalian Cells*, 33(2) Methods 121-125 (2004). Electroporation, also termed electropermeabilization, uses brief, high-voltage, electrical pulses to create transient pores in the membrane through which the nucleic acid molecules enter and can be used effectively for stable and transient transfections of all cell types, see, e.g., M. Golzio et al., *In vitro and in vivo Electric Field-Mediated Permeabilization, Gene Transfer, and Expression*, 33(2) Methods 126-135 (2004); and Oliver Gresch et al., *New Non-Viral Method for Gene Transfer into Primary Cells*, 33(2) Methods 151-163 (2004).

In another aspect of this embodiment, a viral-mediated method, termed transduction, is used to introduce a polynucleotide molecule encoding a modified Clostridial toxin into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, *Lentiviral and MLV based Retroviral Vectors for ex vivo and in vivo Gene Transfer*, 33(2) Methods 164-172 (2004); and Maurizio Federico, *From Lentiviruses to Lentivirus Vectors*, 229 Methods Mol. Biol. 3-15 (2003); E. M. Poeschla, *Non-Primate Lentiviral Vectors*, 5(5) Curr. Opin. Mol. Ther. 529-540 (2003); Karim Benihoud et al, *Adenovirus Vectors for Gene Delivery*, 10(5) Curr. Opin. Biotechnol. 440-447 (1999); H. Bueler, *Adeno-Associated Viral Vectors for Gene Transfer and Gene Therapy*, 380(6) Biol. Chem. 613-622 (1999); Chooi M. Lai et al., *Adenovirus and Adeno-Associated Virus Vectors*, 21(12) DNA Cell Biol. 895-913 (2002); Edward A. Burton et al., *Gene Delivery Using Herpes Simplex Virus Vectors*, 21(12) DNA Cell Biol. 915-936 (2002); Paola Grandi et al., *Targeting HSV Amplicon Vectors*, 33(2) Methods 179-186 (2004); Ilya Frolov et al., *Alphavirus-Based Expression Vectors: Strategies and Applications*, 93(21) Proc. Natl. Acad. Sci. U.S.A. 11371-11377 (1996); Markus U. Ehrengruber, *Alphaviral Gene Transfer in Neurobiology*, 59(1) Brain Res. Bull. 13-22 (2002); Thomas A. Kost & J. Patrick Condreay, *Recombinant Baculoviruses as Mammalian Cell Gene-Delivery Vectors*, 20(4) Trends Biotechnol. 173-180 (2002); and A. Huser & C. Hofmann, *Baculovirus Vectors: Novel Mammalian Cell Gene-Delivery Vehicles and Their Applications*, 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., *Transient Gene Transfer to Neurons and Glia: Analysis of Adenoviral Vector Performance in the CNS and PNS,* 71(1) J. Neurosci. Methods 85-98 (1997); and Hiroyuki Mizuguchi et al., *Approaches for Generating Recombinant Adenovirus Vectors,* 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenoviral vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEaSy™ Adenoviral Vector System (Stratagene, Inc., La Jolla, Calif.) and AdEasy™ Adenoviral Vector System Instruction Manual 064004f, Stratagene, Inc.

Nucleic acid molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., *Transient Production Of Retroviral-and Lentiviral-Based Vectors For the Transduction of Mammalian Cells,* 285 Methods Mol. Biol. 141-148 (2004); Armin Blesch, *Lentiviral and MLV Based Retroviral Vectors for ex vivo and in vivo Gene Transfer,* 33(2) Methods 164-172 (2004); Félix Recillas-Targa, *Gene Transfer and Expression in Mammalian Cell Lines and Transgenic Animals,* 267 Methods Mol. Biol. 417-433 (2004); and Roland Wolkowicz et al., *Lentiviral Vectors for the Delivery of DNA into Mammalian Cells,* 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., *In vivo Gene Delivery and Stable Transduction of Non-Dividing Cells By a Lentiviral Vector,* 272(5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. Patent Nos. Manfred Gossen & Hermann Bujard, Tight Control of Gene Expression in Eukaryotic Cells By Tetracycline-Responsive Promoters, U.S. Pat. No. 5,464,758 (Nov. 7, 1995) and Hermann Bujard & Manfred Gossen, Methods for Regulating Gene Expression, U.S. Pat. No. 5,814,618 (Sep. 29, 1998) David S. Hogness, Polynucleotides Encoding Insect Steroid Hormone Receptor Polypeptides and Cells Transformed With Same, U.S. Pat. No. 5,514,578 (May 7, 1996) and David S. Hogness, Polynucleotide Encoding Insect Ecdysone Receptor, U.S. Pat. No. 6,245,531 (Jun. 12, 2001); Elisabetta Vegeto et al., Progesterone Receptor Having C. Terminal Hormone Binding Domain Truncations, U.S. Pat. No. 5,364,791 (Nov. 15, 1994), Elisabetta Vegeto et al., Mutated Steroid Hormone Receptors, Methods For Their Use and Molecular Switch For Gene Therapy, U.S. Pat. No. 5,874,534 (Feb. 23, 1999) and Elisabetta Vegeto et al., Mutated Steroid Hormone Receptors, Methods For Their Use and Molecular Switch For Gene Therapy, U.S. Pat. No. 5,935,934 (Aug. 10, 1999). Furthermore, such viral delivery systems can be prepared by standard methods and are commercially available, see, e.g., B™ Tet-Off and Tet-On Gene Expression Systems (BD Biosciences-Clontech, Palo Alto, Calif.) and B™ Tet-Off and Tet-On Gene Expression Systems User Manual, PT3001-1, BD Biosciences Clontech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

The methods disclosed in the present specification include, in part, expressing a modified Clostridial toxin from a polynucleotide molecule. It is envisioned that any of a variety of expression systems may be useful for expressing a modified Clostridial toxin from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heter-* ologous Proteins, 80(9) Curr. Sci. 1121-1128, (2001). These protocols are routine procedures well within the scope of one skilled in the art and from the teaching herein.

A variety of cell-based expression procedures are useful for expressing a modified Clostridial toxin encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the ViraPower™ Lentiviral (Invitrogen, Inc., Carlsbad, Calif.), the Adenoviral Expression Systems (Invitrogen, Inc., Carlsbad, Calif.), the AdEaSy™ XL Adenoviral Vector System (Stratagene, La Jolla, Calif.) and the ViraPort® Retroviral Gene Expression System (Stratagene, La Jolla, Calif.). Non-limiting examples of prokaryotic expression systems include the Champion™ pET Expression System (EMD Biosciences-Novagen, Madison, Wis.), the TriEx™ Bacterial Expression Systems (EMD Biosciences-Novagen, Madison, Wis.), the QIAexpress® Expression System (QIAGEN, Inc.), and the Affinity® Protein Expression and Purification System (Stratagene, La Jolla, Calif.). Yeast expression systems include, without limitation, the EasySelect™ *Pichia* Expression Kit (Invitrogen, Inc., Carlsbad, Calif.), the YES-Echo™ Expression Vector Kits (Invitrogen, Inc., Carlsbad, Calif.) and the SPECTRA™ *S. pombe* Expression System (Invitrogen, Inc., Carlsbad, Calif.). Non-limiting examples of baculoviral expression systems include the BaculoDirect™ (Invitrogen, Inc., Carlsbad, Calif.), the Bac-to-Bac® (Invitrogen, Inc., Carlsbad, Calif.), and the BD BaculoGold™ (BD Biosciences-Pharmingen, San Diego, Calif.). Insect expression systems include, without limitation, the *Drosophila* Expression System (DES®) (Invitrogen, Inc., Carlsbad, Calif.), InsectSelect™ System (Invitrogen, Inc., Carlsbad, Calif.) and InsectDirect™ System (EMD Biosciences-Novagen, Madison, Wis.). Non-limiting examples of mammalian expression systems include the T-REx™ (Tetracycline-Regulated Expression) System (Invitrogen, Inc., Carlsbad, Calif.), the Flp-In™ T-REx™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the Exchanger® System, InterPlay™ Mammalian TAP System (Stratagene, La Jolla, Calif.), Complete Control® Inducible Mammalian Expression System (Stratagene, La Jolla, Calif.) and LacSwitch® II Inducible Mammalian Expression System (Stratagene, La Jolla, Calif.).

Another procedure of expressing a modified Clostridial toxin encoded by polynucleotide molecule disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ActivePro In Vitro Translation Kit (Ambion, Inc., Austin, Tex.), the EcoPro™ System (EMD Biosciences-Novagen, Madison, Wis.) and the Expressway™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TnT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINscript® II System (Ambion, Inc., Austin, Tex.) and the TnT® Coupled Reticulocyte Lysate Systems (Promega Corp., Madison, Wis.).

Aspects of the present invention can also be described as follows:
1. A modified Clostridial toxin comprising a Clostridial toxin substrate cleavage site, wherein the Clostridial toxin substrate cleavage site is located within a di-chain loop region.
2. The modified Clostridial toxin according to 1, wherein the Clostridial toxin substrate cleavage site is a Botulinum toxin substrate cleavage site.
3. The modified Clostridial toxin according to 2, wherein the Botulinum toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site and a BoNT/G substrate cleavage site.
4. The modified Clostridial toxin according to 2, wherein the Botulinum toxin substrate cleavage site comprises a BoNT/A cleavage site.
5. The modified Clostridial toxin according to 2, wherein the Botulinum toxin substrate cleavage site comprises at least six consecutive residues of a SNAP-25, said six consecutive residues comprising Gln-Arg.
6. The modified Clostridial toxin according to 2, wherein the Botulinum toxin substrate cleavage site comprises at least six consecutive residues of a SNAP-25, said six consecutive residues comprising Lys-His.
7. The modified Clostridial toxin according to 2, wherein the Botulinum toxin substrate cleavage site comprises SEQ ID NO: 104, SEQ ID NO: 105 or SEQ ID NO: 106.
8. The modified Clostridial toxin according to 2, wherein the Botulinum toxin substrate cleavage site comprises a BoNT/B cleavage site.
9. The modified Clostridial toxin according to 2, wherein the Botulinum toxin substrate cleavage site comprises at least six consecutive residues of a VAMP, said six consecutive residues comprising Gln-Phe.
10. The modified Clostridial toxin according to 2, wherein the Botulinum toxin substrate cleavage site comprises SEQ ID NO: 107, SEQ ID NO: 108, SEQ ID NO: 109, SEQ ID NO: 110, SEQ ID NO: 111 or SEQ ID NO: 112.
11. The modified Clostridial toxin according to 2, wherein the Botulinum toxin substrate cleavage site comprises a BoNT/C1 cleavage site.
12. The modified Clostridial toxin according to 2, wherein the Botulinum toxin substrate cleavage site comprises at least six consecutive residues of a SNAP-25, said six consecutive residues comprising Arg-Ala.
13. The modified Clostridial toxin according to 2, wherein the Botulinum toxin substrate cleavage site comprises at least six consecutive residues of a Syntaxin, said six consecutive residues comprising Lys-Ala.
14. The modified Clostridial toxin according to 2, wherein the Botulinum toxin substrate cleavage site comprises at least six consecutive residues of a Syntaxin, said six consecutive residues comprising Arg-Ala.
15. The modified Clostridial toxin according to 2, wherein the Botulinum toxin substrate cleavage site comprises SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120 or SEQ ID NO: 121.
16. The modified Clostridial toxin according to 2, wherein the Botulinum toxin substrate cleavage site comprises a BoNT/D cleavage site.
17. The modified Clostridial toxin according to 2, wherein the Botulinum toxin substrate cleavage site comprises at least six consecutive residues of a VAMP, said six consecutive residues comprising Lys-Leu.

18. The modified Clostridial toxin according to 2, wherein the Botulinum toxin substrate cleavage site comprises SEQ ID NO: 122 or SEQ ID NO: 123.
19. The modified Clostridial toxin according to 2, wherein the Botulinum toxin substrate cleavage site comprises a BoNT/E cleavage site.
20. The modified Clostridial toxin according to 2, wherein the Botulinum toxin substrate cleavage site comprises at least six consecutive residues of a SNAP-25, said six consecutive residues comprising Arg-Ile.
21. The modified Clostridial toxin according to 2, wherein the Botulinum toxin substrate cleavage site comprises at least six consecutive residues of a SNAP-25, said six consecutive residues comprising Lys-Ile.
22. The modified Clostridial toxin according to 2, wherein the Botulinum toxin substrate cleavage site comprises SEQ ID NO: 124, SEQ ID NO: 125, SEQ ID NO: 126, SEQ ID NO: 127 or SEQ ID NO: 128.
23. The modified Clostridial toxin according to 2, wherein the Botulinum toxin substrate cleavage site comprises a BoNT/F cleavage site.
24. The modified Clostridial toxin according to 2, wherein the Botulinum toxin substrate cleavage site comprises at least six consecutive residues of a VAMP, said six consecutive residues comprising Gln-Lys.
25. The modified Clostridial toxin according to 2, wherein the Botulinum toxin substrate cleavage site comprises SEQ ID NO: 129 or SEQ ID NO: 130.
26. The modified Clostridial toxin according to 2, wherein the Botulinum toxin substrate cleavage site comprises a BoNT/G cleavage site.
27. The modified Clostridial toxin according to 2, wherein the Botulinum toxin substrate cleavage site comprises at least six consecutive residues of a VAMP, said six consecutive residues comprising Ala-Ala.
28. The modified Clostridial toxin according to 2, wherein the Botulinum toxin substrate cleavage site comprises SEQ ID NO: 131 or SEQ ID NO: 132.
29. The modified Clostridial toxin according to 1, wherein the Clostridial toxin substrate cleavage site is a Tetanus toxin substrate cleavage site.
30. The modified Clostridial toxin according to 29, wherein the Tetanus toxin substrate cleavage site comprises at least six consecutive residues of a VAMP, said six consecutive residues comprising Gln-Phe.
31. The modified Clostridial toxin according to 1, wherein the modified Clostridial toxin comprises a Botulinum toxin enzymatic domain, a Botulinum toxin translocation domain and a Botulinum toxin binding domain.
32. The modified Clostridial toxin according to 1, wherein the modified Botulinum toxin comprises a BoNT/A enzymatic domain, a BoNT/A translocation domain and a BoNT/A binding domain.
33. The modified Clostridial toxin according to 1, wherein the modified Botulinum toxin comprises a BoNT/B enzymatic domain, a BoNT/B translocation domain and a BoNT/B binding domain.
34. The modified Clostridial toxin according to 1, wherein the modified Botulinum toxin comprises a BoNT/C1 enzymatic domain, a BoNT/C1 translocation domain and a BoNT/C1 binding domain.
35. The modified Clostridial toxin according to 1, wherein the modified Botulinum toxin comprises a BoNT/D enzymatic domain, a BoNT/D translocation domain and a BoNT/D binding domain.
36. The modified Clostridial toxin according to 1, wherein the modified Botulinum toxin comprises a BoNT/E enzymatic domain, a BoNT/E translocation domain and a BoNT/E binding domain.
37. The modified Clostridial toxin according to 1, wherein the modified Botulinum toxin comprises a BoNT/F enzymatic domain, a BoNT/F translocation domain and a BoNT/F binding domain.
38. The modified Clostridial toxin according to 1, wherein the modified Botulinum toxin comprises a BoNT/G enzymatic domain, a BoNT/G translocation domain and a BoNT/G binding domain.
39. The modified Clostridial toxin according to 1, wherein the modified Clostridial toxin comprises a Tetanus toxin enzymatic domain, a Tetanus toxin translocation domain and a Tetanus toxin binding domain.
40. A modified Clostridial toxin comprising:
    a) a Clostridial toxin substrate cleavage site;
    b) a di-chain loop region
    c) a Clostridial toxin enzymatic domain;
    d) a Clostridial toxin translocation domain; and
    e) an enhanced cell binding activity capable of intoxicating a naturally occurring Clostridial toxin target cell;
    wherein the Clostridial toxin substrate cleavage site is located within the di-chain loop region.
41. A modified Clostridial toxin comprising:
    a) a Clostridial toxin substrate cleavage site;
    b) a di-chain loop region
    c) a Clostridial toxin enzymatic domain;
    d) a Clostridial toxin translocation domain; and
    e) an altered cell binding activity capable of intoxicating a naturally occurring Clostridial toxin target cell;
    wherein the Clostridial toxin substrate cleavage site is located within the di-chain loop region.
42. A modified Clostridial toxin comprising:
    a) a Clostridial toxin substrate cleavage site;
    b) a di-chain loop region
    c) a Clostridial toxin enzymatic domain;
    d) a Clostridial toxin translocation domain; and
    e) an altered cell binding activity capable of intoxicating a non-naturally occurring Clostridial toxin target cell;
    wherein the Clostridial toxin substrate cleavage site is located within the di-chain loop region.
43. The modified Clostridial toxin according to any one of 40-42, wherein the Clostridial toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site and a BuNT substrate cleavage site.
44. The modified Clostridial toxin according to any one of 40-42, wherein the Clostridial toxin enzymatic domain is selected from the group consisting of a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain and a TeNT enzymatic domain, a BaNT enzymatic domain and a BuNT enzymatic domain.
45. The modified Clostridial toxin according to any one of 40-42, wherein the Clostridial toxin translocation domain is selected from the group consisting of a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain and a TeNT translocation domain, a BaNT translocation domain and a BuNT translocation domain.

46. A polynucleotide molecule encoding a modified Clostridial toxin comprising:
 a) a Clostridial toxin substrate cleavage site;
 b) a di-chain loop region
 c) a Clostridial toxin enzymatic domain;
 d) a Clostridial toxin translocation domain; and
 e) an enhanced cell binding activity capable of intoxicating a naturally occurring Clostridial toxin target cell;
 wherein the Clostridial toxin substrate cleavage site is located within the di-chain loop region.

47. A polynucleotide molecule encoding a modified Clostridial toxin comprising:
 a) a Clostridial toxin substrate cleavage site;
 b) a di-chain loop region
 c) a Clostridial toxin enzymatic domain;
 d) a Clostridial toxin translocation domain; and
 e) an altered cell binding activity capable of intoxicating a naturally occurring Clostridial toxin target cell;
 wherein the Clostridial toxin substrate cleavage site is located within the di-chain loop region.

48. A polynucleotide molecule encoding a modified Clostridial toxin comprising:
 a) a Clostridial toxin substrate cleavage site;
 b) a di-chain loop region
 c) a Clostridial toxin enzymatic domain;
 d) a Clostridial toxin translocation domain; and
 e) an altered cell binding activity capable of intoxicating a non-naturally occurring Clostridial toxin target cell;
 wherein the Clostridial toxin substrate cleavage site is located within the di-chain loop region.

49. The polynucleotide molecule according to any one of 46-48, wherein the polynucleotide molecule encoding the Clostridial toxin substrate cleavage site encodes a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site and a BuNT substrate cleavage site.

50. The polynucleotide molecule according to any one of 46-48, wherein the polynucleotide molecule encoding the Clostridial toxin enzymatic domain encodes a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain or a BuNT enzymatic domain.

51. The polynucleotide molecule according to any one of 46-48, wherein the polynucleotide molecule encoding the Clostridial toxin translocation domain encodes a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain or a BuNT translocation domain.

52. A polynucleotide molecule encoding a modified Clostridial toxin comprising a Clostridial toxin substrate cleavage site, wherein the Clostridial toxin substrate cleavage site is located within the di-chain loop region.

53. The polynucleotide molecule according to 52, wherein the polynucleotide molecule encoding the Clostridial toxin substrate cleavage site is a Botulinum toxin substrate cleavage site.

54. The polynucleotide molecule according to 53, wherein the polynucleotide molecule encoding the Botulinum toxin substrate cleavage site is selected from the group consisting of a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site and a BoNT/G substrate cleavage site.

55. The polynucleotide molecule according to 53, wherein the polynucleotide molecule encoding the Botulinum toxin substrate cleavage site comprises a BoNT/A cleavage site.

56. The polynucleotide molecule according to 53, wherein the polynucleotide molecule encoding the Botulinum toxin substrate cleavage site comprises at least six consecutive residues of a SNAP-25, said six consecutive residues comprising Gln-Arg.

57. The polynucleotide molecule according to 53, wherein the polynucleotide molecule encoding the Botulinum toxin substrate cleavage site comprises at least six consecutive residues of a SNAP-25, said six consecutive residues comprising Lys-His.

58. The polynucleotide molecule according to 53, wherein the polynucleotide molecule comprising the Botulinum toxin substrate cleavage site encodes SEQ ID NO: 104, SEQ ID NO: 105 or SEQ ID NO: 106.

59. The polynucleotide molecule according to 53, wherein the polynucleotide molecule encoding the Botulinum toxin substrate cleavage site comprises a BoNT/B cleavage site.

60. The polynucleotide molecule according to 53, wherein the polynucleotide molecule encoding the Botulinum toxin substrate cleavage site comprises at least six consecutive residues of a VAMP, said six consecutive residues comprising Gln-Phe.

61. The polynucleotide molecule according to 53, wherein the polynucleotide molecule comprising the Botulinum toxin substrate cleavage site encodes SEQ ID NO: 107, SEQ ID NO: 108, SEQ ID NO: 109, SEQ ID NO: 110, SEQ ID NO: 111 or SEQ ID NO: 112.

62. The polynucleotide molecule according to 53, wherein the polynucleotide molecule encoding the Botulinum toxin substrate cleavage site comprises a BoNT/C1 cleavage site.

63. The polynucleotide molecule according to 53, wherein the polynucleotide molecule encoding the Botulinum toxin substrate cleavage site comprises at least six consecutive residues of a SNAP-25, said six consecutive residues comprising Arg-Ala.

64. The polynucleotide molecule according to 53, wherein the polynucleotide molecule encoding the Botulinum toxin substrate cleavage site comprises at least six consecutive residues of a Syntaxin, said six consecutive residues comprising Lys-Ala.

65. The polynucleotide molecule according to 53, wherein the polynucleotide molecule encoding the Botulinum toxin substrate cleavage site comprises at least six consecutive residues of a Syntaxin, said six consecutive residues comprising Arg-Ala.

66. The polynucleotide molecule according to 53, wherein the polynucleotide molecule comprising the Botulinum toxin substrate cleavage site encodes SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120 or SEQ ID NO: 121.

67. The polynucleotide molecule according to 53, wherein the polynucleotide molecule encoding the Botulinum toxin substrate cleavage site comprises a BoNT/D cleavage site.

68. The polynucleotide molecule according to 53, wherein the polynucleotide molecule encoding the Botulinum toxin substrate cleavage site comprises at least six consecutive residues of a VAMP, said six consecutive residues comprising Lys-Leu.
69. The polynucleotide molecule according to 53, wherein the polynucleotide molecule comprising the Botulinum toxin substrate cleavage site encodes SEQ ID NO: 122 or SEQ ID NO: 123.
70. The polynucleotide molecule according to 53, wherein the Botulinum toxin substrate cleavage site comprises a BoNT/E cleavage site.
71. The polynucleotide molecule according to 53, wherein the polynucleotide molecule encoding the Botulinum toxin substrate cleavage site comprises at least six consecutive residues of a SNAP-25, said six consecutive residues comprising Arg-Ile.
72. The polynucleotide molecule according to 53, wherein the polynucleotide molecule encoding the Botulinum toxin substrate cleavage site comprises at least six consecutive residues of a SNAP-25, said six consecutive residues comprising Lys-Ile.
73. The polynucleotide molecule according to 53, wherein the polynucleotide molecule comprising the Botulinum toxin substrate cleavage site encodes SEQ ID NO: 124, SEQ ID NO: 125, SEQ ID NO: 126, SEQ ID NO: 127 or SEQ ID NO: 128.
74. The polynucleotide molecule according to 53, wherein the polynucleotide molecule encoding the Botulinum toxin substrate cleavage site comprises a BoNT/F cleavage site.
75. The polynucleotide molecule according to 53, wherein the polynucleotide molecule encoding the Botulinum toxin substrate cleavage site comprises at least six consecutive residues of a VAMP, said six consecutive residues comprising Gln-Lys.
76. The polynucleotide molecule according to 53, wherein the polynucleotide molecule comprising the Botulinum toxin substrate cleavage site encodes SEQ ID NO: 129 or SEQ ID NO: 130.
77. The polynucleotide molecule according to 53, wherein the polynucleotide molecule encoding the Botulinum toxin substrate cleavage site comprises a BoNT/G cleavage site.
78. The polynucleotide molecule according to 53, wherein the polynucleotide molecule encoding the Botulinum toxin substrate cleavage site comprises at least six consecutive residues of a VAMP, said six consecutive residues comprising Ala-Ala.
79. The polynucleotide molecule according to 53, wherein the polynucleotide molecule comprising the Botulinum toxin substrate cleavage site encodes SEQ ID NO: 131 or SEQ ID NO: 132.
80. The polynucleotide molecule according to 52, wherein the polynucleotide molecule encoding the Clostridial toxin substrate cleavage site is a Tetanus toxin substrate cleavage site.
81. The polynucleotide molecule according to 80, wherein the polynucleotide molecule encoding the Tetanus toxin substrate cleavage site comprises at least six consecutive residues of a VAMP, said six consecutive residues comprising Gln-Phe.
82. The polynucleotide molecule according to 80, wherein the polynucleotide molecule encoding the modified Clostridial toxin comprises a polynucleotide molecule encoding a Botulinum toxin enzymatic domain, a polynucleotide molecule encoding a Botulinum toxin translocation domain and a polynucleotide molecule encoding a Botulinum toxin binding domain.
83. The polynucleotide molecule according to 53, wherein the polynucleotide molecule encoding a modified Botulinum toxin comprises a polynucleotide molecule encoding a BoNT/A enzymatic domain, a polynucleotide molecule encoding a BoNT/A translocation domain and a polynucleotide molecule encoding a BoNT/A binding domain.
86. The polynucleotide molecule according to 53, wherein the polynucleotide molecule encoding a modified Botulinum toxin comprises a polynucleotide molecule encoding a BoNT/B enzymatic domain, a polynucleotide molecule encoding a BoNT/B translocation domain and a polynucleotide molecule encoding a BoNT/B binding domain.
87. The polynucleotide molecule according to 53, wherein the polynucleotide molecule encoding a modified Botulinum toxin comprises a polynucleotide molecule encoding a BoNT/C1 enzymatic domain, a polynucleotide molecule encoding a BoNT/C1 translocation domain and a polynucleotide molecule encoding a BoNT/C1 binding domain.
88. The polynucleotide molecule according to 53, wherein the polynucleotide molecule encoding a modified Botulinum toxin comprises a polynucleotide molecule encoding a BoNT/D enzymatic domain, a polynucleotide molecule encoding a BoNT/D translocation domain and a polynucleotide molecule encoding a BoNT/D binding domain.
89. The polynucleotide molecule according to 53, wherein the polynucleotide molecule encoding a modified Botulinum toxin comprises a polynucleotide molecule encoding a BoNT/E enzymatic domain, a polynucleotide molecule encoding a BoNT/E translocation domain and a polynucleotide molecule encoding a BoNT/E binding domain.
90. The polynucleotide molecule according to 53, wherein the polynucleotide molecule encoding a modified Botulinum toxin comprises a polynucleotide molecule encoding a BoNT/F enzymatic domain, a polynucleotide molecule encoding a BoNT/F translocation domain and a polynucleotide molecule encoding a BoNT/F binding domain.
91. The polynucleotide molecule according to 53, wherein the polynucleotide molecule encoding a modified Botulinum toxin comprises a polynucleotide molecule encoding a BoNT/G enzymatic domain, a polynucleotide molecule encoding a BoNT/G translocation domain and a polynucleotide molecule encoding a BoNT/G binding domain.
92. The polynucleotide molecule according to 53, wherein the polynucleotide molecule encoding a modified Clostridial toxin comprises a polynucleotide molecule encoding a Tetanus toxin enzymatic domain, a polynucleotide molecule encoding a Tetanus toxin translocation domain and a polynucleotide molecule encoding a Tetanus toxin binding domain.
93. A method of producing a modified Clostridial toxin comprising the step of expressing a modified Clostridial toxin encoded by a polynucleotide molecule in a cell, wherein the modified Clostridial toxin is defined by any one of 46-92.
94. A methods of producing a modified Clostridial toxin comprising the steps of a) introducing into a cell a polynucleotide molecule encoding a modified Clostridial toxin as defined in any one of 46-92; and b) expressing the modified Clostridial toxin encoded by the polynucleotide molecule.
95. A modified Clostridial toxin comprising:
 a) a Clostridial toxin substrate cleavage site;
 b) a di-chain loop region
 c) a Clostridial toxin enzymatic domain;
 d) a Clostridial toxin translocation domain; and
 e) a Clostridial toxin cell binding domain;

wherein the Clostridial toxin substrate cleavage site is located within the di-chain loop region.

EXAMPLES

The following non-limiting examples are provided for illustrative purposes only in order to facilitate a more complete understanding of disclosed embodiments and are in no way intended to limit any of the embodiments disclosed in the present specification.

Example 1

Construction of Modified Clostridial Toxins Comprising a BoNT/A Substrate Cleavage Site This example illustrates how to make a modified Clostridial toxin comprising a BoNT/A substrate cleavage site located in the di-chain loop region of the toxin.

A polynucleotide molecule (SEQ ID NO: 214) based on BoNT/A-A17 (SEQ ID NO: 203) is synthesized using standard procedures (BlueHeron® Biotechnology, Bothell, Wash.). BoNT/A-A17 is a BoNT/A modified to comprise a 17 amino acid Clostridial toxin substrate cleavage site that can be cleaved by BoNT/A. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-A17. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule (SEQ ID NO: 225) based on BoNT/A-A17 (SEQ ID NO: 203) can be synthesized in order to improve expression in an *Escherichia coli* strain. The polynucleotide molecule encoding the BoNT/A-A17 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006), the contents of all of which are hereby incorporated by reference in their entirety. Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-A17. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Publication No. WO 2006/011966 (Feb. 2, 2006); and Steward, supra, International Patent Publication No. WO 2006/017749 (Feb. 16, 2006).

A similar cloning strategy is used to make pUCBHB1 cloning constructs comprising the polynucleotide molecule of SEQ ID NO: 215 or SEQ ID NO: 226 encoding BoNT/A-A8 of SEQ ID NO: 204. BoNT/A-A8 is a BoNT/A modified to comprise an eight amino acid Clostridial toxin substrate cleavage site that can be cleaved by BoNT/A. In addition, one skilled in the art can modify Clostridial toxins, such as, e.g., BoNT/B, BoNT/C1, BoNT/D. BoNT/E, BoNT/F, BoNT/G and TeNT, using similar cloning strategy described above so that these toxins possess a BoNT/A substrate cleavage site in the di-chain loop region of the toxin.

Figure 7:
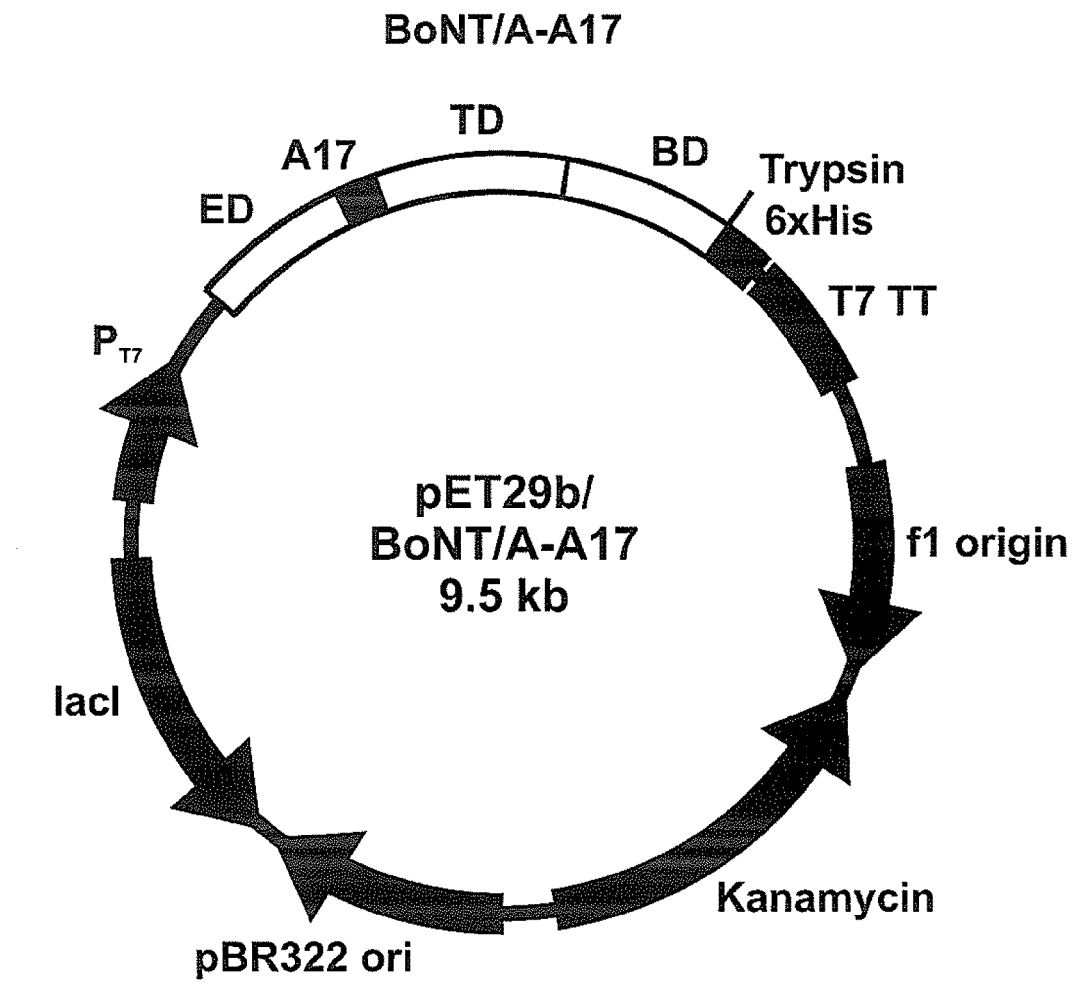

To construct pET29/BoNT/A-A17, a pUCBHB1/BoNT/A-A17 construct is digested with restriction endonucleases that 1) excise the insert comprising the open reading frame encoding BoNT/A-A17, such as, e.g., the polynucleotide molecule of SEQ ID NO: 225; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-A17. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule of SEQ ID NO: 225 encoding the BoNT/A-A17 of SEQ ID NO: 203 operably-linked to a carboxyl terminal polyhistidine affinity binding peptide (FIG. 7).

A similar cloning strategy can be used to make pET29 expression constructs comprising the polynucleotide molecule of SEQ ID NO: 214 encoding BoNT/A-A17 of SEQ ID NO: 203; or the polynucleotide molecules of SEQ ID NO: 215 or SEQ ID NO: 226 encoding BoNT/A-A8 of SEQ ID NO: 204.

Example 2

Construction of Modified Clostridial Toxins Comprising Both a BoNT/B and a TeNT Substrate Cleavage Site This example illustrates how to make a modified Clostridial toxin comprising both a BoNT/B substrate cleavage site and a TeNT substrate cleavage site located in the di-chain loop region of the toxin.

A polynucleotide molecule (SEQ ID NO: 216) based on BoNT/A-BT35 (SEQ ID NO: 205) is synthesized using standard procedures (BlueHeron® Biotechnology, Bothell, Wash.). BoNT/A-BT35 is a BoNT/A modified to comprise a 35 amino acid Clostridial toxin substrate cleavage site that can be cleaved by either BoNT/B or TeNT. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-BT35. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule (SEQ ID NO: 227) based on BoNT/A-BT35 (SEQ ID NO: 205) can be synthesized in order to improve expression in an *Escherichia coli* strain. The polynucleotide molecule encoding the BoNT/A-BT35 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-BT35. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Patent Publication No. WO 2006/011966 (Feb. 2, 2006); and Steward, supra, International Patent Publication No. WO 2006/017749 (Feb. 16, 2006).

A similar cloning strategy is used to make pUCBHB1 cloning constructs comprising the polynucleotide molecule of SEQ ID NO: 217 or SEQ ID NO: 228 encoding BoNT/A-BT8 of SEQ ID NO: 206. BoNT/A-B8 is a BoNT/A modified to comprise an eight amino acid Clostridial toxin substrate cleavage site that can be cleaved by either BoNT/B or TeNT. In addition, one skilled in the art can modify Clostridial toxins, such as, e.g., BoNT/B, BoNT/C1, BoNT/D. BoNT/E, BoNT/F, BoNT/G and TeNT, using similar cloning strategy described above so that these toxins possess both a BoNT/B substrate cleavage site and a TeNT substrate cleavage site in the di-chain loop region of the toxin.

Figure 8:
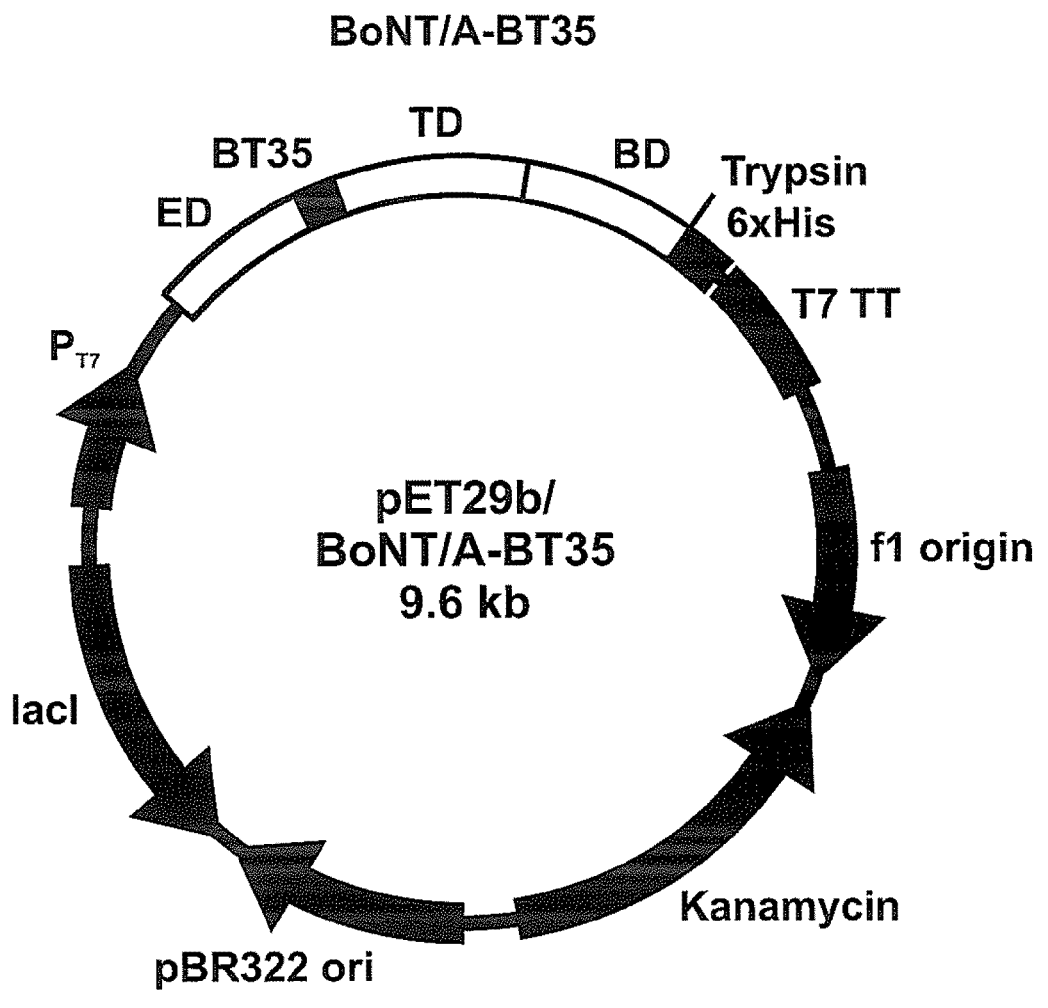

To construct pET29/BoNT/A-BT35, a pUCBHB1/BoNT/A-BT35 construct is digested with restriction endonucleases that 1) excise the insert comprising the open reading frame encoding BoNT/A-BT35, such as, e.g., the polynucleotide molecule of SEQ ID NO: 227; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-BT35. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule of SEQ ID NO: 227 encoding the BoNT/A-BT35 of SEQ ID NO: 205 operably-linked to a carboxyl terminal polyhistidine affinity binding peptide (FIG. 8).

A similar cloning strategy can be used to make pET29 expression constructs comprising the polynucleotide molecule of SEQ ID NO: 216 encoding BoNT/A-BT35 of SEQ ID NO: 205; or the polynucleotide molecules of SEQ ID NO: 217 or SEQ ID NO: 228 encoding BoNT/A-BT8 of SEQ ID NO: 206.

Example 3

Construction of Modified Clostridial Toxins Comprising a BoNT/C1 Substrate Cleavage Site This example illustrates how to make a modified Clostridial toxin comprising a BoNT/C1 substrate cleavage site located in the di-chain loop region of the toxin.

A polynucleotide molecule (SEQ ID NO: 218) based on BoNT/A-Csyn8 (SEQ ID NO: 207) is synthesized using standard procedures (BlueHeron® Biotechnology, Bothell, Wash.). BoNT/A-Csyn8 is a BoNT/A modified to comprise an eight amino acid Clostridial toxin substrate cleavage site that can be cleaved by BoNT/C1. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-Csyn8. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule (SEQ ID NO: 229) based on BoNT/A-Csyn8 (SEQ ID NO: 207) can be synthesized in order to improve expression in an *Escherichia coli* strain. The polynucleotide molecule encoding the BoNT/A-Csyn8 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-Csyn8. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Publication No. WO 2006/011966 (Feb. 2, 2006); and Steward, supra, International Patent Publication No. WO 2006/017749 (Feb. 16, 2006).

A similar cloning strategy is used to make pUCBHB1 cloning constructs comprising the polynucleotide molecule of SEQ ID NO: 219 or SEQ ID NO: 230 encoding BoNT/A-Csnp8 of SEQ ID NO: 208. BoNT/A-Csnp8 is a BoNT/A modified to comprise an eight amino acid Clostridial toxin substrate cleavage site that can be cleaved by BoNT/C1. In addition, one skilled in the art can modify Clostridial toxins, such as, e.g., BoNT/B, BoNT/C1, BoNT/D. BoNT/E, BoNT/F, BoNT/G and TeNT, using similar cloning strategy described above so that these toxins possess a BoNT/C1 substrate cleavage site in the di-chain loop region of the toxin.

To construct pET29/BoNT/A-Csyn8, a pUCBHB1/BoNT/A-Csyn8 construct is digested with restriction endonucleases that 1) excise the insert comprising the open reading frame encoding BoNT/A-Csyn8, such as, e.g., the polynucleotide molecule of SEQ ID NO: 229; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-Csyn8. The ligation mixture is transformed into chemically competent E. coli DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule of SEQ ID NO: 229 encoding the BoNT/A-Csyn8 of SEQ ID NO: 207 operably-linked to a carboxyl terminal polyhistidine affinity binding peptide (FIG. 9).

A similar cloning strategy can be used to make pET29 expression constructs comprising the polynucleotide molecule of SEQ ID NO: 218 encoding BoNT/A-A17 of SEQ ID NO: 207; or the polynucleotide molecules of SEQ ID NO: 219 or SEQ ID NO: 230 encoding BoNT/A-Csyn8 of SEQ ID NO: 208.

Example 4

Construction of Modified Clostridial Toxins Comprising a BoNT/D Substrate Cleavage Site, a BoNT/F Substrate Cleavage Site or Both a BoNT/D and a BoNT/F Substrate Cleavage Site This example illustrates how to make a modified Clostridial toxin comprising a BoNT/D substrate cleavage site located in the di-chain loop region of the toxin, a BoNT/F substrate cleavage site located in the di-chain loop region of the toxin or both a BoNT/D substrate cleavage site and a BoNT/F substrate cleavage site located in the di-chain loop region of the toxin.

A polynucleotide molecule (SEQ ID NO: 220) based on BoNT/A-DF39 (SEQ ID NO: 209) is synthesized using standard procedures (BlueHeron® Biotechnology, Bothell, Wash.). BoNT/A-DF39 is a BoNT/A modified to comprise a 39 amino acid Clostridial toxin substrate cleavage site that can be cleaved by either BoNT/D or BoNT/F. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCHHB1 vector at the SmaI site to generate pUCBHB1/BoNT/A-DF39. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule (SEQ ID NO: 231) based on BoNT/A-DF39 (SEQ ID NO: 209) can be synthesized in order to improve expression in an Escherichia coli strain. The polynucleotide molecule encoding the BoNT/A-DF39 can be modified to 1) contain synonymous codons typically present in native polynucleotide molecules of an Escherichia coli strain; 2) contain a G+C content that more closely matches the average G+C content of native polynucleotide molecules found in an Escherichia coli strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-DF39. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Publication No. WO 2006/011966 (Feb. 2, 2006); and Steward, supra, International Patent Publication No. WO 2006/017749 (Feb. 16, 2006).

A similar cloning strategy is used to make pUCBHB1 cloning constructs comprising the polynucleotide molecule of SEQ ID NO: 221 or SEQ ID NO: 232 encoding BoNT/A-D8 of SEQ ID NO: 210; or constructs comprising the polynucleotide molecule of SEQ ID NO: 223 or SEQ ID NO: 234 encoding BoNT/A-F8 of SEQ ID NO: 212. BoNT/A-D8 is a BoNT/A modified to comprise an eight amino acid Clostridial toxin substrate cleavage site that can be cleaved by BoNT/D. BoNT/A-F8 is a BoNT/A modified to comprise an eight amino acid Clostridial toxin substrate cleavage site that can be cleaved by BoNT/F. In addition, one skilled in the art can modify Clostridial toxins, such as, e.g., BoNT/B, BoNT/

C1, BoNT/D. BoNT/E, BoNT/F, BoNT/G and TeNT, using similar cloning strategy described above so that these toxins comprise a BoNT/D substrate cleavage site in the di-chain loop region of the toxin, comprise a BoNT/B substrate cleavage site in the di-chain loop region of the toxin or comprise both a BoNT/D substrate cleavage site and a BoNT/F substrate cleavage site in the di-chain loop region of the toxin.

Figure 10:
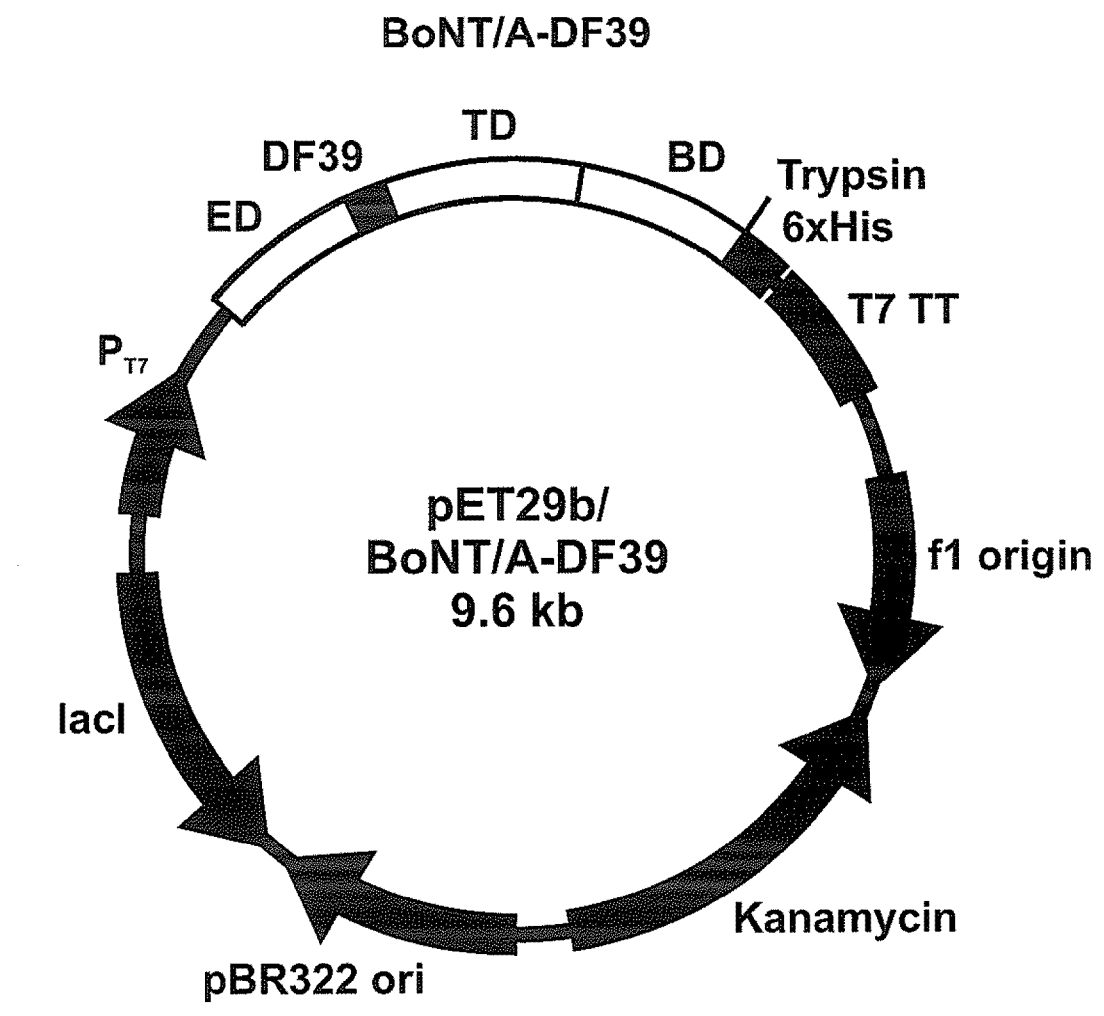

To construct pET29/BoNT/A-DF39, a pUCBHB1/BoNT/A-DF39 construct is digested with restriction endonucleases that 1) excise the insert comprising the open reading frame encoding BoNT/A-DF39, such as, e.g., the polynucleotide molecule of SEQ ID NO: 231; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-DF39. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule of SEQ ID NO: 231 encoding the BoNT/A-DF39 of SEQ ID NO: 209 operably-linked to a carboxyl terminal polyhistidine affinity binding peptide (FIG. 10).

A similar cloning strategy can be used to make pET29 expression constructs comprising the polynucleotide molecule of SEQ ID NO: 220 encoding BoNT/A-DF39 of SEQ ID NO: 209; the polynucleotide molecules of SEQ ID NO: 221 or SEQ ID NO: 232 encoding BoNT/A-D8 of SEQ ID NO: 210; or the polynucleotide molecules of SEQ ID NO: 223 or SEQ ID NO: 234 encoding BoNT/A-F8 of SEQ ID NO: 212.

Example 5

Construction of Modified Clostridial Toxins Comprising a BoNT/E Substrate Cleavage Site This example illustrates how to make a modified Clostridial toxin comprising a BoNT/E substrate cleavage site located in the di-chain loop region of the toxin.

A polynucleotide molecule (SEQ ID NO: 222) based on BoNT/A-E8 (SEQ ID NO: 211) is synthesized using standard procedures (BlueHeron® Biotechnology, Bothell, Wash.). BoNT/A-E8 is a BoNT/A modified to comprise an eight amino acid Clostridial toxin substrate cleavage site that can be cleaved by BoNT/E. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCHB1 vector at the SmaI site to generate pUCBHB1/BoNT/A-E8. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule (SEQ ID NO: 233) based on BoNT/A-E8 (SEQ ID NO: 211) can be synthesized in order to improve expression in an *Escherichia coli* strain. The polynucleotide molecule encoding the BoNT/A-E8 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-E8. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Publication No. WO 2006/011966 (Feb. 2, 2006); and Steward, supra, International Patent Publication No. WO 2006/017749 (Feb. 16, 2006).

One skilled in the art can modify Clostridial toxins, such as, e.g., BoNT/B, BoNT/C1, BoNT/D. BoNT/E, BoNT/F, BoNT/G and TeNT, using similar cloning strategy described above so that these toxins possess a BoNT/E substrate cleavage site in the di-chain loop region of the toxin.

Figure 11:
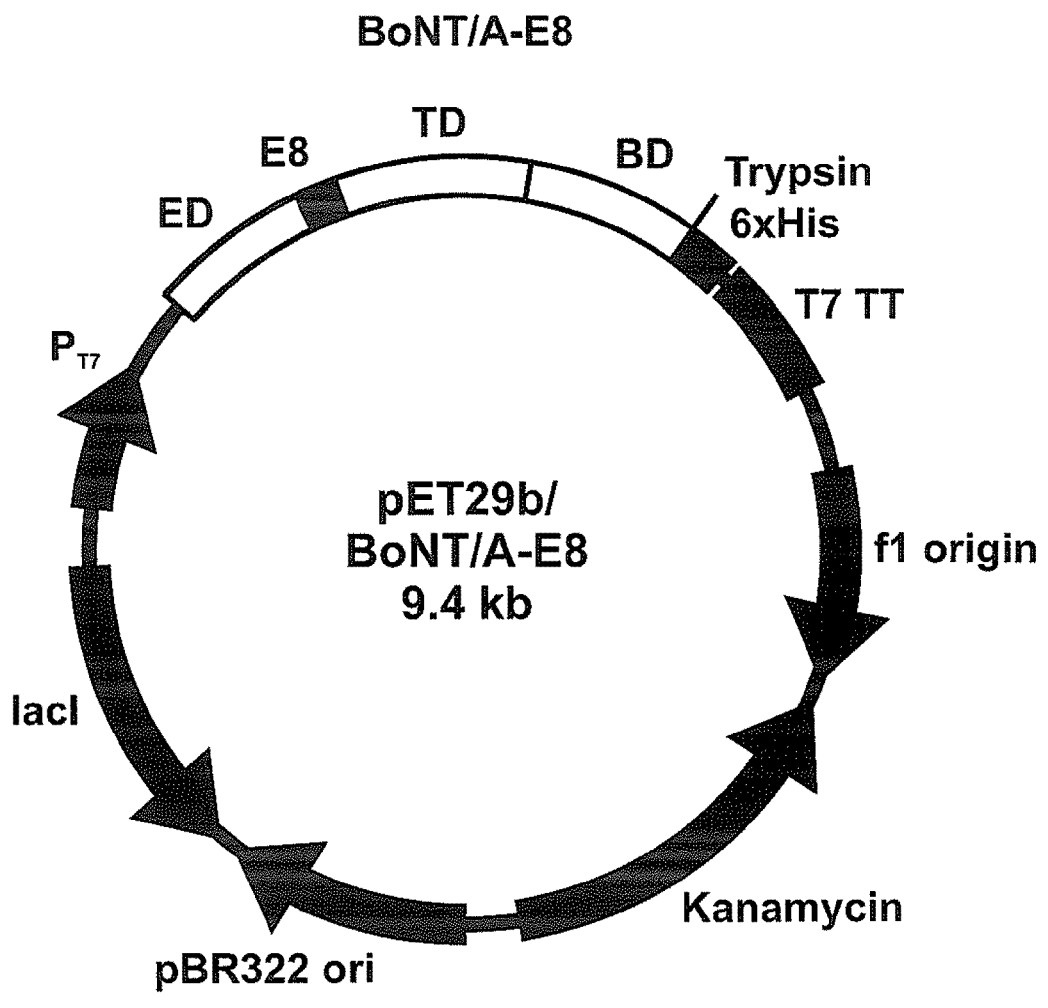

To construct pET29/BoNT/A-E8, a pUCBHB1/BoNT/A-E8 construct is digested with restriction endonucleases that 1) excise the insert comprising the open reading frame encoding BoNT/A-E8, such as, e.g., the polynucleotide molecule of SEQ ID NO: 233; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-E8. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule of SEQ ID NO: 233 encoding the BoNT/A-E8 of SEQ ID NO: 211 operably-linked to a carboxyl terminal polyhistidine affinity binding peptide (FIG. 11).

Example 6

Construction of Modified Clostridial Toxins Comprising a BoNT/G Substrate Cleavage Site This example illustrates how to make a modified Clostridial toxin comprising a BoNT/G substrate cleavage site located in the di-chain loop region of the toxin.

A polynucleotide molecule (SEQ ID NO: 224) based on BoNT/A-G8 (SEQ ID NO: 213) is synthesized using standard procedures (BlueHeron® Biotechnology, Bothell, Wash.). BoNT/A-G8 is a BoNT/A modified to comprise an eight amino acid Clostridial toxin substrate cleavage site that can be cleaved by BoNT/G. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-G8. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule (SEQ ID NO: 235) based on BoNT/A-E8 (SEQ ID NO: 213) can be synthesized in order to improve expression in an *Escherichia coli* strain. The polynucleotide molecule encoding the BoNT/A-D8 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-G8. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Publication No. WO 2006/011966 (Feb. 2, 2006); and Steward, supra, International Patent Publication No. WO 2006/017749 (Feb. 16, 2006).

One skilled in the art can modify Clostridial toxins, such as, e.g., BoNT/B, BoNT/C1, BoNT/D. BoNT/E, BoNT/F, BoNT/G and TeNT, using similar cloning strategy described above so that these toxins possess a BoNT/G substrate cleavage site in the di-chain loop region of the toxin.

To construct pET29/BoNT/A-G8, a pUCBHB1/BoNT/A-G8 construct is digested with restriction endonucleases that 1) excise the insert comprising the open reading frame encoding BoNT/A-E8, such as, e.g., the polynucleotide molecule of SEQ ID NO: 235; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/BoNT/A-G8. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule of SEQ ID NO: 235 encoding the BoNT/A-G8 of SEQ ID NO: 213 operably-linked to a carboxyl terminal polyhistidine affinity binding peptide (FIG. 12).

Example 7

Expression of Modified Clostridial Toxins in a Bacterial Cell

The following example illustrates a procedure useful for expressing any of the modified Clostridial toxins disclosed in the present specification in a bacterial cell.

An expression construct, such as, e.g., pET29/BoNT/A-ED-PAR1Tb, pET29/BoNT/A-TD-PAR1Tb or pET29/BoNT/A-BD-PAR1Tb, see, e.g., Examples 1, 2 and 3, is introduced into chemically competent *E. coli* BL21 (DE3) cells (Invitrogen, Inc, Carlsbad, Calif.) using a heat-shock transformation protocol. The heat-shock reaction is plated onto 1.5% Luria-Bertani agar plates (pH 7.0) containing 50 μg/mL of Kanamycin and is placed in a 37° C. incubator for overnight growth. Kanamycin-resistant colonies of transformed *E. coli* containing the expression construct, such as, e.g., pET29/BoNT/A-A17, pET29/BoNT/A-BT35, pET29/BoNT/A-Csyn8, pET29/BoNT/A-DF39, pET29/BoNT/A-E8 or pET29/BoNT/A-G8, are used to inoculate a baffled flask containing 3.0 mL of PA-0.5 G media containing 50 μg/mL of Kanamycin which is then placed in a 37° C. incubator, shaking at 250 rpm, for overnight growth. The resulting overnight starter culture is in turn used to inoculate a 3 L baffled flask containing ZYP-5052 autoinducing media containing 50 μg/mL of Kanamycin at a dilution of 1:1000. Culture volumes ranged from about 600 mL (20% flask volume) to about 750 mL (25% flask volume). These cultures are grown in a 37° C. incubator shaking at 250 rpm for approximately 5.5 hours and are then transferred to a 16° C. incubator shaking at 250 rpm for overnight expression. Cells are harvested by centrifugation (4,000 rpm at 4° C. for 20-30 minutes) and are used immediately, or stored dry at −80° C. until needed.

Example 8

Purification and Quantification of Modified Clostridial Toxins

The following example illustrates methods useful for purification and quantification of any modified Clostridial toxins disclosed in the present specification.

For immobilized metal affinity chromatography (IMAC) protein purification, E. coli BL21 (DE3) cell pellets used to express a modified Clostridial toxin, as described in Example 4, are resuspended in Column Binding Buffer (25 mM N-(2-hydroxyethyl)piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) Triton-X® 100, 4-octylphenol polyethoxylate; 10% (v/v) glycerol), and then are transferred to a cold Oakridge centrifuge tube. The cell suspension is sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column is prepared using a 20 mL Econo-Pac column support (Bio-Rad Laboratories, Hercules, Calif.) packed with 2.5-5.0 mL of TALON™ SuperFlow Co$^{2+}$ affinity resin (BD Biosciences-Clontech, Palo Alto, Calif.), which is then equilibrated by rinsing with 5 column volumes of deionized, distilled water, followed by 5 column volumes of Column Binding Buffer. The clarified lysate is applied slowly to the equilibrated column by gravity flow (approximately 0.25-0.3 mL/minute). The column is then washed with 5 column volumes of Column Wash Buffer (N-(2-hydroxyethyl)piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The Clostridial toxin is eluted with 20-30 mL of Column Elution Buffer (25 mM N-(2-hydroxyethyl)piperazine-N'-(2-ethanesulfonic acid) (HEPES), pH 7.8; 500 mM sodium chloride; 500 mM imidazole; 0.1% (v/v) Triton-X® 100, 4-octylphenol polyethoxylate; 10% (v/v) glycerol) and is collected in approximately twelve 1 mL fractions. The amount of Clostridial toxin contained in each elution fraction is determined by a Bradford dye assay. In this procedure, 20 µL aliquots of each 1.0 mL fraction is combined with 200 µL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered the elution peak and are combined together. Total protein yield is determined by estimating the total protein concentration of the pooled peak elution fractions using bovine gamma globulin as a standard (Bio-Rad Laboratories, Hercules, Calif.).

For purification of a modified Clostridial toxin using a FPLC desalting column, a HiPrep™ 26/10 size exclusion column (Amersham Biosciences, Piscataway, N.J.) is pre-equilibrated with 80 mL of 4° C. Column Buffer (50 mM sodium phosphate, pH 6.5). After the column is equilibrated, a Clostridial toxin sample is applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified Clostridial toxin sample is collected as a single fraction of approximately 7-12 mL.

For purification of a modified Clostridial toxin using a FPLC ion exchange column, a Clostridial toxin sample that has been desalted following elution from an IMAC column is applied to a 1 mL Q1™ anion exchange column (Bio-Rad Laboratories, Hercules, Calif.) using a BioLogic DuoFlow chromatography system (Bio-Rad Laboratories, Hercules, Calif.). The sample is applied to the column in 4° C. Column Buffer (50 mM sodium phosphate, pH 6.5) and is eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of Clostridial toxin from the column is monitored at 280, 260, and 214 nm, and peaks absorbing above a minimum threshold (0.01 au) at 280 nm are collected. Most of the Clostridial toxin will elute at a sodium chloride concentration of approximately 100 to 200 mM. Average total yields of Clostridial toxin will be determined by a Bradford assay.

Expression of a modified Clostridial toxin is analyzed by polyacrylamide gel electrophoresis. Samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels are stained with SYPRO® Ruby (Bio-Rad Laboratories, Hercules, Calif.) and the separated polypeptides are imaged using a Fluor-S MAX MultiImager (Bio-Rad Laboratories, Hercules, Calif.) for quantification of Clostridial toxin expression levels. The size and amount of the Clostridial toxin is determined by comparison to MagicMark™ protein molecular weight standards (Invitrogen, Inc, Carlsbad, Calif.).

Expression of modified Clostridial toxin is also analyzed by Western blot analysis. Protein samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots are washed three times for 15 minutes each time in Tris-Buffered Saline TWEEN-20®. Washed membranes are incubated at room temperature for 2 hours in Tris-Buffered Saline TWEEN-20® containing an appropriate immunoglobulin G antibody conjugated to horseradish peroxidase as a secondary antibody. Secondary antibody-probed blots are washed three times for 15 minutes each time in Tris-Buffered Saline TWEEN-20®. Signal detection of the labeled Clostridial toxin are visualized using the ECL Plus™ Western Blot Detection System (Amersham Biosciences, Piscataway, N.J.) and are imaged with a Typhoon 9410 Variable Mode Imager (Amersham Biosciences, Piscataway, N.J.) for quantification of modified Clostridial toxin expression levels.

Example 9

Expression of Modified Clostridial Toxins in a Yeast Cell

The following example illustrates a procedure useful for expressing any of the modified Clostridial toxins disclosed in the present specification in a yeast cell.

Figure 13:
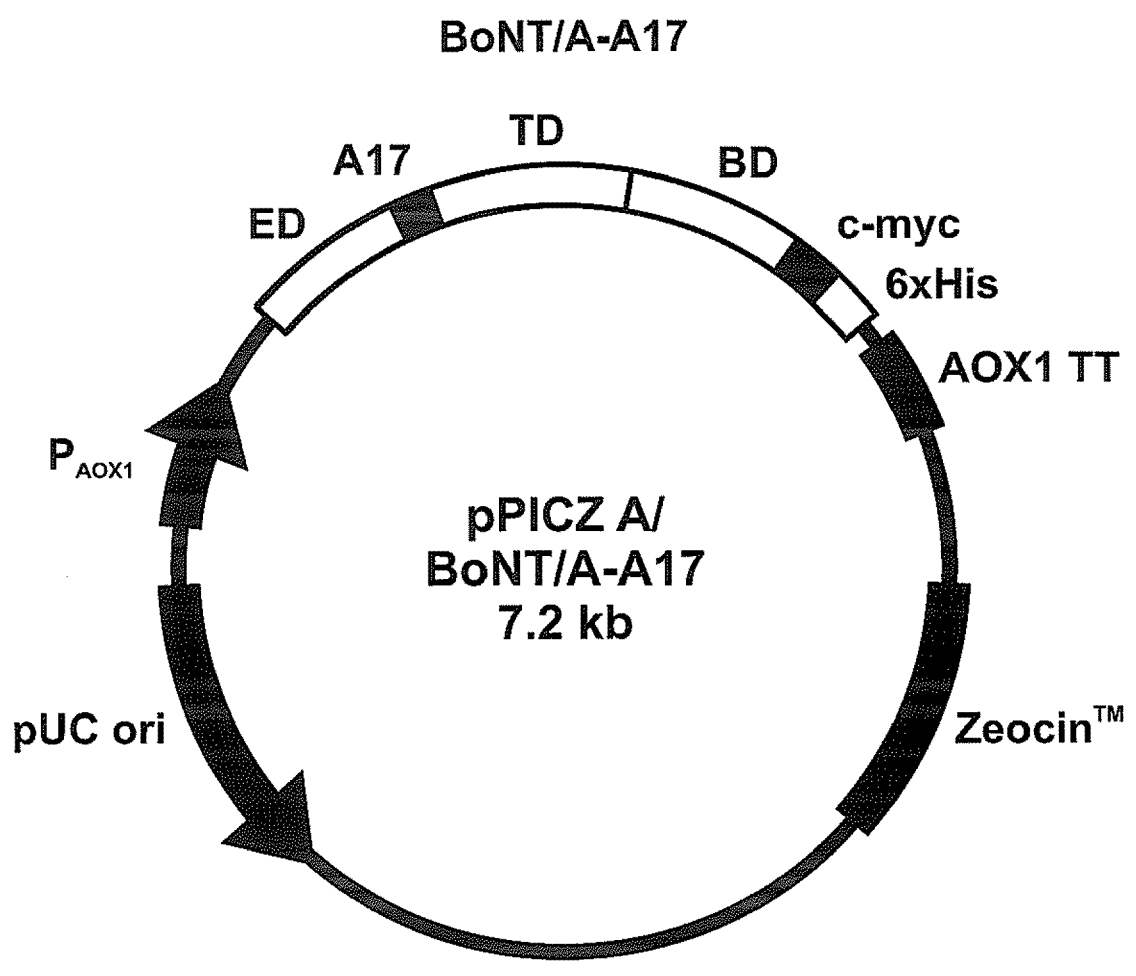

To construct a suitable yeast expression construct encoding a modified Clostridial toxin, restriction endonuclease sites suitable for cloning an operably linked polynucleotide molecule into a pPIC A vector (Invitrogen, Inc, Carlsbad, Calif.) are incorporated into the 5'- and 3' ends of the polynucleotide molecule SEQ ID NO: 236 encoding BoNT/A-A17 of SEQ ID NO: 203. This polynucleotide molecule is synthesized and a pUCBHB1/BoNT/A-A17 construct is obtained as described in Example 1. This construct is digested with restriction enzymes that 1) excise the insert containing the open reading frame of SEQ ID NO: 236 encoding BoNT/A-A17; and 2) enable this insert to be operably-linked to a pPIC A vector. This insert is subcloned using a T4 DNA ligase procedure into a pPIC A vector that is digested with appropriate restriction endonucleases to yield pPIC A/BoNT/A-A17. The ligation mixture is transformed into chemically competent *E. coli* DH5α cells (Invitrogen, Inc, Carlsbad, Calif.) using a heat shock method, plated on 1.5% low salt Luria-Bertani agar plates (pH 7.5) containing 25 µg/mL of Zeocin™, and placed in a 37° C. incubator for overnight growth. Bacteria containing expression constructs are identified as Zeocin™ resistant colonies. Candidate constructs are isolated using an alkaline lysis plasmid mini-preparation procedure and analyzed by restriction endonuclease digest mapping to determine the presence and orientation of the insert. This cloning strategy yielded a pPIC A expression construct comprising the polynucleotide molecule of SEQ ID NO: 236 encoding the BoNT/A-A17 of SEQ ID NO: 203 operably-linked to a carboxyl-terminal c-myc and polyhistidine binding peptides (FIG. 13).

A similar cloning strategy is used to make pPIC A expression constructs encoding BoNT/A-A8 of SEQ ID NO: 204; BoNT/A-BT35 of SEQ ID NO: 205; BoNT/A-BT8 of SEQ ID NO: 206; BoNT/A-Csyn8 of SEQ ID NO: 207; BoNT/A-Csnp8 of SEQ ID NO: 208; BoNT/A-DF39 of SEQ ID NO: 209; BoNT/A-D8 of SEQ ID NO: 210; BoNT/A-E8 of SEQ ID NO: 211; BoNT/A-F8 of SEQ ID NO: 212; or BoNT/A-D8 of SEQ ID NO: 213.

To construct a yeast cell line expressing a modified Clostridial toxin, pPICZ A/BoNT/A-A17 is digested with a suitable restriction endonuclease (i.e., SacI, PmeI or BstXI) and the resulting linearized expression construct is transformed into an appropriate *P. pastoris* Mut$^S$ strain KM71H using an electroporation method. The transformation mixture is plated on 1.5% YPDS agar plates (pH 7.5) containing 100 µg/mL of Zeocin™ and placed in a 28-30° C. incubator for 1-3 days of growth. Selection of transformants integrating the pPICZ A/BoNT/A-A17 at the 5' AOX1 locus is determined by colony resistance to Zeocin™. Cell lines integrating a pPICZ A/BoNT/A-A17 construct is tested for BoNT/A-A17 expression using a small-scale expression test. Isolated colonies from test cell lines that have integrated pPICZ A/BoNT/A-A17 are used to inoculate 1.0 L baffled flasks containing 100 mL of MGYH media and grown at about 28-30° C. in a shaker incubator (250 rpm) until the culture reaches an $OD_{600}$=2-6 (approximately 16-18 hours). Cells are harvested by centrifugation (3,000×g at 22° C. for 5 minutes). To induce expression, the cell pellet is resuspended in 15 mL of MMH media and 100% methanol is added to a final concentration of 0.5%. Cultures are grown at about 28-30° C. in a shaker incubator (250 rpm) for six days. Additional 100% methanol is added to the culture every 24 hours to a final concentration of 0.5%. A 1.0 mL test aliquot is taken from the culture every 24 hours starting at time zero and ending at time 144 hours. Cells are harvested from the aliquots by microcentrifugation to pellet the cells and lysed using three freeze-thaw rounds consisting of −80° C. for 5 minutes, then 37° C. for 5 minutes. Lysis samples are added to 2×LDS Sample Buffer (Invitrogen, Inc, Carlsbad, Calif.) and expression from established cell lines is measured by Western blot analysis (as described in Example 8) using either anti-BoNT/A, anti-myc or anti-His antibodies in order to identify lines expressing BoNT/A-A17. The *P. pastoris* Mut$^S$ KM71H cell line showing the highest expression level of BoNT/A-A17 is selected for large-scale expression using commercial fermentation procedures. Procedures for large-scale expression are as outlined above except the culture volume is approximately 2.5 L MGYH media grown in a 5 L BioFlo 3000 fermentor and concentrations of all reagents will be proportionally increased for this volume. A similar procedure can be used to express a pPICZ A construct encoding any of the modified Clostridial toxins of SEQ ID NO: 204 to SEQ ID NO: 213.

BoNT/A-A17 is purified using the IMAC procedure, as described in Example 8. Expression from each culture is evaluated by a Bradford dye assay, polyacrylamide gel electrophoresis and Western blot analysis (as described in Example 8) in order to determine the amounts of BoNT/A-A17 produced.

Example 10

Expression of Modified Clostridial Toxins in an Insect Cell

The following example illustrates a procedure useful for expressing any of the modified Clostridial toxins disclosed in the present specification in an insect cell.

Figure 14:
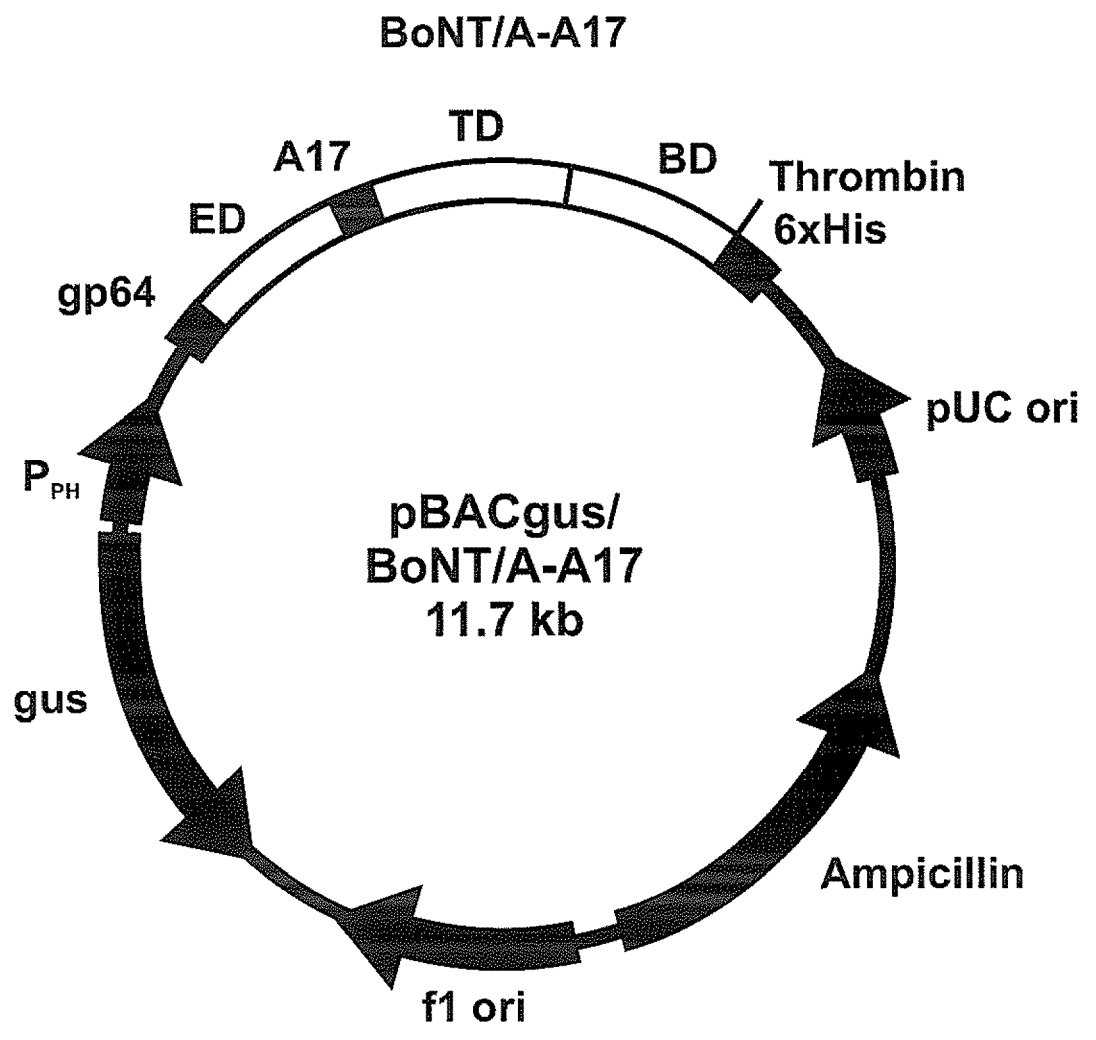

To construct suitable an insect expression construct encoding a modified Clostridial toxin, restriction endonuclease sites suitable for cloning an operably linked polynucleotide molecule into a pBACgus3 vector (EMD Biosciences-Novagen, Madison, Wis.) are incorporated into the 5'- and 3' ends of the polynucleotide molecule SEQ ID NO: 237 encoding BoNT/A-A17 of SEQ ID NO: 203. This polynucleotide molecule is synthesized and a pUCBHB1/BoNT/A-A17 construct is obtained as described in Example 1. This construct is digested with restriction enzymes that 1) excise the insert containing the open reading frame of SEQ ID NO: 237 encoding BoNT/A-A17; and 2) enable this insert to be operably-linked to a pBACgus3 vector. This insert is subcloned using a T4 DNA ligase procedure into a pBACgus3 vector that is digested with appropriate restriction endonucleases to yield pBACgus3/BoNT/A-A17. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yielded a pBACgus3 expression construct comprising the polynucleotide molecule of SEQ ID NO: 237 encoding the BoNT/A-A17 of SEQ ID NO: 203 operably linked to an amino-terminal gp64 signal peptide and a carboxyl-terminal, Thrombin cleavable, polyhistidine affinity binding peptide (FIG. 14).

A similar cloning strategy is used to make pBACgus3 expression constructs encoding BoNT/A-A8 of SEQ ID NO: 204; BoNT/A-BT35 of SEQ ID NO: 205; BoNT/A-BT8 of SEQ ID NO: 206; BoNT/A-Csyn8 of SEQ ID NO: 207; BoNT/A-Csnp8 of SEQ ID NO: 208; BoNT/A-DF39 of SEQ ID NO: 209; BoNT/A-D8 of SEQ ID NO: 210; BoNT/A-E8 of SEQ ID NO: 211; BoNT/A-F8 of SEQ ID NO: 212; or BoNT/A-D8 of SEQ ID NO: 213.

To express a modified Clostridial toxin using a baculoviral expression system, about $2.5 \times 10^6$ Sf9 cells are plated in four 60 mm culture dishes containing 2 mL of BacVector® Insect media (EMD Biosciences-Novagen, Madison, Wis.) and incubated for approximately 20 minutes in a 28° C. incubator. For each transfection, a 50 µL transfection solution is prepared in a 6 mL polystyrene tube by adding 25 µL of BacVector® Insect media containing 100 ng of a pBACgus3 construct encoding a modified Clostridial toxin, such as, e.g., pBACgus3/BoNT/A-A17, and 500 ng TlowE transfer plasmid to 25 µL of diluted Insect GeneJuice® containing 5 µL Insect GeneJuice® (EMD Biosciences-Novagen, Madison, Wis.) and 20 µL nuclease-free water and this solution is incubated for approximately 15 minutes. After the 15 minute incubation, add 450 µL BacVector® media to the transfection solution and mix gently. Using this stock transfection solution as the 1/10 dilution make additional transfection solutions of 1/50, 1/250 and 1/1250 dilutions. Add 100 µL of a transfection solution to the Sf9 cells from one of the four 60 mm culture dishes, twice washed with antibiotic-free, serum-free BacVector® Insect media and incubate at 22° C. After one hour, add 6 mL of 1% BacPlaque agarose-BacVector® Insect media containing 5% bovine serum albumin. After the agarose is solidified, add 2 mL BacVector® Insect media containing 5% bovine serum albumin to the transfected cells and transfer the cells to a 28° C. incubator for 3-5 days until plaques are visible. After 3-5 days post-transfection, plaques in the monolayer will be stained for β-glucuronidase reporter gene activity to test for the presence of recombinant virus plaques containing pBACgus3/BoNT/A-A17 by incubating the washed monolayer with 2 mL of BacVector® Insect media containing 30 µL of 20 mg/mL X-Gluc Solution (EMD Biosciences-Novagen, Madison, Wis.) for approximately 2 hours in a 28° C. incubator.

After identifying candidate recombinant virus plaques, several candidate virus plaques are eluted and plaque purified. To elute a recombinant virus, transfer a plug containing a recombinant virus plaque with a sterile Pasteur pipet to 1 mL BacVector® Insect media (EMD Biosciences-Novagen, Madison, Wis.) in a sterile screw-cap vial. Incubate the vial for approximately 2 hours at 22° C. or for approximately 16 hours at 4° C. For each recombinant virus plaque, $2.5 \times 10^5$ Sf9 cells are plated in 35 mm culture dishes containing 2 mL of BacVector® Insect media (EMD Biosciences-Novagen, Madison, Wis.) and incubated for approximately 20 minutes in a 28° C. incubator. Remove the media and add 200 µL of eluted recombinant virus. After one hour, add 2 mL of 1% BacPlaque agarose-BacVector® Insect media containing 5% bovine serum albumin. After the agarose is solidified, add 1 mL BacVector® Insect media containing 5% bovine serum albumin to the transfected cells and transfer the cells to a 28° C. incubator for 3-5 days until plaques are visible. After 3-5 days post-transfection, plaques in the monolayer will be stained for β-glucuronidase reporter gene activity to test for the presence of recombinant virus plaques containing pBACgus3/BoNT/A-A17 by incubating the washed monolayer with 2 mL of BacVector® Insect media containing 30 µL of 20 mg/mL X-Gluc Solution (EMD Biosciences-Novagen, Madison, Wis.) for approximately 2 hours in a 28° C. incubator.

To prepare a seed stock of virus, elute a recombinant virus by transferring a plug containing a recombinant virus plaque with a sterile Pasteur pipet to 1 mL BacVector® Insect media (EMD Biosciences-Novagen, Madison, Wis.) in a sterile screw-cap vial. Incubate the vial for approximately 16 hours at 4° C. Approximately $5 \times 10^5$ Sf9 cells are plated in T-25 flask containing 5 mL of BacVector® Insect media (EMD Biosciences-Novagen, Madison, Wis.) and are incubated for approximately 20 minutes in a 28° C. incubator. Remove the media and add 300 µL of eluted recombinant virus. After one hour, add 5 mL BacVector® Insect media containing 5% bovine serum albumin to the transfected cells and transfer the cells to a 28° C. incubator for 3-5 days until the majority of cells become unattached and unhealthy. The virus is harvested by transferring the media to 15 mL snap-cap tubes and centrifuging tubes at 1000×g for 5 minutes to remove debris. The clarified supernatant is transferred to fresh 15 mL snap-cap tubes and are stored at 4° C.

To prepare a high titer stock of virus, approximately $2 \times 10^7$ Sf9 cells are plated in T-75 flask containing 10 mL of BacVector® Insect media (EMD Biosciences-Novagen, Madison, Wis.) and are incubated for approximately 20 minutes in a 28° C. incubator. Remove the media and add 500 µL of virus seed stock. After one hour, add 10 mL BacVector® Insect media containing 5% bovine serum albumin to the transfected cells and transfer the cells to a 28° C. incubator for 3-5 days until the majority of cells become unattached and unhealthy. The virus is harvested by transferring the media to 15 mL snap-cap tubes and centrifuging tubes at 1000×g for 5 minutes to remove debris. The clarified supernatant is transferred to fresh 15 mL snap-cap tubes and are stored at 4° C. High titer virus stocks should contain approximately $2 \times 10^8$ to $3 \times 10^9$ pfu of baculovirus.

To express gp64-BoNT/A-A17 using a baculoviral expression system, about $1.25 \times 10^8$ Sf9 cells are seeded in a 1 L flask containing 250 mL of BacVector® Insect media and are grown in an orbital shaker (150 rpm) to a cell density of approximately $5 \times 10^8$. The culture is inoculated with approximately $2.5 \times 10^9$ of high titer stock recombinant baculovirus and incubated for approximately 48 hours in a 28° C. orbital shaker (150 rpm). Media is harvested by transferring the media to tubes and centrifuging tubes at 500×g for 5 minutes to remove debris. Media samples are added to 2×LDS Sample Buffer (Invitrogen, Inc, Carlsbad, Calif.) and expression is measured by Western blot analysis (as described in Example 8) using either anti-BoNT/A or anti-His antibodies in order to identify baculoviral stocks expressing BoNT/A-A17. A similar procedure can be used to express a pBACgus3 construct encoding any of the modified Clostridial toxins of SEQ ID NO: 204 to SEQ ID NO: 213.

BoNT/A-A17 is purified using the IMAC procedure, as described in Example 8. Expression from each culture is evaluated by a Bradford dye assay, polyacrylamide gel electrophoresis and Western blot analysis (as described in Example 8) in order to determine the amounts of BoNT/A-A17 produced.

Example 11

Expression of Modified Clostridial Toxins in a Mammalian Cell

The following example illustrates a procedure useful for expressing any of the modified Clostridial toxins disclosed in the present specification in a mammalian cell.

Figure 15:
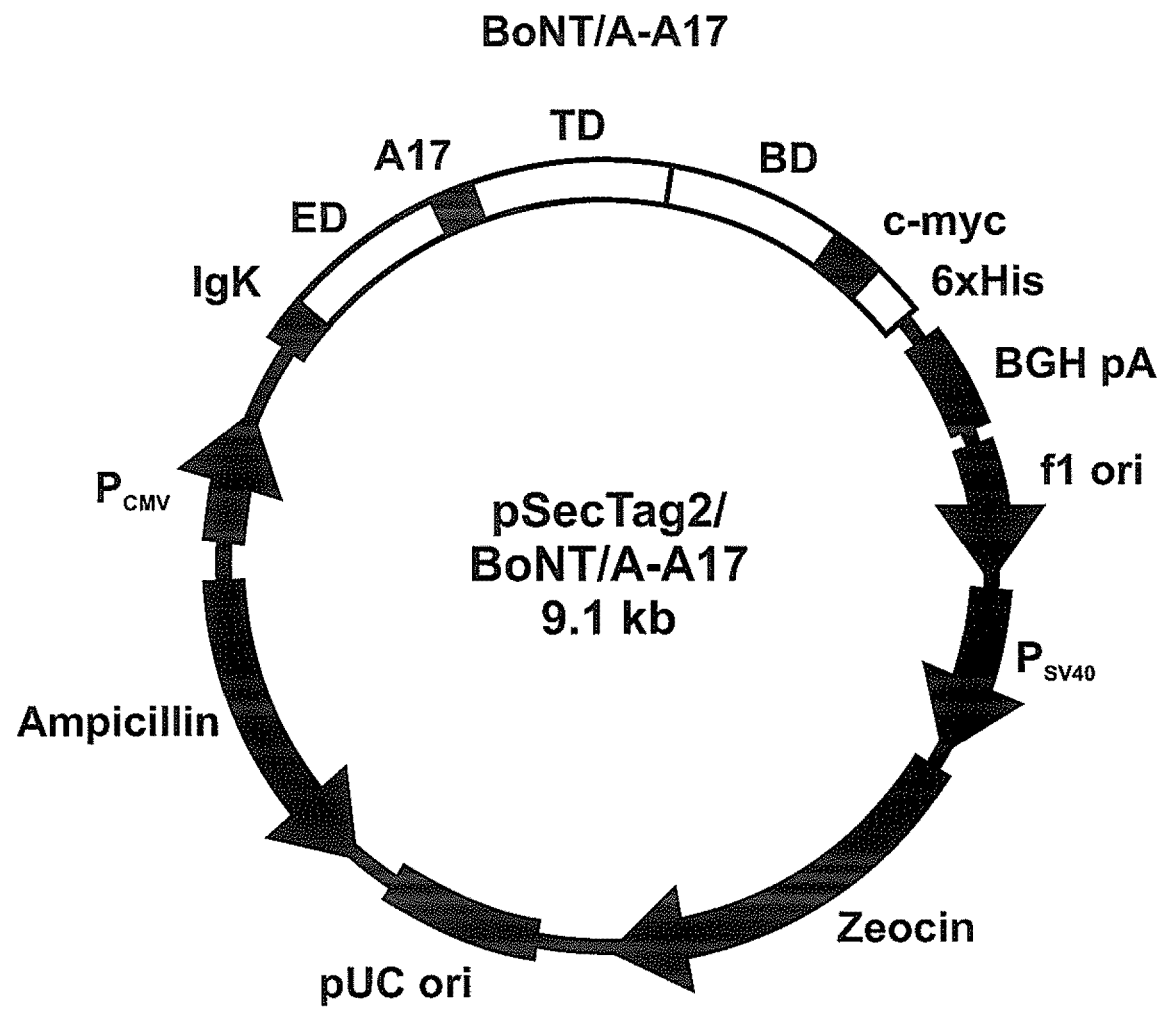

To construct a suitable mammalian expression construct encoding a modified Clostridial toxin, restriction endonuclease sites suitable for cloning an operably linked polynucleotide molecule into a pSecTag2 vector (Invitrogen, Inc, Carlsbad, Calif.) are incorporated into the 5'- and 3' ends of the polynucleotide molecule SEQ ID NO: 238 encoding BoNT/A-A17 of SEQ ID NO: 203. This polynucleotide molecule is synthesized and a pUCBHB1/BoNT/A-A17 construct is obtained as described in Example 1. This construct is digested with restriction enzymes that 1) excise the insert containing the open reading frame of SEQ ID NO: 238 encoding BoNT/A-A17; and 2) enable this insert to be operably-linked to a pSecTag2 vector. This insert is subcloned using a T4 DNA ligase procedure into a pSecTag2 vector that is digested with appropriate restriction endonucleases to yield pSecTag2/BoNT/A-A17. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yielded a pSecTag2 expression construct comprising the polynucleotide molecule of SEQ ID NO: 238 encoding the BoNT/A-A17 of SEQ ID NO: 203 operably-linked to a carboxyl-terminal c-myc and polyhistidine binding peptides (FIG. 15).

A similar cloning strategy is used to make pSecTag2 expression constructs encoding BoNT/A-A8 of SEQ ID NO: 204; BoNT/A-BT35 of SEQ ID NO: 205; BoNT/A-BT8 of SEQ ID NO: 206; BoNT/A-Csyn8 of SEQ ID NO: 207; BoNT/A-Csnp8 of SEQ ID NO: 208; BoNT/A-DF39 of SEQ ID NO: 209; BoNT/A-D8 of SEQ ID NO: 210; BoNT/A-E8 of SEQ ID NO: 211; BoNT/A-F8 of SEQ ID NO: 212; or BoNT/A-D8 of SEQ ID NO: 213.

To transiently express modified Clostridial toxin in a cell line, about $1.5 \times 10^5$ SH-SY5Y cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until cells reach a density of about $5 \times 10^5$ cells/ml (6-16 hours). A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of a pSecTag2 expression construct encoding a modified Clostridial toxin, such as, e.g., pSecTag2/BoNT/A-A17. This transfection is incubated at room temperature for approximately 20 minutes. The complete, supplemented DMEM media is replaced with 2 mL of OPTI-MEM Reduced Serum Medium and the 500 μL transfection solution is added to the SH-SY5Y cells and the cells are incubated in a 37° C. incubator under 5% carbon dioxide for approximately 6 to 18 hours. Transfection media is replaced with 3 mL of fresh complete, supplemented DMEM and the cells are incubated in a 37° C. incubator under 5% carbon dioxide for 48 hours. Both media and cells are collected for expression analysis of BoNT/A-A17. Media is harvested by transferring the media to 15 mL snap-cap tubes and centrifuging tubes at 500×g for 5 minutes to remove debris. Cells are harvested by rinsing cells once with 3.0 mL of 100 mM phosphate-buffered saline, pH 7.4 and lysing cells with a buffer containing 62.6 mM 2-amino-2-hydroxymethyl-1,3-propanediol hydrochloric acid (Tris-HCl), pH 6.8 and 2% sodium lauryl sulfate (SDS). Both media and cell samples are added to 2×LDS Sample Buffer (Invitrogen, Inc, Carlsbad, Calif.) and expression is measured by Western blot analysis (as described in Example 5) using either anti-BoNT/A, anti-c-myc or anti-His antibodies in order to identify pSecTag2 constructs expressing BoNT/A-A17. A similar procedure can be used to transiently express a pSecTag2 construct encoding any of the modified Clostridial toxins of SEQ ID NO: 204 to SEQ ID NO: 213.

To generate a stably-integrated cell line expressing a modified Clostridial toxin, approximately $1.5 \times 10^5$ SH-SY5Y cells are plated in a 35 mm tissue culture dish containing 3 mL of complete DMEM, supplemented with 10% FBS, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until cells reach a density of about $5 \times 10^5$ cells/ml (6-16 hours). A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of a pSecTag2 expression construct encoding a modified Clostridial toxin, such as, e.g., pSecTag2/BoNT/A-A17. This transfection solution is incubated at room temperature for approximately 20 minutes. The complete, supplemented DMEM media is replaced with 2 mL of OPTI-MEM Reduced Serum Medium and the 500 μL transfection solution is added to the SH-SY5Y cells and the cells are incubated in a 37° C. incubator under 5% carbon dioxide for approximately 6 to 18 hours. Transfection media is replaced with 3 mL of fresh complete, supplemented DMEM and cells are incubated in a 37° C. incubator under 5% carbon dioxide for approximately 48 hours. Media is replaced with 3 mL of fresh complete DMEM, containing approximately 5 μg/mL of Zeocin™, 10% FBS, 1× penicillin/streptomycin solution (Invitrogen, Inc, Carlsbad, Calif.) and 1×MEM non-essential amino acids solution (Invitrogen, Inc, Carlsbad, Calif.). Cells are incubated in a 37° C. incubator under 5% carbon dioxide for approximately 3-4 weeks, with old media being replaced with fresh Zeocin™-selective, complete, supplemented DMEM every 4 to 5 days. Once Zeocin™-resistant colonies are established, resistant clones are replated to new 35 mm culture plates containing fresh complete DMEM, supplemented with approximately 5 μg/mL of Zeocin™, 10% FBS, 1× penicillin/streptomycin solution (Invitrogen, Inc, Carlsbad, Calif.) and 1×MEM non-essential amino acids solution (Invitrogen, Inc, Carlsbad, Calif.), until these cells reach a density of 6 to $20 \times 10^5$ cells/mL. To test for expression of BoNT/A-A17 from SH-SY5Y cell lines that have stably-integrated a pSecTag2/BoNT/A-A17, approximately $1.5 \times 10^5$ SH-SY5Y cells from each cell line are plated in a 35 mm tissue culture dish containing 3 mL of Zeocin™-selective, complete, supplemented DMEM and grown in a 37° C. incubator under 5% carbon dioxide until cells reach a density of about $5 \times 10^5$ cells/ml (6-16 hours). Media is replaced with 3 mL of fresh Zeocin™-selective, complete, supplemented DMEM and cells are incubated in a 37° C. incubator under 5% carbon dioxide for 48 hours. Both media and cells are collected for expression analysis of BoNT/A-A17-c-myc-His. Media is harvested by transferring the media to 15 mL snap-cap tubes and centrifuging tubes at 500×g for 5 minutes to remove debris. Cells are harvest by rinsing cells once with 3.0 mL of 100 mM phosphate-buffered saline, pH 7.4 and lysing cells with a buffer containing 62.6 mM 2-amino-2-hydroxymethyl-1,3-propanediol hydrochloric acid (Tris-HCl), pH 6.8 and 2% sodium lauryl sulfate (SDS). Both media and cell samples are added to 2×LDS Sample Buffer (Invitrogen, Inc, Carlsbad, Calif.) and expression is measured by Western blot analysis (as described in Example 5) using either anti-BoNT/A, anti-c-myc or anti-His antibodies in order to identify SH-SY5Y cell lines expressing BoNT/A-A17. The established SH-SY5Y cell line showing the highest expression level of BoNT/A-A17 is selected for large-scale expression using 3 L flasks. Procedures for large-scale expression are as outlined above except the starting volume is approximately 800-1000 mL of complete DMEM and concentrations of all reagents are proportionally increased for this volume. A similar procedure can be used to stably express a pSecTag2 construct encoding any of the modified Clostridial toxin of SEQ ID NO: 204 to SEQ ID NO: 213.

BoNT/A-A17 is purified using the IMAC procedure, as described in Example 8. Expression from each culture is evaluated by a Bradford dye assay, polyacrylamide gel electrophoresis and Western blot analysis (as described in Example 8) in order to determine whether the amounts of BoNT/A-A17 produced.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

What is claimed is:

1. A recombinantly modified Botulinum neurotoxin toxin serotype B (BoNT/B) comprising an enzymatic domain having a zinc-dependent endopeptidase activity which targets a vesicle associated membrane protein (VAMP), a translocation domain, a binding domain and a modified di-chain loop region, the modified di-chain loop region intervening between the enzymatic domain and the translocation domain; wherein the di-chain loop region modification comprises a BoNT/B substrate cleavage site from a VAMP at least six amino acids in length located within the di-chain loop region that is proteolytically cleaved by the enzymatic domain of the recombinantly modified BoNT/B; and wherein expression of the recombinantly modified BoNT/B within a cell results in single chain to di-chain conversion of the recombinantly modified BoNT/B due to proteolytic cleavage of the BoNT/B substrate cleavage site.

2. The modified BoNT/B according to claim 1, wherein the BoNT/B substrate cleavage site comprises at least six consecutive residues of a VAMP, said six consecutive residues comprising Gln-Phe.

3. The modified BoNT/B according to claim 1, wherein the BoNT/B substrate cleavage site comprises SEQ ID NO: 107, SEQ ID NO: 108, SEQ ID NO: 109, SEQ ID NO: 110, SEQ ID NO: 111 or SEQ ID NO: 112.

4. The modified BoNT/B according to claim 1, wherein the modification further comprises a flexible region comprising one or more flexible spacers located within the di-chain loop region.

5. The modified BoNT/B according to claim 4, wherein the one or more flexible spacer are G-spacer, A-spacers or any combination thereof.

* * * * *

UNITED STATES PATENT AND TRADEMARK OFFICE
CERTIFICATE OF CORRECTION

| | | |
|---|---|---|
| PATENT NO. | : 7,815,917 B2 | |
| APPLICATION NO. | : 12/434074 | |
| DATED | : October 19, 2010 | |
| INVENTOR(S) | : Lance E. Steward et al. | |

It is certified that error appears in the above-identified patent and that said Letters Patent is hereby corrected as shown below:

In column 8, line 24, delete "HC($H_N$)" and insert -- HC ($H_N$) --, therefor.

In column 9, line 16, delete "11 (9)" and insert -- 11(9) --, therefor.

In column 40, in table 5, line 6, delete "Ans" and insert -- Asn --, therefor.

In column 43, line 45, delete "amino" and insert -- 15 amino --, therefor.

In column 43, line 54, delete "amino" and insert -- 20 amino --, therefor.

In column 67, line 65, delete "LTINIRGTNIEEFLTF" and insert -- LITNIRGTNIEEFLTF --, therefor.

In column 73, in table 8, line 14, delete "cleavagesite" and insert -- cleavage site --, therefor.

In column 81, line 23, delete "asterisk" and insert -- asterisks --, therefor.

In column 123, line 27, delete "SPECTRA$^{TM}$" and insert -- SpECTRA$^{TM}$ --, therefor.

In column 133, line 41, delete "Patent Patent" and insert -- Patent --, therefor.

In column 142, line 26, delete "MultiImager" and insert -- Multiimager --, therefor.

In column 142, line 50, delete "monolaureate" and insert -- monolaurate --, therefor.

In column 142, line 55, delete "monolaureate" and insert -- monolaurate --, therefor.

In column 317-318, line 12, delete "subtrate" and insert -- substrate --, therefor.

Signed and Sealed this
Nineteenth Day of April, 2011

David J. Kappos
*Director of the United States Patent and Trademark Office*

CERTIFICATE OF CORRECTION (continued)
U.S. Pat. No. 7,815,917 B2

In column 341-342, line 11, delete "hemagluttinin" and insert -- hemagglutinin --, therefor.